US008728731B2

(12) United States Patent
Rohlfs et al.

(10) Patent No.: US 8,728,731 B2
(45) Date of Patent: May 20, 2014

(54) MUTATIONS ASSOCIATED WITH CYSTIC FIBROSIS

(75) Inventors: Elizabeth Rohlfs, Hopkinton, MA (US); Deborah Alexa Sirko-Osadsa, North Grafton, MA (US); Lynne Rosenblum, Hopkinton, MA (US); Narasimhan Nagan, South Grafton, MA (US); Zhaoqing Zhou, Natick, MA (US); Ruth Heim, Shrewsbury, MA (US)

(73) Assignee: Laboratory Corporation of America Holdings, Burlington, NC (US)

(*) Notice: Subject to any disclaimer, the term of this patent is extended or adjusted under 35 U.S.C. 154(b) by 183 days.

(21) Appl. No.: 13/053,626

(22) Filed: Mar. 22, 2011

(65) Prior Publication Data

US 2011/0230365 A1 Sep. 22, 2011

Related U.S. Application Data

(60) Provisional application No. 61/316,321, filed on Mar. 22, 2010, provisional application No. 61/359,029, filed on Jun. 28, 2010.

(51) Int. Cl.

| | |
|---|---|
| ***C12Q 1/68*** | (2006.01) |
| ***C12P 19/34*** | (2006.01) |
| ***C07H 21/02*** | (2006.01) |

(52) U.S. Cl.

USPC ......................... 435/6.11; 435/91.1; 536/23.1

(58) Field of Classification Search

None

See application file for complete search history.

(56) References Cited

U.S. PATENT DOCUMENTS

| | | | | |
|---|---|---|---|---|
| 4,956,778 | A | 9/1990 | Naito | |
| 4,996,617 | A | 2/1991 | Yaeger et al. | |
| 5,019,513 | A | 5/1991 | Kasper et al. | |
| 5,132,405 | A | 7/1992 | Huston et al. | |
| 5,543,399 | A | 8/1996 | Riordan et al. | |
| 5,776,677 | A | 7/1998 | Tsui et al. | |
| 5,846,710 | A | 12/1998 | Bajaj | |
| 5,885,775 | A | 3/1999 | Haff et al. | |
| 5,888,819 | A | 3/1999 | Goelet et al. | |
| 5,945,526 | A | 8/1999 | Lee et al. | |
| 6,201,107 | B1 | 3/2001 | Lap Chee et al. | |
| 6,280,947 | B1 | 8/2001 | Shuber et al. | |
| 6,482,595 | B2 | 11/2002 | Shuber et al. | |
| 6,503,718 | B2 | 1/2003 | Shuber et al. | |
| 6,919,174 | B1 | 7/2005 | Shuber | |
| 7,501,251 | B2 | 3/2009 | Koster | |
| 2002/0150894 | A1 | 10/2002 | Batra et al. | |
| 2003/0235834 | A1 | 12/2003 | Dunlap et al. | |
| 2004/0110138 | A1 | 6/2004 | Lem et al. | |
| 2004/0166760 | A1 | 8/2004 | Kikuchi et al. | |
| 2004/0253636 | A1* | 12/2004 | Soloviev et al. | 435/7.1 |
| 2006/0024692 | A1 | 2/2006 | Nakamura et al. | |
| 2007/0254289 | A1* | 11/2007 | Li et al. | 435/6 |
| 2008/0153088 | A1* | 6/2008 | Sun et al. | 435/6 |

FOREIGN PATENT DOCUMENTS

| | | |
|---|---|---|
| WO | WO 2004/040013 | 5/2004 |
| WO | WO 2005/006951 | 1/2005 |

OTHER PUBLICATIONS

Weiss et al. Gut Jun. 2005 vol. 54 pp. 1456-1460.*

Rowntree et al,. Annals of Human Genetics 2003 vol. 67 pp. 471-485.*

Castellani et al. Journal of Cystic Fibrosis 2008 vol. 7 pp. 179-196.*

Audrezet, M. et al., "Genomic rearrangements in the CFTR gene: extensive allelic heterogeneity and diverse mutational mechanisms," Hum Mutat. 2004: 23(4):343-57.

Ausubel, F. M. et al. 1994, Current Protocols in Molecular Biology, John Wiley & Sons, Secaucus, NJ.

Boat et al., "The Metabolic Basis of Inherited Disease," 1989, 6th ed., pp. 2649-2680, McGraw Hill, NY.

Chu, et al., "Immunohistochemical Staining in the Diagnosis of Pancreatobiliary and Ampulla of Vater Adenocarcinoma," Am J. Surg Pathol., 2005, 29(3):359-367.

Huston, J. et al., "Protein engineering of antibody binding sites: recovery of specific activity in an anti-digoxin single-chain Fv analogue produced in *Escherichia coli*," Proc Natl Acad Sci U S A. Aug. 1988;85(16):5879-83.

Kerem, B. et al., "Identification of the cystic fibrosis gene: genetic analysis," Science. Sep. 8, 1989;245(4922):1073-80.

Lemna, W. et al., "Mutation analysis for heterozygote detection and the prenatal diagnosis of cystic fibrosis," N Engl J Med. Feb. 1, 1990;322(5):291-6.

Noone, P. et al., "'CFTR-opathies': disease phenotypes associated with cystic fibrosis transmembrane regulator gene mutations," Respir Res., 2001;2(6):328-32. Epub Aug. 9, 2001.

Okayama, H. et al., "Rapid, nonradioactive detection of mutations in the human genome by allele-specific amplification," J Lab Clin Med. Aug. 1989;114(2):105-13.

Poddar, S., "Symmetric vs asymmetric PCR and molecular beacon probe in the detection of a target gene of adenovirus," Mol Cell Probes. Feb. 2000;14(1):25-32.

Richards, C. et al., "ACMG recommendations for standards for interpretation and reporting of sequence variations: Revisions 2007," Genet Med. Apr. 2008;10(4):294-300.

Sarkar, G. et al., "Characterization of polymerase chain reaction amplification of specific alleles," Anal Biochem. Apr. 1990;186(1):64-8.

Southern, K. "Cystic fibrosis and formes frustes of CFTR-related disease," Respiration, 2007;74(3):241-51.

Wu, D. et al., "Allele-specific enzymatic amplification of beta-globin genomic DNA for diagnosis of sickle cell anemia," Proc Natl Acad Sci U S A. Apr. 1989;86(8):2757-60.

(Continued)

*Primary Examiner* — Amanda Haney

(74) *Attorney, Agent, or Firm* — Kilpatrick Townsend & Stockton LLP

(57) ABSTRACT

The present invention provides novel mutations identified in the cystic fibrosis transmembrane conductance regulator (CFTR) gene that can be used for a more accurate diagnosis of cystic fibrosis (CF) and CF related disorders. Methods for testing a sample obtained from a subject to determine the presence of one or more mutations in the CFTR gene are provided wherein the presence of one or more mutations indicates that the subject has CF or a CF related disorder, or is a carrier of a CFTR mutation.

29 Claims, 63 Drawing Sheets

(56) References Cited

OTHER PUBLICATIONS

Hoogendoorn, B. et al., "Genotyping single nucleotide polymorphisms by primer extension and high performance liquid chromatography," Hum Genet. Jan. 1999;104(1):89-93.

Ju, J et al., "Fluorescence energy transfer dye-labeled primers for DNA sequencing and analysis," Proc Natl Acad Sci U S A. May 9, 1995;92(10):4347-51.

Landegren, U. et al., "A ligase-mediated gene detection technique," Science. Aug. 26, 1988;241(4869):1077-80.

Mann, D. et al., "Elevated tumour marker CA19-9: clinical interpretation and influence of obstructive jaundice," Eur J Surg Oncol. Aug. 2000;26(5):474-9.

Newton, C. et al., "Analysis of any point mutation in DNA. The amplification refractory mutation system (ARMS)," Nucleic Acids Res. Apr. 11, 1989;17(7):2503-16.

Nickerson, D. et al., "Automated DNA diagnostics using an ELISA-based oligonucleotide ligation assay," Proc Natl Acad Sci U S A. Nov. 1990;87(22):8923-7.

Patent Cooperation Treaty, International Search and Written Opinion, International Application No. PCT/US11/32702, mailed Jun. 14, 2011.

Paul, W. E., Fundamental Immunology, 1993, Raven Press, NY.

Piggee, C. et al., "Capillary electrophoresis for the detection of known point mutations by single-nucleotide primer extension and laser-induced fluorescence detection," J Chromatogr A. Sep. 26, 1997;781(1-2):367-75.

Sambrook et al., Molecular Cloning: A Laboratory Manual, 2nd Edition, 1989, Cold Springs Harbor Press, Plainview, NY.

Stears, R. et al., "A novel, sensitive detection system for high-density microarrays using dendrimer technology," Physiol Genomics. Aug. 9, 2000;3(2):93-9.

Wall, J. et al., "A 31-mutation assay for cystic fibrosis testing in the clinical molecular diagnostics laboratory," Hum Mutat. 1995;5(4):333-8.

Handbook of Fluorescent Probes and Research Products, Haugland eds., 9th Ed., Molecular Probe, Inc., Eugene, OR. 2002.

European Patent Office, Communication Pursuant to Rules 161(2) and 162 EPC, Application No. 11760022, dated Nov. 23, 2012.

Doucet et al., "Applicability of Different Antibodies for the Immunohistochemical Localization of CFTR in Respiratory and Intestinal Tissues of Human and Murine Origin", J. Histochem Cytochem, 51(9):1191-1199, 2003, XP055073665.

Database Geneseq (Online), "Human CFTR probe SEQ ID No. 245", XP002708092, Database accession No. ADW15425 , dated Apr. 7, 2005, web page at http://ibis.internal.epo.org/exam/dbfetch.jsp?id+GSN:ADW15425, as available via the internet and printed Jul. 31, 2013.

Kerem et al., "Identification of the Cystic Fibrosis Gene: Genetic Analysis", Trends in Genetics, Elsevier Science Publishers B.V. Amsterdam, NL, vol. 5, p. 363, 1989, XP025207998.

Anonymous: "Mutation Details for c.1692delA" Cystic Fibrosis Mutation Database XP882788893, web page at http://www.genet.sickkids.on.cajMutationDetailPage.external?sp=1831, as available via the Internet and printed Jul. 30, 2013.

European Patent Office, Extended European Search Report, Application No. E26577EP, mailed Sep. 10, 2013.

State Intellectual Property Office of the People's Republic of China, Notification of the First Office Action, Application No. 201180022402, mailed Oct. 25, 2013.

* cited by examiner

```
   1 aattggaagc aaatgacatc acagcaggtc agagaaaaag ggttgagcgg caggcaccca
  61 gagtagtagg tctttggcat taggagcttg agcccagacg gccctagcag ggaccccagc
 121 gcccgagaga ccatgcagag gtcgcctctg gaaaaggcca gcgttgtctc caaacttttt
 181 ttcaggtgag aaggtggcca accgagcttc ggaaagacac gtgcccacga aagaggaggg
 241 cgtgtgtatg ggttgggttt ggggtaaagg aataagcagt ttttaaaaag atgcgctatc
 301 attcattgtt ttgaaagaaa atgtgggtat tgtagaataa aacagaaagc attaagaaga
 361 gatggaagaa tgaactgaag ctgattgaat agagagccac atctacttgc aactgaaaag
 421 ttagaatctc aagactcaag tacgctacta tgcacttgtt ttatttcatt tttctaagaa
 481 actaaaaata cttgttaata agtacctaag tatggtttat tggttttccc ccttcatgcc
 541 ttggacactt gattgtcttc ttggcacata caggtgccat gcctgcatat agtaagtgct
 601 cagaaaacat ttcttgactg aattcagcca acaaaaattt tggggtaggt agaaaatata
 661 tgcttaaagt atttattgtt atgagactgg atatatctag tatttgtcac aggtaaatga
 721 ttcttcaaaa attgaaagca aatttgttga aatatttatt ttgaaaaaag ttacttcaca
 781 agctataaat tttaaaagcc ataggaatag ataccgaagt tatatccaac tgacatttaa
 841 taaattgtat tcatagccta atgtgatgag ccacagaagc ttgcaaactt taatgagatt
 901 ttttaaaata gcatctaagt tcggaatctt aggcaaagtg ttgttagatg tagcacttca
 961 tatttgaagt gttctttgga tattgcatct actttgttcc tgttattata ctggtgtgaa
1021 tgaatgaata ggtactgctc tctcttggga cattacttga cacataatta cccaatgaat
1081 aagcatactg aggtatcaaa aaagtcaaat atgttataaa tagctcatat atgtgtgtag
1141 gggggaagga atttagcttt cacatctctc ttatgtttag ttctctgcat gtgcagttaa
1201 tcctggaact ccggtgctaa ggagagactg ttggcccttg aaggagagct cctccctgtg
1261 gatgagagag aaggacttta ctctttggaa ttatcttttt gtgttgatgt tatccacctt
1321 ttgttactcc acctataaaa tcggcttatc tattgatctg ttttcctagt ccttataaag
1381 tcaaaatgtt aattggcata aattatagac ttttttttagc agagaacttt gaggaaccta
1441 aatgccaacc agtctaaaaa tgcagttttc agaagaatga atatttcatg gatagttcta
1501 aatactaatg aactttaaaa tagcttacta ttgatctgtc aaagtgggtt tttatataat
1561 tttcttttta caaatcacct gacacattta atataggtta aaaaatgcta tcaggctggt
1621 ttgcaaagaa aatgtattac aaaggctgct aagtgtgtta agagcatact catttctgtt
1681 ctccaaaata tttcataagg tgctttaaga ataggtatgt ttttaaaagt taagttccta
1741 ctatttatag gaactgacaa tcacctaaaa taccaatgat tacaaacttc cttctggcct
1801 tctggactgc aattctaaaa gtgtaaaaaa catattttct gcattaagtt aggcagtatt
1861 gcttagtttt caaagtggta ggctttggag tcagattatt ttgattcaga tcctacatct
1921 actgtttagt agctctgttg cctgaggcag gtcccttaac atctctgtgt gtgacttgac
1981 ctttaaaatt tggagactgt catagggggtt aatcccttga gaaaatgaat gtgaaaagtt
2041 agcctaatgt taactgctat tattatggat taccatattt tcacattcat cacagtacat
2101 gcaccttgtt aatataagat gctcaattca tctttgagta taattttgtg actctcaatc
2161 tggatatgca atgagtgggc ctgtatgaga atttaattta tgaaaaattg tgtttcacat
2221 ggccttacca gatatacagg aaacacgtca catgtttcta ttgtatgttg ttaaatgcct
2281 tagaatttaa ctttctgaat aggatccctt cagtttgaga gtcataaaag agtaaaatta
2341 ttatggtatg agttatagat tgtattgaat atctctttat atgtctaggt tttgtcattg
2401 gaaaaccaaa aagtttggaa aaaaaatcta agttatttct tactttctta attttgtgtg
2461 gatttcacat caagtataaa atttgaagaa catctgaact atcataatcc atatatatat
2521 ataaaataaa cataatctaa gagagaattt caccatgaaa aattcaggta gttcatgact
2581 atcagagcaa acaagtacat taaattgaaa cttttatgaa aataacattt atgaaatagg
2641 aagctatttt taaactagaa gtgatatatt agcatataat ttataattca tatacaagtg
2701 ggattgattt ataaatggtc accaacagag attgtgctat ttaatttggg aaaatttttt
2761 aaatttacat tttctcacaa cttttaaggt agttattcag tttgttcctc tctgtctctt
2821 ctctcatgcc ctgaattttt catatttcgt ttagttgtaa gagtgtatat caaaccgtgt
2881 gtcacatgac ataacttgaa ttttcgtcgt gatatctgtg ctatgtctag gtctatactg
2941 aggaactgtg ggaaccccac agaatccaag tatacagtgc cactgatttc ttacaaggga
3001 tgtggggtct cctgtaaact ctgcagttag tctcaagtaa gaccaaagag taaaatattg
3061 ttaggatcta aggtggaaat tcagcaaaga atcacatagt ctaagtctcg agtttaacag
3121 taagataatt tgagatactt ttgtaattat taaacacaaa gtaatgagag attttaaaac
3181 aaacaaatac acctgaattt atatatcaga ataggtatgg tggttcaaaa tagctatcta
```

FIG. 1 (SEQ ID NO: 1)

```
3241 ataaaaacca cactcctatt ctaaacattt gcctttgatc aaaataattt tgggtctctt
3301 attatgaaat tgcctttcta aataatacat aaatttcttc tcataagtat atattagcca
3361 cattatttta ttgttattgt tttatattca tagcttgctt tagattaaaa attatattac
3421 ccagactggt ctcttggact tgcttccaag tgacttttga ctgtatcaca aaatcaaatt
3481 cactctgaaa atataaagat ttttcatcat aatttccttt gttaacagcc aagtgctacc
3541 taattttagg tgttttcatt aaaaaaaaat gcattgcaaa ctttaaagac aattcttttg
3601 tttgtttgtt tttaaaagac agagtctcac tctgttgccc aggctagagt gcagtgacac
3661 aatcataact cactgcaacc tccacctcct gggctcaagt gagccttcca tcttgcctca
3721 cgagtagctg ggtcttcagg tgtacaggtg tgtaccacca tgcctggcta actttttttt
3781 tttttaagtt atatagagac agtatctcac tatgttgccc aggctgctct tggagctcct
3841 ggcctcaagt tatcctccca ctcagtctcc caaagtgctg ggattacagg cgtaagccac
3901 ctcaccctgt cagcctaaag acagtgctta atgaagagaa atataagtgc tttgagcaat
3961 ggaagtataa ttaaaattat actatgaaag atttataaag atgaccattt tgaatgggac
4021 cacacttatt tggttatata aattatgata cactattaaa aattcatcat gatgattttg
4081 tatttacatt ttatttacat gtttgcaatt tgtgaggaaa gctaaaatta tggctaagcc
4141 ataaatattt ttgcagtttg ttgagggtgt ttgtaaaagt gttgccaagg aagaccagtt
4201 ggctacccaa acaagggttt agtctaggtc tgatcaatac atacacatta tctcaggttt
4261 gtctatcaga aaaaccttag gttatccaaa tcaaaataaa atagatgcat aaaacaaagg
4321 ccaatatgtg ttgaacaatt atattgtgat atacaactgc caagcattcc cgattaccat
4381 gactccattt agtcagtcca tgggcaaatg ccatcaatga ggacagccca gggtttccat
4441 attctctctt ggctttacat cctataggaa ttggaggggc ccacctctgg gataggagcc
4501 cttctgtctt gaacaatgtt gtctgaacac taacaaatgt tgactttcta caccagtccc
4561 tcaatagtct tttctattta tcctttttgct gaccatgttt tgttattaca cagttgagat
4621 ttttcagctg ggaatctgtg ttaattttgt attaattttg attagcttaa ctctcagagt
4681 tctaaaagta cctcctgtac ctgatatatg acaaaaatta taattacatt tatttatata
4741 taaaatatct ttgtatatgt aaaatatctt tgtatatata attatataat tgtttctttt
4801 aattttgcaa attttaaaaa gttctccttt gttttgaagt ttattcctat agttttttat
4861 atgctagtta aattattaat cacttgattc aagtaatatt cttatatact tataaggaat
4921 agtgtagttt taatatttaa ttccttgcta aagagagaag tggaatctat ttttcttagc
4981 tacttcatca atattttatg tttgatgtga cagtcaaaat atccctcaga gctaactgtt
5041 acactaggga aatcacggtt ttccagtttt ccatttatgt gttatgggag ggagtggaac
5101 ttagtgtaat aatattcaat acataaatgt taacacttgt ttaaaggtcc ttgagtgagt
5161 actgctataa aatgcattat tattgctagt gtcatttcac aagagcctat aatttcagtg
5221 tgatagagct acaatataag tatagtattg caaaaccatc aggaagggtg ttaactattt
5281 agcatgcagt tatgtgttgg ttgtcaaaac gttaaaaaca tctctgactc agcagcaatt
5341 ttggcaattt tgatcctgag gcatctgtgt agggcatctt cctggagaaa aacctctgag
5401 atgcaatgag gtcaaaaggg gaaaacagac tatgataaag atcaagttgt ttggagatct
5461 tgtagaaaga ttaatttaca aatatgtcaa gtgcattatc atggaggaaa acattgctat
5521 ttctgttggt tctcttcaga gctctagaat caatttacca catagttgtt tcagtgtgaa
5581 attagcatta cagagtggct ttacggcttt actgtagggc attgtgtcag caaagagctt
5641 aggcttcttt tagcaagaag cttgtaaaaa tttaatttac tcttagattg cttgatgtag
5701 agaattacat tcctacagag ctctgaaaaa tctttttca gagtttttca cagctgtatt
5761 caagttgcaa ggcttgtcaa ctttgctatt tttctgtgca gctctgttaa cttattatta
5821 tcttttgaca taaattatga ttccaaattg taaagctctg gatgtcaggg ccttttctaa
5881 tttgtttagt atgatattca gaccatttca agactcttcc gtggaacaat ttaataaaga
5941 tttttttgtg atgttaatga gttcatggtg atcaacccta gagacctgtg tctattgtag
6001 atcgatgaca ttcaacagtc ctgcagtgct ggcatcattt tgataaaaag gggtcaaagc
6061 aagtgggact gtgggcagat ttttaatgct tagaacaatt attccatcga agtttttcttg
6121 tgtcccttct gccttagcct ttgtaggata gcatgcttgc taatttcttg ctcatggggt
6181 aaggaaatga agatttttgc taggtccgta ggattattag gactactcag gcctgaagct
6241 atgcctggat atagccagaa aactctccca tagcttgctc caaggagctg agatacagca
6301 gtacttcctt tgtaggtcat gattctgggt aacctggaag atgacctcat tcatattctg
6361 tattctatgt gagacgttaa gaaggtagag gtggccaaga aggaaattgt tgctgccttt
6421 atggaacaaa ttatctgaaa cccagctttc tcgagggctt cattgaagta ctcaactggg
6481 gcacttaacc cagtctaagg ctggtcaagg aaggcttgct gggggaagtg tcttttgtat
6541 tcacacctaa aggaggttat tcaattagaa ttatccaaag agggtaggga tgggctagga
6601 aaaatttaaa caggtagtgt ggaggactga caggataagt aagcatggca ccttcaaaat
```

FIG. 1 (cont.) (SEQ ID NO: 1)

```
6661 atcctgagaa gttccctatg acgggaacat aaaatatgtg acagagattt gtgggagatg
6721 ggtctggaaa ctctagcagg ggccagatcg taagggggct ttgtaggctt tgtaggcttt
6781 gtttgggctt tatcatactg gaagtgaaaa gccatggctt ttaaacagga gagggacata
6841 atcagttcat atactgttgc agttttgtaa aagaaaagat gagctgaaag agtggccatg
6901 gtggaggtgg gtggggtggg ggggaggggg cggggagaga gagagagaga gagagatttg
6961 aaagacattt aggaggtaaa atcaactggt ttggtaatca attagtagtt gaaggtgaag
7021 gaaagagaag agttaaggat aacatctata tttgttgatt tggataatag aggggacagt
7081 ggtgctgctt attgaatgag aaaatttaat cggagaagaa ggcatggagc aggagtgcag
7141 acctatgtga ctctacttct ctcaaaacca gaaacggaaa tgatgtatat ggctcagggt
7201 taggtaatat ggttatttga aaatgtatta aagtgattta gagcttagtc ttaggtaaga
7261 gatataagat gtctgaggtg acagttttat aaatatgtag agtgcccact tgtttggcct
7321 tattgtggca tagtgtgacc tgagagtgtt aggaagaagc agctgagttc tagggacagt
7381 actggttaaa ttctacttag aaattatact tagaactctc ctatataacc tgctaactga
7441 tgtctgaacc tcctgataac ttcactcctt taggcagtgc ttttcacatc acgggacaca
7501 acatatgaga gatcatagaa attcaatgtg gtatgaaaat ctgcttggga cttcagatat
7561 tgtctccagt gattgaataa aaataggagc tcacctacta tgatgaggtt tctgtgtgtg
7621 ttaaaagaag gttttcatta cttttgaaaa ggttatgtat ccttgtttta tgttaaaact
7681 ttgagctttg ttaaatatgc agagttctct ttcttagcat ggactacaga ggtgcaacta
7741 cctcctacct gacttcacat ctactcccaa atgcctagtg aaggcttaat aatttcaaaa
7801 agggactcta gaatttcatt tgataccagt cagacaaatg tgtgaaaatt aagcataata
7861 ggcagaatcc caggggtact gacagctgta ttaagaggtg attcaagggc taaaccttag
7921 agtccagcat tggttatggg tgtgacaaga aaatgaagcc tatgttggct gggattagca
7981 accacagttc tagaggaagc aaggtggaga aactatatag gggctccct ttgtacgttt
8041 tatttatttt aaacatctct ataaactcta gaaattaaaa caacaatacc aacacaaaag
8101 catcactttt tcgaccaaag accattgcta tactttttttg tgtaaagggc tagatagtaa
8161 atattttcag ctttgtgggc cacataagtc tctgcaatag acaatatgca aacaaataag
8221 catggctgtg tttcaattaa actttattat gaacattaaa atttgaattt catataactt
8281 ttacatgttg caaaatattc tttatttaaa ttctattgca atatgcttta aaagatacag
8341 tttttagtct ttcttagttt aaaataaaat ctagaaaaaa ttttaagtct tctataactt
8401 tttttcggta actgaataat tttaaaagta agtgaaacat ttagacatgc aaaatggact
8461 tttcagaaga agaaaatggt agcttaacag ttattagatt attgtccaga ataatttttg
8521 acttataagt ctctgttgac catttcattg cctctttttt tggaatatgc atcttttaat
8581 gtgtccttca aggcaaaggc tctatcttat ctatcttgtg tcttgcattt tcccagggca
8641 atgtttttca caattttttt aaaaaacaat actgtaatca attttcaaat aaaatttcc
8701 atgggaccgc agtgtataca aatagcagtg acaataaaag ataataactc tcccataaat
8761 acaaagaaac agttaaccta gtgctctaaa gtaaaggcta cagtgatttt gtataacatt
8821 tatatgtaat tttcttgatc ctacatggtt gtgtttttca cagtgttatg tttctgaaat
8881 cgagatgcct tttataattg atgtcaaaag aaacttgtca gccacaaggc ccaggaataa
8941 gttgtaatat gggaacttag caatacataa aggtatatat actcctgtga cctcagctga
9001 attatttgca ttggttgcat cccacaaggt tgactcttaa ataaatttag tttgttgctt
9061 gaaatttctt gggataaatt actttgtgat gtagttttga aaaaaaaaca ggtaatattt
9121 agtctgaagt ttgtctgaca tactaagcaa tgtaattaaa gtagaagtcg cctaagctca
9181 gcactttatt atgccttgaa attatactgc ctgtcctaca ggtgaaggtg ttatgaatgc
9241 agtttgtcac tgtaactcta ttcatagctc tgaaaggctg agagtgactc agaagaatat
9301 ttttgctctg aatatgaaga acgcttagac taaaacttta attacgatgc tgaagaagaa
9361 agtggtaggt gattgcatga ataagtatgt aatattgtta atttctaaaa actgtgtata
9421 gttaatgtag tgcttctttt tggaaaggct attgttaaat tgatggtaaa ttctataacc
9481 aatatcacct taaagcaagt acgcatgata aagtattata aaaccatgat aatatcatat
9541 gtggcttatt attgttccct gagtgttgta caactctgtt atgctgtgat gaaacctcat
9601 gcaaacaggt atgtcaaaga tatgatgggc tgttaactga gcttggccca catatggtgt
9661 agtgacatgc tcactaatgc agtgcagaga taaccaataa cagatcataa caggtttaaa
9721 tatgtgcaag gagatgtcag cagaagcttt cctacatagt gaatactaaa caagcctgac
9781 agcccaggat catgttcgga tcaatctagt gtgctaaaat taacatatag tcctacattt
9841 gagaatgtgt gattttcttg gttcctgtct ataaaataat attttaaaat acatacattt
9901 caaatcagaa gttggtgaat tcactgaaat atttctagag aacactaggt attggggctc
9961 atagtgtgaa aaccactgac ttaattcttc ccccatcttg gttgttcctg atcttccctt
10021 gtgtccccat tccagccatt tgtatcctta gaaaatgatc tcatattcta cttcatcttt
```

FIG. 1 (cont.) (SEQ ID NO: 1)

```
10081 atcttcattg tcaactgtca ggtagcaata tatgatggaa gaagcatgta ctttggaatc
10141 agacagacct ggctggaatc ctaactctgt cacttattaa caatgtgatc ttaggcaatt
10201 tacttaatct ctctgaacct cagctactct cgtcagtaca atgagttatc cttatcttta
10261 catggcacag tattattatg atatcaaaaa ttcattgagt atttactctg catattagtc
10321 aaggttctcc agagaagtag aaccaatgat acacacacac acacacacac acacacacac
10381 acacacacac acaatttatt ataaggaatt gacttacatg attatgatgg ctaacaagtc
10441 caaaatctgc agtatgggtc agctggcagg aaacccagga gagtcaatgt tccagtttga
10501 gtctgaaggc agtctgttgg ggaatttcgt ccttctctgg gaggccagcc tttttgttct
10561 atacaggcct tcaaccgatt ggatgaagtt cacctttatt agtgagggca atctgcttta
10621 accaaagttt actgatttaa atgttaatct catccaaaaa cacccaccca gttgacacat
10681 aaaattaacc atcactctct gtaagcactt tctatgcatt aagtgatagc aaataatgcc
10741 agacataggg cgtctttaat aaatggtaag cactgttatc agcaacaaca ggattattat
10801 aattagcacc ttttcatctt tctgtctggg ctctgagaaa gtacctctct tctctaaatt
10861 tatccctcct ttcctatgaa ttagacccag tgctttctct gaattatgaa ggtcacactc
10921 ctacaaatgc cccttcccaa ttgcacatct gtcggctttc tttgccattg acttttatct
10981 ctagctttta aatttacagg catatgtcag ttaacaatgg gaatgcgttc tgggtaatat
11041 gtccttaggc aattttatcg ttgtgagaat actatagagt atacctacac aagcctagat
11101 gtcgtatagc ctactacaca cctaggcaat atgacatagt cttttgcttc taggctacaa
11161 acctgtacgg cttgttacta tactgaatac tgcaggcagt tgtgacacag tggtatttgc
11221 atatcggaac atgtctaaac acagaaaagg tgcactaaaa atactatgta gtgatctcat
11281 gggaccacca ttgtatatgc agtctgctgt agactgaaat gtcatgcagt gcataactgt
11341 atcttaaata ctcaaagtat cacctttgtt tgtttgtccc cttgtgtgca tcatcctaac
11401 gtggaatttc tctgttgatt agggccagcg tattagtttg ctagggctac cataacaaaa
11461 taccacaaat ttggtggctt aaataacagg aatttattat cttatggttt tgaagactag
11521 aagtacaaga tcaaggtgtt ggcaggtttt tcttctaagg gccatgagga agagtctatt
11581 ccatgccttt cccctacctt ctggtggttt gctagaaatc cttggcattc cttgacttac
11641 agaggcatca ccctgatctc tgttttcatc ttcacatggc attctccctg tgagcctgtc
11701 tctgtgtcca aacttcttta ctattaatat aaggacacca gtcatattgg attagggtct
11761 actttagtga cctcattgga atgttattac ctctgtaaag atcctatctc taaataaggt
11821 cacatcctta ggtaccgggg gttaggactc aaacatacct tttttggggg aaacacaatt
11881 caacctataa caattgataa cactctttag gagcagaatg cgatatggaa gtaatttgag
11941 accataaagt atatacatgt agggagttaa tctatgaaac ctattgaaag ccatatatac
12001 ctcatgtata gtggtccata aatagcatgg agacattgca gaggatgtta agtgatatga
12061 tacaggaaca atccaagaag gtcataagaa aaaggacctt ttgctcttga gaggactgaa
12121 gaatgacttt ccatttatga aattttggta catgtccact aaaaatagga tgaaggccaa
12181 acttaggaag aatattttga taatggagaa ggttgcatat aaaaacattt tattgaggac
12241 aattaaataa tgttggctgg aagttttagg atgatcatct ttaggactca gaaaaagaga
12301 agaaacatta ttaaagaatt gtccctgaac aagtataggc accctcacat ttgcattgca
12361 tttactatag aattgaaaaa tgttttgacc tttttttttt ggcttttaat atatttgacc
12421 aagagtaaca gctaagcaat acctatttgc aatcagtgtc atcatgtggg ctccaaacat
12481 atcatgtttg tgtaattaat tgattgaccc attaatttgt tcaatttctg ctctgttcca
12541 ggcactgaac aacatgatgg agataaaaga taaatattac acctgccttg tcctcaagaa
12601 gttagtcttc tgagggaaag aaattagcaa acaaattgta atctcagtta tgtgccatgt
12661 tccatgctgg gcacagggga tacagtagtt taaaaaaaac acaagatcta taaggtgttt
12721 cttcttgtgg accttacagt ctagggtgct tggaaacatg ggcgttggc agacaagtaa
12781 atacacattt tgtggtaaag gctcaggtag aagaagtaca ggatagaata gagcacacca
12841 tggggaatta atctagactt cagagaggct cacacataca taatttatgt gtgactattt
12901 caatgcattt gaggtttctt ggaaatagag gttaggtttt attttaagga agttaccatt
12961 tttttttca gtgtgatgtg gttgaaccaa agaatgccat gcccagtgat ggtaatagga
13021 taatcttttt aaaaattaag agccacctaa taaatcaata gtttcattca gcgggagctc
13081 ctgcagagtt caaaaagaag agaatctggc acagcgtttc ctttaaagtt cattttccta
13141 gagtgtgaat ggaagcaaga gattataaca ttttgaggtc aaaaaaattc tgaaatgcct
13201 ataaaaatta ttttctccaa attatcatca tttgtgcttt taatgacctg attgcaaaga
13261 tgaacatttt gaattcttaa attgcttatt aggattggtt aatgaatcaa ttatctatta
13321 ctgtatgttt tgctattgga aaaaatagca acttaagtgt tttgcagacc tttacttagg
13381 tatatgttgc ttttatgaaa aaaaagatgt aaatattaag taaaagggat ttaaagcaag
13441 gcttttgagg tagagtctta ttaattcctt ggtaaacctt gagccaattg ttgtctatgt
```

FIG. 1 (cont.) (SEQ ID NO: 1)

```
13501 tctctgcctc tgtcttgctc cttccttctg ggattcactg tgggaatgcg ggattgttaa
13561 tctggggatg ctgtccaatc ctgcctctct caagctttgc tattgatctc cctcccagtg
13621 ataataaagc ttgaagaaaa tgaaagtagc gttagtattg gtcctcaaac tcaagaacag
13681 gatgaaactt aaatcttgag tcatacaatt gtgtctacat actgctcccc aaaaagagaa
13741 gtaaagaaga tgctaacttt ccctttaat ttgcagtact tagcaatttg ttttcttgag
13801 ggttaagtaa taacagtgga agaaaaaagg gttaaaatgc caccaagaac ccaattccat
13861 gtttagtttg aaagtgggaa atcagctgcc actgggaagt ctgaatccaa tgccatgatg
13921 ttctttgaat ccttctgaga aataatcatg tgtagccata acatacctgt ataacagagc
13981 agagaacata aacaaatgaa ggtgaaggga agattaagac agaagagaaa aattccagaa
14041 tcgactgatc atttttatct gtttagatga tttcaggcag aatcctagag accaacttta
14101 tcacaactga attttaaaaa tcaccagctt tgtcattgtg atgcagcatc agtttcagta
14161 ttatccttgg agtattaatt cttaatcatc ttcatcttag aacatttttg aggtcacttc
14221 tagtctctat ttcaccagtg aagaaacaaa aatccccaaa ctatatcagg tggaattaca
14281 cagtattttt tttttaattt tggggaaagt cgattcaagg cagtaacttg caagctagtg
14341 ttagaaagga tttaataaat agtggttttt ctgtacacat agtgagaggt cattacatca
14401 tttggttgtt gaaagtcata aggatgtcta gcatgcgctt tgcctgtagt ggttcatgcc
14461 aggcagattc ctgactccta taacccagag cttatcagag catttatgtc cccaaagaga
14521 aatgtcacct ccatctttca ataaacactt tagcaaagaa aaatcaagta ctttaattcc
14581 aaatcttgag ttaattccag aataacaatg atggctcgga aaaatatggg tatttctgtc
14641 aaaggacaga gaaacctagt agagagtatt tactttgggt cctagtgatg gtatctgaac
14701 aagctaggtg aacaaagagc ctcaataagg gattttgagg tctagaaaaa gagaggaaat
14761 accaaataaa tggaataatt ataaaataaa taccagcaaa gttaaatcaa tatatcatgt
14821 gggagatatc cttatatcac tcatgtgatt tctattttgt tcctatatta ggccaaggag
14881 aggtggaact tgttttcctt tttccctctc agctacgaat ggacatactt aaaactgttt
14941 ctctgcttct gttctctaaa atgtgattgt ctaacagtaa ccgtgatgac gttttgacag
15001 ttgcacaagt ttctttcttt aagctttaaa aatgccagcc agtaacccag tggcatttct
15061 actataaaat cttaaggcca atccatttcc ccttttcctt attttcttgg tttcaaatat
15121 atttttattg ccaatggaaa taaaaatcct aaattagaga gcaatggcat cccttgtctt
15181 gtgaataaag agctcctaaa tgtgaactta tacaggatgc agcaatttat agggtagtta
15241 atcattcttc tttctagcca gttgttccag ctacagtttt gtggctcttg ttagtggctt
15301 cattcccaga tagaataaaa atcaaaccaa aatcctggaa aggcactctg aggatgcttc
15361 tctaaagtag atgggcatca actataaatc acaatgcttt gtttcctctg ttatgtttca
15421 agatgggtgg gattttttttt gtagcattac ttattattgc ctctcaagtg cttgagtctt
15481 tgaaatccaa gtcatgtgag tgaattagat acagctgtta gaagtggcct ttcaatgcca
15541 atggtacaca ttccttggtt tctttacgat actattgctc ttacaacttt tatctgaagt
15601 cataaattca tagttgtccc agaagttaag ttccttgctt ctagaggaca gaaaacaaac
15661 aatttacaca actcatggtg catgtcacca gtccttagat ctcatgaaat atgcatgaaa
15721 tcttaaatca cttgctgtag ccacccagcc attgacatat ttgaaagact ttagtgtatc
15781 aaagtcacta taatgaaaat tttgatttca ccagttctag gagtgaaaaa tcaaatgttt
15841 agtaaaactt tctaaaatta acactgacag ttgatttctg tatactgttg ttcttaataa
15901 tagctttatt gagatataat tcatattcaa aacaacttac ccatttaaag catacaatcc
15961 aatgattttt tagtatcttc aaagagttgc ctatcaccat aaccaatttt agaacacttt
16021 catcactgta aaaagaaact ccattcctat tagcagtcat tccttattcc aaatcccccct
16081 gctcgcccta gacaactaca aatgtacttt ccatctctat agatttgcct gttctggaaa
16141 ttttatgtaa atagaacaaa gtgttctttt gtgactggct tatttcactt agcatttttt
16201 ttcaaagatt catccctgtt gtagcgtgta tcagtgcatc attctttttt attttttttag
16261 agacagggcc ttgctctgtt gcccaggttg gaatgtgcag tggcatgatc atgggtcact
16321 atagctttga agtcataggc gaaagcggtc ctcccacctc agtctcccga gtagctgaga
16381 ctacaggctt gcaccacatg actgtctaat ttataatttt ctttagagac agggtcttgt
16441 tatgttgtct aggctgctct caaactccag ggctcaagtg gtcctcctcc cacagcatcc
16501 taaagtgctg ggattatagg tgtgagccac agcacctggc ttgcatcatt ctttttattg
16561 ttgaataata tcccacttgt aagaatatgt attttattta tcctttcccc agttaataga
16621 tatttcgatt gttcctaatt cttgtctatt ataaataatg gtgctatgaa catttgtgta
16681 caagtttttg tgcagacatc cattttcctt tcttttgggc atatacctac gagtgtaatg
16741 gatgggccat atagtaactt tatgtttaat attttgagga tttttcaaac tgttttccaa
16801 agtggctgca tcattttaaa ttccttccac cattgtgtga gtgtttcaat ttctccacat
16861 atttgcaaca cttactatta tctactctta aaaattacag ccatcctact gggcatgaag
```

FIG. 1 (cont.) (SEQ ID NO: 1)

16921 tggtatttca ttgtgagttt ttttttctt tttcttttt tcttttttg ctaatgtttg
16981 tggattttct tttcattttc ttgatggtgt cctttgaagc acaaaagtat ttaattttga
17041 taatttccaa tttatttttt gttattgctg tttgtgcttc tggtgttgta tctaagtgta
17101 tgctacttta aaaaattagt tgtaatatgg caaattggat acatgtgtag gctttggtgt
17161 cacaatccta attttaaaat tctgactctg cccttgacaa attaactaat taagcttcct
17221 tagcctcagt ttctcaactg taagttggag atattaccaa gacctacctc ttgaattgtt
17281 gtggggatca gatgaaataa tgtatgtgaa atatttagaa ttatgcaagt ctgtggtaat
17341 gaatactaat gttagctatc attattgtta taatcccaat aataaattct ggtgctttga
17401 aaattaaacc aaagccaagc agttgatatg aagaagcatg taataatgta cagacataat
17461 gctttataga caacattgaa tttggctctc atgaacatca ggaatagtgg tcatggtagt
17521 tattatctcc agcaggaact gtagctgaga gatcttcaga gctttttcca aggcgatatc
17581 actgggaaat aatagagaca aggttacaag ctagggctgt gttttcttct taaaatcttt
17641 agttcagttt ttttcaataa cagatttgta gtaggcatca ggtgactggg gattcgtatt
17701 cttcaagttg aaatattacc ttgttgagaa agaaaccatg tgtgagacaa ccatgttgag
17761 aaagaaaaag tgattttata gaaaattaat attgatagtg agcattatat gaaaatcatg
17821 aagttagaac atatttggcc agaaaattta cattaatagt tacccatagc aattaatgca
17881 ttataattac acatacottt tctttaatga aaaagaattc tttccttcca aagttatgca
17941 tgctattgtt aaacattaga gaatatagag aagcaaaaaa gaaaatatct tttttgatat
18001 tttcttaaca tacgtctgtt cctaataatg tttatagttt agaagcattg catgaaatgg
18061 gtagatcaat tttctattta atgtttggat tcattaggta cgaagttagc aaattaattt
18121 ccattagggt gcctgtatgg ttgtaaatcc tggacctgca gaagattttt cagtattggt
18181 ttgtagtctt ttgtttagca gcaaataatt agttctccag agcttctgaa attaattgac
18241 cactttaatg gtgtttacct acctagagaa agaaaaagaa cttctccaag tcccttggta
18301 aaattaagcc tcatgaacaa ttaactcaaa tatacacaag gcttgtcttt agcgagcata
18361 tactccctaa agttgattaa gctgaccaag tgattactgc ttataaattc accattttat
18421 ggagaagaag caaacactgc taaatacctt gtggaatcag aggaggggaa attagtaact
18481 tgaccccaat actgcgattt taaattgaat tcttgaagcc tacaagtttt acacaggact
18541 ttagagagct ggatagtatc actttgtcaa gtcctacttt tactatgatt ctttgagaaa
18601 aatacatctg actaaataac tctgaatcta aattggataa aataaatgtg acattcaaaa
18661 tgttatttat gattttagaa aaatatcctt atagacacta gatgagtttt agtctcaaat
18721 caatcctccc tatcatagtc acttatcaaa ataactaaag caaagtggta gagctgtgct
18781 ctagaagttt gggatttatg atcacaatct tttccaatga gtcccctctt tcctctgcct
18841 gtcttcaaca tttgtttttt tttttttttg gttaggacta tccagattgt gtggcctatt
18901 tcaaactcat ggcaaataca ttggatgatc agaaattttc taatgtattt gaatttgtct
18961 acacaaacta gagtaattgc tattaattcc tcaagtgtta attatttcat gcaaaaagga
19021 aaaaggctat tagtctttaa gtgtattagt atgtcaatat ttgggagaag tgtcatgcaa
19081 ttagtggttt gaatttccta ttttatttta ttgcatttta ttttatttgc ctagtcaaat
19141 aaaaagtaat gttaaataca tggaagcatg attgttttct acactaaaaa tcattttgac
19201 ttgaaaagat ctgatatcca tgaccttcat ctgaagtttt ggcagatgaa aatgtcagat
19261 gcgtcttttg gattaataaa aggcaaaagt cagatcgaaa aatgagtata agctttaatt
19321 atatgacttt aggaggatat gttatgaaaa tcaaagcttt aatagtgatt ataattggca
19381 agttcttttt ttataaggaa ttacaagtca ctctatacaa aaattggaat ttttgtccta
19441 agaaatgaaa tttactatag tttcatctgt gtgtgtgtgt gtgtgtgtgt gtgtgtgtgt
19501 ttaaaaaatc aagtgatagg gcttttcctc aataaaatct gaaatctctt atagttaagt
19561 gaacagaaca gtgtatctag gatgctagac ttttttttca aagttagttt aaaacttata
19621 catagtaaaa tctgtatgcc ttagggatct ctgtttgcta tcccatagtg aatgattaat
19681 tagtttctgt tagaaatagt cagaactagg ctgggtgtgg tggtggctca tgcctgtaat
19741 tccaggactt tgggaggcca aggcaggagg atctcttaag cccaggaatt tgcaaccagc
19801 ttgggcaggc tggtgagatc ctatctctac aaaaacaaac aaacaaacaa aggacaataa
19861 gaaagaaaga aatagccaga gctttgaaca aaatttctaa gtagaccaat gtaaaagtct
19921 gtcgtcaata tgtagtggct atgaatggag gttatgaatg aaagagaagg ataagatgaa
19981 ctagaggtga gaggggaaga cagcaggccc aagtgaaagg cagagccgag tttattgctt
20041 tttggttatt ccaggtgtgt ctgctttgtc tcatgaaaca cctggatgat cactgatttc
20101 tagtggaaga aatgctgaaa agtccttact gtgcatttaa acattctagg tttaatatac
20161 tcagggtttt tcaaaagaaa gggtggctgg agttttgcac taactaatat ttcataaagt
20221 gtctaagtat agatgtctgg tttttttttg tatttctaag actggcttga ggtaggcatg
20281 gagaattctt tgatggaca taattttctt cctttctttt tttttttttt tttttttttt FIG. 1 (cont.) (SEQ ID NO: 1)

20341 tgagacggag ttttgctctt gttgcccagg ctggagtgca atggcacaat ctcggctcac
20401 tgcaacctcc gcctcccagg ttcaagcaat tctcccacct cagcctcccg cgtagctggg
20461 attacaggca tgtgccccca tgcctggcta atttttttg tatttttagt agagatgggg
20521 tttctccatg ttggtcaggc tggtctcgaa ctccttacct caggtgatcc acccacctcg
20581 gcctcccaaa gtgctgggat tacaggcgtg agccaccgcg cctggcctga tgggacatat
20641 ttttcattca attttattga tttaacctca caaaataaaa tatttcctta agatgactct
20701 gtggtcattg ttgggcagca taagcttaat ggattttagt tatcataatt taccttaaac
20761 ccaatttgta tttcaggata taaatagagg tttattgtag tgaatcttcc aggaaatact
20821 aagtgatact aataattata gatggtgaac ttaagtcttt atattactga atttgtttgg
20881 tttgatgatg ctaggctatg gcattcttgc taatcaaaac gatgtgtcat ggtgtaacat
20941 aacttattaa aatgggcaca gataacacag gaagcttttt ataaaagcag ctcacaaatt
21001 gtgttacttt gaactgaact ggccatttat gggaaaggtc actgggttgt aaataaggac
21061 caaaagagtt acgtttatat tttttaaaag agattgagga gatttatttt tacatttctt
21121 gaaaatgcct tattttggta tggtattgac agatagtgaa attctgctca tttgtaaata
21181 tagtgtcata ttttaataat ttcaaacata ttgaaaatgc agaatttatt aatagtggga
21241 gcacattttc ctttttacta aatgttctac aggttctttt ctttccatcc acacacagtg
21301 ccattaccct cattctaagc ctttcaaaca tctggcagta agtgatctgc tgcacttagc
21361 tctttccagc tgagctgatt tttaaatttt cagaaaattt gtgagctaat tgttaaacat
21421 ggccattatt aaaaattaaa ttatttcaac ttataattaa ataaattata ttaaaacaaa
21481 agtattaaaa actcaaaagt tggctgggcg cactggctca cgtctgtaat cccagcactt
21541 tgggagaccg aggcaggtgg attgcctgaa gtcaggggtt cgagaccaac ctgaccaaca
21601 tggagaaacc ctgtctctac taaaaatata aaaaaatagc cgggcatggt ggtgcatgcc
21661 tgtaatccca gctactcagg aggctgaggc aggagaattg cttgaaccca ggaggtggag
21721 gttgtggtga gctgagattg cgccattgcg ctccagcctg ggcaacaaga gtgaaactct
21781 gtctcaaaaa aaaaaaaaaa aaaaaaaaag aaacaaaaaa aaaaaaaaaa caaaaagcaa
21841 acaaacaaaa aaacaaaaat tatcacttcc taattatttt gcattttact attatctatg
21901 ctattaacgt tatttgcctt cattgtattt gaaaggtgga ctatattcta ttgcactttc
21961 attgtactat attctaatat gcaactgtgt atcccttccc aactctgtgt tcaatgactt
22021 tatatttggt tgctttaaaa tgatgacgat gagagtattt atatcataga aattggcaaa
22081 tgccgtaagt cagtttttgt ttttgttttt gttttccgga gaggggattg ttaaatattt
22141 gcctgcatgc aacaccacta catgcagtct gctatctttt gttcttcctg ctttcaggct
22201 cctctcccag ctgtctgtct agcacaaccc agcataccaa attttcttaa atagggaaag
22261 ttgaacatgg taaaagaatg aatgaagtca aaagaatgtg gaaagaccta ggctttgcca
22321 tttagtaaag tttagcatct ctaagcctcc atctctttat caataaaatt gagcaatgat
22381 ccctttttagt tctacccatt taagaagatt ttcaaatgaa aaccacaacc tgctcatgtt
22441 tatgaaggca ctttggaaag cgctaaatac acgggttttt attagtagta aacacttact
22501 tcaccttttt cacttcttga ctttagttta caagggctca taatctaaat tatatcataa
22561 attgctgtcc cagatttttt tacagcctaa ttgccacctg tatgttcgac tttccttctg
22621 ttctttatgt tagatactgg gatagtatgc accaggtggg tgtgccatca ctttctcaga
22681 tgatgtccac tgaagacctt gcatgatcat ggcattcatt ttcctgctgt attcagactg
22741 gcctcaacta ttttctttat tgctctccag gaaaaattac aaatgaatca gactgggcaa
22801 tgaagggtaa acctaattat cgctctttgt taaagacagc tcttgttaaa atgcggatat
22861 tgcaaattaa tggaaaaaat atgacatagt aaaccatact cacttattaa tatcttagta
22921 aggaataatt gatgaagtta cttaacctta gagccctaat tcagttaagt tttaatgaag
22981 gacaagttgt agagatatcg agaacccagg gcaggtgcct actgaagaag ttccagacca
23041 aggaagtata aagaaggacc tgggtgggag cagtgagatt ggatatgagg gccactggca
23101 aagttttgcc ccagaacagt gtcaaaatgt ttgcatttgg catagccctt tctctttttg
23161 ttctgaatgg ctttgctaga atatcttttc tataatgaat ttatcctgct tctcagatat
23221 tgctaaagca ctccctttttg aattttggtg ctttaacatg cattttgata cattaccaaa
23281 taaggtctga atgacacaaa ttttagaact ctccagagaa aagaaagatg ctgagggaaa
23341 aagcataggt ttgggactca ctaaatccca gttcaattcc tttctttaat aaatatattc
23401 aattttacct gagaaagctc tcgtgctctc gaattttatt tagaaatttc tctttgtaca
23461 tgattgattt cacaatcctt cttctgcctc ctcttctact ttcttctttc tagattttcc
23521 tatctttatg aagattattc tgccttatcc tcaacagtta gaaacaatat ttttgaaaat
23581 cactacggta tcctgcatag tgatttccca tgccaacttt actaatttcc attataaatt
23641 attatttatt gatgcctaga gggcagatga gtgtagctgc tatggagtga ggagacaaaa
23701 cataagaaag ttatgatcct accctcaggt aatgattcag acatgataat taagtcaaca FIG. 1 (cont.) (SEQ ID NO: 1)

```
23761 aattgataga aactaatcac taactctctg gctatagtca ttctttcaat gaatagctca
23821 ttactgagta tgcatgctac agtaacaaaa ttatataagg ctgttgatta aatgttgatt
23881 aagtgcatgt cttattcaga gttttttat atttgaaatg gaagaggctg gacttcagta
23941 atttgctata aactgctagt atatgattat ttgggggcag ttattttta aagaataatt
24001 taaatatgga atgtttagca gtttgttttt tccctgggaa aaaccatact attattccct
24061 cccaatccct ttgacaaagt gacagtcaca ttagttcaga gatattgatg ttttatacag
24121 gtgtagcctg taagagatga agcctggtat ttatagaaat tgacttattt tattctcata
24181 tttacatgtg cataattttc catatgccag aaaagttgaa tagtatcaga ttccaaatct
24241 gtatggagac caaatcaagt gaatatctgt tcctcctctc tttattttag ctggaccaga
24301 ccaattttga ggaaaggata cagacagcgc ctggaattgt cagacatata ccaaatccct
24361 tctgttgatt ctgctgacaa tctatctgaa aaattggaaa ggtatgttca tgtacattgt
24421 ttagttgaag agagaaattc atattattaa ttatttagag aagagaaagc aaacatatta
24481 taagtttaat tcttatattt aaaaatagga gccaagtatg gtggctaatg cctgtaatcc
24541 caactatttg ggaggccaag atgagaggat tgcttgagac caggagtttg ataccagcct
24601 gggcaacata gcaagatgtt atctctacac aaaataaaaa agttagctgg gaatggtagt
24661 gcatgcttgt attcccagct actcaggagg ctgaagcagg agggttactt gagcccagga
24721 gtttgaggtt gcagtgagct atgattgtgc cactgcactc cagcttgggt gacacagcaa
24781 aaccctctct ctctaaaaaa aaaaaaaaaa aggaacatct cattttcaca ctgaaatgtt
24841 gactgaaatc attaaacaat aaaatcataa aagaaaaata atcagtttcc taagaaatga
24901 tttttttcc tgaaaaatac acatttggtt tcagagaatt tgtcttatta gagaccatga
24961 gatggatttt gtgaaaacta aagtaacacc attatgaagt aaatcgtgta tatttgcttt
25021 caaaaccttt atatttgaat acaaatgtac tccctgggaa gtcttaaggt aatggctact
25081 ggttatcaaa caaatgtaaa aattgtatat ttttgagtac ctgttacatg ccaggtagaa
25141 tatctcctct cagccactct gagtggaaag catcattatc tctattttac agaaaagcaa
25201 actgaggctc agagagataa tatactttgc cagttaatga atgatggagc catgattcca
25261 gctgaggtct gtattgcctt gctctctagg aatggtagtc ccccccataa agaatctctc
25321 agtttccttt ccaatcaaaa ggttaggatc cttttgattg ccagtgacag aaacccaatt
25381 tactagctta agtaaataaa aggaacgaat ttattggctc atgaagcctg aactatgtga
25441 agacctaggt ggagaactgg ccttaggaac tcaatgggac caaggactca aatgccacct
25501 ggtggcattt gccttatgct ggttttattt tctcagaccg gaccagcttt ctacataaag
25561 tgggtccctg gttagaactc tttgctccta tctttaagga ccacgaaaga aggagccctt
25621 tgtccttggc taaatgtgaa aaatcccaga gactcttgag tcatagtgct taccccttgg
25681 gccactcata gtctagaatg aactaggctg agtctcgtgc caacagcaca ggcctgatgc
25741 cagataaaag ggtgagtgaa gggggataaa aaataagaca tagctactaa attattgcac
25801 caaagtaaaa acattgagtt gacttgcaat ttgtttcttt taattaaatt catttccttt
25861 ttttggcatt ttgaaggcaa agtaagatat taaactttat ttttattgat tttattcaaa
25921 gaattaagct agtgggagta gcagattcac acttctaaga tcaagggcca gcttctatta
25981 ttgaacactt ggtgtgtgca aatgccatga ggtagggata ctttgttttg tttttattt
26041 tttattgggt tcgatctctt ttgtttatga tgtatcccca agtgcctaga atagggcctg
26101 gcatatggta tatactcaat aaatatttgt tgaatgaatc catgatggaa tgtgaaatgg
26161 ctagcattac atagaaacct gtagcattgc tggagagata aaatatataa acataatcca
26221 ttgcaggtat attgacaagt tcaaaataat ataatgggta ttgaatatct aaatgtttgt
26281 tgttgttgtt gctgttgttt ttgagacaga gtcttgctct gttgcccagg ctggagtgta
26341 atggtgcaat tttggctcac tgcaaacttc gtctcctggg ttcaagtgat tctcctgcct
26401 cagcctctcg agtagctggg tttacaggca ctcgccacaa tgcctggcta atttttgtat
26461 tttagtagat gtggagtttc gccatgttgg ccaggctggt cttgaactcc tgacctcaag
26521 tgatctgccc accttggcct cccaaaatgc tgggattata ggtgtgagcc actatgccca
26581 gctttgaata tctaagtttt aattggatgc tgagggaatg attaatcaga gtagggctgg
26641 gttaattgaa aaatgtgata catttgtatt tatggccaga tagagaacat gaatctgaat
26701 ttgcagaatt atctggctta acattttttt ctttccagtt ttcactgtat cccccatgtt
26761 gattcaattt aaaaaatata cctattttac ttcaattcaa caatgctatg ccagtacaaa
26821 cccatacgtt ctattatttt tgttttgttt tgtttttgta tctccaccct gttacttctt
26881 ttcttataaa attggtattt gaaatttatt gaaatatttt ggaagagtga cataccattt
26941 ttggtacttt gtacctctgc acccttggga agtgaccctg gcttcacatt tcataactgc
27001 cttgtgacca tggccctcaa gtggttgcca gatggttgaa gaacattaac ctatctggct
27061 caattttgtg accatggatt gaatcctcta cataactgca gtgtgcaaac cacacatccg
27121 ttccaagatt gtagtcagga tatgaacttt ttaagaataa aacttcttcc cttctgatct
```

FIG. 1 (cont.) (SEQ ID NO: 1)

```
27181 gggcctggta tgtggtccta ctagaaccac atcacctact cttggtgcta acaatttgtg
27241 gcaccaagtt gttcaagttt cacccattaa agaaattccc cgaccttgcc ttctcctcag
27301 gtaactaccc cattctattt ttctttcat agctaacatt ctctgctctc ctggtctctc
27361 tacttcactt tcatttacat ctcagctcct gaagtatggt ttccaccatg ttcctaaaac
27421 tacattgccc agggtcacta gagacctctt atgaaatata acaacacctt tctacattac
27481 ttccgtgtgg accacttttt cacattgaac ccatttgtt ggtttatgta cacaccccctt
27541 ccttggcttt cccatctgat ccatttctcc tttgatggag aaggtgagtc tgctccatat
27601 ttagcttctt actctgagta accaaatgtt atggatggga ggttagctct gtgtgtgaga
27661 gaaaggtgga gaagcatgtg gggagggaaa tagatgggaa aaggtaatta ggctttatag
27721 aagggctctc attagcaagc ttctagggga tgccaagatc catgcttaga gattgccagg
27781 cttgtcttca aatctcagct gtgtattact cctttatgtt ttttgtttgt ttgtgttgtt
27841 tgtttttgag acagagtctc gctgtgtcac ccaggctgga gtgtagtggt gtgatctcag
27901 ctcactgcaa actctgcctc ctgggttcaa gcgaatctca gtctcctgag tagctgggac
27961 tacaggcatg caccaccagg cctggctaat tttgtagag acggggtttt gctatgctgg
28021 ccaggctggt cttgaactcc tgacctcaag tgatctgccc gccttggcct cccaaagtgt
28081 tgggattagt ggcgtgagcc actgccccgg cctattactc ctttagagtg atttagagcc
28141 atgtttactt atggtaactt gacagtaatg ggaataacca ctgatgaaac gtaaagcctt
28201 tgtctaattg tttacctagt tcttccttgt ggttcatgaa atttttcatc tctgtacagt
28261 ttgaaaatta agatgataat atttagagat attttattcc tttgtgaaga gaaaaaaggc
28321 tttcattaac agaaatcagt ggcaataact taataaatac aatcagctgg tgttcctata
28381 gtatttaaaa gaaaacagaa agtttactag atttcagcca gttttcagac tatttaatgt
28441 ctattcttac tataatagaa aatatataat ttgatcttgt tctcattttt caaagacctt
28501 taatacatga ttttagtagt tgaaaatgaa gtttaatgat agtttatgcc tctactttta
28561 aaaacaaagt ctaacagatt tttctcatgt taaatcacag aaaaagccac ctgacatttt
28621 aacttgtttt tgatttgaca gtgaaatctt ataaatctgc cacagttcta aaccaataaa
28681 gatcaaggta taagggaaaa atgtagaatg tttgtgtgtt tattttttcc accttgttct
28741 aagcacagca atgagcattc gtaaaagcct tactttattt gtccacccctt ttcattgttt
28801 tttagaagcc caacactttt ctttaacaca tacaatgtgg ccttttcatg aaatcaattc
28861 cctgcacagt gatatatggc agagcattga attctgccaa atatctggct gagtgtttgg
28921 tgttgtatgg tctccatgag attttgtctc tataatactt gggttaatct ccttggatat
28981 acttgtgtga atcaaactat gttaagggaa ataggacaac taaaatattt gcacatgcaa
29041 cttattggtc ccacttttta ttcttttgca gagaatggga tagagagctg gcttcaaaga
29101 aaaatcctaa actcattaat gcccttcggc gatgtttttt ctggagattt atgttctatg
29161 gaatcttttt atatttaggg gtaaggatct catttgtaca ttcattatgt atcacataac
29221 tatattcatt tttgtgatta tgaaaagact acgaaatctg gtgaataggt gtaaaaatat
29281 aaaggatgaa tccaactcca aacactaaga aaccacctaa aactctagta aggataagta
29341 aaaatccttt ggaactaaaa tgtcctggaa cacgggtggc aatttacaat ctcaatgggc
29401 tcagcaaaat aaattgcttg cttaaaaaat tattttctgt tatgattcca aatcacatta
29461 tcttactagt acatgagatt actggtgcct ttattttgct gtattcaaca ggagagtgtc
29521 aggagacaat gtcagcagaa ttaggtcaaa tgcagctaat tacatatatg aatgtttgta
29581 atattttgaa atcatatctg catggtgaat tgtttcaaag aaaaacacta aaaatttaaa
29641 gtatagcagc tttaaatact aaataaataa tactaaaaat ttaaagttct cttgcaatat
29701 attttcttaa tatcttacat ctcatcagtg tgaaaagttg cacatctgaa aatccaggct
29761 ttgtggtgtt taagtgcctt gtatgttccc cagttgctgt ccaatgtgac tctgatttat
29821 tattttctac atcatgaaag cattatttga atccttggtt gtaacctata aaaggagaca
29881 gattcaagac ttgtttaatc ttcttgttaa agctgtgcac aatatttgct ttggggcgtt
29941 tacttatcat atggattgac ttgtgtttat attggtcttt atgcctcagg gagttaaaca
30001 gtgtctccca gagaaatgcc atttgtgtta cattgcttga aaaatttcag ttcatacacc
30061 cccatgaaaa atacatttaa aacttatctt aacaaagatg agtacactta ggcccagaat
30121 gttctctaat gctcttgata atttcctaga agaaattttt ctgacttttg aaataataga
30181 tccataatat atattcttat ggaaatctga aaccatttgg gcatttgggg gtaaaaagta
30241 ttttattagt aaatttaaat gaggtagctg gataattaaa ttacttttaa gttacctttg
30301 agatgatttt tctcaatcag agcaccaccc agagctttga gaaacaattt tattcacagc
30361 ttctgattct atttgatgta atttttagaa aataagtttt gctggttgct ttgaatcagg
30421 gtatggagta cagttcactc tgatcctatc atataaatca tgtaagtata taacattttc
30481 aataagtgat tgttggattg aagtgaatga tatttcaagt aattgttatg tcatggccaa
30541 gatttcagtg aaactcaaaa tttctcctgg ttgtgttctc cattgcatgc tgcttctatt
```

FIG. 1 (cont.) (SEQ ID NO: 1)

30601 gattaaccta agcactactg agtagaagct ggaagagggg tctaattaga aggcccettt
30661 ctatgctctg cttggcttgt aaaataattt atttctctag atcccaccaa catagtagtt
30721 tcatgtatgc aaaaacaccc acctaaatgt caaagtttgt atgatacatg gacatatcta
30781 tagaattttt tttggtctgg tgcatgccaa aaaataaaca tgatatagaa gaatttaata
30841 tttattgagt acctaatctg ttccagttca atatgaaggt ctttatgcag attattttac
30901 ttaattttcc tagtaactcc atggagcaaa aattatctct aatttatata acaggaagtt
30961 gagcgtgagg caaattaagt aactttccca aagttacaca tatggtaagt ttgagagata
31021 tcccagtctc tttagctcca aagcctttga ccctttcacc ataccagatt atgattgcta
31081 ttaatatata attataatta taatgattgt atttaggtac tcaacagaat ggtgactcta
31141 gtaaccagcc ttggttctgc tgagcttctc tgcgtcttct caggagacac aggctacaga
31201 gcttgaaggc tgaggattct tccagggtca cttcaggggc aaatctgaaa ctttcttcag
31261 gacaggaatc aacgagatct tctcacttac ttatacctgg gggaggaact gtatgaaatc
31321 cacccaagaa ccagtcatgc taagggccaa acctatagac aaaaaaaggg ataggagaat
31381 ggagtatgta tggagaaaga ctaaattgtt cttaaacttc tcaagcttaa aaatatccca
31441 gcaaaagaga tcgtaaaagc ccttcatggc gtattaatta tccatgcatg gggtgagtg
31501 gaaaggtact cctgagcccg aggctacagc tttggaacta gcagcacctt tgaaggggaa
31561 agcgtgtttc catcatctca actcctactg ataaccaatg gaatattggt gagtaaagga
31621 tcctggggga agaagcagct gaaatgtgta ggtgagaagg cagagagaag aatatttata
31681 ttgggaatgg cacaagtgtg atgaggctgc aggtttttca cccttgtcat agagaaaaaa
31741 ccacgctgac accatgcagt tttaaatagt gagaaatttg caaattgtta gatcttaaat
31801 aatttagata aacatagtgg ccatttagat tattgcagtt ttttcaggat atctgatctc
31861 ttgatttcat tctttttgtc tcttataaga ataaaagggg gggagaaaat ttagccatta
31921 tagtatttct ctacattttc tctgtccttt tacataactt acaccagtgc cttcctattt
31981 atggtattat ttatgggtat ttcttctttt ctttcactga gcaaggataa atgagccagg
32041 gattcttgaa actactgtaa cacttctctt agaaatagat ggtcatactt tcagaatctc
32101 tacacattct tagtccctct aaacaatgat agttgtggca taaaaatatt tgcttggttt
32161 caggactgat agagaaaagt actataaaat ttgctgttaa ctgtgaaagg ttaaaaaaaa
32221 ggaggtgcca tcatgaagga gctaatcttt ctgaagtact gctgtagttt taaatattat
32281 tagctatgac ttctcaccat taactatgca cttgcttttt cttcatctga ctcagcagcc
32341 agatagatgc aacattgtct ttaacattta agactcctag caagtccggg cacgggggct
32401 cacacctgta atcccagcac tttgggaggc cgaggtgggc aaatcacaag gtcaggagtt
32461 tgagaccagc ctggccaata tggtgaaacc ctgtctctac taaaagtaca aaaatcagcc
32521 aggtgtggtg gcgtggtggc gggcacctgt ggtcccagct acttgggagg ctgaggcagg
32581 agaatagctt gaacctggga ggcagaggtt gcagtgagct gagatcgcac cactgcactc
32641 cagcctgggt gacagagcga gactccatct caaaaaaaaa aaaaaaaaaa aagactccta
32701 gcatggaaga gaaactggct gttgaaaacc tgaatgtgag agtcagtcaa ggatagtttg
32761 agggaagcca agtagaggaa gctctcacaa gcagattggt gagagaatat gattatacaa
32821 tgcatttatt atgataagaa attcacaagc attcattcaa aatactcttg attcctaggc
32881 agctctgggc atatttccac caacaaattg aggcatatgt cagtgcagcc taggtcagac
32941 taccttttttt cattaaacct cacaaaatta aaggacatac aggagaagtc ctggtactca
33001 tgttgcagac tacagtctat atggcaaagg aggatctctg tcccttatgt ttggatgaaa
33061 acattgggta ggcatttgaa tacaagccta ctgctaatat ggggctaagg tctttggccc
33121 cctaaaggtt tgctgaaata ttactgacag gaggcagatt gataagagga aaagcacata
33181 aatgtatttg acatgtatac atgggagcct tcaggatgaa gacctacccct ctcagtgcag
33241 tatggaagct tgtataccat cttgaggtta cagaaagaat ggggggtttgg atctttgtaa
33301 aacaggtttc agtggcaaga caggttatga gaaggagaaa ggaagagact tgggtagcaa
33361 agggggtctt gttttgtagg taaatcgttg gcagcccaca gagaaaatag atggagaatg
33421 tttcttttca gaccttggca ggtgtcagat tctcagttaa tctctcctag atttgaaaaa
33481 aaaaaaaaag gtctagaaag ggagagcctg gctgcactaa cacattttct acagatgcaa
33541 atttctccca caaaatacag ctttgcaggt ccacttctat ctgctgggcc tgtggcaacc
33601 atttcaaaat atgtgaatga aatatatgtg ggggtaaact atttttattt acttccctaa
33661 agaagggatg gtgttctctc gggaattctg tgcatagaga gcctgtggct taggcacttt
33721 gatttatgta tatctcttcc tgtgattggc tatctaggga ctgctatctc cagcaaatct
33781 tctaaatgtc tgccatgtag aattcctttc tcatctttct gtctcacccc cttatctagc
33841 tgcttctcta accctagagt gacactgcac tccccacaat ctcctatgtc ctgaatattt
33901 taccccatcc taaactccat ctctaacaca gatgcacttt cttgtgctgc ctactgcatt
33961 gtacatcttc cccttagttc ccatgatgca actctgccct accccagaaa atgtaattta FIG. 1 (cont.) (SEQ ID NO: 1)

34021 attggtctgg gataaaacct gggacactat cattcttgaa atattcccca agcgattcta
34081 attatatagc caaagttgag aactatttgt agacaggcat cagcatgatc acttaatgat
34141 ttgacttttg ctagatctaa ggtgaggaaa ttggagagtg gtatccatag gaagaactgt
34201 ttagtttaat ttttttttta ttttttcttc taaaaaaaaa tccaacaacg agatacatgt
34261 gcggaacatg caggtttgtt acataggtat aatgtgccat ggtagtttgt tgcacctatt
34321 gacccatcct ctaagttccc tcccctactc cttacttccc aacaggccct ggtgtatgtt
34381 gttcccctct ctgggtccac ctgttctcaa tgttcaactc ccttttacga gtgagaacac
34441 atggtgtttg attttctgtt cctgtgttaa tttgctgagg atgatagttt ccagcttcat
34501 ccacgtccct gcaaaggaca tgatctcatt ccttttatg gctgcatagt attccatgat
34561 gtatatgtac cacattttct ttatccagtc tgtcattgat gggcatttgg gttggttcca
34621 tgtctttgct attgtaaata gttctgcagt aaacatatat gtccatgtgt ctttatagta
34681 gaatgattta tattactttg ggtatatacc cagtaatgag attgctgggt caaatggcat
34741 ttctggttct agatacttga ggaatcgcca cactgtcttc cacaatggtt gaactaattt
34801 acactcccac taacagtgta aaagcgttcc tatttctcca cagcctcacc agcatctatt
34861 gtttcctaac attttaataa ctgctattct gactggcatg agatggtatc tcattgtggt
34921 tttgatttgc atttatctga tgatcagtga tgctgagatt tttaaaatat gtttgttggc
34981 catgtaaatg tcttttgtga agtgtctgtt catatccttt gcccacctta atagggtttt
35041 ttttttcttg tgaatttgtt taagtgcctt gtaaattctg gaaattagat ctttgtcaga
35101 tggatagatt gcaaaaattt tctcccattt tgtaggttgc ctgttcactc tgatgatagg
35161 ttcttttgct gtgcagaagc tctttagttt aattagatcc aatttgtcaa ttttggcttt
35221 ttttgcaatt gcttttggca ttttcctcgt gaagtctttg cccgtgccta tgtcctgaat
35281 ggtattgcgt aggttttctt ctagggtttt tatagttttg ggttttacat ttaagtcttt
35341 aatacatctt gagttaattt ttgtataagg tataaggaag ggtccagtt tcagttttat
35401 gcataatggc taggcagttt tcccaccacc atttactgaa taggagatct tttcctcatt
35461 gcttgttttt gtcagatttg tcgaagatca gatggttgta gatgtgtggt gttatttctg
35521 aggtctctgt tctgcaccat tggtctatat gtctgttatc gtaccagtcc catgctgttt
35581 tggttaccgt agccttgtag tatattttga agtctggtag cgtgatgcct ccagctttgt
35641 tctttttgct taggattgtc ttggctatat ggagtcttct ttgattccat atgaaattta
35701 aaataatttt tttttattct gtgaagaatg tcaatggtag tttgatggga atagcattga
35761 aattataaat tactttgggc agtatagcca tgttcacaat attgattctt tctatccgta
35821 aggacgacac tttttccatt tgtttgtgtt ctctcttatt tccttgagca gtggtttgta
35881 gttctcctta aagaggtctt tcacatcctt tgttagctgt gttcctaggt attttgttct
35941 ctttgtagtg attgtgaatg ggaattcatt cttgatttgc ctctctgctg cctgttgttg
36001 gtgtaaacaa aattcatttc ttgttcttat ttgtgaaatt ttggaaccaa atctattttc
36061 aaattagaaa ttgcttgtga taatggtttt gcaacttaga ctggatatga gacgatgaga
36121 tattagttct ttcattcctt tgtaggaata tggtgcatct tgcattattt tagctaacta
36181 gtgtccttta atgactaatg aatatgacat ggtgaaacaa agtaaaatat atatgatgca
36241 ctaagtatgc attgtttcca aaggttcagc attttttttt tgttaactct gctgggatct
36301 gctttatgca ctgataacat aacttatttt atgatcttaa gcaaataaaa acacttatct
36361 ggacctcagt ttccttaact gtacaactga gggaaactgt atagtatagc tatagtacag
36421 tataccatct ttaccgtcac ttccatcttt taaattatgt gtatataaga tagggcctag
36481 ataaatggta tttatcttaa attacagtga tactagctta taacttaatt tgctaggtca
36541 tgttgaactg ataacaatgt gtgaactgat gagcaactga gaagtaacca ggttgtgtta
36601 taacagtttg tttttgattt agggttatca gtgagggtgg cggtggggag gggactttgg
36661 agtctaactg tctagttcaa atattagttt ttgtttattt ttatttttaa tttttgtggg
36721 tacatagtag atgtatatat ttatggggta catgtgatgt tttcatatag gcatgcaatg
36781 tgaaataagc acatcataga gaatggggta tccatcccct caaacactta tcttttgagt
36841 taccaacaat ccaatgacac tctttaagtt atcaaatcac agttttgcca gctactagcc
36901 atgtgatttt gggtaggtta cttaaattct cttcatctca atttcattat tgtaaagtgg
36961 agataatgat agcacatttt ttctttttct tttttctttt attttttatt attatacttt
37021 aagttgtgtg atacatgtgc agaatgtgca ggtttgttac ataggtatca acaactctat
37081 aaaacatgtt ctatccagga aaagaaacta tcatcagagt gaacaggcaa cttacggaat
37141 gggagaaaat gtttgcaatc tagatggcga ttgcaatggc ggttcgctgc atccatcagc
37201 ccatcatcta cattaggtat ttctcctaat gctatccctc cccttgctcc ccaccccctc
37261 acaggcccct gtgtgtgatg ttcccctccc tgtgtccatg tgttctcatt gttcaactcc
37321 cacttatgag tgagaacatg tggtgtttgg ttttctgttc ttgtgttagt ttgctgagaa
37381 tgatggtttc cagcttcatc catgttcctg caaggacatg aactcatcct tttttatggc FIG. 1 (cont.) (SEQ ID NO: 1)

37441 tgtatagtat tccatggtat atatgtgcca cattttcttt atccagtcta tcattggtgg
37501 acatttgggt tggttccaag tctttgctat tgtgaacgct gcagcaatga acatacataa
37561 gcatatgtct ttctagtcaa ataagttata atcctttggg tatgtaccca gtaatgggat
37621 tgctgggtca aatggtattt ctggttctag attcttgagg aatcgccaca ctgtcttcca
37681 caatggttga attaatttac actcccacca acagtgtaga agcattccta tttctccaca
37741 tccgctccag catctgttgt ttcctgactt tttaatgatc accattctaa ctggtgtgag
37801 atggtatctc attgtggttt tgatttgcat ttctctaatg actagtgatg atgagcttct
37861 tttcatgttt gttggctgca taaatgtctt cttttgagaa gtgtctgttc atatcctttc
37921 cccacttttt gatggggttg tttttttcct gtaaatttgt ttaagttcct tgtagatttt
37981 ggatattagc cctttgtcag gtggatagat tgcaaacatt ttctcccatt ctgtaagttg
38041 cctgttcact ctgatgatag tttcttttgc tggatagaac atgttttata gagttgttgt
38101 gagaattaaa tgcattaagc acatagaata gattctggta catagcaagt gctctctcta
38161 tatatggaac tctatatgta gttggtgcaa aagtaattgt ggttttcacc attgaaagta
38221 atggcaaaga ccatcattac cttttcacca atttaaatat atggaaggaa tatatatata
38281 aaacctatat atatatgtca catatatgtc tctaacccat tattataata tataatacaa
38341 tatatattat aattataatt gtatataaca tatgttatat aataatatag taatatttat
38401 tctaaataaa tatataatac tataaataat ataataattt atatatatga ttataatata
38461 taataggcta tattatatat tattaacata tacatatgtg tatatatatg tctttcatag
38521 acttaaatat atagagcaat aataggttag aaaatagcaa acatgtatat ataaacatat
38581 atacatatag aaaacatata taaaaacata tatatatata tatatatgtg tgttttctgc
38641 ctttcatttt tagagacagg gtctcatcat gttgcccagg ctggtctcaa actcctgggc
38701 tcaagtgatc ctactgcttt ggactcccga agtgctggga tttcagacat gagacactgc
38761 acccagtcca gtccctgtct ttttaaatag actctctacc taagtgcaca aatactcatt
38821 atttacattt agttatttct gtatatatgc tataagcaaa tcttgtagca ccagtttgat
38881 ttttataagg cacaagaata tattttacta atgctttaaa atggcagcta gattctagta
38941 ttactttaga aattaaaatt aatattttaa cacatctttc attattgtgt tatctgaacc
39001 aaacctatta ttgctgctat ttcagcaaat ccaggggctt tttcttataa aatatgaaga
39061 atatagctta gatttctagt gaagatgtta ccagtaataa ttaataaaat cagtaagcac
39121 taaaaggaaa ataccaaaac taaagcattt tgaattagtc attgaatcta aaagaaaggt
39181 agattttttt ctgagattct gttctaggtg tggtatatgt gtatttttgc aaaaactata
39241 aacaattgtg gcaaaatgaa ggaaatattt aaaaacaaac ctcttaattc ttcagtggat
39301 taagcgtgaa tatgttttta ttttctatga tgaatatgga aaaattcatt tccttagcaa
39361 tttgtatgag cccaaaaact attgtcagac tctgctgtat caaaatagac aaaaaattga
39421 cactcacttt taccctgcca aaagcaaaat cttaaacttt tgctttagta tataagccag
39481 cattcattgt atcctatgat gggttctgag tgtaggtgta tttgctttct tccatttttt
39541 gtatgcatgt tttcttttta tttattattg taagttgtat gaaattttta tccaaatttt
39601 tattttcttc tgattaataa tcagaataat cagataatta ctggtaaatt tgatgttaat
39661 ccttccagct ttttcccatg ggaatttata cttaataaag gggagaagtc atcattacat
39721 aatgtgcata ttaatctgct tctcccttta atgtgttgtg aatgcctttc catgtcatta
39781 gatgtttttc tacctagtta ctttcatgaa tcatatggct gtaccatgat ttatttaatc
39841 agttcctcat cattgagtat gtaaattgcc tccatttttt tattactata aaaggtcctt
39901 cagtacacac ccctttaaaa gctgactctt agaaggtgtt cttgactctc tacctaagtg
39961 taaaaataca aataaattgc tttccagaaa aggtgcacta ctattttact ttcctgatac
40021 taaactatga aaattcagtc ctaacaatag atatttaaat aaagttttaa aaatgccaag
40081 tgaaaaagag catattatta ttttcatttg cattactttt ggttcctggt gagtttaatc
40141 tgtttttgta tattaattat gcatttatat ttctttttgt gtgtgtgaat tgcctttcat
40201 gttctttgtg tgtttttatt ttgttgtatt tgtctctttc ttgatatatg agagaatatt
40261 ttccctagcc tgtcaattgc cttgtaattt tgtttctagt gagttttttt tttttttttt
40321 acaattaaaa gctttaattt ttgaaaattt tgctggcaaa tctatatatc tttttctttg
40381 ttttctgctt tgacattatt cttttataaa ggcccatgcc acccaaatat tatgtaagca
40441 tgcatctatg tttttattac ttcatctttt acatttaaat atctactcta tttagaattc
40501 attgtgatgc atgtatgagg tagaaatcta atttcaaaaa gatgagtatc cagtttgtcc
40561 atcatttatt gcatgatctc tttctccact gaattaaaat gccgtatttt ataatatatt
40621 aaagtattac atgtgcttgg acatgttcct ggacttttga gataaatcag tctatttctt
40681 tgtcatgtca catattatta tggctttatg atttaatatc cagtaatgta aaccctctga
40741 cacattattc ttattcctca aatgtttttg atgagttttc ttccaaatga aatttataat
40801 cattttattc attgattcaa caaatatttg ttgaatggat attctgtgct tggtattgtg FIG. 1 (cont.) (SEQ ID NO: 1)

```
40861 catggtatta ggattgttgc aaaaattgag actgacagtc cctactctta cggtgctaaa
40921 aattcacttc caaaaaaatc tttaaatgtt gatgaagatt gcactaatct tataaaataa
40981 cttggagggg aatgtaatct ttgcaacatt aagttcttca ttttagaaag ttttaagact
41041 ctccatttat ttgagacttt taaaatatgt cccaataatg ttttgtgaga tgtatatttt
41101 aagatatata tcttattgct attacattgt atcttttgtt atattgttac tatgaatggg
41161 atactcattt aattagatgt catttttggt atatagaaat ctattttctt agcatagtca
41221 tttttaaac ctcgatctat taaattcttg attcatttac atttgttaca caatcatatt
41281 ctatgctgat aatacttctt gcttctttcc aatatttgta cctcgatcat ttttcttgtt
41341 gagttgtatt agctagaagt tctagaaaaa tgttaaatgg tagtaatagc tagtattctg
41401 ttttttcctg actctaaatg taatgcatct agacttttat aattatggca ttgattgtaa
41461 cattttgagg aagaaatcct ttttcaggtt aataatgtat ctttatattc aagtttatta
41521 agaacattta ttggaaacat attgaaattt tatcagattc cttttcagtt gttactgaga
41581 taatcatagg ttcttctgta ttcttttaat taatttctca aaattaaact gtcctattat
41641 tcttggaata acgacatata aagtactgta tatttaaaag aagttaaaat gataatggtg
41701 attttattaa gtgacctcac acaatagaaa acagtgtagc cttagaagtt ttccaagtga
41761 ccattctact tagaaacaac cctgctttgg gatcagaact gtaattttta aagtaaagtt
41821 ttctgggttt aattcattta gtgtaattac aagcatgagt tcaggtttct attttttttca
41881 cctgaacttt ccttcatggt ttgaatatct agaaaaagca gactttccta tctctagact
41941 aaacatttga tcctatctta ggtatgcatt acaatttttt aaccataaat ggttaaagaa
42001 tttagactca tctacaataa ctttgaagct ctggtcttga agaacatgtg agaaatgaga
42061 tataactcct agaagatata ggagacattt ttagtcttcc aaatttttccc tgggaggctg
42121 atctaaattg agtcacaaaa ttgttcccac caggaatgca atcacttgag ctgttttcta
42181 atctgagccc ctctacccag atgatcttct gaactcatac tgttcagact ttcatccttc
42241 tgagtagaaa acagccatag tcatggcagg atgagggcta ggacaattac ccaaggaatt
42301 cttggcctct gccatgggac tctgcagact cagatcatat aatcagagat gttagcactg
42361 gaggggacat cacaattagc tttctccacc tcttagttta tcagtgagga aaactgtcca
42421 gagcgcggaa gagactaaaa taacacagcc aatgtaggta atgtgctgga taagaatttg
42481 gaattcacga ttttgaattc agtgtttatt tcaccatcac gctggcttac acgttggtat
42541 caggcttctt ctattattga agtgagccat taagtgaatt ccatcttgat ttgtgtctga
42601 tacagagtaa taaactattt tattaaatat ccaaataatt atacattcct ccttcttaca
42661 tgcaagccta agtttgcttg tactatttca tgtggtagca aatcaggacg cttcttgtgt
42721 ctctgaaaat actctgagta atggagtaca gtcagctttc ttgtaccaag aatataggga
42781 ctatgtttct cccagtcatt ctggggataa tttttgtgaa ggattgcact tcataggtta
42841 agctaggtat cagttaccag tgttttttcc aaataaaaaa aaaatcaggt gatatctgta
42901 aatggttcca ttgtaaatat taaagaacat gatgcttaaa acagattagg gaaaactata
42961 gaaggggtgg ggtttcggag tgctaatttt gtccttgaat ggtaacagct ccatgtggtg
43021 gtgaggttta tgttggtttg ctgtttgcag atgatcttat tattagaatt tttcataccg
43081 aaaataaact gcattttagt ttgtaaacat gcccttccag agtaatgcta ccagttcttt
43141 gtgaaatagc tactgttgtt caaaggatga ctatgtcctc ttcggttgag gaaagatgac
43201 aacaaactca gtaatgacat gtaaaatagg tattacaaac caggtatggt ggcatgagcc
43261 tgtaatccca gctacttgag aggctaaagc aggaggatct gttgatctat ggatttgagg
43321 ctgtagtgtg ttgtgatggc acctatgaat agcccttgca ctccagccca agcaacaaag
43381 caagactgtc tctgaatttt tgttttgttt tgttttttgt tttttttttt ttgagacaga
43441 gtcttgctct gtcacccagg ctgaagtgca gtggcgcgat ctccactcac tgcaagctcc
43501 gcctcctggg ttcacgccat tctcctgcct cagcctcccg agtagctagg actacaggcg
43561 cccgcctcca cgcccagcta aatttttttgt atttttagta gagacgaggt ttcactgtgt
43621 tagccaggac ggtcttgatc tcctgacctt gtgatcctcc tgcctcggcc tcccaaagtg
43681 ctgggattac aggcgtgagc caccgcgccc ggcccctgtc tctgaatttt ttaaaaaggc
43741 attccactca aattaataca cattttaatt gtgttttgtt gtaaattaca actgaataaa
43801 aattcagcaa ataagtctgt tgtggtaggg aaaagtctat tgtgatctgg aaaatataat
43861 ggagaaatcc agtggaagag atttatttc acattactca aaataaaaaa atcttataca
43921 agtctttaca cttgtaactt gaaaaattct gtgctaaaat ttagcttggt tgctaaaata
43981 tttctctttt tttctcagaa gcttcttttt agcatcctat agacacaagt tactttttaa
44041 aatatttgca tacttgcttt gcaatgtatt gtttatcagt agttctatat tctttgagat
44101 agtctatcca gtctttctgt atttatcgta tgtctgtata gatatatatt agcagataaa
44161 tgagttctga aaggggagaa atgtgattat gctaatcatg atataaagaa ttgactttat
44221 aagcagtgtt cacaggtcat acctttcccg ttactgtctt acagtgaaca agaaatgatg
```

FIG. 1 (cont.) (SEQ ID NO: 1)

```
44281 ctttgtctgg tatgcatggt aaataatgcc ccttgctctc tgcttcatga tcacatgtga
44341 tacttctaac atagatagca catgtaaatc cagtggcctt gactgcaact caagagagca
44401 ttttggccaa gtacaaaccc actagtcatg aaaaaaaaaa aaaaaccaaa tcaaagtaaa
44461 ttgatggtat tgacatttgt ctatgaaaaa caacataata tagaacaatt ctggggtaaa
44521 atattgatct aaaataattt taaggattaa atattgccat tgtaagcata ctatgagcaa
44581 ttatgtttgt aatgcagata tatttataat tttaaatcca agatttacct taattgtaca
44641 ttttcctaat ttaaaaaagt tattttgaaa aaaaaatcct cgaatctaga gaaaggttgg
44701 caaatacata tggaactttg taaaaaacat ccagggcagc actttcactg attgcagtag
44761 cttaggagtg aaaaacaaca caactgctcc aatgtatggc aatgggcaaa tatcccgatt
44821 tattcacagg gtggcatgtt aggcagtgct tagaataaat gagttggtta tacaagtatc
44881 aatagggata aatgtgaaaa acacagtgtt aagtttttaa aaagttgtaa aaagcacagt
44941 aggatgttat ttatataaaa tttaaaaacc tcaaaaacca ttcttctttg atatatattc
45001 taaagatgaa catatatgta atagaagtac aaaacataca taaaataata tacactatgc
45061 agtcatttgt gtacttactt ttcaaaaata tttcagtaga tatagcaaac agttaacatg
45121 taatatttgg ataggaggtt ggcaattttc tttttagcac ctgcctgtct gctatcattc
45181 aaactcacat ttaaaatgtg gctatgtgag atgagagaac tataatattc caggtttgtg
45241 attagtttgg aaacttttta aaagtttgaa tgtggtctga gagatagttt gttataattt
45301 ctgttctttt acatttgctg aggagagctt tacttccaac tatgtggtca attttggaat
45361 aggtgtggtg tggtgctgaa aaaaatgtat attctgttga tttggggtgg agagttctgt
45421 agatgtctat taggtctgct tggtgcagag ctgagttcaa ttcctgggta tccttgttga
45481 ctttctgtct cgttgatctg tctaatgttg acagtggggt gttaaagtct cccattatta
45541 atgtgtggga gtctaagtct ctttgtaggt cactcaggac ttgctttatg aatctgggtg
45601 ctcctgtatt gggtgcataa atatttagga tagttagctc ctcttgttga attgatccct
45661 ttaccattat gtaatggcct tctttgtctc ttttgatctt tgttggttta aagtctgttt
45721 tatcagagac taggattgca acccctgcct ttttttgttt tccattggct tggtagatct
45781 tcctccatcc ttttattttg agcctatgtg tgtctctgca cgtgagatgg gtttcctgaa
45841 tacagcacac tgatgggtct tgactcttta tccaatttgc cagtctgtgt cttttaattg
45901 gagcatttag tccatttata tttaaagtta atattgttat gtgtgaattt gatcctgtca
45961 ttatgatgtt agctggtgat tttgctcatt agttgatgca gtttcttcct agtctcgatg
46021 gtctttacat tttggcatga ttttgcagtg gctggtactg gttgttcctt tccaggttta
46081 gcgcttcctt caggagctct tttagggcag gcctggtggt gacaaaatct ctcagcattt
46141 gcttgtctat aaagtatttt atttctcctt cacttatgaa gcttagtttg gctggatatc
46201 tctcagacca cagtgcaatc aaactagaac tcaggattaa gaatctcact caaagccgct
46261 caactacatg gaaactgaac aacctgctcc tgaatgacta ctgggtacat aacgaaatga
46321 agacagaaat aaagatgttc tttgaaacca acgagaacaa agacaccaca taccagaatc
46381 tctgggatgc attcaaagca gtgtgtagag ggaaatttat agcactaaat gcctacaaga
46441 gaaagcagga aagatccaaa attgacaccc taacatcaca attaaaagaa ctagaaaagc
46501 aagagcaaac acattcaaaa gctagcagaa ggcaagaaat aactaaaatc agagcagaac
46561 tgaaggaaat agagacacaa aaaacccttc aaaaaatcaa tgaatccagg agctggtttt
46621 ttgaaaggat caacaaaatt gatagaccgc tagcaagact aataaagaaa aaaagagaga
46681 agaatcaaat agacacaata aaaaatgata aaggggatat caccaccaat cccacagaaa
46741 tacaaactac catcagagaa tactacaaac acctctacgc aaataaacta gaaaatctag
46801 aagaaatgga tacattcctc gacacataca ctctcccaag actaaaccag gaagaagttg
46861 aatctctgaa tagaccaata acaggctctg aaattgtggc aataatcaat agtttaccaa
46921 ccaaaaagag tccaggacca gatggattca cagccgaatt ctaccagagg tacaaggagg
46981 aactggtacc attccttctg aaactattcc aatcaataga aaaagaggga atcctcccta
47041 actcatttta tgaggccagc atcattctga taccaaagcc gggcagagac acaaccaaaa
47101 aagagaattt tagaccaata tccttgatga acattgatgc aaaaatcctc aataaaatac
47161 tggcaaaccg aatccagcag cacatcaaaa agcttatcca ccatgatcaa gtgggcttca
47221 tccctgggat gcaaggctgg ttcaatatac gcaaatcaat aaatgtaatc cagcatataa
47281 acagagccaa agacaaaaac cacatgatta tctcaataga tgcagaaaaa gcctttgaca
47341 aaattcaaca acccttcatg ctaaaaactc tcaataaatt aggtattgat gggacgtatt
47401 tcaaaataat aagagctatc tatgacaaac ccacagccaa tatcatactg aatgggcaaa
47461 aactggaagc attccctttg aaaactggca caagacaggg atgccctctc tcaccgctcc
47521 tattcaacat agtgttggaa gttctggcca gggcaatcag gcaggagaag gaaataaagg
47581 gtattcaatt aggaaaagag gaagtcaaat tgtccctgtt tgcagacgac atgattgttt
47641 atctagaaaa ccccatcgtc tcagcccaaa atctccttaa gctgataagc aacttcagca
```

FIG. 1 (cont.) (SEQ ID NO: 1)

```
47701 aagtctcagg atacaaaatc aatgtacaaa aatcacaagc attcttatac accaacaaca
47761 gacaaacaga gagccaaatc atgagtgaac tcccattcac aattgcttca aagagaataa
47821 aatacctagg aatccaactt acaagggatg tgaaggacct cttcaaggag aactacaaac
47881 cactgctcaa ggaaataaaa gaggacacaa acaaatggaa gaacattcca tgctcatggg
47941 taggaagaat caatatcgtg aaaatggcca tactgcccaa ggtaatttac agattcaatg
48001 ccatccccat caagctacca atgactttct tcatagaatt ggaaaaaact actttaaagt
48061 tcatatggaa ccaaaaaaga gcccgcatcg ccaagtcaat cgtaagccaa aagaacaaag
48121 ctggaggcat cacgctacct gacttcaaac tatactacaa ggctacagta accaaaacag
48181 catggtactg gtaccaaaac agagatatag atcaatggaa cagaacagag ccctcagaaa
48241 taacgccgca tatctacaac tatctgatct ttgacaaacc tgagaaaaac aagcaatggg
48301 gaaaggattc cctatttaat aaatggtgct gggaaaactg gctagccata tgtagaaagc
48361 tgaaactgga tcccttcctt acaccttata caaaaatcaa ttcaagatgg attaaagatt
48421 taaacgttag acctaaaacc ataaaaaccc tagaagaaaa cctaggtatt accattcagg
48481 acataggcgt gggcaaggac ttcatgtcca aaacaccaaa agcaatggca acaaaagcca
48541 aaattgacaa atgggatcta attaaactaa agagcttctg caaagcaaaa gaaactacca
48601 tcagagtgaa caggcaacct acaacatggg agaaaatttt cgcaacctac tcatctgaca
48661 aagggctaat atccagaatc tacaatgaac tcaaacaaat ttacaagaaa aaaacaaaca
48721 accccatcaa aaagtgggcg aaggacatga acagacacta ctcaaaagaa gacatttatg
48781 cagccaaaaa acacatgaag aaatgctcat catcactggc catcagagaa atgcaaatca
48841 aaaccactat gagatatcat ctcacaccag ttagaatggc aatcattaaa aagtcaggaa
48901 acaacaggtg ctggagagga tgtggagaaa taggaacact tttacactgt tggtgggact
48961 gtaaactagt tcaaccattg tggaagtcag tgtggcgatt cctcagggat ctagaactag
49021 aaataccatt tgacccagcc atcccattac tgggtatata cccaaaggac tataaatcat
49081 gctgctataa agacacatgc acacgtatgt ttattgcggc actattcaca ataggaaaga
49141 cttggaacca acccaaatgt ccaacaatga tagactggat taagaaaatg tggcacatat
49201 acaccatgga atactataca gccataaaaa atgatgagtt catgtccttt gtagagacat
49261 ggatgaaatt ggaaaccatc attctcagta aactatcgca agaacaaaaa accaaacacc
49321 gcatattctc actcataggt gggaattgaa caatgagatc acatggacac aggaagggga
49381 atatcacact ctggggactg tggtggggtc gggggagggg ggagggatag cattgggaga
49441 tatacctaat gctagatgac acgttagtgg gtgcagcgca ccagcatggc acatgtatac
49501 atatgtaact aacctgcaca atgtgcacat gtaccctaaa acttagagta taaaaaaaaa
49561 aaaaaaaaaa gtttgaatgt tttcttgcat tcagagcctt ggttgacata gttaattaaa
49621 aataaaacat tgtatataaa gcacagaatg agcagctaca caaagctgct caatcaatga
49681 cagctctata tgggttaggg tttcttgtgg ggatgacatt gatgtagaaa gcatggtcat
49741 ctattgagaa tgatggggct ggaggtattg gatacttgag gtttagaaaa tacattgtag
49801 aaaatggaca aaaacccctc aaattaaggg atgaggcaga ataatgcttg gcaataccag
49861 gggtaggctg cagtctttct tggaaatata tattttaaat ggaaccaatt atcatagcat
49921 catttcctct cagggttacc ctctgatccc tattttacta aatcgttata aaacaaaatg
49981 aggaattatg tgtccttccc ttttgaagcc aatgtaacaa gatgggtaag aattagacct
50041 cctgagttca aaatccctgg attcagatct attcctgtat attcaggaga agtggtaata
50101 aattcgatgg acaatttggt ttagtagtcg attgaggacc ctgatgaggt atatttggga
50161 aaacataact tccgctctct ctcattgact cacgggcctt tgaggagtcc aggagtcatt
50221 ggaatctggc ctgaggttga ggctgctggc aaaactcctt ccccaaagtc cattcctatt
50281 gctgactgag aagggactag cattggaagt ggctgatttt aaataccgct agtgctggtg
50341 tgctcctccc tcccattccc agctctgctt tgtgtagttg ccttgagaag ctaagttcat
50401 tctgaaaata atgccattgc acaaaacact tttgaaagtt ctagtttgaa attacatcag
50461 gtcacttggt ctgtgtggcc tcagtttctt catctgccat gtgaaaataa taatgcctac
50521 tctgtagcaa agaaagtctc tatagtaaac aaaaaaaaag cctactctga tactgaaagt
50581 tgttatgaaa aataaaaaag ggaaatgctt tagaaactgt taagtgctat gtagatgtta
50641 ctaattaaca aaccatttca gaaactatac tttttatttt atggccacta ttcactgttt
50701 aacttaaaat acctcatatg taaacttgtc tcccactgtt gctataacaa atcccaagtc
50761 ttatttcaaa gtaccaagat attgaaaata gtgctaagag tttcacatat ggtatgaccc
50821 tctatataaa ctcattttaa gtctcctcta aagatgaaaa gtcttgtgtt gaaattctca
50881 gggtatttta tgagaaataa atgaaattta atttctctgt ttttcccctt ttgtaggaag
50941 tcaccaaagc agtacagcct ctcttactgg gaagaatcat agcttcctat gacccggata
51001 acaaggagga acgctctatc gcgatttatc taggcatagg cttatgcctt ctctttattg
51061 tgaggacact gctcctacac ccagccattt ttggccttca tcacattgga atgcagatga
```

FIG. 1 (cont.) (SEQ ID NO: 1)

```
51121 gaatagctat gtttagtttg atttataaga aggtaatact tccttgcaca ggccccatgg
51181 cacatatatt ctgtatcgta catgttttaa tgtcataaat taggtagtga gctggtacaa
51241 gtaagggata aatgctgaaa ttaatttaat atgcctatta aataaatggc aggaataatt
51301 aatgctctta attatccttg ataatttaat tgacttaaac tgataattat tgagtatctt
51361 ctgtaaactg cctctgttgt agtttttttt ttctcctaat catgttatca ttttttttgga
51421 atccatggtt tcctgttaag atgactcaca cagcctacat aaaagtaatt gacaaaatat
51481 catcttatag taaaatgcca catatcttta tgttcagcaa gaagagtata atatatgatt
51541 gttaatgata acccaaacaa caaaagattt caccttaact ggttgtcata agtagtagta
51601 tccaccgcct tattttgagt tggattttta tcatcctatg agccctacaa atttaaagtt
51661 tttggaacag cacgtgcatt gaacccataa gaacctactc tgcttttctg catgtattgt
51721 ccagacaaga gaccaaattg ccgaggcatc atttaggtga attctaatta acatttagct
51781 accttacaac cacaattcaa ggttgtttca aaggcatgtg cttgcatcat cctgattcac
51841 taccatgtgt tactaacttg gatctgcaaa gtcattataa aaagctgttt tgatggactt
51901 atttggatat tgctttaccc ttcttctctc ttttctttta tcaatgtaaa aacattatat
51961 gttaaatact tggcttttaa gagcatagat ctgaaatctg cctctagcaa ataacccata
52021 acacttctaa gatataccctg caaggtcaat tgtgttgtaa aaccttgata accatacttt
52081 attgttcaaa aaagcctttt atgaaggcag aagttaaaaa aaaaaaacaa aaaaaacaga
52141 gtccacagtt atcacctcag ctacaatctc atcagttcac aagtaccagc aaaacatgtg
52201 ataagtcaac aaatgtttta tttcaatctg aacattttac gtaagtgaag actttgttag
52261 atatcatttg gaatgtggaa tctacacagt tggcatatca gagaaggttg aattcagttt
52321 aataaatgtt tatagaaagt gcttgttatc ataatgataa tagctcagga tgtgcatgac
52381 aagcttttaa gcgattgggt acactatctc atttgatctt ctgcacaact attaatggta
52441 ggtactatta tccctatctt atggataagt aaactaagat ttaaaaagta cagaacatgg
52501 tgtgaacact gcttcaaaat ttctaaaata ggtaaatcac gatctctaaa ctggagggtt
52561 gtccaaccac tagggacaat agagtactga tatttagtgg tcagactgta atgcgggaag
52621 agacaggcat gggctaaacg ggtgtagaga tcaaataagg ggcaggttag tttgtaaaca
52681 tgtccatatg taacatttag cacaaataca ggatataggt gctttcagac ccagctgcat
52741 tgataaaaag ttaggtggta ttgtatctgt cttcctttct caatgttgca tatctgtgtt
52801 cttgcccagt ttgcttcatc tctctagcca cacttattgg cctacaatgg catcatcacc
52861 aaagaaggca atcccatctc cgtgtggctt tggtttgctc cctaaagtaa accttgtgtt
52921 tacttttccc aggtctcatg ctttcccata tctgacctgt tttgtcctca tggccaggat
52981 atgtgggacc tttcctacaa tgttccaaag tttgtaatag agctcttctc tgctttgttc
53041 caaattctgc aacattttac tttaaataat gaatttaaat acaaacaaac ttgagctttg
53101 cctatacttt tcaagaatgc agagataact aaattaataa aaatattcat tgagtcctta
53161 ctgtgcacac agctctatgt taagccttgt gcagaactca aagtcactcg agattaagcc
53221 tgttactaag ttatgtgcaa tttagctcag tggatttccc ccacttcata ttgctctgat
53281 aatgttttgg aattaactgc cttgattcct tcttttctct gcttgtctat acactattta
53341 ttattctaca ccatctcaaa ttctaactcc tcaagaaaat ccttccagat gatttttcta
53401 accaggagtt ttaacttcct tttaactacc ctattacttt ctacttcctt aactcatcta
53461 tcatattata tttagttatt tatatactag gtcgccttga agaaggggatt gtgttttcat
53521 aaatcttaat aatccctgag gcatcaagta cagtgatttg catttactaa atgctcaaca
53581 aatatgtgag ggattcactt gaaactaata ttagataatt cccagtcaaa gtgatctaat
53641 agcaaatcaa ttcttcagtt ttataggcaa agtatgactc tggttttcca taatcataat
53701 taatttgtca actttataat tttaattaag taaatttaat tggtagataa ataagtagat
53761 aaaaaataat ttacctgctt aactacgttt catatagcat tgcattttc tttgtaaaat
53821 ttaagaattt tgtattaata aactttttta caaaagtatt aattattcag ttattcatca
53881 tatactttta ttgacttaaa agtaatttta ttcaaaagag ttagtatagg actacatgaa
53941 aaattcaagg ccaaggctta atttcaaatt tcactgcctt tggctctatc ttttaaaaca
54001 aaacaaaaaa ctcccgcaca atatcaatgg gtatttaagt ataatatcat tctcattgtg
54061 aggagaaaaa ataattattt ctgcctagat gctgggaaat aaaacaacta gaagcatgcc
54121 agtataatat tgactgttga aagaaacatt tatgaacctg agaagatagt aagctagatg
54181 aatagaatat aattttcatt acctttactt aataatgaat gcataataac tgaattagtc
54241 atattataat tttacttata atatatttgt attttgtttg ttgaaattat ctaactttcc
54301 atttttcttt tagactttaa agctgtcaag ccgtgttcta gataaaataa gtattggaca
54361 acttgttagt ctcctttcca acaacctgaa caaatttgat gaagtatgta cctattgatt
54421 taatctttta ggcactattg ttataaatta tacaactgga aaggcggagt tttcctgggt
54481 cagataatag taattagtgg ttaagtcttg ctcagctcta gcttccctat tctggaaact
```

FIG. 1 (cont.) (SEQ ID NO: 1)

```
54541 aagaaaggtc aattgtatag cagagcacca ttctggggtc tggtagaacc acccaactca
54601 aaggcacctt agcctgttgt taataagatt tttcaaaact taattcttat cagaccttgc
54661 ttctttttaa aactttaaat ctgttatgta ctttggccag atatgatacc tgagcaattc
54721 ttgttctggg ttgtcttatg tgaaaaataa attcaaggtc cttgggacag ataatgtgtt
54781 ttatttatct ttgcatatcc attacttaaa acagcattgg acccacagct ggtacaaaat
54841 taattactgt tgaattgagc aaatatttat tctaaatgtc tctgtcaaat gacagagtgt
54901 ggttgtgtgg attaagtccc tggagagagt tctttgttct ctcatgttct atgctgtggt
54961 tcttgcttta tgcaaaaaga agtaagttac ttaaaacctg gacatgatac ttaagatgtc
55021 caatcttgat tccactgaat aaaaatatgc ttaaaaatgc actgacttga aatttgtttt
55081 ttgggaaaac cgattctatg tgtagaatgt ttaagcacat tgctatgtgc tccatgtaat
55141 gattacctag atttagtgt gctcagaacc acgaagtgtt tgatcatata agctcctttt
55201 acttgctttc tttcatatat gattgttagt ttctaggggt ggaagataca atgacacctg
55261 tttttgctgt gcttttattt tccagggact tgcattggca catttcgtgt ggatcgctcc
55321 tttgcaagtg gcactcctca tggggctaat ctgggagttg ttacaggcgt ctgccttctg
55381 tggacttggt ttcctgatag tccttgccct ttttcaggct gggctaggga gaatgatgat
55441 gaagtacagg tagcaaccta ttttcataac ttgaaagttt taaaaattat gttttcaaaa
55501 agcccacttt agtaaaacca ggactgctct atgcatagaa cagtgatctt cagtgtcatt
55561 aaattttttt tttttttttt tttttgagac agagtctaga tctgtcaccc aggctggagt
55621 gcagtggcac gatcttggct cactgcactg caacttctgc ctcccaggct caagcaattc
55681 tcctgcctca gcctccggag tagctgggat tagaggcgca tgccaccaca cccagctaat
55741 ttttgtattt tagtagagac agggtttcac caggttgccc aggctggtct cgaatgcctg
55801 acctcaggtg atccgcccac ctcggcctcc caaagtactg atattacagg catgagctac
55861 cgcgcccggc ctaaaaaata ctttttaaga tggtgtaaat attactttct gtatcaatgg
55921 tacatttttt acttgtcagt ctctagaatt tctttataaa tatgttgatt cagttcattt
55981 ttgtagatta taaaacaggt aaaaaaggat aaaacattta tgtgaattaa agggaatacc
56041 taatttttgt gtagagttta ttagctttta ctactctggt ttatggatca tcacaccaga
56101 gccttagtta ctttgtgtta cagaataact aatatgagtg aatgaatgac ttacacaagt
56161 cactgcttag gataaagggc ttgagtttgt cagctagagt atgacagaaa gtatctaagt
56221 tttggagtca aatagcactt tgtttgaatc ccagattgca tgcttactag ttatgtgacc
56281 ttagtcaagc cacttcacct cactgagtct ttgctttttt catctctaaa atagagatac
56341 ccaccgctca taggctgtca taagggatag agatagcata tggaatgagt ctgtacagcg
56401 tctggcacat aggaggcatt taccaaacag tagttattat ttttgttacc atctatttga
56461 taataaaata atgcccatct gttgaataaa agaaatatga cttaaaacct tgagcagttc
56521 ttaatagata atttgacttg tttttactat tagattgatt gattgattga ttgattgatt
56581 tacagagatc agagagctgg gaagatcagt gaaagacttg tgattacctc agaaatgatt
56641 gaaaatatcc aatctgttaa ggcatactgc tgggaagaag caatggaaaa aatgattgaa
56701 aacttaagac agtaagttgt tccaataatt tcaatattgt tagtaattct gtccttaatt
56761 ttttaaaaat atgtttatca tggtagactt ccacctcata tttgatgttt gtgacaatca
56821 aatgattgca tttaagttct gtcaatattc atgcattagt tgcacaaatt cactttcatg
56881 ggctgtagtt ttatgtagtt ggtccagggt gttattttat gctgcaagta tattatactg
56941 atacgttatt aaagaatttc ctacatatgt tcactgctgc tcaatacatt tatttcgtta
57001 aaacaattat caagatactg aaggctgatt ggtaactcac atggaactgg gagagtatac
57061 aattctgaac caaatagatg attctctatt attatatctt aatttatgtg ttatggtata
57121 ttaaacatga aaaaaattgt atttggttag aatatgtttg ctcttcctta actcgggaat
57181 gacatagggt aatattcaca gattgggttc ctataaatcc tccacttgaa gtgaagtcag
57241 ttcaagtaat gaaagctacc tcctgagata gaatcagtac ttggcaccta tctctagtgt
57301 tctttcacct catataacct ttcactgatt agtaaagatt atatccaaca aagaaagtac
57361 agcacagact gagatatgat tactgagata aatttggca aaatataaac tacagcattt
57421 ctgtagcaat gagaccattt ttcttcagtt gagctccatg ttctacaaac ttcaatcaaa
57481 aaaggttcta ggagactcag tgaaagttga tacactgttc aaggaacaaa taatttcagc
57541 acatgggaat ttcacaggga aaaatatact aaaaagagag gtaccatttt ggatggtgtc
57601 aatatgggtt atgaggaatt caggctgctg agtccagtgt acaatggaaa ctgagctgca
57661 ggtgtgtgat tgtaacaaca aaagaaatgc tgaaatatta agtcctttgc catgtaaata
57721 gaaaaagagt atttatttcc caaacattat tgctcacctg tttttgttat gcctttcaag
57781 ataaatccag gaaaggaatt gcattttctt tccagaaaac aagttcttgg gggaattgtt
57841 caattggtag atgttgtttt tctcattaac aagtgagtgc tccatcacac ttgctgagtg
57901 ctccatcaca cttgctctct gcattactcc tctgcctgca aacacatata tagcaagggt
```

FIG. 1 (cont.) (SEQ ID NO: 1)

```
57961 gatgacaagg atatcagagg gtctggtttt ctcaaactca tgataaactc atggctgggt
58021 cattcttggt gctgatttta ctttgttttt tgttgttatt gttccctctt cctcaaaaga
58081 tgaaatctat ccctcttact tggaatttct ctttgatata tagcgaatgt ttggttgtaa
58141 cctgtataat ctggcatgaa attgtcactc gaaaaggcta gaagtgttga cataaatatg
58201 ggacagcaag agttgctcct actcaagaga gcaaatataa tgttctggaa gagattggca
58261 gaattcacat caaaggagtg attacttcag cctgggccac tgttgtactg gtcaaaaggc
58321 tgtgcaaagc tctctgaaaa tccactcttt tattgctctt tagtaataaa gtcactttca
58381 attttaaaaa taacaaactg atatattttt atgactcata aaatgttagc aattatatta
58441 tggagaatct actttctggg tgattcttac aaatgttctt ggatctattt tttttttctta
58501 tagtacctat tcttcccatt tttctcagct ctagttaata tatttcaaca acagttcaac
58561 aaatttaaca tttttataaa aagtgtttcc tatcatttta taaataccag cctagtccat
58621 gttattcctt ttcttgttga ggagaaagga cacacattgt aaattcaaat atagacctct
58681 actgtgctat ttaatcttgg taacaactcc acaaaggaga tgacatgttt tccttctata
58741 gaggtagatt ctgtaaagtt agagggaaga gtgacttgct taagatggca taagctgtaa
58801 ctggcagaac caggattcaa agccaggtgg gatgccaaaa tcataatctg tcttcagtgt
58861 caagttactg aaattggtaa acattagacc taaatagacg gaattgcaat ccgggttggg
58921 cacattaaac tccattttct tcatcaatgt gctcagatta cattttactt ttcaggctaa
58981 aaatggaaaa aaagagtccc tcttagttct gcacttgaga atgagaatag cttttctgaa
59041 ttatacaagg aagaagaact aatgcccaaa tgccaggtac ccacatgcac tatgccatgg
59101 cacagctgtt gcccccttc accagagccc tctctctgta tcctggttga cctttccttg
59161 ggcaagagct gggtggggag gatcacaagt gactccaatt tggatggctt cgggaagact
59221 gggaccgagc tgaaggcagt gttgtcctct gcactccctg ttttctgtct gctggagcac
59281 tgaagcctca catatgtatt aaaaaaataa tttccatttg catttcagac tagaagattg
59341 aacgtatagt gtaatgtgat tgcaaataat tatattgaaa tgagacagag aggatgtagt
59401 atctactgtc ataattttc aaaacccacc tgcaacttga attaaaagaa ccacttgggt
59461 ttttttttt gtttcaaacg caaatcctgg aaacctactg agactcattc agtcagtatc
59521 tctaagaggc aagcttgaga ctgtatattt aaaaagcatc tcaggtgatt tttacacatg
59581 ctaaggctta agaaccactt ctctgtagct tatatgttat tttcaatgtt cctcaaagcc
59641 aagttagaat ttccaaagtg ttaagaatcc attagacaat cacagaattg tctttttcct
59701 ttataaatct tgcaatgttg ttctcatttc catacttaat tacttaaaac accaaccaac
59761 caacaagcaa aaaatgatta gtctaactaa tattacaagt taataatgaa gtaaaggttt
59821 aaaaataatg tcataataat gttaataaca aattattaat tataatttaa aaataatatt
59881 tataatttaa aaataatatt tacaagtact acaagcaaaa cactggtact ttcattgtta
59941 tcttttcata taaggtaact gaggcccaga gagattaaat aacatgccca aggtcacaca
60001 ggtcatatga tgtggagcca ggttaaaaat ataggcagaa agactctaga gaccatgctc
60061 agatcttcca ttccaagatc cctgatattt gaaaaataaa ataacatcct gaattttatt
60121 gttattgttt tttatagaac agaactgaaa ctgactcgga aggcagccta tgtgagatac
60181 ttcaatagct cagccttctt cttctcaggg ttctttgtgg tgtttttatc tgtgcttccc
60241 tatgcactaa tcaaaggaat catcctccgg aaaatattca ccaccatctc attctgcatt
60301 gttctgcgca tggcggtcac tcggcaattt ccctgggctg tacaaacatg gtatgactct
60361 cttggagcaa taaacaaaat acaggtaatg taccataatg ctgcattata tactatgatt
60421 taaataatca gtcaatagat cagttctaat gaactttgca aaaatgtgcg aaaagataga
60481 aaaagaaatt tccttcacta ggaagttata aaagttgcca gctaatacta ggaatgttca
60541 ccttaaactt ttcctagcat ttctctggac agtatgatgg atgagagtgg cattttatgc
60601 caaattacct taaaatccca ataatactga tgtagctagc agctttgaga aattctaaag
60661 ttttcaagtg ataagactca atttatacaa agctaattgg ataaacttgt atatgattaa
60721 gaagcaaata aatacttatt atgctttttt gctgtttatt taaatattta acccagaaaa
60781 taagtcactg tgacagaaat aaaaatgaga gagaagggtg agccactctt aggtagttct
60841 ggcattattt aatctaggcc agaggttgca aatggtgtcc catagaacta attttggctc
60901 ctagacctgt cttatttaac ctttcattta aaaaatttgt attggttgcc agcaattaaa
60961 aattgggaga tgtctcacac acacacacac ataaacacac acactcatgt gtgcagcctc
61021 ttttgaagaa ttggaataac tagtcaactg cgtcctcctt ttccacaagc tgtgacagct
61081 ccctgctcac agagcacctg ccctctcctg ttcatcatgc tctcttctca gtcccattcc
61141 ttcattatat cacctatttg gtcctgagac taagtgagtt tgagatctgt gatttagaca
61201 aagtggtgaa tctagctctg aatcatagta agtagctctg ggaatcatct tgtcttctgt
61261 tagcccattg agagagaaat agagagagag agagagagaa agaaagaaga agaaacagat
61321 ctggggagag tcactgaatg ggagcataga gacagagaaa cagatctaga aaaccaaact
```

FIG. 1 (cont.) (SEQ ID NO: 1)

```
61381 gggagaaaat gagagaaacc aaaagagagg tagagaggag cagagaagaa aatgaagaag
61441 caaggcaagg accaggcttt ttcattattt cttatggcca agacttcagt atgcgtggac
61501 ttaattcttc cttatgctcc taccttccct agggaaactg atttggagtc tctaatagag
61561 cccttctttt agaatcacag tttgatgcct taaaactagt tatatacctt cacatgcttc
61621 cttaacccac agaagtgatg ctaatgaggc ccttaataag gagcgtgcta ttaagatgaa
61681 gacattcatt ttttttctcc gtccaatgtt ggattaaggc acattagtgg gtaattcagg
61741 gttgctttgt aaattcatca ctaaggttag catgtaatag tacaaggaag aatcagttgt
61801 atgttaaatc taatgtataa aaagttttat aaaatatcat atgtttagag agtatatttc
61861 aaatatgatg aatcctagtg cttggcaaat taactttaga acactaataa aattatttta
61921 ttaagaaata attactattt cattattaaa attcatatat aagatgtagc acaatgagag
61981 tataaagtag atgtaataat gcattaatgc tattctgatt ctataatatg tttttgctct
62041 cttttataaa taggatttct tacaaaagca agaatataag acattggaat ataacttaac
62101 gactacagaa gtagtgatgg agaatgtaac agccttctgg gaggaggtca gaatttttaa
62161 aaaattgttt gctctaaaca cctaactgtt ttcttctttg tgaatatgga tttcatccta
62221 atggcgaata aaattagaat gatgatataa ctggtagaac tggaaggagg atcactcact
62281 tattttctag attaagaagt agaggaatgg ccaggtgctc atggttgtaa tcccagcact
62341 ttgggagacc aaggcgggtg gatcacctga ggtcaggagt tcaagaccag cctggccaac
62401 atggtaaaac ccggtctcta ctaaaaatac aaaaaattaa ctgggcatgg tggcagatgc
62461 tgtagtccca gctgctcggg aggctgaggc aggagaatca cttgaacctg ggaggcggag
62521 gttgcagtga gctaagatca cgccactgca ctccagcctg ggcaacaagg cgagactctg
62581 tctgaaaaag aaaaaaaaat aaaaataaaa ataaaaagaa gtggaggaat attaaatgca
62641 atataaaagc tttttttatt tttaagtcat acaatttgtt tcacataaca gatcaggaaa
62701 taatacagag atcataagtt ttggagctgg gtttgaatcc tggctctgcc atttactttc
62761 tgtgtaatct aagtcaagtt actgaacttt gtgggccctc tggctctcca tgtgtaaaat
62821 ggagaatatt aatatttacc ttgcaagttt gttgtgaaga ctgaaggaga gaatttaggt
62881 aaaacattca tcagagtacc atgcacacag ttgttcctca ataaacatta gcttctctga
62941 ttgcaagttc cagtctaaag tgctttatat ataccagcca ataaaaggat gcgagagaga
63001 tataccagtg tattgttttc taccatttta aacctatttt catccactgt tacaaattct
63061 atcatactgc tccacataaa aaatattatc aatgattttt agtctctgaa gtgcaatatt
63121 tgattattga gcacacctgt tgaagtttta gtttcttctc acttacatgg gttgtgtaaa
63181 ggtaggaggt ataaaaccag tgtcctaggt ctaaatcttt cttaatgtca tactttggat
63241 tcattgatat aagtaacttg agcaccagcg cttcatttta cttcattttt taaagatata
63301 gtaagagtaa ttcccatctg cctagcaaaa ttgttttgta gaaaagtttg tggatcagat
63361 ttattttact ttgattttag gaatttcaag tgtcttcgtc ggcatgaagg aaaaatatgc
63421 agtttgacat tttctactac tttcaggtca ttattttcct actctggtgc aaaaaccctc
63481 aattcctgtc tcactccatc taatcaaata ggtagcatgc ttgagccctt actatgtgcc
63541 aggcactagg ataagcactt tatatgtttt gtcccaatta attctcacag catttctatg
63601 acctaaataa aattaatatt ttcatttcac caataataaa atggaggctt caaaaagttt
63661 agggacttgg ctcagctcac acaactggca aggactgaaa atggatttta gtcccaaatg
63721 tcataggcta gagccctttc actaaactgt tgtcttccat ctggtggcat cctcttcctc
63781 cagtctttgt cacctaaact ctgggcaccc cttgatggca tttacttatg atggtgatgc
63841 ttgttaaact tcctgtttgc gacttcaacg tccatataaa tgagtcttcc aatactgtac
63901 ttagaactta tattttgtag tgacttcttt aaaagctttc tctcttagtc atatcctgag
63961 ttttgttagc acctggactt accttacttt ggaaatgttg cactctgaaa tctctttctc
64021 agcttggaat ttcctaatct tccaactgtt tgagtctttt aattctacat ttactgcctt
64081 tccatttcat caggatttct agtctcttta attcttcctt ttgaactcct cctgatttaa
64141 cctctgctta ttcgaagaac aataatttta ttctctcagc tgcactctca attccctttt
64201 ccttttggtg atttttcttt ttcctacaga acacttactt tatcagtttt ggagaaggaa
64261 gtgctatctg ggtaacagta gtgctatctg ttgactctag tcaactgtaa gttttataca
64321 tttattgttt aaaccttata tgggtctata atccttcttg ggaaatcctt tcatttgtct
64381 ttaatttcct ttaccatttc cctaaaggct attccagatt tttatcacat tcacaaaatt
64441 cccgtctttt ctcaggatct gttcaccccc agtagatagc cttgtctccc acaatacatg
64501 gagaaaatag aggccaccgt catatttgaa tgtttccaac ttctctcttc acctttggaa
64561 ttatcttttt cttcttttgt gtctaagaga aagatgtata cttcttctta cccttgtctg
64621 aactactcta ttttgcttca tcttctcaga acaggggacc agcaattatt cttcctccag
64681 aagcttcaac atcttttgtc aactgactcc ttctcatgtt taaatatttt caagttaaac
64741 aatttctttc ctgactttcg ctcacgcaac ctcatgccca aaaccttatc actcttcttc
```

FIG. 1 (cont.) (SEQ ID NO: 1)

64801 cctttgctgt caaggctgtt ctcacttctt cactttttgt ggacttctcc ccactacaac
64861 atagattctg ctatcaccaa tctattaaaa ctgttatact cttgtggaat ttatcattta
64921 atttagcttc agtgaaccgt tctttccaga ttattttggc ctcagaccat gacttctaag
64981 tctgccgtgc ttgccactta agtgatgatg ggccagtggg tccccaccta ggcctctgtg
65041 ttagtctgtt ttcatgttgc tgataaagac atacccaaga atgggcaatt tacagaagaa
65101 aggggtttga gggactcaca gttccatgtg actggggagg cctcacaatc atggtggatg
65161 atgaaaggca tgtctcacat ggaggcagat aagagcatag aacttgtgca gggaaacttc
65221 cctttattaa accaccaggt cttgtgagac ttcttcacta tcacgagaat aggatgggca
65281 agaccctccc ccatgattca attatctccc actgggtccc tcccacaaca catgggaatt
65341 atgggagcta taattcaaga tgagatttgg gtgaggacat agccaaacca tatcagcctc
65401 cttctggctt tttatgttct ccgtgggtga cctctctcag gctcaagtga taaccaatgt
65461 gctgatgact ctcaaatgcg catctctggc ttcagtttct tccttgaact tcatacatat
65521 gtttccaaat ttcctgcgtg tacctcaagg ttcttgttca tcacttccca agcttcataa
65581 acgcactcat tttagtgtat tctctgtctc ctttgatagc atccctgaga ggcaagtccc
65641 tggtgagtta tatacaactc ctccccttgct ccaaacctga gagtaagtaa cattcctatt
65701 aacatattag gaagctgagg cttagacagt ttaagtaact caagcatggt tacacaacta
65761 gctagggcag agctaaaatg tcaggctagg cttctgtgac tccaaagccc tttctcactt
65821 agcatatcat cacttatttt ttttttaat cacatatatg attttttttt ctttaagaga
65881 tagaatcttg ctctatcacg tgggctggag tgcagtggca caatcatagc tcactgtaac
65941 cttgaacttg ggctcaagtg atcctcctgc cttagcctac tgagtagcta gggctacaga
66001 cacacaccac catgcctagc taattttatt ttattttatt ttattttttg agacagagtc
66061 tcactctgtc acccaggctg gagtgcagtg gtgcgatctt ggctcactgg aacctctgct
66121 gcccgggttc aagcgattct cctgcctcag cctcctgagt agctgggatt acaggtgcct
66181 gccactgtgc ccagctaatt tttgtatttt tagtagagac ggggtttcac catcttggcc
66241 aggcttgtct tgaactcctg acctcgtgat ccactcgcct cggcctccca aagtgctggg
66301 attacaggtg tgagccacca cgcctggcca cctacctaat ttttaatttt tttgtagaga
66361 cagggtctca ctacgttgcc caggctggtc ttgaactcct gttctcaaac aatcctcctg
66421 cctcggacac cccaagtgca gggattacag gcatgagtca ttgcagctga cctgtatata
66481 tgatttttag tatatgtaaa tatacatatt tattaaatgt aaatataaat ataaatgtgt
66541 ggagtgatat ccattgaaat gttaaacata gttctcagtg gtacaactac aggtgatttc
66601 tcttttctta tttctggttt tctgtgtttt ccaaatttct tgaaatgtgt cttctgtaat
66661 cagaaataaa agttattagt aacaacagtc ttccactggt acaagtgctt attggataaa
66721 agtcccactt ctaagcatga tactcacaac ttttaggtta atagcctttg tcaccttgcc
66781 atatacatct gatccagcca ctcacaccat tcctgagata tattttgttc ctttgtgcct
66841 aaatcattgt gcatgcagat ccatcttcct ggaacaccta taaccatttc ttagtcctgt
66901 gaaatcctac ttacatcctt catagcctag catgtatgtc atttatttgg tcaagggtga
66961 gttggttgtt ctcttgaatg tactgccata tgacgtggtg tgatttcaat tgtagcacca
67021 agctcattgc aatattaatt cgtttgtcat tctcccatgt aggatgtttg aagtagtttc
67081 taacacagag attatactca ataaatattt attagataaa taaatgaata agggaataac
67141 aaatgccttt gtctcatttt aaaatacttt cattgttagc tacccatata ataaaaaact
67201 aaaagcagta gttttcaagc atgattgttt atgtatgcct taaaagaatt ttgaaaacct
67261 atgtacccct gacacacttt taagttaact tataaatttt tcaacatagt tttaagtggt
67321 ggcaaatgat gtagtttctt gtgtatttta aactgcttaa gtatgctata catggatttc
67381 ttcaaaaccc tgaagctgca gtttcagtgc attcaattta tggaaaagaa attaatttat
67441 aaaattggtt cttattgtca agtcaatcag ctaaatataa cttgctttct gtcaggaaaa
67501 gtctgacttt aaaatacaga taagtaataa ctattattaa ttaattaaat tattaaaatt
67561 aaaataatta aataatttgt taattaaaat gccttattcc cctacttatt tctgcaattt
67621 gactctaaga atagatagga catgtagatt gccttaggtt tgaaatctgg gtgaaataag
67681 atactgcctc cttcagtatt tctgcctttg cttttatggg agcctctttc aagaaaaagt
67741 cattctctca tggtcccttt gtttgagtcc cagaggtttt cctactccag aaagtgcaac
67801 gtagtgagac tagtactata ctccccttgca tggtaagtga gaaggctgtc tgtataaaat
67861 gagggaagga ctcatgagag ggaagtaggt caggagaaat gataggttct caggcaggtt
67921 aattttagga aagagtgaat agagtccctt aaaacaaggt gcatctgctt cctcctgatc
67981 aatctttagg actgtttact ttgatttgaa gaccactatg ctaaagcttc ccacgggggc
68041 aatagtgagg caaggaattt ttaaaaggga attacttctt cgtagctact tttgtgaaat
68101 gaattcattt gaattatctg gcaatctctt catatttata ttcaacaata attacttaaa
68161 gaaatgcttt gagcttctca gaggagggtg ctaccagtgt gatggagtag aattcagatt FIG. 1 (cont.) (SEQ ID NO: 1)

```
68221 tgggtagtga ctttaaagct gtgtgacttt agtcatttaa ctgctgagtc acagtctaca
68281 gctttgaaag aggaggatta taaaatctat ctcatgttaa tgctgaagat taaataatag
68341 tgtttatgta ccccgcttat aggagaagag ggtgtgtgtg tgtgtgtgtg tgtgtgtgtg
68401 tgtatgtgta tgtatacatg tatgtattca gtctttactg aaattaaaaa atctttaact
68461 tgataatggg caaatatctt agttttagat catgtcctct agaaaccgta tgctatataa
68521 ttatgtacta taaagtaata atgtatacag tgtaatggat catgggccat gtgcttttca
68581 aactaattgt acataaaaca agcatctatt gaaaatatct gacaaactca tcttttattt
68641 ttgatgtgtg tgtgtgtgtg tgtgtgtttt tttaacaggg atttggggaa ttatttgaga
68701 aagcaaaaca aaacaataac aatagaaaaa cttctaatgg tgatgacagc ctcttcttca
68761 gtaatttctc acttcttggt actcctgtcc tgaaagatat taatttcaag atagaaagag
68821 gacagttgtt ggcggttgct ggatccactg gagcaggcaa ggtagttctt ttgttcttca
68881 ctattaagaa cttaatttgg tgtccatgtc tctttttttt tctagtttgt agtgctggaa
68941 ggtatttttg gagaaattct tacatgagca ttaggagaat gtatgggtgt agtgtcttgt
69001 ataatagaaa ttgttccact gataatttac tctagttttt tatttcctca tattattttc
69061 agtggctttt tcttccacat ctttatattt tgcaccacat tcaacactgt atcttgcaca
69121 tggcgagcat tcaataactt tattgaataa acaaatcatc cattttatcc attcttaacc
69181 agaacagaca ttttttcaga gctggtccag gaaaatcatg acttacattt tgccttagta
69241 accacataaa caaaaggtct ccatttttgt taacattaca attttcagaa tagatttaga
69301 tttgcttatg atatattata aggaaaaatt atttagtggg atagtttttt gaggaaatac
69361 ataggaatgt taatttattc agtggtcatc ctcttctcca tatcccaccc taagaacaac
69421 ttaacctggc atatttggag atacatctga aaaaatagta gattagaaag aaaaaacagc
69481 aaaaggacca aaactttatt gtcaggagaa gactttgtag tgatcttcaa gaatataacc
69541 cattgtgtag ataatggtaa aaacttgctc tcttttaact attgaggaaa taaatttaaa
69601 gacatgaaag aatcaaatta gagatgagaa agagctttct agtattagaa tgggctaaag
69661 ggcaataggt atttgcttca gaagtctata aaatggttcc ttgttcccat ttgattgtca
69721 ttttagctgt ggtactttgt agaaatgtga gaaaaagttt agtggtctct tgaagctttt
69781 caaaatactt tctagaatta taccgaataa tctaagacaa acagaaaaag aaagagagga
69841 aggaagaaag aaggaaatga ggaagaaagg aagtaggagg aaggaaggaa ggaaagaagg
69901 aaggaagtaa gagggaagca gtgctgctgc tgtaggtaaa aatgttaatg aaaatagaaa
69961 ttaagaaaga ctcctgaaag gcaattattt atcaatatct aagatgagga gaaccatatt
70021 ttgaagaatt gaatatgaga cttgggaaac aaaatgccac aaaaaatttc cactcaataa
70081 atttggtgtc aggctgggtg cagtggctca cacttgtaat cctagcactt ttggaggcag
70141 aggcaggtga attgcttgag tccaggagtt tgagaccagc gtgggcaaca tggcaaaccc
70201 cacctctaca aaaaacacaa acaaaagaaa atagctgggt gtggtggtgt gtgcctgtag
70261 tcccagctac ttgggaggct gaggtgggag gatcacctga gcctgagaag tggaggctgc
70321 agtgagccat gattgcacca ctgtacccta gcctaggtga taggctcaaa aaaaaaaaaa
70381 attggtgttt gcaatgctaa taatacaatt tggttgtttc tctctccagt tgttttccta
70441 catacgaaac agcttttaaa acaaaatagc tggaattgtg catttttttct tacaaaaaca
70501 ttttctttct taaaatgtta ttatttttct tttatatctt gtatattatt actagcagtg
70561 ttcactatta aaaaattata ctataggagg ggctgatact aaataagtta gcaatggtct
70621 aaacaaggat gtttatttat gaaaaggtag taattgtgtt tcatagaatt tttaaaatta
70681 attctgcgta tgtcttcaag atcaattcta tgatagatgt gcaaaaatag ctttggaatt
70741 acaaattcca agacttactg gcaattaaat ttcaggcagt tttattaaaa ttgatgagca
70801 gataattact ggctgacagt gcagttatag cttatgaaaa gcagctatga aggcagagtt
70861 agaggaaggc agtggtccct tgggaatatt taaacacttc tgagaaacgg agtttactaa
70921 ctcaatctag gaggctgcct tttagtagta ttaggaatgg aacactttat agtttttttt
70981 ggacaaaaga tctagctaaa atataagatt gaataattga aaatattaac attttaagtt
71041 aaatcttacc cactcaatac aatttggtaa tttgtatcag aagcttaaaa gataacctaa
71101 tagttcttct acttctataa cttacccaaa tatgtttgca gagatcttat gtaaagctct
71161 tcattataac actgctttca ggagccaaaa attgggtggg ggagccccat aaatgttgaa
71221 taataggggt ttgattagat aaattttggt gtagttctat aatggcgtgt tattcagcca
71281 ataaaaggtt tgttaaagaa tgactgtgac ggatgtatat gatatactct taagtgaata
71341 aagagttaca aaatgttatg tacaagttac aaaatgtatg tacattatga tccatttttc
71401 ataaaatcat atgtatgtat atatgtgtgt ctggaaggat aaatttatca agttgttatc
71461 tctgaaattt tgggtatatt ttatatttct agattttctg ttactttgtt actttactga
71521 taaagtaata acgttgttga cttttgtcac tctcccctat taataatcat ctaggctgca
71581 aaaggatcat gtcttcttta tttttatatt ccaaggactg tcaacaagtg cctagcactt
```

FIG. 1 (cont.) (SEQ ID NO: 1)

```
71641 gacaggtata ttatagaaat ttaactgaat atctttagga aatagatttt tgtttgtagt
71701 tgttctagtc tacattaaat gtcttgcgct tatgaaactt ccttgaatta ttttagtgaa
71761 gcaatattag tatagaattt tgcatcactg gatgcccttg actgaaagct ggcttatggc
71821 atctcaccag tgtgtgggga gtttcagtcc ttctgttgtc tgcatcacag ctgaagcagt
71881 gctgttgctg acaattcctg acaccacctt gtctctatta ttgatcattg cctcactatg
71941 gtactgagtt ttagcttatt cttgtaataa ctgggactca tatgtataga ataagctatt
72001 agctcacgtt tttgcttgct ttttatacag aatacatgtc tgcaaatagt tttatcaata
72061 ttttggaatt ttgggagata tgaagttaaa aacatcattg aatatatata tatacacaca
72121 cacatatata tatgacacta tacatgattt attttattta atttttaaaa ttttattctt
72181 tttagagatt aggtcttact ctgtcaccca ggctgaactt cagtggtgtg atcatagctc
72241 actgtaacct tgaactcctg ggctcaattg acctttccgc ttcagcctcc caaagtgctg
72301 ggtttatagg catgagccac tgtgtctggt ccaatatgca tatatatatt tttaacctgg
72361 attatcagag ctatattgtg tttaggttta taaagctgta ctatgtgaaa atatcacttc
72421 taggtttaat tttgtacaaa ggaattttat atagaaatga ggtaattcag atttttttccc
72481 atgtaataag aattgtaaaa tttactgaaa caaacatcaa aaagatatct gttacatgac
72541 cttcctttct tttgaatata tttcaggtga tattatttat taaaatttaa aaatgaaaat
72601 taaaatatat aaaaagttga aaattattcc tttctttact gtctctcatc tgtccatttt
72661 ccattctcct gcattccctc atccaaccaa ggtagccaat ccaggtaact tttttttagta
72721 tcttcccaga gatgtttctc tctatatata taatcaatat acattttttta ttattcccca
72781 cctctctttt tatgtaacaa tatgcagagt tttgcttctt gcttttccca ctatcttgga
72841 caactttcca tattcaaagc acagaggact tgcacatatg ttcagactgc tgaatatttc
72901 tgtctctccc ctgccattca tatgttgaaa tcctaattcc caaggtgatg gtattgcagg
72961 gtggggcctt tgggaggtga ttagtccatg agggtgaagt ctttagtaaa tgagattagt
73021 gtctttataa aagaaacctt agagagaccc tcacacctta gagagaccct cacccctttc
73081 tgccatgtga gaacacagca ggaagacagc tggctatcca ggattcagga gtctcttagc
73141 agacccaaat ctgctggcac cttgatcttg gacttcccag cctccagaac tgtgagaaat
73201 aaattcctgt tgtttataag ccacacagtt catggtattt tgttatagca gcctgaacaa
73261 ggacacacac acacacacac acacatgcac acacatttaa atagatgcat agtattctat
73321 catatggatg gatattctat gatataatga atcactattg attgacattt gggttgtttc
73381 caatattttg ttaacacaaa gaacaacact acaaataact ttatatacat atcatttagc
73441 acatctgcaa ttgtatcagt aggcttccta taagtggtca agcatttgtg tacttgtgat
73501 tttggtagat gttgtcaaat gtccttccct gaaatttgta ccaattcgta ctcatgccat
73561 acactctaaa tagagtgctg atttccccac agcattacta acagatgata ttatctaatt
73621 taaaaagttt ctcatcttat agggaaaata gtatgtcaat gtattcttaa cttgcatttc
73681 ttttattata agtagtgtaa aatatcattt caacttatac acaggaggaa tttctctcta
73741 tataaagtga tcctagaatc ataatgaaaa atatcaccaa ctcattagga aaatgtacaa
73801 aggattgaat agatatctca tcaaaaataa aaatataagt ggcctttaaa cattgaaagg
73861 taacatttga acaaagactt gcaggaggtg agggattagg gaatgcagac tctgggaaga
73921 gtcttccaag tagcaggtga agcaagtgca aagctttcag atgggactga ctatacctgt
73981 ctggtttgaa gaacagtaag gaggtcactg aggctggcat agagtaagac agggagggta
74041 gaatactgtc agagaagtaa tcggcggtgg aggtaggggg taaaccataa agtgctcgta
74101 aagactaagg cttatttctc tgggtgagat tagaggccac tggagagttt taaacagaag
74161 taacagggcc actttggcta atgtttttag gctattctgt agggagacaa gggaggaagc
74221 aaggagatga gttaggagtc tattgtgcca gttcaggcaa gtgatgatgg tggcttgatc
74281 caggtagtag tggaagtagt atagtaggaa gtgatcagat tcaggacatg ctttgaagga
74341 agatccaata ggattaatgg ataagttgaa caatggcata tgagaaaagt cacagaggag
74401 tcaaagatga ttccaagctt tctggactga gtaactggaa ggataaatgt gccgtttact
74461 agaaagataa tgggagaaac aggttttgga tggagcttgg tttgggaata ttaagtttga
74521 aatgcctatt tgacatccaa atagagatgt tagttggatg tacaagtcta gtttcaagga
74581 agagggggct ggtagtgtga agatggggct ggataagatt ctaaaggaaa gagggttgat
74641 aagaagagaa aggggtgtag gggttagcct aagggcattc taagtattag aggttaagga
74701 ggtgggtgaa gaaaacccaa taaaataaaa gtctgagaag acaaagctag tgaatgaatg
74761 tggtatcccg gaacccaact gatgtcaagc agaagggtgt tatcaactag gtcaaatgct
74821 cattcatcaa gtaagatgaa actgttataa ttaaccggtg tcttctgaaa tacggagata
74881 actcgtgact taatgaaagc aatagtagag aaggtcaaac ttgaccagaa tgaaattaga
74941 aagaataaga ggaaagaaaa gaccaaatac agacaaccat tgatgcctta ttcttttgat
75001 atactcctgg agtccacttg ctaatacaat tgacccttaa acaatacagg cttgaactgc
```

FIG. 1 (cont.) (SEQ ID NO: 1)

75061 atgggtccac ttatttgtga atttttttc agttaataca ttggaaaatt tttggggttt
75121 tttgacaatt tgaaaaaact cacaaactgt ctagcctaga aataccgaga aaattaagaa
75181 aaagtaagat atgccatgaa tgcataaaat atatgtagac actagcctat tttatcattt
75241 gctactataa aatatacaca atctattata aaaagttaaa atttatcaaa acttaacaca
75301 cactaacacc taccctacct ggcaccattc acagtaaaga gaaatgtaaa taaacataaa
75361 aatgtagtat taaaccataa tggcataaaa ctaattgtag tacatatggt actactgtaa
75421 taatttggaa gccacttcct gttgctatta cggtaagctc aagcattgtg gatagccatt
75481 taaaacacca cgtgatgcta atcatctccg tgtgagcagt tctctctcca gtaaattgca
75541 tattgcagta aaaagtgatc tctagtggtt ctcgcatatt tttcatcatg tttagtgcaa
75601 tgccataaac cttgaataac atcaagcaat ccatacaaag tgccactagt gatgcacgga
75661 aaagttgtaa cagtacaaga aaaaagttga gttgcttggt atttaccata tattgaggtc
75721 tgcagctaca gttgcctgca atttcgagat aaatgaaccc agtataaaga ctgttgtaac
75781 aaaagaaaag aaaatgtgaa accatcagtg cagctatgcc agcaggtgtg aagtcttgca
75841 ctttttgcaa aatacaaaat atgaaatatg tgttaattga ctgtttatgt tatctgtaag
75901 gtttccactc aacaataggc tattagtagt taagtttttg tggagtcaaa aattatacgt
75961 ggatttttga ctatacagtg ggttggcacc cctaaccttc atgttgataa agggtcaatg
76021 gtatattatt taattttttt gtatttatat tcataaataa gattaaatct atatttccaa
76081 gtaatctcta taagattttg ttattaatat tactattatt tttgagacag agtcttactg
76141 tcaccaggct ggagcacagt ggtgcgatct cggctcactg caacctctgc ctcccgggct
76201 caagcaattc tcctgcctca ccctcccaag tagctgggac tacaggcacg cacaaccaca
76261 ctcagctaat ttttgtattt ttagtagaga cggggtttca ccatgttggc caggatggta
76321 ttgatctctt gacctcatga tctgcctgcc tcggcctccc aaagtgttgg gattacaggc
76381 atgagccact gtgcacagcc attaatatta ttgttaccca ataaaaaaaa tttggaaact
76441 tgtcttcttt tcccctgatt ctgtttaaat agcactggag ttacctgttt tgaatttttt
76501 ttccaagcgg tcccttatga gttttctcta tgttttattt gtttcatttc tttttttttt
76561 tttttttttt tttttgagac ggagtctcgc tctgtcgccc aggctggagt gcagtggcgg
76621 gatctcggct cactgcaagc tccgcctccc gggttcacgc cattctcctg cctcagcctc
76681 ccaagtagct gggactacag gcgcccgcca ctacgcccgg ctaatttttt gtatttttag
76741 tagagacggg gtttcaccgt tttagccggg atggtctcga tctcctgacc tcgtgatccg
76801 cccgcctcgg cctcccaaag tgctgggatt acaggcgtga gccaccgcgc ccggcctgtt
76861 tcatttctta tatcgtattt ttgcaactcc tttattgata cttttcttcc tgattaggtt
76921 tctactaaaa ccaaacaagc tttccatgaa ttagctttta gatttactta ttagtttaac
76981 tgttctgttg tattgtaact cattaattta taattttatc tttattaatt attctatttt
77041 tcttcgcttt tttgttgttt ttctagtttt tgagttagat gtttgacgct tttttaaaaa
77101 gctgtgcatt ttcctctggg taatacttta gctgtatatt atgtattctg atatatagtg
77161 tttccattac attgttttct agaaaatctg tagctttgat ttatatttgt ttcctctttg
77221 acctaagata tcctaaggga aaatttaaca ttttccagaa agaaaacaaa ttttctttgt
77281 tttccaagaa tgttgttcaa attatttcta ctgcttggaa tttttatcat ttttgtgtat
77341 ccagtaaata gtcaatattt gtacttgctc tctgaccaca taaaagaata tattcgtgta
77401 gtttctatta atagattaga gttcaattca gatattaaat gtacatcatt attcatgata
77461 tttaggtctt ctacatcttc acttatcttt tttctacttg ctttgccatt aacagataaa
77521 gttgaattaa aggcttctac tacatacatt tctccctgtt attccttata ggttctgtaa
77581 tttttgcttc aagaatattg ctttttaaat ttaatatata gatacttata attacactct
77641 agcattataa agagcctttt ctttttcatt gaatgtattt gggcctgcat atgtctaaca
77701 tgaaaattat agtccttttt ttgtttcttt gtttgtattt acagttttaa gttccatttt
77761 caacctttat gcactctttg ctttaggtgt gtctctttta gttagcataa agttaggttt
77821 gtctttaatt tcacctgaag tcttttcctc ttaatagatg ggttaagcca actgaaaaat
77881 aaaactgact tatatacttt tatttcaagt atgtcctcca caaatatttt ttgaatagat
77941 tagcttatat actttggaat ttgttaaaaa aagattttta taaaaaataa ttgtggtgaa
78001 atgtacataa cataaaattt atcattttga ccatttttaa gggcatagct ctgtggcata
78061 aagtatactc acatagttgt gcaactatca cctccttttg attttttttt actaattttg
78121 taaatttgtt tcatctgagc tgtcttatta tgttttgttt tatgtttttc tttcctttat
78181 tatgaagtca ctgtattgtc tgtaggctat atgtatctgt gagtgtgtgt gtatatgtgt
78241 gtattatggt ttttaaaaaa gtctatattt gttttccagt ggctatactt aatactaata
78301 actttatgtt aaatttttca ttctatgtga ctctagttca ctaatatgag ctctgataaa
78361 atcagtgctt tttcgaggtt aggagatcaa gaccatcctg gctaacacag tgaaactccg
78421 tctctactaa aaatacaaaa aattagccag acgtgatggc gggtgcccgt agtcccagct FIG. 1 (cont.) (SEQ ID NO: 1)

78481 actcgggagg ctgaggcagg agaatggcgt gaacccagga ggcagaactt gcagtgagcc
78541 gagatcgcgc cactgcactc tagcctgggt gacagagtga gactctgtct ctaaataaat
78601 aaataaataa ataaataaat aaataaaatc agtgcttttt cttcctctgc tacctccttt
78661 ccttctactc agttttagtc agtagtatta tctttttca gatttatctt tgtattgtta
78721 aatctgctta tgcttctatt actttattta ttagctttaa atgatacctt ttgactttca
78781 gcttttctta ataaagcaat cagcaaattt cctttacact ccacacttat accccatttc
78841 ctttgtttgt ttatttggtt tttacttcta acttttctta ttgtcaggac atataacata
78901 tttaaacttt gtttttcaac tcgaattctg ccattagttt taatttttgt tcacagttat
78961 ataaatcttt gttcactgat agtccttttg tactatcatc tcttaaatga ctttatactc
79021 caagaaaggc tcatgggaac aatattacct gaatatgtct ctattactta atctgtacct
79081 aataatatga aggtaatcta ctttgtagga tttctgtgaa gattaaataa attaatatag
79141 ttaaagcaca tagaacagca ctcgacacag agtgagcact tggcaactgt tagctgttac
79201 taacctttcc cattcttcct ccaaacctat tccaactatc tgaatcatgt gccccttctc
79261 tgtgaacctc tatcataata cttgtcacac tgtattgtaa ttgtctcttt tactttccct
79321 tgtatctttt gtgcatagca gagtacctga aacaggaagt attttaaata ttttgaatca
79381 aatgagttaa tagaatcttt acaaataaga atatacactt ctgcttagga tgataattgg
79441 aggcaagtga atcctgagcg tgatttgata atgacctaat aatgatgggt tttatttcca
79501 gacttcactt ctaatggtga ttatgggaga actggagcct tcagagggta aaattaagca
79561 cagtggaaga atttcattct gttctcagtt ttcctggatt atgcctggca ccattaaaga
79621 aaatatcatc tttggtgttt cctatgatga atatagatac agaagcgtca tcaaagcatg
79681 ccaactagaa gaggtaagaa actatgtgaa aactttttga ttatgcatat gaacccttca
79741 cactacccaa attatatatt tggctccata ttcaatcggt tagtctacat atatttatgt
79801 ttcctctatg ggtaagctac tgtgaatgga tcaattaata aaacacatga cctatgcttt
79861 aagaagcttg caaacacatg aaataaatgc aatttatttt ttaaataatg ggttcatttg
79921 atcacaataa atgcatttta tgaaatggtg agaattttgt tcactcatta gtgagacaaa
79981 cgtcctcaat ggttatttat atggcatgca tataagtgat atgtggtatc tttttaaaag
80041 ataccacaaa atatgcatct ttaaaaatat actccaaaaa ttattaagat tattttaata
80101 attttaataa tactatagcc taatggaatg agcattgatc tgccagcaga gaattagagg
80161 ggtaaaattg tgaagatatt gtatccctgg ctttgaacaa ataccatata acttctagtg
80221 actgcaattc tttgatgcag aggcaaaatg aagatgatgt cattactcat ttcacaacaa
80281 tattggagaa tgagctaatt atctgaaaat tacatgaagt attccaagag aaaccagtat
80341 atggatcttg tgctgttcac tatgtaaatt gtgtgatggt gggttcagta gttattgctg
80401 taaatgttag ggcagggaat atgttactat gaagtttatt gacagtatac tccaaatagt
80461 gtttgtgatt caaaagcaat atctttgata gttggcattt gcaattcctt tatataatct
80521 tttatgaaaa aaattgcaga gaaagtaaaa tgtagcttaa aatacagtat ccaaaaaaat
80581 ggaaaagggc aaaccgtgga ttagatagaa atggcaattc ttataaaaag ggttgcatgc
80641 ttacatgaat ggctttccat gtatatactc agtcattcaa cagtttttt tttagagccc
80701 cattcttatt ttttatacac tttgagagca taatgaaaag aaaagctacc tgcaaaagtt
80761 ttggacttac ctcaaagagg atatacttca ttcctcaaaa ggccttcttc caggaatagt
80821 atttcataac ctggaggttg gaaaaatctg gatttgttac aaaaaaatct gagtgtttct
80881 agcggacaca gatatttgtc taggagggga ctaggttgta gcagtggtag tgccttacaa
80941 gataaatcat gggctttatt tacttacgag tggaaaagtt gcggaaggtg ccttacagac
81001 tttttttttg cgttaagtat gtgttttccc ataggaatta atttataaat ggtggtttga
81061 tttcctcaag tcaaccttta aaagtatatt tagccaaaat atagcttaaa tatattacta
81121 gtaataaatt tagtactgtg ggtctctcat tctcaaaatg agcatttact aatttctgaa
81181 cactgtgcta ggtcctggga ataccaaatt gaataagaca tagtctattt ttctgaaggg
81241 tttatagcag agtcccctgt gttaataatg aaggagtgtg tggtatgtga atcatatatc
81301 aatagggttg ttaaaaataa tgaaaaaagg agaagaggaa gaacatcttt tttttttctg
81361 attgcacggg cagccttaaa attattttg aagtgtacaa ttcagtgttt ttttagcata
81421 ttcacagggt tgtattatca tcaccatatt tttggcctct tgaaaagaaa tcctgtgcct
81481 attagcatcc aattaccgtt cctttgtagc taagtctccc ccattccagc tttaaacaat
81541 cacccatcta ctttctgtct ctataaattt gtctcttttg gacatttcac ataaatgaaa
81601 taatataata gggtttttttg tgcctaaata agcttctaaa gaagaataag gtaaggaatc
81661 atcattcagc aaatatttat taagacttgc tttattttat acagtgtact aggagctgga
81721 gatgaaaata tgtgtagaac atgaatcata tacttcggga atttgtggac tagtgggaaa
81781 gattgacata tcaataacaa atcgaattag tgatgtaata gaggcatttt tacaggagta
81841 aaatgaggta gcatggactc tatctgggtc tgaataatgt gaggagtaac ctccttacac FIG. 1 (cont.) (SEQ ID NO: 1)

81901 aaagaggcac aaggctaatg tcctctgatg gaatgattca ccatgcaatt ctaagggtga
81961 caagaatgaa agttagggcc ttgaagaaat attttgatta agagctgcca ataaagtaga
82021 gtaaagatta gattgatgtg aagaagtggg agattaatga gtaaatggtc actggcttgt
82081 tgagaagatt aaatgagatg tacatgtaat gtacctaaca caacgtcttg tacaaagtag
82141 ccattcagta gagactagct tgtattatct ccctttgagg taaagaaaac tgttagaaat
82201 agtatttcta ctactgatag tatttcttct acttatgcct ccctttgagg tgaagaatac
82261 tgttagaaaa catgacatag gagaaatacc cctgagagac agttcttatt agtgactact
82321 gtgcagaaaa gatggaggtt ggtgtaatta aggagaagga aagccatgaa gccaaagtat
82381 tatgaaaaag catcaatatg aattttcatg ttgacaaagt ggtataaaag ataattataa
82441 agatggtcac ttataaatac ggtagttctg tgtgacacaa tttacagaag ttggtatatc
82501 gtgtggaaga aaacagcata agatcctgaa ggtttgaact gtgggcacat tggctccatg
82561 ctcaggaaat ggcaatgggg ttgggaagtg attccacttt atgtcccttt cagacacata
82621 aaaattactt gtgtgagtat cttatgccag acactattca ctgtgtagtg agcatggtgg
82681 gtatgaaatg acaactttat tgtctttcct gtcaaagaac ttgtaggctg gttgggggaa
82741 agagaccatt tcaatatgaa gtgctgagct agaggtaccc ttagggcact acagaagcct
82801 agctgatggc ttttagcctg gctagacagt tcaggatctc taaaagcagg tgccttgaag
82861 gctgagtcaa atacaaaaat gtattttgga cagaggaaat tgtatgaaca gaaacacaga
82921 acatgaaact acttggttgg tgcagggtat catcagcata gaaccagaca gaaccagagt
82981 gtaaataagc cagaaggcca tgtcatggag gccttgtata ccagtctcag gaatttggtt
83041 gtggagagct ttcatcaggg gaatgatgta atcagcttgg aaatgtagat atatcactga
83101 ctgtgatagt gaggagcaga attaaggtgg acgtgattag aagctttgtg aatagcagaa
83161 agaacataga ttttgaaagc tggcagacgt aggttactga agaaagttac ttaaccttgc
83221 tatgtcttta gttttatcct ctgcaatatg gggataatac tgcctatttt gtagagtctt
83281 gtggattctt ctggcatata taatagaaaa taaaacagct attattatta ttgttgatgg
83341 tactatttgc tatatctgac tacaaggaga aagactaata ggaaaccatt tcaggaatcc
83401 agatatggtc atgatggaca ggaagagaca agagttacat agaggaattc tgggaagata
83461 agaaatgtca tttttatgta ctgtttgcat ccatcagaca aggcatcagg aaaaatgatc
83521 cttcaggaaa gagtgatttt ttttcttcaa gaaattagaa gaggggagaa attggtttaa
83581 gattaaggac tccatgcata agagaaactg ggagggaaga caggtagaaa tgctatgggg
83641 ttaggaagga agaatgcaga ggtggattac ttagaattga gacatctgat caagacagag
83701 ggatcacagc ttttgctaac aaagtactag tggaggatgc cactaggtga ggtttaataa
83761 ataattgttg acaataagtt ccatttaaaa aataaacaat ttatgcttct tctttgccta
83821 agtgtcaaat aaaacattca gatttttatt tcaaagtatc cctgagtccc tgttcccttt
83881 tttgtcctgc tgacttttgg aactgattta ggcttcctta gtcatctcat aatagaaaaa
83941 atcagccagg tatttcctac atttcttgta ttttaaaaaa atgtaatgga tgtaatgaat
84001 tttaagcaaa tgtaatgaat acaataagta acttagtata tgctgttttc ttctctatgc
84061 tgaatgtttc atacatgtta ttttctatac aactacatgg tcaattcctt gaaaatatca
84121 actccaaaat ctttattttg gtatactcca cgtagcacat tgagagagtt ttaaactctt
84181 gttggatgac tgtttcaaaa gtgttttgaa gtaggcatgt cagttgcaaa aagtttgctc
84241 agcaaatgtt gttctgtctc acagtctcag acattgagca gatgattaca tgacagcacg
84301 tgattgctgg gagtaacaga caaaagtaac tgaaagtgct cggttatctt gacagtcaaa
84361 atcaaaagtg tcccctattt tcagtgacct aagagtttct ttttgtgttt ttggtattgt
84421 tgttaaataa gtgttctcac ctttgaaaag gtcaataaga attcaataca gtataatgtc
84481 tgtgtgccaa atgaaggtgc cccttatttt taagtgtgga ggagttttga tcataagaac
84541 ttgaaatacc tacagaatcc ttgatggtta agcagctggt gccagcacaa gaatccctca
84601 atatgttctc tatgaagccc cgatcaccaa atgcaaacat tcatgattca gtatattttc
84661 atcttgactg ccaaagttga tctgtttctt aatatattac atctagactt ggaactggag
84721 atgagaacag aatattatct tcctcatttt tgtgtttttg ttcaactcta atgtctgcaa
84781 agcacttgcg tatgtaatga tgctcagtgt cataggagca ggcaggtaag tgtaaatttg
84841 tctggatagg agaaagcatg cacaacatat ttcacatagt tttctgattt cagtttgttt
84901 ttgcaaatta ttcactcagt gagatagctt aaagacgtta tcacagggaa aggcatggag
84961 atagttctgt gttgatagaa aacttgtaat gtacagccat gagtgagaag tcaggttcag
85021 attcttcacc ttcagtcctc ctctttcata aacagctcca tgtcctattt tacatatcct
85081 actttaaaac gagattatag aagaatgaat ttctaggcaa agtgacactt attttaaaat
85141 actattacgt atccctgtgc ccattaactt atcctaccat ttttcttccc ctgtgtccaa
85201 accacettta gaatctccta aatatttgta gctattgtaa acagcactgg agactttgct
85261 agtttaaaag gagaaatcaa cgcaattaag ccctagttaa tttacttatc ccttatgaga FIG. 1 (cont.) (SEQ ID NO: 1)

85321 ttataattgt attttgttat taaaaggggg acagagtaca ctgttctctt gcctttttaa
85381 tttccagact accacttctc ctgcacttga caataccgca gtctaccacg tagtcccatg
85441 gctgacagga ggagaattct aggcaggcca gtgtttgagt agtgagtaat tggactgtct
85501 ttacccagca actcactgtt ttgtaaatgt acctgagttt ggagaagtaa ttggctttta
85561 taaggggtgc ggggtggagg gttggggtgg ggagagtgag aaggaggtca gagctttagg
85621 atatataatt ggtctccaca aagttgttgt gatacttttg gaaccacgta atggtcttca
85681 ttaactaagt gtctgtcatg acagccatta catatgcatt ataataaaaa tttatttaca
85741 gtgtaagttg aagaaggtaa aatctggatg tagtttctaa actctgcttg gcagttttca
85801 tatttaagcc actagaagaa aaaaattggg agggaagctg agaagaattt actgaaagaa
85861 aaaaatactt gggagggaaa ttggcaagaa gtatgaaaaa gcttgggagg gaagtaagca
85921 aataaatgag ttaatgactg ttctggaaaa taaactctat catgcagata tcacatgact
85981 gattaaattt gaatttgacc tcctgctttc caggtctggt aaaaactaac ctgtaagaac
86041 ttgaaactta gcctttgaat ggtcaatcca ccactgtagg agaatttatg aatgttcagt
86101 tgagagaact gaaaataaag aagtaccata ggaattaaca tttgcattca gtagccaaga
86161 tataatggac atctgaaaca ggtatttgag gccaggcgtg gtgtctcatg cctgtaataa
86221 tagcactttg ggaggccgag gtgggtggat cacaggaggc caggagttca agaccagcct
86281 actaaaacac acacacacac acacacacac acacacacac acactagcca ggcgtggtgg
86341 tgcacgtttg tagtccaagc tacttgggag gctgaggcat gagaatagct tgaacccaga
86401 aggcggaggt tgctgtgagc tgagattgcg ccactgcact ctagcctggg tgacagagtg
86461 agactctgtc tcaaaaataa aataaaacat atatttgaaa cacattgaat tatgtccctt
86521 aaacaagaat aaacatcact aaatgactgt accttgaact acctgtaatt ttctcctgat
86581 aggtaattaa gcttcaaagt actgacactt atttactgta atatgaagca ataacttaaa
86641 aaaaaaaaaa aactattgaa ccagaaccaa acaggaatgc catagcattt tgtaaactaa
86701 actgctattt catttcattt gagccctgga acttgaaaat aaatgctagc taacatctgt
86761 gaacagaaca tacccatcag tactgtgcta agcacctttc atgaactggt cattaaatcc
86821 tcactttcca tttatttagt gacaacttca cccagagttt gcagtcaaag tgaaaatgtg
86881 ctgaattcca aaagtgtgag ctaggtttta gaagttaatc acaattctgg aacaaattac
86941 tagcttaaca aatgagagtt cttatgtctc taaaaccaaa atagccctaa gtctgtccct
87001 cccagtaaga tttgggccag tcaatggaac agtaatatac aaatataatt acagctgtct
87061 aggagcaaac tatcctatga atagataata aaattaagac acttaagcca tgttttcata
87121 ttaaaacaca aagtaaaaaa tcattgtttt ccaaagataa aagccatact gtatcatgac
87181 atatatatgc ccgatgtttc gaccctcttg aagaattgag attctcgact ctacactctt
87241 agcgttttct atattgaaca gatgtttaat ttaaggaggt caagagaaat cttacactta
87301 ttttttaatg gtaccttaga catagaagga acctcagaaa tctctggctg aatatttcca
87361 tctgcagatg atcatgtcat taggcttctg actctatagc catagaaaaa tattcatgaa
87421 gacctttcag gaagggaatg ttggtatttc taaaaattga gtacaagtat tctctagaca
87481 aaacagctct tgaaatggca gattgtattc ccattattat atttcagaat caagacatta
87541 atacctactt tttatttacc aggtttagtt atccttgaat tagattttat aaattaaaga
87601 aatagatttc aataaatatt tgttgagttc ctagtatgga aacatcgtgt ttggcaccag
87661 ggatgttgcc tgcaagtata acaggagttc gtatttgtaa tgagtttatg atttacagat
87721 atttgggggg caaagatatc attcggtaaa tacttatgag tgcaaacttt gaactaggga
87781 ctgggccaaa ctctaggaac atatttgatg acagagacac aatccctgtc ctcaaggagc
87841 tttcattcta gtagagaaga tgaaaaccag tacagtttgg taagttagat gatattggtt
87901 aatgtagggt tcttatgtaa gtctagagaa gtagcattta atctgttctt agaaggtcag
87961 gaaagatttc cctggaggaa gtgacattta agctgagaga ggatggataa acaggagtca
88021 tctgagtgaa caacagggag aacattccag aaagagaaca aaatgtacga ggcctgatgc
88081 caagagagaa cattcattgc attggggaac tatagtcact tctgtgtggc tgggatgtag
88141 aatgaaatga gcctggaccc aagagagcac tttgcccttt ggggaagctg taggtattac
88201 agtaaggttg gagtctggaa agaaaggggt atattgtgag atctgaattg ggagaggaca
88261 gttatatcca gacctttata tgctccagta agaagactga actttacact gggggccatg
88321 ggactcactg aatggcatta aatttgagag tggtcatatg accagatttg cattttacaa
88381 agattgtcat tgactgcaac atgaagtatg gagtattgga ggagcggtaa ggctggtggc
88441 agggagataa tttaggaggc tttaggtgag ggatgataat gacttgccag gtaggaagga
88501 gtaaatttct tctcagtgga taattagaag attgaatgga tggacttggt cactatttgg
88561 tatagaaggg gaaaaaagat gtcaaagatg atgccaattt ttaaaaataa tttaacattt
88621 atttttaaat attttttcag ccttattaag gtataatgga caacaattgt aggtatatgt
88681 catttacaac atgatgtttt gatttatgta tacattgtga aatgactgcc atagtcaagc FIG. 1 (cont.) (SEQ ID NO: 1)

```
88741 tcattaacat atccatcact cacataatta acattttgtg tgtatgcagt gagaacatca
88801 ggctctactc tcttagcaat tttcaagtat agattacatt tgttaccaac tatagtggcc
88861 acactataca atagagctcc aggacttatt catcctgcct aactaaaact ttgtactctt
88921 tgaccaacat cttcccattc gtctctcctc cccatgccaa gtttccatct tggtcagttg
88981 ggtggatagt agtactatct gccgaggcag gttggtaggg tgaaaacaat gtgttccctt
89041 ttggaaatgc tgaggtgacc agggaacttc caagggaatc tgtctggatc tagagcttag
89101 aagagatgtt tgggctggaa acagacatca ggtattcttc agtatatggg ttgtaaatga
89161 agtcacagga gtgggtgata tcaccaatgg tgagtgtagt ataagaagac tggactgagg
89221 acagatttcc aaggaatttc aatacttaag aggtacgcag agaaaagagg ggctgtgaag
89281 gacaccaagg aggagactaa gagccaggag ggaaaacttt caagagagta ttgcattatg
89341 gaagggaaga agagagaaca ttttaaatga tacgcaatgc tcaataatgg tatccgcttt
89401 ggagaggcca agtaagattc ctaagtaccc attggatcaa ggtccttaat cttacaaaaa
89461 cttatgcaaa tcaataataa agagatgata acccgataat caaaaataga caaggcatat
89521 aagaagaaaa tgaattaaaa atattcaaag cattcaacat atacaaatgc gctcaatctg
89581 atatataatg aaagaaaagt aaattaaaac aacaatgggc atgactaaat aacagtatga
89641 gggagcctga ggagaaggag catttgaaat ttcagtacag aagagaaaag gggtgactta
89701 tagaaaaagg agacagaaac catagaacat gtttggagga taagactcaa acaggtagtg
89761 gggacccttt tctagagtag gatgaaaaca ggtaatgtgt gtggatgcaa atatgaggta
89821 ggatgtaatg ggaagttgag cgaattcata tttagtcatt cattcaaaaa tacttaattg
89881 agttactgct gtgtggcaag catcattcta caaacagagg gcacagtgat aagcaagcca
89941 gtttgtactc tcgtgtaact tacattctac tttgagaaga cagattataa ataggttaaa
90001 aagtcaataa tatgatgttt cagcatcaac aataaaaaat tagggtgata tatagagtgc
90061 cagggaaagt gctttcatgg acctcttcat tctctcctct cctggtgtca taagctactc
90121 cttcatccat gctgccattt ctcttggttt acggttccag tatagtactc atcacattat
90181 tactatagag ccatccacct tatgaaggtg aaggtgtcca tctccttact taaaaaaaaa
90241 aaaaacaaac aaaaaaacaa aaaacccgaa aaacaaaaaa agaggcagaa agacagaagg
90301 tcctccacta actttcacgt gccatgtaac cagcgaaatc caattatttt acagcattct
90361 agctatagaa gagtttggga agcgtagtgc ttagtgttct agcctttgta gcacaggaaa
90421 gggcctggaa ggaaaggaat tgtgtcttcc gcagttgctt ttctttatgg ggaagtgcta
90481 tagcccaaac aatattttag gaattttcat ctattgtcaa tatgcaaact ggaaggggat
90541 aatgaaaatg ttgtggttag aagtttatga aatattgtta ttcacatttt aaagtaaaaa
90601 gagggaatgt ttaagagact tgtttaagat cacatgtctc ataattggtg ggaccagcaa
90661 tacaatccaa atctaactac ttatcttttt gctatgccct attagtgttc atattagaaa
90721 agaaattcta tctcagacac taatgatttg ttctttggac accaatgact ttaagttaaa
90781 acttcatact agttaattta attatggtgt agcagtatta ttaaactatc aagactataa
90841 attttctatt tgtaaaggag attatgatac caaagattag tgaactaatg atattgagaa
90901 ttctatgaca taattttgaa aaatatttgc aggatattta tttttgtgta aatgatgctt
90961 tcaagctacc ataatcctaa gtaagtgtat atttgggaaa accacctatt ctaacacact
91021 tgaaatttaa ataagtcagg aaatttttt ccagatcttc tcccaaatta tcttcatctt
91081 tttcctctcc ccttgggaaa gaatctcttc atgcctcata atatcaaatt taaactatgg
91141 aagtccaggt ggtggacagt cagcaaaggg gaagatgaga agcttgtgtt ataaagccag
91201 ctcttgtcag aataaggatc tggtaggaac ttcagaagtg atgggtaggt aagtatgaag
91261 gccaggtcct aagatctaaa ttacaaagca gaagacttac ttaccaggga gctggaaaac
91321 atgttaggaa atccagagca ggaacagatt tcaagatagc acaataatat agcagtgaag
91381 tactgagaaa agagtttttt tcacgggttg gatttattct agcattttag gcagcatttg
91441 ggcatttcta agtggtcaga cttagaggag atagttaagg aattagcagc tgctaaatgc
91501 caattcttag accagttgaa tcaaaatcat ctaaaaagct ttcagaaacc agacttttta
91561 agggccattt gagagactct caaatctgga atccagaaat ctatagctag atgagtttaa
91621 ggtagagcca gaataagaaa aataaaatag tttgtttgtt tcaggtatct tttccaatat
91681 tatttccgaa cctaccccaa acaccttaaa tcactgcatt ctatagccat tcttttaaaa
91741 atgcttgagt tattagtttt caaaaacaaa tacaaatctg cacacataca gaaataaaca
91801 ttaaagagac ataaagatat taaacagagt tacatatact tacaacttca tacatatata
91861 ttatatataa aactgaatat taagtgtttg atattagtga caaaatctgt aacatccatt
91921 atattagtgc tttttgtact ttttgttggg tgtagtaaaa attgcattcg aatttgagtt
91981 ttctgctata tatttggtca gttcctatca gtgaaggaaa aacctttttt tattatttta
92041 ttgttttttt attttttgag acggagtcct gctctgttgt ccaggctgga gtgcagtggc
92101 atgatcttgg ctcactccaa cctctgcctc ccgggttcaa gcgattctcc tgcctcagcc
```

FIG. 1 (cont.) (SEQ ID NO: 1)

92161 tcctgagtag ctgggactac aggcacctgc caccaggtcc agctaatttt tgtattttta
92221 gtagaaatgg ggttttgcca tgttggccaa gttggtctgg aactcctgac ctcaggtgat
92281 ctgcctggct tggcctccca aagtgctgga attacaggtg taagtcacca cgcctggccc
92341 ctttttattt tttaagctga ttgaagattc ttagttctca tgctttctag tggtgattaa
92401 tctttagcca atatttctat atacagttat tagtaatcat gtttgactta ggtcaacaaa
92461 caatctttcc taaaaaaaca gaaccccaat tttaatttct gaattattta gtatctattt
92521 tctgctgtgg aagttgaatt atgttgatag atatcataca gggccatgta acactctcag
92581 atacacgttc acatgtatag tagctgtata caaaaatgtt acttcattct ctctctcttt
92641 ataatactct tggctctctt acgttctctc acacactcta ctcttccctt cctctgttct
92701 ttctacttgt tccctctgct cctaccacac ttattccccc cttgtccatt ttccttgtgc
92761 ataaagcaca agtgcttagt aattatcaaa tattaataac aatgacacta accacccaat
92821 gatttagtgt taatgacatg ctttattgaa tggcattacc tctaaagttc atgtttcctt
92881 tacccaacca agcttcttac cctcctccct taccacaagc atctatattg tcaaggttgt
92941 tataaagagt aataagccag ccattaaaaa agggtttatg gtattttcct atctacaaag
93001 tcacaggaag ctcaaatgta ctcagtaaat attgcaaaat tacacaggac cattaaatgt
93061 aacactccac cctttctctc tctctctctc tctcttgctc tctctctctc tttctgtcaa
93121 tatagcaaca ccctatatca ttgccctttg tatgtgcaaa tcagagttaa taagctttat
93181 attagcaatt actccttaac aacttctggt ttgtttggtc cagttgaata atgtaagcac
93241 ttaaaaaaat gaaattataa acatttatgt gaaaagtgca tatatcacat tggatatgtt
93301 gttatgcact ccttaataat aaagtaagtt aatctttatt gcacacttat tataatatta
93361 ctttgaccct ctctagtact ctttatctaa gtattctcaa gtgctttaca atctcaaaca
93421 gacccaatgt gttgtataca cagaatcctt tgaagctgac atttgccttt ctgaccagct
93481 tgttgtaaag gaaatcagcc aaaaaacaag tatctagatg agtagctcaa acattagtac
93541 acatagtaat cacaggtcaa aatgcagata gattaccctg tccaaattct cctgagtaag
93601 agtaggtgaa acatttttaa ataagctccc caggtgattc tgaaattggt ccaaggacca
93661 catattaaga actaatgatc caaacaattt gactttttat tgtagattaa accatgctga
93721 gaaaattatt aaaaattgaa atggcagtgg aggatggttt gaaagaaagg tttttcaggg
93781 ccctttcaac aataaaatta attgaacaca atattaaaac tctatatttg atttaagact
93841 aaggttttca ttgtttttaa atctcagtaa tttttatgta acaggtcaat tcatacccag
93901 catcttaatt ccaatgaatg atttcccaca acaatttttg tggataactc caagggaact
93961 cgaaggaagt tgtagtatga acaaagagaa gtagaatttg tccctgtgtg taaggcttct
94021 ctgataagca gcacaggctc tcatactgct ttttaaaaaa attatgatag catcaagtgg
94081 aattaatttt ttttagatta tactttcatg gaagggaaga tctactgtga aggctggaaa
94141 accaacaccc ttaagataaa tatattacca gatttgagcg ctcttagtaa tcagcaaaga
94201 taaatgttta acagtgcata caaaatgaag tgttttatgt taaatcaaat agagaaagcc
94261 aaacactaat aatgtggtta caaatgaaca ataaattagg taatcagaac aggtacagac
94321 attaatagca ggatattggt attattaatg tattttgttt taaaataatg aacttaatta
94381 caattctcct catcctaccc cactatttta ttttattcca gattcagcag cttcatatta
94441 tgtctctgaa acacttatta ttaaagttat ccaaatgtac acatttctct ttatataaat
94501 gtttcagtcc agaaaaggag gccaaataca ttagctcaga acatcaaatc ttctcagatg
94561 tgggaatctt ttattttcac acttttaaag gtaatctgta tttctagcgt ctattataga
94621 cagaaaactt tcatatgaca acattcctat tttcttaact gccttgatag gggcgaagac
94681 aaattctaag taggactttt taccccattc ttcttaccat cattctttca caaaaccccc
94741 agctttagac aatcgctatt atgaatttga catgtactat tccaatccat tcccataaat
94801 ttacacccat atatacatat agttatctat gaacaatatt tagtagcttt tttgtgtgtg
94861 gctttaaaat ttacataaat tgtataattt gtgcacattc ttctttaatt tgccttcttg
94921 gctacggtta tctttttgag atctagctat gctgctggta tgtagaattc tatttcattc
94981 ttttttcatt gttgttttgt acccataacg tgtcacattt tatttatacc ttctgttcct
95041 gatggacatt tagattcttc caggatttta ctcaatactg caatgaaaat ctttgaattt
95101 ttctcttttg cacatattca agagactttt ctgacatata tatctatagg tgaattgtgt
95161 agtcatatga tacatacaca cattttaaat ttcactagat actgccaatt tgccctttga
95221 aatagccata caatttatag taccaccagc cacttatgaa agttcccatt tcctcaaatc
95281 tttgaaagtt cttattataa acagacatat taattcttgc cattctgatt tgtaaatcag
95341 aatctctatt gttctacctc tagttctaat ttggaattcc ccaattactt gtaagatgct
95401 atatattttc atgtttgtta gtcattctga tttcatatcc tttaccaatt atctttttgg
95461 taagttattg tggtggccat gagatgtgcc ttacagaggc cttgctagag ggaatgtgat
95521 tgaatgagag ccccagatgc tgtgtattaa aatcctgcac tgagtttgtc tcaagatttc FIG. 1 (cont.) (SEQ ID NO: 1)

95581 ttgcacgtga atgaatgagt acagctggga tactaaagca gatgtgtatt tgggagatat
95641 gagacttctt tagtggctga tttttggctc ataaatgact ttgccaaacc ttccttagac
95701 tgctcagtgt tctaacatct tccatccagc cttctaccct tctttccttt actaggggat
95761 tgaatttaca ttgaggtctc atagccttct ctgcctctct ccttatttcc ttttatacaa
95821 atatttcccc taataaatcc atgcacattt aataccattt tgctatttgc aacctgcagg
95881 tcctggacta acacagttct atacattgca ttaccattct ctagagtggg atcttttgtt
95941 gtagagagtt ttaaaatttt tatgtagtca cttttatcca tatttttctt tatggtttat
96001 atttttgtgt cttctcttta acacatcttt tctagcagaa ttcataaata tattattcta
96061 tattgccaaa agtttgaaag ttgcaatcat tagaattaat ttttgtatat tgtgtaagtt
96121 aagaatctaa ttttattgtt tttcattgga aagccatttg tcccaagata attttttagt
96181 agtccctcct tcccctattg tcattctgac atattttttc taggttccga tctatgcatg
96241 tgtttcttta tggaagagtt ggccctttgt atctttgagt ttcaaatcca tggattcaat
96301 caaccacaga tagaaaatat ttagaaaagc gtcagaattg aacatgtaca tacattttgc
96361 ttgtcattat tccctaaaca atatagtata acaactattt atgtaggatt tacattgtat
96421 taggtattgt aagtaatcta gagatgattt aaagtataca ggaagatgtg catatgttac
96481 atgcaaatac taccccattt atataagggt cttgagcatt catggatttt ggtatccaca
96541 gagagtcctg gaaccaattc cccacagatg ccaaggcaca actgtattta ttctatcatc
96601 tacttgttta atctcacatc agtatctact tttgaaataa caataacttt attatttaac
96661 tttttttatt acttaggatt agagaatttc ctctggtgag gcatcatagt gtctcaagct
96721 ggccataaag acaagtgagg gctaggatcg gtaagactgg gcagaggaag atacaacaga
96781 tctcctatgc atgaagcaaa agtgcagctc agaagccagc tctttcatta agttgtcctc
96841 tataccctca ctagattgta agctcttgaa atgagaggct ataccttaat tgtctctgtt
96901 atctaaaata cttccactca ctgcttggaa catattgcct gcaataatta agcttgccct
96961 ggctcccaaa gcatagagca aatcacactc ctccccttgc ctttgagaag ctcacagtct
97021 tcgaaggtag agatatgtga acagataaga aaatggatga caggagaaca gaaacgcatg
97081 actgtcagag aagtcattgg agactttaca gaggaaatta aatttttatt gatcttgaaa
97141 gagtttgcca gatgaagtag aggacaggca ttttagacaa agggaacagg aaatgtgaaa
97201 acacaaagtg atggaagtca tggtgagttt ggagaactat aaaacttcaa tgtggctgaa
97261 gggtaaggtg gatatagagg agtgctggga ggtgaggctg aagaaataag ctaggaaatg
97321 tctttttatg ccatttttta aagtttggac tttattctga agttcacatg gatccaatat
97381 tttttgtttt gtgttgtttt aagcagaagc gtgacatgat cagcttgaat gatgaacaac
97441 ttgaattgtt taaagtggat cacacagtct actgttttac agttattctt tgaccaagat
97501 attctttatt aactgaggaa aaaaagggct ttcctgaatt ttgcagtcat gggatatatg
97561 ataagcattc ttgatttatc atcttcaatc ctgttacata acataataac cattgttatt
97621 acctttagca atgctttcct cagtattatc taatggccta taaaatgtga ctttcatttg
97681 caaatacagt acatctaaca agaacttacc acagctgcta tgcaaaatac caatacaatt
97741 gacccttgga caatgtgggg gttaggggtg ctgattcccc atgcagttga acatgttaca
97801 taacataata cataaccatt gttattatgt aacaggattg aaaatgataa atctttggaa
97861 agtggggcaa atgaattctt atgaattcca tatcttccac atgtgtttta ctttttttgat
97921 aagaagtagt aacctagttc agaaagaaaa taatcatccc cttttactta tgcaggatac
97981 caagtctatc ttagcaccat aatagtgaat gataggaatc aagctctatg aatacattca
98041 catgtacata tatatggcta tataggacac atgcatgcac atatacatat atacacttgc
98101 atatatgtgt atatacatgt acatatatgc atgtatattc aattgtatat gtgtatatag
98161 ccaagttatt gtacagttga cctttgaaca acacgggttt gaactatgca ggtccactta
98221 cacgtatttt tttttccgt ttctgacacc cctaaggcaa caaggccaac tcctcccctt
98281 gctcttcctc ctcagctgac tcaacatgaa aactatgagg acgaagacct ttatgaagat
98341 tcacctccac ttaatgaata gtacatacat ttctttttcc ccatggtttt cttaataaca
98401 ttttcttttc tctagcttgc tttattgtaa taatatagta tataatacat ataacatacc
98461 aagtatgtgt taattgactg cttatgttat cagtaaggct tctggtcaac agtagactat
98521 tgctagttaa gtttctggta gttacaagtt atatgtgggt gttcgactgc atggggagtc
98581 agcaccccaa ccctcatgtt gtccaagggc gttgtccaag ggtcagttgt aattggtatt
98641 ttggatagca gctgtggtaa attctggtta gatgtactat atttataaat gaaactcaca
98701 ttttataggc cattaaatat tattgaggag agcatttcta agggtaaaat cttgtctaat
98761 gcttgaaaca tcttcatttt cctgtcagtt tagatctttt tgaagtaatt ctgaaaatct
98821 ctcttttaag ctaaatttaa cacaaccaaa tagccaaata tttaagttcc actaatgaag
98881 atatctaaat ttctgttaaa aatttaagat atatgttaaa cccttctaat ataactcttc
98941 tctcagtcaa actttttttt ttaacagttg ctttgcttct tctttcaaag tcatacttca FIG. 1 (cont.) (SEQ ID NO: 1)

```
99001 acaaagttgc tattgaatat gtctgactaa acatgttagc tatatgataa gatggctgga
99061 taagagataa atatagaaaa tgtagctttt tttctacttg caataaccct ttaggaatta
99121 aaatggaaaa ctaataacta tttgattcat aatagtagca aaccgtaaaa tatttagaca
99181 taaatctact aagaaattta taagacatat atggagaaaa ttcaattgaa taaaccgtta
99241 ttgaagtata taaaataaga tctggatgaa tagaaagatc ataattttta ataaaatttt
99301 gcatcttaaa aagtgaaccc tctccaaata tatgcacatt taataaaatt ataaatacat
99361 cccaatgagg ttggttttga aattttgtta attggaactt aaatttcacc taagaagaaa
99421 aaataaagaa tagttaagag tgcatgcttt gtagacaaat tgccttagtt agaatcctgg
99481 ctctatcatc tattagctat gttatctttg ggataacatt catcttttct tatagatatg
99541 cttaaaacag tgcctgacat atagtaagca caaatatcca ttagctattc ttcttattat
99601 ttatgttatt agtattgtta atatttgtta ttatatggaa gactaaatga ccaaagagag
99661 tcaagaaatt tatgaataag atttatgcgt tgttagatat tagagccatt aaaaaaaaaa
99721 aaaccaaagt gccaaaaaac ctagcacagt gttaatacag gaataaaaaa atggatcaga
99781 ggaaccaaac agaaaagcca gaaatggatc ttaggaaaca tgagaatatg atatatgata
99841 gatgctaaat gaattcagta taaaaatatt aatgtaataa atcatgcttg ctattcaagt
99901 aaaagaaaat gaggttagat tcatgtctca taccaaatat aaccataaat tataccttga
99961 ttaaattttt taattaaaaa gcaataatat ttgaaaagaa atataggata ctcaatgtat
100021 aacctgaagg ttgggtagta cttttcaaca aatataggaa tttttcactt gaaatactag
100081 aagaaaaaaa gatagcaaac aaatacagga attccaattt caagcagata taatgatttc
100141 atgaaatgtt aactgtgcac atgatagatg gtctatggat agtgcaaaag aaaaagagaa
100201 aagaaaaaat gtttttttaac atatgcagca aaaaaggttt ttaacatcta ttacatacaa
100261 ataaaaatga atgtataaca cagacttcaa taaaaatagg catttcacag gagaacaatt
100321 cagatggcca gtatttacaa tttcataggt attaaggaaa atacaaatta aaatggcaaa
100381 ttagcaaaaa ttgaggtgtg attatattaa tatctgttgg tggtggtgat tatggggaaa
100441 agggtacttt caaaacttgc taatataaat ataattcttt tggttgtttt gtaaaggaac
100501 ctgacaatat cttttaaaaa taaagaaaac gcatactttt gacctagcca tcccattcat
100561 gagggtatgt cttagaaaaa taagatcaca aaatcataga gatttatgtg caatgatatt
100621 attggtaggt catttttatg aggaggggtg tggatagtaa atgccagggt aaatcacata
100681 gcatctaata aacgtattta tgaactacaa aagcttacac tttcagtcta gtctagtcca
100741 gactgcaaat aaatgtgagc aagtgaattc aagcacagaa gtgcttgaag gcaggtttca
100801 taaatctact ttcttacagt atcctgatat tgacttatcg agacagttac tgtggggttg
100861 attattaaaa tatttatgta tctaggtatt tttcattcag tagtatgtta ttcaattagc
100921 aacaagtgtg gggatttaaa gatattcttg tttgttttta ctgctgaaac atattctagt
100981 ggaaatttcg aataaacgat tagtcatcct aaaagcaaga tacattttct cagaaaagac
101041 aaggtaaaga acttgtatat cctccctcaa ttcgtttata aggtaataag atgaataaaa
101101 atatcatagt acaatttagc attgtaaaat aaaattaatt ggtcatctct agtgtggtcg
101161 tgcttggaag gtgaaagaag ccaagatctt gtctgggaat atcatgtcta ccttgacctc
101221 acccttaaga atcctagcct ttagtttaaa atcacatggc tacatacata ccaacttcaa
101281 caatagtaca tctggcaagg tcatgcaaac ctgggacttg agcttctgat tctaagtcca
101341 gtgctttttg tgtacatcat ctcttgtaca taccttatga tgatatgcta ataaaagcta
101401 cgtgatcagg ccttaaaaat ctgctttttt tttgtaatgg tagaatgggg catattatca
101461 catcaggtaa acactctatt caaggataaa tggaaatgaa tgtcatatat agatcattga
101521 taaatatctc attacaaaat tatgagagtt accaatgttt gagtgtatat tatgggccag
101581 ccctttatat taaattactt caaattttta caactgttaa aggaagatat tattataccc
101641 atttatagaa tggacaagtt agggccagaa aagacttcct caaagctgtt agtccagtaa
101701 tggagacagg gctagaaaac aggtcatttt gctctttgac taatgttact actcatgttt
101761 tgtattttgt ttaaagtttt attttatttt gctttattta tttttgaga caagatctta
101821 ctctgtcacc caggctggag tgcaatggag tgatcacggt tcattgcagc cttgacctcc
101881 tgggctcaag cgatcctccc acctctcaat ctccagagta gctaggacta ctacaggtgt
101941 gtgccaccat acctggctaa attttgcatt ttttgtgggg acagggtttc actatgttgc
102001 ccaggctggt cttgaactcc tgggctccag cgattcacct gccttgacct cccaaagtgc
102061 cagtatcaca ggcttgagcc accatgtcca gccaagtttt attttagaat taaaaaaaat
102121 tccacttgga ttgttacatt ttatctcatt gctttatatt tatagaatta ctttataaat
102181 gccactttct taattttcat agttagcact ctttatgaaa cataaactat tatttgaccc
102241 aggtttttgt tagaggaatt gagtcagaga gctgttaagt aactgagatt tcacaataag
102301 ccagacagac cagggttcaa attctgggtc tcacattatc caattcaata ttccagcttt
102361 gttacttatt gagcaaccac tacaagcaca gtttacatga catctgatag ctctcaaaat
```

FIG. 1 (cont.) (SEQ ID NO: 1)

```
102421 gaattttaca aacataattc agatttcaac tcagcagtga ctcaggagaa aggacacttg
102481 gatgcatttc tttatggcat ttttcccagg gtacacgcaa cctggaagat ctcccaagta
102541 tgggggaagg tttcaccctg aggaatccca ttccctctaa tctgggacaa gggggaggag
102601 agtactgtct cttatcagcc atctccccag ggaggcctgg gccctcctgg aatgcatacc
102661 atggcttact gactcaaagt gttgaaaaga ccaggcattg ggacacacaa cactactctt
102721 aaaataaaaa aagaatcaga gtagcttgtg gttataattg aaatggacag agtaacatgg
102781 taccaagaaa ctattagcaa ttccttccct aaatccctca ttttcttaaa gcatttctct
102841 cttttcctca acaagcttta agttggattt gaagaatgat aagactaaaa ggagggctgt
102901 ttctggtctt tggaggaatt tgatattcca ttcgatctga gtgtgcaaag cctgagttca
102961 catgaactct tctgatctct ttctctaata ttttttcacc ttattcatat gggaaagaag
103021 gaggggaata ctttagttcc attctccctc ctcctatttc cttgacttgt ttaaaatata
103081 aatgttatag acacctaaga tagaaatttg actgaaacag cctcttaatt attgtcttaa
103141 aaaattggta taatgaaatt gcatttgtag tctttggaca tttaaatcca gaagggatat
103201 tttctttttc tttttaaaa atttaattca atagtttttg ggctacaggt ggtttttggt
103261 tacatggata agtgctttag tggtgatttc tgagattttg atatacccat cacctgagca
103321 gtgtgcactg tacccaatat gtagtctttt atcccccccc cgctccaccc ttcctttatc
103381 gtccccaaag cacattatat aattattatg cctttgcagc ctcattggtt agctcccact
103441 tgtaagtgag aacatgcgat atttggtttt ccattcctga gttacttcat ttagaataaa
103501 ttgtctctag ctccattcaa gttgctgcaa aggccattat ttcattccgt tttttggctg
103561 aatagtattc catagtgtat atatgccaca ttttctttat ccacttgttg attgataggc
103621 atttaggttg gacccatatt ttcgcaatta tgaattgtac tgctgtaaac atgagtgtgc
103681 tttttttttt tccatataat gacttctttt cctttgggta gatacccagc agtgggactg
103741 ctggatcgaa tggtagttct ccttttagtt ctttaaggaa tctccatact gttttccaca
103801 gtggttgtac tagtttacaa ccccaccagc agtgtaaaac tgttccattt tcagcacatc
103861 catgccaaca tctattattt tttgactttt taattgtggc tattcttgca ggagtaagat
103921 ggtatctcat tgtggtttta atttgcattt ccctgataat cagtgatgtt gagcattttt
103981 tcctgtgttt gttatttgtt tgtatatctt gagaattatc tattctgtcc tttgcccact
104041 ttttgatgga attatttgtt ttttttttctt gctgatttgt ttgagttcct tgtagatcct
104101 ggatactagt cctttatcgg atgcatagtt tatgaatatt ctttcccact ctgtaggttg
104161 tctgtttacc atgctaatta tttattttgc tgtgcaaaag cttttcagtt taattatttc
104221 ccatctattt atttttgttt ctgttttatt tgcttttggg atcttagtca tgaacttttt
104281 acctaaacca atgactataa gagtttttcc aatgttatct tctagaatgc ttatgttttc
104341 tggtcttaga tttaagtctt tgattcatct tgagttaatt tttgtataag gtgagcattg
104401 aggatccagt ttcattcttc tacgtgtggc ttgccagttt tcccagcacc atttattaga
104461 tagggtatcc tgtccccact ttatgttttt gtatgctttg tcaaagatca gttgacttta
104521 agtatttggc tttatttctg ggttctctat tctgttccat tgtctacttg cctatttgtg
104581 taccagtacc aggctgtttt agtaactata gccttgtagt ataatttgaa gtcgggtaat
104641 atgatgcctc cagatttgtt ctttttgctt agtattcctt tagctatgtg ggctcttttt
104701 tagttcccta tgaattttag gatttttttc tagttctgtg aagaattatg atgatatttt
104761 gatgggaatt gtattgaatt tgtagattgc ttttggcagt atggtcattt tcatagtatt
104821 gattctaccc atccatgagc atgggatgtg tttccatttg tttgtgtcac ctgtgatttc
104881 tttgagcagc atttgtagt tttccttgta gagatcttta acctccttgg ttaagtatat
104941 tttcatgtat tttagttttt tttttttgtt tgttttgttt tgttttgttt tgtttttgca
105001 gctgttgtaa aagggattga gttcttgatt tgattctcag cttggttgtt gtcagcaggg
105061 acattttcta aagtatagac tgtagttcct tatcttctat ctgtttctta ctgtcccctt
105121 cagtattctt gtccttttt cccgctatta tctttttgac cttttaatat atagatatct
105181 acttctactt ctgacaattt ttgcttctcc aattttcttt ctttttctcc tctgcacaca
105241 tttatttatt ttcttctatg tacttcttta tttttaactt aatatttgat taacttccct
105301 tccctgtctc ttttccttct ttccataaat cttcattaat tgcctgcact gagctaggat
105361 tctatactct ctaaatcaat aatctatttt ctatagtcaa ctgtgttata atcgtactgt
105421 caagataact acttattttt aatacttaaa aatattttga aattttaacc aatttaatta
105481 atacaatgtt gagttcaaat ttgaaaaaaa caatggaaaa ctgtaataat tctagcaacc
105541 tcctgctttt taataatgta ttagaaaatt tgcctctttt tcaaaagcct acagtgaatc
105601 tattcataca aggcaaaagc aaaccattct cttcattctc tttttttctc caaaagattt
105661 aagtgttttt tgtttgtttg ttttgttttg ttttttagat attgagtctt gctctgtcat
105721 ccaggctgca gtgcagtggt gtgatcatag ctcgctatag cctcgaattc ctgggttcaa
105781 gcaatcctcc tccctcaccc tcctgagtag ctggggctac aggtgcatgc taccatgccc
```

FIG. 1 (cont.) (SEQ ID NO: 1)

```
105841 agctaattta aaaggaaaaa aattgtgtag agatgggtct tgctatgttg cccaggctgg
105901 tctcaaactt ccaatctcaa gcatttctcc cacccagcat cctgaagtgc tgagattata
105961 agtgagccac tatgcccaac cagatttagt ttttaaaaag agaatacgat ttgaaaaagg
106021 aaaaatgtga ggcaggagag aagaaataca cacacgagct gttttgtaat tgctgtaaaa
106081 ctgaaatctt cagcctcact aaaggagcac ttgcatgaac acctctaaat taccttatta
106141 ccttctaaat taggtgtgaa gtctaacttc taaattatga gtgaaatcca ctgcaattct
106201 tgttatttgg atggaatcct aggtatgtgg tccagttcat gagttgaaca aaagcatgct
106261 catttaggcc aggtagaaag aaataaagac ctatgtttta catgtctcat aaccactgaa
106321 ggtccttctc ataagcagtg cttatgggta ttaacgacct ctctatattt tacttctcca
106381 gtgcctaagt agccgagtcc actgagtcct gctacatctc ctccaacatg tcagcatttt
106441 tttcacaggc cttttgttac tctagatcag aaatgttgat agcaacagtt ccttgagggc
106501 agcagctagc atgatgccag ccaacaggaa ccaccaaatg gttcttaata taaattacta
106561 cttattaatc tatttacttt gtgcatttgg agttttgcat gtaaagtcct atttatgtcc
106621 atatggtaga taaatggaac aaatgaataa cagaagtaac cattttgata ctttagatat
106681 agataatatt ggattatttc tggattgtga aagaagaagg aagaagcata tggaagagaa
106741 gttttagtag aggggaggaa ggaggaggtg gaaacgaatg tacaaggatg ggaggagaaa
106801 agggagagag actttttttt ttttaaggcg agagtttact acctatctaa ctcttcgcat
106861 tcttgaagtc tcagaccaaa tcccatcggt ttgaaagcct ctagggtatt ctatctattg
106921 tatacttctg ttatgtacaa aattaatttg ccaattaatt gtgaactgtt ttataaacta
106981 tcttaaaatg gttagttaaa tctttgggat agtatttagc tttctccagg attatgactt
107041 accttctaaa ttagacatac aatgcctagg agtcaaggac tattttgcat aaattccagt
107101 cttcttttac aatgcctaga atgattgtta ccacagaaat attcattacc tgggagaaag
107161 gatgacagga ggggcagaat gaatggagag aggtcgtgag aatgaggtgc tgaggatgga
107221 cgaggaagaa agctgtttta gttgggagga taggtgacag aagcatggaa aggaattgcc
107281 ttggacccat ggaagcccag tgaagatact tagatcctgc aggggtgtga ataatgttct
107341 tttagtttct cttcttagga ggtttgttca ttttgggaga tttcttttga aaagagtgaa
107401 cttaaattgg agaaaagtac attttagtat gttgataaca tttgaatttg taaaatggac
107461 ctatggatga tctacacata tttatatacc cataaatata cacatatttt aatttttggt
107521 attttataat tattatttaa tgatcattca tgacatttta aaaattacag aaaaatttac
107581 atctaaaatt tcagcaatgt tgtttttgac caactaaata aattgcattt gaaataatgg
107641 agatgcaatg ttcaaaattt caactgtggt taaagcaata gtgtgatata tgattacatt
107701 agaaggaaga tgtgcctttc aaattcagat tgagcatact aaaagtgact ctctaatttt
107761 ctatttttgg taataggaca tctccaagtt tgcagagaaa gacaatatag ttcttggaga
107821 aggtggaatc acactgagtg gaggtcaacg agcaagaatt tctttagcaa ggtgaataac
107881 taattattgg tctagcaagc atttgctgta aatgtcattc atgtaaaaaa attacagaca
107941 tttctctatt gctttatatt ctgtttctgg aattgaaaaa atcctggggt tttatggcta
108001 gtgggttaag aatcacattt aagaactata aataatggta tagtatccag atttggtaga
108061 gattatggtt actcagaatc tgtgcccgta tcttggtgtc agtgtatttg tttgcctcat
108121 agtatagttt actacaaatg gaaaactcta ggattctgca taatactgga cagagaagat
108181 gtaaatatct gttagttcca tcatagaccc tgccactcca atgtacacac cagctttagg
108241 cttcttggta tagataaaca tacattttca aaatttttca tcataatttt cataacaaaa
108301 taggaaggca aatgatgtca cttggcttaa aatctataat atttaaaata aacaggacaa
108361 atgcattaac attgttgggg gaggaggtcc cttagtagaa acactcttgg tccaagcatt
108421 ttaaagctgt caaagagatg taaatataga taatgtatgt caaggagaga gctttgtggt
108481 taaactgtaa ctttcagttt aaacaattat tggtgactct gatgtcaaat gtttctcaag
108541 ctttatctga acaaaattct tctcactttg ttgccaaagt cgttaacaag aaatcacatt
108601 gactcattga tgttttggct cctttccctt actttctgtt gctttccaaa agctgagaca
108661 ggaaactaac cctaactgag cacctgcaat tgcctggtag tattctagtc atgtgtgtac
108721 ttttgtgtgt atgtaatccc cttacagctc tgcaaagtaa gaattgttct ccctgcttta
108781 cagaagagat cataagataa ttgaggctgt tagatgttaa cttgccaaaa gccatacagg
108841 aaaatggtag agtcacagtt tgaaccaggt ccttttgatt ctttacatta aaccatgctt
108901 tgatcttgga aatacactgt aaggcaataa atcaatagat acggataatt cacaggcttc
108961 taaataaatg gaagttgatt gtttttatct gtgagccaaa gtaagactta ttctaagaat
109021 tccacaaatt tagataagat agagtatatg gcttctagac atccaacata gaactgagtt
109081 tgtgttatca gtttaagatt tggttttgct gtaaggtgca cacactttga ggaactaaaa
109141 ataattgtct gttcttattc tgatcagaat gtgtaatgtg ttgtccagtt ttggatgatg
109201 aatttcttat ttctaatctc ataagaaact tgtcatagat gtgagggaga gaattaagaa
```

FIG. 1 (cont.) (SEQ ID NO: 1)

```
109261 cagagtgtgg ggaagaaact gtgtacattt tgatgggatc cattatgtag ctcttgcata
109321 ctgtcttcaa aaataagtta cactataaag gttgttttag acttttaaag ttttgccatt
109381 ggtttttaaa aaaattttta aattggcttt aaaaatttct taattgtgtg ctgaatacaa
109441 ttttctttat tacagaagta ccaacaatta catgtataaa cagagaatcc tatgtacttg
109501 agatataagt aaggttacta tcaatcacac ctgaaaaatt taaatgttat gaagaaatta
109561 tctcatttct attaatatgg gaactgtgtc ttcatcttta ttactgttct aaggtcaact
109621 caatgtagat tttacttgct tatggtttca tattttagct aaatagtaaa ataatatgga
109681 tatacatttt gttgtgactt actcatactt tccttatttg gaacttttat gaatatgata
109741 tagagactga aactacaagg aacaaaatgc aatatcaatt atacagttgt ggcagcactg
109801 ctatcaattt gttgatagtg gttaacactt agaaaaacat tttaaaaata atttcacata
109861 agtaatgtaa tttattagct gtctctgaca ttttacagtt tggaatagtt tattttcttt
109921 ttggtgtcct caccaaaacc caacatcttc aagggcagga actgtataat ttttgccatt
109981 gtattttgag cacatagcat ggtacttgcc tctaaataga tactattgtt aaaatatttt
110041 ttaaggtaat attttaaagt gtatgctatg gtacagttca gtttgtgact tttgctagtt
110101 tatgccactt acagttagca aaatcacttc agcagttctt ggaatgttgt gaaaagtgat
110161 aaaaatcttc tgcaacttat tcctttattc ctcatttaaa ataatctacc atagtaaaaa
110221 catgtataaa agtgctactt ctgcaccact tttgagaata gtgttatttc agtgaatcga
110281 tgtggtgacc atattgtaat gcatgtagtg aactgtttaa ggcaaatcat ctacactaga
110341 tgaccaggaa atagagagga aatgtaattt aatttccatt ttctttttag agcagtatac
110401 aaagatgctg atttgtattt attagactct ccttttggat acctagatgt tttaacagaa
110461 aaagaaatat ttgaaaggta tgttctttga ataccttact tataatgctc atgctaaaat
110521 aaaagaaaga cagactgtcc catcatagat tgcattttac ctcttgagaa atatgttcac
110581 cattgttggt atggcagaat gtagcatggt attaactcaa atctgatctg ccctactggg
110641 ccaggattca agattacttc cattaaaacc ttttctcacc gcctcatgct aaaccagttt
110701 ctctcattgc tatactgtta tagcaattgc tatctatgta gtttttgcag tatcattgcc
110761 ttgtgatata tattacttta attattatta tacttaacat ttttatttac tttttgtgtt
110821 agtattttat tctgtcttct ccttagatag taaccttctt aagaaaatat atatgctaag
110881 tgttttactg gtttaatatg cttagactac tcatctacct caatacttcc ttggagatct
110941 cctcctcagt cacacagagc tcaggactta tatttccttg gaactcctgt tagggtccaa
111001 tgtacatgaa attccctaga cagacagaca gtcagttata tggcttgatt tcaaagtttc
111061 aaaatgattt aatggactat caagtagttt attaggagaa cagttattat actcttctaa
111121 aaataaagac tttaagcaat aaagatgtat atgtatataa aatggctggg ttattcctag
111181 aagtaccttt cttagaattt agttaaattt aatatccaag atactatctt ttcaaccctg
111241 agattgtgaa aagtaacttc tatcaatata aactttacta catttgtatt gtgttagtgt
111301 gttacagtat aatctagaac aatgtgtctt tctatatgat atatgacatt ttaatgccta
111361 aaaaaactga tatgtcttag atgattctag tcaggattta cttctagaat agattaaaat
111421 tctatttgag gagagtcaaa ttaattatcg aattctcagt tgttattatt gctgttttat
111481 ttttagtgaa acagattagt cttaatgtaa acacttgaga aataaattga tggtcaacct
111541 aaaatgtaaa aaagaaatta atagaaaatt taaagagcaa caaagctctg acatttaaaa
111601 gaaatgaagt acaaatctct agggacctta aagatcatct aataatttcc tcattttcta
111661 gataaataaa ctgagagacc ccgaggataa atgatttgct caaagtcaaa tatctactta
111721 atataggaaa tttaatttca ttctcagtct gttaacatgc aacttttcaa tatagcatgt
111781 tatttcatgc tatcagaatt cacaaggtac caatttaatt actacagagt acttatagaa
111841 tcatttaaaa tataataaaa ttgtatgata gagattatat gcaataaaac attaacaaaa
111901 tgctaaaata cgagacatat tgcaataaag tatttataaa attgatattt atatgttttt
111961 atatcttaaa gctgtgtctg taaactgatg gctaacaaaa ctaggatttt ggtcacttct
112021 aaaatggaac atttaaagaa agctgacaaa atattaattt tgcatgaagg tagcagctat
112081 ttttatggga cattttcaga actccaaaat ctacagccag actttagctc aaaactcatg
112141 ggatgtgatt ctttcgacca atttagtgca gaaagaagaa attcaatcct aactgagacc
112201 ttacaccgtt tctcattaga aggagatgct cctgtctcct ggacagaaac aaaaaaacaa
112261 tcttttaaac agactggaga gtttggggaa aaaaggaaga attctattct caatccaatc
112321 aactctatac gaaaattttc cattgtgcaa aagactccct tacaaatgaa tggcatcgaa
112381 gaggattctg atgagccttt agagagaagg ctgtccttag taccagattc tgagcaggga
112441 gaggcgatac tgcctcgcat cagcgtgatc agcactggcc ccacgcttca ggcacgaagg
112501 aggcagtctg tcctgaacct gatgacacac tcagttaacc aaggtcagaa cattcaccga
112561 aagacaacag catccacacg aaaagtgtca ctggcccctc aggcaaactt gactgaactg
112621 gatatatatt caagaaggtt atctcaagaa actggcttgg aaataagtga agaaattaac
```

FIG. 1 (cont.) (SEQ ID NO: 1)

112681 gaagaagact taaaggtagg tatacatcgc ttgggggtat ttcaccccac agaatgcaat
112741 tgagtagaat gcaatatgta gcatgtaaca aaatttacta aaatcatagg attaggataa
112801 ggtgtatctt aaaactcaga aagtatgaag ttcattaatt atacaagcaa cgttaaaatg
112861 taaaataaca aatgatttct ttttgcaatg gacatatctc ttcccataaa atgggaaagg
112921 atttagtttt tggtcctcta ctaagccagt gataactgtg actataagtt agaaagcatt
112981 tgctttatta ccatcttgaa ccctctgtgg gaagaggtgc agtataaata actgtataaa
113041 taaatagtag ctttcattat ttatagctcg caaaataatc tgtatggaag tagcatatat
113101 aaggtatata aacatttagc ctcttgatag gactaactca cattctggtt tgtatatcag
113161 tcttgcctga atttagctag tgtgggcttt tttttatctt gtgagtttgc tttatacatt
113221 gggtttctga aaagatttct tttagagaat gtatataagc ttaacatgta ctagtgccaa
113281 tcttcagaca gaaattttgt tctattaggt tttaagaata aaagcatttt atttttaaaa
113341 caggaaataa tataaaaagg agagtttttg ttgttttagt agaaaactta atgccttgga
113401 tgaaatgagc catgggcagg gttgtaatga attgatatgt ttaatagtat agatcatttg
113461 tgaataatat gacctttgac aagacacaag ccattaacat ctgtaggcag aagtttcctt
113521 ctttgtaaaa tgagggaata aaatagatcc ctaaagtgtg taattttagt atttctaaac
113581 tttatgaagg tttcctaaat gataattcat ctatatagtg tttttttgtg tgtttgtttg
113641 tttgtttgtt tgagatggag tctcgctctg tcacctaggc tggagtgcaa tggtgcaacc
113701 tcggctcact gcaacctctg cctcctgggt tcaagctaat ctcctgcctc agcctcctga
113761 gtagctgaga ttacaggcat gcaccaccat gccgagctaa tttttgtatt tttagtagag
113821 aaggggtttc atcatgttga ccaggctggt cttgaactcc tgaccttgtg atccacccac
113881 ctcagcctcc caaagtgctg gtattacagg cgtgtgccac cacgtccagc ctgagccact
113941 gcgcccagcc catctatata gtttaatatc aatctaaatg aatttctcag tcctgagcct
114001 aaaaatttag ttgtaaagaa tgatatcctt gactaataat agtttctatt aatggattgc
114061 atctagtgct aggtggcata tatttagtcc ccacaactac cctggaaggt atttaaaatt
114121 tttcacattt gcagataagg aaactaaagt tcagagttcg gcaacatgct tgaattcaag
114181 cagctcctag gatgttaatg gtggaggttg ggttcaaatc cagatctgtc tgactcaaaa
114241 aatgcatact cctaaccagt gcactatatc ccaattccat aggagccctt ctttgtgatt
114301 catagcactt tcccatgagt tttgttgatt ttgtgagaaa caaaactctt tttcctttgg
114361 actgtctgga atctctcttt ttcaaatttt tgaaatgtat ttctatgcca aaagacaaag
114421 atttctagag gaatatgcct aggatgagaa ttatgtaatt taaatcacag ctggaaagag
114481 agaaagtcct aagttactaa gaaatgttca aacacaaatg agctttcagt ctattggaag
114541 acctttatag ctagaagtat actgaactgt acttgtccat ggacccctga agaaacaggt
114601 taaatcaaag agagttctgg gaaacttcat ttagatggta tcattcattt gataaaaggt
114661 atgccactgt taagccttta atggtaaaat tgtccaataa taatacagtt atataatcag
114721 tgatacattt ttagaatttt gaaaaattac gatgtttctc atttttaata aagctgtgtt
114781 gctccagtag acattattct ggctatagaa tgacatcata catggcattt ataatgattt
114841 atatttgtta aaatacactt agattcaagt aatactattc ttttattttc atatattaaa
114901 aataaaacca caatggtggc atgaaactgt actgtcttat tgtaatagcc ataattcttt
114961 tattcaggag tgcttttttg atgatatgga gagcatacca gcagtgacta catggaacac
115021 ataccttcga tatattactg tccacaagag cttaattttt gtgctaattt ggtgcttagt
115081 aatttttctg gcagaggtaa gaatgttcta ttgtaaagta ttactggatt taaagttaaa
115141 ttaagatagt ttggggatgt atacatatat atgcacacac ataaatatgt atatatacac
115201 atgtatacat gtataagtat gcatatatac acacatatat cactatatgt atatatgtat
115261 atattacata tatttgtgat tttacagtat ataatggtat agattcatat agttcttagc
115321 ttctgaaaaa tcaacaagta gaaccactac tgatatttta ttatttcata ttacatataa
115381 aatatattta aatacaaata taagaagagt ttttaataga tttttaataa taaaggttaa
115441 gagattcgaa agctcaaagt agaaggcttt tatttggatt gaaattaaac aattagaatc
115501 actgttgata ttttattatt tcatattaca tataaaatat atttaaatat aaagataaga
115561 gtttttaata gattttataa taaatgttaa gagattaaaa aactgaaaat agaaggcttt
115621 tatttggatt gaaattaaag gccaggcatg gtggttcatg cctgtaatcc cagaatttta
115681 ggagactgag tggggaggat tgcttgagcc caggggtcaa gaccagcctg ggcaacacag
115741 tgagacaccg tatctacaaa ataattaaaa aattagctgg gcatggtggt gtgtgcctgt
115801 atgctaccat taactaagga ggctgaggtg ggagaatcgc ttgagcctgg gaggtcaagg
115861 ctgccctgaa ctgtgattgt gccattgcat tccagcctgg gtgccagaga gagaccctat
115921 ctctaaataa ataaataagt aaataaataa acagcaacaa caaaaacact caaagcaaat
115981 ctgtactaaa ttttgaattc attctgagag gtgacagcat gctggcagtc ctggcagccc
116041 tcgctcactc tcagggcctc cttgaccttg acgcccactc tggctgtgcg tgaggagccc FIG. 1 (cont.) (SEQ ID NO: 1)

116101 ttcagccctc ccctgcactg tgggagcccc tttctgggct ggccaaggcc agagccggct
116161 ccctcagctt gcggggaggt gtggagggag aggcgctggg ggaactgggg ctgcgggtgc
116221 cttgtgggcc agcgcgagtt ctgggtgggt gtgggctggg caggccccgc actcggagca
116281 gccggccggc cccgcgagcc ccaggcagtg aggggcttag cacctgggcc agcagctgct
116341 gtactcgatt tctcactggg ccttagctgc ctccctgcgg ggcagggctc gggacctgca
116401 gcctgccatg cctgagcctc cccccaacct gccgctgcag tgggctcctg cgtggcccaa
116461 gcctcctgac gagcaccgcc ccctgctcca cggcacccag tcccatagac cgcccaaggg
116521 ctgaggagtg tgggtgcagg gcgcagggct ggcaggcagc tccacctgca gccccagtgc
116581 gggatccact gggtgaagcc agctgggctt ctgagtctgg tggggacttg gaggatcttt
116641 atgtctagct aagggattgt aaatacacca atcagcactc tgtatctagc tcaaggtttg
116701 taaacacacc aatcagcacc ctgtgtctag ctcagggttt gtgaatgcac caatcagcac
116761 tctgtatcta gttaatctgg tggagacttg gagaaccttt atgtctagct aagggattgt
116821 aaatatacca atgtgcactc tgtatctagc tcaaggtttg taaatacacc aatcagcact
116881 ctctgtctag ctcagggttt gtaaatacac caatggacac tttgtatcta gctaatctag
116941 tgaggaggtg gagaactttt gtgtctagct cagggattgt aaacgcacca atcagcaccc
117001 tgtcaaaacg gaccaatcag ctctctgtaa aaccaatctg ctgtctgtaa aatggaccaa
117061 tcagcaggat gtgggtgggg ccagataaga gaataaaagc aggctgcctg agccagaagt
117121 ggcaacctgc tggggtctgt agaagctttg ttcttttgtt ctttgcaata aattttgcta
117181 ctgctcactt tttgggtccg cattgcgttt atgagctgtg acactcactg ggaaggtctg
117241 cagcttcact cctgaagcca gcgagatcac gaacccacca gaagaaagaa actcctaaca
117301 catccgaaca tcagaaggaa caaactcagg acacgcggcc tttaagaact ataacactca
117361 ctgcaagggt ccttggcttc attctcgaag tcagtgagac caagaaccca ccaattccgg
117421 acacaatttg actgcagaaa atggatgtcc aaccctgtgg tttccctggg ccacattgga
117481 agaagaaagg agttgtcttg ggccacacat aaaatacact tactatagca gatgagctaa
117541 agaaaagaaa aaagtccatg cgtaatcttt gtgatatgtg ccaccaccaa taagcaaaat
117601 tgttctctta ttcaaaaggt tggacacagc tgctctagat attttattat taaatatgca
117661 ggcaattact gtttaaatga agatttcctc acagaatgag attaaaagta tatattagtg
117721 gcttagcatt cattttagac aaccatttta gagattcaaa tcacacactt gcttacagaa
117781 attttgttgt cttcaatgtc cccattgtgg tttctttacc aagcctctac tgttcttcac
117841 atcaccaagt taaaaaaaaa aaaggggcgg gggggcagaa tgaaaattgc atggtaggcc
117901 acaagttcag atcctcatcg acacaagagg tgcctgaagc agtggatgag gcttttctat
117961 ggatcatgag cagccacata aatgcttaaa agggcctggc agggagcatc agtgggtgat
118021 gtggctggga ggctgaatgg agagcatttg ttcttcagtt atctatagaa ggcagctgtc
118081 actcagcacc agctaagggc ttcccatgag ggaactgggg atcaggtttc ccagatcttt
118141 ttatgtaaca ggataagaca gagatccagc tttttttggg taattatttc ctattttaaa
118201 atacgggtag ttgattaaat aaaaacaaac gaatgaacac catatgggca caacaaaaca
118261 catctgtggc ttggattcag cttgtgaatg attactgcag atatttattc tagaggacac
118321 ccctgggtat gtcctaatat aaaacctaaa tctaaactca agtcccatgc taccttcaga
118381 gaataaatga cccagaaaaa gaaccacctc tcctaaggaa gtataaattt gtaaataact
118441 gagacccaaa cttacaactg tacatttttc ttattgttgg gctgttgcta acctcaatta
118501 agaaggcttg atgatatttg taaagtgtca tcactccacc atggtccagt aacatctgat
118561 cactccacca tggtccagta acatctgaat ggtcaagaaa tatctaaacg tatgtaccaa
118621 aaatttgtgt atactactgt accaataaac catttgtttc catttgatct ctgagtgtgg
118681 taatacatgt tatttgccct gctgttgtaa ataaacaaac caaatggagg cttgatgcaa
118741 gatgcagtgt agcatagtgc caactctgga ctccgactac tcagggtgta aattctaact
118801 ctgttctatt aacaccatga aactgagcaa gttagttaaa actcgctggg cccattttct
118861 catttataca atggagattt taatagtaca gctacatagg ccattttgtg gtttaaaata
118921 catcatgatt atgaaacact taatgtaggg cttgctacat aatgagcaag gtttgttgct
118981 gttatcatta atatccttaa ttctcattat tataaaactt gagatagtat gaggtgaaca
119041 agttcataac agcaatataa tgaaaatttt aataattcct tttatacttt aacaaaaata
119101 cgagattggg taatttatta tttttacatg agtaataaat attgcattaa aatatattta
119161 aaatttacca cattaatgtc tgccagtcat gccaaatgac caacatgaat gtgaataaaa
119221 ctcagtctgt gcccatttaa tcttaaccaa ccctttataa ttgttaatga tttgaacctc
119281 tgccttgaaa gatcacatta cttgattgtc ttcaacttat ctgaatgtgg tagtgatttc
119341 tgtaaattta taggaccttt gtctcatgca gctccatgga gttgaactta tgcaccttta
119401 aaatggtata tacttaatta attaagtgtt gatctgcttc acatgtgtat aatattatta
119461 gctcactaaa ccaagaaaac agtggtcctt tagggaaaga aactaaatta caacagagaa FIG. 1 (cont.) (SEQ ID NO: 1)

119521 tataaatacc atataaatat ctattattta ttgaactgtc acaattattg caaaaaatta
119581 ccttttagtg gacaaaacaa ttgatattgc ccttttctgg aaaagaaata atgtaatata
119641 tgatgaatag ttttggccag tatcctctag accttgccag ttaactggct ctcaaaattt
119701 tgaataataa aaacttggtg atagtagaaa aatagtaatt ttttaaaagt atgtgcacaa
119761 ttatacaact aaacaattca ttcaccagtg ttcacaattc tattgccttc tttgaatcaa
119821 aatttacata gtttttcttt tagactaagc tcctttatga taccagtgtg cccatttctc
119881 attaccattg aaatgtctca tgagcatgtc acattctggt acaactgcta atccaggatg
119941 acagtttagt tcttttaaat ccaattgaga gccttctact catgaccaga gaacctaaag
120001 aaaggttaag atacatttat tccttggtgt aagtgatttg tctattttta gttttcctaa
120061 gggtcatatt tcaatttaga tttttttta taggttaggt aaaataggct tcccttttgc
120121 aatatgaaat atgtagtctt ttaaaaaatt tcttcaaagc tattaaactg aaaaaaaatt
120181 aatttggtct attcagtttg ttagcactta ccattttgga aagagagtga ctctactttt
120241 gtatttggta acattttccc tactacaggg cagtatcttt tgtaagttct tagatattag
120301 caccaaataa ataggcaaaa aaaatctatt atgttaattc ttagaacccc tgcttggcag
120361 tgcatcattg actagatgga gaagaaatga aaataataca ttaggaagca gtttcctggt
120421 tcttttgaaa acaactagag agtcttgttg ttgactggaa tatctgaaga tcctgtttaa
120481 tgctttcatt ctatgattgt taagaatatg tcatagaact gctgtatcct gtttctttat
120541 gtcttccctt ctgtttgttg attagaaatc cctgagtggc tttacattat tagtacagta
120601 gatatgtagt atattcccat aataccactg ctgctattga ctaatagtaa taattttagg
120661 gcagctttat gacagttggt ttatgtttta gggtgtcatt tgacttgtga agcattgaaa
120721 tctgggtatt aagcacactg ttttctatgt ggtatggaat gattcttaaa gccctgagaa
120781 aatggaaaat aaaaatattt ttcctttttta ccataatcac ctatgactgt cactctatca
120841 taaactgcat aaactttata acctcaaaac attttggaaa tgaaatgaca gaacttgctt
120901 actcaattgc ttctatatac accaaatatt tttttaaagt attatgttaa gtccttgaaa
120961 atattttgtt ctactcaata gaagcagttt aggttggtag ttctatgtgg aaaccgtgag
121021 gaaataattt tatattatga tgactagacc agtctttgaa catcactttg gttattgttc
121081 cattagtaaa tattataatt atttctgaga tttactcacc ttcaaagaat gttggcaatg
121141 ccagcattat taacactcct ctagttagaa caaagaggaa atgtaataac aaaacataat
121201 aatagccaaa taaagagtga cttagaatgt acacccttat ctaggatcct gagtaattcg
121261 attattctta ggaaatacac ttttgtgcta gaacaaagac ttttgaaata gctaatttct
121321 gggtttcttt tcattttgaa ttaacttgaa tttcaaggaa acaagggtag tttttacaga
121381 tacagtgcat agaagctctg tgtacaatga agaaaagtag gaaagtgaga aaaatgccat
121441 tagatttttc atcgttatac tatctgatat gtgaatttaa ctaaaactta tatacctcat
121501 tatagtactt cctaatgtaa tttcttaatt taagtgttcc ccataaggtt tttttttata
121561 taaacttaag tactgttaaa tatttaaggc aaattcaggt ataaaataag acttgttgat
121621 atcttattcc aagcatattt gtttctctcc tatttatttt tattctgtgt tcatttccaa
121681 aattgtttta ctcacaactg tttgtttttt ctgtttcatt ctgtggtaaa ggtatcattt
121741 ggctaattgt ataatttcag tgtcatttct aatattccaa ttgtgatagt atcaacacaa
121801 gattaaattt ctctacatgg tttatgagaa tggaatgcca aattgaaata gaacagagca
121861 cagatgatct aaatataaaa agaactacaa aaatcacagt tgtttaaaaa ggttttttgt
121921 ttgtttatat atggtgcaga acatttgttc cttagccaaa tgtttccacc ttgagaaagc
121981 tatagagatt ctatgtagtc ctagtaccaa taatatgttt taacctgaat gtaccttatc
122041 tttattcata aactgtgact ttttacactg ctgaaacttt ttttttaag acaatctcac
122101 tctgtcgtcc agtctggagt gcagcagtgg tgtgatcttg gctcactgca acctctacct
122161 tctgtgttca agcaattctg gtgcctcggc cacctgagta gttgggatca caggtgtaca
122221 ccaccaggcc tggctaatag tttttgatat ttctagtaga gatgagtttt gccacattgg
122281 ccaggctggc ctgaaactcc tggcctcaag tgatctgcct gccttggcct cccaaagtgt
122341 tggtattaca agtgtgagcc actgtgcctg gcctgaaact cataattcat ttccattaat
122401 attaatctca ccttttccaa taattaattg atttcacaag tattagtccc ctataatcat
122461 tgaatggcta ataaaattat ttatagcaaa cagattaatt atctgccagc agtctgagat
122521 tagtttcttt aaaaaatgtt tattatttaa aacattcagc tgtgatcttg gctttcttgt
122581 gaggttcaat agtttctatt gagtaaagga gagaaatggc agagaattta cttcagtgaa
122641 atttgaattc cattaactta atgtggtctc atcacaaata atagtactta gaacacctag
122701 tacagctgct ggacccagga acacaaagca aaggaagatg aaattgtgtg taccttgata
122761 ttggtacaca catcaaatgg tgtgatgtga atttagatgt gggcatggga ggaataggtg
122821 aagatgttag aaaaaaaatc aactgtgtct tgttccattc caggtggctg cttctttggt
122881 tgtgctgtgg ctccttggaa agtgagtatt ccatgtccta ttgtgtagat tgtgttttat FIG. 1 (cont.) (SEQ ID NO: 1)

```
122941 ttctgttgat taaatattgt aatccactat gtttgtatgt attgtaatcc actttgtttc
123001 atttctccca agcattatgg tagtggaaag ataaggtttt ttgtttaaat gatgaccatt
123061 agttgggtga ggtgacacat tcctgtagtc ctagctcctc cacaggctga cgcaggagga
123121 tcacttgagc ccaggagttc agggctgtag tgttgtatca ttgtgagtag ccaccgcact
123181 ccagcctgga caatatagtg agatcctata tctaaaataa aataaaataa aatgaataaa
123241 ttgtgagcat gtgcagctcc tgcagtttct aaagaatata gttctgttca gtttctgtga
123301 aacacaataa aaatatttga aataacatta catatttagg gttttcttca aattttttaa
123361 tttaataaag aacaactcaa tctctatcaa tagtgagaaa acatatctat tttcttgcaa
123421 taatagtatg attttgaggt taagggtgca tgctcttcta atgcaaaata ttgtatttat
123481 ttagactcaa gtttagttcc atttacatgt attggaaatt cagtaagtaa ctttggctgc
123541 caaataacga tttcctattt gctttacagc actcctcttc aagacaaagg gaatagtact
123601 catagtagaa ataacagcta tgcagtgatt atcaccagca ccagttcgta ttatgtgttt
123661 tacatttacg tgggagtagc cgacactttg cttgctatgg gattcttcag aggtctacca
123721 ctggtgcata ctctaatcac agtgtcgaaa attttacacc acaaaatgtt acattctgtt
123781 cttcaagcac ctatgtcaac cctcaacacg ttgaaagcag gtactttact aggtctaaga
123841 aatgaaactg ctgatccacc atcaataggg cctgtggttt tgttggtttt ctaatggcag
123901 tgctggcttt tgcacagagg catgtgccct ttgttgaacc tccatttgac tggcatgcac
123961 atgtctcaga tattataggt tatcatatat tgttgctcct aatatttctg tgttagataa
124021 ttagagtagc ttggtttgta agaatgtgat gttggtggga ctgtagcaga acaagaaggc
124081 ccttatgggt cagtcatacc tctcttttca aatatttggt ctagctctct tctgggcatc
124141 ttgttgccaa tatatagtat tgctcaaaag ggcaggagat ttgaagtgat caaggaaaat
124201 atatttttc tattgattaa gtcttttgat ggggtagaat aatctaattt catgtaactg
124261 ctcaaagtta tatggtaggg ggatcccaaa tgtattttaa aactattttt atatcatcat
124321 atttgaagta atagaaagtc agagtagcag aataaaggta ctaaaaattt taaaaactaa
124381 taaggtactt tgaaagaaat caattatgtt gattcctcat taaacaaatt tgcacttaaa
124441 gactgaggtt aataaggatt tccccaagtt ttttcatagc aacctgtgag cactttctct
124501 gttgaggcat ttatggtatg aaaagatgag taaggcacag ttcttgccct ggagaaggtc
124561 acaggtgaga ggaggagttg acacagaaac atttgatata aagcaaggaa taaattccaa
124621 gactaaaatt ttcagaaatc taaaaaactc aagataagaa aaacccatta tattttctgg
124681 gtaacaaaat ttcagtgtta ttaacatgta ggaagatctt gatatttatt ctgaagccca
124741 tgtgtgttgc tgaaatattg ccgcatttgc atatactcat caccatcctc tgttttggag
124801 ctaagaattt tagactcaag atgtctaatt aagttgatcc attgatttta ttttttatgg
124861 aaatctgaga cccacagaag gcaggggatt tgcccacatt tctagaagag tcagacatga
124921 gcgatgaggc acagtggaaa gaacatgagc attgcctgag ctctgagttg gcgctataag
124981 agcagtgatc atgggcaagt gactcttctg agccttggcc tcctcacctg ttaagtgaag
125041 aaaagaatat ttcagaagat ctttgtgaga atgaaacaag gcaatttact tgcctgctac
125101 atagccaatg ggaaatcaat ataagttccc cgtggttccc ttctgtgggg ttttgttccc
125161 acagagggtg cactggccat tccacttctt cttttccaag ctcctcattc cctttaacgc
125221 tgttcatagt tggttccaaa ccatttgaaa tataataagc accaggatgg ttttttcttt
125281 ccaccaaagc aaatttcatt ttctaaacac tgtttataaa tatcaatggc tattttttca
125341 atttttgatt atcatgaaaa tatacaaata tgtttaatta aatatgctaa agaatgtatt
125401 aataaatatg tattaaataa ttcctacata taaggccttt ttgcttgggg tatgggtgat
125461 acaaaataaa tgtggcatga acccactgac ctctagcaat ttataaccta gaaaaagagt
125521 tatgatatgt ttataagttc ctgtgatata agacatgcat atagtcatta taacagaggt
125581 gcaaacaaga tgtatcaagt atgtccagag gaggaagaga ttaatcccag ctggaggaaa
125641 cactgatgct ttcttgcagc aggggcattt gagttgagaa agggaggaaa catagatttt
125701 gacaatgaga gctgagggga aaggggtttc aggtggaggg aaccgcatgt ggaaagcagg
125761 gaggtaggaa agtgtagagt gtgtttaaag aatagaccag tttggctgaa acaggatatt
125821 tgagcagagg aagcttgtac taggtaggtg ggttgaggcc aaattatgca aggcattaaa
125881 tattaaacta ggaattttgg actttatcct gcagtttatg gggggtaaat gataagattc
125941 aatatcactt tatttgtaca gtattatgtt acattttatc taattgtttg tttaattcct
126001 gtctagacaa tgaattcctc aagggcaagg agcatggctt attcacctca gtaatttcag
126061 tgcctagcat tgtgcctggt acaaagtgga cacttgtata taacctttt taattgaagc
126121 aacaagttgt caaccttaca aatgtgaatc cgtgattcag atgacaggtt gaaatgtaga
126181 ttgtctgcga agagggcaga aagagagtat gacaaaggag gacaagacag tggggcaggc
126241 agggagagag agcagccagg gtttcggtag aggtatgtca aaaaggtatg gaagtcagag
126301 gagaaggaga cccctatgtt atagaataca aatggaaggg aaatgatgac aacagtaagt
```

FIG. 1 (cont.) (SEQ ID NO: 1)

126361 tgtcattaaa tgcaaggttg caaaagtaag attgtaaagc aggatgagta cccacctatt
126421 cctgacataa tttatagtaa aagctatttc agagaaattg gtcgttactt gaatcttaca
126481 agaatctgaa acttttaaaa aggtttaaaa gtaaaagaca ataacttgaa cacataatta
126541 tttagaatgt ttggaaagaa acaaaaattt ctaagtctat ctgattctat ttgctaattc
126601 ttatttgggt tctgaatgcg tctactgtga tccaaactta gtattgaata tattgatata
126661 tctttaaaaa attagtgttt tttgaggaat ttgtcatctt gtatattata ggtgggattc
126721 ttaatagatt ctccaaagat atagcaattt tggatgacct tctgcctctt accatatttg
126781 acttcatcca ggtatgtaaa aataagtacc gttaagtatg tctgtattat taaaaaaaca
126841 ataacaaaag caaatgtgat tttgttttca tttttattt gattgagggt tgaagtcctg
126901 tctattgcat taattttgta attatccaaa gccttcaaaa tagacataag tttagtaaat
126961 tcaataataa gtcagaactg cttacctggc ccaaacctga ggcaatccca catttagatg
127021 taatagctgt ctacttggga gtgatttgag aggcacaaag gaccatcttt cccaaaatca
127081 ctggccacaa agtgtgacat tttggcattg gcatcactat ttgatggaag ccaacctccc
127141 cccaaaaggc ctgtattaga atgaagatgg attccctggg tgggttacac ttgaaactag
127201 cctcacccat gaacactttg gcacagatta gctagcccat tcccccacag taaggaccat
127261 aaggaaggga cagaagcaaa gataagtttt agaacaaaag agaggggaaa gaaaaaatct
127321 agggttttat gagggctgtc cctgagtgat agatgtgaat aggcctccag ggcaggctgg
127381 ctcagaggct gactctttgg gttggggtga ctgattggtg gtgaggatgg agaagaaaag
127441 gggagtggag gaggtgaaag tgaccttggg acattaggtc tccataagtg acaggattta
127501 aggagtgttg taagctgtgg ttgttggacc aggtttaagc acagcttcct gagcttcctg
127561 actggtttag gtcaagctcc agagagcaaa tgccacagtc tcagtgatct ccttggagaa
127621 acagttggaa taggatgttg cccatgttgg gatgagtcat tgtccgctct tgctctttcc
127681 ctacccctgc aaaataataa tactgtattt gattgaacat ataaaacaaa agaaggatta
127741 tcacataagt atgtatatat aaccaacatt ggcaggtgca gaaaaaccag actgtcagtt
127801 tgcctcatct gaaatgattg acacaaacaa atatatttac tgtcccaagt gaactttggc
127861 attttggata tccttcagtt gttctgttta aagatataac ttagaagcag ctgatggaat
127921 atttaaatcc atgcgttgaa ttcatgcatt caaagaaaca tgtcctgagt cactaaatgc
127981 tgacatttgt ttttcatgtt aagagtgtaa ataactggtc ccaaatataa tattattaca
128041 tcagataaaa actggaatgt gaacctctta acttgattgt gaaagtattt gccaatggtg
128101 cctcttgata attatttgag gctcacttca gaactcctct ggaagggtta atttttaaat
128161 agtcatttta taaattaaca tttttgacat atgtgatggc tctcaaattt tttcttttat
128221 gccagtttga atcatttctg ctcaattttt tttttaatt gggatggagt ctcactctgt
128281 tgcccaggct ggagtgcagt gatgcaatct tggctgactg caacctccac ctcctcggtt
128341 caagcgattc tctcgcatca gcctccagag tagctgggat tacaggcgcg caccaccatg
128401 cctggataat ttttgtatta ttactagaga tggggtttca ccacgttggc caggctggtc
128461 ttgaactcct gaactcctga cctcaagtga tccacctgcc tcagcctctt aaagagctgg
128521 aattataggt gtgagccact gcaccaggcc ctgttcaact tttaatgcta agattcattt
128581 gttgttgttt cacaagtgat taggcagagg tcttttatat taatttaccc attttatttg
128641 taagagagtc tcatattaag gaagcataat atatgacaat ccaaatacag tacaaatttg
128701 gttaatttttg attttgttaa ataattaatc acaggggtcc ttcaaattgt gagctcctct
128761 ggttatactt atgttttacc tctggttata cttaatttca aacaaatgaa atttcattct
128821 attcatgata tttcagaagc agatctgttg cacaaaataa agcataccta taaattttct
128881 ttttttaaaa aaaagtctct gttcactcta ttttctatta tttttctctt tttaaaattt
128941 gaattttatt gtggcaagtc cacttaacat gagatttacc ctcttaacag atttttatgt
129001 gtaaaataca atattgttca ccatgggtaa atgttgcaca gcagatctct ggaacttatt
129061 cattttgcac tactgaaatt ttatacctgt tgattagtat ctccccattt ccctctctcc
129121 cctgtcctgt tacccatggt tctgttcttt gcttctttga gtttgagtat tttgatacct
129181 catgtaatct tcattctatt ttctaacttt gacaatgttc tgacaaattt gctttccgga
129241 ttggagcact gtatagtgaa aattgaaaat cttggttatt ttctacagat tcccactatt
129301 ttaccttgag cagacactta tcttgaaggg tctcagattt gtcacttgta gaatggggaa
129361 tataaacctg ataatggtcc ctttcagttc taaagttata tcagttgaaa atacatgtgt
129421 cacttatggt aacgggtaga gaactggctc actgaacagc atatggatat tataaagtgg
129481 tttttttaa tcctttctgc agacagttac tttatacttt attcaaatgg attattgtga
129541 agtacatgtt agcggacttt gtacctttta aaaatgtatg tatttggtgt aatgtagaaa
129601 tatagaaatt tattaagtat gatttatttc aatgttaagc atgagaaaat atgctccgaa
129661 aggttagata gcttgcctaa atgacaagct tgtatttcaa gcagaacttt ctgaatcaaa
129721 agactccaag acgaatgccc agctttcaaa aactgtctaa ccaaaataaa tcctaagatt FIG. 1 (cont.) (SEQ ID NO: 1)

129781 caccttcata ctaaaattat ttaaaaatag tttattttaa attaatattc acttaaaatg
129841 tatttatcat gcaatacttt aaagtgtctg ggaaatgaaa atatccaaag atcaaagaac
129901 accatgtttt caaacttcaa aaatgttatc agtgacctaa acaattttta aaattttcat
129961 agagcctatg aaaaatgtac ttgcaaatgg ctactttctg actaggaata gaatggggag
130021 agtatttagt ccaacaatga tagactggat taagaaaatg tggcacatat acaccatgga
130081 acactatgca gccataaaaa atgatgagtt catgtccttt gtagggacat ggatgaaatt
130141 ggaaaacatc attctcagta aactatcgca agaacaaaaa accaaacacc gcatattctc
130201 actcataggt gggaattgaa caatgagatc acatggacac aggaagggga atatcacact
130261 ctggggactg ttgtggggtg gggggagggg ggagggatag cactgggaga tatacctaat
130321 gctagatgac gagttagtgg gtgcagtgca ccagcatggc acatgtatac atatgtaact
130381 aacctgcaca atgtgcacat gtaccctaaa acttaaagta taataaaaaa aataaaaaaa
130441 agtttgaggt gtttaaagta tgcaaaaaaa aaaaaagaaa taaatcactg acacactttg
130501 tccactttgc aatgtgaaaa tgtttactca ccaacatgtt ttctttgatc ttacagttgt
130561 tattaattgt gattggagct atagcagttg tcgcagtttt acaaccctac atctttgttg
130621 caacagtgcc agtgatagtg gcttttatta tgttgagagc atatttcctc caaacctcac
130681 agcaactcaa acaactggaa tctgaaggta tgacagtgaa tgtgcgatac tcatcttgta
130741 aaaaagctat aagagctatt tgagattctt tattgttaat ctacttaaaa aaaattctgc
130801 ttttaaactt ttacatcata taacaataat ttttttctac atgcatgtgt atataaaagg
130861 aaactatatt acaaagtaca catggatttt ttttcttaat taatgaccat gtgacttcat
130921 tttggtttta aaataggtat atagaatctt accacagttg gtgtacagga cattcattta
130981 taataaactt atatcagtca aattaaacaa ggatagtgct gctattacta aaggtttctc
131041 tgggttccca aatgatactt gaccaaattt gtccctttgg cttgttgtct tcagacaccc
131101 tttcttcatg tgttggagct gccatttcgt gtgcccccaa actctacttg agctgttagg
131161 gaatcacatt ttgcagtgac agccttagtg tgggtgcatt ttcaggcaat actttttcag
131221 tatatttctg ctttgtagat tattagctaa atcaagtcac ataaacttcc ttaatttaga
131281 tacttgaaaa aattgtctta aaagaaaatt tttttagtaa gaattaattt agaattagcc
131341 agaaaactcc cagtggtagc caagaaagag gaataaatat tggtggtaat tttttaagtt
131401 cccatctctg gtagccaagt aaaaaaagag ggtaactcat taataaaata acaaatcata
131461 tctattcaaa gaatggcacc agtgtgaaaa aaagcttttt aaccaatgac atttgtgata
131521 tgattattct aatttagtct ttttcaggta caagatatta tgaaattaca ttttgtgttt
131581 atgttatttg caatgttttc tatggaaata tttcacaggc aggagtccaa ttttcactca
131641 tcttgttaca agcttaaaag gactatggac acttcgtgcc ttcggacggc agccttactt
131701 tgaaactctg ttccacaaag ctctgaattt acatactgcc aactggttct tgtacctgtc
131761 aacactgcgc tggttccaaa tgagaataga aatgattttt gtcatcttct tcattgctgt
131821 taccttcatt tccattttaa caacaggtac tatgaactca ttaactttag ctaagcattt
131881 aagtaaaaaa ttttcaatga ataaaatgct gcattctata ggttatcaat tttgatatc
131941 tttagagttt agtaattaac aaatttgttg gtttattatt gaacaagtga tttctttgaa
132001 tttccattgt tttattgtta aacaaataat ttccttgaaa tcggatatat atatatatat
132061 gtatatatat atatatatat atatatatat acatatatat atatagtatt atccctgttt
132121 tcacagtttt aaaaaccgat gcacacagat tgtcagatag caattctgtg attgaagggg
132181 aaatatgtca cctcttcata ctcatattgg tgaagggtcc tagcttcaaa attaatagat
132241 tcctaaagag gggaaatgaa acatccgcat ttacacacac acacacacac acacacacag
132301 agttcctctt gtcggtaagt tttgtttttt ttaaatctct actagataaa atttgttatc
132361 taattgtgag ttttacacaa agaaaaactg tcacagaaaa gaaagacagt gtcacatttt
132421 tcaaaagaaa aagaagaaaa gaaagtgcca tgtttttcaa atacaaatgt tctggattga
132481 ttttaggatc tttagtgaaa aacaaagtat ttcataataa gtaaaataaa aatctatgta
132541 ggtaaatttg tttctctaat ttaagaattt gaatttctga gtatttatga taagtgttga
132601 aataacttct tatatgtgac agtgaatact ggcagagcaa atgccaaatc aatgccaaat
132661 ctgtaggatc atttgattgt aggaacagaa ttctactcaa accgaaagca ggcatttgct
132721 ggagttacag aaaggcctca tggaacaccg agaaggtggt gccattcgac tcttaaagaa
132781 gctgcaacag gcacaagaga gtcagctgca gctcttcttc ttgagtctat atctgtcctg
132841 ggtccattcc tttttgtggt tgcttcattc ctttctctct ctgaagactg gtttttctgg
132901 tctaccaggg ctatgccaca ttgactttat gtagtgtctc cattctggcc tcctgaattt
132961 acaggagagt tcctctgtac aaactcaaag tcctggagag aacagaaaac agcttccttt
133021 tggctcaggg gtccaactgc agtctactct gctgctatga ggatagtggg ttcaccacct
133081 ttgttgttct ctcagctagg gcagtgggaa atgactctat gaaaggaata tacatgggca
133141 ggcaaatgta ctaatcctca tcagtactgt aattttaagc aactttaaaa aattctttta FIG. 1 (cont.) (SEQ ID NO: 1)

133201 agttatttga aaataagatc aaagaaggct gaattacata aatgaagatt tgttaacaat
133261 taattcaaac caatataaca catgctataa catggttgag tgtgattgag tcttgattta
133321 ttaggggcaa taatcaaaac atttaacaat cattatagta cagaacttac caatcaaatc
133381 agatgctcag ccggagtgga tgttggccac ccagctatta ttatccctgg ctcaattggt
133441 cttcagctgt gttaacttgc aaacattaat taactatcta agcccctcat tttcctcaag
133501 tgtaaataga cacaataata ttacctattc cataggtgtg gggtgaatag taaatgtaat
133561 aatttgtcca aaacacttag tatagtgcct ggtccatggt aaatactaaa taaatgttat
133621 ctgacttatt attaaaattt tatcttctca gcttaacctt cagaacagta atatattggg
133681 gtctagataa atcttgccta tatgaaaata atttaatact acatgcagat atatgctgtg
133741 tatattatgc cttctgttag aggaattgca gaaacaaaaa tttcaattaa taataagatg
133801 aattatttct cccaattgta gaatcttttg acaattttat catgcattac agatgtaaga
133861 actcttgatt gggacttgat agtctaactt tataataatt taagaacatt cctcttagag
133921 aatttctatg gccataatac tgaacacatg aattttaatt agctgtcctc tttagcccta
133981 aaaaaaaaat tactgtaatt taacacttaa gtgttgttct tcccaggtac agtaatcttt
134041 ttttttttt ttttttttt ttgcatagag ggtaatcttt tctctttcca aatggcagaa
134101 ctgttagttt tctgactgtc cggtgaaatt ctaagtccac ttacttccca atagcatgca
134161 attagcaaag gtcctccttg caaaggcaca gaacacacct aaacatcttg cagatgctgt
134221 ttggacactc ttcccctgct tttggtctct ttgtaaagca gctcatctgg atacaggatc
134281 tcttttcccc attgcccatt ctaatatatg ttaccgttat tacttataga ataatagtag
134341 aagagacaaa tatggtacct acccattacc aacaacacct ccaataccag taacattttt
134401 taaaaagggc aacactttcc taatattcaa tcgctctttg atttaaaatc ctggttgaat
134461 acttactata tgcagagcat tattctatta gtagatgctg tgatgaactg agatttaaaa
134521 attgttaaaa ttagcataaa attgaaatgt aaatttaatg tgatatgtgc cctaggagaa
134581 gtgtgaataa agtcgttcac agaagagaga aataacatga ggttcattta cgtcttttgt
134641 gcatctatag gagaaggaga aggaagagtt ggtattatcc tgactttagc catgaatatc
134701 atgagtacat tgcagtgggc tgtaaactcc agcatagatg tggatagctt ggtaagtctt
134761 atcatctttt taacttttat gaaaaaaatt cagacaagta acaaagtatg agtaatagca
134821 tgaggaagaa ctatataccg tatattgagc ttaagaaata aaacattaca gataaattga
134881 gggtcactgt gtatctgtca ttaaatcctt atctcttctt tccttctcat agatagccac
134941 tatgaagatc taatactgca gtgagcattc tttcacctgt ttccttattc aggattttct
135001 aggagaaata cctaggggtt gtattgctgg gtcataggat tcacccatgc ttaactgagt
135061 ggtgccaaat tgtcctcaag tctgttgtac tgatatatat ccccatcaag agagtacaag
135121 aattctcata gctatgtatc ttcaacaaca cttggtgtct ggtagatgtg aagtgattac
135181 taaaaatata gggaagctgc atacataatt attggctttt gctgttctct tacattaatt
135241 tcttattcat gttgattact catttgtcac ctagtttttt cttccttaat taaattgtag
135301 gaatttatga attatggatt gatcatcagc tctatacatt tcaaacataa tccctcagtc
135361 agtggcttgg cttatagagt cttttgatga aaagaagctt ttaagtttaa taaagttcaa
135421 tttattgtct tttcctttat gttttgtgct tttggtatct tgattaagaa ctccttcctt
135481 atattgggtt ctcaaattta gcagcataac attttcatac tattatttaa attttttca
135541 cattatttag tgatagcacc tttcttattc ctaaagtgtt tatcattgcc ttctgtcttt
135601 ctgcttgata aatattgcca cacatttgta tactttatta gtgtgtacaa agaccacatt
135661 ttagttgtgt tatttctctt gttttggttt tctagaatgc agagccatta atattatagt
135721 aatgcttatg tgctaatacc atatcagggg cacaaatccc attgcagcgg gactgagaaa
135781 ttaaaggaaa tgatgcacat ttactcattt ttgtttaaaa aatcaaatgc atatttttca
135841 atcagactat atggttggtc tggatagctt catcattgaa tttttaaagt atttttgtac
135901 tactgtattt aaaattattc attcaccact gcttttgtag atggtttaga aacccaagtt
135961 aggaatgact gtgcaacact attattatac tctttttaaa attatacttt ttgcttaagt
136021 ttctttcctt gttctctgag acagtgttca tgttcccaaa ccacacacat ttattcagct
136081 ataaaatttg tatgatcaac tcctgtcaga acaaacatca ttataaaaaa tatctccagg
136141 aaaaagaaaa cccttttaat gctctcttct ggttcatgtg tcttcttatt ttctttaagc
136201 attttcataa cccattgagc tgtaatttaa ttggaacatg atttatacta aagttggttt
136261 ctttaccttt aacttttttt tttagtttga tcagctctct ttagcttctg tagttcggtc
136321 tttaattcca ttccagtatg cttttggagt tgggtctcat aaatgtatag aaatgtttct
136381 gttgggaaac agcaggagaa tattaaataa atattgtgct tacatctatt taattctttg
136441 cccaactttc tacaactttg actttacatt taagctcctc atgcacttac atgtttcttt
136501 acctaaaaat atcttttcac catgggtgtg tacaattcct ttgtccttgc tgtattaatt
136561 ttcttggttt acatagtagc ctctacacat tgatgtcaaa acctctgttt ggtgcatttc FIG. 1 (cont.) (SEQ ID NO: 1)

```
136621 tactctgcgt gttcaatctc catgaaagtt tctgtaaggt attttcattc ctctagtttt
136681 tcacatgtgc atcctggctt tgtgacctgt gctttgatat cgtgcctttc atcttgtggc
136741 attgaaggat ctttgcaagg acctattgtg ttataataca gtctatgaaa aatatcaata
136801 tttgcatttg atcacattta aaaaaatcac attcttttgt ttgaatatca aagctaatat
136861 gtgagtgatt tccctgccaa atagcacaag tagcctttcc tgggtgttta tgggcattta
136921 tctggttaat gattcccatc atagtgctgt cacccatgcc attgctaaac ttatacagta
136981 actttttgt tttcacctca gcatatgttg agagtaggaa atagatagga ctatgccctc
137041 aaattttacg tttatatgat gttaatccta aaggtccttg tgacttctga agtaaaaact
137101 cagtgttgtc attttactta ctgaattgtt agctgagttt agagttgagt ttacaatgga
137161 gtaaacaagg tgtttagttt gatgtatgct tttagtcttt cagaaaaaaa tgtttatact
137221 tggaaagaat agtttattta cccatctggc ctagtttaga caaaaacaca gagtcaaatg
137281 tcaacagaat tctgaagtta taaaaatgac agtgtggctt ttttttttt taaccttcca
137341 cctggtgctt atgcccaagt gcctagcttt ctttagctct caactaataa aggtaatgtt
137401 tagataacat ttaacgttaa gttgcattgt gtttatgatc acatatctca aatattggta
137461 cacgaaactg tacaacaacc tttttatta gattttccta cgaaattcct tattatattc
137521 cctaagatag ctttttccca ccttcttctt ccttctccct tctcaggtgc tccaataatt
137581 ccaacccctg cagccagtga ctttattata tctttttta aaaatctaaa aaaaaaaatt
137641 gatgcaacca ggaagaattt tctcatttct ctccaccagt tgtaccagcc tactgcacct
137701 ctcctcatgc accaccttct gcctgtgttc ttgctcctat attcaggagc aagtaatatg
137761 caatacctcc ctctttgtgg gatctttctc attagcataa aaatactttc ccttgatctc
137821 cagctactac cccatttctt tgacctacat atagcaaaat atttgagaaa ggaccacttt
137881 ccatcttttc ctcaatctac ttccattttt ttctcaatcc actttcattt cattgttctc
137941 ctcaacccat tctttccaca acctacttca ttttatttcc atcagcccca taactcagga
138001 tcaacatctt gccagagcca atttccttgt ctcccttaac agctccagca gtatttatgc
138061 catggacaaa ttattcttct tgtgatactt tctctcttgc ttccatgaca ctactcccac
138121 ttcattttct ttctacctct ctggctcttc cttggtccct tttcctggcc ccttctctct
138181 ttcagatctc taaacatcag ctatatctca gccctgttct actgacactc tctagctgtt
138241 attttctaaa cccatgtttc agaaaccata tcttgatgaa tcttggaagg ccgaggcagg
138301 cgaattactt gaggtcggga gtttgagacc agcctggcca acgtggtgaa accccatctc
138361 tcctaaaaat acaaaaatta cctggccgtg gtggcatgca cccagctact tgagaggctg
138421 aggcacaaga atcgcttgaa cctgggaggt ggaggtttca gtgagccgag atcctgccac
138481 tgcactccag cctgagcaat agaggagact ccgtctcaca cacacacaca cacacacaca
138541 cacaaagaaa ataaaccatc tcttgatgaa tcataaattt gtgtctctag tttagacctc
138601 tatcctgctc tctaaatgat gtatccaact atcatcttga caccatcata tgttcataaa
138661 acataattat agaatatctt tcagtaggct tgacatttta aggcatgagt ttccgttcag
138721 tatctcctta aaatataccc agggtctcag gagactattc aaacaggaca aagcttctat
138781 tctacttact aatgtgtctg gccctatttg gcaggttgga taaaaagtca tctgaacatt
138841 gtcactttat gaataatata gtttaatagt ttgtgaatca cccctgcaat ttaaaaaata
138901 gtaaaattat cagaatctaa tttaataatt cctattggaa cacccccatgt taggggattt
138961 ccagttattt caattgatat ctcaatgttt taaagattgt ttatttctat tactaattca
139021 ctctttattt taacataaat tgtggctatc tatctctatt catttcaatt atatttctca
139081 taccattcta tagatggggt gaaaagaaaa gtgttaattt tttaaaactc catacctcaa
139141 atactatatg aatttatagt tgttattgct aaagcaatta tcttacatct tttcctccaa
139201 aacaaagtta tgtgctggtt tattttcttt gtactcataa gatgccttcc atttttagta
139261 acataagtct tgtctttctc ctattcttag ctacttaagc attatgtagc ttaaataagc
139321 actaaagatt cctatctgta tgaaaaaata aagattaaat aaataagatc tagaaagggt
139381 gacaaggtga tgcttcaaaa tgaaccatac caagccatct agcgattgat aaattactca
139441 cactcataat cacattgttg gaaagaagcc attgacaatt cagtttgttt cacaactgtc
139501 tatcacatag tgagcacaac taaaagacta ctttttgtct tttactgctt gttttgttga
139561 tcaagtgact gattgtacaa tgaccaacaa gaagtctgat gtgtagagaa aaggggaacc
139621 tggcttttct gccttactcc tgatgcctaa ttctgagcat gtgaatatta ttctgtttct
139681 ttaattctcc aagtgaagca gcagataaac catccttgtt tccattagct gtctaccctg
139741 ttcaactgtg tgtttctaat aacataagaa taagaaagcc accagggtga gcagggaagg
139801 caatgagtct gcaaggcttg tggatagatt tctgttagtg aggctctaga aagttcttcc
139861 aagattgatg caatctgaga agagttttct gtcaatacaa actccctggg tttctccttt
139921 gtccttttac tgcctgtgtt tgttttgggt tccagtaaag atcaagtgac tgattgtacc
139981 atgaccaaca agaagcctga tgtgtggaga aaaggggaac ctggcttttc tgcattactc
```

FIG. 1 (cont.) (SEQ ID NO: 1)

140041 ctaatgccta attttcttgt actgaaagta gtttttgctg taagaatctg aggggaggag
140101 tcatttcttc aattttttttt tttggtctcc ttttaatggt ttcttgatca tgtctatcct
140161 tatttttctg ttttcacaaa tttttgtggt atattttcct ctcatgacct ctgtctcaag
140221 acttctttcc atccatctct tctcatttca tcctgtagag tgtctgtggt aagagccctg
140281 cattctactc tggccttgcc atgtgtggcc ttgggcaagt cctagcctcc ttgagggtct
140341 tatttttctc atttgtaaaa tgaaacagtt tgatgagaag ttttctaagg ttccttcaag
140401 ctttgacaat ctctctcttc tggatctttt tcccatgaaa aatttcaact cttgattagc
140461 atgtaggcag ggattattcc acatccttat aggaatcaca tttctgctac tgtccctgaa
140521 tgctagagtc cattgattaa gttattcact gctgcaattg tcagagctga tcaaagaact
140581 ctgaaccagt gtgttactag aactaacaaa gaaaatgcca ttatgatgtt ctagagtctt
140641 gaattagtag aagaggttta ataagaaccc taagggattg ctagaatgtt aaaaacaaac
140701 aaacaaaaaa aaaggttgaa aagtttagaa aattcactgg tctttgtgcc catcatttta
140761 cttccagggt ttagataatc tcatttttgc aatgaaggaa tggattagat cacaagttct
140821 catcctagta gcacatgcag aatctttata aaaacacaga gtagccaggt gcggtggctc
140881 atgcctgtaa tcccagcact ttgagagcct ggggcaggtg gatcacttga gaataggagt
140941 tgaagaccaa gctggtcaac atggcaaaac cctgtatcta ctaaaaattc aaaaattagc
141001 caggcatgat ggcacatgcc tcccagctac tggggaggct gaggcaggag aatcgattga
141061 acccgggaga tggaggttgc agggagctga gatagctcca ctgcactcca gcctggtgac
141121 agggtgagac tccatcacaa acaaaacaaa acaaaagaaa gcaaaaacac agattactca
141181 gggtccacta agaccagtga agtcagttct cttggtaggg ggcagggtga ctgagcatga
141241 tgtttgtaat tttaaaagtg ctccaggtga ttctagcgtg tatcaagcaa gacttgtgaa
141301 ccactgaact acatgctaag actcatttta gctctgattt tctgtgagtc atagcagagg
141361 gctcagcaaa ctttttctat aaatgctaag atagtaaata ttttcagctt tgtgggctgt
141421 atcgtcttta tgacaactca actcagtctt tgtagagaaa agcagctgta cataatatgt
141481 aaactaatgg gagtagctag atgtgtcctg tgggccatag ttttgctgac tcctggtcta
141541 tgtcatagaa tttccttttg aattgatgga ccaccagcaa atgattttttg tcctgtatca
141601 atcaatgata catacataaa tctctacaag acatgtaaag gatgaggctt aatgacagag
141661 tactttgggg aagacataat attgcaaaat taagatgctt agagaaaaat catattaaaa
141721 tagtgaaaac tgtgagaagg tattttgatt tgttgttttg gattcctctt tttgcaaatt
141781 cttttgaaat attttcagtg gaagctacat agatccaatt gtattcacca agctagattg
141841 taattaagct ccagagtaag taatagattt gatgagtgat gtccaacctt ttacatggaa
141901 gagtaagttt gagtcttcct ttgcccattg acacacttag taccatgttt accaaagttc
141961 ttagttattg aaatgggcac cagcatattt tgaaacgttg gtgttaactt gggatatgcc
142021 ttttgtcatg ttgcaaatag attttgtttc tgttttgtga agatcaccat ctctgtcact
142081 tctgatagaa aaagtgacac tgacttctca agtgatttga cacaggttaa aatatgtaaa
142141 ccatttctgt agagagcaag ctgtaataat atactaaagg gctaggttta tagtataata
142201 taaataactc atttatgctg ttaataattt atagcaacat ggcatttgac tgacttttta
142261 tgtgctctag tcatgtaagt aatagatgtg gaaacataga ccagagtttc aagaacatgt
142321 tttgggcaga gtctgttttc ttgctattat ctcttaagtt tatgttcatg gcctaaagat
142381 tatgctaatg gatctgcctt ggtcttgggt gtcaggtctg tgttagcgag tattgaaaag
142441 catagttttt gcctactggg aaggatttat gatttaaaag ccctaaatct ccccttttat
142501 gtacttcata cttagaaaat ttttcctgta aactgtgtga ctttttttaca ttgtgccagt
142561 tttctagatg actctcgtca tatttatttc ttgcaatcct tctataacta tcagttatga
142621 agtctcttta tagtgttgcc agccaggtct caggtgtgtg aaatgtattt tctattatgg
142681 attttggggt atgatggcac atagtttggg tgttaatgcc taatcttgat gtactggctt
142741 ctgaacaacc aaaaggatga aaggaaatag aacaaatatt tttgtgaggg agaggagtct
142801 ggcttcttga cttactctag aaaaagcctg taagcctcct cttccctcct tgtcacacaa
142861 agtgacaaag aaaatcaaga attgttttct tcttggctta aatgcatccc ttataaagta
142921 aggctgagat caggctgtga agctatcttt ttgtcaagac tgtcataatt ccaaaacact
142981 ttgttcttct aatgcttagg ttagtaactt taaacatttt tataaagata gtgaggtcca
143041 gttttaagga ttgacccctt ctcaaggggc tcagaagagg ttttggagaa taataaaatt
143101 aaataatgaa accaataatt taaaccagat catgatcctt aagaaaaaat cccatcaaat
143161 ttgggctaaa ctctaatata cagaggtctg cacaacttat gtcaagtatt cttccccaca
143221 aatgaagaat ggggttcatt gtgtcattgg ttgggtctca ttttggcttc atcttctatt
143281 tctcaaagtc taagaaaagt gctcctacgg aagtgggtgt tggctatcat gagactttgc
143341 tgctggcagg ccagcttgct gctctagaca gagatatccc tcgatcctcc ttggacaact
143401 gttttctgtg cacaggaagc agcaggctgg ggttaaggag tttgccaatc cagtcattct FIG. 1 (cont.) (SEQ ID NO: 1)

143461 gataattgct gaatatgaat ttctatccag cacaatctag gtagctacaa tggcacagta
143521 gtttttatgt atcaggtgaa aatgtttaat aggcactcta aatgagagaa aaggttaagt
143581 gaggttaaaa gctcaatgaa aacaaataga tgagactaaa aatagttcaa taggttgtaa
143641 cttccatctc atccaaacag caatgaatat tttgaggctg aggcgctgag gggtaaaatt
143701 gcagcctgga ctacttgcta atgtagacct acagcactgt cattcttact gcacagacac
143761 tgctttctgc ataggaggta gaataatgaa ttcatttatt attaacaaag atttattaag
143821 tgactgcatg gtgctaacca ctagatgggg agggatgttt tgaactgtcc attgtttgac
143881 tataacaagg aacgctttga acgaggttac tatcataggc agaatttgtt taacatgaag
143941 cctatgagac ataagccaca ggtcctctca cgtgcaggaa ctcctttgaa ggccctatac
144001 ttaattttat atgcatagtt tggatttgga ttcttttttt tttaagagtt ccccaaatta
144061 cttaagcttc aggctccaca aaacctggat ctacccctgg tagcagctat gaatctttga
144121 ctatgaaatt aagtgtacaa gaaatatgac tttacttttt ctgtgattga gtttattttc
144181 tatttgagca cgcattccac tgagtgaaag aaataatatc attgaattca gagattttgc
144241 tgggttctaa gtggagttta cagaatgcca tgatattagg aattaaggag tgtgttgccc
144301 tacatcatct tttgtccgtg ctcactgtct ctgaggcact gatgttccta tgtgacctag
144361 aggggcatgg tccaggtaga tggagtctgt ccttgttctc actgtgagct ctcgcttgct
144421 gacccttctt cagtttcttc catgcccctg aggggtaaaa agattcaaat ctgaagctat
144481 atcaagccat ctgtgcatag acattccaag caaccatgtt cactctactg ctcccatgtc
144541 atgcaaggca caggaagctt cactatggca tgagtatttc ctgggctttg ccttggaatt
144601 gaggcacggg cctcctttgt tctaaaattc cccaaatcta cttgaggata gaaccaggat
144661 ttggttgcaa ggcagaactt ttcttagagg acctggtatc taaaccctct tgttaccccc
144721 atttatggac cccatttatg gggtgaggag agtgactgct tctaatccat cataattttt
144781 gtctatggct actgtttttg catagacact atgttttgag tccttaggct ttggcttttg
144841 gcgcttaatg gccaatattc acatggctca aaattttcaa atgatccata tctgacttga
144901 gtttcaaaag tcagtttttg aaacttaaat gatcagaatt gatttgttct gctctggttc
144961 tgatgtggcc tctccttcca gaggtactgg aggtagaata tccaaggtgg aaagcccacg
145021 actacaagga attggttagt aattcataat gttagctgtc cacatctatt cagtaatggc
145081 atttcagtgg ctgcacaact gaccatggtg aaagtgtctg cacaagccac tttttcttcc
145141 tgtcagaaaa tgttctcacc cactgaattg aatgactgtc tgctcatatg ctgtgaatga
145201 gtgcccagtc ttaagattaa atcacacgtt cttggctatg catatttggg catgctgtgg
145261 ggagttataa taggctgtct tagagtcaca ttaagcagct agacagacaa tgagttggaa
145321 agttacattt tctaaatttg attggtacat tccatttgtc acatttgaca ttagaagttc
145381 tggattcacc ctctatggtg agcttcacta atggagaatg taatttgcaa tgctcaaaca
145441 caagtcctaa acagaaaaca ttgtatgtta cattccagtg ctaccaaaat agtggttttg
145501 aaagtcctta ttttctaata ctactatgtg taattttgag tcatttagat agcaacagtt
145561 aaatgtttta tagattgttt ggaagtatta aaatgtgaag gatttttgtt atatagtgtc
145621 tttcctatct tgcttaataa aatataagtt tagaattgtg tatagaatta acatgcaaaa
145681 atatcaagtc tcaactttat acagttaatc tacatttgtg tatacccttc aattatttca
145741 agagagggat actattctta tgcaggataa atacaataag atattttaaa tgaattttaa
145801 ctacatctct ggcagtttca tctcaatagt agttgtaatt ttatctccca gaccttatta
145861 tagactagca gctctctatg aaaattagtg acagtgtgag tgtattttaa ttcaaagtta
145921 atcaagaatg actgagtcaa gagttagcta cccctgaaag taactcataa ttcagaattt
145981 aaaatattac atgtggaaca atcatgacta tatgcctttt actttctcta tcattattta
146041 ggttgtgggc tttgggtcct tttcacatcc gttaacagtg ggcttgactt caaaggatta
146101 ttttcttgaa tcttgaataa ttgctgaaga caatttgaag atattttcaa gatgaaggaa
146161 actgaagcac agaatcacta gagtgaaaaa agaacttcac aaacagtgca ggcttgatca
146221 atggcatggg aaaacaggca atacagttag aattgctaag atggaatttt aacgttcaat
146281 taaggatcta tctctaaact cctctgcttt atccaccaat cattccatat taaagatgaa
146341 gaattgttcc catttcacct tttgataagg aaaaatagaa ataacagaag caaatacact
146401 tttgcccaca tttttttcca aaaagaataa tttttgaagt ctaaacgttt ggtgtaaata
146461 agatgatgtg ttaatattgt aaaggaaagc tagttaagtt tttgactgaa taaagccagc
146521 atcaataatt actagtaaga ctaaaaataa gagcagtaaa attgtgtcta atcagctact
146581 aatatctggg aaggattgag ccacaggatc aaagatggta tcttttaaaa atagaagttg
146641 agtgaattcg gtcttcaaat tctttctttt tattcattta tatttattta ctcattagta
146701 tattcattcc tttattcatg tattgttcaa atatatattg ggtacttatt atatgccaag
146761 ttgtttttaa aatcacattc caaattcccg taagtcataa ttattcagag atgtatgttt
146821 tttttaaaaa aaattgaaca cctttaaaaa ttatcaagtc cttttatttc tgtatgcatt FIG. 1 (cont.) (SEQ ID NO: 1)

146881 aaagataaac tttactaaat gttacatgaa tagatttata aagcagataa atatttaatt
146941 tcaaatataa cccttatatg caattatatt ttccttagca ctaaaaatga atatttaagt
147001 aatttatatt aaaagtgtaa ttatttaact gcagatgtat gccaatgact taaattgttt
147061 aaagattata gcaaagttgt ttaaaattgt ctaatcatga agagttcact taaccacctg
147121 gttgacacat aaaattatag ttagttacta aggtagttcg agagaaagag aagaatcttc
147181 agtagtggtt ttgaggtgtg gtacatttta ttataatata ccggttatac agcattgtgc
147241 agtgctgctc atagtagaaa taaattttct ctttgatgtc atctattccc ttgtgtggct
147301 tacataactg agaattaggt gatcacaaaa ataaacaggc ctatacagag cccatttata
147361 taagtcctgg ttatttctct tcagttaaac ttttaattat atccaattat ttcctgttag
147421 ttcattgaaa agcccgacaa ataaccaagt gacaaatagc aagtgttgca ttttacaagt
147481 tattttttag gaagcatcaa actaattgtg aaattgtctg ccattcttaa aaacaaaaat
147541 gttgttattt ttatttcaga tgcgatctgt gagccgagtc tttaagttca ttgacatgcc
147601 aacagaaggt aaacctacca agtcaaccaa accatacaag aatggccaac tctcgaaagt
147661 tatgattatt gagaattcac acgtgaagaa agatgacatc tggccctcag gggccaaat
147721 gactgtcaaa gatctcacag caaaatacac agaaggtgga aatgccatat tagagaacat
147781 ttccttctca ataagtcctg gccagagggt gagatttgaa cactgcttgc tttgttagac
147841 tgtgttcagt aagtgaatcc cagtagcctg aagcaatgtg ttagcagaat ctatttgtaa
147901 cattattatt gtacagtaga atcaatatta aacacacatg ttttattata tggagtcatt
147961 atttttaata tgaaatttaa tttgcagagt cctgaaccta tataatgggt ttattttaaa
148021 tgtgattgta cttgcagaat atctaattaa ttgctaggtt aataactaaa gaagccatta
148081 aataaatcaa aattgtaaca tgttttagat ttcccatctt gaaaatgtct tccaaaaata
148141 tcttattgct gactccatct attgtcttaa attttatcta agttccattc tgccaaacaa
148201 gtgatacttt ttttctagct tttttcagtt tgtttgtttt gtttttcttt gaagttttaa
148261 ttcagacata gattattttt tcccagttat ttactatatt tattaagcat gagtaattga
148321 cattattttg aaatccttct tatggatccc agcactgggc tgaacacata gaaggaactt
148381 aatatatact gatttctgga attgattctt ggagacaggg atggtcatta tccatatact
148441 tcaggctcca taaacatatt tcttaattgc cttcaaatcc ctattctgga ctgctctata
148501 aatctagaca agagtattat atattttgat tgatattttt tagataaaat aaaagggagc
148561 tgaaaactga attgcaaact gaattttaaa actttatctc tctgtggtta attgcaaaca
148621 cagatacaaa aatatagaga gagatacagt tagtaaagat gttaggtcac cgttactaac
148681 actgacatag aaacagtttt gctcatgagt ttcagaatat atgagtttga ttttgcccat
148741 ggattttaga atatttgata aacatttaat gcattgtaca aattctgtga aaacatatat
148801 ataggatgtg cgaaaagtcc ctgtgtatca tgtgaaatgg cttaaaacag aacaccatag
148861 gtattcatat cagtgaatac cataggtagc tgaaagtgtt ttttcctggg gtcgccaaga
148921 tgaatgccaa aagtgatatc attattataa acaatagcca gaataggttg gtataaacct
148981 ggtagaaagc cttgataaat tgactttctc tcctcctgac atcctgccac cccttttgctt
149041 tgctgatgct catttgtcca ctaaattaaa ctcaagcaag ccctagtaaa gtaatagaat
149101 ttgtggagtc ctcattagta taggaagttt ccctgatgtg agattagtaa ttagagatgt
149161 agcaaaatga gaaagaagta atatgcttag atatttcatt ttctctgaac ctgtatatac
149221 aaaataggcc atgcgtgttc agtaactatt cactgcaagg cactctctag gtactttggg
149281 ggaattggaa attactcaca taaggctatg gattgtgcca tttgtcaaaa gacaaaatga
149341 caacaaattt agtttaaaga cctcagtcag ctttattttc tattctagat ttggacagtc
149401 cttcatttca caaattggag taagtgttcc aataagttga gcaaaggagc ttggctttat
149461 agacccaaaa aaagggccaa aggaagcaga aacaaagaac aataagagaa ttggtcattt
149521 caaagttact tttcttgaaa ggtggggaca aggagacaga ataatagaaa agtcactgat
149581 tggttaacat tggattaaga attaaaacag aggaaacttt aagattgaag tttgaaactg
149641 acttgtttgg gaaatcaggc tgtcttcttt cttgatttct tagaaggccg gataacaact
149701 gagttttgct ttggtgaaca tgggtgactc catttttact tttagtctgg tctgttgagg
149761 cctcgtgaga gagcttaatc taaaacaatg acttcctata atttttgttt gacacatcca
149821 aagagggact ctaatattta ttgagagctt atcatatctt aagtactgtt taaacacttt
149881 tatttgctat tacatttgat cttattataa ctctaaaggc agaaatgatt gcttttattt
149941 tccacaatgg aggaaactga ggttcaatta agtgagtaag gaagcaggga tcttaaaccc
150001 agataccatt gctcctcttt aaaggtggaa gaacagaaaa catggggcag gggaagagag
150061 aaagtttctg tcccaggaca tgataatcta aaagggaaaa cgtaagatcc actgaaacct
150121 gaggcagatt tattgtggca ataacaaagc ttaagtttca cagaccttca tttgcctgag
150181 ccaactttga aggccatgta tctaattttg tttttataat tctataatct ttattcttga
150241 aaagagccct ccctccaaat ttacaagctt tgggccccca aaatccttga aatgcccttg FIG. 1 (cont.) (SEQ ID NO: 1)

```
150301 aataagagat atccaggtaa atgctatggg aattcagagg aggaagcagt tagtatcagt
150361 tggcggagag ttaggctatt aagagaaggt tttatatagg aagtggcatt tagaatgaag
150421 ctttgagaac tgagctgtgt atttgaacaa gtaaaggtgg tgttgcagaa ttttgctcct
150481 tagttctatt aaaaacccgg gttcttgtca catgatccgg aaaatttagg cacacagata
150541 cattgaagca tgagtagagc aggattttat tgggcaaaaa ggaaaaaaag aaaactcagc
150601 aaatcgagat ggagtcttgc tcacagattg aatcccaggc caccacaaag gaactgaaga
150661 gatcgggctt ctcccctgca taaggtgcaa attccccatg gctccaccca cttcccctta
150721 gtgtgcatgt ggggctccag tccacggtgg gcatgcccag acaagccttg ggcaggttcc
150781 ctcatctgtg caaaagcatc tgatgtaaac acttgagggg tggttcggag attctctggg
150841 acccttttat tttcttatct gcctaggcat ttggctgtct cagtgggtgg gaaagggtgc
150901 tccaggcaaa gggcataaca tgaggcaaag ggcatgcaca gaaaacagtg actggttcag
150961 tcaggttggg ggatgccaaa ggaagtaatg ggagacaaga ttggagcaag atagataaga
151021 gattgtggat ttttttctt ttttatctat ataaatacag agacagggtc tcactatgtt
151081 gcccaggctg gtctcaaact cctggcctca agtgatcctc ccacctcatc ctcccaaagt
151141 gctaggatta caggcatgag gcactgtgcc caacctccaa ttttggattt tgagagctaa
151201 agcaatatag tcgaaaactc agataatcca ggtagatttt gctattaggt gctatttggt
151261 tcctggtaca gagctaaaac ccttggaatt tcctaagtga taagagctac aggagcatct
151321 tttgttatat gtttcccccc ctagttcctg aaatagctct agagaaatac aggtgaataa
151381 catcctttgt tattcatatc aagcccctat caaccatacc ccagtttcta tttatgaagt
151441 ggcttttggg aagtccctaa agacaggagt ggggaaaggc tggttgtcag gggggatgggt
151501 tgaaactttc atcttccccc cttgacctcc agggagggat gagtggctga aaattgtgta
151561 aaatcaacaa tggccagtga tttaatcaac catgcctatg taatgaagcc acccgataag
151621 ccttaactgg aactttttgg agagcctcca ggctggtgaa gacattgagg tgctcagaag
151681 gtggtattcc agagagagca cagaatctct gttccccttc ccacattcat tttgctatgc
151741 atctctccca tctggctgtt cttgagaggt atccgtttat aataaactgg taacctagta
151801 agtaaactgt taccctgagt tctgtgagcc attctagcaa attatcaaac ctaaagagtt
151861 catggatacg tgcaatttac agatgcacag tcagaagcac agatgacaat ctgggcttgc
151921 cattggcatt tgaagtgtgt tgggaggcag tcttacagga atgagccctt atcctgtggg
151981 gtctatgcta ataacagaca gttgtcagca ttgcttggtg tcgaaaaccc acattgttgg
152041 tgtcagaagt attgtcagta ggatagggaa aacagtttgt tttcttttt tagtggtctt
152101 tggtcatctt taagagcagg gcttctcaaa gtgtggtcct tgaaccagca tcacctgtac
152161 cacgtaagaa cttatgagaa atgttcattc ttgggcccca acaaagaatt aaaaattctg
152221 agggtgtgaa cggggtctga gtttcagcac aacttcccga ccatgctgat gcattcttgc
152281 ccaagcatga aagccctccc ttgtttaaga aggccattag ggccgggtgt ggtggctcat
152341 gcttgtaatc gagcactttg agaggacata gtgggaggat cacttgagcc ctggagttct
152401 agacaagcct gggcaacatg gcaaaatgct gtctccacaa aaatcacaaa aattaggtgg
152461 gcgtgtgttg tgtgcctata ggcccagcta cttaggagac tgaggcagga ggatcgcttg
152521 agcccaggag attaaggctg cagcgagctg tgatggcacc actacagcct ggatgacaga
152581 gtgagacact gtctcaaaaa aaaaaaagaa aaagaaaaag aaaaaagaaa ggaaaatgaa
152641 aaagaacgcc attaggtata aaggagcaat ggtaaaagac cagttgcaaa aggttaggga
152701 atgggtggtt actgaaataa gaagctatgt agaacactag tgttggtggc aggaagtaga
152761 aagcaagagc actgctctgt gggggatggt catagcaaat gcaatatgga ggcatttgcc
152821 tctgcactga ggagaaaact atcttttcca agataggagg aaaggagata agtggaatta
152881 aagagaacct ttgagcacag agttgggaaa ctgaaggtat ttgtgttgtg ctccctcaat
152941 cttttaattc aactataagc taaacccatg aaacttgagt agtttcagtt atctgacttt
153001 tttcttctct tttgatacag tgttggctat tctgggtctt ttgcctctct ttatgtactt
153061 aagaatcagt ttgccaatgt atgcaaaata actggctggg attttgattg tgattggctt
153121 gaatctatag atggagttgg gaaggactga catcttgaca atgttgaagc ttcctattca
153181 tcattatgaa atatttctcc atttgtttga ttctttgatt tcttttatca gaatttagtt
153241 ttcctcatat agtcttttaa aatattttgt tatattttgt tcaagtattt tgtttttgag
153301 gaatgccaat gtaaatggta ttgtgatttt aatttcaaat tccaattttt cattgctgtt
153361 atataggaaa atgatttttt ttgcatgtta gccttatatc tttcaacttt gctataatca
153421 attattgata gtttcaagga ttttttggtc aattattttg aatcttctac atagattatc
153481 atcatctgaa cttagtttta tttcttcctt cccaatctgt atacctttat ctcctttctt
153541 tatttcatta gctaggactt ccagtatgat gttgaaagta gtggtgagag gggatatctt
153601 ggtcttgttc ttgatcttag tgggaaaact tcaagtttct tatcattaag tatgatttta
153661 gctggagggt ttttgtagaa gttttttttt tttaagttga agaagtctcc ttctattttt
```

FIG. 1 (cont.) (SEQ ID NO: 1)

153721 agtttgctga tttttaaaaa gaatcaggaa tgggtgttaa attttgtgaa atgcttttct
153781 gcaactattg atttgagcac tttatttttc ttctttggct tgttgatgtg aagtacatta
153841 attgattttt gaatgctgaa tcaacctttt gtacctgaga ttaatcccgt ttggttgtgg
153901 tatataatta tttgtataca tgttgagttc gatttgctaa tactttttga gaatttttgc
153961 attggtgttc atgaaaaaat attggtgtgt agttttttgt gacatcttta tctgcttatg
154021 gttttaaggt aatgctggcc tcatagcatg agttagggag tatttcctct acttttacat
154081 ttgagaagag attgcagaga attagtaaaa ttcctacttt aaatattttg tggaattcac
154141 cagtgaaccc atctggacct ggtgctttct gttttggaag gtcattaatt attttaaaat
154201 agatataggc ctattcagat tacctatttt ttctcatgcg agttttagca gattgtcttt
154261 caaggaattg gtctatttca tttaggttat caaatatgtc aacgtagagt tattcatagt
154321 attcttttat tatcctttta atgtgcaagg gatctgtagt gatgtcccct tttttgtttt
154381 attgatatta gcaatttgtg tcacatcttt tattttgctt tgttagccag gctagagata
154441 tctctatttt tgatgttttt gatgaaccaa ctttttgttt tattgatttt ctctgttgat
154501 ttcgtgattt caatttcatg atttttaaat tatgcttaca tttgatttaa tttgatcttc
154561 ttttgctagt tatccaaggt ggaagcttat attgttaaga tcctttttgca ttcttatgca
154621 ttcaatgatg taaatttccc tctaagcact gctttttctg catctcacaa atattcatga
154681 gttgtatttt catgttcatt tagtttgaaa tatttttaaa tttctcttga tatttctctt
154741 ttgacccatg tgttacttag aagtgtgttg tttaatcacc atttttaaaa attttctagc
154801 tatctttctg ttattgattt ctagtttaat tccattgtgg tctgagagca tatattgtat
154861 aattttaatt tttataaaat ttgttaaggt gtgatttatg gcccagaatg tggtctatct
154921 tggtgaatgt tccatgtaag ctttggaaga ctgtgtattc tgctatattt gaatgaggta
154981 gtctatagac atcaattatg tccagttgat tgatggtgct gttgaattca actatgtcct
155041 tactgatttt ccacctgcta gatctgtcca ttctttgcag agggacactg aagtctccaa
155101 ctctagtagt gaatattcta tttcttgtta cagttttatc aacttctgct tcatgtcttt
155161 tgatgctttg ttgctagaaa catacacatg aagaattggt atgtcttttg gagcatgacc
155221 catttatcct catataatgc ccctcattat ttcctcgccc tgatgtctgt tctctctgaa
155281 agaaatatag cctctccagg tctcttttgg ttggtgttaa aatgacttaa ctttctttat
155341 ccccccttact tttagtttat atgtggtttt aaatttaaag tgggtttctt gtagacagca
155401 aatagttcag agttgttttt cgatccactt tgacaatctt tgtcttttaa ttggtatatt
155461 tggactattg atattttaag tgattattga tatagttaga taaacatcta ctatatttat
155521 tactgttttc tgtctgttac actacttgtt ctttgtttat atttttattg tctactcttt
155581 ttctttccat tgtggtttta atcgagcatt ttatatgttt ccattttctt ttcttagcat
155641 agtaattctt ctttaaaaaa acattttttta gtggttgccc ctagagtttg caatatacat
155701 ttacaactaa tctaagtcca ttttcaaata atactaaata atttcatgtg tagtgcaagt
155761 accttttaat aataaaacac tcccagttcc accttccagt ctcttgtatt atagctataa
155821 tttagttcac ttacatatat gggtatacct aagtatatac attatcatat ttatgattga
155881 atatattgat gaaattattt tgaaaaaact gttatcgtta aatcaattaa gagtaagaaa
155941 aatagttcta attttattat aaaatgaaat accttcattt attcattctc taatacactt
156001 tctttcttta tgtagatcca agtttctgac ctgtataatt ttccttttct ctcttcagct
156061 tctttgaaca tttcttacca gccagaccta ctgacaacaa ttttccccaa tttttgtttg
156121 tctgatagag actttatttc ttcttgactt ttgaagaata attccacagg gcacagaact
156181 ctagattggt gatttcttcc cctcaaaccc ttaaatattt cattccactg ccttcttgct
156241 tgcattgttt ctgagaagtt agatataatt cttatctttg cctttctata ggtaagatgt
156301 tttttcctct ggcttctatc aagatttttt ctttatgaac atgatatgcc tttctttttg
156361 aacatgatat gcctttcttt ttgaacatga tatgcctttg tgtcggattt tttttggcat
156421 tattctgctt ggttttctct gagtttcttg gatatgtggt atggtatctg acactaattt
156481 ggaaaaattc tcagtcatta ttgcttcaaa tatttcttct gttctttttt ttcctttatt
156541 ctccttctgg tattcccatt acatgtatgt tacagttttt gtagtcatcc cgctgttttg
156601 gatattctgt ttttttcagt tttttttcc ttcgcatttc agtgttggaa gtttctattg
156661 acatattctc aacctcagag attctttctt cagctgtgtt cagtctacca atgagtccat
156721 caaaggcatt ttacattttt attacagaat ttttgaccta tagaatttct tttgattcca
156781 tctttgaatc tccatttctc ttctgctttt catctgttct tgcatgttgc ctactttttc
156841 catgaaaacc tttagctttt tttttttttc tttttgaggt ggagtctcac tgttgcccag
156901 gctggagtgc agtggtgtga tcttggctca ctgcaacctc tgcctcctgg gttcaagtga
156961 ttctcctcct cagcctccca agtagctggg attacaggtg cctgccacca tgcctgagta
157021 atttttgtat ttttagtaga gatggggttt tatcatgttg gccaggcggg tcttgaactc
157081 ctaacctcaa gtgatctgcc caccttagcc tcccaaattg ctgggattat aggtgtgagc FIG. 1 (cont.) (SEQ ID NO: 1)

157141 caccatgccc tgcctttagc atgttaatca tagttgtttt aaattcctga tctgttaatt
157201 ccaacatccc tgtcatatct gactgtggtt ctgatgcttg ctctgtgttt tcaaatggtg
157261 tttttttttt tttgcctttt agtaagcctt gtaatttttt attgaaaggt ggacatgatg
157321 tgctgggtaa aaggaactgt agtaaatagg cctttagtaa tgtactggta ggtgtagcag
157381 agggtgaggg aagtattctg tagtcctatg attaggtttt agtcttttag tgagcctgtg
157441 cgcctgcagc ttggaagcac ttgtgaagtg ttttttcacc ccttttggtg ggacatagtg
157501 actagtgtga gcgggagttg agtatttccc ttcccctagg tcagttaggc tctgaaaaaa
157561 ccctgatagg ttaggcatgg taaaatagtc tcttttgagg gcaggcattg ttataagaat
157621 agaatgctct ggggccaggt gcggtggctc acgcctgtaa tccccgcact ttgggaggct
157681 aaggcaggtg gatcacctga ggtcaggagt tcgagaccag cctggccaac atggtgaaac
157741 cccgtctcta ctaaaaatac aaaaatcagc caggtgtggt ggcacacacc tataatccca
157801 gctactcagg aggctgaggc aggagaactg cttgaaccca gtaagtggag gttacagtga
157861 cccaagattg tgccactgca gtctagtctg ggtgacagag caagactccg tctcaaaaaa
157921 aaaagaatgc tctggcatat ttgaaaatgg ttacttttcc cttttttttct ctgatcttca
157981 ctgtgagaac ctggtaagca tcctataggc aaaattcata aaagtataga agtcggccag
158041 tgacttggac ccacttggaa ttttcttgct ctcacatcat gcacactgaa tctccagcaa
158101 tttttcactt acagtttagg ttttcctacc ctactactgg ttctctcaga ggtttctgct
158161 tattggtttc tgttttgtaa gttgtgattc tctgtaccta actgcctgtc tcccattttg
158221 gggggcagtg gtttgccctg tgacctcact tctctgacag atctaagaaa agttgtttat
158281 ttttcagtgt gctctgcttt ttacttgtta cgatgaagcc aaccactttc agaatttcta
158341 caaaccagat cagaatctgg aagtcctgtt tttttatttt ttttatccct ttgtttagca
158401 tgttacctat cttaacacat tttaaataag tgaatgcata gcttatatct acttctaggt
158461 tatatgcttc cttagaatag gaattgattc ttaaaatgtc gttctgctca cgcctgtaat
158521 tccagcactt tgggaggcca aggcaggcgg atcacttggg gtcaggagtt caagaccagc
158581 ctggtcaaca tggtaaaacc ctgtgcctgc aaaaaataca aaaattagct gggcatggtg
158641 gtggccatct gtaatcccag ctactaggga agctaaggca tgagaatcac ttgaacctgg
158701 gaggtggagg ttgcagtgag ctgagatcgc gccactgcac tccagcctgg gtgacaagag
158761 caaaactcca tctcataaat aaataaataa ataaataaat aaataataaa aataaaaaaa
158821 taaaataaaa caaaaatttt attctgagca gtctctgaag aatataaatt ctactgcctt
158881 gcctttagaa cttataacag catctcgcaa actatcacaa gatgctccaa acatacttct
158941 tatgtgctga attaagaagt caactcaaat ttagtatact agtaatattt ttggatatcc
159001 caaaacactg ccagctcagc tttaggctgc ccttcttggg ggggaaaaaa gcagttgaaa
159061 tttaggactt aagtgggcat ctcgtttaat ttttaatgga tttctatgtt gttggttatg
159121 gtgaagaggt gaaaagaata aatattctgt gcagaaaaat tattcagtct tcatgtgaaa
159181 acactttgtc catagcaatt actttatgaa aaagatgtgg tattactttc tttgctctta
159241 actgagacct ttaatttaaa gaacctatac tttacaagtt tttattttca atgcatgaaa
159301 aatgtagcag ctatttcaca acctttactt ttaaaatcca tttttctttt taatctcaaa
159361 tagtttttttc ttaaaacctt ttgacttttt atctaaattg taatagccag agcaccttcc
159421 cacaactaga atatctcatc ctttttgtct tttctttttc ctctcaaaat gcctactggg
159481 aacttaattt ggagtcagat tcttcatgat aaatctggac ttaatcaaaa ttcctcatat
159541 ggtatattgt atatatcaca gtactggata gtcctctgat taaatagata tttgatagta
159601 ctttaaggtc tatactttttg gatgaactta actgctttct ccatttgtag tctcttgaaa
159661 atacagaaat ttcagaaata atttataaga atatcaagga ttcaaatcat atcagcacaa
159721 acacctaaat acttgtttgc tttgttaaac acatatccca ttttctatct tgataaacat
159781 tggtgtaaag tagttgaatc attcagtggg tataagcagc atattctcaa tactatgttt
159841 cattaataat taatagagat atatgaacac ataaaagatt caattataat caccttgtgg
159901 atctaaattt cagttgactt gtcatcttga tttctggaga ccacaaggta atgaaaaata
159961 attacaagag tcttccatct gttgcagtat taaaatggcg agtaagacac cctgaaagga
160021 aatgttctat tcatggtaca atgcaattac agctagcacc aaattcaaca ctgtttaact
160081 ttcaacatat tattttgatt tatcttgatc caacattctc agggaggagg tgcattgaag
160141 ttattagaaa acactgactt agatttaggg tatgtcttaa aagcttattt gcgggaagta
160201 ctctagcctt attcaacaga tcactgagaa gcctggaaaa acaaatcccg gaaactaatt
160261 attatgtgcc agttatataa acaagaagac tttgttgggt acaaaccagt gattccttgc
160321 ctttgaaaaa tgtgtcagat atcatgcatt accagcagtt caatgatata aggaaaccag
160381 agtaatagct aaaaccttta aagctaaacc aaagatttac aaattgcctc ttcatccagt
160441 ctttcccaac ctaaaaactg agttctctaa aaattttagt attttttttct gaagaaaagg
160501 gaacatggac atttatctaa tcctcattag aaatctgact aatgataaca aggatttaga FIG. 1 (cont.) (SEQ ID NO: 1)

160561 cctcaagcac ttcttaccaa aattcttgat atgaccttat agcaaattac tttcacctgt
160621 tgaactttcc tttcttttat tcccctgtac ctcacctgca ctgggcatat tcaagttgct
160681 tatacaacac tttactattg tgttagaaaa atcatgacac atgatgaatg tgtttgtgca
160741 acatgagctg attcataaat gaaaatgtgc attgaaattc cacaatattt taaaattagg
160801 agtttatcta gcaattgaac aaaattgatt aaatccatta tttgttagat cagctaaatt
160861 acataagttc attcatctgc tcataaatcc atccattctt ccatctggct atcccttagt
160921 caattcaaat aaatatttat ggggcacttt gggtaagcca ggtgctaaga attcaatgca
160981 aaacaagata gactcccctg tccttgttga acttatattt ttggtacaaa caaaagcaat
161041 aatcaagaaa aaataaaaaa agtactgatt gtgattaata atatgaagaa attcaacaga
161101 gtattgtact taacatttga ttgatctgat ttctcagtt gtctgagaac aaacatttgt
161161 gaaaatctca ttgtagagtt cttacgatgg ataggggtc aactgtgtca ttattgctta
161221 tcagcttatc ccaaagacct agtttattac cagattgcaa atagtgttca ataaattatt
161281 cttattaagg gttgttatgt actctaaaac atttattgtg gtcccttcac tggttctggt
161341 ttacaaactt actttctat gatgacatag tatagaaatt gagagtgaat atttagaagt
161401 tcatttttat tatatatttt tgaagtattg atatgtagtg aattagaaat ttaaaaagaa
161461 aacaaaactg tccttcacta cagattgaaa agcattatac taaaagacca tttgctcagt
161521 tatagtatat aaaggccaaa tgacttaaaa acaaattatg taaggagaag gaaacaacca
161581 tttattcagt gccactaact gtcagccagt tttttcagtg gtcagttaat gactgcagta
161641 gtgttctacc ttgctcaaag caccctcctc aagttctggc atctaagctg acatcagaac
161701 acagagttgg ggctctctgt gggtcacctc tagcacttga tctcctcatg cagtgcatgg
161761 tgctctcacg tctatgctat gttcttatgg tctttaggta acaagaataa ttttctttct
161821 tttccttact atacattttg ctttctgaaa ttcccttctc gccaatccag gtgaatgtca
161881 gaatgtgatt tgacaactgt ccaaagtact cattcactga ggagtggtaa ggccttcgcc
161941 caacctgcct tctctgggaa tatactgctg cctgaacata tcattgttta ttgccaggct
162001 tgaacttcac caaattaatt tattagggtc aacatctaaa tattagaact atttcagatt
162061 aatttttaag tcgtatccac tttgggtact agatcaaatt gcaggtctct gcttctggct
162121 tgagcctatg tttagagatg atgtgcatga agacactctt tgcttttcct ttatgcaaaa
162181 tgggcatttt caatcttttt gtcattagta aaggtcagtg ataaaggaag tctgcatcag
162241 gggtccaatt ccttatggcc agtttctcta ttctgttcca aggttgtttg tctccatata
162301 tcaacattgg tcaggattga aagtgtgcaa caaggtttga atgaataagt gaaaatcttc
162361 cactggtgac aggataaaat attccaatgg tttttattga agtacaatac tgaattatgt
162421 ttatggcatg gtacctatat gtcacagaag tgatcccatc acttttacct tataggtggg
162481 cctcttggga agaactggat cagggaagag tactttgtta tcagcttttt tgagactact
162541 gaacactgaa ggagaaatcc agatcgatgg tgtgtcttgg gattcaataa ctttgcaaca
162601 gtggaggaaa gcctttggag tgataccaca ggtgagcaaa aggacttagc cagaaaaaag
162661 gcaactaaat tatatttttt actgctattt gatacttgta ctcaagaaat tcatattact
162721 ctgcaaaata tatttgttat gcattgctgt ctttttctc cagtgcagtt ttctcatagg
162781 cagaaaagat gtctctaaaa gtttggaatt ctcaaattct ggttattgaa atgttcatag
162841 ctttgatagt gtttttcaga agaccaaatt tacagtggga gccttgggct tttgtttttt
162901 aacagctctt ttttgttcct gcttcagtgg cctgacctcc aagttagcaa tcgccaggtt
162961 gagaaatgct ttgcgagaca taacagatgc tcctgaaata acaaacactt ggaatcatga
163021 ggtagtggaa ttgaaaatag aaagtgtagt gattgttttt tgttatttgg atgggatgaa
163081 caatgtcaga ttagtctgta actattttt tttaatgtca ctctgatttg gtcacaaagg
163141 atctctagtc tcattgcctt agtatcattc tacgaattag aatgtgttac tgtgtaagag
163201 cacttcttgt atatgagaga aatagcaaca gttccagttt aaagtgatat aaatggaaac
163261 caagaaatgt ctttactggg accaaatctg gacagcattt actgtatttt tgctggtatt
163321 ttctctagtc tttccgggta tattcacatt taatgatcac ttttctccct ttgtgctaat
163381 ggacactgaa tccattccac taccatagtt cttgctaata ctactctact ttttacacaa
163441 aattaaaatg ccaggagcac ctccaggtag actgactata aatctagact gaaaaaaaag
163501 cttgtatttc ttaacagatt accttgtgga acatttgctc ctttcaacta atgaggcact
163561 aaatattgta actgctcaac tggtgctttt aatttatttg tctagacttt gtcatgttgc
163621 cagaagcttt atcctggttg gagttttgaa aacagtattg tttcttcaga aagaaaaaag
163681 ggattgtcag atgatctaaa aataaagaaa cactggaaat acaagtatcc caaggtgata
163741 gcattaggca agataaaaat gttgaaaagc gaaaaagaac tggttgatag agaagtgttg
163801 ttattcagta gaacctaagt cttgtggtcc catttttaat gaaaaatggt gaattttttg
163861 gtttttattg ttcttgttca cacaaatctg cccattagaa taagccaagc cctaaaaatt
163921 aatttcagtt tcactgggaa tcctttagtt tatctactat gtagtagaga ggttttgttt FIG. 1 (cont.) (SEQ ID NO: 1)

```
163981 tattgcatgt ttgacgtagg aacgtatata tgcaagacat ggaggaaaac caagtgggcc
164041 agagttttga aaattcttta tcttttcttt ctgccaaagt gagtctccca agtttgtctt
164101 ttttttttca tttccactct tctatggttt ctagcattat ataaaccaaa caaaaaaaat
164161 acgttcagag attccttcag aaatgctgga tgatcttgat atcgatgctt ttcatatatg
164221 tgtttatgat gctggtttct ggggctggct ctcagtatca caaagatgtc tgtaaacaga
164281 atatgctatt tcttctttgt gacaaatttt gaacattatg tgaatgtcca agaaagagca
164341 aaagagggca aacttctcat acatttttga tgtcgaaacc aagagacgct tttattttcc
164401 taacttttct ttgaaagttc aaattaagta attttatcct gtcctaaagt ttaaaaagaa
164461 aaaaaaaagg aagaaggaat taaaaatcca aagaaaatta tgtttgtttg cttttctgtt
164521 tttttcttcc ttccaactcc gagactttgc aagggcatag ttctgaagat ctctgacact
164581 gagacattag agatctctgt atcaatggat catttgtttt cagacatatg aaacaggaac
164641 tttgaacaag aaatttcccc tctttttctc atagtgatcc tgagacatca gctgtggaat
164701 cacaacacgt cattagtttt ggcaggtcct tgcaggtgtt ttgttttgtt ttattaatgt
164761 tcttccctcc tgtagctaga cagcaatctt ggagaatctg ccagcttgga agactattgt
164821 gtaaatttca aggtggagcc tcctttaatt tgttctgtgt tacctgtgag ctgtgaggtc
164881 atgaagagga gacaatgagg ctaatcatga gagccccatt ggtttaggca attagaacaa
164941 caagatctaa aatggtttat tagccttgaa ttgtgttaag cacataattc ataaaaaaca
165001 gaaaaaatat ttttaaatgt atgtctaaat cttcagttac aagtttgaaa ggtgacaaac
165061 tattctgagg aaatgattag gcctattctt gcaacgagtc tttatgatct gaaaagaatc
165121 tatgtccaca cataactccc acctcaaaga tggggcatct tttgctctgg gagatatcaa
165181 atgcgaccaa aacaagtgtt tgtagatttg aatgatgatt cagcagtgta gcagttctca
165241 ctcattttat aataattaac aacttaataa ttaattatta aactcctaca tgcttaacat
165301 tataagtatg ataacttctg tggttacata aaagatatac atagcacttg tccttgatct
165361 gtcacagtga ggtcccaatc caacctatga gcttcaaatg aaaagttcaa aattacactc
165421 attgtcataa gtcagagatc aaaggaagaa aggatttaac caaaatgata aattaaatat
165481 aggtgattaa atatagtcat ggttcaaggc atgggccagt tagggagtgt gatgtgggta
165541 attatgaaag gccagctccc aagccctgtt gttgctactc ccccacatca gtcatccttc
165601 ctttttttct acttctactg cagtgccttc ctcatctttt cccttgcatc cctccattat
165661 atgagtcata caaattagac ttttcaaagc aacattaaca ttgtgtgaat ttggggtttt
165721 tgactaatcc caacattcca cccccacatt ccagtcccac atgggatttg gagccttgtt
165781 tataaacctg gcacttctaa tatatcttat cttagagtaa tccttgtatt tgtttaattt
165841 ccacttagca ttgtaaatac ttgcaggtat cctagttaag aaagcaaggt ttaaacacaa
165901 aatcatcacc aattaaagca ggctagataa agaatgtaat agaaatgcta gataaaacag
165961 atttttttctt actaagtttt ctgtccctta tagagtgcat aacacaataa cttgcttgat
166021 aagaattcaa tgtacattgt tttgtgctga atcactaaat gcttgatttc tgtaacaaga
166081 gattgtggtt ccatcagtat ctggatttta gtctgtgtaa tcttaggcaa gttatttgat
166141 ttctctgtgc ctctgttttc ttgtctgtaa aatgagtata atggtagtaa ctaattcatt
166201 gtgtttttgt gaggattaaa tgagttaata actagtactc ctccctggca catagtaagt
166261 acaatatgct gtgctgtggt ggttgttatt attttttata gttccttgag caaaagaaat
166321 aatgtcccca tcttagtata atattggagg tatataccat agaagtgaac aaaagaatat
166381 agtttcacaa agaaagtgat aattaaggcg gttcataaag ggtcataaag cttgtagatt
166441 ttagaaatgt gggggcatga ggatgtggag agggtattcc aggatgccag acagggagat
166501 tatggatgag tactaagatg agaactagaa aaagctgagg ggcaaaaggt cagaggaggc
166561 cacaagttag ggagtattag gaaaaagaag ttaatacttg acaagtgcca acatggcttc
166621 acgaggaatg ggttgggcct ttttgagtga ggaagaggct ggtgaaaggg tggtggagga
166681 cactgctgct gctgatggca tggggtgtag gtggcaggag aggcagggac atgagctagg
166741 aaactctcca gctatgaagt gatgagtctg gagtaatata aggacagtag gggtggagtg
166801 ctgaacttaa gggaggagag aaaaataatt ggtatggaag taggtacaat gcaattttat
166861 tatttctgag cctaaaaatg tgaaattttt gattatttgg tcagaccagg gaagtatttt
166921 cttttatgct atctctgaaa atgtatacac taaaaagttg tagtataaaa aggttgtaaa
166981 gcattaagta attttagagg aaacaataat ttggatattt tacatgcaat catttatatg
167041 caaatatatg taaatattac aaaattattc tctatttgtt acaaacctta aatatttttg
167101 actgaggaat attttattca tctaattata gctactttgt tctaactaat agatattctt
167161 gaaaacaaag caacactttt ttggagacag agtcttgcac tgtcacctag acttgagtgt
167221 gttaccttga actccagggc tccagtgatc ctcccacctc agtctcttgg gtaggtggat
167281 tacaggccca cactaccatg cccagctgta ttagtccatc ctttcattgc tataaagaaa
167341 taccggaaac tgggtaattt ataaagaaaa taaatgtaac tggctcacgg ttcttcaggc
```

FIG. 1 (cont.) (SEQ ID NO: 1)

167401 tgtacgggaa gcatagcagc atctgcttct gaggaggcct caggaagttt tcaatcatgg
167461 tggaaggcaa ataagaagca ggcatgttac acgacgaatc aggagcaaga caaagtgagg
167521 gaggaggtgc cacacacttt gaaatgagca gatctcatga gaacagcgcc aagaggatgg
167581 tgctataccg ttcatgagaa atccaccccc atgatccagt tacctcccac caggccccgc
167641 ctccaacact gggaattaca attcaacatg agatttgggc agagacacag atccaaacca
167701 taccaccagc taataccaaa aaaaaaaaaa aattttttt ttaagacatg gtcttactat
167761 gttctacagg ctggtcttaa actcctggcc tcaagtgatc ctcccacctt ggcctcccaa
167821 agcactggga attcagacat gagtaacagt gcctggccaa tacttatttt taaacattct
167881 ctaccataaa cttaggatct tgatttgttc acattgaaca gatttttatt atacagattg
167941 aatttataag aaaatgttgc agacattgtc aaaaagggac gtccaaacca ctgtgatatt
168001 tataagcatt tgggccacat tttgatagaa ctatacacgg agtgtgtgtg tgtgtgtgtg
168061 tgtatatata tatacacaca cacattattt atatatatgt atatatgtat atatatatat
168121 gtatttatat atatatgtgt atatgtatgt acacattatt tacctaccta ctgtgtgagt
168181 gtgtgcatat atacacgcac acacacacac acaaatatat atatttccct tctgagacaa
168241 agccaaacag cactgtatgc ttaaagaaaa acagtcacac ttcccactta tgtaatttat
168301 attacatcca gtcaccacac cagccaaact gctttattgt tttttgtttg acatccaatg
168361 ctaaagcata atgcctgttg cagtgaaata tacatgagca accctgagaa ctcaatatag
168421 cctcacgtgt tgccactgag ttgagttgag gagtcaagct gtagcaaaaa ggtttgtcac
168481 cgggtgagta atggtgctct tatttttctc tgggtctcaa gaagtgctct ttatgacata
168541 tatggcatta aataaatatc agatatttgc acatcctaac tttcctattg gtgaagtttc
168601 ttaaaagaga gataaagggc cattgtgtga ttgatagttt caggtatatt tttgctgcac
168661 agtcagtccg agtgtaccac gtagggcaaa ccacgtaact tctcagggcc ttgactgttt
168721 catttgtaaa ccagagaaaa ggacttgggt gacctccaaa gacctttcaa atttggagat
168781 gagtttgtgg aaagttcaaa cagtttagaa aacagaacta agacacccac tggcacccct
168841 ggaagcaaga gagtgccagg tactatttgt aatacaggaa tgaaatacct aattgtatga
168901 aattgaattc taactgaacc agtttgttca gttaaatttt ttttttcaat tagagtgctt
168961 acttcagtat ctaacactag acagtaaact gtagacaaaa gacctacaga atttctgaat
169021 ggtatcaaat tcaccacact taaaactttg ggatgtctaa tttcaaccaa cagctttctt
169081 tcttcataat gttgaatata tgtgtatcta ttttagctaa atttaatata tatcaatata
169141 ctttgataga tattttatat aaactattag actatagtat tatgagtaaa agacccacca
169201 tttcccaagc aattataaag aacgatcaaa attttaatgg gttgttagta ttatttcttt
169261 aaagattgtg atactgataa atatttggcc acattttaat agaattatac atgggatgtg
169321 tgtgtgtgtg tgtgtgtgtg tatatgtgtg tgtgtatata tatatggcag tagagatata
169381 tatatctaca cacatctaga tatatatata catgtatatc tatatataca cacatatatc
169441 tgtgtgtata tatacatatg tatatatacc tacatacata tgtacatata catacatgca
169501 tatatctgta catatatata tagtgtgtgt gtgtgtatat atatatatat atatatattt
169561 tttttttcct gagccaaaac aaaatactag gttgtaatag ctgttctttc agaaggaaga
169621 aaaacaacat gtgctgaact ctgagtttga tgtttttgta ttttacttcc tattttcata
169681 tcagtccatt tatttattca ggaagaattt attgagcata tattatgaac acagcttttg
169741 ctaaggacag ggtatgcagc agttatggcc tagtaggaga tatggatgtt aaaaacaaaa
169801 tgctcacaaa tgcacatata atcttaatac tcattgtaag ctatgaaagc agagtgtgag
169861 tattatgaga ccatatgttg ggagatttta tttggtattg aggatcagga aagatacccc
169921 tgaggaagtg atatttaatt tgaaacctaa agaaagcagt tggccatggg aagaaggtag
169981 ggaatgagat tcccaagcaa taggaatcca atgtgtgaag aagctgaggg agtgaaagaa
170041 agctagtgtg gtggcaggaa gaaagagaag agaatggaga agggcactaa atgagtcaga
170101 gaagtaggag gggctaaacc atgtagggtc gtgtaggcca tcttaaaggc ctgagtgtag
170161 tggaaaacct ttgaaggttt gttaaaaggt caatgaaatg ttctaatttc tgttgtagtg
170221 aattgctttg attgctgaat gcgaatggat gggtagagat gcaagagtga aagggaagaa
170281 atcaattagg aggctcttgc cctgctccag ataggactga taattaattt tatttgggaa
170341 gatcagggag aaagataagt catgaatgac tcccaagttt ctggattgaa gaaatgaagg
170401 taccatacac tgagatggga aagcctaggg gtagagtagc tttgagaaga aaggtagcat
170461 ttccccattt cataaaacat ggaagaacaa agaggctgga ttcctgtttg tagacatacc
170521 ttccaggcca gaactgcatt actacaacat ctttgcaagc cacattgcct ttcataactc
170581 tgtgtcagtg ttgatgccgt aacatctttg gccttccccc taccatcctc ccgcagtcct
170641 ccatgataat gccattattc cgtttcaaat tgtgtgcttc cattggatgt gtgagtctcc
170701 ttgaaagtta taatgaggct gtagcccata tgaaatgctt caactcaggt cctgcatagg
170761 aagaggaagc taatctctcc aggaactgag cctgtggcta gagggatgga taattgttta FIG. 1 (cont.) (SEQ ID NO: 1)

170821 aataaagaat atgctgctga gtactgatgg gctctttatg tacccatttg gctgctgctg
170881 cccaaccttt aatctttcct gagctttaaa taggaaggaa aaaatggtcc acaaaggatt
170941 tgagccattt tgctgtggtg atgaggagca cgggtttaga gacaaacact cctgtgtttg
171001 aattccagct cctactatct cctagctaag tgaccttgga caagtcactt accttctcca
171061 acctgctgtt tcttcatgta cgtaatagga tttacctcat gaggttgaca tgaagattga
171121 aagaggtaac atatagaatg agcctgtccc aggacatggt tcatgataag tctgccataa
171181 atgggagcta tgtgtcccac ccttttggag gagataactg ttctgtagca ggtaatatat
171241 tgtttgatac ttggttaacc cttacaatta tcatttcctg ttcttctcaa taatgctaga
171301 aaccttttat ttaaagaacc acaatataaa atgaaaaata tataaaaaaa gcaaatggaa
171361 aaattctatt ggcaaggctt tttaacttta tatactaaat aaatccaatt gcttaaataa
171421 tgaactgact caagttctca gcactgcttc ttgtttaatt ctctttagtt tttcagaatt
171481 ctccaataat gacctttgtc tactctcttc agtttattca gaaattactt ttatttacat
171541 agaagtttgg aagtggatac acaaacatat ccctcacata tcttatgatc ctatgagtca
171601 tatactcatc tcttatattc cctctgtaaa gcaatgtagg tacctttcag gaaggtgatt
171661 tttatgtagg ttgagaaata tcagcatgga ggtcctagct gacctctcta gagagtttct
171721 gagacatttg acaacaactt tttctttaag tcatcagtta tgccccgggg tatgaaattt
171781 ctaacatgat cctcagtaaa cttggctgcc ttgctgagga tactctccat ctgcctgaga
171841 gacacagaca ccattaattg ggaattgact tgacttgtgt ggttccttgt ggaccagatg
171901 gccactaaat attctcattt caaggcaatt ggtaaaaact acacttcaag aaatttcatt
171961 cttaattccc cttagtggat gttattaacc aaaggcaaaa gaaaaaaagg gtaaaaaaaa
172021 tattctaaat gttaatatca aaaatattat tttcaattca ccccaggcac agagaactaa
172081 gtattattat tgctattgca ccggcattcc ccaatgagac agtgattttc ttttaagaca
172141 tttttaaata atataggcag aattaagtag acggtgatct ggtaagtaga tgtttcaggg
172201 taacagctgt gcaatgctcc atgcagggaa ttagattgtc attttattcc ttaccaggaa
172261 catacattca gttaaacaat tatttgactt ctgctcttcc actgatttct aagttgaggc
172321 tctctcttgt gcctgtctga tcagataagt agagttgtgc cttggtttat agatgagata
172381 aatgtgtatt tgaataagca taagttaaag aaattttaaa atcccttagg aagctaggct
172441 tatcagagaa atccaaggaa atacattaac aaactaggaa tttgttctaa caggttaatt
172501 ataactcata aacttattgg gttttttttac cttttaattt tatattacat ttgcttataa
172561 taaggaatat tgctaggaat aaaatttttt aatattctac aattaacaat tatctcaatt
172621 tctttattct aaagacattg ggattagaaa aatgttcaca agggactcca aatattgctg
172681 tagtatttgt ttcttaaaag aatgatacaa agcagacatg ataaaatatt aaaatttgag
172741 agaacttgat ggtaagtaca tgggtgtttc ttattttaaa ataattttttc tacttgaaat
172801 attttacaat acaataaggg aaaaataaaa agttatttaa gttattcata ctttcttctt
172861 cttttctttt ttgctataga aagtatttat tttttctgga acatttagaa aaaacttgga
172921 tccctatgaa cagtggagtg atcaagaaat atggaaagtt gcagatgagg taaggctgct
172981 aactgaaatg attttgaaag ggtaactcca taccaacaca aatggctgat atagctgaca
173041 tcattctaca cactttgtgt gcatgtatgt gtgtgcacaa ctttaaaatg gagtacccta
173101 acatacctgg agcaacaggt actttgact ggacctaccc ctaactgaaa tgattttgaa
173161 agaggtaact cataccaaca caaatggttg atatggctaa gatcattcta cacactttgt
173221 gtgcatgtat ttctgtgcac aacttcaaaa tggagtaccc taaaatacct ggcgcgacaa
173281 gtacttttga ctgagcctac ttctctcctc actggtatgg ctccaaccat caggccctat
173341 cttggtccat ttaggctgct aaaataaaat accaaagact gagctgctta taagcaatct
173401 ttggaggctg agaagtcaaa gatcaaggtg ccagcaggtt tgctgtctcg tgagagcata
173461 cttcctggtt cattgatggt gctttcttgc tgtgtcctca cataatggaa agggcaagac
173521 ctctctggtg tctcttttac aatggcacta atcccatcat gagggctttg ttctcatgac
173581 ctaatcacct cccacatgtc ctacattcta atactatcac cttgggggtt aggattttaa
173641 catatgaatt tgaggaggtg gcgggggga cacaaatatt tagaccatag catttcactc
173701 ctgacctcca aagttcatgt cttcttcaca tgcaaaatac attcattcca tcccaatagc
173761 ccccaaagtc ttaacttgtt ccagcatcaa cttacaaggc taaagtccaa ggtttcatct
173821 aaatatcagc taaatcagca caaacagcta aatcaggtag agtgggactt aaggtgtgat
173881 tcctctttag gcagattgct ctccaactat gaaattgtga aatcaaacct attatgtact
173941 ttcaaaataa aatggtgaaa caggcacagg ctagacagtc ccatttcaaa aaagagaaat
174001 agaaaagaaa aaaggagtga caggtctcta taagtctaaa actttaaggc ttgagaataa
174061 tttgctttgc tttgcctcca ggctcactgg ggtggtgtct tacctctgga cacactgggg
174121 tggaggctct atcctcatgg atttgagtgt ctcattcttt gtggcaggtc tgtgctccaa
174181 tcccacacct atggctccct gagtgtgcaa ttgcatgcct ggtggttcta ctggtctggg FIG. 1 (cont.) (SEQ ID NO: 1)

174241 attgcatagg tggcccagcc ttcatagctc cactgggcat tgccctaatg tgggctctat
174301 gtggtgacct cacccctggg cctctacctg ggccctgtga ctccctgggt tcttgaaatc
174361 taggtggagg cagccatccc cctacagttg tgctgagtgt agtgcatgag tgctggggtc
174421 tgctagagct atacctaggg tggtggagat gtatggcaat ggagtatggg gagctgatat
174481 ggtttgggtg tgtccccacc caaatcttgt cttgaattat aatttccata atctccatgt
174541 gttgagggag ggacctggtg agaggtgact ggatcatggg catggttttc ccatgctgtt
174601 catgtgatag tgagtgagtt ctcacgagat ccaatggttt cataaggcag ttttccctgc
174661 tcttgcaccc tctttcttgc ctgtcaccat gtaagacata actctttccc ttccgccatg
174721 attgtaagtt tcctgaggcc ttcccagcca tgtggaactg tgagtcaatt aaacctcttt
174781 tctttataaa ttacccagtc tctttacagc aatgtgaaaa tgtgctaata caggagcaaa
174841 gactgcagtg tgaggtggca atgtgaagtc tgcaatgtga ggtggcacgg ggcagttgta
174901 gcccctcctt tgaaatcttt cttccctacc ccaggcctct gcactctgaa ctatgatggg
174961 aaaggcagct tggaagatct ccaaatggct ttggagtcat tcttccattg tcttggacta
175021 taaattctgg cttctgttta ggtggctgac taatatcccc actgtctgaa tgcatagcac
175081 ctagtttctg ttgagatggc tagtccatag taatttactt atcaaatttg gccacaccct
175141 ttgtattctc tcctgagcag gctttctcat ctttcacaat atggataggc tgagaatttt
175201 ccaaattttg aagttctgct tccctttttga tcaataattc cattttaaag tcatttctca
175261 tcttgaattt tactatgagc agtcaagagt aactaagctg ctccttcaac tttgcttgga
175321 tatttcctca gtcaaacatt caatttcatt gctttcaagt tctgccttcc acaaaaacact
175381 aggacacaaa cagctcagcc aagttctttg acattttata agaaggatag cttttcctcc
175441 attgtccaat aacatgttcc tcatttccat ctgaaaaccc atcagattgg cctttaccgt
175501 ccatatttct gggaacattc tgctcatgac cacttaggta ttcggtaaga agatagtagc
175561 tttctctata gctctcctcc tctctggagc cctcaccaga atggccttta attgtccatt
175621 cacagcaatg taggcttttt ctagcatgta cctgaaaact cttccagcct ctactcatta
175681 ccttgttcca aagctgcttc cacattgagt atttgttaca gcagtaccca gatcccagta
175741 ccaatattct gtcttagtcc attggggcta ctacacgatg tcttataaac aacagtaaaa
175801 tttatttttc acagttgtgg aggctgggaa gttcaaaatc tggtgccagc agattttgtg
175861 tctggtgaag gccttcttcc tcacagatgg ctgtgttctc actgtgttgt tacatggcag
175921 aagagtgggc aggctagctc tctgggatgt cttttataag ggcagtaatc caaatcatgg
175981 gtttagggta gagccctcat gacctaaatc acctcccaaa ggccccacct cctaatacca
176041 gcatctttga agttaggatt tcaacatatg actttggcag ggggacagaa gctttcagtt
176101 tatagcaaac cctataggta gcactacttt gtcctttcct aatcaatttg cgtcaatgaa
176161 acatgaatta gaagagacct aggcgactcc actatactgg gattattccc agtataaatt
176221 atcatctctc cacaccttct catctactcc ctatctgagt tctgaagctc tccactacaa
176281 gaaggaggct ttggtttgac ttgatatact tctctgggaa acaggtttag cataaaacag
176341 tgatgctcat tctagaacac ctgcaaatga caatagtttt ctttcgaagt cgccaggaat
176401 cgtctgcctt tgggtatgtg gctgtgagca ctgccgggca aaatgccata tgacctagat
176461 gaggcatatg ccatcctttg aagccattag gacattatat aggaaatata ttaactaaaa
176521 tggaataaaa ttttctaaat aacaccttat gtttatccaa caggtggttc attatacttg
176581 agagcattat acagaggaat ttgatgggga ggagagctgg agaaattctc gaaattctgg
176641 gtttctttaa cagaatactc tagctataaa cttataattt taaaaaataa gcattatatt
176701 aaagaaaagg gaacataaat tattttgttt tattaaactt aagtccaaag gtctggattg
176761 tggcagaata ggatcagggg acctaaaatg ttgagcctca aaggtcttct tagagaacaa
176821 ctgtattcca ctattagcgc ttttggtcct tttagcccaa tttctgttta tcccaaatgt
176881 tcttcccttt tctgccttcc ttcacagtgg accctgccag gagctttgaa atgcctgtga
176941 gtgttaaaca cttaccccatt gagtgcccaa ccttaacatg cccctaataa aatgtactta
177001 gattaaccgt tttcattatc aaagtttcct tattacccaa caaacacagg cgctttaaag
177061 aaaacattaa ctaaattgca agtgacacat tttaagatct ttgatatgac ttcagagaat
177121 gcactatagg aacacaatgc aatgggaggg aaacttggga gggaagacat tagcctttat
177181 aaaatctgca agtattgcca aatcaaaata aaatttacag gaaagcagga tcataaatat
177241 aatctaaaat cttagaacct gtggttatga ttttaaatac taatacaatg caaaattttt
177301 acctgtttag gtttttattt catcagttca tatttaggta tatactttta ctgttctcct
177361 tttttataat ttaccattca caaagatgat gatgttagtc taactttaat gtcatgagtg
177421 ctttgagtag tagtgctaag tttttgttga gtagtagtgt gctttttttga ttagtagtga
177481 taggtttttg atgagtaagc ctgctagcag catacaaaca aacaagcaag tatcagccta
177541 gagaagcaga aaaggcattt gggtttcaaa gtcacaaggc ctaggcttta gtctaataca
177601 gctgataata caatttgtcc aaacaggaca tttttgggtg tgtcaaacac taaactggac FIG. 1 (cont.) (SEQ ID NO: 1)

177661 aggacattat gacaaaagtg caaagcagga ctttccgggg caaaccagga tgtatgtcat
177721 ctcactgagt cctctctttg tccttgccat gactagtatc tctagaggta aatgaacaga
177781 gtaatgacaa atagccagac acctgaatct tatcccaaca gcacctccta cataattccc
177841 cattatccca aatggaaatt aaaaatatat acagtgataa ttccaggcca agaaatgctt
177901 tatttctagc ttggacttgg cttccatgtc cagtgtagaa tcttatcctt gctgatctgg
177961 actgtatctc atgaagccat gacttgtacc tagttactag ctggaaggct tagaacaaaa
178021 gctggtccag agagcctcct ttttccttat ttcctgggtc cacaccttta ccatggcagt
178081 ctgcctatca tttgatggag gaatttaaag caagtccaag ggaagggaag agagtttcta
178141 aaatctagaa cttggatagt ttaatttacc tatcccaaaa cagcttaggc ccagacagct
178201 tctctccaag attggtgcca aactgaaatt accagctgtg tagaccaaag agaatttcaa
178261 aagaaactga atcccaagag aaaaaaaaaa gacttctggc attgtggccc aataaattgg
178321 taggattgtt gtgacttttc aagtttacat gtaaaatggg cccagcgcag tgcctggcaa
178381 atatgggtac taagtaaaag taactataat catgtttttt taatctggac ttcacttggt
178441 catcctttaa atggtgtctg acagaatcct agttcttgtc tcactttact tagtttccct
178501 gggaaatttc atgtgtcctt ttggctttaa ttaatatctc tattttgatg acctccatta
178561 tctgcctatt cccagagctt tccacctgat atctcagcac atgaaaagca ccttatgtca
178621 ataagtgagt tccttccctg ccccaccaca tacctgtcct gtgttcctaa ttccactgaa
178681 tggcatccca tcctccagtt tcccaaggcc aagacctggg actcatcttt cactctcaag
178741 ttcctccacg ggtacccaca tgtcacatcc tgtcaatgct gtccctgggg agtatctgaa
178801 atatattcac ttttcttcat ttccacctga caccactatt aacacttgca caaatttctg
178861 aggttcctgg ctcatttccc tcattgaccc ccaatagttc attctgctct ttgcagctct
178921 ggtgatcttt ccaaacccca catctgatca cttgtttctt cccttcatat ggctccttaa
178981 tgccttctgg actaagtcca cactgcttaa ggtggcttac caggtccttc atgattttgt
179041 ctttgtttgg ctttctacac tcactgccca acttcccctt acttcccatg attcagttat
179101 actgaatttc tttggttctc taaagcacat gtgctttctg ttctgcagag gctttttttgt
179161 tcacttgcta ttctctacct gggaaactcc cccagccctt cactgcctcc ttctaccatc
179221 tttcaggcct ctccttacac atcacttctt tccaaaaatc tgccttgaca ctccaggtct
179281 cggtttccta ggtgtaccct ataactccac ccctttcata gcatttctca ctctggctgg
179341 agatttacct tttaacttgt ccatgtcccc cactggagtg gaagttcctg gaggtcaggg
179401 attatatcct attaattgtt gtatttccag tgcctagagt agtcttgcat acatggatgg
179461 tattcaataa atattggttg aatgaataag gagttctttc atttcatatg taatagatca
179521 tggaaatagc cttgtgattg atacacagca ggtattacca tcctcacttt agaatgagga
179581 ctcagagcct tgagatgtct gagggccttg actgggacag ctggcagatg caggagcaga
179641 gctgcatcac ccctgtgggc tatctcaggg ttgtctgtaa tctaagtaca atgtctgttg
179701 attttggact gaaggctttt tgggtaattg tttgcttttt caatacttat aaaatagttt
179761 ccatccttac tcattgatag taaggttagt tattttagaa aacaagctaa atagcagaaa
179821 tagtggcctt ttaagttgaa aatttaccct gaaaaatcta cagagtagca aacagagtat
179881 caaaaggagt tgactgtatc tatttttata actgccactt atggattatt cagtaaaacc
179941 acaattcact tttatgattt tttttcatgt ttctctgtca caagagcaaa ctcttgctcc
180001 ataataacat tccagaatac agcaatagca aaagtcaaca ttttgaatcc tttacaaact
180061 cttagacatt tttttttttt tagtttaaca tgttacaaaa caaaatttct tcttttttca
180121 cagcagtttg ggaagtacat actatttatt agctcatcag catgaagctg gaaaattctt
180181 tttcctaaag ttctttatat ctacaaactg ttgatgtttt catttattta tttttaatgc
180241 tacgttgtaa tgaaaatcat tggaaaactt tagattctag taattttgaa gtcttcttag
180301 tttggacagg actgagctaa agtttgtact ttttttaatt tattgaaaaa tggtttctaa
180361 tgatagtatt aacaagatta tattgggggc aggacgcagt ggctcacact tgtaatccta
180421 gcactttggg aggccgaggc ggttggatca cctgaggtca ggagttcaag accagcctgg
180481 ccaacatgta gaaatcccct ctccactaaa atacaaaaat tagctgggca tggtggcagg
180541 cactgtaatc ccagctactt gggaggctga ggcaggagaa ttgtttgaac ctgggagtcg
180601 gaggttgcag tgagcccaga tcgcaccact gcactccagc ctgggcaata gagcaagatt
180661 ctgtctcaaa aaggaagaaa gaaagattat attggggata tatatgtgtg tgtgtgtgtg
180721 tgtgtgtata tacacacaca tatatatata catatataca tatatataca tatttaaagg
180781 ataaaggatt ctgctgccac agatcactaa atcagatgat ctctagcaat ttcctgtttg
180841 tttgtttttt gcccatagtg cttatctctt tgaacagtaa ttttccactt actatttttc
180901 tccccttttg gaccataatt tcctttaagg cagagcctcc tgttactcat ctttgaatct
180961 ggggtctgtc agagtaccta gaatttaata aactctcatt aagagccagt tgaaagaata
181021 tatgactaag cagtcattta catccaaaag atccgtagga gaattcttat cagcacatgt FIG. 1 (cont.) (SEQ ID NO: 1)

181081 gattggtaac aataactttg tacttttcaa aaacaattac taatctatct tgctttccat
181141 tatctcacca aaacctatta gcatgtctgg cagaaaatag atacttaata aatttcttaa
181201 atgtttactg acttcaattt taagttttat taactatgtt gacttttctc taatgaagat
181261 gattctaaaa agctttttac tatacttcac agtgaataaa acagtgagat aggaatattg
181321 caaaatgtcc cctgtgttgg tcagtcttag tgtcattcat tttaaaaatt ctgttctcta
181381 aatattgaca gttatatata aatttatgta attgtttact tctaataaag aatttcatct
181441 ggggaaaaac atactttgct cagctctttg ccacaagtgc aaagtctaag acagtcaaat
181501 agctttccta gtacggcctt aggaacttag tatatgactg gtgtgaatct agagggagca
181561 tactgcattc tgaccaaaat ctccaccctg ttactatggc catcactaac ttcgcagtat
181621 tgcagtactt cctgctagct tagttcccaa ggcaacttgt gaaggaaaat ttttacaaag
181681 ctgttgtcac acaaaggtag tgtttcagtt cctgagccca tgtccttgga gttgcccagg
181741 ctccaataat actaataatt actgtacatt aggtacttac catgtgccat attctgtggg
181801 agccgctttc cacaaattat ctctggtaat ccttgtaaca accctttgac atcaatatta
181861 ttattttctc catttttta catatgagat aaatgagact taaaataatg tgcctgatat
181921 catcagcaaa tgagctgagg agggcagatt caaagctgat tgtgtttgac tctagagctg
181981 cagtcttaag ccagaccttt tcttgctggt taattttact gaaaaaaaaa aaaaaaaaaa
182041 aaaaccctca aatactgctg attgatctaa agtactaaca tttctatcag tgttagggaa
182101 attttaattt tataatttga ttttgtgaga aatttatagc atcttgaata ctcacatgca
182161 aagtgatatg tcttagataa cattttacaa tggcagagct taagccagtg ctcagtcatt
182221 cattcatcct caagttttga ttcatttatc attcatcaaa actctgtttt gtttggccac
182281 ccacattcta ggagctcagt acatatttga taaatgaatg aattgttgag gttgacagtt
182341 acccaggact ggcattagga acacagagct gaagagcacg tttttaccct caagaagctt
182401 acagtctaac gagggaactt gcacaaatac tactatcact aggtgcctgg ttgaatggct
182461 taagagatga tcagggatat tcagaaggat atgtcaggct cagcaatggc atcacttgag
182521 agcatcaagg tgtttaggga actacaagat gtttggttct gctgggaata agagtgaagg
182581 gggctccatt tggatgcctc atacaccagg tgagagatct tagattttat tccaccagga
182641 ggagaactac cataggattt aaaacagaaa tgatatggtc aaacctacat cttaggaaga
182701 tccctggggt gtttgtatgg tggacttgca atttgactaa ttgagatttg taggatgatt
182761 cttaagagat gatgatgacc cagactggga tcactataat agagttggta aggaggagaa
182821 tgatttaaaa agtagttgga agaattctag ggatggagat aaacatttga aaattattaa
182881 cttataggtg gtcatcaata ccctgaaaat gactgggatc tcagaggaga gtctggagag
182941 ttggaaatga caaagactaa tattcaaggg ggcaggaaga gggagagttg ttcacacatg
183001 acaataggaa gaaatggcca tagagtgtgt ggtttctctc aagccaagga atagatgttt
183061 taagaaagga aaattcttgt ggtgggaagc agtagagatg acagatacac attaatttct
183121 tgagatttct agatgactaa atgggcagat gttgaatgat agctaaagga gaacccagaa
183181 acaagggagg gattttgttt ttgtttttta aaaaagatag accatagcag cttcatagac
183241 tgaaacaata aaaaagttga aggcacaaag aaagacacag gtcctctaac tccctgccca
183301 gtgcccttta ttcatattct cagcacttgt atttctaagt tttatgtttg agtcttcggg
183361 gatacatcag agtagtcccc cttgtctaat aaatgtgttt acatttcctg ccataccaga
183421 aacccttctc aaactttaat gaatttctac aaggtgagat tactttaatg agaaaccaac
183481 caaggaaagg agtatcatct gcaatatact ttcaaatgtt ttttgcttgt ttgtttcttg
183541 tccagctaaa aaaaaaaaaa aaaaacaagc cattggtcct aacacaactt tcatattcta
183601 ccccaatatc aaagaggctt aaaatctcct ggtcgtgtga tgggcacaca gttaattttt
183661 tgtgaacaaa cacagtgtta tgggccattt ctgaatttat ctctgaaatc ataagattct
183721 ttctgagcca ttatctcatt ctatattaca gtcaggtgga gcccatctta cctcctcata
183781 ctaaattcta gacttctcaa gggcaggaga caatcatctg tatatctctt tggccttcat
183841 acactcagga gtacttgcca aaaataaaca tttaatgcac atttatttga ataattgata
183901 agatccaata cttcaataac tttgtcatat ttttatagaa tgggtttcta tatctcattt
183961 gcattttcaa actttacttt tactgtctag ctttaaaaaa aaagcctttg actctaatac
184021 agccctcata ttctacccca atatctaaga ggctttatat ctcctagtgt tgtaccacta
184081 ttttaactcc agtatttttt acttcatagt tttacctatt tgttacagtt agtttttatg
184141 aattcaagag atgaatagca attttccata tgtaatttaa aaaaccccac agttgactat
184201 tttatgctat cttttgtcct cagtcatgac agagtagaag atgggaggta gcaccaagga
184261 tgatgtcata cctccatcct ttatgctaca ttctatcttc tgtctacata agatgtcata
184321 ctagagggca tatctgcaat gtatacatat tatcttttcc agcatgcatt cagttgtgtt
184381 ggaataattt atgtacacct ttataaacgc tgagcctcac aagagccatg tgccacgtat
184441 tgttttctta ctactttttg ggatacctgg cacgtaatag acactcattg aaagtttcct FIG. 1 (cont.) (SEQ ID NO: 1)

184501 aatgaatgaa gtacaaagat aaaacaagtt atagactgat tcttttgagc tgtcaaggtt
184561 gtaaatagac ttttgctcaa tcaattcaaa tggtggcagg tagtgggggt agagggattg
184621 gtatgaaaaa cataagcttt cagaactcct gtgtttattt ttagaatgtc aactgcttga
184681 gtgtttttaa ctctgtggta tctgaactat cttctctaac tgcaggttgg gctcagatct
184741 gtgatagaac agtttcctgg gaagcttgac tttgtccttg tggatggggg ctgtgtccta
184801 agccatggcc acaagcagtt gatgtgcttg gctagatctg ttctcagtaa ggcgaagatc
184861 ttgctgcttg atgaacccag tgctcatttg gatccagtgt gagtttcaga tgttctgtta
184921 cttaatagca cagtgggaac agaatcatta tgcctgcttc atggtgacac atatttctat
184981 taggctgtca tgtctgcgtg tgggggtctc ccccaagata tgaaataatt gcccagtgga
185041 aatgagcata aatgcatatt tccttgctaa gagtcttgtg ttttcttccg aagatagttt
185101 ttagtttcat acaaactctt ccccccttgtc aacacatgat gaagctttta aatacatggg
185161 cctaatctga tccttatgat ttgcctttgt atcccattta taccataagc atgtttatag
185221 ccccaaataa agaagtactg gtgattctac ataatgaaaa atgtactcat ttattaaagt
185281 ttctttgaaa tatttgtcct gtttatttat ggatacttag agtctacccc atggttgaaa
185341 agctgattgt ggctaacgct atatcaacat tatgtgaaaa gaacttaaag aaataagtaa
185401 tttaaagaga taatagaaca atagacatat tatcaaggta aatacagatc attactgttc
185461 tgtgatatta tgtgtggtat tttctttctt ttctagaaca taccaaataa ttagaagaac
185521 tctaaaacaa gcatttgctg attgcacagt aattctctgt gaacacagga tagaagcaat
185581 gctggaatgc caacaatttt tggtgagtct ttataacttt acttaagatc tcattgccct
185641 tgtaattctt gataacaatc tcacatgtga tagttcctgc aaattgcaac aatgtacaag
185701 ttcttttcaa aaatatgtat catacagcca tccagcttta ctcaaaatag ctgcacaagt
185761 ttttcacttt gatctgagcc atgtggtgag gttgaaatat agtaaatcta aaatggcagc
185821 atattactaa gttatgttta taaataggat atatatactt tttgagccct ttatttgggg
185881 accaagtcat acaaaatact ctactgttta agattttaaa aaaggtccct gtgattcttt
185941 caataactaa atgtcccatg gatgtggtct gggacaggcc tagttgtctt acagtctgat
186001 ttatggtatt aatgacaaag ttgagaggca catttcattt ttctagccat gatttgggtt
186061 caggtagtac ctttctcaac caccttctca ctgttcttaa aaaaactgtc acatggccag
186121 gcacagtggc ttacatctgt aatcccaata ctttgggagg ctgaggtggg gggattactt
186181 gaggccagga attcaagacc agcccaggca acatagtgag gccccatctg tctttattaa
186241 aacaaaacaa aactgtcaca gcttctttca agtgatgttt acaaattccc tatggtttag
186301 tcacaaggaa gttctgagga tgatgtatca cgtcatttct gttcaggctt ttgagcctcc
186361 tggaggtaaa tggtttcctt actgaaggct tgttattacc atgattatca ctaagcttga
186421 agtaacaaat tagggggca gactcacaac ctcttgccct gccatggaca agttcaagaa
186481 tctaagtaaa gtcctctatt gtctgatctt ggatttgctc aacctgaaca agccaaggag
186541 gtgtattaaa ctcaggcaca tcctgaccaa tttggaattc ttaagcttca gatcactgtg
186601 gaagaggctc aactctttat ggtgctgtag acttacgctc attttctagg taatttataa
186661 gggacctaat attttgtttt caaagcaact tcagttctac taaacctccc tgaagaatct
186721 tccagctgct gagtagaaaa tcacaactaa tttcacagat ggtagaacct ccttagagca
186781 aaaggacaca gcagttaaat gtgacatacc tgattgttca aaatgcaagg ctctggacat
186841 tgcattcttt gacttttatt ttcctttgag cctgtgccag tttctgtccc tgctctggtc
186901 tgacctgcct tctgtcccag atctcactaa cagccatttc cctaggtcat agaagagaac
186961 aaagtgcggc agtacgattc catccagaaa ctgctgaacg agaggagcct cttccggcaa
187021 gccatcagcc cctccgacag ggtgaagctc tttccccacc ggaactcaag caagtgcaag
187081 tctaagcccc agattgctgc tctgaaagag gagacagaag aagaggtgca agatacaagg
187141 ctttagagag cagcataaat gttgacatgg gacatttgct catggaattg gagctcgtgg
187201 gacagtcacc tcatggaatt ggagctcgtg gaacagttac ctctgcctca gaaaacaagg
187261 atgaattaag tttttttta aaaaagaaac atttggtaag gggaattgag gacactgata
187321 tgggtcttga taaatggctt cctggcaata gtcaaattgt gtgaaaggta cttcaaatcc
187381 ttgaagattt accacttgtg ttttgcaagc cagattttcc tgaaaaccct tgccatgtgc
187441 tagtaattgg aaaggcagct ctaaatgtca atcagcctag ttgatcagct tattgtctag
187501 tgaaactcgt taatttgtag tgttggagaa gaactgaaat catacttctt agggttatga
187561 ttaagtaatg ataactggaa acttcagcgg tttatataag cttgtattcc tttttctctc
187621 ctctccccat gatgtttaga aacacaacta tattgtttgc taagcattcc aactatctca
187681 tttccaagca agtattagaa taccacagga accacaagac tgcacatcaa aatatgcccc
187741 attcaacatc tagtgagcag tcaggaaaga gaacttccag atcctggaaa tcagggttag
187801 tattgtccag gtctaccaaa aatctcaata tttcagataa tcacaataca tcccttacct
187861 gggaaagggc tgttataatc tttcacaggg gacaggatgg ttcccttgat gaagaagttg FIG. 1 (cont.) (SEQ ID NO: 1)

```
187921 atatgccttt tcccaactcc agaaagtgac aagctcacag acctttgaac tagagtttag
187981 ctggaaaagt atgttagtgc aaattgtcac aggacagccc ttctttccac agaagctcca
188041 ggtagagggt gtgtaagtag ataggccatg ggcactgtgg gtagacacac atgaagtcca
188101 agcatttaga tgtataggtt gatggtggta tgttttcagg ctagatgtat gtacttcatg
188161 ctgtctacac taagagagaa tgagagacac actgaagaag caccaatcat gaattagttt
188221 tatatgcttc tgttttataa ttttgtgaag caaaattttt tctctaggaa atatttattt
188281 taataatgtt tcaaacatat ataacaatgc tgtattttaa aagaatgatt atgaattaca
188341 tttgtataaa ataattttta tatttgaaat attgactttt tatggcacta gtatttctat
188401 gaaatattat gttaaaactg ggacagggga gaacctaggg tgatattaac caggggccat
188461 gaatcacctt ttggtctgga gggaagcctt ggggctgatg cagttgttgc ccacagctgt
188521 atgattccca gccagcacag cctcttagat gcagttctga agaagatggt accaccagtc
188581 tgactgtttc catcaagggt acactgcctt ctcaactcca aactgactct taagaagact
188641 gcattatatt tattactgta agaaaatatc acttgtcaat aaaatccata catttgtgtg
188701 aaa
```

FIG. 1 (cont.) (SEQ ID NO: 1)

| | | | | | | |
|---|---|---|---|---|---|---|
| 1 | aattggaagc | aaatgacatc | acagcaggtc | agagaaaaag | ggttgagcgg | caggcaccca |
| 61 | gagtagtagg | tctttggcat | taggagcttg | agcccagacg | gccctagcag | ggaccccagc |
| 121 | gcccgagaga | ccatgcagag | gtcgcctctg | gaaaaggcca | gcgttgtctc | caaacttttt |
| 181 | ttcagctgga | ccagaccaat | tttgaggaaa | ggatacagac | agcgcctgga | attgtcagac |
| 241 | atataccaaa | tcccttctgt | tgattctgct | gacaatctat | ctgaaaaatt | ggaaagagaa |
| 301 | tgggatagag | agctggcttc | aaagaaaaat | cctaaactca | ttaatgccct | tcggcgatgt |
| 361 | tttttctgga | gatttatgtt | ctatggaatc | tttttatatt | taggggaagt | caccaaagca |
| 421 | gtacagcctc | tcttactggg | aagaatcata | gcttcctatg | acccggataa | caaggaggaa |
| 481 | cgctctatcg | cgatttatct | aggcataggc | ttatgccttc | tctttattgt | gaggacactg |
| 541 | ctcctacacc | cagccatttt | tggccttcat | cacattggaa | tgcagatgag | aatagctatg |
| 601 | tttagtttga | tttataagaa | gactttaaag | ctgtcaagcc | gtgttctaga | taaaataagt |
| 661 | attggacaac | ttgttagtct | cctttccaac | aacctgaaca | aatttgatga | aggacttgca |
| 721 | ttggcacatt | tcgtgtggat | cgctcctttg | caagtggcac | tcctcatggg | gctaatctgg |
| 781 | gagttgttac | aggcgtctgc | cttctgtgga | cttggtttcc | tgatagtcct | tgcccttttt |
| 841 | caggctgggc | tagggagaat | gatgatgaag | tacagagatc | agagagctgg | gaagatcagt |
| 901 | gaaagacttg | tgattacctc | agaaatgatt | gaaaatatcc | aatctgttaa | ggcatactgc |
| 961 | tgggaagaag | caatggaaaa | aatgattgaa | aacttaagac | aaacagaact | gaaactgact |
| 1021 | cggaaggcag | cctatgtgag | atacttcaat | agctcagcct | tcttcttctc | agggttcttt |
| 1081 | gtggtgtttt | tatctgtgct | tccctatgca | ctaatcaaag | gaatcatcct | ccggaaaata |
| 1141 | ttcaccacca | tctcattctg | cattgttctg | cgcatggcgg | tcactcggca | atttccctgg |
| 1201 | gctgtacaaa | catggtatga | ctctcttgga | gcaataaaca | aaatacagga | tttcttacaa |
| 1261 | aagcaagaat | ataagacatt | ggaatataac | ttaacgacta | cagaagtagt | gatggagaat |
| 1321 | gtaacagcct | tctgggagga | gggatttggg | gaattatttg | agaaagcaaa | acaaaacaat |
| 1381 | aacaatagaa | aaacttctaa | tggtgatgac | agcctcttct | tcagtaattt | ctcacttctt |
| 1441 | ggtactcctg | tcctgaaaga | tattaatttc | aagatagaaa | gaggacagtt | gttggcggtt |
| 1501 | gctggatcca | ctggagcagg | caagacttca | cttctaatga | tgattatggg | agaactggag |
| 1561 | ccttcagagg | gtaaaattaa | gcacagtgga | agaatttcat | tctgttctca | gttttcctgg |
| 1621 | attatgcctg | gcaccattaa | agaaaatatc | atctttggtg | tttcctatga | tgaatataga |
| 1681 | tacagaagcg | tcatcaaagc | atgccaacta | gaagaggaca | tctccaagtt | tgcagagaaa |
| 1741 | gacaatatag | ttcttggaga | aggtggaatc | acactgagtg | gaggtcaacg | agcaagaatt |
| 1801 | tctttagcaa | gagcagtata | caaagatgct | gatttgtatt | tattagactc | tccttttgga |
| 1861 | tacctagatg | ttttaacaga | aaaagaaata | tttgaaagct | gtgtctgtaa | actgatggct |
| 1921 | aacaaaacta | ggattttggt | cacttctaaa | atggaacatt | taaagaaagc | tgacaaaata |
| 1981 | ttaattttgc | atgaaggtag | cagctatttt | tatgggacat | tttcagaact | ccaaaatcta |
| 2041 | cagccagact | ttagctcaaa | actcatggga | tgtgattctt | tcgaccaatt | tagtgcagaa |
| 2101 | agaagaaatt | caatcctaac | tgagacctta | caccgtttct | cattagaagg | agatgctcct |
| 2161 | gtctcctgga | cagaaacaaa | aaaacaatct | tttaaacaga | ctggagagtt | tggggaaaaa |
| 2221 | aggaagaatt | ctattctcaa | tccaatcaac | tctatacgaa | aattttccat | tgtgcaaaag |
| 2281 | actcccttac | aaatgaatgg | catcgaagag | gattctgatg | agcctttaga | gagaaggctg |
| 2341 | tccttagtac | cagattctga | gcagggagag | gcgatactgc | ctcgcatcag | cgtgatcagc |
| 2401 | actggcccca | cgcttcaggc | acgaaggagg | cagtctgtcc | tgaacctgat | gacacactca |
| 2461 | gttaaccaag | gtcagaacat | tcaccgaaag | acaacagcat | ccacacgaaa | agtgtcactg |
| 2521 | gccccctcagg | caaacttgac | tgaactggat | atatattcaa | gaaggttatc | tcaagaaact |
| 2581 | ggcttggaaa | taagtgaaga | aattaacgaa | gaagacttaa | aggagtgctt | ttttgatgat |
| 2641 | atggagagca | taccagcagt | gactacatgg | aacacatacc | ttcgatatat | tactgtccac |

FIG. 2 (SEQ ID NO: 2)

| | | | | | | |
|---|---|---|---|---|---|---|
| 2701 | aagagcttaa | tttttgtgct | aatttggtgc | ttagtaattt | ttctggcaga | ggtggctgct |
| 2761 | tctttggttg | tgctgtggct | ccttggaaac | actcctcttc | aagacaaagg | gaatagtact |
| 2821 | catagtagaa | ataacagcta | tgcagtgatt | atcaccagca | ccagttcgta | ttatgtgttt |
| 2881 | tacatttacg | tgggagtagc | cgacactttg | cttgctatgg | gattcttcag | aggtctacca |
| 2941 | ctggtgcata | ctctaatcac | agtgtcgaaa | attttacacc | acaaaatgtt | acattctgtt |
| 3001 | cttcaagcac | ctatgtcaac | cctcaacacg | ttgaaagcag | gtgggattct | taatagattc |
| 3061 | tccaaagata | tagcaatttt | ggatgacctt | ctgcctctta | ccatatttga | cttcatccag |
| 3121 | ttgttattaa | ttgtgattgg | agctatagca | gttgtcgcag | ttttacaacc | ctacatcttt |
| 3181 | gttgcaacag | tgccagtgat | agtggctttt | attatgttga | gagcatattt | cctccaaacc |
| 3241 | tcacagcaac | tcaaacaact | ggaatctgaa | ggcaggagtc | caattttcac | tcatcttgtt |
| 3301 | acaagcttaa | aaggactatg | gacacttcgt | gccttcggac | ggcagcctta | ctttgaaact |
| 3361 | ctgttccaca | aagctctgaa | tttacatact | gccaactggt | tcttgtacct | gtcaacactg |
| 3421 | cgctggttcc | aaatgagaat | agaaatgatt | tttgtcatct | tcttcattgc | tgttaccttc |
| 3481 | atttccattt | taacaacagg | agaaggagaa | ggaagagttg | gtattatcct | gactttagcc |
| 3541 | atgaatatca | tgagtacatt | gcagtgggct | gtaaactcca | gcatagatgt | ggatagcttg |
| 3601 | atgcgatctg | tgagccgagt | ctttaagttc | attgacatgc | caacagaagg | taaacctacc |
| 3661 | aagtcaacca | aaccatacaa | gaatggccaa | ctctcgaaag | ttatgattat | tgagaattca |
| 3721 | cacgtgaaga | aagatgacat | ctggccctca | gggggccaaa | tgactgtcaa | agatctcaca |
| 3781 | gcaaaataca | cagaaggtgg | aaatgccata | ttagagaaca | tttccttctc | aataagtcct |
| 3841 | ggccagaggg | tgggcctctt | gggaagaact | ggatcaggga | agagtacttt | gttatcagct |
| 3901 | tttttgagac | tactgaacac | tgaaggagaa | atccagatcg | atggtgtgtc | ttgggattca |
| 3961 | ataactttgc | aacagtggag | gaaagccttt | ggagtgatac | cacagaaagt | atttattttt |
| 4021 | tctggaacat | ttagaaaaaa | cttggatccc | tatgaacagt | ggagtgatca | agaaatatgg |
| 4081 | aaagttgcag | atgaggttgg | gctcagatct | gtgatagaac | agtttcctgg | gaagcttgac |
| 4141 | tttgtccttg | tggatggggg | ctgtgtccta | agccatggcc | acaagcagtt | gatgtgcttg |
| 4201 | gctagatctg | ttctcagtaa | ggcgaagatc | ttgctgcttg | atgaacccag | tgctcatttg |
| 4261 | gatccagtaa | cataccaaat | aattagaaga | actctaaaac | aagcatttgc | tgattgcaca |
| 4321 | gtaattctct | gtgaacacag | gatagaagca | atgctggaat | gccaacaatt | tttggtcata |
| 4381 | gaagagaaca | aagtgcggca | gtacgattcc | atccagaaac | tgctgaacga | gaggagcctc |
| 4441 | ttccggcaag | ccatcagccc | ctccgacagg | gtgaagctct | ttccccaccg | gaactcaagc |
| 4501 | aagtgcaagt | ctaagcccca | gattgctgct | ctgaaagagg | agacagaaga | agaggtgcaa |
| 4561 | gatacaaggc | tttagagagc | agcataaatg | ttgacatggg | acatttgctc | atggaattgg |
| 4621 | agctcgtggg | acagtcacct | catggaattg | gagctcgtgg | aacagttacc | tctgcctcag |
| 4681 | aaaacaagga | tgaattaagt | ttttttttaa | aaaagaaaca | tttggtaagg | ggaattgagg |
| 4741 | acactgatat | gggtcttgat | aaatggcttc | ctggcaatag | tcaaattgtg | tgaaaggtac |
| 4801 | ttcaaatcct | tgaagattta | ccacttgtgt | tttgcaagcc | agattttcct | gaaaaccctt |
| 4861 | gccatgtgct | agtaattgga | aaggcagctc | taaatgtcaa | tcagcctagt | tgatcagctt |
| 4921 | attgtctagt | gaaactcgtt | aatttgtagt | gttggagaag | aactgaaatc | atacttctta |
| 4981 | gggttatgat | taagtaatga | taactggaaa | cttcagcggt | ttatataagc | ttgtattcct |
| 5041 | ttttctctcc | tctccccatg | atgtttagaa | acacaactat | attgtttgct | aagcattcca |
| 5101 | actatctcat | ttccaagcaa | gtattagaat | accacaggaa | ccacaagact | gcacatcaaa |
| 5161 | atatgcccca | ttcaacatct | agtgagcagt | caggaaagag | aacttccaga | tcctggaaat |
| 5221 | cagggttagt | attgtccagg | tctaccaaaa | atctcaatat | ttcagataat | cacaatacat |
| 5281 | cccttacctg | ggaaagggct | gttataatct | ttcacagggg | acaggatggt | tcccttgatg |
| 5341 | aagaagttga | tatgcctttt | cccaactcca | gaaagtgaca | agctcacaga | cctttgaact |
| 5401 | agagtttagc | tggaaaagta | tgttagtgca | aattgtcaca | ggacagccct | tctttccaca |

FIG. 2 (cont.) (SEQ ID NO: 2)

| | | | | | | |
|---|---|---|---|---|---|---|
| 5461 | gaagctccag | gtagagggtg | tgtaagtaga | taggccatgg | gcactgtggg | tagacacaca |
| 5521 | tgaagtccaa | gcatttagat | gtataggttg | atggtggtat | gttttcaggc | tagatgtatg |
| 5581 | tacttcatgc | tgtctacact | aagagagaat | gagagacaca | ctgaagaagc | accaatcatg |
| 5641 | aattagtttt | atatgcttct | gttttataat | tttgtgaagc | aaaatttttt | ctctaggaaa |
| 5701 | tatttatttt | aataatgttt | caaacatata | ttacaatgct | gtattttaaa | agaatgatta |
| 5761 | tgaattacat | ttgtataaaa | taatttttat | atttgaaata | ttgacttttt | atggcactag |
| 5821 | tattttttatg | aaatattatg | ttaaaactgg | gacaggggag | aacctagggt | gatattaacc |
| 5881 | aggggccatg | aatcaccttt | tggtctggag | ggaagccttg | gggctgatcg | agttgttgcc |
| 5941 | cacagctgta | tgattcccag | ccagacacag | cctcttagat | gcagttctga | agaagatggt |
| 6001 | accaccagtc | tgactgtttc | catcaagggt | acactgcctt | ctcaactcca | aactgactct |
| 6061 | taagaagact | gcattatatt | tattactgta | agaaaatatc | acttgtcaat | aaaatccata |
| 6121 | catttgtgta | | | | | |

FIG. 2 (cont.) (SEQ ID NO: 2)

| | | | | | | |
|---|---|---|---|---|---|---|
| 1 | mqrsplekas | vvsklffswt | rpilrkgyrq | rlelsdiyqi | psvdsadnls | eklerewdre |
| 61 | laskknpkli | nalrrcffwr | fmfygiflyl | gevtkavqpl | llgriiasyd | pdnkeersia |
| 121 | iylgiglcll | fivrtlllhp | aifglhhigm | qmriamfsli | ykktlklssr | vldkisigql |
| 181 | vsllsnnlnk | fdeglalahf | vwiaplqval | lmgliwellq | asafcglgfl | ivlalfgagl |
| 241 | grmmmkyrdq | ragkiserlv | itsemieniq | svkaycweea | mekmienlrq | telkltrkaa |
| 301 | yvryfnssaf | ffsgffvvfl | svlpyalikg | iilrkiftti | sfcivlrmav | trqfpwavqt |
| 361 | wydslgaink | iqdflqkqey | ktleynlttt | evvmenvtaf | weegfgelfe | kakqnnnnrk |
| 421 | tsngddslff | snfsllgtpv | lkdinfkier | gqllavagst | gagktsllmm | imgelepseg |
| 481 | kikhsgrisf | csqfswimpg | tikeniifgv | sydeyryrsv | ikacqleedi | skfaekdniv |
| 541 | lgeggitlsg | gqrarislar | avykdadlyl | ldspfgyldv | ltekeifesc | vcklmanktr |
| 601 | ilvtskmehl | kkadkililh | egssyfygtf | selqnlqpdf | ssklmgcdsf | dqfsaerrns |
| 661 | iltetlhrfs | legdapvswt | etkkqsfkqt | gefgekrkns | ilnpinsirk | fsivqktplq |
| 721 | mngieedsde | plerrlslvp | dseqgeailp | risvistgpt | lqarrrqsvl | nlmthsvnqg |
| 781 | qnihrkttas | trkvslapqa | nlteldiysr | rlsqetglei | seeineedlk | ecffddmesi |
| 841 | pavttwntyl | ryitvhksli | fvliwclvif | laevaaslvv | lwllgntplq | dkgnsthsrn |
| 901 | nsyaviitst | ssyyvfyiyv | gvadtllamg | ffrglplvht | litvskilhh | kmlhsvlqap |
| 961 | mstlntlkag | gilnrfskdi | ailddllplt | ifdfiqllli | vigaiavvav | lqpyifvatv |
| 1021 | pvivafimlr | ayflqtsqql | kqlesegrsp | ifthlvtslk | glwtlrafgr | qpyfetlfhk |
| 1081 | alnlhtanwf | lylstlrwfq | mriemifvif | fiavtfisil | ttgegegrvg | iiltlamnim |
| 1141 | stlqwavnss | idvdslmrsv | srvfkfidmp | tegkptkstk | pykngqlskv | miienshvkk |
| 1201 | ddiwpsggqm | tvkdltakyt | eggnaileni | sfsispgqrv | gllgrtgsgk | stllsaflrl |
| 1261 | lntegeigid | gvswdsitlq | qwrkafgvip | qkvfifsgtf | rknldpyeqw | sdqeiwkvad |
| 1321 | evglrsvieq | fpgkldfvlv | dggcvlshgh | kqlmclarsv | lskakillld | epsahldpvt |
| 1381 | yqiirrtlkq | afadctvilc | ehrieamlec | qqflvieenk | vrqydsiqkl | lnerslfrqa |
| 1441 | ispsdrvklf | phrnsskcks | kpqiaalkee | teevqdtrl | | |

FIG. 3 (SEQ ID NO: 3)

1 gaattcaaag gaaaacataa gatgcaattc gtgcctccaa ggaggttgta gggaagaggg
61 gttatgaatg tatgtaaata gaagttggtg tgcgtgtgtg tttataaaca gaattgtcag
121 accaaacatt attttggaag cagtaaaagt aaactagaat ctggcctagt catgtcccag
181 gacacctctt tcaagtcctg aaacatcttt gtaagactgt aatgtgtgtt tacatcctag
241 gtaatcactg tggccccactg ttgaagagct gtggctgttc ttacccttct agttagataa
301 acttataagc acaaccagac tacatatatg aagctgaaga gaccttgtct tttttaacg
361 agcttttctt cccgatagga gtgactattt cttttcttct tccacatttt caggttttag
421 tgtacttgtg attgctaccc acttatcact attaaagtct actcaggaga gaatctgaga
481 aacactctca aattaagttg aacatgatgg ataagtaaag tattgtgaaa gttcactctc
541 atgatttcta atggtgaaac ctggcagggt gactaatctt tgacgagaag gttatcactt
601 ataatctttc atatattgag atcatttgta agaagcaccc agcacattgc tgaacacaaa
661 gtaggtatta aataaatgtt ggcttccttt tctcctactc atcctcgctc ttctttttaa
721 tataccttta aaatgatgcc acagaaatgg ccacccaatc ttctatattt aaggtcagtt
781 cttgcattag gaaattctat aggggaagta tgtgaagtat gtgtagtcag tcattaaatg
841 cttgggctct ggccacagat tgtttaggtt taaatcccag tttcctcttt tattattaat
901 tgtgcaactt gcttgggaaa acatgaaact tgtttttcct caggttcatt atctgtaata
961 tatagtgaat gaagaagttt cctgtcccat gaaggtgttg taaagattaa aaaaggcaaa
1021 ttaggctgtg tatttgtcat aataattggc atatatggta agtgaccaac aaccataagg
1081 tattataaaa ttgttataaa atgatatgag ctatcattga gcagcatgaa agaagagctt
1141 cactgtttca cctactatca ccctggccca ttaatctctt tcctgttcct gacatttcag
1201 agatacgttt aggatttcaa tcatgacctt aagccacatt tgaacaattt tctggtggat
1261 aagtcctcat tcccacatta tgtatgtacc tagatgcaaa tcctgaatat catgtcgcaa
1321 ttagtgcatc tggacatgct tgctaactgt gttaaagctc tgaataatgg taaagtttta
1381 tttctaccaa aacaaatttg ggctgtaatg ttttatgata aaaatctgtg gtcttcctat
1441 gtacatgtgt gtgtacatgc ttaaaatgca atgttatagt taaatgtaat tcattaaaag
1501 tatgtaactc cagtggctac ttagtttggc tacttggttt gtagatttct gctttcctgt
1561 ttcattgtta aacaggtcta gaagttatta tttcatgaaa ctaatgtgag gaaaaagact
1621 atgttgatat ataagtgaca ttatataaat acatgaggga tgatttgatt agaagcagta
1681 ttacacagtg ataggagtaa tggtttagaa ctagactcag gtttgaatct tagctctatc
1741 attataggca tttacttaac ttttcttgtt tgcttaactg aaaactgaag ataataacac
1801 ctatttacat ggttgttata agggttatat gaataatgtc tggcaaatag taagaactca
1861 agtaactgtt tcactctttc cagaaggaga ttggctgaaa aatatttgga gtctcctcca
1921 gccatattcc ttggtcagct tctatgatcc tctttggagc ttaattctta atccctttat
1981 tttcacttgc ttgttgataa caaagaagaa ctaattatta atttatttca aaatgcatgt
2041 attatatttg atgggccaca ctaacagtta taaaccaaac aacagattgg gaatggggaa
2101 gtggatgtgg tgagttcaat cacatgtctg ggaaaagtca atagtgaaga cagagtctca
2161 caattttttg tcataatgga gagatgaaaa cacaggtaga ggatttcaaa caacagagtg
2221 gatggtgagt taaaaatgct gaaattcttt cctggtgtct aacttaatgc aatgtggttt
2281 atctctttgc tcttttctct actattcaaa tttaggataa taaagattaa atgtttctaa
2341 atcttacttt acaatatcaa gaaaaaaagg tatgcttttg cccacggaag ggcaaagcag
2401 agctatgaaa acctgctgaa cacattcttt attttcaaca caggttcttg tctttccatc
2461 atgaaatgca cattttattt gtactgtatt tgggtgacca caagtcaaca acaagataat
2521 tcacaagacc cttgccttag atgtgtcggc aataaagtaa tcaggccaaa atttttactt
2581 tcctttgaat ttttcaattc aaacacaatg tatgcttgct tttacacagt agggttcagg
2641 gattagaggg ttggctcctt taaaaccgtc agagacacag gcaatcctac acaaaattct
2701 cagaaggaag gcgcctacgc ctgggaatgc ccagatgccc ctcagagagt tgaagatggc

FIG. 4 (SEQ ID NO: 4)

2761 gtttctctga gtcaggtcaa agttaacaca ttaccttcgc ttcaaagact gcttggcttc
2821 ctttcggtgg attagtcaag atgttttgct gactgagact aggaaatcta taggagggcg
2881 ggttagttta cattgttcct tgtcattatc gctaaaacac tccaaagcct tccttaaaaa
2941 tgcgcactgg gctaaaaagg atagacaagg aacacatcct gggccggtaa ttacgcaaag
3001 cattatctcc tcttacctcc ttgcagattt ttttttctct ttcagtacgt gtcctaagat
3061 ttctgtgcca cccttggagt tcactcacct aaacctgaaa ctaataaagc ttggttcttt
3121 tctccgacac gcaaaggaag cgctaaggta aatgcatcag acccacactg ccgcggaact
3181 tttcggctct ctaaggctgt attttgatat acgaaaggca cattttcctt cccttttcaa
3241 aatgcacctt gcaaacgtaa caggaacccg actaggatca tcgggaaaag gaggaggagg
3301 aggaaggcag gctccgggga agctggtggc agcgggtcct gggtctggcg gaccctgacg
3361 cgaaggaggg tctaggaagc tctccgggga gccggttctc ccgccggtgg cttcttctgt
3421 cctccagcgt tgccaactgg acctaaagag aggccgcgac tgtcgcccac ctgcgggatg
3481 ggcctggtgc tgggcggtca ggacactgac ctggaaggag cgcgcgcgag ggagggaggc
3541 tgggagtcag aatcgggaaa gggaggtgcg gggcggcgag ggagcgaagg aggagaggag
3601 gaaggagcgg gaggggtgct ggcggggggtg cgtagtgggt ggagaaagcc gctagagcaa
3661 atttggggcc ggaccaggca gcactcggct tttaacctgg gcagtgaagg cgggggaaag
3721 agcaaaagga aggggtggtg tgcggagtag gggtgggtgg ggggaattgg aagcaaatga
3781 catcacagca ggtcagagaa aaagggttga gcggcaggca cccagagtag taggtctttg
3841 gcattaggag cttgagccca gacggcccta gcagggaccc cagcgcccga gagaccatgc
3901 agaggtcgcc tctggaaaag gccagcgttg tctccaaact ttttttcagg tgagaaggtg
3961 gccaaccgag cttcggaaag acacgtgccc acgaaagagg agggcgtgtg tatgggttgg
4021 gtttggggta aaggaataag cagtttttaa aaagatgcgc tatcattcat tgttttgaaa
4081 gaaaatgtgg gtattgtaga ataaaacaga aagcattaag aagagatgga agaatgaact
4141 gaagctgatt gaatagagag ccacatctac ttgcaactga aaagttagaa tctcaagact
4201 caagtacgct actatgcact tgttttattt catttttcta agaaactaaa aatacttgtt
4261 aataagtacc taagtatggt ttattggttt tcccccttca tgccttggac acttgattgt
4321 cttcttggca catacaggtg ccatgcctgc atatagtaag tgctcagaaa acatttcttg
4381 actgaattc FIG. 4 (cont.) (SEQ ID NO: 4)

SEQUENCE LISTING

```
<160> NUMBER OF SEQ ID NOS: 72

<210> SEQ ID NO 1
<211> LENGTH: 188703
<212> TYPE: DNA
<213> ORGANISM: Homo sapiens

<400> SEQUENCE: 1

aattggaagc aaatgacatc acagcaggtc agagaaaaag ggttgagcgg caggcaccca      60

gagtagtagg tctttggcat taggagcttg agcccagacg gccctagcag ggaccccagc     120

gcccgagaga ccatgcagag gtcgcctctg gaaaaggcca gcgttgtctc caaacttttt     180

ttcaggtgag aaggtggcca accgagcttc ggaaagacac gtgcccacga aagaggaggg     240

cgtgtgtatg ggttgggttt ggggtaaagg aataagcagt ttttaaaaag atgcgctatc     300

attcattgtt ttgaaagaaa atgtgggtat tgtagaataa aacagaaagc attaagaaga     360

gatggaagaa tgaactgaag ctgattgaat agagagccac atctacttgc aactgaaaag     420

ttagaatctc aagactcaag tacgctacta tgcacttgtt ttatttcatt tttctaagaa     480

actaaaaata cttgttaata agtacctaag tatggtttat tggttttccc ccttcatgcc     540

ttggacactt gattgtcttc ttggcacata caggtgccat gcctgcatat agtaagtgct     600
```

```
cagaaaacat ttcttgactg aattcagcca acaaaaattt tggggtaggt agaaaatata    660
tgcttaaagt atttattgtt atgagactgg atatatctag tatttgtcac aggtaaatga    720
ttcttcaaaa attgaaagca aatttgttga aatatttatt ttgaaaaaag ttacttcaca    780
agctataaat tttaaaagcc ataggaatag ataccgaagt tatatccaac tgacatttaa    840
taaattgtat tcatagccta atgtgatgag ccacagaagc ttgcaaactt taatgagatt    900
ttttaaaata gcatctaagt tcggaatctt aggcaaagtg ttgttagatg tagcacttca    960
tatttgaagt gttctttgga tattgcatct actttgttcc tgttattata ctggtgtgaa   1020
tgaatgaata ggtactgctc tctcttggga cattacttga cacataatta cccaatgaat   1080
aagcatactg aggtatcaaa aaagtcaaat atgttataaa tagctcatat atgtgtgtag   1140
gggggaagga atttagcttt cacatctctc ttatgtttag ttctctgcat gtgcagttaa   1200
tcctggaact ccggtgctaa ggagagactg ttggcccttg aaggagagct cctccctgtg   1260
gatgagagag aaggacttta ctctttggaa ttatcttttt gtgttgatgt tatccacctt   1320
ttgttactcc acctataaaa tcggcttatc tattgatctg ttttcctagt ccttataaag   1380
tcaaaatgtt aattggcata aattatagac ttttttagc agagaacttt gaggaaccta   1440
aatgccaacc agtctaaaaa tgcagttttc agaagaatga atatttcatg gatagttcta   1500
aatactaatg aactttaaaa tagcttacta ttgatctgtc aaagtgggtt tttatataat   1560
tttcttttta caaatcacct gacacattta atataggtta aaaaatgcta tcaggctggt   1620
ttgcaaagaa aatgtattac aaaggctgct aagtgtgtta agagcatact catttctgtt   1680
ctccaaaata tttcataagg tgctttaaga ataggtatgt ttttaaaagt taagttccta   1740
ctatttatag gaactgacaa tcacctaaaa taccaatgat tacaaacttc cttctggcct   1800
tctggactgc aattctaaaa gtgtaaaaaa catattttct gcattaagtt aggcagtatt   1860
gcttagtttt caaagtggta ggctttggag tcagattatt ttgattcaga tcctacatct   1920
actgtttagt agctctgttg cctgaggcag gtcccttaac atctctgtgt gtgacttgac   1980
ctttaaaatt tggagactgt cataggggtt aatcccttga gaaaatgaat gtgaaaagtt   2040
agcctaatgt taactgctat tattatggat taccatattt tcacattcat cacagtacat   2100
gcaccttgtt aatataagat gctcaattca tctttgagta taattttgtg actctcaatc   2160
tggatatgca atgagtgggc ctgtatgaga atttaattta tgaaaaattg tgtttcacat   2220
ggccttacca gatatacagg aaacacgtca catgtttcta ttgtatgttg ttaaatgcct   2280
tagaatttaa ctttctgaat aggatccctt cagtttgaga gtcataaaag agtaaaatta   2340
ttatggtatg agttatagat tgtattgaat atctctttat atgtctaggt tttgtcattg   2400
gaaaaccaaa aagtttggaa aaaaaatcta agttatttct tactttctta attttgtgtg   2460
gatttcacat caagtataaa atttgaagaa catctgaact atcataatcc atatatatat   2520
ataaaataaa cataatctaa gagagaattt caccatgaaa aattcaggta gttcatgact   2580
atcagagcaa acaagtacat taaattgaaa cttttatgaa aataacattt atgaaatagg   2640
aagctatttt taaactagaa gtgatatatt agcatataat ttataattca tatacaagtg   2700
ggattgattt ataaatggtc accaacagag attgtgctat ttaatttggg aaaatttttt   2760
aaatttacat tttctcacaa cttttaaggt agttattcag tttgttcctc tctgtctctt   2820
ctctcatgcc ctgaattttt catatttcgt ttagttgtaa gagtgtatat caaaccgtgt   2880
gtcacatgac ataacttgaa ttttcgtcgt gatatctgtg ctatgtctag gtctatactg   2940
aggaactgtg ggaaccccac agaatccaag tatacagtgc cactgatttc ttacaaggga   3000
```

-continued

```
tgtggggtct cctgtaaact ctgcagttag tctcaagtaa gaccaaagag taaaatattg   3060
ttaggatcta aggtggaaat tcagcaaaga atcacatagt ctaagtctcg agtttaacag   3120
taagataatt tgagatactt ttgtaattat taaacacaaa gtaatgagag attttaaaac   3180
aaacaaatac acctgaattt atatatcaga ataggtatgg tggttcaaaa tagctatcta   3240
ataaaaacca cactcctatt ctaaacattt gcctttgatc aaaataattt tgggtctctt   3300
attatgaaat tgcctttcta aataatacat aaatttcttc tcataagtat atattagcca   3360
cattatttta ttgttattgt tttatattca tagcttgctt tagattaaaa attatattac   3420
ccagactggt ctcttggact tgcttccaag tgacttttga ctgtatcaca aaatcaaatt   3480
cactctgaaa atataaagat ttttcatcat aatttccttt gttaacagcc aagtgctacc   3540
taattttagg tgttttcatt aaaaaaaaat gcattgcaaa ctttaaagac aattcttttg   3600
tttgtttgtt tttaaaagac agagtctcac tctgttgccc aggctagagt gcagtgacac   3660
aatcataact cactgcaacc tccacctcct gggctcaagt gagccttcca tcttgcctca   3720
cgagtagctg ggtcttcagg tgtacaggtg tgtaccacca tgcctggcta acttttttt   3780
tttttaagtt atatagagac agtatctcac tatgttgccc aggctgctct tggagctcct   3840
ggcctcaagt tatcctccca ctcagtctcc caaagtgctg ggattacagg cgtaagccac   3900
ctcaccctgt cagcctaaag acagtgctta atgaagagaa atataagtgc tttgagcaat   3960
ggaagtataa ttaaaattat actatgaaag atttataaag atgaccattt tgaatgggac   4020
cacacttatt tggttatata aattatgata cactattaaa aattcatcat gatgattttg   4080
tatttacatt ttatttacat gtttgcaatt tgtgaggaaa gctaaaatta tggctaagcc   4140
ataaatattt ttgcagtttg ttgagggtgt ttgtaaaagt gttgccaagg aagaccagtt   4200
ggctacccaa acaagggttt agtctaggtc tgatcaatac atacacatta tctcaggttt   4260
gtctatcaga aaaaccttag gttatccaaa tcaaaataaa atagatgcat aaaacaaagg   4320
ccaatatgtg ttgaacaatt atattgtgat atacaactgc caagcattcc cgattaccat   4380
gactccattt agtcagtcca tgggcaaatg ccatcaatga ggacagccca gggtttccat   4440
attctctctt ggctttacat cctataggaa ttggaggggc ccacctctgg gataggagcc   4500
cttctgtctt gaacaatgtt gtctgaacac taacaaatgt tgactttcta caccagtccc   4560
tcaatagtct tttctattta tccttttgct gaccatgttt tgttattaca cagttgagat   4620
ttttcagctg ggaatctgtg ttaattttgt attaattttg attagcttaa ctctcagagt   4680
tctaaaagta cctcctgtac ctgatatatg acaaaaatta taattacatt tatttatata   4740
taaaatatct ttgtatatgt aaaatatctt tgtatatata attatataat tgtttctttt   4800
aattttgcaa attttaaaaa gttctccttt gttttgaagt ttattcctat agttttttat   4860
atgctagtta aattattaat cacttgattc aagtaatatt cttatatact tataaggaat   4920
agtgtagttt taatatttaa ttccttgcta aagagagaag tggaatctat ttttcttagc   4980
tacttcatca atattttatg tttgatgtga cagtcaaaat atccctcaga gctaactgtt   5040
acactaggga aatcacggtt ttccagtttt ccatttatgt gttatgggag ggagtggaac   5100
ttagtgtaat aatattcaat acataaatgt taacacttgt ttaaaggtcc ttgagtgagt   5160
actgctataa aatgcattat tattgctagt gtcatttcac aagagcctat aatttcagtg   5220
tgatagagct acaatataag tatagtattg caaaaccatc aggaagggtg ttaactattt   5280
agcatgcagt tatgtgttgg ttgtcaaaac gttaaaaaca tctctgactc agcagcaatt   5340
ttggcaattt tgatcctgag gcatctgtgt agggcatctt cctggagaaa aacctctgag   5400
```

-continued

```
atgcaatgag gtcaaaaggg gaaaacagac tatgataaag atcaagttgt ttggagatct   5460
tgtagaaaga ttaatttaca aatatgtcaa gtgcattatc atggaggaaa acattgctat   5520
ttctgttggt tctcttcaga gctctagaat caatttacca catagttgtt tcagtgtgaa   5580
attagcatta cagagtggct ttacggcttt actgtagggc attgtgtcag caaagagctt   5640
aggcttcttt tagcaagaag cttgtaaaaa tttaatttac tcttagattg cttgatgtag   5700
agaattacat tcctacagag ctctgaaaaa tcttttttca gagtttttca cagctgtatt   5760
caagttgcaa ggcttgtcaa ctttgctatt tttctgtgca gctctgttaa cttattatta   5820
tcttttgaca taaattatga ttccaaattg taaagctctg gatgtcaggg ccttttctaa   5880
tttgtttagt atgatattca gaccatttca agactcttcc gtggaacaat ttaataaaga   5940
tttttttgtg atgttaatga gttcatggtg atcaacccta gagacctgtg tctattgtag   6000
atcgatgaca ttcaacagtc ctgcagtgct ggcatcattt tgataaaaag gggtcaaagc   6060
aagtgggact gtgggcagat ttttaatgct tagaacaatt attccatcga agtttttcttg   6120
tgtcccttct gccttagcct ttgtaggata gcatgcttgc taatttcttg ctcatggggt   6180
aaggaaatga agatttttgc taggtccgta ggattattag gactactcag gcctgaagct   6240
atgcctggat atagccagaa aactctccca tagcttgctc caaggagctg agatacagca   6300
gtacttcctt tgtaggtcat gattctgggt aacctggaag atgacctcat tcatattctg   6360
tattctatgt gagacgttaa gaaggtagag gtggccaaga aggaaattgt tgctgccttt   6420
atggaacaaa ttatctgaaa cccagctttc tcgagggctt cattgaagta ctcaactggg   6480
gcacttaacc cagtctaagg ctggtcaagg aaggcttgct gggggaagtg tcttttgtat   6540
tcacacctaa aggaggttat tcaattagaa ttatccaaag agggtaggga tgggctagga   6600
aaaatttaaa caggtagtgt ggaggactga caggataagt aagcatggca ccttcaaaat   6660
atcctgagaa gttccctatg acgggaacat aaaatatgtg acagagattt gtgggagatg   6720
ggtctggaaa ctctagcagg ggccagatcg taagggggct ttgtaggctt tgtaggcttt   6780
gtttgggctt tatcatactg gaagtgaaaa gccatggctt ttaaacagga gagggacata   6840
atcagttcat atactgttgc agttttgtaa aagaaaagat gagctgaaag agtggccatg   6900
gtggaggtgg gtggggtggg ggggaggggg cggggagaga gagagagaga gagagatttg   6960
aaagacattt aggaggtaaa atcaactggt ttggtaatca attagtagtt gaaggtgaag   7020
gaaagagaag agttaaggat aacatctata tttgttgatt tggataatag aggggacagt   7080
ggtgctgctt attgaatgag aaaatttaat cggagaagaa ggcatggagc aggagtgcag   7140
acctatgtga ctctacttct ctcaaaacca gaaacggaaa tgatgtatat ggctcagggt   7200
taggtaatat ggttatttga aaatgtatta aagtgattta gagcttagtc ttaggtaaga   7260
gatataagat gtctgaggtg acagttttat aaatatgtag agtgcccact tgtttggcct   7320
tattgtggca tagtgtgacc tgagagtgtt aggaagaagc agctgagttc tagggacagt   7380
actggttaaa ttctacttag aaattatact tagaactctc ctatataacc tgctaactga   7440
tgtctgaacc tcctgataac ttcactcctt taggcagtgc ttttcacatc acgggacaca   7500
acatatgaga gatcatagaa attcaatgtg gtatgaaaat ctgcttggga cttcagatat   7560
tgtctccagt gattgaataa aaataggagc tcacctacta tgatgaggtt tctgtgtgtg   7620
ttaaaagaag gttttcatta cttttgaaaa ggttatgtat ccttgtttta tgttaaaact   7680
ttgagctttg ttaaatatgc agagttctct ttcttagcat ggactacaga ggtgcaacta   7740
cctcctacct gacttcacat ctactcccaa atgcctagtg aaggcttaat aatttcaaaa   7800
```

```
agggactcta gaatttcatt tgataccagt cagacaaatg tgtgaaaatt aagcataata   7860
ggcagaatcc caggggtact gacagctgta ttaagaggtg attcaagggc taaaccttag   7920
agtccagcat tggttatggg tgtgacaaga aaatgaagcc tatgttggct gggattagca   7980
accacagttc tagaggaagc aaggtggaga aactatatag ggggctccct ttgtacgttt   8040
tatttatttt aaacatctct ataaactcta gaaattaaaa caacaatacc aacacaaaag   8100
catcactttt tcgaccaaag accattgcta tactttttg tgtaaagggc tagatagtaa   8160
atattttcag ctttgtgggc cacataagtc tctgcaatag acaatatgca aacaaataag   8220
catggctgtg tttcaattaa actttattat gaacattaaa atttgaattt catataactt   8280
ttacatgttg caaaatattc tttatttaaa ttctattgca atatgcttta aaagatacag   8340
tttttagtct ttcttagttt aaaataaaat ctagaaaaaa ttttaagtct tctataactt   8400
tttttcggta actgaataat tttaaaagta agtgaaacat ttagacatgc aaaatggact   8460
tttcagaaga agaaaatggt agcttaacag ttattagatt attgtccaga ataatttttg   8520
acttataagt ctctgttgac catttcattg cctctttttt tggaatatgc atcttttaat   8580
gtgtccttca aggcaaaggc tctatcttat ctatcttgtg tcttgcattt tcccagggca   8640
atgtttttca caattttttt aaaaaacaat actgtaatca attttcaaat aaaattttcc   8700
atgggaccgc agtgtataca aatagcagtg acaataaaag ataataactc tcccataaat   8760
acaaagaaac agttaaccta gtgctctaaa gtaaaggcta cagtgatttt gtataacatt   8820
tatatgtaat tttcttgatc ctacatggtt gtgtttttca cagtgttatg tttctgaaat   8880
cgagatgcct tttataattg atgtcaaaag aaacttgtca gccacaaggc ccaggaataa   8940
gttgtaatat gggaacttag caatacataa aggtatatat actcctgtga cctcagctga   9000
attatttgca ttggttgcat cccacaaggt tgactcttaa ataaatttag tttgttgctt   9060
gaaatttctt gggataaatt actttgtgat gtagttttga aaaaaaaaca ggtaatattt   9120
agtctgaagt ttgtctgaca tactaagcaa tgtaattaaa gtagaagtcg cctaagctca   9180
gcactttatt atgccttgaa attatactgc ctgtcctaca ggtgaaggtg ttatgaatgc   9240
agtttgtcac tgtaactcta ttcatagctc tgaaaggctg agagtgactc agaagaatat   9300
ttttgctctg aatatgaaga acgcttagac taaaacttta attacgatgc tgaagaagaa   9360
agtggtaggt gattgcatga ataagtatgt aatattgtta atttctaaaa actgtgtata   9420
gttaatgtag tgcttctttt tggaaaggct attgttaaat tgatggtaaa ttctataacc   9480
aatatcacct taaagcaagt acgcatgata aagtattata aaaccatgat aatatcatat   9540
gtggcttatt attgttccct gagtgttgta caactctgtt atgctgtgat gaaacctcat   9600
gcaaacaggt atgtcaaaga tatgatgggc tgttaactga gcttggccca catatggtgt   9660
agtgacatgc tcactaatgc agtgcagaga taaccaataa cagatcataa caggtttaaa   9720
tatgtgcaag gagatgtcag cagaagcttt cctacatagt gaatactaaa caagcctgac   9780
agcccaggat catgttcgga tcaatctagt gtgctaaaat taacatatag tcctacattt   9840
gagaatgtgt gattttcttg gttcctgtct ataaaataat attttaaaat acatacattt   9900
caaatcagaa gttggtgaat tcactgaaat atttctagag aacactaggt attggggctc   9960
atagtgtgaa aaccactgac ttaattcttc ccccatcttg gttgttcctg atcttccctt  10020
gtgtccccat tccagccatt tgtatcctta gaaaatgatc tcatattcta cttcatcttt  10080
atcttcattg tcaactgtca ggtagcaata tatgatggaa gaagcatgta ctttggaatc  10140
agacagacct ggctggaatc ctaactctgt cacttattaa caatgtgatc ttaggcaatt  10200
```

-continued

```
tacttaatct ctctgaacct cagctactct cgtcagtaca atgagttatc cttatcttta  10260
catggcacag tattattatg atatcaaaaa ttcattgagt atttactctg catattagtc  10320
aaggttctcc agagaagtag aaccaatgat acacacacac acacacacac acacacacac  10380
acacacacac acaatttatt ataaggaatt gacttacatg attatgatgg ctaacaagtc  10440
caaaatctgc agtatgggtc agctggcagg aaacccagga gagtcaatgt tccagtttga  10500
gtctgaaggc agtctgttgg ggaatttcgt ccttctctgg gaggccagcc tttttgttct  10560
atacaggcct tcaaccgatt ggatgaagtt cacctttatt agtgagggca atctgcttta  10620
accaaagttt actgatttaa atgttaatct catccaaaaa cacccaccca gttgacacat  10680
aaaattaacc atcactctct gtaagcactt tctatgcatt aagtgatagc aaataatgcc  10740
agacataggg cgtctttaat aaatggtaag cactgttatc agcaacaaca ggattattat  10800
aattagcacc ttttcatctt tctgtctggg ctctgagaaa gtacctctct tctctaaatt  10860
tatccctcct ttcctatgaa ttagacccag tgctttctct gaattatgaa ggtcacactc  10920
ctacaaatgc cccttcccaa ttgcacatct gtcggctttc tttgccattg acttttatct  10980
ctagctttta aatttacagg catatgtcag ttaacaatgg gaatgcgttc tgggtaatat  11040
gtccttaggc aattttatcg ttgtgagaat actatagagt atacctacac aagcctagat  11100
gtcgtatagc ctactacaca cctaggcaat atgacatagt cttttgcttc taggctacaa  11160
acctgtacgg cttgttacta tactgaatac tgcaggcagt tgtgacacag tggtatttgc  11220
atatcggaac atgtctaaac acagaaaagg tgcactaaaa atactatgta gtgatctcat  11280
gggaccacca ttgtatatgc agtctgctgt agactgaaat gtcatgcagt gcataactgt  11340
atcttaaata ctcaaagtat cacctttgtt tgtttgtccc cttgtgtgca tcatcctaac  11400
gtggaatttc tctgttgatt agggccagcg tattagtttg ctagggctac cataacaaaa  11460
taccacaaat ttggtggctt aaataacagg aatttattat cttatggttt tgaagactag  11520
aagtacaaga tcaaggtgtt ggcaggtttt tcttctaagg gccatgagga agagtctatt  11580
ccatgccttt cccctacctt ctggtggttt gctagaaatc cttggcattc cttgacttac  11640
agaggcatca ccctgatctc tgttttcatc ttcacatggc attctccctg tgagcctgtc  11700
tctgtgtcca aacttcttta ctattaatat aaggacacca gtcatattgg attagggtct  11760
actttagtga cctcattgga atgttattac ctctgtaaag atcctatctc taaataaggt  11820
cacatcctta ggtaccgggg gttaggactc aaacatacct ttttttgggg aaacacaatt  11880
caacctataa caattgataa cactctttag gagcagaatg cgatatggaa gtaatttgag  11940
accataaagt atatacatgt agggagttaa tctatgaaac ctattgaaag ccatatatac  12000
ctcatgtata gtggtccata aatagcatgg agacattgca gaggatgtta agtgatatga  12060
tacaggaaca atccaagaag gtcataagaa aaaggacctt ttgctcttga gaggactgaa  12120
gaatgacttt ccatttatga aattttggta catgtccact aaaaatagga tgaaggccaa  12180
acttaggaag aatattttga taatggagaa ggttgcatat aaaaacattt tattgaggac  12240
aattaaataa tgttggctgg aagttttagg atgatcatct ttaggactca gaaaaagaga  12300
agaaacatta ttaaagaatt gtccctgaac aagtataggc accctcacat ttgcattgca  12360
tttactatag aattgaaaaa tgttttgacc tttttttttt ggcttttaat atatttgacc  12420
aagagtaaca gctaagcaat acctatttgc aatcagtgtc atcatgtggg ctccaaacat  12480
atcatgtttg tgtaattaat tgattgaccc attaatttgt tcaatttctg ctctgttcca  12540
ggcactgaac aacatgatgg agataaaaga taaatattac acctgccttg tcctcaagaa  12600
```

-continued

```
gttagtcttc tgagggaaag aaattagcaa acaaattgta atctcagtta tgtgccatgt  12660
tccatgctgg gcacagggga tacagtagtt taaaaaaaac acaagatcta taaggtgttt  12720
cttcttgtgg accttacagt ctagggtgct tggaaacatg gggcgttggc agacaagtaa  12780
atacacattt tgtggtaaag gctcaggtag aagaagtaca ggatagaata gagcacacca  12840
tggggaatta atctagactt cagagaggct cacacataca taatttatgt gtgactattt  12900
caatgcattt gaggtttctt ggaaatagag gttaggtttt attttaagga agttaccatt  12960
ttttttttca gtgtgatgtg gttgaaccaa agaatgccat gcccagtgat ggtaatagga  13020
taatcttttt aaaaattaag agccacctaa taaatcaata gtttcattca gcgggagctc  13080
ctgcagagtt caaaaagaag agaatctggc acagcgtttc ctttaaagtt cattttccta  13140
gagtgtgaat ggaagcaaga gattataaca ttttgaggtc aaaaaaattc tgaaatgcct  13200
ataaaaatta ttttctccaa attatcatca tttgtgcttt taatgacctg attgcaaaga  13260
tgaacatttt gaattcttaa attgcttatt aggattggtt aatgaatcaa ttatctatta  13320
ctgtatgttt tgctattgga aaaaatagca acttaagtgt tttgcagacc tttacttagg  13380
tatatgttgc ttttatgaaa aaaaagatgt aaatattaag taaaagggat ttaaagcaag  13440
gcttttgagg tagagtctta ttaattcctt ggtaaacctt gagccaattg ttgtctatgt  13500
tctctgcctc tgtcttgctc cttccttctg ggattcactg tgggaatgcg ggattgttaa  13560
tctggggatg ctgtccaatc ctgcctctct caagctttgc tattgatctc cctcccagtg  13620
ataataaagc ttgaagaaaa tgaaagtagc gttagtattg gtcctcaaac tcaagaacag  13680
gatgaaactt aaatcttgag tcatacaatt gtgtctacat actgctcccc aaaaagagaa  13740
gtaaagaaga tgctaacttt ccccttttaat ttgcagtact tagcaatttg ttttcttgag  13800
ggttaagtaa taacagtgga agaaaaaagg gttaaaatgc caccaagaac ccaattccat  13860
gtttagtttg aaagtgggaa atcagctgcc actgggaagt ctgaatccaa tgccatgatg  13920
ttctttgaat ccttctgaga aataatcatg tgtagccata acatacctgt ataacagagc  13980
agagaacata aacaaatgaa ggtgaaggga agattaagac agaagagaaa aattccagaa  14040
tcgactgatc atttttatct gtttagatga tttcaggcag aatcctagag accaacttta  14100
tcacaactga attttaaaaa tcaccagctt tgtcattgtg atgcagcatc agtttcagta  14160
ttatccttgg agtattaatt cttaatcatc ttcatcttag aacatttttg aggtcacttc  14220
tagtctctat ttcaccagtg aagaaacaaa aatccccaaa ctatatcagg tggaattaca  14280
cagtattttt tttttaattt tggggaaagt cgattcaagg cagtaacttg caagctagtg  14340
ttagaaagga tttaataaat agtggttttt ctgtacacat agtgagaggt cattacatca  14400
tttggttgtt gaaagtcata aggatgtcta gcatgcgctt tgcctgtagt ggttcatgcc  14460
aggcagattc ctgactccta taacccagag cttatcagag catttatgtc cccaaagaga  14520
aatgtcacct ccatctttca ataaacactt tagcaaagaa aaatcaagta ctttaattcc  14580
aaatcttgag ttaattccag aataacaatg atggctcgga aaaatatggg tatttctgtc  14640
aaaggacaga gaaacctagt agagagtatt tactttgggt cctagtgatg gtatctgaac  14700
aagctaggtg aacaaagagc ctcaataagg gattttgagg tctagaaaaa gagaggaaat  14760
accaaataaa tggaataatt ataaaataaa taccagcaaa gttaaatcaa tatatcatgt  14820
gggagatatc cttatatcac tcatgtgatt tctattttgt tcctatatta ggccaaggag  14880
aggtggaact tgttttcctt tttccctctc agctacgaat ggacatactt aaaactgttt  14940
ctctgcttct gttctctaaa atgtgattgt ctaacagtaa ccgtgatgac gttttgacag  15000
```

ttgcacaagt ttctttcttt aagctttaaa aatgccagcc agtaacccag tggcatttct 15060
actataaaat cttaaggcca atccatttcc ccttttcctt attttcttgg tttcaaatat 15120
atttttattg ccaatggaaa taaaaatcct aaattagaga gcaatggcat cccttgtctt 15180
gtgaataaag agctcctaaa tgtgaactta tacaggatgc agcaatttat agggtagtta 15240
atcattcttc tttctagcca gttgttccag ctacagtttt gtggctcttg ttagtggctt 15300
cattcccaga tagaataaaa atcaaaccaa aatcctggaa aggcactctg aggatgcttc 15360
tctaaagtag atgggcatca actataaatc acaatgcttt gtttcctctg ttatgtttca 15420
agatgggtgg gatttttttt gtagcattac ttattattgc ctctcaagtg cttgagtctt 15480
tgaaatccaa gtcatgtgag tgaattagat acagctgtta gaagtggcct ttcaatgcca 15540
atggtacaca ttccttggtt tctttacgat actattgctc ttacaacttt tatctgaagt 15600
cataaattca tagttgtccc agaagttaag ttccttgctt ctagaggaca gaaaacaaac 15660
aatttacaca actcatggtg catgtcacca gtccttagat ctcatgaaat atgcatgaaa 15720
tcttaaatca cttgctgtag ccacccagcc attgacatat ttgaaagact ttagtgtatc 15780
aaagtcacta taatgaaaat tttgatttca ccagttctag gagtgaaaaa tcaaatgttt 15840
agtaaaactt tctaaaatta acactgacag ttgatttctg tatactgttg ttcttaataa 15900
tagctttatt gagatataat tcatattcaa aacaacttac ccatttaaag catacaatcc 15960
aatgattttt tagtatcttc aaagagttgc ctatcaccat aaccaatttt agaacacttt 16020
catcactgta aaaagaaact ccattcctat tagcagtcat tccttattcc aaatccccct 16080
gctcgcccta gacaactaca aatgtacttt ccatctctat agatttgcct gttctggaaa 16140
ttttatgtaa atagaacaaa gtgttctttt gtgactggct tatttcactt agcatttttt 16200
ttcaaagatt catccctgtt gtagcgtgta tcagtgcatc attctttttt attttttttag 16260 agacagggcc ttgctctgtt gcccaggttg gaatgtgcag tggcatgatc atgggtcact 16320
atagctttga agtcataggc gaaagcggtc ctcccacctc agtctcccga gtagctgaga 16380
ctacaggctt gcaccacatg actgtctaat ttataatttt ctttagagac agggtcttgt 16440
tatgttgtct aggctgctct caaactccag ggctcaagtg gtcctcctcc cacagcatcc 16500
taaagtgctg ggattatagg tgtgagccac agcacctggc ttgcatcatt ctttttattg 16560
ttgaataata tcccacttgt aagaatatgt attttattta tcctttcccc agttaataga 16620
tatttcgatt gttcctaatt cttgtctatt ataaataatg gtgctatgaa catttgtgta 16680
caagtttttg tgcagacatc cattttcctt tcttttgggc atatacctac gagtgtaatg 16740
gatgggccat atagtaactt tatgtttaat attttgagga tttttcaaac tgttttccaa 16800
agtggctgca tcattttaaa ttccttccac cattgtgtga gtgtttcaat ttctccacat 16860
atttgcaaca cttactatta tctactctta aaaattacag ccatcctact gggcatgaag 16920
tggtatttca ttgtgagttt tttttttctt tttctttttt tctttttttg ctaatgtttg 16980
tggattttct tttcattttc ttgatggtgt cctttgaagc acaaaagtat ttaattttga 17040
taatttccaa tttatttttt gttattgctg tttgtgcttc tggtgttgta tctaagtgta 17100
tgctacttta aaaaattagt tgtaatatgg caaattggat acatgtgtag gctttggtgt 17160
cacaatccta attttaaaat tctgactctg cccttgacaa attaactaat taagcttcct 17220
tagcctcagt ttctcaactg taagttggag atattaccaa gacctacctc ttgaattgtt 17280
gtggggatca gatgaaataa tgtatgtgaa atatttagaa ttatgcaagt ctgtggtaat 17340
gaatactaat gttagctatc attattgtta taatcccaat aataaattct ggtgctttga 17400

-continued

```
aaattaaacc aaagccaagc agttgatatg aagaagcatg taataatgta cagacataat  17460
gctttataga caacattgaa tttggctctc atgaacatca ggaatagtgg tcatggtagt  17520
tattatctcc agcaggaact gtagctgaga gatcttcaga gctttttcca aggcgatatc  17580
actgggaaat aatagagaca aggttacaag ctagggctgt gttttcttct taaaatcttt  17640
agttcagttt ttttcaataa cagatttgta gtaggcatca ggtgactggg gattcgtatt  17700
cttcaagttg aaatattacc ttgttgagaa agaaaccatg tgtgagacaa ccatgttgag  17760
aaagaaaaag tgattttata gaaaattaat attgatagtg agcattatat gaaaatcatg  17820
aagttagaac atatttggcc agaaaattta cattaatagt tacccatagc aattaatgca  17880
ttataattac acataccttt tctttaatga aaaagaattc tttccttcca aagttatgca  17940
tgctattgtt aaacattaga gaatatagag aagcaaaaaa gaaaatatct tttttgatat  18000
tttcttaaca tacgtctgtt cctaataatg tttatagttt agaagcattg catgaaatgg  18060
gtagatcaat tttctattta atgtttggat tcattaggta cgaagttagc aaattaattt  18120
ccattagggt gcctgtatgg ttgtaaatcc tggacctgca gaagattttt cagtattggt  18180
ttgtagtctt ttgtttagca gcaaataatt agttctccag agcttctgaa attaattgac  18240
cactttaatg gtgtttacct acctagagaa agaaaaagaa cttctccaag tcccttggta  18300
aaattaagcc tcatgaacaa ttaactcaaa tatacacaag gcttgtcttt agcgagcata  18360
tactccctaa agttgattaa gctgaccaag tgattactgc ttataaattc accattttat  18420
ggagaagaag caaacactgc taaatacctt gtggaatcag aggaggggaa attagtaact  18480
tgaccccaat actgcgattt taaattgaat tcttgaagcc tacaagtttt acacaggact  18540
ttagagagct ggatagtatc actttgtcaa gtcctacttt tactatgatt ctttgagaaa  18600
aatacatctg actaaataac tctgaatcta aattggataa aataaatgtg acattcaaaa  18660
tgttatttat gattttagaa aaatatcctt atagacacta gatgagtttt agtctcaaat  18720
caatcctccc tatcatagtc acttatcaaa ataactaaag caaagtggta gagctgtgct  18780
ctagaagttt gggatttatg atcacaatct tttccaatga gtcccctctt tcctctgcct  18840
gtcttcaaca tttgtttttt tttttttttg gttaggacta tccagattgt gtggcctatt  18900
tcaaactcat ggcaaataca ttggatgatc agaaattttc taatgtattt gaatttgtct  18960
acacaaacta gagtaattgc tattaattcc tcaagtgtta attatttcat gcaaaaagga  19020
aaaaggctat tagtctttaa gtgtattagt atgtcaatat ttgggagaag tgtcatgcaa  19080
ttagtggttt gaatttccta ttttatttta ttgcatttta ttttatttgc ctagtcaaat  19140
aaaaagtaat gttaaataca tggaagcatg attgttttct acactaaaaa tcattttgac  19200
ttgaaaagat ctgatatcca tgaccttcat ctgaagtttt ggcagatgaa aatgtcagat  19260
gcgtcttttg gattaataaa aggcaaaagt cagatcgaaa aatgagtata agctttaatt  19320
atatgacttt aggaggatat gttatgaaaa tcaaagcttt aatagtgatt ataattggca  19380
agttcttttt ttataaggaa ttacaagtca ctctatacaa aaattggaat ttttgtccta  19440
agaaatgaaa tttactatag tttcatctgt gtgtgtgtgt gtgtgtgtgt gtgtgtgtgt  19500
ttaaaaaatc aagtgatagg gcttttcctc aataaaatct gaaatctctt atagttaagt  19560
gaacagaaca gtgtatctag gatgctagac tttttttca aagttagttt aaaacttata  19620
catagtaaaa tctgtatgcc ttagggatct ctgtttgcta tcccatagtg aatgattaat  19680
tagtttctgt tagaaatagt cagaactagg ctgggtgtgg tggtggctca tgcctgtaat  19740
tccaggactt tgggaggcca aggcaggagg atctcttaag cccaggaatt tgcaaccagc  19800
```

```
ttgggcaggc tggtgagatc ctatctctac aaaaacaaac aaacaaacaa aggacaataa  19860
gaaagaaaga aatagccaga gctttgaaca aaatttctaa gtagaccaat gtaaaagtct  19920
gtcgtcaata tgtagtggct atgaatggag gttatgaatg aaagagaagg ataagatgaa  19980
ctagaggtga gaggggaaga cagcaggccc aagtgaaagg cagagccgag tttattgctt  20040
tttggttatt ccaggtgtgt ctgctttgtc tcatgaaaca cctggatgat cactgatttc  20100
tagtggaaga aatgctgaaa agtccttact gtgcatttaa acattctagg tttaatatac  20160
tcagggtttt tcaaaagaaa gggtggctgg agttttgcac taactaatat ttcataaagt  20220
gtctaagtat agatgtctgg tttttttttg tatttctaag actggcttga ggtaggcatg  20280
gagaattctt tgatgggaca taattttctt cctttctttt tttttttttt tttttttttt  20340
tgagacggag ttttgctctt gttgcccagg ctggagtgca atggcacaat ctcggctcac  20400
tgcaacctcc gcctcccagg ttcaagcaat tctcccacct cagcctcccg cgtagctggg  20460
attacaggca tgtgcccca tgcctggcta attttttttg tatttttagt agagatgggg  20520
tttctccatg ttggtcaggc tggtctcgaa ctccttacct caggtgatcc acccacctcg  20580
gcctcccaaa gtgctgggat tacaggcgtg agccaccgcg cctggcctga tgggacatat  20640
ttttcattca attttattga tttaacctca caaaataaaa tatttcctta agatgactct  20700
gtggtcattg ttgggcagca taagcttaat ggattttagt tatcataatt taccttaaac  20760
ccaatttgta tttcaggata taaatagagg tttattgtag tgaatcttcc aggaaatact  20820
aagtgatact aataattata gatggtgaac ttaagtcttt atattactga atttgtttgg  20880
tttgatgatg ctaggctatg gcattcttgc taatcaaaac gatgtgtcat ggtgtaacat  20940
aacttattaa aatgggcaca gataacacag gaagcttttt ataaaagcag ctcacaaatt  21000
gtgttacttt gaactgaact ggccatttat gggaaaggtc actgggttgt aaataaggac  21060
caaaagagtt acgtttatat tttttaaaag agattgagga gatttatttt tacatttctt  21120
gaaaatgcct tattttggta tggtattgac agatagtgaa attctgctca tttgtaaata  21180
tagtgtcata ttttaataat ttcaaacata ttgaaaatgc agaatttatt aatagtggga  21240
gcacattttc ctttttacta aatgttctac aggttctttt ctttccatcc acacacagtg  21300
ccattaccct cattctaagc ctttcaaaca tctggcagta agtgatctgc tgcacttagc  21360
tctttccagc tgagctgatt tttaaatttt cagaaaattt gtgagctaat tgttaaacat  21420
ggccattatt aaaaattaaa ttatttcaac ttataattaa ataaattata ttaaaacaaa  21480
agtattaaaa actcaaaagt tggctgggcg cactggctca cgtctgtaat cccagcactt  21540
tgggagaccg aggcaggtgg attgcctgaa gtcaggggtt cgagaccaac ctgaccaaca  21600
tggagaaacc ctgtctctac taaaaatata aaaaaatagc cgggcatggt ggtgcatgcc  21660
tgtaatccca gctactcagg aggctgaggc aggagaattg cttgaaccca ggaggtggag  21720
gttgtggtga gctgagattg cgccattgcg ctccagcctg ggcaacaaga gtgaaactct  21780
gtctcaaaaa aaaaaaaaaa aaaaaaaaag aaacaaaaaa aaaaaaaaaa caaaaagcaa  21840
acaaacaaaa aaacaaaaat tatcacttcc taattatttt gcattttact attatctatg  21900
ctattaacgt tatttgcctt cattgtattt gaaaggtgga ctatattcta ttgcactttc  21960
attgtactat attctaatat gcaactgtgt atcccttccc aactctgtgt tcaatgactt  22020
tatatttggt tgctttaaaa tgatgacgat gagagtattt atatcataga aattggcaaa  22080
tgccgtaagt cagtttttgt ttttgttttt gttttccgga gaggggattg ttaaatattt  22140
gcctgcatgc aacaccacta catgcagtct gctatctttt gttcttcctg ctttcaggct  22200
```

-continued

```
cctctcccag ctgtctgtct agcacaaccc agcataccaa attttcttaa atagggaaag  22260
ttgaacatgg taaaagaatg aatgaagtca aaagaatgtg gaaagaccta ggctttgcca  22320
tttagtaaag tttagcatct ctaagcctcc atctctttat caataaaatt gagcaatgat  22380
ccctttagt tctacccatt taagaagatt ttcaaatgaa aaccacaacc tgctcatgtt  22440
tatgaaggca ctttggaaag cgctaaatac acgggttttt attagtagta aacacttact  22500
tcaccttttt cacttcttga ctttagttta caagggctca taatctaaat tatatcataa  22560
attgctgtcc cagatttttt tacagcctaa ttgccacctg tatgttcgac tttccttctg  22620
ttctttatgt tagatactgg gatagtatgc accaggtggg tgtgccatca ctttctcaga  22680
tgatgtccac tgaagacctt gcatgatcat ggcattcatt ttcctgctgt attcagactg  22740
gcctcaacta ttttctttat tgctctccag gaaaaattac aaatgaatca gactgggcaa  22800
tgaagggtaa acctaattat cgctctttgt taaagacagc tcttgttaaa atgcggatat  22860
tgcaaattaa tggaaaaaat atgacatagt aaaccatact cacttattaa tatcttagta  22920
aggaataatt gatgaagtta cttaacctta gagccctaat tcagttaagt tttaatgaag  22980
gacaagttgt agagatatcg agaacccagg gcaggtgcct actgaagaag ttccagacca  23040
aggaagtata aagaaggacc tgggtgggag cagtgagatt ggatatgagg gccactggca  23100
aagttttgcc ccagaacagt gtcaaaatgt ttgcatttgg catagccctt tctctttttg  23160
ttctgaatgg ctttgctaga atatcttttc tataatgaat ttatcctgct tctcagatat  23220
tgctaaagca ctccctttg aattttggtg ctttaacatg cattttgata cattaccaaa  23280
taaggtctga atgacacaaa ttttagaact ctccagagaa aagaaagatg ctgagggaaa  23340
aagcataggt ttgggactca ctaaatccca gttcaattcc tttctttaat aaatatattc  23400
aattttacct gagaaagctc tcgtgctctc gaattttatt tagaaatttc tctttgtaca  23460
tgattgattt cacaatcctt cttctgcctc ctcttctact ttcttctttc tagattttcc  23520
tatctttatg aagattattc tgccttatcc tcaacagtta gaaacaatat ttttgaaaat  23580
cactacggta tcctgcatag tgatttccca tgccaacttt actaatttcc attataaatt  23640
attatttatt gatgcctaga gggcagatga gtgtagctgc tatggagtga ggagacaaaa  23700
cataagaaag ttatgatcct accctcaggt aatgattcag acatgataat taagtcaaca  23760
aattgataga aactaatcac taactctctg gctatagtca ttctttcaat gaatagctca  23820
ttactgagta tgcatgctac agtaacaaaa ttatataagg ctgttgatta aatgttgatt  23880
aagtgcatgt cttattcaga gttttttat atttgaaatg gaagaggctg gacttcagta  23940
atttgctata aactgctagt atatgattat ttgggggcag ttattttta aagaataatt  24000
taaatatgga atgtttagca gtttgttttt tccctgggaa aaaccatact attattccct  24060
cccaatccct ttgacaaagt gacagtcaca ttagttcaga gatattgatg ttttatacag  24120
gtgtagcctg taagagatga agcctggtat ttatagaaat tgacttattt tattctcata  24180
tttacatgtg cataattttc catatgccag aaaagttgaa tagtatcaga ttccaaatct  24240
gtatggagac caaatcaagt gaatatctgt tcctcctctc tttattttag ctggaccaga  24300
ccaattttga ggaaaggata cagacagcgc ctggaattgt cagacatata ccaaatccct  24360
tctgttgatt ctgctgacaa tctatctgaa aaattggaaa ggtatgttca tgtacattgt  24420
ttagttgaag agagaaattc atattattaa ttatttagag aagagaaagc aaacatatta  24480
taagtttaat tcttatattt aaaaatagga gccaagtatg gtggctaatg cctgtaatcc  24540
caactatttg ggaggccaag atgagaggat tgcttgagac caggagtttg ataccagcct  24600
```

-continued

```
gggcaacata gcaagatgtt atctctacac aaaataaaaa agttagctgg gaatggtagt  24660
gcatgcttgt attcccagct actcaggagg ctgaagcagg agggttactt gagcccagga  24720
gtttgaggtt gcagtgagct atgattgtgc cactgcactc cagcttgggt gacacagcaa  24780
aaccctctct ctctaaaaaa aaaaaaaaaa aggaacatct cattttcaca ctgaaatgtt  24840
gactgaaatc attaaacaat aaaatcataa aagaaaaata atcagtttcc taagaaatga  24900
tttttttcc tgaaaaatac acatttggtt tcagagaatt tgtcttatta gagaccatga  24960
gatggatttt gtgaaaacta aagtaacacc attatgaagt aaatcgtgta tatttgcttt  25020
caaaaccttt atatttgaat acaaatgtac tccctgggaa gtcttaaggt aatggctact  25080
ggttatcaaa caaatgtaaa aattgtatat ttttgagtac ctgttacatg ccaggtagaa  25140
tatctcctct cagccactct gagtggaaag catcattatc tctattttac agaaaagcaa  25200
actgaggctc agagagataa tatactttgc cagttaatga atgatggagc catgattcca  25260
gctgaggtct gtattgcctt gctctctagg aatggtagtc ccccccataa agaatctctc  25320
agtttccttt ccaatcaaaa ggttaggatc cttttgattg ccagtgacag aaacccaatt  25380
tactagctta agtaaataaa aggaacgaat ttattggctc atgaagcctg aactatgtga  25440
agacctaggt ggagaactgg ccttaggaac tcaatgggac caaggactca aatgccacct  25500
ggtggcattt gccttatgct ggttttattt tctcagaccg gaccagcttt ctacataaag  25560
tgggtccctg gttagaactc tttgctccta tctttaagga ccacgaaaga aggagccctt  25620
tgtccttggc taaatgtgaa aaatcccaga gactcttgag tcatagtgct taccccttgg  25680
gccactcata gtctagaatg aactaggctg agtctcgtgc caacagcaca ggcctgatgc  25740
cagataaaag ggtgagtgaa gggggataaa aaataagaca tagctactaa attattgcac  25800
caaagtaaaa acattgagtt gacttgcaat ttgtttcttt taattaaatt catttccttt  25860
ttttggcatt ttgaaggcaa agtaagatat taaactttat ttttattgat tttattcaaa  25920
gaattaagct agtgggagta gcagattcac acttctaaga tcaagggcca gcttctatta  25980
ttgaacactt ggtgtgtgca aatgccatga ggtagggata ctttgttttg ttttttattt  26040
tttattgggt tcgatctctt ttgtttatga tgtatcccca agtgcctaga atagggcctg  26100
gcatatggta tatactcaat aaatatttgt tgaatgaatc catgatggaa tgtgaaatgg  26160
ctagcattac atagaaacct gtagcattgc tggagagata aaatatataa acataatcca  26220
ttgcaggtat attgacaagt tcaaaataat ataatgggta ttgaatatct aaatgtttgt  26280
tgttgttgtt gctgttgttt ttgagacaga gtcttgctct gttgcccagg ctggagtgta  26340
atggtgcaat tttggctcac tgcaaacttc gtctcctggg ttcaagtgat tctcctgcct  26400
cagcctctcg agtagctggg tttacaggca ctcgccacaa tgcctggcta atttttgtat  26460
tttagtagat gtggagtttc gccatgttgg ccaggctggt cttgaactcc tgacctcaag  26520
tgatctgccc accttggcct cccaaaatgc tgggattata ggtgtgagcc actatgccca  26580
gctttgaata tctaagtttt aattggatgc tgagggaatg attaatcaga gtagggctgg  26640
gttaattgaa aaatgtgata catttgtatt tatggccaga tagagaacat gaatctgaat  26700
ttgcagaatt atctggctta acattttttt ctttccagtt ttcactgtat cccccatgtt  26760
gattcaattt aaaaaatata cctattttac ttcaattcaa caatgctatg ccagtacaaa  26820
cccatacgtt ctattatttt tgttttgttt tgtttttgta tctccaccct gttacttctt  26880
ttcttataaa attggtattt gaaatttatt gaaatatttt ggaagagtga cataccattt  26940
ttggtacttt gtacctctgc acccttggga agtgaccctg gcttcacatt tcataactgc  27000
```

-continued

```
cttgtgacca tggccctcaa gtggttgcca gatggttgaa gaacattaac ctatctggct  27060
caattttgtg accatggatt gaatcctcta cataactgca gtgtgcaaac cacacatccg  27120
ttccaagatt gtagtcagga tatgaacttt ttaagaataa aacttcttcc cttctgatct  27180
gggcctggta tgtggtccta ctagaaccac atcacctact cttggtgcta acaatttgtg  27240
gcaccaagtt gttcaagttt cacccattaa agaaattccc cgaccttgcc ttctcctcag  27300
gtaactaccc cattctattt tttctttcat agctaacatt ctctgctctc ctggtctctc  27360
tacttcactt tcatttacat ctcagctcct gaagtatggt ttccaccatg ttcctaaaac  27420
tacattgccc agggtcacta gagacctctt atgaaatata acaacacctt tctacattac  27480
ttccgtgtgg accacttttt cacattgaac ccattttgtt ggtttatgta cacacccctt  27540
ccttggcttt cccatctgat ccatttctcc tttgatggag aaggtgagtc tgctccatat  27600
ttagcttctt actctgagta accaaatgtt atggatggga ggttagctct gtgtgtgaga  27660
gaaaggtgga gaagcatgtg gggagggaaa tagatgggaa aaggtaatta ggctttatag  27720
aagggctctc attagcaagc ttctagggga tgccaagatc catgcttaga gattgccagg  27780
cttgtcttca aatctcagct gtgtattact cctttatgtt ttttgtttgt ttgtgttgtt  27840
tgtttttgag acagagtctc gctgtgtcac ccaggctgga gtgtagtggt gtgatctcag  27900
ctcactgcaa actctgcctc ctgggttcaa gcgaatctca gtctcctgag tagctgggac  27960
tacaggcatg caccaccagg cctggctaat ttttgtagag acggggtttt gctatgctgg  28020
ccaggctggt cttgaactcc tgacctcaag tgatctgccc gccttggcct cccaaagtgt  28080
tgggattagt ggcgtgagcc actgccccgg cctattactc ctttagagtg atttagagcc  28140
atgtttactt atggtaactt gacagtaatg ggaataacca ctgatgaaac gtaaagcctt  28200
tgtctaattg tttacctagt tcttccttgt ggttcatgaa atttttcatc tctgtacagt  28260
ttgaaaatta agatgataat atttagagat attttattcc tttgtgaaga gaaaaaaggc  28320
tttcattaac agaaatcagt ggcaataact taataaatac aatcagctgg tgttcctata  28380
gtatttaaaa gaaaacagaa agtttactag atttcagcca gttttcagac tatttaatgt  28440
ctattcttac tataatagaa aatatataat ttgatcttgt tctcattttt caaagacctt  28500
taatacatga ttttagtagt tgaaaatgaa gtttaatgat agtttatgcc tctactttta  28560
aaaacaaagt ctaacagatt tttctcatgt taaatcacag aaaaagccac ctgacatttt  28620
aacttgtttt tgatttgaca gtgaaatctt ataaatctgc cacagttcta aaccaataaa  28680
gatcaaggta taagggaaaa atgtagaatg tttgtgtgtt tattttttcc accttgttct  28740
aagcacagca atgagcattc gtaaaagcct tactttattt gtccaccctt ttcattgttt  28800
tttagaagcc caacactttt ctttaacaca tacaatgtgg ccttttcatg aaatcaattc  28860
cctgcacagt gatatatggc agagcattga attctgccaa atatctggct gagtgtttgg  28920
tgttgtatgg tctccatgag attttgtctc tataatactt gggttaatct ccttggatat  28980
acttgtgtga atcaaactat gttaagggaa ataggacaac taaaatattt gcacatgcaa  29040
cttattggtc ccacttttta ttcttttgca gagaatggga tagagagctg gcttcaaaga  29100
aaaatcctaa actcattaat gcccttcggc gatgtttttt ctggagattt atgttctatg  29160
gaatcttttt atatttaggg gtaaggatct catttgtaca ttcattatgt atcacataac  29220
tatattcatt tttgtgatta tgaaaagact acgaaatctg gtgaataggt gtaaaaatat  29280
aaaggatgaa tccaactcca aacactaaga aaccacctaa aactctagta aggataagta  29340
aaaatccttt ggaactaaaa tgtcctggaa cacgggtggc aatttacaat ctcaatgggc  29400
```

-continued

```
tcagcaaaat aaattgcttg cttaaaaaat tattttctgt tatgattcca aatcacatta  29460
tcttactagt acatgagatt actggtgcct ttattttgct gtattcaaca ggagagtgtc  29520
aggagacaat gtcagcagaa ttaggtcaaa tgcagctaat tacatatatg aatgtttgta  29580
atattttgaa atcatatctg catggtgaat tgtttcaaag aaaaacacta aaaatttaaa  29640
gtatagcagc tttaaatact aaataaataa tactaaaaat ttaaagttct cttgcaatat  29700
attttcttaa tatcttacat ctcatcagtg tgaaaagttg cacatctgaa aatccaggct  29760
ttgtggtgtt taagtgcctt gtatgttccc cagttgctgt ccaatgtgac tctgatttat  29820
tattttctac atcatgaaag cattatttga atccttggtt gtaacctata aaaggagaca  29880
gattcaagac ttgtttaatc ttcttgttaa agctgtgcac aatatttgct ttggggcgtt  29940
tacttatcat atggattgac ttgtgtttat attggtcttt atgcctcagg gagttaaaca  30000
gtgtctccca gagaaatgcc atttgtgtta cattgcttga aaaatttcag ttcatacacc  30060
cccatgaaaa atacatttaa aacttatctt aacaaagatg agtacactta ggcccagaat  30120
gttctctaat gctcttgata atttcctaga agaaattttt ctgacttttg aaataataga  30180
tccataatat atattcttat ggaaatctga aaccatttgg gcatttgggg gtaaaaagta  30240
ttttattagt aaatttaaat gaggtagctg gataattaaa ttacttttaa gttacctttg  30300
agatgatttt tctcaatcag agcaccaccc agagctttga gaaacaattt tattcacagc  30360
ttctgattct atttgatgta atttttagaa aataagtttt gctggttgct ttgaatcagg  30420
gtatggagta cagttcactc tgatcctatc atataaatca tgtaagtata taacattttc  30480
aataagtgat tgttggattg aagtgaatga tatttcaagt aattgttatg tcatggccaa  30540
gatttcagtg aaactcaaaa tttctcctgg ttgtgttctc cattgcatgc tgcttctatt  30600
gattaaccta agcactactg agtagaagct ggaagagggg tctaattaga aggccccttt  30660
ctatgctctg cttggcttgt aaaataattt atttctctag atcccaccaa catagtagtt  30720
tcatgtatgc aaaaacaccc acctaaatgt caaagtttgt atgatacatg gacatatcta  30780
tagaattttt tttggtctgg tgcatgccaa aaaataaaca tgatatagaa gaatttaata  30840
tttattgagt acctaatctg ttccagttca atatgaaggt ctttatgcag attattttac  30900
ttaattttcc tagtaactcc atggagcaaa aattatctct aatttatata acaggaagtt  30960
gagcgtgagg caaattaagt aactttccca aagttacaca tatggtaagt ttgagagata  31020
tcccagtctc tttagctcca aagcctttga ccctttcacc ataccagatt atgattgcta  31080
ttaatatata attataatta taatgattgt atttaggtac tcaacagaat ggtgactcta  31140
gtaaccagcc ttggttctgc tgagcttctc tgcgtcttct caggagacac aggctacaga  31200
gcttgaaggc tgaggattct tccagggtca cttcaggggc aaatctgaaa ctttcttcag  31260
gacaggaatc aacgagatct tctcacttac ttatacctgg gggaggaact gtatgaaatc  31320
cacccaagaa ccagtcatgc taagggccaa acctatagac aaaaaaaggg ataggagaat  31380
ggagtatgta tggagaaaga ctaaattgtt cttaaacttc tcaagcttaa aaatatccca  31440
gcaaaagaga tcgtaaaagc ccttcatggc gtattaatta tccatgcatg ggggtgagtg  31500
gaaaggtact cctgagcccg aggctacagc tttggaacta gcagcacctt tgaaggggaa  31560
agcgtgtttc catcatctca actcctactg ataaccaatg gaatattggt gagtaaagga  31620
tcctggggga agaagcagct gaaatgtgta ggtgagaagg cagagagaag aatatttata  31680
ttgggaatgg cacaagtgtg atgaggctgc aggtttttca cccttgtcat agagaaaaaa  31740
ccacgctgac accatgcagt tttaaatagt gagaaatttg caaattgtta gatcttaaat  31800
```

```
aatttagata aacatagtgg ccatttagat tattgcagtt ttttcaggat atctgatctc  31860
ttgatttcat tctttttgtc tcttataaga ataaaagggg gggagaaaat ttagccatta  31920
tagtatttct ctacattttc tctgtccttt tacataactt acaccagtgc cttcctattt  31980
atggtattat ttatgggtat ttcttctttt ctttcactga gcaaggataa atgagccagg  32040
gattcttgaa actactgtaa cacttctctt agaaatagat ggtcatactt tcagaatctc  32100
tacacattct tagtccctct aaacaatgat agttgtggca taaaaatatt tgcttggttt  32160
caggactgat agagaaaagt actataaaat ttgctgttaa ctgtgaaagg ttaaaaaaaa  32220
ggaggtgcca tcatgaagga gctaatcttt ctgaagtact gctgtagttt taaatattat  32280
tagctatgac ttctcaccat taactatgca cttgcttttt cttcatctga ctcagcagcc  32340
agatagatgc aacattgtct ttaacattta agactcctag caagtccggg cacgggggct  32400
cacacctgta atcccagcac tttgggaggc cgaggtgggc aaatcacaag gtcaggagtt  32460
tgagaccagc ctggccaata tggtgaaacc ctgtctctac taaaagtaca aaaatcagcc  32520
aggtgtggtg gcgtggtggc gggcacctgt ggtcccagct acttgggagg ctgaggcagg  32580
agaatagctt gaacctggga ggcagaggtt gcagtgagct gagatcgcac cactgcactc  32640
cagcctgggt gacagagcga gactccatct caaaaaaaaa aaaaaaaaaa aagactccta  32700
gcatggaaga gaaactggct gttgaaaacc tgaatgtgag agtcagtcaa ggatagtttg  32760
agggaagcca agtagaggaa gctctcacaa gcagattggt gagagaatat gattatacaa  32820
tgcatttatt atgataagaa attcacaagc attcattcaa aatactcttg attcctaggc  32880
agctctgggc atatttccac caacaaattg aggcatatgt cagtgcagcc taggtcagac  32940
tacctttttt cattaaacct cacaaaatta aaggacatac aggagaagtc ctggtactca  33000
tgttgcagac tacagtctat atggcaaagg aggatctctg tcccttatgt ttggatgaaa  33060
acattgggta ggcatttgaa tacaagccta ctgctaatat ggggctaagg tctttggccc  33120
cctaaaggtt tgctgaaata ttactgacag gaggcagatt gataagagga aaagcacata  33180
aatgtatttg acatgtatac atgggagcct tcaggatgaa gacctaccct ctcagtgcag  33240
tatggaagct tgtataccat cttgaggtta cagaaagaat gggggtttgg atctttgtaa  33300
aacaggtttc agtggcaaga caggttatga gaaggagaaa ggaagagact tgggtagcaa  33360
agggggtctt gttttgtagg taaatcgttg gcagcccaca gagaaaatag atggagaatg  33420
tttcttttca gaccttggca ggtgtcagat tctcagttaa tctctcctag atttgaaaaa  33480
aaaaaaaaag gtctagaaag ggagagcctg gctgcactaa cacattttct acagatgcaa  33540
atttctccca caaaatacag ctttgcaggt ccacttctat ctgctgggcc tgtggcaacc  33600
atttcaaaat atgtgaatga aatatatgtg ggggtaaact atttttattt acttccctaa  33660
agaagggatg gtgttctctc gggaattctg tgcatagaga gcctgtggct taggcacttt  33720
gatttatgta tatctcttcc tgtgattggc tatctaggga ctgctatctc cagcaaatct  33780
tctaaatgtc tgccatgtag aattcctttc tcatctttct gtctcacccc cttatctagc  33840
tgcttctcta accctagagt gacactgcac tccccacaat ctcctatgtc ctgaatattt  33900
taccccatcc taaactccat ctctaacaca gatgcacttt cttgtgctgc ctactgcatt  33960
gtacatcttc cccttagttc ccatgatgca actctgccct accccagaaa atgtaattta  34020
attggtctgg gataaaacct gggacactat cattcttgaa atattcccca agcgattcta  34080
attatatagc caaagttgag aactatttgt agacaggcat cagcatgatc acttaatgat  34140
ttgacttttg ctagatctaa ggtgaggaaa ttggagagtg gtatccatag gaagaactgt  34200
```

```
ttagtttaat ttttttttta ttttttcttc taaaaaaaaa tccaacaacg agatacatgt  34260
gcggaacatg caggtttgtt acataggtat aatgtgccat ggtagtttgt tgcacctatt  34320
gacccatcct ctaagttccc tcccctactc cttacttccc aacaggccct ggtgtatgtt  34380
gttcccctct ctgggtccac ctgttctcaa tgttcaactc ccttttacga gtgagaacac  34440
atggtgtttg attttctgtt cctgtgttaa tttgctgagg atgatagttt ccagcttcat  34500
ccacgtccct gcaaaggaca tgatctcatt cctttttatg gctgcatagt attccatgat  34560
gtatatgtac cacattttct ttatccagtc tgtcattgat gggcatttgg gttggttcca  34620
tgtctttgct attgtaaata gttctgcagt aaacatatat gtccatgtgt ctttatagta  34680
gaatgattta tattactttg ggtatatacc cagtaatgag attgctgggt caaatggcat  34740
ttctggttct agatacttga ggaatcgcca cactgtcttc cacaatggtt gaactaattt  34800
acactcccac taacagtgta aaagcgttcc tatttctcca cagcctcacc agcatctatt  34860
gtttcctaac attttaataa ctgctattct gactggcatg agatggtatc tcattgtggt  34920
tttgatttgc atttatctga tgatcagtga tgctgagatt tttaaaatat gtttgttggc  34980
catgtaaatg tcttttgtga agtgtctgtt catatccttt gcccacctta atagggtttt  35040
tttttcttg tgaatttgtt taagtgcctt gtaaattctg gaaattagat ctttgtcaga  35100
tggatagatt gcaaaaattt tctcccattt tgtaggttgc ctgttcactc tgatgatagg  35160
ttcttttgct gtgcagaagc tctttagttt aattagatcc aatttgtcaa ttttggcttt  35220
ttttgcaatt gcttttggca ttttcctcgt gaagtctttg cccgtgccta tgtcctgaat  35280
ggtattgcgt aggttttctt ctagggtttt tatagttttg ggttttacat ttaagtcttt  35340
aatacatctt gagttaattt ttgtataagg tataaggaag ggtccagtt tcagttttat  35400
gcataatggc taggcagttt tcccaccacc atttactgaa taggagatct tttcctcatt  35460
gcttgttttt gtcagatttg tcgaagatca gatggttgta gatgtgtggt gttatttctg  35520
aggtctctgt tctgcaccat tggtctatat gtctgttatc gtaccagtcc catgctgttt  35580
tggttaccgt agccttgtag tatattttga agtctggtag cgtgatgcct ccagctttgt  35640
tctttttgct taggattgtc ttggctatat ggagtcttct ttgattccat atgaaattta  35700
aaataatttt tttttattct gtgaagaatg tcaatggtag tttgatggga atagcattga  35760
aattataaat tactttgggc agtatagcca tgttcacaat attgattctt tctatccgta  35820
aggacgacac tttttccatt tgtttgtgtt ctctcttatt tccttgagca gtggtttgta  35880
gttctcctta aagaggtctt tcacatcctt tgttagctgt gttcctaggt attttgttct  35940
ctttgtagtg attgtgaatg ggaattcatt cttgatttgc ctctctgctg cctgttgttg  36000
gtgtaaacaa aattcatttc ttgttcttat ttgtgaaatt ttggaaccaa atctattttc  36060
aaattagaaa ttgcttgtga taatggtttt gcaacttaga ctggatatga gacgatgaga  36120
tattagttct ttcattcctt tgtaggaata tggtgcatct tgcattattt tagctaacta  36180
gtgtccttta atgactaatg aatatgacat ggtgaaacaa agtaaaatat atatgatgca  36240
ctaagtatgc attgtttcca aaggttcagc attttttttt tgttaactct gctgggatct  36300
gctttatgca ctgataacat aacttatttt atgatcttaa gcaaataaaa acacttatct  36360
ggacctcagt ttccttaact gtacaactga gggaaactgt atagtatagc tatagtacag  36420
tataccatct ttaccgtcac ttccatcttt taaattatgt gtatataaga tagggcctag  36480
ataaatggta tttatcttaa attacagtga tactagctta taacttaatt tgctaggtca  36540
tgttgaactg ataacaatgt gtgaactgat gagcaactga gaagtaacca ggttgtgtta  36600
```

```
taacagtttg tttttgattt agggttatca gtgagggtgg cggtggggag gggactttgg  36660
agtctaactg tctagttcaa atattagttt ttgtttattt ttatttttaa tttttgtggg  36720
tacatagtag atgtatatat ttatggggta catgtgatgt tttcatatag gcatgcaatg  36780
tgaaataagc acatcataga gaatggggta tccatcccct caaacactta tcttttgagt  36840
taccaacaat ccaatgacac tctttaagtt atcaaatcac agttttgcca gctactagcc  36900
atgtgatttt gggtaggtta cttaaattct cttcatctca atttcattat tgtaaagtgg  36960
agataatgat agcacatttt ttcttttttct tttttcttt attttttatt attatacttt  37020
aagttgtgtg atacatgtgc agaatgtgca ggtttgttac ataggtatca acaactctat  37080
aaaacatgtt ctatccagga aaagaaacta tcatcagagt gaacaggcaa cttacggaat  37140
gggagaaaat gtttgcaatc tagatggcga ttgcaatggc ggttcgctgc atccatcagc  37200
ccatcatcta cattaggtat ttctcctaat gctatccctc cccttgctcc ccaccccctc  37260
acaggcccct gtgtgtgatg ttcccctccc tgtgtccatg tgttctcatt gttcaactcc  37320
cacttatgag tgagaacatg tggtgtttgg ttttctgttc ttgtgttagt ttgctgagaa  37380
tgatggtttc cagcttcatc catgttcctg caaggacatg aactcatcct tttttatggc  37440
tgtatagtat tccatggtat atatgtgcca cattttcttt atccagtcta tcattggtgg  37500
acatttgggt tggttccaag tctttgctat tgtgaacgct gcagcaatga acatacataa  37560
gcatatgtct ttctagtcaa ataagttata atcctttggg tatgtaccca gtaatgggat  37620
tgctgggtca aatggtattt ctggttctag attcttgagg aatcgccaca ctgtcttcca  37680
caatggttga attaatttac actcccacca acagtgtaga agcattccta tttctccaca  37740
tccgctccag catctgttgt ttcctgactt tttaatgatc accattctaa ctggtgtgag  37800
atggtatctc attgtggttt tgatttgcat ttctctaatg actagtgatg atgagcttct  37860
tttcatgttt gttggctgca taaatgtctt cttttgagaa gtgtctgttc atatcctttc  37920
cccacttttt gatggggttg tttttttcct gtaaatttgt ttaagttcct tgtagatttt  37980
ggatattagc cctttgtcag gtggatagat tgcaaacatt ttctcccatt ctgtaagttg  38040
cctgttcact ctgatgatag tttcttttgc tggatagaac atgttttata gagttgttgt  38100
gagaattaaa tgcattaagc acatagaata gattctggta catagcaagt gctctctcta  38160
tatatggaac tctatatgta gttggtgcaa aagtaattgt ggttttcacc attgaaagta  38220
atggcaaaga ccatcattac cttttcacca atttaaatat atggaaggaa tatatatata  38280
aaacctatat atatatgtca catatatgtc tctaacccat tattataata tataatacaa  38340
tatatattat aattataatt gtatataaca tatgttatat aataatatag taatatttat  38400
tctaaataaa tatataatac tataaataat ataataattt atatatatga ttataatata  38460
taataggcta tattatatat tattaacata tacatatgtg tatatatatg tctttcatag  38520
acttaaatat atagagcaat aataggttag aaaatagcaa acatgtatat ataaacatat  38580
atacatatag aaaacatata taaaaacata tatatatata tatatatgtg tgttttctgc  38640
ctttcatttt tagagacagg gtctcatcat gttgcccagg ctggtctcaa actcctgggc  38700
tcaagtgatc ctactgcttt ggactcccga agtgctggga tttcagacat gagacactgc  38760
acccagtcca gtccctgtct ttttaaatag actctctacc taagtgcaca aatactcatt  38820
atttacattt agttatttct gtatatatgc tataagcaaa tcttgtagca ccagtttgat  38880
ttttataagg cacaagaata tattttacta atgctttaaa atggcagcta gattctagta  38940
ttactttaga aattaaaatt aatattttaa cacatctttc attattgtgt tatctgaacc  39000
```

```
aaacctatta ttgctgctat ttcagcaaat ccaggggctt tttcttataa aatatgaaga  39060
atatagctta gatttctagt gaagatgtta ccagtaataa ttaataaaat cagtaagcac  39120
taaaaggaaa ataccaaaac taaagcattt tgaattagtc attgaatcta aaagaaaggt  39180
agattttttt ctgagattct gttctaggtg tggtatatgt gtatttttgc aaaaactata  39240
aacaattgtg gcaaaatgaa ggaaatattt aaaaacaaac ctcttaattc ttcagtggat  39300
taagcgtgaa tatgttttta ttttctatga tgaatatgga aaaattcatt tccttagcaa  39360
tttgtatgag cccaaaaact attgtcagac tctgctgtat caaaatagac aaaaaattga  39420
cactcacttt taccctgcca aaagcaaaat cttaaacttt tgctttagta tataagccag  39480
cattcattgt atcctatgat gggttctgag tgtaggtgta tttgctttct tccatttttt  39540
gtatgcatgt tttcttttta tttattattg taagttgtat gaaattttta tccaaatttt  39600
tattttcttc tgattaataa tcagaataat cagataatta ctggtaaatt tgatgttaat  39660
ccttccagct ttttcccatg ggaatttata cttaataaag gggagaagtc atcattacat  39720
aatgtgcata ttaatctgct tctcccttta atgtgttgtg aatgcctttc catgtcatta  39780
gatgtttttc tacctagtta ctttcatgaa tcatatggct gtaccatgat ttatttaatc  39840
agttcctcat cattgagtat gtaaattgcc tccatttttt tattactata aaaggtcctt  39900
cagtacacac ccctttaaaa gctgactctt agaaggtgtt cttgactctc tacctaagtg  39960
taaaaataca aataaattgc tttccagaaa aggtgcacta ctattttact ttcctgatac  40020
taaactatga aaattcagtc ctaacaatag atatttaaat aaagttttaa aaatgccaag  40080
tgaaaaagag catattatta ttttcatttg cattactttt ggttcctggt gagtttaatc  40140
tgtttttgta tattaattat gcatttatat ttctttttgt gtgtgtgaat tgcctttcat  40200
gttctttgtg tgtttttatt ttgttgtatt tgtctctttc ttgatatatg agagaatatt  40260
ttccctagcc tgtcaattgc cttgtaattt tgtttctagt gagttttttt tttttttttt  40320
acaattaaaa gctttaattt ttgaaaattt tgctggcaaa tctatatatc tttttctttg  40380
ttttctgctt tgacattatt cttttataaa ggcccatgcc acccaaatat tatgtaagca  40440
tgcatctatg tttttattac ttcatctttt acatttaaat atctactcta tttagaattc  40500
attgtgatgc atgtatgagg tagaaatcta atttcaaaaa gatgagtatc cagtttgtcc  40560
atcatttatt gcatgatctc tttctccact gaattaaaat gccgtatttt ataatatatt  40620
aaagtattac atgtgcttgg acatgttcct ggacttttga gataaatcag tctatttctt  40680
tgtcatgtca catattatta tggctttatg atttaatatc cagtaatgta aaccctctga  40740
cacattattc ttattcctca aatgtttttg atgagttttc ttccaaatga aatttataat  40800
cattttattc attgattcaa caaatatttg ttgaatggat attctgtgct tggtattgtg  40860
catggtatta ggattgttgc aaaaattgag actgacagtc cctactctta cggtgctaaa  40920
aattcacttc caaaaaaatc tttaaatgtt gatgaagatt gcactaatct tataaaataa  40980
cttggagggg aatgtaatct ttgcaacatt aagttcttca ttttagaaag ttttaagact  41040
ctccatttat ttgagacttt taaaatatgt cccaataatg ttttgtgaga tgtatatttt  41100
aagatatata tcttattgct attacattgt atcttttgtt atattgttac tatgaatggg  41160
atactcattt aattagatgt catttttggt atatagaaat ctattttctt agcatagtca  41220
ttttttaaac ctcgatctat taaattcttg attcatttac atttgttaca caatcatatt  41280
ctatgctgat aatacttctt gcttctttcc aatatttgta cctcgatcat ttttcttgtt  41340
gagttgtatt agctagaagt tctagaaaaa tgttaaatgg tagtaatagc tagtattctg  41400
```

-continued

```
tttttttcctg actctaaatg taatgcatct agacttttat aattatggca ttgattgtaa  41460
cattttgagg aagaaatcct ttttcaggtt aataatgtat ctttatattc aagtttatta  41520
agaacattta ttggaaacat attgaaattt tatcagattc cttttcagtt gttactgaga  41580
taatcatagg ttcttctgta ttcttttaat taatttctca aaattaaact gtcctattat  41640
tcttggaata acgacatata aagtactgta tatttaaaag aagttaaaat gataatggtg  41700
attttattaa gtgacctcac acaatagaaa acagtgtagc cttagaagtt ttccaagtga  41760
ccattctact tagaaacaac cctgctttgg gatcagaact gtaattttta aagtaaagtt  41820
ttctgggttt aattcattta gtgtaattac aagcatgagt tcaggtttct atttttttca  41880
cctgaacttt ccttcatggt ttgaatatct agaaaaagca gactttccta tctctagact  41940
aaacatttga tcctatctta ggtatgcatt acaatttttt aaccataaat ggttaaagaa  42000
tttagactca tctacaataa ctttgaagct ctggtcttga agaacatgtg agaaatgaga  42060
tataactcct agaagatata ggagacattt ttagtcttcc aaatttttccc tgggaggctg  42120
atctaaattg agtcacaaaa ttgttcccac caggaatgca atcacttgag ctgttttcta  42180
atctgagccc ctctacccag atgatcttct gaactcatac tgttcagact ttcatccttc  42240
tgagtagaaa acagccatag tcatggcagg atgagggcta ggacaattac ccaaggaatt  42300
cttggcctct gccatgggac tctgcagact cagatcatat aatcagagat gttagcactg  42360
gaggggacat cacaattagc tttctccacc tcttagttta tcagtgagga aaactgtcca  42420
gagcgcggaa gagactaaaa taacacagcc aatgtaggta atgtgctgga taagaatttg  42480
gaattcacga ttttgaattc agtgtttatt tcaccatcac gctggcttac acgttggtat  42540
caggcttctt ctattattga agtgagccat taagtgaatt ccatcttgat ttgtgtctga  42600
tacagagtaa taaactattt tattaaatat ccaaataatt atacattcct ccttcttaca  42660
tgcaagccta agtttgcttg tactatttca tgtggtagca aatcaggacg cttcttgtgt  42720
ctctgaaaat actctgagta atggagtaca gtcagctttc ttgtaccaag aatataggga  42780
ctatgtttct cccagtcatt ctggggataa tttttgtgaa ggattgcact tcataggtta  42840
agctaggtat cagttaccag tgtttttttcc aaataaaaaa aaaatcaggt gatatctgta  42900
aatggttcca ttgtaaatat taaagaacat gatgcttaaa acagattagg gaaaactata  42960
gaaggggtgg ggtttcggag tgctaatttt gtccttgaat ggtaacagct ccatgtggtg  43020
gtgaggttta tgttggtttg ctgtttgcag atgatcttat tattagaatt tttcataccg  43080
aaaataaact gcattttagt ttgtaaacat gcccttccag agtaatgcta ccagttcttt  43140
gtgaaatagc tactgttgtt caaaggatga ctatgtcctc ttcggttgag gaaagatgac  43200
aacaaactca gtaatgacat gtaaaatagg tattacaaac caggtatggt ggcatgagcc  43260
tgtaatccca gctacttgag aggctaaagc aggaggatct gttgatctat ggatttgagg  43320
ctgtagtgtg ttgtgatggc acctatgaat agcccttgca ctccagccca agcaacaaag  43380
caagactgtc tctgaatttt tgttttgttt tgttttttgt tttttttttt ttgagacaga  43440
gtcttgctct gtcacccagg ctgaagtgca gtggcgcgat ctccactcac tgcaagctcc  43500
gcctcctggg ttcacgccat tctcctgcct cagcctcccg agtagctagg actacaggcg  43560
cccgcctcca cgcccagcta aattttttgt atttttagta gagacgaggt ttcactgtgt  43620
tagccaggac ggtcttgatc tcctgacctt gtgatcctcc tgcctcggcc tcccaaagtg  43680
ctgggattac aggcgtgagc caccgcgccc ggcccctgtc tctgaatttt ttaaaaaggc  43740
attccactca aattaataca cattttaatt gtgttttgtt gtaaattaca actgaataaa  43800
```

-continued

```
aattcagcaa ataagtctgt tgtggtaggg aaaagtctat tgtgatctgg aaaatataat  43860
ggagaaatcc agtggaagag attttatttc acattactca aaataaaaaa atcttataca  43920
agtctttaca cttgtaactt gaaaaattct gtgctaaaat ttagcttggt tgctaaaata  43980
tttctctttt tttctcagaa gcttcttttt agcatcctat agacacaagt tactttttaa  44040
aatatttgca tacttgcttt gcaatgtatt gtttatcagt agttctatat tctttgagat  44100
agtctatcca gtctttctgt atttatcgta tgtctgtata gatatatatt agcagataaa  44160
tgagttctga aaggggagaa atgtgattat gctaatcatg atataaagaa ttgactttat  44220
aagcagtgtt cacaggtcat acctttcccg ttactgtctt acagtgaaca agaaatgatg  44280
ctttgtctgg tatgcatggt aaataatgcc ccttgctctc tgcttcatga tcacatgtga  44340
tacttctaac atagatagca catgtaaatc cagtggcctt gactgcaact caagagagca  44400
ttttggccaa gtacaaaccc actagtcatg aaaaaaaaaa aaaaaccaaa tcaaagtaaa  44460
ttgatggtat tgacatttgt ctatgaaaaa caacataata tagaacaatt ctggggtaaa  44520
atattgatct aaaataattt taaggattaa atattgccat tgtaagcata ctatgagcaa  44580
ttatgtttgt aatgcagata tatttataat tttaaatcca agatttacct taattgtaca  44640
ttttcctaat ttaaaaaagt tattttgaaa aaaaaatcct cgaatctaga gaaaggttgg  44700
caaatacata tggaactttg taaaaaacat ccagggcagc actttcactg attgcagtag  44760
cttaggagtg aaaaacaaca caactgctcc aatgtatggc aatgggcaaa tatcccgatt  44820
tattcacagg gtggcatgtt aggcagtgct tagaataaat gagttggtta tacaagtatc  44880
aatagggata aatgtgaaaa acacagtgtt aagtttttaa aaagttgtaa aaagcacagt  44940
aggatgttat ttatataaaa tttaaaaacc tcaaaaacca ttcttctttg atatatattc  45000
taaagatgaa catatatgta atagaagtac aaaacataca taaaataata tacactatgc  45060
agtcatttgt gtacttactt ttcaaaaata tttcagtaga tatagcaaac agttaacatg  45120
taatatttgg ataggaggtt ggcaatttc tttttagcac ctgcctgtct gctatcattc  45180
aaactcacat ttaaaatgtg gctatgtgag atgagagaac tataatattc caggtttgtg  45240
attagtttgg aaacttttta aaagtttgaa tgtggtctga gagatagttt gttataattt  45300
ctgttctttt acatttgctg aggagagctt tacttccaac tatgtggtca attttggaat  45360
aggtgtggtg tggtgctgaa aaaaatgtat attctgttga tttggggtgg agagttctgt  45420
agatgtctat taggtctgct tggtgcagag ctgagttcaa ttcctgggta tccttgttga  45480
ctttctgtct cgttgatctg tctaatgttg acagtggggt gttaaagtct cccattatta  45540
atgtgtggga gtctaagtct ctttgtaggt cactcaggac ttgctttatg aatctgggtg  45600
ctcctgtatt gggtgcataa atatttagga tagttagctc ctcttgttga attgatccct  45660
ttaccattat gtaatggcct tctttgtctc ttttgatctt tgttggttta aagtctgttt  45720
tatcagagac taggattgca acccctgcct tttttgtttt tccattggct tggtagatct  45780
tcctccatcc ttttattttg agcctatgtg tgtctctgca cgtgagatgg gtttcctgaa  45840
tacagcacac tgatgggtct tgactcttta tccaatttgc cagtctgtgt cttttaattg  45900
gagcatttag tccatttata tttaaagtta atattgttat gtgtgaattt gatcctgtca  45960
ttatgatgtt agctggtgat tttgctcatt agttgatgca gtttcttcct agtctcgatg  46020
gtctttacat tttggcatga ttttgcagtg gctggtactg gttgttcctt tccaggttta  46080
gcgcttcctt caggagctct tttagggcag gcctggtggt gacaaaatct ctcagcattt  46140
gcttgtctat aaagtatttt atttctcctt cacttatgaa gcttagtttg gctggatatc  46200
```

```
tctcagacca cagtgcaatc aaactagaac tcaggattaa gaatctcact caaagccgct  46260
caactacatg gaaactgaac aacctgctcc tgaatgacta ctgggtacat aacgaaatga  46320
agacagaaat aaagatgttc tttgaaacca acgagaacaa agacaccaca taccagaatc  46380
tctgggatgc attcaaagca gtgtgtagag ggaaatttat agcactaaat gcctacaaga  46440
gaaagcagga aagatccaaa attgacaccc taacatcaca attaaaagaa ctagaaaagc  46500
aagagcaaac acattcaaaa gctagcagaa ggcaagaaat aactaaaatc agagcagaac  46560
tgaaggaaat agagacacaa aaaacccttc aaaaaatcaa tgaatccagg agctggtttt  46620
ttgaaaggat caacaaaatt gatagaccgc tagcaagact aataaagaaa aaaagagaga  46680
agaatcaaat agacacaata aaaaatgata aaggggatat caccaccaat cccacagaaa  46740
tacaaactac catcagagaa tactacaaac acctctacgc aaataaacta gaaaatctag  46800
aagaaatgga tacattcctc gacacataca ctctcccaag actaaaccag gaagaagttg  46860
aatctctgaa tagaccaata acaggctctg aaattgtggc aataatcaat agtttaccaa  46920
ccaaaaagag tccaggacca gatggattca cagccgaatt ctaccagagg tacaaggagg  46980
aactggtacc attccttctg aaactattcc aatcaataga aaaagaggga atcctcccta  47040
actcatttta tgaggccagc atcattctga taccaaagcc gggcagagac acaaccaaaa  47100
aagagaattt tagaccaata tccttgatga acattgatgc aaaaatcctc aataaaatac  47160
tggcaaaccg aatccagcag cacatcaaaa agcttatcca ccatgatcaa gtgggcttca  47220
tccctgggat gcaaggctgg ttcaatatac gcaaatcaat aaatgtaatc cagcatataa  47280
acagagccaa agacaaaaac cacatgatta tctcaataga tgcagaaaaa gcctttgaca  47340
aaattcaaca acccttcatg ctaaaaactc tcaataaatt aggtattgat gggacgtatt  47400
tcaaaataat aagagctatc tatgacaaac ccacagccaa tatcatactg aatgggcaaa  47460
aactggaagc attccctttg aaaactggca caagacaggg atgccctctc tcaccgctcc  47520
tattcaacat agtgttggaa gttctggcca gggcaatcag gcaggagaag gaaataaagg  47580
gtattcaatt aggaaaagag gaagtcaaat tgtccctgtt tgcagacgac atgattgttt  47640
atctagaaaa ccccatcgtc tcagcccaaa atctccttaa gctgataagc aacttcagca  47700
aagtctcagg atacaaaatc aatgtacaaa aatcacaagc attcttatac accaacaaca  47760
gacaaacaga gagccaaatc atgagtgaac tcccattcac aattgcttca aagagaataa  47820
aatacctagg aatccaactt acaagggatg tgaaggacct cttcaaggag aactacaaac  47880
cactgctcaa ggaaataaaa gaggacacaa acaaatggaa gaacattcca tgctcatggg  47940
taggaagaat caatatcgtg aaaatggcca tactgcccaa ggtaatttac agattcaatg  48000
ccatccccat caagctacca atgactttct tcatagaatt ggaaaaaact actttaaagt  48060
tcatatggaa ccaaaaaaga gcccgcatcg ccaagtcaat cgtaagccaa aagaacaaag  48120
ctggaggcat cacgctacct gacttcaaac tatactacaa ggctacagta accaaaacag  48180
catggtactg gtaccaaaac agagatatag atcaatggaa cagaacagag ccctcagaaa  48240
taacgccgca tatctacaac tatctgatct ttgacaaacc tgagaaaaac aagcaatggg  48300
gaaaggattc cctatttaat aaatggtgct gggaaaactg gctagccata tgtagaaagc  48360
tgaaactgga tcccttcctt acaccttata caaaaatcaa ttcaagatgg attaaagatt  48420
taaacgttag acctaaaacc ataaaaaccc tagaagaaaa cctaggtatt accattcagg  48480
acataggcgt gggcaaggac ttcatgtcca aaacaccaaa agcaatggca acaaaagcca  48540
aaattgacaa atgggatcta attaaactaa agagcttctg caaagcaaaa gaaactacca  48600
```

-continued

```
tcagagtgaa caggcaacct acaacatggg agaaaatttt cgcaacctac tcatctgaca  48660
aagggctaat atccagaatc tacaatgaac tcaaacaaat ttacaagaaa aaaacaaaca  48720
accccatcaa aaagtgggcg aaggacatga acagacacta ctcaaaagaa gacatttatg  48780
cagccaaaaa acacatgaag aaatgctcat catcactggc catcagagaa atgcaaatca  48840
aaaccactat gagatatcat ctcacaccag ttagaatggc aatcattaaa aagtcaggaa  48900
acaacaggtg ctggagagga tgtggagaaa taggaacact tttacactgt tggtgggact  48960
gtaaactagt tcaaccattg tggaagtcag tgtggcgatt cctcagggat ctagaactag  49020
aaataccatt tgacccagcc atcccattac tgggtatata cccaaaggac tataaatcat  49080
gctgctataa agacacatgc acacgtatgt ttattgcggc actattcaca ataggaaaga  49140
cttggaacca acccaaatgt ccaacaatga tagactggat taagaaaatg tggcacatat  49200
acaccatgga atactataca gccataaaaa atgatgagtt catgtccttt gtagagacat  49260
ggatgaaatt ggaaaccatc attctcagta aactatcgca agaacaaaaa accaaacacc  49320
gcatattctc actcataggt gggaattgaa caatgagatc acatggacac aggaagggga  49380
atatcacact ctggggactg tggtggggtc gggggagggg ggagggatag cattgggaga  49440
tatacctaat gctagatgac acgttagtgg gtgcagcgca ccagcatggc acatgtatac  49500
atatgtaact aacctgcaca atgtgcacat gtaccctaaa acttagagta taaaaaaaaa  49560
aaaaaaaaaa gtttgaatgt tttcttgcat tcagagcctt ggttgacata gttaattaaa  49620
aataaaacat tgtatataaa gcacagaatg agcagctaca caaagctgct caatcaatga  49680
cagctctata tgggttaggg tttcttgtgg ggatgacatt gatgtagaaa gcatggtcat  49740
ctattgagaa tgatggggct ggaggtattg gatacttgag gtttagaaaa tacattgtag  49800
aaaatggaca aaaacccctc aaattaaggg atgaggcaga ataatgcttg gcaataccag  49860
gggtaggctg cagtctttct tggaaatata tattttaaat ggaaccaatt atcatagcat  49920
catttcctct cagggttacc ctctgatccc tattttacta aatcgttata aaacaaaatg  49980
aggaattatg tgtccttccc ttttgaagcc aatgtaacaa gatgggtaag aattagacct  50040
cctgagttca aaatccctgg attcagatct attcctgtat attcaggaga agtggtaata  50100
aattcgatgg acaatttggt ttagtagtcg attgaggacc ctgatgaggt atatttggga  50160
aaacataact tccgctctct ctcattgact cacgggcctt tgaggagtcc aggagtcatt  50220
ggaatctggc ctgaggttga ggctgctggc aaaactcctt ccccaaagtc cattcctatt  50280
gctgactgag aagggactag cattggaagt ggctgatttt aaataccgct agtgctggtg  50340
tgctcctccc tcccattccc agctctgctt tgtgtagttg ccttgagaag ctaagttcat  50400
tctgaaaata atgccattgc acaaaacact tttgaaagtt ctagtttgaa attacatcag  50460
gtcacttggt ctgtgtggcc tcagtttctt catctgccat gtgaaaataa taatgcctac  50520
tctgtagcaa agaaagtctc tatagtaaac aaaaaaaaag cctactctga tactgaaagt  50580
tgttatgaaa aataaaaaag ggaaatgctt tagaaactgt taagtgctat gtagatgtta  50640
ctaattaaca aaccatttca gaaactatac tttttatttt atggccacta ttcactgttt  50700
aacttaaaat acctcatatg taaacttgtc tcccactgtt gctataacaa atcccaagtc  50760
ttatttcaaa gtaccaagat attgaaaata gtgctaagag tttcacatat ggtatgaccc  50820
tctatataaa ctcattttaa gtctcctcta aagatgaaaa gtcttgtgtt gaaattctca  50880
gggtatttta tgagaaataa atgaaattta atttctctgt ttttcccctt ttgtaggaag  50940
tcaccaaagc agtacagcct ctcttactgg gaagaatcat agcttcctat gacccggata  51000
```

```
acaaggagga acgctctatc gcgatttatc taggcatagg cttatgcctt ctctttattg  51060
tgaggacact gctcctacac ccagccattt ttggccttca tcacattgga atgcagatga  51120
gaatagctat gtttagtttg atttataaga aggtaatact tccttgcaca ggccccatgg  51180
cacatatatt ctgtatcgta catgttttaa tgtcataaat taggtagtga gctggtacaa  51240
gtaagggata aatgctgaaa ttaatttaat atgcctatta aataaatggc aggaataatt  51300
aatgctctta attatccttg ataatttaat tgacttaaac tgataattat tgagtatctt  51360
ctgtaaactg cctctgttgt agtttttttt ttctcctaat catgttatca tttttttgga  51420
atccatggtt tcctgttaag atgactcaca cagcctacat aaaagtaatt gacaaaatat  51480
catcttatag taaaatgcca catatcttta tgttcagcaa gaagagtata atatatgatt  51540
gttaatgata acccaaacaa caaaagattt caccttaact ggttgtcata agtagtagta  51600
tccaccgcct tattttgagt tggattttta tcatcctatg agccctacaa atttaaagtt  51660
tttggaacag cacgtgcatt gaacccataa gaacctactc tgcttttctg catgtattgt  51720
ccagacaaga gaccaaattg ccgaggcatc atttaggtga attctaatta acatttagct  51780
accttacaac cacaattcaa ggttgtttca aaggcatgtg cttgcatcat cctgattcac  51840
taccatgtgt tactaacttg gatctgcaaa gtcattataa aaagctgttt tgatggactt  51900
atttggatat tgctttaccc ttcttctctc ttttctttta tcaatgtaaa aacattatat  51960
gttaaatact tggcttttaa gagcatagat ctgaaatctg cctctagcaa ataacccata  52020
acacttctaa gatatacctg caaggtcaat tgtgttgtaa aaccttgata accatacttt  52080
attgttcaaa aaagcctttt atgaaggcag aagttaaaaa aaaaaaacaa aaaaaacaga  52140
gtccacagtt atcacctcag ctacaatctc atcagttcac aagtaccagc aaaacatgtg  52200
ataagtcaac aaatgtttta tttcaatctg aacattttac gtaagtgaag actttgttag  52260
atatcatttg gaatgtggaa tctacacagt tggcatatca gagaaggttg aattcagttt  52320
aataaatgtt tatagaaagt gcttgttatc ataatgataa tagctcagga tgtgcatgac  52380
aagcttttaa gcgattgggt acactatctc atttgatctt ctgcacaact attaatggta  52440
ggtactatta tccctatctt atggataagt aaactaagat ttaaaaagta cagaacatgg  52500
tgtgaacact gcttcaaaat ttctaaaata ggtaaatcac gatctctaaa ctggagggtt  52560
gtccaaccac tagggacaat agagtactga tatttagtgg tcagactgta atgcgggaag  52620
agacaggcat gggctaaacg ggtgtagaga tcaaataagg ggcaggttag tttgtaaaca  52680
tgtccatatg taacatttag cacaaataca ggatataggt gctttcagac ccagctgcat  52740
tgataaaaag ttaggtggta ttgtatctgt cttcctttct caatgttgca tatctgtgtt  52800
cttgcccagt ttgcttcatc tctctagcca cacttattgg cctacaatgg catcatcacc  52860
aaagaaggca atcccatctc cgtgtggctt tggtttgctc cctaaagtaa accttgtgtt  52920
tacttttccc aggtctcatg ctttcccata tctgacctgt tttgtcctca tggccaggat  52980
atgtgggacc tttcctacaa tgttccaaag tttgtaatag agctcttctc tgctttgttc  53040
caaattctgc aacattttac tttaaataat gaatttaaat acaaacaaac ttgagctttg  53100
cctatacttt tcaagaatgc agagataact aaattaataa aaatattcat tgagtcctta  53160
ctgtgcacac agctctatgt taagccttgt gcagaactca aagtcactcg agattaagcc  53220
tgttactaag ttatgtgcaa tttagctcag tggatttccc ccacttcata ttgctctgat  53280
aatgttttgg aattaactgc cttgattcct tcttttctct gcttgtctat acactattta  53340
ttattctaca ccatctcaaa ttctaactcc tcaagaaaat ccttccagat gatttttcta  53400
```

```
accaggagtt ttaacttcct tttaactacc ctattacttt ctacttcctt aactcatcta  53460
tcatattata tttagttatt tatatactag gtcgccttga agaagggatt gtgttttcat  53520
aaatcttaat aatccctgag gcatcaagta cagtgatttg catttactaa atgctcaaca  53580
aatatgtgag ggattcactt gaaactaata ttagataatt cccagtcaaa gtgatctaat  53640
agcaaatcaa ttcttcagtt ttataggcaa agtatgactc tggttttcca taatcataat  53700
taatttgtca actttataat tttaattaag taaatttaat tggtagataa ataagtagat  53760
aaaaaataat ttacctgctt aactacgttt catatagcat tgcatttttc tttgtaaaat  53820
ttaagaattt tgtattaata aacttttta caaaagtatt aattattcag ttattcatca  53880
tatactttta ttgacttaaa agtaatttta ttcaaaagag ttagtatagg actacatgaa  53940
aaattcaagg ccaaggctta atttcaaatt tcactgcctt tggctctatc ttttaaaaca  54000
aaacaaaaaa ctcccgcaca atatcaatgg gtatttaagt ataatatcat tctcattgtg  54060
aggagaaaaa ataattattt ctgcctagat gctgggaaat aaaacaacta gaagcatgcc  54120
agtataatat tgactgttga aagaaacatt tatgaacctg agaagatagt aagctagatg  54180
aatagaatat aattttcatt acctttactt aataatgaat gcataataac tgaattagtc  54240
atattataat tttacttata atatatttgt attttgtttg ttgaaattat ctaactttcc  54300
atttttcttt tagactttaa agctgtcaag ccgtgttcta gataaaataa gtattggaca  54360
acttgttagt ctcctttcca acaacctgaa caaatttgat gaagtatgta cctattgatt  54420
taatctttta ggcactattg ttataaatta tacaactgga aaggcggagt tttcctgggt  54480
cagataatag taattagtgg ttaagtcttg ctcagctcta gcttccctat tctggaaact  54540
aagaaaggtc aattgtatag cagagcacca ttctggggtc tggtagaacc acccaactca  54600
aaggcacctt agcctgttgt taataagatt tttcaaaact taattcttat cagaccttgc  54660
ttctttttaa aactttaaat ctgttatgta ctttggccag atatgatacc tgagcaattc  54720
ttgttctggg ttgtcttatg tgaaaaataa attcaaggtc cttgggacag ataatgtgtt  54780
ttatttatct ttgcatatcc attacttaaa acagcattgg acccacagct ggtacaaaat  54840
taattactgt tgaattgagc aaatatttat tctaaatgtc tctgtcaaat gacagagtgt  54900
ggttgtgtgg attaagtccc tggagagagt tctttgttct ctcatgttct atgctgtggt  54960
tcttgcttta tgcaaaaaga agtaagttac ttaaaacctg gacatgatac ttaagatgtc  55020
caatcttgat tccactgaat aaaaatatgc ttaaaaatgc actgacttga aatttgtttt  55080
ttgggaaaac cgattctatg tgtagaatgt ttaagcacat tgctatgtgc tccatgtaat  55140
gattacctag attttagtgt gctcagaacc acgaagtgtt tgatcatata agctcctttt  55200
acttgctttc tttcatatat gattgttagt ttctaggggt ggaagataca atgacacctg  55260
tttttgctgt gcttttattt tccagggact tgcattggca catttcgtgt ggatcgctcc  55320
tttgcaagtg gcactcctca tggggctaat ctgggagttg ttacaggcgt ctgccttctg  55380
tggacttggt ttcctgatag tccttgccct ttttcaggct gggctaggga gaatgatgat  55440
gaagtacagg tagcaaccta ttttcataac ttgaaagttt taaaaattat gttttcaaaa  55500
agcccacttt agtaaaacca ggactgctct atgcatagaa cagtgatctt cagtgtcatt  55560
aaattttttt tttttttttt tttttgagac agagtctaga tctgtcaccc aggctggagt  55620
gcagtggcac gatcttggct cactgcactg caacttctgc ctcccaggct caagcaattc  55680
tcctgcctca gcctccggag tagctgggat tagaggcgca tgccaccaca cccagctaat  55740
ttttgtattt tagtagagac agggtttcac caggttgccc aggctggtct cgaatgcctg  55800
```

```
acctcaggtg atccgcccac ctcggcctcc caaagtactg atattacagg catgagctac  55860
cgcgcccggc ctaaaaaata ctttttaaga tggtgtaaat attactttct gtatcaatgg  55920
tacatttttt acttgtcagt ctctagaatt tctttataaa tatgttgatt cagttcattt  55980
ttgtagatta taaaacaggt aaaaaaggat aaaacattta tgtgaattaa agggaatacc  56040
taatttttgt gtagagttta ttagctttta ctactctggt ttatggatca tcacaccaga  56100
gccttagtta ctttgtgtta cagaataact aatatgagtg aatgaatgac ttacacaagt  56160
cactgcttag gataaagggc ttgagtttgt cagctagagt atgacagaaa gtatctaagt  56220
tttggagtca aatagcactt tgtttgaatc ccagattgca tgcttactag ttatgtgacc  56280
ttagtcaagc cacttcacct cactgagtct ttgctttttt catctctaaa atagagatac  56340
ccaccgctca taggctgtca taagggatag agatagcata tggaatgagt ctgtacagcg  56400
tctggcacat aggaggcatt taccaaacag tagttattat ttttgttacc atctatttga  56460
taataaaata atgcccatct gttgaataaa agaaatatga cttaaaacct tgagcagttc  56520
ttaatagata atttgacttg tttttactat tagattgatt gattgattga ttgattgatt  56580
tacagagatc agagagctgg gaagatcagt gaaagacttg tgattacctc agaaatgatt  56640
gaaaatatcc aatctgttaa ggcatactgc tgggaagaag caatggaaaa aatgattgaa  56700
aacttaagac agtaagttgt tccaataatt tcaatattgt tagtaattct gtccttaatt  56760
ttttaaaaat atgtttatca tggtagactt ccacctcata tttgatgttt gtgacaatca  56820
aatgattgca tttaagttct gtcaatattc atgcattagt tgcacaaatt cactttcatg  56880
ggctgtagtt ttatgtagtt ggtccagggt gttattttat gctgcaagta tattatactg  56940
atacgttatt aaagaatttc ctacatatgt tcactgctgc tcaatacatt tatttcgtta  57000
aaacaattat caagatactg aaggctgatt ggtaactcac atggaactgg gagagtatac  57060
aattctgaac caaatagatg attctctatt attatatctt aatttatgtg ttatggtata  57120
ttaaacatga aaaaaattgt atttggttag aatatgtttg ctcttcctta actcgggaat  57180
gacatagggt aatattcaca gattgggttc ctataaatcc tccacttgaa gtgaagtcag  57240
ttcaagtaat gaaagctacc tcctgagata gaatcagtac ttggcaccta tctctagtgt  57300
tctttcacct catataacct ttcactgatt agtaaagatt atatccaaca aagaaagtac  57360
agcacagact gagatatgat tactgagata aatttgggca aaatataaac tacagcattt  57420
ctgtagcaat gagaccattt ttcttcagtt gagctccatg ttctacaaac ttcaatcaaa  57480
aaaggttcta ggagactcag tgaaagttga tacactgttc aaggaacaaa taatttcagc  57540
acatggaaat ttcacaggga aaaatatact aaaaagagag gtaccatttt ggatggtgtc  57600
aatatgggtt atgaggaatt caggctgctg agtccagtgt acaatggaaa ctgagctgca  57660
ggtgtgtgat tgtaacaaca aaagaaatgc tgaaatatta agtcctttgc catgtaaata  57720
gaaaaagagt atttatttcc caaacattat tgctcacctg tttttgttat gcctttcaag  57780
ataaatccag gaaaggaatt gcattttctt tccagaaaac aagttcttgg gggaattgtt  57840
caattggtag atgttgtttt tctcattaac aagtgagtgc tccatcacac ttgctgagtg  57900
ctccatcaca cttgctctct gcattactcc tctgcctgca aacacatata tagcaagggt  57960
gatgacaagg atatcagagg gtctggtttt ctcaaactca tgataaactc atggctgggt  58020
cattcttggt gctgatttta ctttgttttt tgttgttatt gttccctctt cctcaaaaga  58080
tgaaatctat ccctcttact tggaatttct ctttgatata tagcgaatgt ttggttgtaa  58140
cctgtataat ctggcatgaa attgtcactc gaaaaggcta gaagtgttga cataaatatg  58200
```

```
ggacagcaag agttgctcct actcaagaga gcaaatataa tgttctggaa gagattggca  58260
gaattcacat caaaggagtg attacttcag cctgggccac tgttgtactg gtcaaaaggc  58320
tgtgcaaagc tctctgaaaa tccactcttt tattgctctt tagtaataaa gtcactttca  58380
attttaaaaa taacaaactg atatattttt atgactcata aaatgttagc aattatatta  58440
tggagaatct actttctggg tgattcttac aaatgttctt ggatctattt tttttcttta  58500
tagtacctat tcttcccatt tttctcagct ctagttaata tatttcaaca acagttcaac  58560
aaatttaaca tttttataaa aagtgtttcc tatcatttta taaataccag cctagtccat  58620
gttattcctt ttcttgttga ggagaaagga cacacattgt aaattcaaat atagacctct  58680
actgtgctat ttaatcttgg taacaactcc acaaaggaga tgacatgttt tccttctata  58740
gaggtagatt ctgtaaagtt agagggaaga gtgacttgct taagatggca taagctgtaa  58800
ctggcagaac caggattcaa agccaggtgg gatgccaaaa tcataatctg tcttcagtgt  58860
caagttactg aaattggtaa acattagacc taaatagacg gaattgcaat ccgggttggg  58920
cacattaaac tccattttct tcatcaatgt gctcagatta cattttactt ttcaggctaa  58980
aaatggaaaa aaagagtccc tcttagttct gcacttgaga atgagaatag cttttctgaa  59040
ttatacaagg aagaagaact aatgcccaaa tgccaggtac ccacatgcac tatgccatgg  59100
cacagctgtt gcccccttc accagagccc tctctctgta tcctggttga cctttccttg  59160
ggcaagagct gggtggggag gatcacaagt gactccaatt tggatggctt cgggaagact  59220
gggaccgagc tgaaggcagt gttgtcctct gcactccctg ttttctgtct gctggagcac  59280
tgaagcctca catatgtatt aaaaaaataa tttccatttg catttcagac tagaagattg  59340
aacgtatagt gtaatgtgat tgcaaataat tatattgaaa tgagacagag aggatgtagt  59400
atctactgtc ataatttttc aaaacccacc tgcaacttga attaaaagaa ccacttgggt  59460
ttttttttt gtttcaaacg caaatcctgg aaacctactg agactcattc agtcagtatc  59520
tctaagaggc aagcttgaga ctgtatattt aaaaagcatc tcaggtgatt tttacacatg  59580
ctaaggctta agaaccactt ctctgtagct tatatgttat tttcaatgtt cctcaaagcc  59640
aagttagaat ttccaaagtg ttaagaatcc attagacaat cacagaattg tctttttcct  59700
ttataaatct tgcaatgttg ttctcatttc catacttaat tacttaaaac accaaccaac  59760
caacaagcaa aaaatgatta gtctaactaa tattacaagt taataatgaa gtaaaggttt  59820
aaaaataatg tcataataat gttaataaca aattattaat tataatttaa aaataatatt  59880
tataatttaa aaataatatt tacaagtact acaagcaaaa cactggtact ttcattgtta  59940
tcttttcata taaggtaact gaggcccaga gagattaaat aacatgccca aggtcacaca  60000
ggtcatatga tgtggagcca ggttaaaaat ataggcagaa agactctaga gaccatgctc  60060
agatcttcca ttccaagatc cctgatattt gaaaaataaa ataacatcct gaattttatt  60120
gttattgttt tttatagaac agaactgaaa ctgactcgga aggcagccta tgtgagatac  60180
ttcaatagct cagccttctt cttctcaggg ttctttgtgg tgtttttatc tgtgcttccc  60240
tatgcactaa tcaaaggaat catcctccgg aaaatattca ccaccatctc attctgcatt  60300
gttctgcgca tggcggtcac tcggcaattt ccctgggctg tacaaacatg gtatgactct  60360
cttggagcaa taaacaaaat acaggtaatg taccataatg ctgcattata tactatgatt  60420
taaataatca gtcaatagat cagttctaat gaactttgca aaaatgtgcg aaaagataga  60480
aaaagaaatt tccttcacta ggaagttata aaagttgcca gctaatacta ggaatgttca  60540
ccttaaactt ttcctagcat ttctctggac agtatgatgg atgagagtgg cattttatgc  60600
```

caaattacct taaaatccca ataatactga tgtagctagc agctttgaga aattctaaag 60660
ttttcaagtg ataagactca atttatacaa agctaattgg ataaacttgt atatgattaa 60720
gaagcaaata aatacttatt atgctttttt gctgtttatt taaatattta acccagaaaa 60780
taagtcactg tgacagaaat aaaaatgaga gagaagggtg agccactctt aggtagttct 60840
ggcattattt aatctaggcc agaggttgca aatggtgtcc catagaacta attttggctc 60900
ctagacctgt cttatttaac ctttcattta aaaaatttgt attggttgcc agcaattaaa 60960
aattgggaga tgtctcacac acacacacac ataaacacac acactcatgt gtgcagcctc 61020
ttttgaagaa ttggaataac tagtcaactg cgtcctcctt ttccacaagc tgtgacagct 61080
ccctgctcac agagcacctg ccctctcctg ttcatcatgc tctcttctca gtcccattcc 61140
ttcattatat cacctatttg gtcctgagac taagtgagtt tgagatctgt gatttagaca 61200
aagtggtgaa tctagctctg aatcatagta agtagctctg ggaatcatct tgtcttctgt 61260
tagcccattg agagagaaat agagagagag agagagagaa agaaagaaga agaaacagat 61320
ctggggagag tcactgaatg ggagcataga gacagagaaa cagatctaga aaaccaaact 61380
gggagaaaat gagagaaacc aaaagagagg tagagaggag cagagaagaa aatgaagaag 61440
caaggcaagg accaggcttt ttcattattt cttatggcca agacttcagt atgcgtggac 61500
ttaattcttc cttatgctcc taccttccct agggaaactg atttggagtc tctaatagag 61560
cccttctttt agaatcacag tttgatgcct taaaactagt tatataccctt cacatgcttc 61620
cttaacccac agaagtgatg ctaatgaggc ccttaataag gagcgtgcta ttaagatgaa 61680
gacattcatt tttttctcc gtccaatgtt ggattaaggc acattagtgg gtaattcagg 61740
gttgctttgt aaattcatca ctaaggttag catgtaatag tacaaggaag aatcagttgt 61800
atgttaaatc taatgtataa aaagttttat aaaatatcat atgtttagag agtatatttc 61860
aaatatgatg aatcctagtg cttggcaaat taactttaga acactaataa aattatttta 61920
ttaagaaata attactattt cattattaaa attcatatat aagatgtagc acaatgagag 61980
tataaagtag atgtaataat gcattaatgc tattctgatt ctataatatg tttttgctct 62040
cttttataaa taggatttct tacaaaagca agaatataag acattggaat ataacttaac 62100
gactacagaa gtagtgatgg agaatgtaac agccttctgg gaggaggtca gaatttttaa 62160
aaaattgttt gctctaaaca cctaactgtt ttcttctttg tgaatatgga tttcatccta 62220
atggcgaata aaattagaat gatgatataa ctggtagaac tggaaggagg atcactcact 62280
tattttctag attaagaagt agaggaatgg ccaggtgctc atggttgtaa tcccagcact 62340
ttgggagacc aaggcgggtg gatcacctga ggtcaggagt tcaagaccag cctggccaac 62400
atggtaaaac ccggtctcta ctaaaaatac aaaaaattaa ctgggcatgg tggcagatgc 62460
tgtagtccca gctgctcggg aggctgaggc aggagaatca cttgaacctg ggaggcggag 62520
gttgcagtga gctaagatca cgccactgca ctccagcctg ggcaacaagg cgagactctg 62580
tctgaaaaag aaaaaaaaat aaaaataaaa ataaaaagaa gtggaggaat attaaatgca 62640
atataaaagc ttttttatt tttaagtcat acaatttgtt tcacataaca gatcaggaaa 62700
taatacagag atcataagtt ttggagctgg gtttgaatcc tggctctgcc atttactttc 62760
tgtgtaatct aagtcaagtt actgaacttt gtgggccctc tggctctcca tgtgtaaaat 62820
ggagaatatt aatatttacc ttgcaagttt gttgtgaaga ctgaaggaga gaatttaggt 62880
aaaacattca tcagagtacc atgcacacag ttgttcctca ataaacatta gcttctctga 62940
ttgcaagttc cagtctaaag tgctttatat ataccagcca ataaaaggat gcgagagaga 63000

```
tataccagtg tattgttttc taccatttta aacctatttt catccactgt tacaaattct  63060
atcatactgc tccacataaa aaatattatc aatgattttt agtctctgaa gtgcaatatt  63120
tgattattga gcacacctgt tgaagtttta gtttcttctc acttacatgg gttgtgtaaa  63180
ggtaggaggt ataaaaccag tgtcctaggt ctaaatcttt cttaatgtca tactttggat  63240
tcattgatat aagtaacttg agcaccagcg cttcatttta cttcattttt taaagatata  63300
gtaagagtaa ttcccatctg cctagcaaaa ttgttttgta gaaaagtttg tggatcagat  63360
ttattttact ttgattttag gaatttcaag tgtcttcgtc ggcatgaagg aaaaatatgc  63420
agtttgacat tttctactac tttcaggtca ttattttcct actctggtgc aaaaaccctc  63480
aattcctgtc tcactccatc taatcaaata ggtagcatgc ttgagccctt actatgtgcc  63540
aggcactagg ataagcactt tatatgtttt gtcccaatta attctcacag catttctatg  63600
acctaaataa aattaatatt ttcatttcac caataataaa atggaggctt caaaaagttt  63660
agggacttgg ctcagctcac acaactggca aggactgaaa atggatttta gtcccaaatg  63720
tcataggcta gagccctttc actaaactgt tgtcttccat ctggtggcat cctcttcctc  63780
cagtctttgt cacctaaact ctgggcaccc cttgatggca tttacttatg atggtgatgc  63840
ttgttaaact tcctgtttgc gacttcaacg tccatataaa tgagtcttcc aatactgtac  63900
ttagaactta tattttgtag tgacttcttt aaaagctttc tctcttagtc atatcctgag  63960
ttttgttagc acctggactt accttacttt ggaaatgttg cactctgaaa tctctttctc  64020
agcttggaat ttcctaatct tccaactgtt tgagtctttt aattctacat ttactgcctt  64080
tccatttcat caggatttct agtctcttta attcttcctt ttgaactcct cctgatttaa  64140
cctctgctta ttcgaagaac aataatttta ttctctcagc tgcactctca attccctttt  64200
ccttttggtg atttttcttt ttcctacaga acacttactt tatcagtttt ggagaaggaa  64260
gtgctatctg ggtaacagta gtgctatctg ttgactctag tcaactgtaa gttttataca  64320
tttattgttt aaaccttata tggtctata atccttcttg ggaaatcctt tcatttgtct  64380
ttaatttcct ttaccatttc cctaaaggct attccagatt tttatcacat tcacaaaatt  64440
cccgtctttt ctcaggatct gttcaccccc agtagatagc cttgtctccc acaatacatg  64500
gagaaaatag aggccaccgt catatttgaa tgtttccaac ttctctcttc acctttggaa  64560
ttatcttttt cttcttttgt gtctaagaga aagatgtata cttcttctta cccttgtctg  64620
aactactcta ttttgcttca tcttctcaga acaggggacc agcaattatt cttcctccag  64680
aagcttcaac atcttttgtc aactgactcc ttctcatgtt taaatatttt caagttaaac  64740
aatttctttc ctgactttcg ctcacgcaac ctcatgccca aaaccttatc actcttcttc  64800
cctttgctgt caaggctgtt ctcacttctt cactttttgt ggacttctcc ccactacaac  64860
atagattctg ctatcaccaa tctattaaaa ctgttatact cttgtggaat ttatcattta  64920
atttagcttc agtgaaccgt tctttccaga ttattttggc ctcagaccat gacttctaag  64980
tctgccgtgc ttgccactta agtgatgatg ggccagtggg tccccaccta ggcctctgtg  65040
ttagtctgtt ttcatgttgc tgataaagac atacccaaga atgggcaatt tacagaagaa  65100
aggggtttga gggactcaca gttccatgtg actggggagg cctcacaatc atggtggatg  65160
atgaaaggca tgtctcacat ggaggcagat aagagcatag aacttgtgca gggaaacttc  65220
cctttattaa accaccaggt cttgtgagac ttcttcacta tcacgagaat aggatgggca  65280
agaccctccc ccatgattca attatctccc actgggtccc tcccacaaca catgggaatt  65340
atgggagcta taattcaaga tgagatttgg gtgaggacat agccaaacca tatcagcctc  65400
```

-continued

```
cttctggctt tttatgttct ccgtgggtga cctctctcag gctcaagtga taaccaatgt  65460
gctgatgact ctcaaatgcg catctctggc ttcagtttct tccttgaact tcatacatat  65520
gtttccaaat ttcctgcgtg tacctcaagg ttcttgttca tcacttccca agcttcataa  65580
acgcactcat tttagtgtat tctctgtctc ctttgatagc atccctgaga ggcaagtccc  65640
tggtgagtta tatacaactc ctcccttgct ccaaacctga gagtaagtaa cattcctatt  65700
aacatattag gaagctgagg cttagacagt ttaagtaact caagcatggt tacacaacta  65760
gctagggcag agctaaaatg tcaggctagg cttctgtgac tccaaagccc tttctcactt  65820
agcatatcat cacttatttt ttttttaat cacatatatg attttttttt ctttaagaga  65880
tagaatcttg ctctatcacg tgggctggag tgcagtggca caatcatagc tcactgtaac  65940
cttgaacttg ggctcaagtg atcctcctgc cttagcctac tgagtagcta gggctacaga  66000
cacacaccac catgcctagc taattttatt ttattttatt ttattttttg agacagagtc  66060
tcactctgtc acccaggctg gagtgcagtg gtgcgatctt ggctcactgg aacctctgct  66120
gcccgggttc aagcgattct cctgcctcag cctcctgagt agctgggatt acaggtgcct  66180
gccactgtgc ccagctaatt tttgtatttt tagtagagac ggggtttcac catcttggcc  66240
aggcttgtct tgaactcctg acctcgtgat ccactcgcct cggcctccca aagtgctggg  66300
attacaggtg tgagccacca cgcctggcca cctacctaat ttttaatttt tttgtagaga  66360
cagggtctca ctacgttgcc caggctggtc ttgaactcct gttctcaaac aatcctcctg  66420
cctcggacac cccaagtgca gggattacag gcatgagtca ttgcagctga cctgtatata  66480
tgatttttag tatatgtaaa tatacatatt tattaaatgt aaatataaat ataaatgtgt  66540
ggagtgatat ccattgaaat gttaaacata gttctcagtg gtacaactac aggtgatttc  66600
tcttttctta tttctggttt tctgtgtttt ccaaatttct tgaaatgtgt cttctgtaat  66660
cagaaataaa agttattagt aacaacagtc ttccactggt acaagtgctt attggataaa  66720
agtcccactt ctaagcatga tactcacaac ttttaggtta atagcctttg tcaccttgcc  66780
atatacatct gatccagcca ctcacaccat tcctgagata tattttgttc ctttgtgcct  66840
aaatcattgt gcatgcagat ccatcttcct ggaacaccta taaccatttc ttagtcctgt  66900
gaaatcctac ttacatcctt catagcctag catgtatgtc atttatttgg tcaagggtga  66960
gttggttgtt ctcttgaatg tactgccata tgacgtggtg tgatttcaat tgtagcacca  67020
agctcattgc aatattaatt cgtttgtcat tctcccatgt aggatgtttg aagtagtttc  67080
taacacagag attatactca ataaatattt attagataaa taaatgaata agggaataac  67140
aaatgccttt gtctcatttt aaaatacttt cattgttagc tacccatata ataaaaaact  67200
aaaagcagta gttttcaagc atgattgttt atgtatgcct taaaagaatt ttgaaaacct  67260
atgtacccct gacacacttt taagttaact tataaatttt tcaacatagt tttaagtggt  67320
ggcaaatgat gtagtttctt gtgtatttta aactgcttaa gtatgctata catggatttc  67380
ttcaaaaccc tgaagctgca gtttcagtgc attcaattta tggaaaagaa attaatttat  67440
aaaattggtt cttattgtca agtcaatcag ctaaatataa cttgctttct gtcaggaaaa  67500
gtctgacttt aaaatacaga taagtaataa ctattattaa ttaattaaat tattaaaatt  67560
aaaataatta aataatttgt taattaaaat gccttattcc cctacttatt tctgcaattt  67620
gactctaaga atagatagga catgtagatt gccttaggtt tgaaatctgg gtgaaataag  67680
atactgcctc cttcagtatt tctgcctttg cttttatggg agcctctttc aagaaaaagt  67740
cattctctca tggtcccttt gtttgagtcc cagaggtttt cctactccag aaagtgcaac  67800
```

gtagtgagac tagtactata ctcccttgca tggtaagtga gaaggctgtc tgtataaaat 67860
gagggaagga ctcatgagag ggaagtaggt caggagaaat gataggttct caggcaggtt 67920
aattttagga aagagtgaat agagtccctt aaaacaaggt gcatctgctt cctcctgatc 67980
aatctttagg actgtttact ttgatttgaa gaccactatg ctaaagcttc ccacgggggc 68040
aatagtgagg caaggaattt ttaaaaggga attacttctt cgtagctact tttgtgaaat 68100
gaattcattt gaattatctg gcaatctctt catatttata ttcaacaata attacttaaa 68160
gaaatgcttt gagcttctca gaggagggtg ctaccagtgt gatggagtag aattcagatt 68220
tgggtagtga ctttaaagct gtgtgacttt agtcatttaa ctgctgagtc acagtctaca 68280
gctttgaaag aggaggatta taaaatctat ctcatgttaa tgctgaagat taaataatag 68340
tgtttatgta ccccgcttat aggagaagag ggtgtgtgtg tgtgtgtgtg tgtgtgtgtg 68400
tgtatgtgta tgtatacatg tatgtattca gtctttactg aaattaaaaa atctttaact 68460
tgataatggg caaatatctt agttttagat catgtcctct agaaaccgta tgctatataa 68520
ttatgtacta taaagtaata atgtatacag tgtaatggat catgggccat gtgcttttca 68580
aactaattgt acataaaaca agcatctatt gaaaatatct gacaaactca tcttttattt 68640
ttgatgtgtg tgtgtgtgtg tgtgtgtttt tttaacaggg atttggggaa ttatttgaga 68700
aagcaaaaca aaacaataac aatagaaaaa cttctaatgg tgatgacagc ctcttcttca 68760
gtaatttctc acttcttggt actcctgtcc tgaaagatat taatttcaag atagaaagag 68820
gacagttgtt ggcggttgct ggatccactg gagcaggcaa ggtagttctt ttgttcttca 68880
ctattaagaa cttaatttgg tgtccatgtc tcttttttttt tctagtttgt agtgctggaa 68940
ggtatttttg gagaaattct tacatgagca ttaggagaat gtatgggtgt agtgtcttgt 69000
ataatagaaa ttgttccact gataatttac tctagttttt tatttcctca tattattttc 69060
agtggctttt tcttccacat ctttatattt tgcaccacat tcaacactgt atcttgcaca 69120
tggcgagcat tcaataactt tattgaataa acaaatcatc cattttatcc attcttaacc 69180
agaacagaca ttttttcaga gctggtccag gaaaatcatg acttacattt tgccttagta 69240
accacataaa caaaaggtct ccatttttgt taacattaca attttcagaa tagatttaga 69300
tttgcttatg atatattata aggaaaaatt atttagtggg atagtttttt gaggaaatac 69360
ataggaatgt taatttattc agtggtcatc ctcttctcca tatcccaccc taagaacaac 69420
ttaacctggc atatttggag atacatctga aaaaatagta gattagaaag aaaaaacagc 69480
aaaaggacca aaactttatt gtcaggagaa gactttgtag tgatcttcaa gaatataacc 69540
cattgtgtag ataatggtaa aaacttgctc tcttttaact attgaggaaa taaatttaaa 69600
gacatgaaag aatcaaatta gagatgagaa agagctttct agtattagaa tgggctaaag 69660
ggcaataggt atttgcttca gaagtctata aaatggttcc ttgttcccat ttgattgtca 69720
ttttagctgt ggtactttgt agaaatgtga gaaaaagttt agtggtctct tgaagctttt 69780
caaaatactt tctagaatta taccgaataa tctaagacaa acagaaaaag aaagagagga 69840
aggaagaaag aaggaaatga ggaagaaagg aagtaggagg aaggaaggaa ggaaagaagg 69900
aaggaagtaa gagggaagca gtgctgctgc tgtaggtaaa aatgttaatg aaaatagaaa 69960
ttaagaaaga ctcctgaaag gcaattattt atcaatatct aagatgagga gaaccatatt 70020
ttgaagaatt gaatatgaga cttgggaaac aaaatgccac aaaaaatttc cactcaataa 70080
atttggtgtc aggctgggtg cagtggctca cacttgtaat cctagcactt ttggaggcag 70140
aggcaggtga attgcttgag tccaggagtt tgagaccagc gtgggcaaca tggcaaaccc 70200

-continued

```
cacctctaca aaaaacacaa acaaaagaaa atagctgggt gtggtggtgt gtgcctgtag  70260
tcccagctac ttgggaggct gaggtgggag gatcacctga gcctgagaag tggaggctgc  70320
agtgagccat gattgcacca ctgtacccta gcctaggtga taggctcaaa aaaaaaaaaa  70380
attggtgttt gcaatgctaa taatacaatt tggttgtttc tctctccagt tgttttccta  70440
catacgaaac agcttttaaa acaaaatagc tggaattgtg catttttttct tacaaaaaca  70500
ttttctttct taaaatgtta ttatttttct tttatatctt gtatattatt actagcagtg  70560
ttcactatta aaaaattata ctataggagg ggctgatact aaataagtta gcaatggtct  70620
aaacaaggat gtttatttat gaaaaggtag taattgtgtt tcatagaatt tttaaaatta  70680
attctgcgta tgtcttcaag atcaattcta tgatagatgt gcaaaaatag ctttggaatt  70740
acaaattcca agacttactg gcaattaaat ttcaggcagt tttattaaaa ttgatgagca  70800
gataattact ggctgacagt gcagttatag cttatgaaaa gcagctatga aggcagagtt  70860
agaggaaggc agtggtccct tgggaatatt taaacacttc tgagaaacgg agtttactaa  70920
ctcaatctag gaggctgcct tttagtagta ttaggaatgg aacactttat agtttttttt  70980
ggacaaaaga tctagctaaa atataagatt gaataattga aaatattaac attttaagtt  71040
aaatcttacc cactcaatac aatttggtaa tttgtatcag aagcttaaaa gataacctaa  71100
tagttcttct acttctataa cttacccaaa tatgtttgca gagatcttat gtaaagctct  71160
tcattataac actgctttca ggagccaaaa attgggtggg ggagccccat aaatgttgaa  71220
taatagggggt ttgattagat aaattttggt gtagttctat aatggcgtgt tattcagcca  71280
ataaaaggtt tgttaaagaa tgactgtgac ggatgtatat gatatactct taagtgaata  71340
aagagttaca aaatgttatg tacaagttac aaaatgtatg tacattatga tccatttttc  71400
ataaaatcat atgtatgtat atatgtgtgt ctggaaggat aaatttatca agttgttatc  71460
tctgaaattt tgggtatatt ttatatttct agattttctg ttactttgtt actttactga  71520
taaagtaata acgttgttga cttttgtcac tctcccctat taataatcat ctaggctgca  71580
aaaggatcat gtcttcttta tttttatatt ccaaggactg tcaacaagtg cctagcactt  71640
gacaggtata ttatagaaat ttaactgaat atctttagga aatagatttt tgtttgtagt  71700
tgttctagtc tacattaaat gtcttgcgct tatgaaactt ccttgaatta ttttagtgaa  71760
gcaatattag tatagaattt tgcatcactg gatgcccttg actgaaagct ggcttatggc  71820
atctcaccag tgtgtgggga gtttcagtcc ttctgttgtc tgcatcacag ctgaagcagt  71880
gctgttgctg acaattcctg acaccacctt gtctctatta ttgatcattg cctcactatg  71940
gtactgagtt ttagcttatt cttgtaataa ctgggactca tatgtataga ataagctatt  72000
agctcacgtt tttgcttgct ttttatacag aatacatgtc tgcaaatagt tttatcaata  72060
ttttggaatt ttgggagata tgaagttaaa aacatcattg aatatatata tatacacaca  72120
cacatatata tatgacacta tacatgattt attttattta atttttaaaa ttttattctt  72180
tttagagatt aggtcttact ctgtcaccca ggctgaactt cagtggtgtg atcatagctc  72240
actgtaacct tgaactcctg ggctcaattg acctttccgc ttcagcctcc caaagtgctg  72300
ggtttatagg catgagccac tgtgtctggt ccaatatgca tatatatatt tttaacctgg  72360
attatcagag ctatattgtg tttaggttta taaagctgta ctatgtgaaa atatcacttc  72420
taggtttaat tttgtacaaa ggaattttat atagaaatga ggtaattcag attttttccc  72480
atgtaataag aattgtaaaa tttactgaaa caaacatcaa aaagatatct gttacatgac  72540
cttcctttct tttgaatata tttcaggtga tattatttat taaaatttaa aaatgaaaat  72600
```

taaaatatat aaaaagttga aaattattcc tttctttact gtctctcatc tgtccatttt 72660
ccattctcct gcattccctc atccaaccaa ggtagccaat ccaggtaact tttttagta 72720
tcttcccaga gatgtttctc tctatatata taatcaatat acattttta ttattcccca 72780
cctctctttt tatgtaacaa tatgcagagt tttgcttctt gcttttccca ctatcttgga 72840
caactttcca tattcaaagc acagaggact tgcacatatg ttcagactgc tgaatatttc 72900
tgtctctccc ctgccattca tatgttgaaa tcctaattcc caaggtgatg gtattgcagg 72960
gtggggcctt tgggaggtga ttagtccatg agggtgaagt ctttagtaaa tgagattagt 73020
gtctttataa aagaaacctt agagagaccc tcacacctta gagagaccct cacccctttc 73080
tgccatgtga gaacacagca ggaagacagc tggctatcca ggattcagga gtctcttagc 73140
agacccaaat ctgctggcac cttgatcttg gacttcccag cctccagaac tgtgagaaat 73200
aaattcctgt tgtttataag ccacacagtt catggtattt tgttatagca gcctgaacaa 73260
ggacacacac acacacacac acacatgcac acacatttaa atagatgcat agtattctat 73320
catatggatg gatattctat gatataatga atcactattg attgacattt gggttgtttc 73380
caatattttg ttaacacaaa gaacaacact acaaataact ttatatacat atcatttagc 73440
acatctgcaa ttgtatcagt aggcttccta taagtggtca agcatttgtg tacttgtgat 73500
tttggtagat gttgtcaaat gtccttccct gaaatttgta ccaattcgta ctcatgccat 73560
acactctaaa tagagtgctg atttccccac agcattacta acagatgata ttatctaatt 73620
taaaaagttt ctcatcttat agggaaaata gtatgtcaat gtattcttaa cttgcatttc 73680
ttttattata agtagtgtaa aatatcattt caacttatac acaggaggaa tttctctcta 73740
tataaagtga tcctagaatc ataatgaaaa atatcaccaa ctcattagga aaatgtacaa 73800
aggattgaat agatatctca tcaaaaaataa aaatataagt ggcctttaaa cattgaaagg 73860
taacatttga acaaagactt gcaggaggtg agggattagg gaatgcagac tctgggaaga 73920
gtcttccaag tagcaggtga agcaagtgca aagctttcag atgggactga ctatacctgt 73980
ctggtttgaa gaacagtaag gaggtcactg aggctggcat agagtaagac agggagggta 74040
gaatactgtc agagaagtaa tcggcggtgg aggtaggggg taaaccataa agtgctcgta 74100
aagactaagg cttatttctc tgggtgagat tagaggccac tggagagttt taaacagaag 74160
taacagggcc actttggcta atgtttttag gctattctgt agggagacaa gggaggaagc 74220
aaggagatga gttaggagtc tattgtgcca gttcaggcaa gtgatgatgg tggcttgatc 74280
caggtagtag tggaagtagt atagtaggaa gtgatcagat tcaggacatg ctttgaagga 74340
agatccaata ggattaatgg ataagttgaa caatggcata tgagaaaagt cacagaggag 74400
tcaaagatga ttccaagctt tctggactga gtaactggaa ggataaatgt gccgtttact 74460
agaaagataa tgggagaaac aggttttgga tggagcttgg tttgggaata ttaagtttga 74520
aatgcctatt tgacatccaa atagagatgt tagttggatg tacaagtcta gtttcaagga 74580
agagggggct ggtagtgtga agatggggct ggataagatt ctaaaggaaa gagggttgat 74640
aagaagagaa aggggtgtag gggttagcct aagggcattc taagtattag aggttaagga 74700
ggtgggtgaa gaaaacccaa taaaataaaa gtctgagaag acaaagctag tgaatgaatg 74760
tggtatcccg gaacccaact gatgtcaagc agaagggtgt tatcaactag gtcaaatgct 74820
cattcatcaa gtaagatgaa actgttataa ttaaccggtg tcttctgaaa tacggagata 74880
actcgtgact taatgaaagc aatagtagag aaggtcaaac ttgaccagaa tgaaattaga 74940
aagaataaga ggaaagaaaa gaccaaatac agacaaccat tgatgcctta ttcttttgat 75000
atactcctgg agtccacttg ctaatacaat tgacccttaa acaatacagg cttgaactgc 75060
atgggtccac ttatttgtga attttttttc agttaataca ttggaaaatt tttggggttt 75120
tttgacaatt tgaaaaaact cacaaactgt ctagcctaga aataccgaga aaattaagaa 75180
aaagtaagat atgccatgaa tgcataaaat atatgtagac actagcctat tttatcattt 75240
gctactataa aatatacaca atctattata aaaagttaaa atttatcaaa acttaacaca 75300
cactaacacc taccctacct ggcaccattc acagtaaaga gaaatgtaaa taaacataaa 75360
aatgtagtat taaaccataa tggcataaaa ctaattgtag tacatatggt actactgtaa 75420
taatttggaa gccacttcct gttgctatta cggtaagctc aagcattgtg gatagccatt 75480
taaaacacca cgtgatgcta atcatctccg tgtgagcagt tctctctcca gtaaattgca 75540
tattgcagta aaaagtgatc tctagtggtt ctcgcatatt tttcatcatg tttagtgcaa 75600
tgccataaac cttgaataac atcaagcaat ccatacaaag tgccactagt gatgcacgga 75660
aaagttgtaa cagtacaaga aaaaagttga gttgcttggt atttaccata tattgaggtc 75720
tgcagctaca gttgcctgca atttcgagat aaatgaaccc agtataaaga ctgttgtaac 75780
aaaagaaaag aaaatgtgaa accatcagtg cagctatgcc agcaggtgtg aagtcttgca 75840
ctttttgcaa aatacaaaat atgaaatatg tgttaattga ctgtttatgt tatctgtaag 75900
gtttccactc aacaataggc tattagtagt taagtttttg tggagtcaaa aattatacgt 75960
ggatttttga ctatacagtg ggttggcacc cctaaccttc atgttgataa agggtcaatg 76020
gtatattatt taattttttt gtatttatat tcataaataa gattaaatct atatttccaa 76080
gtaatctcta taagattttg ttattaatat tactattatt tttgagacag agtcttactg 76140
tcaccaggct ggagcacagt ggtgcgatct cggctcactg caacctctgc ctcccgggct 76200
caagcaattc tcctgcctca ccctcccaag tagctgggac tacaggcacg cacaaccaca 76260
ctcagctaat ttttgtattt ttagtagaga cggggtttca ccatgttggc caggatggta 76320
ttgatctctt gacctcatga tctgcctgcc tcggcctccc aaagtgttgg gattacaggc 76380
atgagccact gtgcacagcc attaatatta ttgttaccca ataaaaaaaa tttggaaact 76440
tgtcttcttt tcccctgatt ctgtttaaat agcactggag ttacctgttt tgaatttttt 76500
ttccaagcgg tcccttatga gtttctctca tgttttattt gtttcatttc tttttttttt 76560
tttttttttt tttttgagac ggagtctcgc tctgtcgccc aggctggagt gcagtggcgg 76620
gatctcggct cactgcaagc tccgcctccc gggttcacgc cattctcctg cctcagcctc 76680
ccaagtagct gggactacag gcgcccgcca ctacgcccgg ctaatttttt gtatttttag 76740
tagagacggg gtttcaccgt tttagccggg atggtctcga tctcctgacc tcgtgatccg 76800
cccgcctcgg cctcccaaag tgctgggatt acaggcgtga gccaccgcgc ccggcctgtt 76860
tcatttctta tatcgtattt ttgcaactcc tttattgata cttttcttcc tgattaggtt 76920
tctactaaaa ccaaacaagc tttccatgaa ttagctttta gatttactta ttagtttaac 76980
tgttctgttg tattgtaact cattaattta taattttatc tttattaatt attctatttt 77040
tcttcgcttt tttgttgttt ttctagtttt tgagttagat gtttgacgct tttttaaaaa 77100
gctgtgcatt ttcctctggg taatacttta gctgtatatt atgtattctg atatatagtg 77160
tttccattac attgttttct agaaaatctg tagctttgat ttatatttgt ttcctctttg 77220
acctaagata tcctaaggga aaatttaaca ttttccagaa agaaaacaaa ttttctttgt 77280
tttccaagaa tgttgttcaa attatttcta ctgcttggaa tttttatcat ttttgtgtat 77340
ccagtaaata gtcaatattt gtacttgctc tctgaccaca taaaagaata tattcgtgta 77400

```
gtttctatta atagattaga gttcaattca gatattaaat gtacatcatt attcatgata  77460
tttaggtctt ctacatcttc acttatcttt tttctacttg ctttgccatt aacagataaa  77520
gttgaattaa aggcttctac tacatacatt tctccctgtt attccttata ggttctgtaa  77580
tttttgcttc aagaatattg ctttttaaat ttaatatata gatacttata attacactct  77640
agcattataa agagcctttt ctttttcatt gaatgtattt gggcctgcat atgtctaaca  77700
tgaaaattat agtccttttt ttgtttcttt gtttgtattt acagttttaa gttccatttt  77760
caacctttat gcactctttg ctttaggtgt gtctctttta gttagcataa agttaggttt  77820
gtctttaatt tcacctgaag tcttttcctc ttaatagatg ggttaagcca actgaaaaat  77880
aaaactgact tatatacttt tatttcaagt atgtcctcca caaatatttt ttgaatagat  77940
tagcttatat actttggaat ttgttaaaaa aagattttta taaaaaaataa ttgtggtgaa  78000
atgtacataa cataaaattt atcattttga ccatttttaa gggcatagct ctgtggcata  78060
aagtatactc acatagttgt gcaactatca cctccttttg attttttttt actaattttg  78120
taaatttgtt tcatctgagc tgtcttatta tgttttgttt tatgtttttc tttcctttat  78180
tatgaagtca ctgtattgtc tgtaggctat atgtatctgt gagtgtgtgt gtatatgtgt  78240
gtattatggt ttttaaaaaa gtctatattt gttttccagt ggctatactt aatactaata  78300
actttatgtt aaatttttca ttctatgtga ctctagttca ctaatatgag ctctgataaa  78360
atcagtgctt tttcgaggtt aggagatcaa gaccatcctg gctaacacag tgaaactccg  78420
tctctactaa aaatacaaaa aattagccag acgtgatggc gggtgcccgt agtcccagct  78480
actcgggagg ctgaggcagg agaatggcgt gaacccagga ggcagaactt gcagtgagcc  78540
gagatcgcgc cactgcactc tagcctgggt gacagagtga gactctgtct ctaaataaat  78600
aaataaataa ataaataaat aaataaaatc agtgcttttt cttcctctgc tacctccttt  78660
ccttctactc agttttagtc agtagtatta tctttttttca gatttatctt tgtattgtta  78720
aatctgctta tgcttctatt actttattta ttagctttaa atgatacctt ttgactttca  78780
gcttttctta ataaagcaat cagcaaattt cctttacact ccacacttat accccatttc  78840
ctttgtttgt ttatttggtt tttacttcta acttttctta ttgtcaggac atataacata  78900
tttaaacttt gtttttcaac tcgaattctg ccattagttt taatttttgt tcacagttat  78960
ataaatcttt gttcactgat agtccttttg tactatcatc tcttaaatga ctttatactc  79020
caagaaaggc tcatgggaac aatattacct gaatatgtct ctattactta atctgtacct  79080
aataatatga aggtaatcta ctttgtagga tttctgtgaa gattaaataa attaatatag  79140
ttaaagcaca tagaacagca ctcgacacag agtgagcact tggcaactgt tagctgttac  79200
taacctttcc cattcttcct ccaaacctat tccaactatc tgaatcatgt gccccttctc  79260
tgtgaacctc tatcataata cttgtcacac tgtattgtaa ttgtctcttt tactttccct  79320
tgtatctttt gtgcatagca gagtacctga aacaggaagt attttaaata ttttgaatca  79380
aatgagttaa tagaatcttt acaaataaga atatacactt ctgcttagga tgataattgg  79440
aggcaagtga atcctgagcg tgatttgata atgacctaat aatgatgggt tttatttcca  79500
gacttcactt ctaatggtga ttatgggaga actggagcct tcagagggta aaattaagca  79560
cagtggaaga atttcattct gttctcagtt ttcctggatt atgcctggca ccattaaaga  79620
aaatatcatc tttggtgttt cctatgatga atatagatac agaagcgtca tcaaagcatg  79680
ccaactagaa gaggtaagaa actatgtgaa aactttttga ttatgcatat gaacccttca  79740
cactacccaa attatatatt tggctccata ttcaatcggt tagtctacat atatttatgt  79800
```

-continued

```
ttcctctatg ggtaagctac tgtgaatgga tcaattaata aaacacatga cctatgcttt  79860
aagaagcttg caaacacatg aaataaatgc aatttatttt ttaaataatg ggttcatttg  79920
atcacaataa atgcatttta tgaaatggtg agaattttgt tcactcatta gtgagacaaa  79980
cgtcctcaat ggttatttat atggcatgca tataagtgat atgtggtatc tttttaaaag  80040
ataccacaaa atatgcatct ttaaaaatat actccaaaaa ttattaagat tattttaata  80100
attttaataa tactatagcc taatggaatg agcattgatc tgccagcaga gaattagagg  80160
ggtaaaattg tgaagatatt gtatccctgg ctttgaacaa ataccatata acttctagtg  80220
actgcaattc tttgatgcag aggcaaaatg aagatgatgt cattactcat ttcacaacaa  80280
tattggagaa tgagctaatt atctgaaaat tacatgaagt attccaagag aaaccagtat  80340
atggatcttg tgctgttcac tatgtaaatt gtgtgatggt gggttcagta gttattgctg  80400
taaatgttag ggcagggaat atgttactat gaagtttatt gacagtatac tccaaatagt  80460
gtttgtgatt caaaagcaat atctttgata gttggcattt gcaattcctt tatataatct  80520
tttatgaaaa aaattgcaga gaaagtaaaa tgtagcttaa aatacagtat ccaaaaaaat  80580
ggaaaagggc aaaccgtgga ttagatagaa atggcaattc ttataaaaag ggttgcatgc  80640
ttacatgaat ggctttccat gtatatactc agtcattcaa cagttttttt tttagagccc  80700
cattcttatt ttttatacac tttgagagca taatgaaaag aaaagctacc tgcaaaagtt  80760
ttggacttac ctcaaagagg atatacttca ttcctcaaaa ggccttcttc caggaatagt  80820
atttcataac ctggaggttg gaaaaatctg gatttgttac aaaaaaatct gagtgtttct  80880
agcggacaca gatatttgtc taggagggga ctaggttgta gcagtggtag tgccttacaa  80940
gataaatcat gggctttatt tacttacgag tggaaaagtt gcggaaggtg ccttacagac  81000
tttttttttg cgttaagtat gtgttttccc ataggaatta atttataaat ggtggtttga  81060
tttcctcaag tcaaccttta aaagtatatt tagccaaaat atagcttaaa tatattacta  81120
gtaataaatt tagtactgtg ggtctctcat tctcaaaatg agcatttact aatttctgaa  81180
cactgtgcta ggtcctggga ataccaaatt gaataagaca tagtctattt ttctgaaggg  81240
tttatagcag agtcccctgt gttaataatg aaggagtgtg tggtatgtga atcatatatc  81300
aatagggttg ttaaaaataa tgaaaaaagg agaagaggaa gaacatcttt tttttttctg  81360
attgcacggg cagccttaaa attattttttg aagtgtacaa ttcagtgttt ttttagcata  81420
ttcacagggt tgtattatca tcaccatatt tttggcctct tgaaaagaaa tcctgtgcct  81480
attagcatcc aattaccgtt cctttgtagc taagtctccc ccattccagc tttaaacaat  81540
cacccatcta ctttctgtct ctataaattt gtctcttttg gacatttcac ataaatgaaa  81600
taatataata gggtttttttg tgcctaaata agcttctaaa gaagaataag gtaaggaatc  81660
atcattcagc aaatatttat taagacttgc tttattttat acagtgtact aggagctgga  81720
gatgaaaata tgtgtagaac atgaatcata tacttcggga atttgtggac tagtgggaaa  81780
gattgacata tcaataacaa atcgaattag tgatgtaata gaggcatttt tacaggagta  81840
aaatgaggta gcatggactc tatctgggtc tgaataatgt gaggagtaac ctccttacac  81900
aaagaggcac aaggctaatg tcctctgatg gaatgattca ccatgcaatt ctaagggtga  81960
caagaatgaa agttagggcc ttgaagaaat attttgatta agagctgcca ataaagtaga  82020
gtaaagatta gattgatgtg aagaagtggg agattaatga gtaaatggtc actggcttgt  82080
tgagaagatt aaatgagatg tacatgtaat gtacctaaca caacgtcttg tacaaagtag  82140
ccattcagta gagactagct tgtattatct ccctttgagg taaagaaaac tgttagaaat  82200
```

agtatttcta ctactgatag tatttcttct acttatgcct ccctttgagg tgaagaatac 82260
tgttagaaaa catgacatag gagaaatacc cctgagagac agttcttatt agtgactact 82320
gtgcagaaaa gatggaggtt ggtgtaatta aggagaagga aagccatgaa gccaaagtat 82380
tatgaaaaag catcaatatg aattttcatg ttgacaaagt ggtataaaag ataattataa 82440
agatggtcac ttataaatac ggtagttctg tgtgacacaa tttacagaag ttggtatatc 82500
gtgtggaaga aaacagcata agatcctgaa ggtttgaact gtgggcacat tggctccatg 82560
ctcaggaaat ggcaatgggg ttgggaagtg attccacttt atgtcccttt cagacacata 82620
aaaattactt gtgtgagtat cttatgccag acactattca ctgtgtagtg agcatggtgg 82680
gtatgaaatg acaactttat tgtctttcct gtcaaagaac ttgtaggctg gttgggggaa 82740
agagaccatt tcaatatgaa gtgctgagct agaggtaccc ttagggcact acagaagcct 82800
agctgatggc ttttagcctg gctagacagt tcaggatctc taaaagcagg tgccttgaag 82860
gctgagtcaa atacaaaaat gtattttgga cagaggaaat tgtatgaaca gaaacacaga 82920
acatgaaact acttggttgg tgcagggtat catcagcata gaaccagaca gaaccagagt 82980
gtaaataagc cagaaggcca tgtcatggag gccttgtata ccagtctcag gaatttggtt 83040
gtggagagct ttcatcaggg gaatgatgta atcagcttgg aaatgtagat atatcactga 83100
ctgtgatagt gaggagcaga attaaggtgg acgtgattag aagctttgtg aatagcagaa 83160
agaacataga ttttgaaagc tggcagacgt aggttactga agaaagttac ttaaccttgc 83220
tatgtcttta gttttatcct ctgcaatatg gggataatac tgcctatttt gtagagtctt 83280
gtggattctt ctggcatata taatagaaaa taaaacagct attattatta ttgttgatgg 83340
tactatttgc tatatctgac tacaaggaga aagactaata ggaaaccatt tcaggaatcc 83400
agatatggtc atgatggaca ggaagagaca agagttacat agaggaattc tgggaagata 83460
agaaatgtca tttttatgta ctgtttgcat ccatcagaca aggcatcagg aaaaatgatc 83520
cttcaggaaa gagtgatttt ttttcttcaa gaaattagaa gaggggagaa attggtttaa 83580
gattaaggac tccatgcata agagaaactg ggagggaaga caggtagaaa tgctatgggg 83640
ttaggaagga agaatgcaga ggtggattac ttagaattga gacatctgat caagacagag 83700
ggatcacagc ttttgctaac aaagtactag tggaggatgc cactaggtga ggtttaataa 83760
ataattgttg acaataagtt ccatttaaaa aataaacaat ttatgcttct tctttgccta 83820
agtgtcaaat aaaacattca gatttttatt tcaaagtatc cctgagtccc tgttcccttt 83880
tttgtcctgc tgacttttgg aactgattta ggcttcctta gtcatctcat aatagaaaaa 83940
atcagccagg tatttcctac atttcttgta ttttaaaaaa atgtaatgga tgtaatgaat 84000
tttaagcaaa tgtaatgaat acaataagta acttagtata tgctgttttc ttctctatgc 84060
tgaatgtttc atacatgtta ttttctatac aactacatgg tcaattcctt gaaaatatca 84120
actccaaaat ctttattttg gtatactcca cgtagcacat tgagagagtt ttaaactctt 84180
gttggatgac tgtttcaaaa gtgttttgaa gtaggcatgt cagttgcaaa aagtttgctc 84240
agcaaatgtt gttctgtctc acagtctcag acattgagca gatgattaca tgacagcacg 84300
tgattgctgg gagtaacaga caaaagtaac tgaaagtgct cggttatctt gacagtcaaa 84360
atcaaaagtg tcccctattt tcagtgacct aagagtttct ttttgtgttt ttggtattgt 84420
tgttaaataa gtgttctcac ctttgaaaag gtcaataaga attcaataca gtataatgtc 84480
tgtgtgccaa atgaaggtgc cccttatttt taagtgtgga ggagttttga tcataagaac 84540
ttgaaatacc tacagaatcc ttgatggtta agcagctggt gccagcacaa gaatccctca 84600

```
atatgttctc tatgaagccc cgatcaccaa atgcaaacat tcatgattca gtatattttc  84660
atcttgactg ccaaagttga tctgtttctt aatatattac atctagactt ggaactggag  84720
atgagaacag aatattatct tcctcatttt tgtgtttttg ttcaactcta atgtctgcaa  84780
agcacttgcg tatgtaatga tgctcagtgt cataggagca ggcaggtaag tgtaaatttg  84840
tctggatagg agaaagcatg cacaacatat ttcacatagt tttctgattt cagtttgttt  84900
ttgcaaatta ttcactcagt gagatagctt aaagacgtta tcacagggaa aggcatggag  84960
atagttctgt gttgatagaa aacttgtaat gtacagccat gagtgagaag tcaggttcag  85020
attcttcacc ttcagtcctc ctctttcata aacagctcca tgtcctattt tacatatcct  85080
actttaaaac gagattatag aagaatgaat ttctaggcaa agtgacactt attttaaaat  85140
actattacgt atccctgtgc ccattaactt atcctaccat ttttcttccc ctgtgtccaa  85200
accaccttta gaatctccta aatatttgta gctattgtaa acagcactgg agactttgct  85260
agtttaaaag gagaaatcaa cgcaattaag ccctagttaa tttacttatc ccttatgaga  85320
ttataattgt attttgttat taaaaggggg acagagtaca ctgttctctt gccttttttaa  85380
tttccagact accacttctc ctgcacttga caataccgca gtctaccacg tagtcccatg  85440
gctgacagga ggagaattct aggcaggcca gtgtttgagt agtgagtaat tggactgtct  85500
ttacccagca actcactgtt ttgtaaatgt acctgagttt ggagaagtaa ttggctttta  85560
taaggggtgc ggggtggagg gttggggtgg ggagagtgag aaggaggtca gagctttagg  85620
atatataatt ggtctccaca aagttgttgt gatacttttg gaaccacgta atggtcttca  85680
ttaactaagt gtctgtcatg acagccatta catatgcatt ataataaaaa tttatttaca  85740
gtgtaagttg aagaaggtaa aatctggatg tagtttctaa actctgcttg gcagttttca  85800
tatttaagcc actagaagaa aaaaattggg agggaagctg agaagaattt actgaaagaa  85860
aaaaatactt gggagggaaa ttggcaagaa gtatgaaaaa gcttgggagg gaagtaagca  85920
aataaatgag ttaatgactg ttctggaaaa taaactctat catgcagata tcacatgact  85980
gattaaattt gaatttgacc tcctgctttc caggtctggt aaaaactaac ctgtaagaac  86040
ttgaaactta gcctttgaat ggtcaatcca ccactgtagg agaatttatg aatgttcagt  86100
tgagagaact gaaaataaag aagtaccata ggaattaaca tttgcattca gtagccaaga  86160
tataatggac atctgaaaca ggtatttgag gccaggcgtg gtgtctcatg cctgtaataa  86220
tagcactttg ggaggccgag gtgggtggat cacaggaggc caggagttca agaccagcct  86280
actaaaacac acacacacac acacacacac acacacacac acactagcca ggcgtggtgg  86340
tgcacgtttg tagtccaagc tacttgggag gctgaggcat gagaatagct tgaacccaga  86400
aggcggaggt tgctgtgagc tgagattgcg ccactgcact ctagcctggg tgacagagtg  86460
agactctgtc tcaaaaataa aataaaacat atatttgaaa cacattgaat tatgtccctt  86520
aaacaagaat aaacatcact aaatgactgt accttgaact acctgtaatt ttctcctgat  86580
aggtaattaa gcttcaaagt actgacactt atttactgta atatgaagca ataacttaaa  86640
aaaaaaaaaa aactattgaa ccagaaccaa acaggaatgc catagcattt tgtaaactaa  86700
actgctattt catttcattt gagccctgga acttgaaaat aaatgctagc taacatctgt  86760
gaacagaaca tacccatcag tactgtgcta agcacctttc atgaactggt cattaaatcc  86820
tcactttcca tttatttagt gacaacttca cccagagttt gcagtcaaag tgaaaatgtg  86880
ctgaattcca aaagtgtgag ctaggtttta gaagttaatc acaattctgg aacaaattac  86940
tagcttaaca aatgagagtt cttatgtctc taaaaccaaa atagccctaa gtctgtccct  87000
```

cccagtaaga tttgggccag tcaatggaac agtaatatac aaatataatt acagctgtct 87060
aggagcaaac tatcctatga atagataata aaattaagac acttaagcca tgttttcata 87120
ttaaaacaca aagtaaaaaa tcattgtttt ccaaagataa aagccatact gtatcatgac 87180
atatatatgc ccgatgtttc gaccctcttg aagaattgag attctcgact ctacactctt 87240
agcgttttct atattgaaca gatgtttaat ttaaggaggt caagagaaat cttacactta 87300
ttttttaatg gtaccttaga catagaagga acctcagaaa tctctggctg aatatttcca 87360
tctgcagatg atcatgtcat taggcttctg actctatagc catagaaaaa tattcatgaa 87420
gacctttcag gaagggaatg ttggtatttc taaaaattga gtacaagtat tctctagaca 87480
aaacagctct tgaaatggca gattgtattc ccattattat atttcagaat caagacatta 87540
atacctactt tttatttacc aggtttagtt atccttgaat tagattttat aaattaaaga 87600
aatagatttc aataaatatt tgttgagttc ctagtatgga aacatcgtgt ttggcaccag 87660
ggatgttgcc tgcaagtata acaggagttc gtatttgtaa tgagtttatg atttacagat 87720
atttgggggg caaagatatc attcggtaaa tacttatgag tgcaaacttt gaactaggga 87780
ctgggccaaa ctctaggaac atatttgatg acagagacac aatccctgtc ctcaaggagc 87840
tttcattcta gtagagaaga tgaaaaccag tacagtttgg taagttagat gatattggtt 87900
aatgtagggt tcttatgtaa gtctagagaa gtagcattta atctgttctt agaaggtcag 87960
gaaagatttc cctggaggaa gtgacattta agctgagaga ggatggataa acaggagtca 88020
tctgagtgaa caacagggag aacattccag aaagagaaca aaatgtacga ggcctgatgc 88080
caagagagaa cattcattgc attggggaac tatagtcact tctgtgtggc tgggatgtag 88140
aatgaaatga gcctggaccc aagagagcac tttgcccttt ggggaagctg taggtattac 88200
agtaaggttg gagtctggaa agaaaggggt atattgtgag atctgaattg ggagaggaca 88260
gttatatcca gacctttata tgctccagta agaagactga actttacact gggggccatg 88320
ggactcactg aatggcatta aatttgagag tggtcatatg accagatttg cattttacaa 88380
agattgtcat tgactgcaac atgaagtatg gagtattgga ggagcggtaa ggctggtggc 88440
agggagataa tttaggaggc tttaggtgag ggatgataat gacttgccag gtaggaagga 88500
gtaaatttct tctcagtgga taattagaag attgaatgga tggacttggt cactatttgg 88560
tatagaaggg gaaaaaagat gtcaaagatg atgccaattt ttaaaaataa tttaacattt 88620
atttttaaat attttttcag ccttattaag gtataatgga caacaattgt aggtatatgt 88680
catttacaac atgatgtttt gatttatgta tacattgtga aatgactgcc atagtcaagc 88740
tcattaacat atccatcact cacataatta acattttgtg tgtatgcagt gagaacatca 88800
ggctctactc tcttagcaat tttcaagtat agattacatt tgttaccaac tatagtggcc 88860
acactataca atagagctcc aggacttatt catcctgcct aactaaaact ttgtactctt 88920
tgaccaacat cttcccattc gtctctcctc cccatgccaa gtttccatct tggtcagttg 88980
ggtggatagt agtactatct gccgaggcag gttggtaggg tgaaaacaat gtgttccctt 89040
ttggaaatgc tgaggtgacc agggaacttc caagggaatc tgtctggatc tagagcttag 89100
aagagatgtt tgggctggaa acagacatca ggtattcttc agtatatggg ttgtaaatga 89160
agtcacagga gtgggtgata tcaccaatgg tgagtgtagt ataagaagac tggactgagg 89220
acagatttcc aaggaatttc aatacttaag aggtacgcag agaaaagagg ggctgtgaag 89280
gacaccaagg aggagactaa gagccaggag ggaaaacttt caagagagta ttgcattatg 89340
gaagggaaga agagagaaca ttttaaatga tacgcaatgc tcaataatgg tatccgcttt 89400

```
ggagaggcca agtaagattc ctaagtaccc attggatcaa ggtccttaat cttacaaaaa  89460
cttatgcaaa tcaataataa agagatgata acccgataat caaaaataga caaggcatat  89520
aagaagaaaa tgaattaaaa atattcaaag cattcaacat atacaaatgc gctcaatctg  89580
atatataatg aaagaaaagt aaattaaaac aacaatgggc atgactaaat aacagtatga  89640
gggagcctga ggagaaggag catttgaaat ttcagtacag aagagaaaag gggtgactta  89700
tagaaaaagg agacagaaac catagaacat gtttggagga taagactcaa acaggtagtg  89760
gggacccttt tctagagtag gatgaaaaca ggtaatgtgt gtggatgcaa atatgaggta  89820
ggatgtaatg ggaagttgag cgaattcata tttagtcatt cattcaaaaa tacttaattg  89880
agttactgct gtgtggcaag catcattcta caaacagagg gcacagtgat aagcaagcca  89940
gtttgtactc tcgtgtaact tacattctac tttgagaaga cagattataa ataggttaaa  90000
aagtcaataa tatgatgttt cagcatcaac aataaaaaat tagggtgata tatagagtgc  90060
cagggaaagt gctttcatgg acctcttcat tctctcctct cctggtgtca taagctactc  90120
cttcatccat gctgccattt ctcttggttt acggttccag tatagtactc atcacattat  90180
tactatagag ccatccacct tatgaaggtg aaggtgtcca tctccttact taaaaaaaaa  90240
aaaaacaaac aaaaaaacaa aaaacccgaa aaacaaaaaa agaggcagaa agacagaagg  90300
tcctccacta actttcacgt gccatgtaac cagcgaaatc caattatttt acagcattct  90360
agctatagaa gagtttggga agcgtagtgc ttagtgttct agcctttgta gcacaggaaa  90420
gggcctggaa ggaaaggaat tgtgtcttcc gcagttgctt ttctttatgg ggaagtgcta  90480
tagcccaaac aatattttag gaattttcat ctattgtcaa tatgcaaact ggaaggggat  90540
aatgaaaatg ttgtggttag aagtttatga aatattgtta ttcacatttt aaagtaaaaa  90600
gagggaatgt ttaagagact tgtttaagat cacatgtctc ataattggtg ggaccagcaa  90660
tacaatccaa atctaactac ttatcttttt gctatgccct attagtgttc atattagaaa  90720
agaaattcta tctcagacac taatgatttg ttctttggac accaatgact ttaagttaaa  90780
acttcatact agttaattta attatggtgt agcagtatta ttaaactatc aagactataa  90840
attttctatt tgtaaaggag attatgatac caaagattag tgaactaatg atattgagaa  90900
ttctatgaca taattttgaa aaatatttgc aggatattta tttttgtgta aatgatgctt  90960
tcaagctacc ataatcctaa gtaagtgtat atttgggaaa accacctatt ctaacacact  91020
tgaaatttaa ataagtcagg aaattttttt ccagatcttc tcccaaatta tcttcatctt  91080
tttcctctcc ccttgggaaa gaatctcttc atgcctcata atatcaaatt taaactatgg  91140
aagtccaggt ggtggacagt cagcaaaggg gaagatgaga agcttgtgtt ataaagccag  91200
ctcttgtcag aataaggatc tggtaggaac ttcagaagtg atgggtaggt aagtatgaag  91260
gccaggtcct aagatctaaa ttacaaagca gaagacttac ttaccaggga gctggaaaac  91320
atgttaggaa atccagagca ggaacagatt tcaagatagc acaataatat agcagtgaag  91380
tactgagaaa agagtttttt tcacgggttg gatttattct agcattttag gcagcatttg  91440
ggcatttcta agtggtcaga cttagaggag atagttaagg aattagcagc tgctaaatgc  91500
caattcttag accagttgaa tcaaaatcat ctaaaaagct ttcagaaacc agacttttta  91560
agggccattt gagagactct caaatctgga atccagaaat ctatagctag atgagtttaa  91620
ggtagagcca gaataagaaa aataaaatag tttgtttgtt tcaggtatct tttccaatat  91680
tatttccgaa cctaccccaa acaccttaaa tcactgcatt ctatagccat tcttttaaaa  91740
atgcttgagt tattagtttt caaaaacaaa tacaaatctg cacacataca gaaataaaca  91800
```

ttaaagagac ataaagatat taaacagagt tacatatact tacaacttca tacatatata 91860
ttatatataa aactgaatat taagtgtttg atattagtga caaaatctgt aacatccatt 91920
atattagtgc tttttgtact ttttgttggg tgtagtaaaa attgcattcg aatttgagtt 91980
ttctgctata tatttggtca gttcctatca gtgaaggaaa aaccttttt tattatttta 92040 ttgtttttttt attttttgag acggagtcct gctctgttgt ccaggctgga gtgcagtggc 92100
atgatcttgg ctcactccaa cctctgcctc ccgggttcaa gcgattctcc tgcctcagcc 92160
tcctgagtag ctgggactac aggcacctgc caccaggtcc agctaatttt tgtattttta 92220
gtagaaatgg ggttttgcca tgttggccaa gttggtctgg aactcctgac ctcaggtgat 92280
ctgcctggct tggcctccca aagtgctgga attacaggtg taagtcacca cgcctggccc 92340
ctttttattt tttaagctga ttgaagattc ttagttctca tgctttctag tggtgattaa 92400
tctttagcca atatttctat atacagttat tagtaatcat gtttgactta ggtcaacaaa 92460
caatctttcc taaaaaaaca gaaccccaat tttaatttct gaattattta gtatctattt 92520
tctgctgtgg aagttgaatt atgttgatag atatcataca gggccatgta acactctcag 92580
atacacgttc acatgtatag tagctgtata caaaaatgtt acttcattct ctctctcttt 92640
ataatactct tggctctctt acgttctctc acacactcta ctcttccctt cctctgttct 92700
ttctacttgt tccctctgct cctaccacac ttattccccc cttgtccatt ttccttgtgc 92760
ataaagcaca agtgcttagt aattatcaaa tattaataac aatgacacta accacccaat 92820
gatttagtgt taatgacatg ctttattgaa tggcattacc tctaaagttc atgtttcctt 92880
tacccaacca agcttcttac cctcctccct taccacaagc atctatattg tcaaggttgt 92940
tataaagagt aataagccag ccattaaaaa agggtttatg gtattttcct atctacaaag 93000
tcacaggaag ctcaaatgta ctcagtaaat attgcaaaat tacacaggac cattaaatgt 93060
aacactccac cctttctctc tctctctctc tctcttgctc tctctctctc tttctgtcaa 93120
tatagcaaca ccctatatca ttgccctttg tatgtgcaaa tcagagttaa taagctttat 93180
attagcaatt actccttaac aacttctggt ttgtttggtc cagttgaata atgtaagcac 93240
ttaaaaaaat gaaattataa acatttatgt gaaaagtgca tatatcacat tggatatgtt 93300
gttatgcact ccttaataat aaagtaagtt aatctttatt gcacacttat tataatatta 93360
ctttgaccct ctctagtact ctttatctaa gtattctcaa gtgctttaca atctcaaaca 93420
gacccaatgt gttgtataca cagaatcctt tgaagctgac atttgccttt ctgaccagct 93480
tgttgtaaag gaaatcagcc aaaaaacaag tatctagatg agtagctcaa acattagtac 93540
acatagtaat cacaggtcaa aatgcagata gattaccctg tccaaattct cctgagtaag 93600
agtaggtgaa acatttttaa ataagctccc caggtgattc tgaaattggt ccaaggacca 93660
catattaaga actaatgatc caaacaattt gactttttat tgtagattaa accatgctga 93720
gaaaattatt aaaaattgaa atggcagtgg aggatggttt gaaagaaagg tttttcaggg 93780
ccctttcaac aataaaatta attgaacaca atattaaaac tctatatttg atttaagact 93840
aaggttttca ttgtttttaa atctcagtaa tttttatgta acaggtcaat tcatacccag 93900
catcttaatt ccaatgaatg atttcccaca acaattttg tggataactc caagggaact 93960
cgaaggaagt tgtagtatga acaaagagaa gtagaatttg tccctgtgtg taaggcttct 94020
ctgataagca gcacaggctc tcatactgct ttttaaaaaa attatgatag catcaagtgg 94080
aattaatttt ttttagatta tactttcatg gaagggaaga tctactgtga aggctggaaa 94140
accaacaccc ttaagataaa tatattacca gatttgagcg ctcttagtaa tcagcaaaga 94200

-continued taaatgttta acagtgcata caaaatgaag tgttttatgt taaatcaaat agagaaagcc 94260
aaacactaat aatgtggtta caaatgaaca ataaattagg taatcagaac aggtacagac 94320
attaatagca ggatattggt attattaatg tattttgttt taaaataatg aacttaatta 94380
caattctcct catcctaccc cactatttta ttttattcca gattcagcag cttcatatta 94440
tgtctctgaa acacttatta ttaaagttat ccaaatgtac acatttctct ttatataaat 94500
gtttcagtcc agaaaaggag gccaaataca ttagctcaga acatcaaatc ttctcagatg 94560
tgggaatctt ttattttcac acttttaaag gtaatctgta tttctagcgt ctattataga 94620
cagaaaactt tcatatgaca acattcctat tttcttaact gccttgatag gggcgaagac 94680
aaattctaag taggactttt taccccattc ttcttaccat cattctttca caaaaccccc 94740
agctttagac aatcgctatt atgaatttga catgtactat tccaatccat tcccataaat 94800
ttacacccat atatacatat agttatctat gaacaatatt tagtagcttt tttgtgtgtg 94860
gctttaaaat ttacataaat tgtataattt gtgcacattc ttctttaatt tgccttcttg 94920
gctacggtta tctttttgag atctagctat gctgctggta tgtagaattc tatttcattc 94980
ttttttcatt gttgttttgt acccataacg tgtcacattt tatttatacc ttctgttcct 95040
gatggacatt tagattcttc caggatttta ctcaatactg caatgaaaat ctttgaattt 95100
ttctcttttg cacatattca agagactttt ctgacatata tatctatagg tgaattgtgt 95160
agtcatatga tacatacaca cattttaaat ttcactagat actgccaatt tgccctttga 95220
aatagccata caatttatag taccaccagc cacttatgaa agttcccatt tcctcaaatc 95280
tttgaaagtt cttattataa acagacatat taattcttgc cattctgatt tgtaaatcag 95340
aatctctatt gttctacctc tagttctaat ttggaattcc ccaattactt gtaagatgct 95400
atatattttc atgtttgtta gtcattctga tttcatatcc tttaccaatt atctttttgg 95460
taagttattg tggtggccat gagatgtgcc ttacagaggc cttgctagag ggaatgtgat 95520
tgaatgagag ccccagatgc tgtgtattaa aatcctgcac tgagtttgtc tcaagatttc 95580
ttgcacgtga atgaatgagt acagctggga tactaaagca gatgtgtatt tgggagatat 95640
gagacttctt tagtggctga tttttggctc ataaatgact ttgccaaacc ttccttagac 95700
tgctcagtgt tctaacatct tccatccagc cttctaccct tctttccttt actaggggat 95760
tgaatttaca ttgaggtctc atagccttct ctgcctctct ccttatttcc ttttatacaa 95820
atatttcccc taataaatcc atgcacattt aataccattt tgctatttgc aacctgcagg 95880
tcctggacta acacagttct atacattgca ttaccattct ctagagtggg atcttttgtt 95940
gtagagagtt ttaaaatttt tatgtagtca cttttatcca tatttttctt tatggtttat 96000
atttttgtgt cttctcttta acacatcttt tctagcagaa ttcataaata tattattcta 96060
tattgccaaa agtttgaaag ttgcaatcat tagaattaat ttttgtatat tgtgtaagtt 96120
aagaatctaa ttttattgtt tttcattgga aagccatttg tcccaagata attttttagt 96180
agtccctcct tcccctattg tcattctgac atattttttc taggttccga tctatgcatg 96240
tgtttcttta tggaagagtt ggccctttgt atctttgagt ttcaaatcca tggattcaat 96300
caaccacaga tagaaaatat ttagaaaagc gtcagaattg aacatgtaca tacattttgc 96360
ttgtcattat tccctaaaca atatagtata acaactattt atgtaggatt tacattgtat 96420
taggtattgt aagtaatcta gagatgattt aaagtataca ggaagatgtg catatgttac 96480
atgcaaatac taccccattt atataagggt cttgagcatt catggatttt ggtatccaca 96540
gagagtcctg gaaccaattc cccacagatg ccaaggcaca actgtattta ttctatcatc 96600

-continued

```
tacttgttta atctcacatc agtatctact tttgaaataa caataacttt attatttaac  96660
ttttttttatt acttaggatt agagaatttc ctctggtgag gcatcatagt gtctcaagct  96720
ggccataaag acaagtgagg gctaggatcg gtaagactgg gcagaggaag atacaacaga  96780
tctcctatgc atgaagcaaa agtgcagctc agaagccagc tctttcatta agttgtcctc  96840
tatacctca ctagattgta agctcttgaa atgagaggct ataccttaat tgtctctgtt  96900
atctaaaata cttccactca ctgcttggaa catattgcct gcaataatta agcttgccct  96960
ggctcccaaa gcatagagca aatcacactc ctccccttgc ctttgagaag ctcacagtct  97020
tcgaaggtag agatatgtga acagataaga aaatggatga caggagaaca gaaacgcatg  97080
actgtcagag aagtcattgg agactttaca gaggaaatta aatttttatt gatcttgaaa  97140
gagtttgcca gatgaagtag aggacaggca ttttagacaa agggaacagg aaatgtgaaa  97200
acacaaagtg atggaagtca tggtgagttt ggagaactat aaaacttcaa tgtggctgaa  97260
gggtaaggtg gatatagagg agtgctggga ggtgaggctg aagaaataag ctaggaaatg  97320
tctttttatg ccattttta aagtttggac tttattctga agttcacatg gatccaatat  97380
tttttgtttt gtgttgtttt aagcagaagc gtgacatgat cagcttgaat gatgaacaac  97440
ttgaattgtt taaagtggat cacacagtct actgttttac agttattctt tgaccaagat  97500
attctttatt aactgaggaa aaaaagggct ttcctgaatt ttgcagtcat gggatatatg  97560
ataagcattc ttgatttatc atcttcaatc ctgttacata acataataac cattgttatt  97620
acctttagca atgctttcct cagtattatc taatggccta taaaatgtga ctttcatttg  97680
caaatacagt acatctaaca agaacttacc acagctgcta tgcaaaatac caatacaatt  97740
gacccttgga caatgtgggg gttaggggtg ctgattcccc atgcagttga acatgttaca  97800
taacataata cataaccatt gttattatgt aacaggattg aaaatgataa atctttggaa  97860
agtggggcaa atgaattctt atgaattcca tatcttccac atgtgtttta ctttttttgat  97920
aagaagtagt aacctagttc agaaagaaaa taatcatccc cttttactta tgcaggatac  97980
caagtctatc ttagcaccat aatagtgaat gataggaatc aagctctatg aatacattca  98040
catgtacata tatatggcta tataggacac atgcatgcac atatacatat atacacttgc  98100
atatatgtgt atatacatgt acatatatgc atgtatattc aattgtatat gtgtatatag  98160
ccaagttatt gtacagttga cctttgaaca acacgggttt gaactatgca ggtccactta  98220
cacgtatttt tttttccgt ttctgacacc cctaaggcaa caaggccaac tcctcccctt  98280
gctcttcctc ctcagctgac tcaacatgaa aactatgagg acgaagacct ttatgaagat  98340
tcacctccac ttaatgaata gtacatacat ttctttttcc ccatggtttt cttaataaca  98400
ttttcttttc tctagcttgc tttattgtaa taatatagta tataatacat ataacatacc  98460
aagtatgtgt taattgactg cttatgttat cagtaaggct tctggtcaac agtagactat  98520
tgctagttaa gtttctggta gttacaagtt atatgtgggt gttcgactgc atggggagtc  98580
agcaccccaa ccctcatgtt gtccaagggc gttgtccaag ggtcagttgt aattggtatt  98640
ttggatagca gctgtggtaa attctggtta gatgtactat atttataaat gaaactcaca  98700
ttttataggc cattaaatat tattgaggag agcatttcta agggtaaaat cttgtctaat  98760
gcttgaaaca tcttcatttt cctgtcagtt tagatctttt tgaagtaatt ctgaaaatct  98820
ctcttttaag ctaaatttaa cacaaccaaa tagccaaata tttaagttcc actaatgaag  98880
atatctaaat ttctgttaaa aatttaagat atatgttaaa cccttctaat ataactcttc  98940
tctcagtcaa acttttttt ttaacagttg ctttgcttct tctttcaaag tcatacttca  99000
```

```
acaaagttgc tattgaatat gtctgactaa acatgttagc tatatgataa gatggctgga  99060
taagagataa atatagaaaa tgtagctttt tttctacttg caataaccct ttaggaatta  99120
aaatggaaaa ctaataacta tttgattcat aatagtagca aaccgtaaaa tatttagaca  99180
taaatctact aagaaattta taagacatat atggagaaaa ttcaattgaa taaaccgtta  99240
ttgaagtata taaaataaga tctggatgaa tagaaagatc ataattttta ataaaatttt  99300
gcatcttaaa aagtgaaccc tctccaaata tatgcacatt taataaaatt ataaatacat  99360
cccaatgagg ttggttttga aattttgtta attggaactt aaatttcacc taagaagaaa  99420
aaataaagaa tagttaagag tgcatgcttt gtagacaaat tgccttagtt agaatcctgg  99480
ctctatcatc tattagctat gttatctttg ggataacatt catcttttct tatagatatg  99540
cttaaaacag tgcctgacat atagtaagca caaatatcca ttagctattc ttcttattat  99600
ttatgttatt agtattgtta atatttgtta ttatatggaa gactaaatga ccaaagagag  99660
tcaagaaatt tatgaataag atttatgcgt tgttagatat tagagccatt aaaaaaaaaa  99720
aaaccaaagt gccaaaaaac ctagcacagt gttaatacag gaataaaaaa atggatcaga  99780
ggaaccaaac agaaaagcca gaaatggatc ttaggaaaca tgagaatatg atatatgata  99840
gatgctaaat gaattcagta taaaaatatt aatgtaataa atcatgcttg ctattcaagt  99900
aaaagaaaat gaggttagat tcatgtctca taccaaatat aaccataaat tataccttga  99960
ttaaattttt taattaaaaa gcaataatat ttgaaaagaa atataggata ctcaatgtat 100020
aacctgaagg ttgggtagta cttttcaaca aatataggaa tttttcactt gaaatactag 100080
aagaaaaaaa gatagcaaac aaatacagga attccaattt caagcagata taatgatttc 100140
atgaaatgtt aactgtgcac atgatagatg gtctatggat agtgcaaaag aaaaagagaa 100200
aagaaaaaat gttttttaac atatgcagca aaaaaggttt ttaacatcta ttacatacaa 100260
ataaaaatga atgtataaca cagacttcaa taaaaatagg catttcacag gagaacaatt 100320
cagatggcca gtatttacaa tttcataggt attaaggaaa atacaaatta aaatggcaaa 100380
ttagcaaaaa ttgaggtgtg attatattaa tatctgttgg tggtggtgat tatggggaaa 100440
agggtacttt caaaacttgc taatataaat ataattcttt tggttgtttt gtaaaggaac 100500
ctgacaatat cttttaaaaa taaagaaaac gcatactttt gacctagcca tcccattcat 100560
gagggtatgt cttagaaaaa taagatcaca aaatcataga gatttatgtg caatgatatt 100620
attggtaggt catttttatg aggaggggtg tggatagtaa atgccagggt aaatcacata 100680
gcatctaata aacgtattta tgaactacaa aagcttacac tttcagtcta gtctagtcca 100740
gactgcaaat aaatgtgagc aagtgaattc aagcacagaa gtgcttgaag gcaggtttca 100800
taaatctact ttcttacagt atcctgatat tgacttatcg agacagttac tgtggggttg 100860
attattaaaa tatttatgta tctaggtatt tttcattcag tagtatgtta ttcaattagc 100920
aacaagtgtg gggatttaaa gatattcttg tttgttttta ctgctgaaac atattctagt 100980
ggaaatttcg aataaacgat tagtcatcct aaaagcaaga tacattttct cagaaaagac 101040
aaggtaaaga acttgtatat cctccctcaa ttcgtttata aggtaataag atgaataaaa 101100
atatcatagt acaatttagc attgtaaaat aaaattaatt ggtcatctct agtgtggtcg 101160
tgcttggaag gtgaaagaag ccaagatctt gtctgggaat atcatgtcta ccttgacctc 101220
acccttaaga atcctagcct ttagtttaaa atcacatggc tacatacata ccaacttcaa 101280
caatagtaca tctggcaagg tcatgcaaac ctgggacttg agcttctgat tctaagtcca 101340
gtgctttttg tgtacatcat ctcttgtaca taccttatga tgatatgcta ataaaagcta 101400
```

cgtgatcagg ccttaaaaat ctgctttttt tttgtaatgg tagaatgggg catattatca 101460
catcaggtaa acactctatt caaggataaa tggaaatgaa tgtcatatat agatcattga 101520
taaatatctc attacaaaat tatgagagtt accaatgttt gagtgtatat tatgggccag 101580
ccctttatat taaattactt caaattttta caactgttaa aggaagatat tattataccc 101640
attttataga tggacaagtt agggccagaa aagacttcct caaagctgtt agtccagtaa 101700
tggagacagg gctagaaaac aggtcatttt gctctttgac taatgttact actcatgttt 101760
tgtattttgt ttaaagtttt attttatttt gctttattta ttttttgaga caagatctta 101820
ctctgtcacc caggctggag tgcaatggag tgatcacggt tcattgcagc cttgacctcc 101880
tgggctcaag cgatcctccc acctctcaat ctccagagta gctaggacta ctacaggtgt 101940
gtgccaccat acctggctaa attttgcatt ttttgtgggg acagggtttc actatgttgc 102000
ccaggctggt cttgaactcc tgggctccag cgattcacct gccttgacct cccaaagtgc 102060
cagtatcaca ggcttgagcc accatgtcca gccaagtttt attttagaat taaaaaaaat 102120
tccacttgga ttgttacatt ttatctcatt gctttatatt tatagaatta ctttataaat 102180
gccactttct taattttcat agttagcact ctttatgaaa cataaactat tatttgaccc 102240
aggtttttgt tagaggaatt gagtcagaga gctgttaagt aactgagatt tcacaataag 102300
ccagacagac cagggttcaa attctgggtc tcacattatc caattcaata ttccagcttt 102360
gttacttatt gagcaaccac tacaagcaca gtttacatga catctgatag ctctcaaaat 102420
gaattttaca aacataattc agatttcaac tcagcagtga ctcaggagaa aggacacttg 102480
gatgcatttc tttatggcat ttttcccagg gtacacgcaa cctggaagat ctcccaagta 102540
tgggggaagg tttcaccctg aggaatccca ttccctctaa tctgggacaa gggggaggag 102600
agtactgtct cttatcagcc atctccccag ggaggcctgg gccctcctgg aatgcatacc 102660
atggcttact gactcaaagt gttgaaaaga ccaggcattg ggacacacaa cactactctt 102720
aaaataaaaa aagaatcaga gtagcttgtg gttataattg aaatggacag agtaacatgg 102780
taccaagaaa ctattagcaa ttccttccct aaatccctca ttttcttaaa gcattttctc 102840
cttttcctca acaagcttta agttggattt gaagaatgat aagactaaaa ggagggctgt 102900
ttctggtctt tggaggaatt tgatattcca ttcgatctga gtgtgcaaag cctgagttca 102960
catgaactct tctgatctct ttctctaata ttttttcacc ttattcatat gggaaagaag 103020
gaggggaata ctttagttcc attctccctc ctcctatttc cttgacttgt ttaaaatata 103080
aatgttatag acacctaaga tagaaatttg actgaaacag cctcttaatt attgtcttaa 103140
aaaattggta taatgaaatt gcatttgtag tctttggaca tttaaatcca gaagggatat 103200
tttctttttc ttttttaaaa atttaattca atagtttttg ggctacaggt ggtttttggt 103260
tacatggata agtgctttag tggtgatttc tgagattttg atatacccat cacctgagca 103320
gtgtgcactg tacccaatat gtagtctttt atcccccccc cgctccaccc ttcctttatc 103380
gtccccaaag cacattatat aattattatg cctttgcagc ctcattggtt agctcccact 103440
tgtaagtgag aacatgcgat atttggtttt ccattcctga gttacttcat ttagaataaa 103500
ttgtctctag ctccattcaa gttgctgcaa aggccattat ttcattccgt tttttggctg 103560
aatagtattc catagtgtat atatgccaca ttttctttat ccacttgttg attgataggc 103620
atttaggttg gacccatatt ttcgcaatta tgaattgtac tgctgtaaac atgagtgtgc 103680
tttttttttt tccatataat gacttctttt cctttgggta gatacccagc agtgggactg 103740
ctggatcgaa tggtagttct ccttttagtt ctttaaggaa tctccatact gttttccaca 103800
gtggttgtac tagtttacaa ccccaccagc agtgtaaaac tgttccattt tcagcacatc 103860
catgccaaca tctattattt tttgactttt taattgtggc tattcttgca ggagtaagat 103920
ggtatctcat tgtggtttta atttgcattt ccctgataat cagtgatgtt gagcattttt 103980
tcctgtgttt gttatttgtt tgtatatctt gagaattatc tattctgtcc tttgcccact 104040
ttttgatgga attatttgtt tttttttctt gctgatttgt ttgagttcct tgtagatcct 104100
ggatactagt cctttatcgg atgcatagtt tatgaatatt ctttcccact ctgtaggttg 104160
tctgtttacc atgctaatta tttattttgc tgtgcaaaag cttttcagtt taattatttc 104220
ccatctattt atttttgttt ctgttttatt tgcttttggg atcttagtca tgaacttttt 104280
acctaaacca atgactataa gagtttttcc aatgttatct tctagaatgc ttatgttttc 104340
tggtcttaga tttaagtctt tgattcatct tgagttaatt tttgtataag gtgagcattg 104400
aggatccagt ttcattcttc tacgtgtggc ttgccagttt tcccagcacc atttattaga 104460
tagggtatcc tgtccccact ttatgttttt gtatgctttg tcaaagatca gttgacttta 104520
agtatttggc tttatttctg ggttctctat tctgttccat tgtctacttg cctatttgtg 104580
taccagtacc aggctgtttt agtaactata gccttgtagt ataatttgaa gtcgggtaat 104640
atgatgcctc cagatttgtt ctttttgctt agtattcctt tagctatgtg ggctcttttt 104700
tagttcccta tgaattttag gatttttttc tagttctgtg aagaattatg atgatatttt 104760
gatgggaatt gtattgaatt tgtagattgc ttttggcagt atggtcattt tcatagtatt 104820
gattctaccc atccatgagc atgggatgtg tttccatttg tttgtgtcac ctgtgatttc 104880
tttgagcagc attttgtagt tttccttgta gagatcttta acctccttgg ttaagtatat 104940
tttcatgtat tttagttttt tttttttgtt tgttttgttt tgttttgttt tgtttttgca 105000
gctgttgtaa aagggattga gttcttgatt tgattctcag cttggttgtt gtcagcaggg 105060
acattttcta aagtatagac tgtagttcct tatcttctat ctgtttctta ctgtcccctt 105120
cagtattctt gtcctttttt cccgctatta tctttttgac cttttaatat atagatatct 105180
acttctactt ctgacaattt ttgcttctcc aatttttcttt ctttttctcc tctgcacaca 105240
tttatttatt ttcttctatg tacttcttta tttttaactt aatatttgat taacttccct 105300
tccctgtctc ttttccttct ttccataaat cttcattaat tgcctgcact gagctaggat 105360
tctatactct ctaaatcaat aatctatttt ctatagtcaa ctgtgttata atcgtactgt 105420
caagataact acttattttt aatacttaaa aatattttga aattttaacc aatttaatta 105480
atacaatgtt gagttcaaat ttgaaaaaaa caatggaaaa ctgtaataat tctagcaacc 105540
tcctgctttt taataatgta ttagaaaatt tgcctctttt tcaaaagcct acagtgaatc 105600
tattcataca aggcaaaagc aaaccattct cttcattctc ttttttttctc caaaagattt 105660 aagtgttttt tgtttgtttg ttttgttttg ttttttagat attgagtctt gctctgtcat 105720
ccaggctgca gtgcagtggt gtgatcatag ctcgctatag cctcgaattc ctgggttcaa 105780
gcaatcctcc tccctcaccc tcctgagtag ctggggctac aggtgcatgc taccatgccc 105840
agctaattta aaaggaaaaa aattgtgtag agatgggtct tgctatgttg cccaggctgg 105900
tctcaaactt ccaatctcaa gcatttctcc cacccagcat cctgaagtgc tgagattata 105960
agtgagccac tatgcccaac cagatttagt ttttaaaaag agaatacgat ttgaaaaagg 106020
aaaaatgtga ggcaggagag aagaaataca cacacgagct gttttgtaat tgctgtaaaa 106080
ctgaaatctt cagcctcact aaaggagcac ttgcatgaac acctctaaat taccttatta 106140
ccttctaaat taggtgtgaa gtctaacttc taaattatga gtgaaatcca ctgcaattct 106200
tgttatttgg atggaatcct aggtatgtgg tccagttcat gagttgaaca aaagcatgct 106260
catttaggcc aggtagaaag aaataaagac ctatgtttta catgtctcat aaccactgaa 106320
ggtccttctc ataagcagtg cttatgggta ttaacgacct ctctatattt tacttctcca 106380
gtgcctaagt agccgagtcc actgagtcct gctacatctc ctccaacatg tcagcatttt 106440
tttcacaggc cttttgttac tctagatcag aaatgttgat agcaacagtt ccttgagggc 106500
agcagctagc atgatgccag ccaacaggaa ccaccaaatg gttcttaata taaattacta 106560
cttattaatc tatttacttt gtgcatttgg agttttgcat gtaaagtcct atttatgtcc 106620
atatggtaga taaatggaac aaatgaataa cagaagtaac cattttgata ctttagatat 106680
agataatatt ggattatttc tggattgtga aagaagaagg aagaagcata tggaagagaa 106740
gttttagtag aggggaggaa ggaggaggtg gaaacgaatg tacaaggatg ggaggagaaa 106800
agggagagag actttttttt ttttaaggcg agagtttact acctatctaa ctcttcgcat 106860
tcttgaagtc tcagaccaaa tcccatcggt ttgaaagcct ctagggtatt ctatctattg 106920
tatacttctg ttatgtacaa aattaatttg ccaattaatt gtgaactgtt ttataaacta 106980
tcttaaaatg gttagttaaa tctttgggat agtatttagc tttctccagg attatgactt 107040
accttctaaa ttagacatac aatgcctagg agtcaaggac tattttgcat aaattccagt 107100
cttcttttac aatgcctaga atgattgtta ccacagaaat attcattacc tgggagaaag 107160
gatgacagga ggggcagaat gaatggagag aggtcgtgag aatgaggtgc tgaggatgga 107220
cgaggaagaa agctgtttta gttgggagga taggtgacag aagcatggaa aggaattgcc 107280
ttggacccat ggaagcccag tgaagatact tagatcctgc aggggtgtga ataatgttct 107340
tttagtttct cttcttagga ggtttgttca ttttgggaga tttcttttga aaagagtgaa 107400
cttaaattgg agaaaagtac attttagtat gttgataaca tttgaatttg taaaatggac 107460
ctatggatga tctacacata tttatatacc cataaatata cacatatttt aatttttggt 107520
attttataat tattatttaa tgatcattca tgacatttta aaaattacag aaaaatttac 107580
atctaaaatt tcagcaatgt tgtttttgac caactaaata aattgcattt gaaataatgg 107640
agatgcaatg ttcaaaattt caactgtggt taaagcaata gtgtgatata tgattacatt 107700
agaaggaaga tgtgcctttc aaattcagat tgagcatact aaaagtgact ctctaatttt 107760
ctatttttgg taataggaca tctccaagtt tgcagagaaa gacaatatag ttcttggaga 107820
aggtggaatc acactgagtg gaggtcaacg agcaagaatt tctttagcaa ggtgaataac 107880
taattattgg tctagcaagc atttgctgta aatgtcattc atgtaaaaaa attacagaca 107940
tttctctatt gctttatatt ctgtttctgg aattgaaaaa atcctggggt tttatggcta 108000
gtgggttaag aatcacattt aagaactata aataatggta tagtatccag atttggtaga 108060
gattatggtt actcagaatc tgtgcccgta tcttggtgtc agtgtatttg tttgcctcat 108120
agtatagttt actacaaatg gaaaactcta ggattctgca taatactgga cagagaagat 108180
gtaaatatct gttagttcca tcatagaccc tgccactcca atgtacacac cagctttagg 108240
cttcttggta tagataaaca tacattttca aaatttttca tcataatttt cataacaaaa 108300
taggaaggca aatgatgtca cttggcttaa aatctataat atttaaaata aacaggacaa 108360
atgcattaac attgttgggg gaggaggtcc cttagtagaa acactcttgg tccaagcatt 108420
ttaaagctgt caaagagatg taaatataga taatgtatgt caaggagaga gctttgtggt 108480
taaactgtaa ctttcagttt aaacaattat tggtgactct gatgtcaaat gtttctcaag 108540
ctttatctga acaaaattct tctcactttg ttgccaaagt cgttaacaag aaatcacatt 108600
gactcattga tgttttggct cctttccctt actttctgtt gctttccaaa agctgagaca 108660
ggaaactaac cctaactgag cacctgcaat tgcctggtag tattctagtc atgtgtgtac 108720
ttttgtgtgt atgtaatccc cttacagctc tgcaaagtaa gaattgttct ccctgcttta 108780
cagaagagat cataagataa ttgaggctgt tagatgttaa cttgccaaaa gccatacagg 108840
aaaatggtag agtcacagtt tgaaccaggt ccttttgatt ctttacatta aaccatgctt 108900
tgatcttgga aatacactgt aaggcaataa atcaatagat acggataatt cacaggcttc 108960
taaataaatg gaagttgatt gtttttatct gtgagccaaa gtaagactta ttctaagaat 109020
tccacaaatt tagataagat agagtatatg gcttctagac atccaacata gaactgagtt 109080
tgtgttatca gtttaagatt tggttttgct gtaaggtgca cacactttga ggaactaaaa 109140
ataattgtct gttcttattc tgatcagaat gtgtaatgtg ttgtccagtt ttggatgatg 109200
aatttcttat ttctaatctc ataagaaact tgtcatagat gtgagggaga gaattaagaa 109260
cagagtgtgg ggaagaaact gtgtacattt tgatgggatc cattatgtag ctcttgcata 109320
ctgtcttcaa aaataagtta cactataaag gttgttttag acttttaaag ttttgccatt 109380
ggtttttaaa aaaattttta aattggcttt aaaaatttct taattgtgtg ctgaatacaa 109440
ttttctttat tacagaagta ccaacaatta catgtataaa cagagaatcc tatgtacttg 109500
agatataagt aaggttacta tcaatcacac ctgaaaaatt taaatgttat gaagaaatta 109560
tctcatttct attaatatgg gaactgtgtc ttcatcttta ttactgttct aaggtcaact 109620
caatgtagat tttacttgct tatggtttca tattttagct aaatagtaaa ataatatgga 109680
tatacatttt gttgtgactt actcatactt tccttatttg gaacttttat gaatatgata 109740
tagagactga aactacaagg aacaaaatgc aatatcaatt atacagttgt ggcagcactg 109800
ctatcaattt gttgatagtg gttaacactt agaaaaacat tttaaaaata atttcacata 109860
agtaatgtaa tttattagct gtctctgaca ttttacagtt tggaatagtt tattttcttt 109920
ttggtgtcct caccaaaacc caacatcttc aagggcagga actgtataat ttttgccatt 109980
gtattttgag cacatagcat ggtacttgcc tctaaataga tactattgtt aaaatatttt 110040
ttaaggtaat attttaaagt gtatgctatg gtacagttca gtttgtgact tttgctagtt 110100
tatgccactt acagttagca aaatcacttc agcagttctt ggaatgttgt gaaaagtgat 110160
aaaaatcttc tgcaacttat tcctttattc ctcatttaaa ataatctacc atagtaaaaa 110220
catgtataaa agtgctactt ctgcaccact tttgagaata gtgttatttc agtgaatcga 110280
tgtggtgacc atattgtaat gcatgtagtg aactgtttaa ggcaaatcat ctacactaga 110340
tgaccaggaa atagagagga aatgtaattt aatttccatt ttctttttag agcagtatac 110400
aaagatgctg atttgtattt attagactct ccttttggat acctagatgt tttaacagaa 110460
aaagaaatat ttgaaaggta tgttctttga ataccttact tataatgctc atgctaaaat 110520
aaaagaaaga cagactgtcc catcatagat tgcattttac ctcttgagaa atatgttcac 110580
cattgttggt atggcagaat gtagcatggt attaactcaa atctgatctg ccctactggg 110640
ccaggattca agattacttc cattaaaacc ttttctcacc gcctcatgct aaaccagttt 110700
ctctcattgc tatactgtta tagcaattgc tatctatgta gtttttgcag tatcattgcc 110760
ttgtgatata tattacttta attattatta tacttaacat ttttatttac tttttgtgtt 110820
agtattttat tctgtcttct ccttagatag taaccttctt aagaaaatat atatgctaag 110880
tgttttactg gtttaatatg cttagactac tcatctacct caatacttcc ttggagatct 110940
cctcctcagt cacacagagc tcaggactta tatttccttg gaactcctgt tagggtccaa 111000

-continued tgtacatgaa attccctaga cagacagaca gtcagttata tggcttgatt tcaaagtttc 111060
aaaatgattt aatggactat caagtagttt attaggagaa cagttattat actcttctaa 111120
aaataaagac tttaagcaat aaagatgtat atgtatataa aatggctggg ttattcctag 111180
aagtaccttt cttagaattt agttaaattt aatatccaag atactatctt ttcaaccctg 111240
agattgtgaa aagtaacttc tatcaatata aactttacta catttgtatt gtgttagtgt 111300
gttacagtat aatctagaac aatgtgtctt tctatatgat atatgacatt ttaatgccta 111360
aaaaaactga tatgtcttag atgattctag tcaggattta cttctagaat agattaaaat 111420
tctatttgag gagagtcaaa ttaattatcg aattctcagt tgttattatt gctgttttat 111480
ttttagtgaa acagattagt cttaatgtaa acacttgaga aataaattga tggtcaacct 111540
aaaatgtaaa aaagaaatta atagaaaatt taaagagcaa caaagctctg acatttaaaa 111600
gaaatgaagt acaaatctct agggacctta aagatcatct aataatttcc tcattttcta 111660
gataaataaa ctgagagacc ccgaggataa atgatttgct caaagtcaaa tatctactta 111720
atataggaaa tttaatttca ttctcagtct gttaacatgc aacttttcaa tatagcatgt 111780
tatttcatgc tatcagaatt cacaaggtac caatttaatt actacagagt acttatagaa 111840
tcatttaaaa tataataaaa ttgtatgata gagattatat gcaataaaac attaacaaaa 111900
tgctaaaata cgagacatat tgcaataaag tatttataaa attgatattt atatgttttt 111960
atatcttaaa gctgtgtctg taaactgatg gctaacaaaa ctaggatttt ggtcacttct 112020
aaaatggaac atttaaagaa agctgacaaa atattaattt tgcatgaagg tagcagctat 112080
ttttatggga cattttcaga actccaaaat ctacagccag actttagctc aaaactcatg 112140
ggatgtgatt ctttcgacca atttagtgca gaaagaagaa attcaatcct aactgagacc 112200
ttacaccgtt tctcattaga aggagatgct cctgtctcct ggacagaaac aaaaaaacaa 112260
tcttttaaac agactggaga gtttggggaa aaaaggaaga attctattct caatccaatc 112320
aactctatac gaaaatttc cattgtgcaa aagactccct tacaaatgaa tggcatcgaa 112380
gaggattctg atgagccttt agagagaagg ctgtccttag taccagattc tgagcaggga 112440
gaggcgatac tgcctcgcat cagcgtgatc agcactggcc ccacgcttca ggcacgaagg 112500
aggcagtctg tcctgaacct gatgacacac tcagttaacc aaggtcagaa cattcaccga 112560
aagacaacag catccacacg aaaagtgtca ctggcccctc aggcaaactt gactgaactg 112620
gatatatatt caagaaggtt atctcaagaa actggcttgg aaataagtga agaaattaac 112680
gaagaagact taaaggtagg tatacatcgc ttgggggtat ttcaccccac agaatgcaat 112740
tgagtagaat gcaatatgta gcatgtaaca aaatttacta aaatcatagg attaggataa 112800
ggtgtatctt aaaactcaga aagtatgaag ttcattaatt atacaagcaa cgttaaaatg 112860
taaaataaca aatgatttct ttttgcaatg gacatatctc ttcccataaa atgggaaagg 112920
atttagtttt tggtcctcta ctaagccagt gataactgtg actataagtt agaaagcatt 112980
tgctttatta ccatcttgaa ccctctgtgg gaagaggtgc agtataaata actgtataaa 113040
taaatagtag ctttcattat ttatagctcg caaaataatc tgtatggaag tagcatatat 113100
aaggtatata aacatttagc ctcttgatag gactaactca cattctggtt tgtatatcag 113160
tcttgcctga atttagctag tgtgggcttt tttttatctt gtgagtttgc tttatacatt 113220
gggtttctga aaagatttct tttagagaat gtatataagc ttaacatgta ctagtgccaa 113280
tcttcagaca gaaattttgt tctattaggt tttaagaata aaagcatttt atttttaaaa 113340
caggaaataa tataaaaagg agagtttttg ttgttttagt agaaaactta atgccttgga 113400
tgaaatgagc catgggcagg gttgtaatga attgatatgt ttaatagtat agatcatttg 113460
tgaataatat gacctttgac aagacacaag ccattaacat ctgtaggcag aagtttcctt 113520
ctttgtaaaa tgagggaata aaatagatcc ctaaagtgtg taattttagt atttctaaac 113580
tttatgaagg tttcctaaat gataattcat ctatatagtg tttttttgtg tgtttgtttg 113640
tttgtttgtt tgagatggag tctcgctctg tcacctaggc tggagtgcaa tggtgcaacc 113700
tcggctcact gcaacctctg cctcctgggt tcaagctaat ctcctgcctc agcctcctga 113760
gtagctgaga ttacaggcat gcaccaccat gccgagctaa tttttgtatt tttagtagag 113820
aaggggtttc atcatgttga ccaggctggt cttgaactcc tgaccttgtg atccacccac 113880
ctcagcctcc caaagtgctg gtattacagg cgtgtgccac cacgtccagc ctgagccact 113940
gcgcccagcc catctatata gtttaatatc aatctaaatg aatttctcag tcctgagcct 114000
aaaaatttag ttgtaaagaa tgatatcctt gactaataat agtttctatt aatggattgc 114060
atctagtgct aggtggcata tatttagtcc ccacaactac cctggaaggt atttaaaatt 114120
tttcacattt gcagataagg aaactaaagt tcagagttcg gcaacatgct tgaattcaag 114180
cagctcctag gatgttaatg gtggaggttg ggttcaaatc cagatctgtc tgactcaaaa 114240
aatgcatact cctaaccagt gcactatatc ccaattccat aggagccctt ctttgtgatt 114300
catagcactt tcccatgagt tttgttgatt ttgtgagaaa caaaactctt tttcctttgg 114360
actgtctgga atctctcttt ttcaaatttt tgaaatgtat ttctatgcca aaagacaaag 114420
atttctagag gaatatgcct aggatgagaa ttatgtaatt taaatcacag ctggaaagag 114480
agaaagtcct aagttactaa gaaatgttca aacacaaatg agctttcagt ctattggaag 114540
acctttatag ctagaagtat actgaactgt acttgtccat ggacccctga agaaacaggt 114600
taaatcaaag agagttctgg gaaacttcat ttagatggta tcattcattt gataaaaggt 114660
atgccactgt taagccttta atggtaaaat tgtccaataa taatacagtt atataatcag 114720
tgatacattt ttagaatttt gaaaaattac gatgtttctc atttttaata aagctgtgtt 114780
gctccagtag acattattct ggctatagaa tgacatcata catggcattt ataatgattt 114840
atatttgtta aaatacactt agattcaagt aatactattc ttttattttc atatattaaa 114900
aataaaacca caatggtggc atgaaactgt actgtcttat tgtaatagcc ataattcttt 114960
tattcaggag tgctttttg atgatatgga gagcatacca gcagtgacta catggaacac 115020
ataccttcga tatattactg tccacaagag cttaattttt gtgctaattt ggtgcttagt 115080
aatttttctg gcagaggtaa gaatgttcta ttgtaaagta ttactggatt taaagttaaa 115140
ttaagatagt ttggggatgt atacatatat atgcacacac ataaatatgt atatatacac 115200
atgtatacat gtataagtat gcatatatac acacatatat cactatatgt atatatgtat 115260
atattacata tatttgtgat tttacagtat ataatggtat agattcatat agttcttagc 115320
ttctgaaaaa tcaacaagta gaaccactac tgatatttta ttatttcata ttacatataa 115380
aatatattta aatacaaata taagaagagt ttttaataga tttttaataa taaaggttaa 115440
gagattcgaa agctcaaagt agaaggcttt tatttggatt gaaattaaac aattagaatc 115500
actgttgata ttttattatt tcatattaca tataaaatat atttaaatat aaagataaga 115560
gtttttaata gattttataa taaatgttaa gagattaaaa aactgaaaat agaaggcttt 115620
tatttggatt gaaattaaag gccaggcatg gtggttcatg cctgtaatcc cagaatttta 115680
ggagactgag tggggaggat tgcttgagcc caggggtcaa gaccagcctg ggcaacacag 115740
tgagacaccg tatctacaaa ataattaaaa aattagctgg gcatggtggt gtgtgcctgt 115800
atgctaccat taactaagga ggctgaggtg ggagaatcgc ttgagcctgg gaggtcaagg 115860
ctgccctgaa ctgtgattgt gccattgcat tccagcctgg gtgccagaga gagaccctat 115920
ctctaaataa ataaataagt aaataaataa acagcaacaa caaaaacact caaagcaaat 115980
ctgtactaaa ttttgaattc attctgagag gtgacagcat gctggcagtc ctggcagccc 116040
tcgctcactc tcagggcctc cttgaccttg acgcccactc tggctgtgcg tgaggagccc 116100
ttcagccctc ccctgcactg tgggagcccc tttctgggct ggccaaggcc agagccggct 116160
ccctcagctt gcggggaggt gtggagggag aggcgctggg ggaactgggg ctgcgggtgc 116220
cttgtgggcc agcgcgagtt ctgggtgggt gtgggctggg caggccccgc actcggagca 116280
gccggccggc cccgcgagcc ccaggcagtg aggggcttag cacctgggcc agcagctgct 116340
gtactcgatt tctcactggg ccttagctgc ctccctgcgg ggcagggctc gggacctgca 116400
gcctgccatg cctgagcctc cccccaacct gccgctgcag tgggctcctg cgtggcccaa 116460
gcctcctgac gagcaccgcc ccctgctcca cggcacccag tcccatagac cgcccaaggg 116520
ctgaggagtg tgggtgcagg gcgcagggct ggcaggcagc tccacctgca gccccagtgc 116580
gggatccact gggtgaagcc agctgggctt ctgagtctgg tggggacttg gaggatcttt 116640
atgtctagct aagggattgt aaatacacca atcagcactc tgtatctagc tcaaggtttg 116700
taaacacacc aatcagcacc ctgtgtctag ctcagggttt gtgaatgcac caatcagcac 116760
tctgtatcta gttaatctgg tggagacttg gagaaccttt atgtctagct aagggattgt 116820
aaatatacca atgtgcactc tgtatctagc tcaaggtttg taaatacacc aatcagcact 116880
ctctgtctag ctcagggttt gtaaatacac caatggacac tttgtatcta gctaatctag 116940
tgaggaggtg gagaactttt gtgtctagct cagggattgt aaacgcacca atcagcaccc 117000
tgtcaaaacg gaccaatcag ctctctgtaa aaccaatctg ctgtctgtaa aatggaccaa 117060
tcagcaggat gtgggtgggg ccagataaga gaataaaagc aggctgcctg agccagaagt 117120
ggcaacctgc tggggtctgt agaagctttg ttcttttgtt ctttgcaata aattttgcta 117180
ctgctcactt tttgggtccg cattgcgttt atgagctgtg acactcactg ggaaggtctg 117240
cagcttcact cctgaagcca gcgagatcac gaacccacca gaagaaagaa actcctaaca 117300
catccgaaca tcagaaggaa caaactcagg acacgcggcc tttaagaact ataacactca 117360
ctgcaagggt ccttggcttc attctcgaag tcagtgagac caagaaccca ccaattccgg 117420
acacaatttg actgcagaaa atggatgtcc aaccctgtgg tttccctggg ccacattgga 117480
agaagaaagg agttgtcttg ggccacacat aaaatacact tactatagca gatgagctaa 117540
agaaaagaaa aaagtccatg cgtaatcttt gtgatatgtg ccaccaccaa taagcaaaat 117600
tgttctctta ttcaaaaggt tggacacagc tgctctagat attttattat taaatatgca 117660
ggcaattact gtttaaatga agatttcctc acagaatgag attaaaagta tatattagtg 117720
gcttagcatt cattttagac aaccatttta gagattcaaa tcacacactt gcttacagaa 117780
attttgttgt cttcaatgtc cccattgtgg tttctttacc aagcctctac tgttcttcac 117840
atcaccaagt taaaaaaaaa aaagggggcgg gggggcagaa tgaaaattgc atggtaggcc 117900
acaagttcag atcctcatcg acacaagagg tgcctgaagc agtggatgag gcttttctat 117960
ggatcatgag cagccacata aatgcttaaa agggcctggc agggagcatc agtgggtgat 118020
gtggctggga ggctgaatgg agagcatttg ttcttcagtt atctatagaa ggcagctgtc 118080
actcagcacc agctaagggc ttcccatgag ggaactgggg atcaggtttc ccagatcttt 118140
ttatgtaaca ggataagaca gagatccagc tttttttggg taattatttc ctattttaaa 118200
atacgggtag ttgattaaat aaaaacaaac gaatgaacac catatgggca caacaaaaca 118260
catctgtggc ttggattcag cttgtgaatg attactgcag atatttattc tagaggacac 118320
ccctgggtat gtcctaatat aaaacctaaa tctaaactca agtcccatgc taccttcaga 118380
gaataaatga cccagaaaaa gaaccacctc tcctaaggaa gtataaattt gtaaataact 118440
gagacccaaa cttacaactg tacatttttc ttattgttgg gctgttgcta acctcaatta 118500
agaaggcttg atgatatttg taaagtgtca tcactccacc atggtccagt aacatctgat 118560
cactccacca tggtccagta acatctgaat ggtcaagaaa tatctaaacg tatgtaccaa 118620
aaatttgtgt atactactgt accaataaac catttgtttc catttgatct ctgagtgtgg 118680
taatacatgt tatttgccct gctgttgtaa ataaacaaac caaatggagg cttgatgcaa 118740
gatgcagtgt agcatagtgc caactctgga ctccgactac tcagggtgta aattctaact 118800
ctgttctatt aacaccatga aactgagcaa gttagttaaa actcgctggg cccattttct 118860
catttataca atggagattt taatagtaca gctacatagg ccattttgtg gtttaaaata 118920
catcatgatt atgaaacact taatgtaggg cttgctacat aatgagcaag gtttgttgct 118980
gttatcatta atatccttaa ttctcattat tataaaactt gagatagtat gaggtgaaca 119040
agttcataac agcaatataa tgaaaatttt aataattcct tttatacttt aacaaaaata 119100
cgagattggg taatttatta tttttacatg agtaataaat attgcattaa aatatattta 119160
aaatttacca cattaatgtc tgccagtcat gccaaatgac caacatgaat gtgaataaaa 119220
ctcagtctgt gcccatttaa tcttaaccaa ccctttataa ttgttaatga tttgaacctc 119280
tgccttgaaa gatcacatta cttgattgtc ttcaacttat ctgaatgtgg tagtgatttc 119340
tgtaaattta taggaccttt gtctcatgca gctccatgga gttgaactta tgcaccttta 119400
aaatggtata tacttaatta attaagtgtt gatctgcttc acatgtgtat aatattatta 119460
gctcactaaa ccaagaaaac agtggtcctt tagggaaaga aactaaatta caacagagaa 119520
tataaatacc atataaatat ctattattta ttgaactgtc acaattattg caaaaaatta 119580
ccttttagtg gacaaaacaa ttgatattgc ccttttctgg aaaagaaata atgtaatata 119640
tgatgaatag ttttggccag tatcctctag accttgccag ttaactggct ctcaaaattt 119700
tgaataataa aaacttggtg atagtagaaa aatagtaatt ttttaaaagt atgtgcacaa 119760
ttatacaact aaacaattca ttcaccagtg ttcacaattc tattgccttc tttgaatcaa 119820
aatttacata gtttttcttt tagactaagc tcctttatga taccagtgtg cccatttctc 119880
attaccattg aaatgtctca tgagcatgtc acattctggt acaactgcta atccaggatg 119940
acagtttagt tcttttaaat ccaattgaga gccttctact catgaccaga gaacctaaag 120000
aaaggttaag atacatttat tccttggtgt aagtgatttg tctattttta gttttcctaa 120060
gggtcatatt tcaatttaga tttttttta taggttaggt aaaataggct tccctttgc 120120 aatatgaaat atgtagtctt ttaaaaaatt tcttcaaagc tattaaactg aaaaaaaatt 120180
aatttggtct attcagtttg ttagcactta ccattttgga aagagagtga ctctactttt 120240
gtatttggta acattttccc tactacaggg cagtatcttt tgtaagttct tagatattag 120300
caccaaataa ataggcaaaa aaaatctatt atgttaattc ttagaacccc tgcttggcag 120360
tgcatcattg actagatgga gaagaaatga aaataataca ttaggaagca gtttcctggt 120420
tcttttgaaa acaactagag agtcttgttg ttgactggaa tatctgaaga tcctgtttaa 120480
tgctttcatt ctatgattgt taagaatatg tcatagaact gctgtatcct gtttctttat 120540
gtcttccctt ctgtttgttg attagaaatc cctgagtggc tttacattat tagtacagta 120600
gatatgtagt atattcccat aataccactg ctgctattga ctaatagtaa taattttagg 120660
gcagctttat gacagttggt ttatgtttta gggtgtcatt tgacttgtga agcattgaaa 120720
tctgggtatt aagcacactg ttttctatgt ggtatggaat gattcttaaa gccctgagaa 120780
aatggaaaat aaaaatattt ttccttttta ccataatcac ctatgactgt cactctatca 120840
taaactgcat aaactttata acctcaaaac attttggaaa tgaaatgaca gaacttgctt 120900
actcaattgc ttctatatac accaaatatt tttttaaagt attatgttaa gtccttgaaa 120960
atattttgtt ctactcaata gaagcagttt aggttggtag ttctatgtgg aaaccgtgag 121020
gaaataattt tatattatga tgactagacc agtctttgaa catcactttg gttattgttc 121080
cattagtaaa tattataatt atttctgaga tttactcacc ttcaaagaat gttggcaatg 121140
ccagcattat taacactcct ctagttagaa caaagaggaa atgtaataac aaaacataat 121200
aatagccaaa taaagagtga cttagaatgt acacccttat ctaggatcct gagtaattcg 121260
attattctta ggaaatacac ttttgtgcta gaacaaagac ttttgaaata gctaatttct 121320
gggtttcttt tcattttgaa ttaacttgaa tttcaaggaa acaagggtag tttttacaga 121380
tacagtgcat agaagctctg tgtacaatga agaaaagtag gaaagtgaga aaaatgccat 121440
tagattttc atcgttatac tatctgatat gtgaatttaa ctaaaactta tatacctcat 121500
tatagtactt cctaatgtaa tttcttaatt taagtgttcc ccataaggtt tttttttata 121560
taaacttaag tactgttaaa tatttaaggc aaattcaggt ataaaataag acttgttgat 121620
atcttattcc aagcatattt gtttctctcc tatttatttt tattctgtgt tcatttccaa 121680
aattgtttta ctcacaactg tttgtttttt ctgtttcatt ctgtggtaaa ggtatcattt 121740
ggctaattgt ataatttcag tgtcatttct aatattccaa ttgtgatagt atcaacacaa 121800
gattaaattt ctctacatgg tttatgagaa tggaatgcca aattgaaata gaacagagca 121860
cagatgatct aaatataaaa agaactacaa aaatcacagt tgtttaaaaa ggtttttttgt 121920
ttgtttatat atggtgcaga acatttgttc cttagccaaa tgtttccacc ttgagaaagc 121980
tatagagatt ctatgtagtc ctagtaccaa taatatgttt taacctgaat gtaccttatc 122040
tttattcata aactgtgact ttttacactg ctgaaacttt ttttttaag acaatctcac 122100
tctgtcgtcc agtctggagt gcagcagtgg tgtgatcttg gctcactgca acctctacct 122160
tctgtgttca agcaattctg gtgcctcggc cacctgagta gttgggatca caggtgtaca 122220
ccaccaggcc tggctaatag tttttgatat ttctagtaga gatgagtttt gccacattgg 122280
ccaggctggc ctgaaactcc tggcctcaag tgatctgcct gccttggcct cccaaagtgt 122340
tggtattaca agtgtgagcc actgtgcctg gcctgaaact cataattcat ttccattaat 122400
attaatctca ccttttccaa taattaattg atttcacaag tattagtccc ctataatcat 122460
tgaatggcta ataaaattat ttatagcaaa cagattaatt atctgccagc agtctgagat 122520
tagtttcttt aaaaaatgtt tattatttaa aacattcagc tgtgatcttg gctttcttgt 122580
gaggttcaat agtttctatt gagtaaagga gagaaatggc agagaattta cttcagtgaa 122640
atttgaattc cattaactta atgtggtctc atcacaaata atagtactta gaacacctag 122700
tacagctgct ggacccagga acacaaagca aaggaagatg aaattgtgtg taccttgata 122760
ttggtacaca catcaaatgg tgtgatgtga atttagatgt gggcatggga ggaataggtg 122820
aagatgttag aaaaaaaatc aactgtgtct tgttccattc caggtggctg cttctttggt 122880
tgtgctgtgg ctccttggaa agtgagtatt ccatgtccta ttgtgtagat tgtgttttat 122940
ttctgttgat taaatattgt aatccactat gtttgtatgt attgtaatcc actttgtttc 123000
atttctccca agcattatgg tagtggaaag ataaggtttt ttgtttaaat gatgaccatt 123060
agttgggtga ggtgacacat tcctgtagtc ctagctcctc cacaggctga cgcaggagga 123120
tcacttgagc ccaggagttc agggctgtag tgttgtatca ttgtgagtag ccaccgcact 123180
ccagcctgga caatatagtg agatcctata tctaaaataa aataaaataa aatgaataaa 123240
ttgtgagcat gtgcagctcc tgcagtttct aaagaatata gttctgttca gtttctgtga 123300
aacacaataa aaatatttga aataacatta catatttagg gttttcttca aatttttttaa 123360
tttaataaag aacaactcaa tctctatcaa tagtgagaaa acatatctat tttcttgcaa 123420
taatagtatg attttgaggt taagggtgca tgctcttcta atgcaaaata ttgtatttat 123480
ttagactcaa gtttagttcc atttacatgt attggaaatt cagtaagtaa ctttggctgc 123540
caaataacga tttcctattt gctttacagc actcctcttc aagacaaagg gaatagtact 123600
catagtagaa ataacagcta tgcagtgatt atcaccagca ccagttcgta ttatgtgttt 123660
tacatttacg tgggagtagc cgacactttg cttgctatgg gattcttcag aggtctacca 123720
ctggtgcata ctctaatcac agtgtcgaaa attttacacc acaaaatgtt acattctgtt 123780
cttcaagcac ctatgtcaac cctcaacacg ttgaaagcag gtactttact aggtctaaga 123840
aatgaaactg ctgatccacc atcaataggg cctgtggttt tgttggtttt ctaatggcag 123900
tgctggcttt tgcacagagg catgtgccct ttgttgaacc tccatttgac tggcatgcac 123960
atgtctcaga tattataggt tatcatatat tgttgctcct aatatttctg tgttagataa 124020
ttagagtagc ttggtttgta agaatgtgat gttggtggga ctgtagcaga acaagaaggc 124080
ccttatgggt cagtcatacc tctcttttca aatatttggt ctagctctct tctgggcatc 124140
ttgttgccaa tatatagtat tgctcaaaag ggcaggagat ttgaagtgat caaggaaaat 124200
atattttttc tattgattaa gtcttttgat ggggtagaat aatctaattt catgtaactg 124260
ctcaaagtta tatggtaggg ggatcccaaa tgtattttaa aactattttt atatcatcat 124320
atttgaagta atagaaagtc agagtagcag aataaaggta ctaaaaattt taaaaactaa 124380
taaggtactt tgaaagaaat caattatgtt gattcctcat taaacaaatt tgcacttaaa 124440
gactgaggtt aataaggatt tccccaagtt ttttcatagc aacctgtgag cactttctct 124500
gttgaggcat ttatggtatg aaaagatgag taaggcacag ttcttgccct ggagaaggtc 124560
acaggtgaga ggaggagttg acacagaaac atttgatata aagcaaggaa taaattccaa 124620
gactaaaatt ttcagaaatc taaaaaactc aagataagaa aaacccatta tattttctgg 124680
gtaacaaaat ttcagtgtta ttaacatgta ggaagatctt gatatttatt ctgaagccca 124740
tgtgtgttgc tgaaatattg ccgcatttgc atatactcat caccatcctc tgttttggag 124800
ctaagaattt tagactcaag atgtctaatt aagttgatcc attgatttta ttttttatgg 124860
aaatctgaga cccacagaag gcaggggatt tgcccacatt tctagaagag tcagacatga 124920
gcgatgaggc acagtggaaa gaacatgagc attgcctgag ctctgagttg gcgctataag 124980
agcagtgatc atgggcaagt gactcttctg agccttggcc tcctcacctg ttaagtgaag 125040
aaaagaatat ttcagaagat ctttgtgaga atgaaacaag gcaatttact tgcctgctac 125100
atagccaatg ggaaatcaat ataagttccc cgtggttccc ttctgtgggg ttttgttccc 125160
acagagggtg cactggccat tccacttctt cttttccaag ctcctcattc cctttaacgc 125220
tgttcatagt tggttccaaa ccatttgaaa tataataagc accaggatgg ttttttcttt 125280
ccaccaaagc aaatttcatt ttctaaacac tgtttataaa tatcaatggc tattttttca 125340
atttttgatt atcatgaaaa tatacaaata tgtttaatta aatatgctaa agaatgtatt 125400

-continued aataaatatg tattaaataa ttcctacata taaggccttt ttgcttgggg tatgggtgat 125460
acaaaataaa tgtggcatga acccactgac ctctagcaat ttataaccta gaaaaagagt 125520
tatgatatgt ttataagttc ctgtgatata agacatgcat atagtcatta taacagaggt 125580
gcaaacaaga tgtatcaagt atgtccagag gaggaagaga ttaatcccag ctggaggaaa 125640
cactgatgct ttcttgcagc aggggcattt gagttgagaa agggaggaaa catagatttt 125700
gacaatgaga gctgagggga aaggggtttc aggtggaggg aaccgcatgt ggaaagcagg 125760
gaggtaggaa agtgtagagt gtgtttaaag aatagaccag tttggctgaa acaggatatt 125820
tgagcagagg aagcttgtac taggtaggtg ggttgaggcc aaattatgca aggcattaaa 125880
tattaaacta ggaattttgg actttatcct gcagtttatg gggggtaaat gataagattc 125940
aatatcactt tatttgtaca gtattatgtt acattttatc taattgtttg tttaattcct 126000
gtctagacaa tgaattcctc aagggcaagg agcatggctt attcacctca gtaatttcag 126060
tgcctagcat tgtgcctggt acaaagtgga cacttgtata taaccttttt taattgaagc 126120
aacaagttgt caaccttaca aatgtgaatc cgtgattcag atgacaggtt gaaatgtaga 126180
ttgtctgcga agagggcaga aagagagtat gacaaaggag gacaagacag tggggcaggc 126240
agggagagag agcagccagg gtttcggtag aggtatgtca aaaaggtatg gaagtcagag 126300
gagaaggaga cccctatgtt atagaataca aatggaaggg aaatgatgac aacagtaagt 126360
tgtcattaaa tgcaaggttg caaaagtaag attgtaaagc aggatgagta cccacctatt 126420
cctgacataa tttatagtaa aagctatttc agagaaattg gtcgttactt gaatcttaca 126480
agaatctgaa acttttaaaa aggtttaaaa gtaaaagaca ataacttgaa cacataatta 126540
tttagaatgt ttggaaagaa acaaaaattt ctaagtctat ctgattctat ttgctaattc 126600
ttatttgggt tctgaatgcg tctactgtga tccaaactta gtattgaata tattgatata 126660
tctttaaaaa attagtgttt tttgaggaat ttgtcatctt gtatattata ggtgggattc 126720
ttaatagatt ctccaaagat atagcaattt tggatgacct tctgcctctt accatatttg 126780
acttcatcca ggtatgtaaa aataagtacc gttaagtatg tctgtattat taaaaaaaca 126840
ataacaaaag caaatgtgat tttgttttca tttttttattt gattgagggt tgaagtcctg 126900
tctattgcat taattttgta attatccaaa gccttcaaaa tagacataag tttagtaaat 126960
tcaataataa gtcagaactg cttacctggc ccaaacctga ggcaatccca catttagatg 127020
taatagctgt ctacttggga gtgatttgag aggcacaaag gaccatcttt cccaaaatca 127080
ctggccacaa agtgtgacat tttggcattg gcatcactat ttgatggaag ccaacctccc 127140
cccaaaaggc ctgtattaga atgaagatgg attccctggg tgggttacac ttgaaactag 127200
cctcacccat gaacactttg gcacagatta gctagcccat tcccccacag taaggaccat 127260
aaggaaggga cagaagcaaa gataagtttt agaacaaaag agaggggaaa gaaaaaatct 127320
agggttttat gagggctgtc cctgagtgat agatgtgaat aggcctccag ggcaggctgg 127380
ctcagaggct gactctttgg gttggggtga ctgattggtg gtgaggatgg agaagaaaag 127440
gggagtggag gaggtgaaag tgaccttggg acattaggtc tccataagtg acaggattta 127500
aggagtgttg taagctgtgg ttgttggacc aggtttaagc acagcttcct gagcttcctg 127560
actggtttag gtcaagctcc agagagcaaa tgccacagtc tcagtgatct ccttggagaa 127620
acagttggaa taggatgttg cccatgttgg gatgagtcat tgtccgctct tgctctttcc 127680
ctacccctgc aaaataataa tactgtattt gattgaacat ataaaacaaa agaaggatta 127740
tcacataagt atgtatatat aaccaacatt ggcaggtgca gaaaaaccag actgtcagtt 127800
tgcctcatct gaaatgattg acacaaacaa atatatttac tgtcccaagt gaactttggc 127860
attttggata tccttcagtt gttctgttta aagatataac ttagaagcag ctgatggaat 127920
atttaaatcc atgcgttgaa ttcatgcatt caaagaaaca tgtcctgagt cactaaatgc 127980
tgacatttgt ttttcatgtt aagagtgtaa ataactggtc ccaaatataa tattattaca 128040
tcagataaaa actggaatgt gaacctctta acttgattgt gaaagtattt gccaatggtg 128100
cctcttgata attatttgag gctcacttca gaactcctct ggaagggtta atttttaaat 128160
agtcatttta taaattaaca tttttgacat atgtgatggc tctcaaattt tttcttttat 128220
gccagtttga atcatttctg ctcaattttt ttttttaatt gggatggagt ctcactctgt 128280
tgcccaggct ggagtgcagt gatgcaatct tggctgactg caacctccac ctcctcggtt 128340
caagcgattc tctcgcatca gcctccagag tagctgggat tacaggcgcg caccaccatg 128400
cctggataat ttttgtatta ttactagaga tggggtttca ccacgttggc caggctggtc 128460
ttgaactcct gaactcctga cctcaagtga tccacctgcc tcagcctctt aaagagctgg 128520
aattataggt gtgagccact gcaccaggcc ctgttcaact tttaatgcta agattcattt 128580
gttgttgttt cacaagtgat taggcagagg tcttttatat taatttaccc attttatttg 128640
taagagagtc tcatattaag gaagcataat atatgacaat ccaaatacag tacaaatttg 128700
gttaattttg attttgttaa ataattaatc acaggggtcc ttcaaattgt gagctcctct 128760
ggttatactt atgttttacc tctggttata cttaatttca aacaaatgaa atttcattct 128820
attcatgata tttcagaagc agatctgttg cacaaaataa agcataccta taaattttct 128880
ttttttaaaa aaaagtctct gttcactcta ttttctatta tttttctctt tttaaaattt 128940
gaattttatt gtggcaagtc cacttaacat gagatttacc ctcttaacag atttttatgt 129000
gtaaaataca atattgttca ccatgggtaa atgttgcaca gcagatctct ggaacttatt 129060
cattttgcac tactgaaatt ttatacctgt tgattagtat ctccccattt ccctctctcc 129120
cctgtcctgt tacccatggt tctgttcttt gcttctttga gtttgagtat tttgatacct 129180
catgtaatct tcattctatt ttctaacttt gacaatgttc tgacaaattt gctttccgga 129240
ttggagcact gtatagtgaa aattgaaaat cttggttatt ttctacagat tcccactatt 129300
ttaccttgag cagacactta tcttgaaggg tctcagattt gtcacttgta gaatggggaa 129360
tataaacctg ataatggtcc ctttcagttc taaagttata tcagttgaaa atacatgtgt 129420
cacttatggt aacgggtaga gaactggctc actgaacagc atatggatat tataaagtgg 129480 tttttttaa tcctttctgc agacagttac tttatacttt attcaaatgg attattgtga 129540
agtacatgtt agcggacttt gtacctttta aaaatgtatg tatttggtgt aatgtagaaa 129600
tatagaaatt tattaagtat gatttatttc aatgttaagc atgagaaaat atgctccgaa 129660
aggttagata gcttgcctaa atgacaagct tgtatttcaa gcagaacttt ctgaatcaaa 129720
agactccaag acgaatgccc agctttcaaa aactgtctaa ccaaaataaa tcctaagatt 129780
caccttcata ctaaaattat ttaaaaatag tttattttaa attaatattc acttaaaatg 129840
tatttatcat gcaatacttt aaagtgtctg ggaaatgaaa atatccaaag atcaaagaac 129900
accatgtttt caaacttcaa aaatgttatc agtgacctaa acaattttta aaattttcat 129960
agagcctatg aaaaatgtac ttgcaaatgg ctactttctg actaggaata gaatggggag 130020
agtatttagt ccaacaatga tagactggat taagaaaatg tggcacatat acaccatgga 130080
acactatgca gccataaaaa atgatgagtt catgtccttt gtagggacat ggatgaaatt 130140
ggaaaacatc attctcagta aactatcgca agaacaaaaa accaaacacc gcatattctc 130200
actcataggt gggaattgaa caatgagatc acatggacac aggaagggga atatcacact 130260
ctggggactg ttgtggggtg gggggagggg ggagggatag cactgggaga tatacctaat 130320
gctagatgac gagttagtgg gtgcagtgca ccagcatggc acatgtatac atatgtaact 130380
aacctgcaca atgtgcacat gtaccctaaa acttaaagta taataaaaaa aataaaaaaa 130440
agtttgaggt gtttaaagta tgcaaaaaaa aaaaaagaaa taaatcactg acacactttg 130500
tccactttgc aatgtgaaaa tgtttactca ccaacatgtt ttctttgatc ttacagttgt 130560
tattaattgt gattggagct atagcagttg tcgcagtttt acaaccctac atctttgttg 130620
caacagtgcc agtgatagtg gcttttatta tgttgagagc atatttcctc caaacctcac 130680
agcaactcaa acaactggaa tctgaaggta tgacagtgaa tgtgcgatac tcatcttgta 130740
aaaaagctat aagagctatt tgagattctt tattgttaat ctacttaaaa aaaattctgc 130800
ttttaaactt ttacatcata taacaataat ttttttctac atgcatgtgt atataaaagg 130860
aaactatatt acaaagtaca catggatttt ttttcttaat taatgaccat gtgacttcat 130920
tttggtttta aaataggtat atagaatctt accacagttg gtgtacagga cattcattta 130980
taataaactt atatcagtca aattaaacaa ggatagtgct gctattacta aaggtttctc 131040
tgggttccca aatgatactt gaccaaattt gtccctttgg cttgttgtct tcagacaccc 131100
tttcttcatg tgttggagct gccatttcgt gtgcccccaa actctacttg agctgttagg 131160
gaatcacatt ttgcagtgac agccttagtg tgggtgcatt ttcaggcaat actttttcag 131220
tatatttctg ctttgtagat tattagctaa atcaagtcac ataaacttcc ttaatttaga 131280
tacttgaaaa aattgtctta aaagaaaatt tttttagtaa gaattaattt agaattagcc 131340
agaaaactcc cagtggtagc caagaaagag gaataaatat tggtggtaat tttttaagtt 131400
cccatctctg gtagccaagt aaaaaaagag ggtaactcat taataaaata acaaatcata 131460
tctattcaaa gaatggcacc agtgtgaaaa aaagcttttt aaccaatgac atttgtgata 131520
tgattattct aatttagtct ttttcaggta caagatatta tgaaattaca ttttgtgttt 131580
atgttatttg caatgtttc tatggaaata tttcacaggc aggagtccaa ttttcactca 131640
tcttgttaca agcttaaaag gactatggac acttcgtgcc ttcggacggc agccttactt 131700
tgaaactctg ttccacaaag ctctgaattt acatactgcc aactggttct tgtacctgtc 131760
aacactgcgc tggttccaaa tgagaataga aatgattttt gtcatcttct tcattgctgt 131820
taccttcatt tccattttaa caacaggtac tatgaactca ttaactttag ctaagcattt 131880
aagtaaaaaa ttttcaatga ataaaatgct gcattctata ggttatcaat ttttgatatc 131940
tttagagttt agtaattaac aaatttgttg gtttattatt gaacaagtga tttctttgaa 132000
tttccattgt tttattgtta aacaaataat ttccttgaaa tcggatatat atatatatat 132060
gtatatatat atatatatat atatatatat acatatatat atatagtatt atccctgttt 132120
tcacagtttt aaaaaccgat gcacacagat tgtcagatag caattctgtg attgaagggg 132180
aaatatgtca cctcttcata ctcatattgg tgaagggtcc tagcttcaaa attaatagat 132240
tcctaaagag gggaaatgaa acatccgcat ttacacacac acacacacac acacacacag 132300
agttcctctt gtcggtaagt tttgtttttt ttaaatctct actagataaa atttgttatc 132360
taattgtgag ttttacacaa agaaaaactg tcacagaaaa gaaagacagt gtcacatttt 132420
tcaaaagaaa aagaagaaaa gaaagtgcca tgtttttcaa atacaaatgt tctggattga 132480
ttttaggatc tttagtgaaa aacaaagtat ttcataataa gtaaaataaa aatctatgta 132540
ggtaaatttg tttctctaat ttaagaattt gaatttctga gtatttatga taagtgttga 132600
aataacttct tatatgtgac agtgaatact ggcagagcaa atgccaaatc aatgccaaat 132660
ctgtaggatc atttgattgt aggaacagaa ttctactcaa accgaaagca ggcatttgct 132720
ggagttacag aaaggcctca tggaacaccg agaaggtggt gccattcgac tcttaaagaa 132780
gctgcaacag gcacaagaga gtcagctgca gctcttcttc ttgagtctat atctgtcctg 132840
ggtccattcc tttttgtggt tgcttcattc ctttctctct ctgaagactg gtttttctgg 132900
tctaccaggg ctatgccaca ttgactttat gtagtgtctc cattctggcc tcctgaattt 132960
acaggagagt tcctctgtac aaactcaaag tcctggagag aacagaaaac agcttccttt 133020
tggctcaggg gtccaactgc agtctactct gctgctatga ggatagtggg ttcaccacct 133080
ttgttgttct ctcagctagg gcagtgggaa atgactctat gaaaggaata tacatgggca 133140
ggcaaatgta ctaatcctca tcagtactgt aattttaagc aactttaaaa aattctttta 133200
agttatttga aaataagatc aaagaaggct gaattacata aatgaagatt tgttaacaat 133260
taattcaaac caatataaca catgctataa catggttgag tgtgattgag tcttgattta 133320
ttaggggcaa taatcaaaac atttaacaat cattatagta cagaacttac caatcaaatc 133380
agatgctcag ccggagtgga tgttggccac ccagctatta ttatccctgg ctcaattggt 133440
cttcagctgt gttaacttgc aaacattaat taactatcta agcccctcat tttcctcaag 133500
tgtaaataga cacaataata ttacctattc cataggtgtg gggtgaatag taaatgtaat 133560
aatttgtcca aaacacttag tatagtgcct ggtccatggt aaatactaaa taaatgttat 133620
ctgacttatt attaaaattt tatcttctca gcttaacctt cagaacagta atatattggg 133680
gtctagataa atcttgccta tatgaaaata atttaatact acatgcagat atatgctgtg 133740
tatattatgc cttctgttag aggaattgca gaaacaaaaa tttcaattaa taataagatg 133800
aattatttct cccaattgta gaatcttttg acaattttat catgcattac agatgtaaga 133860
actcttgatt gggacttgat agtctaactt tataataatt taagaacatt cctcttagag 133920
aatttctatg gccataatac tgaacacatg aattttaatt agctgtcctc tttagcccta 133980
aaaaaaaaat tactgtaatt taacacttaa gtgttgttct tcccaggtac agtaatcttt 134040
ttttttttt ttttttttt ttgcatagag ggtaatcttt tctctttcca aatggcagaa 134100
ctgttagttt tctgactgtc cggtgaaatt ctaagtccac ttacttccca atagcatgca 134160
attagcaaag gtcctccttg caaaggcaca gaacacacct aaacatcttg cagatgctgt 134220
ttggacactc ttcccctgct tttggtctct ttgtaaagca gctcatctgg atacaggatc 134280
tcttttcccc attgcccatt ctaatatatg ttaccgttat tacttataga ataatagtag 134340
aagagacaaa tatggtacct acccattacc aacaacacct ccaataccag taacattttt 134400
taaaaagggc aacactttcc taatattcaa tcgctctttg atttaaaatc ctggttgaat 134460
acttactata tgcagagcat tattctatta gtagatgctg tgatgaactg agatttaaaa 134520
attgttaaaa ttagcataaa attgaaatgt aaatttaatg tgatatgtgc cctaggagaa 134580
gtgtgaataa agtcgttcac agaagagaga aataacatga ggttcattta cgtcttttgt 134640
gcatctatag gagaaggaga aggaagagtt ggtattatcc tgactttagc catgaatatc 134700
atgagtacat tgcagtgggc tgtaaactcc agcatagatg tggatagctt ggtaagtctt 134760
atcatctttt taacttttat gaaaaaaatt cagacaagta acaaagtatg agtaatagca 134820
tgaggaagaa ctatataccg tatattgagc ttaagaaata aaacattaca gataaattga 134880
gggtcactgt gtatctgtca ttaaatcctt atctcttctt tccttctcat agatagccac 134940
tatgaagatc taatactgca gtgagcattc tttcacctgt ttccttattc aggattttct 135000
aggagaaata cctaggggtt gtattgctgg gtcataggat tcacccatgc ttaactgagt 135060
ggtgccaaat tgtcctcaag tctgttgtac tgatatatat ccccatcaag agagtacaag 135120
aattctcata gctatgtatc ttcaacaaca cttggtgtct ggtagatgtg aagtgattac 135180
taaaaatata gggaagctgc atacataatt attggctttt gctgttctct tacattaatt 135240
tcttattcat gttgattact catttgtcac ctagtttttt cttccttaat taaattgtag 135300
gaatttatga attatggatt gatcatcagc tctatacatt tcaaacataa tccctcagtc 135360
agtggcttgg cttatagagt cttttgatga aaagaagctt ttaagtttaa taaagttcaa 135420
tttattgtct tttcctttat gttttgtgct tttggtatct tgattaagaa ctccttcctt 135480
atattgggtt ctcaaattta gcagcataac attttcatac tattatttaa atttttttca 135540
cattatttag tgatagcacc tttcttattc ctaaagtgtt tatcattgcc ttctgtcttt 135600
ctgcttgata aatattgcca cacatttgta tactttatta gtgtgtacaa agaccacatt 135660
ttagttgtgt tatttctctt gttttggttt tctagaatgc agagccatta atattatagt 135720
aatgcttatg tgctaatacc atatcagggg cacaaatccc attgcagcgg gactgagaaa 135780
ttaaaggaaa tgatgcacat ttactcattt ttgtttaaaa aatcaaatgc atatttttca 135840
atcagactat atggttggtc tggatagctt catcattgaa tttttaaagt atttttgtac 135900
tactgtattt aaaattattc attcaccact gcttttgtag atggtttaga aacccaagtt 135960
aggaatgact gtgcaacact attattatac tctttttaaa attatacttt ttgcttaagt 136020
ttctttcctt gttctctgag acagtgttca tgttcccaaa ccacacacat ttattcagct 136080
ataaaatttg tatgatcaac tcctgtcaga acaaacatca ttataaaaaa tatctccagg 136140
aaaaagaaaa cccttttaat gctctcttct ggttcatgtg tcttcttatt ttctttaagc 136200
attttcataa cccattgagc tgtaatttaa ttggaacatg atttatacta aagttggttt 136260
ctttaccttt aacttttttt tttagtttga tcagctctct ttagcttctg tagttcggtc 136320
tttaattcca ttccagtatg cttttggagt tgggtctcat aaatgtatag aaatgtttct 136380
gttgggaaac agcaggagaa tattaaataa atattgtgct tacatctatt taattctttg 136440
cccaactttc tacaactttg actttacatt taagctcctc atgcacttac atgtttcttt 136500
acctaaaaat atcttttcac catgggtgtg tacaattcct ttgtccttgc tgtattaatt 136560
ttcttggttt acatagtagc ctctacacat tgatgtcaaa acctctgttt ggtgcatttc 136620
tactctgcgt gttcaatctc catgaaagtt tctgtaaggt attttcattc ctctagtttt 136680
tcacatgtgc atcctggctt tgtgacctgt gctttgatat cgtgcctttc atcttgtggc 136740
attgaaggat ctttgcaagg acctattgtg ttataataca gtctatgaaa aatatcaata 136800
tttgcatttg atcacattta aaaaaatcac attcttttgt ttgaatatca aagctaatat 136860
gtgagtgatt tccctgccaa atagcacaag tagcctttcc tgggtgttta tgggcattta 136920
tctggttaat gattcccatc atagtgctgt cacccatgcc attgctaaac ttatacagta 136980
actttttgt tttcacctca gcatatgttg agagtaggaa atagatagga ctatgccctc 137040
aaattttacg tttatatgat gttaatccta aaggtccttg tgacttctga agtaaaaact 137100
cagtgttgtc attttactta ctgaattgtt agctgagttt agagttgagt ttacaatgga 137160
gtaaacaagg tgtttagttt gatgtatgct tttagtcttt cagaaaaaaa tgtttatact 137220
tggaaagaat agtttattta cccatctggc ctagtttaga caaaaacaca gagtcaaatg 137280
tcaacagaat tctgaagtta taaaaatgac agtgtggctt ttttttttt taaccttcca 137340
cctggtgctt atgcccaagt gcctagcttt ctttagctct caactaataa aggtaatgtt 137400
tagataacat ttaacgttaa gttgcattgt gtttatgatc acatatctca aatattggta 137460
cacgaaactg tacaacaacc ttttttatta gattttccta cgaaattcct tattatattc 137520
cctaagatag ctttttccca ccttcttctt ccttctccct tctcaggtgc tccaataatt 137580
ccaacccctg cagccagtga ctttattata tcttttttta aaaatctaaa aaaaaaaatt 137640
gatgcaacca ggaagaattt tctcatttct ctccaccagt tgtaccagcc tactgcacct 137700
ctcctcatgc accaccttct gcctgtgttc ttgctcctat attcaggagc aagtaatatg 137760
caatacctcc ctctttgtgg gatctttctc attagcataa aaatactttc ccttgatctc 137820
cagctactac cccatttctt tgacctacat atagcaaaat atttgagaaa ggaccacttt 137880
ccatcttttc ctcaatctac ttccattttt ttctcaatcc actttcattt cattgttctc 137940
ctcaacccat tctttccaca acctacttca ttttatttcc atcagcccca taactcagga 138000
tcaacatctt gccagagcca atttccttgt ctcccttaac agctccagca gtatttatgc 138060
catggacaaa ttattcttct tgtgatactt tctctcttgc ttccatgaca ctactcccac 138120
ttcattttct ttctacctct ctggctcttc cttggtccct tttcctggcc ccttctctct 138180
ttcagatctc taaacatcag ctatatctca gccctgttct actgacactc tctagctgtt 138240
attttctaaa cccatgtttc agaaaccata tcttgatgaa tcttggaagg ccgaggcagg 138300
cgaattactt gaggtcggga gtttgagacc agcctggcca acgtggtgaa accccatctc 138360
tcctaaaaat acaaaaatta cctggccgtg gtggcatgca cccagctact tgagaggctg 138420
aggcacaaga atcgcttgaa cctgggaggt ggaggtttca gtgagccgag atcctgccac 138480
tgcactccag cctgagcaat agaggagact ccgtctcaca cacacacaca cacacacaca 138540
cacaaagaaa ataaaccatc tcttgatgaa tcataaattt gtgtctctag tttagacctc 138600
tatcctgctc tctaaatgat gtatccaact atcatcttga caccatcata tgttcataaa 138660
acataattat agaatatctt tcagtaggct tgacatttta aggcatgagt ttccgttcag 138720
tatctcctta aaatataccc agggtctcag gagactattc aaacaggaca aagcttctat 138780
tctacttact aatgtgtctg gccctatttg gcaggttgga taaaaagtca tctgaacatt 138840
gtcactttat gaataatata gtttaatagt ttgtgaatca cccctgcaat ttaaaaaata 138900
gtaaaattat cagaatctaa tttaataatt cctattggaa caccccatgt taggggattt 138960
ccagttattt caattgatat ctcaatgttt taaagattgt ttatttctat tactaattca 139020
ctctttattt taacataaat tgtggctatc tatctctatt catttcaatt atatttctca 139080
taccattcta tagatggggt gaaaagaaaa gtgttaattt tttaaaactc catacctcaa 139140
atactatatg aatttatagt tgttattgct aaagcaatta tcttacatct tttcctccaa 139200
aacaaagtta tgtgctggtt tattttcttt gtactcataa gatgccttcc atttttagta 139260
acataagtct tgtctttctc ctattcttag ctacttaagc attatgtagc ttaaataagc 139320
actaaagatt cctatctgta tgaaaaaata aagattaaat aaataagatc tagaaagggt 139380
gacaaggtga tgcttcaaaa tgaaccatac caagccatct agcgattgat aaattactca 139440
cactcataat cacattgttg gaaagaagcc attgacaatt cagtttgttt cacaactgtc 139500
tatcacatag tgagcacaac taaaagacta ctttttgtct tttactgctt gttttgttga 139560
tcaagtgact gattgtacaa tgaccaacaa gaagtctgat gtgtagagaa aaggggaacc 139620
tggcttttct gccttactcc tgatgcctaa ttctgagcat gtgaatatta ttctgtttct 139680
ttaattctcc aagtgaagca gcagataaac catccttgtt tccattagct gtctaccctg 139740
ttcaactgtg tgtttctaat aacataagaa taagaaagcc accagggtga gcagggaagg 139800
caatgagtct gcaaggcttg tggatagatt tctgttagtg aggctctaga aagttcttcc 139860
aagattgatg caatctgaga agagttttct gtcaatacaa actccctggg tttctccttt 139920
gtccttttac tgcctgtgtt tgttttgggt tccagtaaag atcaagtgac tgattgtacc 139980
atgaccaaca agaagcctga tgtgtggaga aaaggggaac ctggcttttc tgcattactc 140040
ctaatgccta attttcttgt actgaaagta gtttttgctg taagaatctg aggggaggag 140100
tcatttcttc aatttttttt tttggtctcc ttttaatggt ttcttgatca tgtctatcct 140160
tatttttctg ttttcacaaa tttttgtggt atattttcct ctcatgacct ctgtctcaag 140220
acttctttcc atccatctct tctcatttca tcctgtagag tgtctgtggt aagagccctg 140280
cattctactc tggccttgcc atgtgtggcc ttgggcaagt cctagcctcc ttgagggtct 140340
tatttttctc atttgtaaaa tgaaacagtt tgatgagaag ttttctaagg ttccttcaag 140400
ctttgacaat ctctctcttc tggatctttt tcccatgaaa aatttcaact cttgattagc 140460
atgtaggcag ggattattcc acatccttat aggaatcaca tttctgctac tgtccctgaa 140520
tgctagagtc cattgattaa gttattcact gctgcaattg tcagagctga tcaaagaact 140580
ctgaaccagt gtgttactag aactaacaaa gaaaatgcca ttatgatgtt ctagagtctt 140640
gaattagtag aagaggttta ataagaaccc taagggattg ctagaatgtt aaaaacaaac 140700
aaacaaaaaa aaaggttgaa aagtttagaa aattcactgg tctttgtgcc catcatttta 140760
cttccagggt ttagataatc tcatttttgc aatgaaggaa tggattagat cacaagttct 140820
catcctagta gcacatgcag aatctttata aaaacacaga gtagccaggt gcggtggctc 140880
atgcctgtaa tcccagcact ttgagagcct ggggcaggtg gatcacttga gaataggagt 140940
tgaagaccaa gctggtcaac atggcaaaac cctgtatcta ctaaaaattc aaaaattagc 141000
caggcatgat ggcacatgcc tcccagctac tggggaggct gaggcaggag aatcgattga 141060
acccgggaga tggaggttgc agggagctga gatagctcca ctgcactcca gcctggtgac 141120
agggtgagac tccatcacaa acaaaacaaa acaaaagaaa gcaaaaacac agattactca 141180
gggtccacta agaccagtga agtcagttct cttggtaggg ggcagggtga ctgagcatga 141240
tgtttgtaat tttaaaagtg ctccaggtga ttctagcgtg tatcaagcaa gacttgtgaa 141300
ccactgaact acatgctaag actcatttta gctctgattt tctgtgagtc atagcagagg 141360
gctcagcaaa ctttttctat aaatgctaag atagtaaata ttttcagctt tgtgggctgt 141420
atcgtcttta tgacaactca actcagtctt tgtagagaaa agcagctgta cataatatgt 141480
aaactaatgg gagtagctag atgtgtcctg tgggccatag ttttgctgac tcctggtcta 141540
tgtcatagaa tttcctttg aattgatgga ccaccagcaa atgatttttg tcctgtatca 141600
atcaatgata catacataaa tctctacaag acatgtaaag gatgaggctt aatgacagag 141660
tactttgggg aagacataat attgcaaaat taagatgctt agagaaaaat catattaaaa 141720
tagtgaaaac tgtgagaagg tattttgatt tgttgttttg gattcctctt tttgcaaatt 141780
cttttgaaat attttcagtg gaagctacat agatccaatt gtattcacca agctagattg 141840
taattaagct ccagagtaag taatagattt gatgagtgat gtccaacctt ttacatggaa 141900
gagtaagttt gagtcttcct ttgcccattg acacacttag taccatgttt accaaagttc 141960
ttagttattg aaatgggcac cagcatattt tgaaacgttg gtgttaactt gggatatgcc 142020
ttttgtcatg ttgcaaatag attttgtttc tgttttgtga agatcaccat ctctgtcact 142080
tctgatagaa aaagtgacac tgacttctca agtgatttga cacaggttaa aatatgtaaa 142140
ccatttctgt agagagcaag ctgtaataat atactaaagg gctaggttta tagtataata 142200

-continued taaataactc atttatgctg ttaataattt atagcaacat ggcatttgac tgacttttta 142260
tgtgctctag tcatgtaagt aatagatgtg gaaacataga ccagagtttc aagaacatgt 142320
tttgggcaga gtctgttttc ttgctattat ctcttaagtt tatgttcatg gcctaaagat 142380
tatgctaatg gatctgcctt ggtcttgggt gtcaggtctg tgttagcgag tattgaaaag 142440
catagttttt gcctactggg aaggatttat gatttaaaag ccctaaatct cccctttat 142500
gtacttcata cttagaaaat ttttcctgta aactgtgtga ctttttaca ttgtgccagt 142560
tttctagatg actctcgtca tatttatttc ttgcaatcct tctataacta tcagttatga 142620
agtctcttta tagtgttgcc agccaggtct caggtgtgtg aaatgtattt tctattatgg 142680
attttggggt atgatggcac atagtttggg tgttaatgcc taatcttgat gtactggctt 142740
ctgaacaacc aaaaggatga aaggaaatag aacaaatatt tttgtgaggg agaggagtct 142800
ggcttcttga cttactctag aaaaagcctg taagcctcct cttccctcct tgtcacacaa 142860
agtgacaaag aaaatcaaga attgttttct tcttggctta aatgcatccc ttataaagta 142920
aggctgagat caggctgtga agctatcttt ttgtcaagac tgtcataatt ccaaaacact 142980
ttgttcttct aatgcttagg ttagtaactt taaacatttt tataaagata gtgaggtcca 143040
gttttaagga ttgacccctt ctcaaggggc tcagaagagg ttttggagaa taataaaatt 143100
aaataatgaa accaataatt taaaccagat catgatcctt aagaaaaaat cccatcaaat 143160
ttgggctaaa ctctaatata cagaggtctg cacaacttat gtcaagtatt cttccccaca 143220
aatgaagaat ggggttcatt gtgtcattgg ttgggtctca ttttggcttc atcttctatt 143280
tctcaaagtc taagaaaagt gctcctacgg aagtgggtgt tggctatcat gagactttgc 143340
tgctggcagg ccagcttgct gctctagaca gagatatccc tcgatcctcc ttggacaact 143400
gttttctgtg cacaggaagc agcaggctgg ggttaaggag tttgccaatc cagtcattct 143460
gataattgct gaatatgaat ttctatccag cacaatctag gtagctacaa tggcacagta 143520
gtttttatgt atcaggtgaa aatgtttaat aggcactcta aatgagagaa aaggttaagt 143580
gaggttaaaa gctcaatgaa aacaaataga tgagactaaa aatagttcaa taggttgtaa 143640
cttccatctc atccaaacag caatgaatat tttgaggctg aggcgctgag gggtaaaatt 143700
gcagcctgga ctacttgcta atgtagacct acagcactgt cattcttact gcacagacac 143760
tgctttctgc ataggaggta gaataatgaa ttcatttatt attaacaaag atttattaag 143820
tgactgcatg gtgctaacca ctagatgggg agggatgttt tgaactgtcc attgtttgac 143880
tataacaagg aacgctttga acgaggttac tatcataggc agaatttgtt taacatgaag 143940
cctatgagac ataagccaca ggtcctctca cgtgcaggaa ctcctttgaa ggccctatac 144000
ttaattttat atgcatagtt tggatttgga ttcttttttt tttaagagtt ccccaaatta 144060
cttaagcttc aggctccaca aaacctggat ctacccctgg tagcagctat gaatctttga 144120
ctatgaaatt aagtgtacaa gaaatatgac tttactttt ctgtgattga gtttattttc 144180
tatttgagca cgcattccac tgagtgaaag aaataatatc attgaattca gagattttgc 144240
tgggttctaa gtggagttta cagaatgcca tgatattagg aattaaggag tgtgttgccc 144300
tacatcatct tttgtccgtg ctcactgtct ctgaggcact gatgttccta tgtgacctag 144360
aggggcatgg tccaggtaga tggagtctgt ccttgttctc actgtgagct ctcgcttgct 144420
gacccttctt cagtttcttc catgcccctg aggggtaaaa agattcaaat ctgaagctat 144480
atcaagccat ctgtgcatag acattccaag caaccatgtt cactctactg ctcccatgtc 144540
atgcaaggca caggaagctt cactatggca tgagtatttc ctgggctttg ccttggaatt 144600
gaggcacggg cctcctttgt tctaaaattc cccaaatcta cttgaggata gaaccaggat 144660
ttggttgcaa ggcagaactt ttcttagagg acctggtatc taaaccctct tgttacccccc 144720
atttatggac cccatttatg gggtgaggag agtgactgct tctaatccat cataattttt 144780
gtctatggct actgtttttg catagacact atgttttgag tccttaggct ttggcttttg 144840
gcgcttaatg gccaatattc acatggctca aaattttcaa atgatccata tctgacttga 144900
gtttcaaaag tcagtttttg aaacttaaat gatcagaatt gatttgttct gctctggttc 144960
tgatgtggcc tctccttcca gaggtactgg aggtagaata tccaaggtgg aaagcccacg 145020
actacaagga attggttagt aattcataat gttagctgtc cacatctatt cagtaatggc 145080
atttcagtgg ctgcacaact gaccatggtg aaagtgtctg cacaagccac tttttcttcc 145140
tgtcagaaaa tgttctcacc cactgaattg aatgactgtc tgctcatatg ctgtgaatga 145200
gtgcccagtc ttaagattaa atcacacgtt cttggctatg catatttggg catgctgtgg 145260
ggagttataa taggctgtct tagagtcaca ttaagcagct agacagacaa tgagttggaa 145320
agttacattt tctaaatttg attggtacat tccatttgtc acatttgaca ttagaagttc 145380
tggattcacc ctctatggtg agcttcacta atggagaatg taatttgcaa tgctcaaaca 145440
caagtcctaa acagaaaaca ttgtatgtta cattccagtg ctaccaaaat agtggttttg 145500
aaagtcctta ttttctaata ctactatgtg taattttgag tcatttagat agcaacagtt 145560
aaatgtttta tagattgttt ggaagtatta aaatgtgaag gatttttgtt atatagtgtc 145620
tttcctatct tgcttaataa aatataagtt tagaattgtg tatagaatta acatgcaaaa 145680
atatcaagtc tcaactttat acagttaatc tacatttgtg tataccttc aattatttca 145740
agagagggat actattctta tgcaggataa atacaataag atattttaaa tgaattttaa 145800
ctacatctct ggcagtttca tctcaatagt agttgtaatt ttatctccca gaccttatta 145860
tagactagca gctctctatg aaaattagtg acagtgtgag tgtattttaa ttcaaagtta 145920
atcaagaatg actgagtcaa gagttagcta cccctgaaag taactcataa ttcagaattt 145980
aaaatattac atgtggaaca atcatgacta tatgcctttt actttctcta tcattattta 146040
ggttgtgggc tttgggtcct tttcacatcc gttaacagtg ggcttgactt caaaggatta 146100
ttttcttgaa tcttgaataa ttgctgaaga caatttgaag atattttcaa gatgaaggaa 146160
actgaagcac agaatcacta gagtgaaaaa agaacttcac aaacagtgca ggcttgatca 146220
atggcatggg aaaacaggca atacagttag aattgctaag atggaatttt aacgttcaat 146280
taaggatcta tctctaaact cctctgcttt atccaccaat cattccatat taaagatgaa 146340
gaattgttcc catttcacct tttgataagg aaaaatagaa ataacagaag caaatacact 146400
tttgcccaca tttttttcca aaaagaataa tttttgaagt ctaaacgttt ggtgtaaata 146460
agatgatgtg ttaatattgt aaaggaaagc tagttaagtt tttgactgaa taaagccagc 146520
atcaataatt actagtaaga ctaaaaataa gagcagtaaa attgtgtcta atcagctact 146580
aatatctggg aaggattgag ccacaggatc aaagatggta tcttttaaaa atagaagttg 146640
agtgaattcg gtcttcaaat tctttctttt tattcattta tatttattta ctcattagta 146700
tattcattcc tttattcatg tattgttcaa atatatattg ggtacttatt atatgccaag 146760
ttgtttttaa aatcacattc caaattcccg taagtcataa ttattcagag atgtatgttt 146820
tttttaaaaa aaattgaaca cctttaaaaa ttatcaagtc cttttatttc tgtatgcatt 146880
aaagataaac tttactaaat gttacatgaa tagatttata aagcagataa atatttaatt 146940
tcaaatataa cccttatatg caattatatt ttccttagca ctaaaaatga atatttaagt 147000

```
aatttatatt aaaagtgtaa ttatttaact gcagatgtat gccaatgact taaattgttt 147060
aaagattata gcaaagttgt ttaaaattgt ctaatcatga agagttcact taaccacctg 147120
gttgacacat aaaattatag ttagttacta aggtagttcg agagaaagag aagaatcttc 147180
agtagtggtt ttgaggtgtg gtacatttta ttataatata ccggttatac agcattgtgc 147240
agtgctgctc atagtagaaa taaattttct ctttgatgtc atctattccc ttgtgtggct 147300
tacataactg agaattaggt gatcacaaaa ataaacaggc ctatacagag cccatttata 147360
taagtcctgg ttatttctct tcagttaaac ttttaattat atccaattat ttcctgttag 147420
ttcattgaaa agcccgacaa ataaccaagt gacaaatagc aagtgttgca ttttacaagt 147480
tattttttag gaagcatcaa actaattgtg aaattgtctg ccattcttaa aaacaaaaat 147540
gttgttattt ttatttcaga tgcgatctgt gagccgagtc tttaagttca ttgacatgcc 147600
aacagaaggt aaacctacca agtcaaccaa accatacaag aatggccaac tctcgaaagt 147660
tatgattatt gagaattcac acgtgaagaa agatgacatc tggccctcag ggggccaaat 147720
gactgtcaaa gatctcacag caaaatacac agaaggtgga aatgccatat tagagaacat 147780
ttccttctca ataagtcctg gccagagggt gagatttgaa cactgcttgc tttgttagac 147840
tgtgttcagt aagtgaatcc cagtagcctg aagcaatgtg ttagcagaat ctatttgtaa 147900
cattattatt gtacagtaga atcaatatta aacacacatg ttttattata tggagtcatt 147960
atttttaata tgaaatttaa tttgcagagt cctgaaccta tataatgggt ttattttaaa 148020
tgtgattgta cttgcagaat atctaattaa ttgctaggtt aataactaaa gaagccatta 148080
aataaatcaa aattgtaaca tgttttagat ttcccatctt gaaaatgtct tccaaaaata 148140
tcttattgct gactccatct attgtcttaa attttatcta agttccattc tgccaaacaa 148200
gtgatacttt ttttctagct tttttcagtt tgtttgtttt gtttttcttt gaagttttaa 148260
ttcagacata gattattttt tcccagttat ttactatatt tattaagcat gagtaattga 148320
cattattttg aaatccttct tatggatccc agcactgggc tgaacacata gaaggaactt 148380
aatatatact gatttctgga attgattctt ggagacaggg atggtcatta tccatatact 148440
tcaggctcca taaacatatt tcttaattgc cttcaaatcc ctattctgga ctgctctata 148500
aatctagaca agagtattat atattttgat tgatattttt tagataaaat aaaagggagc 148560
tgaaaactga attgcaaact gaattttaaa actttatctc tctgtggtta attgcaaaca 148620
cagatacaaa aatatagaga gagatacagt tagtaaagat gttaggtcac cgttactaac 148680
actgacatag aaacagtttt gctcatgagt ttcagaatat atgagtttga ttttgcccat 148740
ggattttaga atatttgata aacatttaat gcattgtaca aattctgtga aaacatatat 148800
ataggatgtg cgaaaagtcc ctgtgtatca tgtgaaatgg cttaaaacag aacaccatag 148860
gtattcatat cagtgaatac cataggtagc tgaaagtgtt ttttcctggg gtcgccaaga 148920
tgaatgccaa aagtgatatc attattataa acaatagcca gaataggttg gtataaacct 148980
ggtagaaagc cttgataaat tgactttctc tcctcctgac atcctgccac ccctttgctt 149040
tgctgatgct catttgtcca ctaaattaaa ctcaagcaag ccctagtaaa gtaatagaat 149100
ttgtggagtc ctcattagta taggaagttt ccctgatgtg agattagtaa ttagagatgt 149160
agcaaaatga gaaagaagta atatgcttag atatttcatt ttctctgaac ctgtatatac 149220
aaaataggcc atgcgtgttc agtaactatt cactgcaagg cactctctag gtactttggg 149280
ggaattggaa attactcaca taaggctatg gattgtgcca tttgtcaaaa gacaaaatga 149340
caacaaattt agtttaaaga cctcagtcag ctttattttc tattctagat ttggacagtc 149400
```

cttcatttca caaattggag taagtgttcc aataagttga gcaaaggagc ttggctttat 149460
agacccaaaa aaagggccaa aggaagcaga aacaaagaac aataagagaa ttggtcattt 149520
caaagttact tttcttgaaa ggtggggaca aggagacaga ataatagaaa agtcactgat 149580
tggttaacat tggattaaga attaaaacag aggaaacttt aagattgaag tttgaaactg 149640
acttgtttgg gaaatcaggc tgtcttcttt cttgatttct tagaaggccg gataacaact 149700
gagttttgct ttggtgaaca tgggtgactc catttttact tttagtctgg tctgttgagg 149760
cctcgtgaga gagcttaatc taaaacaatg acttcctata atttttgttt gacacatcca 149820
aagagggact ctaatattta ttgagagctt atcatatctt aagtactgtt taaacacttt 149880
tatttgctat tacatttgat cttattataa ctctaaaggc agaaatgatt gcttttattt 149940
tccacaatgg aggaaactga ggttcaatta agtgagtaag gaagcaggga tcttaaaccc 150000
agataccatt gctcctcttt aaaggtggaa gaacagaaaa catggggcag gggaagagag 150060
aaagtttctg tcccaggaca tgataatcta aaagggaaaa cgtaagatcc actgaaacct 150120
gaggcagatt tattgtggca ataacaaagc ttaagtttca cagaccttca tttgcctgag 150180
ccaactttga aggccatgta tctaattttg tttttataat tctataatct ttattcttga 150240
aaagagccct ccctccaaat ttacaagctt tgggccccca aaatccttga aatgcccttg 150300
aataagagat atccaggtaa atgctatggg aattcagagg aggaagcagt tagtatcagt 150360
tggcggagag ttaggctatt aagagaaggt tttatatagg aagtggcatt tagaatgaag 150420
ctttgagaac tgagctgtgt atttgaacaa gtaaaggtgg tgttgcagaa ttttgctcct 150480
tagttctatt aaaaacccgg gttcttgtca catgatccgg aaaatttagg cacacagata 150540
cattgaagca tgagtagagc aggattttat tgggcaaaaa ggaaaaaaag aaaactcagc 150600
aaatcgagat ggagtcttgc tcacagattg aatcccaggc caccacaaag gaactgaaga 150660
gatcgggctt ctcccctgca taaggtgcaa attccccatg gctccaccca cttcccctta 150720
gtgtgcatgt ggggctccag tccacggtgg gcatgcccag acaagccttg ggcaggttcc 150780
ctcatctgtg caaaagcatc tgatgtaaac acttgagggg tggttcggag attctctggg 150840
accctttat tttcttatct gcctaggcat ttggctgtct cagtgggtgg gaaagggtgc 150900
tccaggcaaa gggcataaca tgaggcaaag ggcatgcaca gaaaacagtg actggttcag 150960
tcaggttggg ggatgccaaa ggaagtaatg ggagacaaga ttggagcaag atagataaga 151020
gattgtggat ttttttcttt ttttatctat ataaatacag agacagggtc tcactatgtt 151080
gcccaggctg gtctcaaact cctggcctca agtgatcctc ccacctcatc ctcccaaagt 151140
gctaggatta caggcatgag gcactgtgcc caacctccaa ttttggattt tgagagctaa 151200
agcaatatag tcgaaaactc agataatcca ggtagatttt gctattaggt gctatttggt 151260
tcctggtaca gagctaaaac ccttggaatt tcctaagtga taagagctac aggagcatct 151320
tttgttatat gtttcccccc ctagttcctg aaatagctct agagaaatac aggtgaataa 151380
catcctttgt tattcatatc aagcccctat caaccatacc ccagtttcta tttatgaagt 151440
ggcttttggg aagtccctaa agacaggagt ggggaaaggc tggttgtcag gggggatgggt 151500
tgaaactttc atcttccccc cttgacctcc agggagggat gagtggctga aaattgtgta 151560
aaatcaacaa tggccagtga tttaatcaac catgcctatg taatgaagcc acccgataag 151620
ccttaactgg aactttttgg agagcctcca ggctggtgaa gacattgagg tgctcagaag 151680
gtggtattcc agagagagca cagaatctct gttccccttc ccacattcat tttgctatgc 151740
atctctccca tctggctgtt cttgagaggt atccgtttat aataaactgg taacctagta 151800

```
agtaaactgt taccctgagt tctgtgagcc attctagcaa attatcaaac ctaaagagtt 151860
catggatacg tgcaatttac agatgcacag tcagaagcac agatgacaat ctgggcttgc 151920
cattggcatt tgaagtgtgt tgggaggcag tcttacagga atgagccctt atcctgtggg 151980
gtctatgcta ataacagaca gttgtcagca ttgcttggtg tcgaaaaccc acattgttgg 152040
tgtcagaagt attgtcagta ggatagggaa aacagtttgt tttctttttt tagtggtctt 152100
tggtcatctt taagagcagg gcttctcaaa gtgtggtcct tgaaccagca tcacctgtac 152160
cacgtaagaa cttatgagaa atgttcattc ttgggcccca acaaagaatt aaaaattctg 152220
agggtgtgaa cggggtctga gtttcagcac aacttcccga ccatgctgat gcattcttgc 152280
ccaagcatga aagccctccc ttgtttaaga aggccattag ggccgggtgt ggtggctcat 152340
gcttgtaatc gagcactttg agaggacata gtgggaggat cacttgagcc ctggagttct 152400
agacaagcct gggcaacatg gcaaaatgct gtctccacaa aaatcacaaa aattaggtgg 152460
gcgtgtgttg tgtgcctata ggcccagcta cttaggagac tgaggcagga ggatcgcttg 152520
agcccaggag attaaggctg cagcgagctg tgatggcacc actacagcct ggatgacaga 152580
gtgagacact gtctcaaaaa aaaaaaagaa aaagaaaaag aaaaaagaaa ggaaaatgaa 152640
aaagaacgcc attaggtata aaggagcaat ggtaaaagac cagttgcaaa aggttaggga 152700
atgggtggtt actgaaataa gaagctatgt agaacactag tgttggtggc aggaagtaga 152760
aagcaagagc actgctctgt gggggatggt catagcaaat gcaatatgga ggcatttgcc 152820
tctgcactga ggagaaaact atcttttcca agataggagg aaaggagata agtggaatta 152880
aagagaacct ttgagcacag agttgggaaa ctgaaggtat ttgtgttgtg ctccctcaat 152940
cttttaattc aactataagc taaacccatg aaacttgagt agtttcagtt atctgacttt 153000
tttcttctct tttgatacag tgttggctat tctgggtctt ttgcctctct ttatgtactt 153060
aagaatcagt ttgccaatgt atgcaaaata actggctggg attttgattg tgattggctt 153120
gaatctatag atggagttgg gaaggactga catcttgaca atgttgaagc ttcctattca 153180
tcattatgaa atatttctcc atttgtttga ttctttgatt tcttttatca gaatttagtt 153240
ttcctcatat agtcttttaa aatattttgt tatattttgt tcaagtattt tgtttttgag 153300
gaatgccaat gtaaatggta ttgtgatttt aatttcaaat tccaattttt cattgctgtt 153360
atataggaaa atgatttttt ttgcatgtta gccttatatc tttcaacttt gctataatca 153420
attattgata gtttcaagga ttttttggtc aattattttg aatcttctac atagattatc 153480
atcatctgaa cttagtttta tttcttcctt cccaatctgt ataccttat ctccttttct 153540
tatttcatta gctaggactt ccagtatgat gttgaaagta gtggtgagag gggatatctt 153600
ggtcttgttc ttgatcttag tgggaaaact tcaagtttct tatcattaag tatgatttta 153660
gctggagggt ttttgtagaa gttttttttt tttaagttga agaagtctcc ttctattttt 153720
agtttgctga tttttaaaaa gaatcaggaa tgggtgttaa attttgtgaa atgcttttct 153780
gcaactattg atttgagcac tttatttttc ttctttggct tgttgatgtg aagtacatta 153840
attgattttt gaatgctgaa tcaacctttt gtacctgaga ttaatcccgt ttggttgtgg 153900
tatataatta tttgtataca tgttgagttc gatttgctaa tactttttga gaatttttgc 153960
attggtgttc atgaaaaaat attggtgtgt agttttttgt gacatcttta tctgcttatg 154020
gttttaaggt aatgctggcc tcatagcatg agttagggag tatttcctct actttacat 154080
ttgagaagag attgcagaga attagtaaaa ttcctacttt aaatattttg tggaattcac 154140
cagtgaaccc atctggacct ggtgctttct gttttggaag gtcattaatt attttaaaat 154200
```

agatataggc ctattcagat tacctatttt ttctcatgcg agttttagca gattgtcttt 154260
caaggaattg gtctatttca tttaggttat caaatatgtc aacgtagagt tattcatagt 154320
attcttttat tatcctttta atgtgcaagg gatctgtagt gatgtcccct tttttgtttt 154380
attgatatta gcaatttgtg tcacatcttt tattttgctt tgttagccag gctagagata 154440
tctctatttt tgatgttttt gatgaaccaa ctttttgttt tattgatttt ctctgttgat 154500
ttcgtgattt caatttcatg atttttaaat tatgcttaca tttgatttaa tttgatcttc 154560
ttttgctagt tatccaaggt ggaagcttat attgttaaga tcctttttgca ttcttatgca 154620 ttcaatgatg taaatttccc tctaagcact gctttttctg catctcacaa atattcatga 154680
gttgtatttt catgttcatt tagtttgaaa tatttttaaa tttctcttga tatttctctt 154740
ttgacccatg tgttacttag aagtgtgttg tttaatcacc atttttaaaa attttctagc 154800
tatctttctg ttattgattt ctagtttaat tccattgtgg tctgagagca tatattgtat 154860
aattttaatt tttataaaat ttgttaaggt gtgatttatg gcccagaatg tggtctatct 154920
tggtgaatgt tccatgtaag ctttggaaga ctgtgtattc tgctatattt gaatgaggta 154980
gtctatagac atcaattatg tccagttgat tgatggtgct gttgaattca actatgtcct 155040
tactgatttt ccacctgcta gatctgtcca ttctttgcag agggacactg aagtctccaa 155100
ctctagtagt gaatattcta tttcttgtta cagttttatc aacttctgct tcatgtcttt 155160
tgatgctttg ttgctagaaa catacacatg aagaattggt atgtcttttg gagcatgacc 155220
catttatcct catataatgc ccctcattat ttcctcgccc tgatgtctgt tctctctgaa 155280
agaaatatag cctctccagg tctcttttgg ttggtgttaa aatgacttaa ctttctttat 155340 ccccccttact tttagtttat atgtggtttt aaatttaaag tgggtttctt gtagacagca 155400
aatagttcag agttgttttt cgatccactt tgacaatctt tgtcttttaa ttggtatatt 155460
tggactattg atattttaag tgattattga tatagttaga taaacatcta ctatatttat 155520
tactgttttc tgtctgttac actacttgtt ctttgtttat atttttattg tctactcttt 155580
ttctttccat tgtggtttta atcgagcatt ttatatgttt ccatttttctt ttcttagcat 155640 agtaattctt ctttaaaaaa acattttttta gtggttgccc ctagagtttg caatatacat 155700
ttacaactaa tctaagtcca ttttcaaata atactaaata atttcatgtg tagtgcaagt 155760
accttttaat aataaaacac tcccagttcc accttccagt ctcttgtatt atagctataa 155820
tttagttcac ttacatatat gggtatacct aagtatatac attatcatat ttatgattga 155880
atatattgat gaaattattt tgaaaaaact gttatcgtta aatcaattaa gagtaagaaa 155940
aatagttcta attttattat aaaatgaaat accttcattt attcattctc taatacactt 156000
tctttcttta tgtagatcca agtttctgac ctgtataatt ttccttttct ctcttcagct 156060
tctttgaaca tttcttacca gccagaccta ctgacaacaa ttttccccaa tttttgtttg 156120
tctgatagag actttatttc ttcttgactt ttgaagaata attccacagg gcacagaact 156180
ctagattggt gatttcttcc cctcaaaccc ttaaatattt cattccactg ccttcttgct 156240
tgcattgttt ctgagaagtt agatataatt cttatctttg cctttctata ggtaagatgt 156300
tttttcctct ggcttctatc aagatttttt ctttatgaac atgatatgcc tttctttttg 156360
aacatgatat gcctttcttt ttgaacatga tatgcctttg tgtcggattt tttttggcat 156420
tattctgctt ggttttctct gagtttcttg gatatgtggt atggtatctg acactaattt 156480 ggaaaaaattc tcagtcatta ttgcttcaaa tatttcttct gttcttttttt ttcctttatt 156540 ctccttctgg tattcccatt acatgtatgt tacagttttt gtagtcatcc cgctgttttg 156600
gatattctgt ttttttcagt ttttttttcc ttcgcatttc agtgttggaa gtttctattg 156660
acatattctc aacctcagag attctttctt cagctgtgtt cagtctacca atgagtccat 156720
caaaggcatt ttacattttt attacagaat ttttgaccta tagaatttct tttgattcca 156780
tctttgaatc tccatttctc ttctgctttt catctgttct tgcatgttgc ctactttttc 156840
catgaaaacc tttagctttt tttttttttc tttttgaggt ggagtctcac tgttgcccag 156900
gctggagtgc agtggtgtga tcttggctca ctgcaacctc tgcctcctgg gttcaagtga 156960
ttctcctcct cagcctccca agtagctggg attacaggtg cctgccacca tgcctgagta 157020
atttttgtat ttttagtaga gatggggttt tatcatgttg gccaggcggg tcttgaactc 157080
ctaacctcaa gtgatctgcc caccttagcc tcccaaattg ctgggattat aggtgtgagc 157140
caccatgccc tgcctttagc atgttaatca tagttgtttt aaattcctga tctgttaatt 157200
ccaacatccc tgtcatatct gactgtggtt ctgatgcttg ctctgtgttt tcaaatggtg 157260
tttttttttt tttgcctttt agtaagcctt gtaatttttt attgaaaggt ggacatgatg 157320
tgctgggtaa aaggaactgt agtaaatagg cctttagtaa tgtactggta ggtgtagcag 157380
agggtgaggg aagtattctg tagtcctatg attaggtttt agtcttttag tgagcctgtg 157440
cgcctgcagc ttggaagcac ttgtgaagtg tttttttcacc ccttttggtg ggacatagtg 157500
actagtgtga gcgggagttg agtatttccc ttcccctagg tcagttaggc tctgaaaaaa 157560
ccctgatagg ttaggcatgg taaaatagtc tcttttgagg gcaggcattg ttataagaat 157620
agaatgctct ggggccaggt gcggtggctc acgcctgtaa tccccgcact ttgggaggct 157680
aaggcaggtg gatcacctga ggtcaggagt tcgagaccag cctggccaac atggtgaaac 157740
cccgtctcta ctaaaaatac aaaaatcagc caggtgtggt ggcacacacc tataatccca 157800
gctactcagg aggctgaggc aggagaactg cttgaaccca gtaagtggag gttacagtga 157860
cccaagattg tgccactgca gtctagtctg ggtgacagag caagactccg tctcaaaaaa 157920
aaaagaatgc tctggcatat ttgaaaatgg ttacttttcc ctttttttct ctgatcttca 157980
ctgtgagaac ctggtaagca tcctataggc aaaattcata aaagtataga agtcggccag 158040
tgacttggac ccacttggaa ttttcttgct ctcacatcat gcacactgaa tctccagcaa 158100
tttttcactt acagtttagg ttttcctacc ctactactgg ttctctcaga ggtttctgct 158160
tattggtttc tgttttgtaa gttgtgattc tctgtaccta actgcctgtc tcccattttg 158220
gggggcagtg gtttgccctg tgacctcact tctctgacag atctaagaaa agttgtttat 158280
ttttcagtgt gctctgcttt ttacttgtta cgatgaagcc aaccactttc agaatttcta 158340
caaaccagat cagaatctgg aagtcctgtt tttttatttt ttttatccct ttgtttagca 158400
tgttacctat cttaacacat tttaaataag tgaatgcata gcttatatct acttctaggt 158460
tatatgcttc cttagaatag gaattgattc ttaaaatgtc gttctgctca cgcctgtaat 158520
tccagcactt tgggaggcca aggcaggcgg atcacttggg gtcaggagtt caagaccagc 158580
ctggtcaaca tggtaaaacc ctgtgcctgc aaaaaataca aaaattagct gggcatggtg 158640
gtggccatct gtaatcccag ctactaggga agctaaggca tgagaatcac ttgaacctgg 158700
gaggtggagg ttgcagtgag ctgagatcgc gccactgcac tccagcctgg gtgacaagag 158760
caaaactcca tctcataaat aaataaataa ataaataaat aaataataaa aataaaaaaa 158820
taaaataaaa caaaaatttt attctgagca gtctctgaag aatataaatt ctactgcctt 158880
gcctttagaa cttataacag catctcgcaa actatcacaa gatgctccaa acatacttct 158940
tatgtgctga attaagaagt caactcaaat ttagtatact agtaatattt ttggatatcc 159000
caaaacactg ccagctcagc tttaggctgc ccttcttggg ggggaaaaaa gcagttgaaa 159060
tttaggactt aagtgggcat ctcgtttaat ttttaatgga tttctatgtt gttggttatg 159120
gtgaagaggt gaaaagaata aatattctgt gcagaaaaat tattcagtct tcatgtgaaa 159180
acactttgtc catagcaatt actttatgaa aaagatgtgg tattactttc tttgctctta 159240
actgagacct ttaatttaaa gaacctatac tttacaagtt tttattttca atgcatgaaa 159300
aatgtagcag ctatttcaca acctttactt ttaaaatcca tttttctttt taatctcaaa 159360
tagtttttc ttaaaacctt ttgacttttt atctaaattg taatagccag agcaccttcc 159420
cacaactaga atatctcatc ctttttgtct tttctttttc ctctcaaaat gcctactggg 159480
aacttaattt ggagtcagat tcttcatgat aaatctggac ttaatcaaaa ttcctcatat 159540
ggtatattgt atatatcaca gtactggata gtcctctgat taaatagata tttgatagta 159600
ctttaaggtc tatacttttg gatgaactta actgctttct ccatttgtag tctcttgaaa 159660
atacagaaat ttcagaaata atttataaga atatcaagga ttcaaatcat atcagcacaa 159720
acacctaaat acttgtttgc tttgttaaac acatatccca ttttctatct tgataaacat 159780
tggtgtaaag tagttgaatc attcagtggg tataagcagc atattctcaa tactatgttt 159840
cattaataat taatagagat atatgaacac ataaaagatt caattataat caccttgtgg 159900
atctaaattt cagttgactt gtcatcttga tttctggaga ccacaaggta atgaaaaata 159960
attacaagag tcttccatct gttgcagtat taaaatggcg agtaagacac cctgaaagga 160020
aatgttctat tcatggtaca atgcaattac agctagcacc aaattcaaca ctgtttaact 160080
ttcaacatat tattttgatt tatcttgatc caacattctc agggaggagg tgcattgaag 160140
ttattagaaa acactgactt agatttaggg tatgtcttaa aagcttattt gcgggaagta 160200
ctctagcctt attcaacaga tcactgagaa gcctggaaaa acaaatcccg gaaactaatt 160260
attatgtgcc agttatataa acaagaagac tttgttgggt acaaaccagt gattccttgc 160320
ctttgaaaaa tgtgtcagat atcatgcatt accagcagtt caatgatata aggaaaccag 160380
agtaatagct aaaaccttta aagctaaacc aaagatttac aaattgcctc ttcatccagt 160440
ctttcccaac ctaaaaactg agttctctaa aaattttagt atttttttct gaagaaaagg 160500
gaacatggac atttatctaa tcctcattag aaatctgact aatgataaca aggatttaga 160560
cctcaagcac ttcttaccaa aattcttgat atgaccttat agcaaattac tttcacctgt 160620
tgaactttcc tttcttttat tcccctgtac ctcacctgca ctgggcatat tcaagttgct 160680
tatacaacac tttactattg tgttagaaaa atcatgacac atgatgaatg tgtttgtgca 160740
acatgagctg attcataaat gaaaatgtgc attgaaattc cacaatattt taaaattagg 160800
agtttatcta gcaattgaac aaaattgatt aaatccatta tttgttagat cagctaaatt 160860
acataagttc attcatctgc tcataaatcc atccattctt ccatctggct atcccttagt 160920
caattcaaat aaatatttat ggggcacttt gggtaagcca ggtgctaaga attcaatgca 160980
aaacaagata gactcccctg tccttgttga acttatattt ttggtacaaa caaaagcaat 161040
aatcaagaaa aaataaaaaa agtactgatt gtgattaata atatgaagaa attcaacaga 161100
gtattgtact taacatttga ttgatctgat tttctcagtt gtctgagaac aaacatttgt 161160
gaaaatctca ttgtagagtt cttacgatgg atagggggtc aactgtgtca ttattgctta 161220
tcagcttatc ccaaagacct agtttattac cagattgcaa atagtgttca ataaattatt 161280
cttattaagg gttgttatgt actctaaaac atttattgtg gtcccttcac tggttctggt 161340
ttacaaactt acttttctat gatgacatag tatagaaatt gagagtgaat atttagaagt 161400
tcatttttat tatatatttt tgaagtattg atatgtagtg aattagaaat ttaaaaagaa 161460
aacaaaactg tccttcacta cagattgaaa agcattatac taaaagacca tttgctcagt 161520
tatagtatat aaaggccaaa tgacttaaaa acaaattatg taaggagaag gaaacaacca 161580
tttattcagt gccactaact gtcagccagt tttttcagtg gtcagttaat gactgcagta 161640
gtgttctacc ttgctcaaag caccctcctc aagttctggc atctaagctg acatcagaac 161700
acagagttgg ggctctctgt gggtcacctc tagcacttga tctcctcatg cagtgcatgg 161760
tgctctcacg tctatgctat gttcttatgg tctttaggta acaagaataa ttttctttct 161820
tttccttact atacattttg ctttctgaaa ttcccttctc gccaatccag gtgaatgtca 161880
gaatgtgatt tgacaactgt ccaaagtact cattcactga ggagtggtaa ggccttcgcc 161940
caacctgcct tctctgggaa tatactgctg cctgaacata tcattgttta ttgccaggct 162000
tgaacttcac caaattaatt tattagggtc aacatctaaa tattagaact atttcagatt 162060
aatttttaag tcgtatccac tttgggtact agatcaaatt gcaggtctct gcttctggct 162120
tgagcctatg tttagagatg atgtgcatga agacactctt tgcttttcct ttatgcaaaa 162180
tgggcatttt caatcttttt gtcattagta aaggtcagtg ataaaggaag tctgcatcag 162240
gggtccaatt ccttatggcc agtttctcta ttctgttcca aggttgtttg tctccatata 162300
tcaacattgg tcaggattga aagtgtgcaa caaggtttga atgaataagt gaaaatcttc 162360
cactggtgac aggataaaat attccaatgg tttttattga agtacaatac tgaattatgt 162420
ttatggcatg gtacctatat gtcacagaag tgatcccatc acttttacct tataggtggg 162480
cctcttggga agaactggat cagggaagag tactttgtta tcagcttttt tgagactact 162540
gaacactgaa ggagaaatcc agatcgatgg tgtgtcttgg gattcaataa ctttgcaaca 162600
gtggaggaaa gcctttggag tgataccaca ggtgagcaaa aggacttagc cagaaaaaag 162660
gcaactaaat tatatttttt actgctattt gatacttgta ctcaagaaat tcatattact 162720
ctgcaaaata tatttgttat gcattgctgt ctttttttctc cagtgcagtt ttctcatagg 162780
cagaaaagat gtctctaaaa gtttggaatt ctcaaattct ggttattgaa atgttcatag 162840
ctttgatagt gtttttcaga agaccaaatt tacagtggga gccttgggct tttgtttttt 162900
aacagctctt ttttgttcct gcttcagtgg cctgacctcc aagttagcaa tcgccaggtt 162960
gagaaatgct ttgcgagaca taacagatgc tcctgaaata acaaacactt ggaatcatga 163020
ggtagtggaa ttgaaaatag aaagtgtagt gattgttttt tgttatttgg atgggatgaa 163080
caatgtcaga ttagtctgta actatttttt tttaatgtca ctctgatttg gtcacaaagg 163140
atctctagtc tcattgcctt agtatcattc tacgaattag aatgtgttac tgtgtaagag 163200
cacttcttgt atatgagaga aatagcaaca gttccagttt aaagtgatat aaatggaaac 163260
caagaaatgt ctttactggg accaaatctg gacagcattt actgtatttt tgctggtatt 163320
ttctctagtc tttccgggta tattcacatt taatgatcac ttttctccct ttgtgctaat 163380
ggacactgaa tccattccac taccatagtt cttgctaata ctactctact ttttacacaa 163440
aattaaaatg ccaggagcac ctccaggtag actgactata aatctagact gaaaaaaaag 163500
cttgtatttc ttaacagatt accttgtgga acatttgctc ctttcaacta atgaggcact 163560
aaatattgta actgctcaac tggtgctttt aatttatttg tctagacttt gtcatgttgc 163620
cagaagcttt atcctggttg gagttttgaa aacagtattg tttcttcaga aagaaaaaag 163680
ggattgtcag atgatctaaa aataaagaaa cactggaaat acaagtatcc caaggtgata 163740
gcattaggca agataaaaat gttgaaaagc gaaaaagaac tggttgatag agaagtgttg 163800
ttattcagta gaacctaagt cttgtggtcc catttttaat gaaaaatggt gaatttttg 163860
gtttttattg ttcttgttca cacaaatctg cccattagaa taagccaagc cctaaaaatt 163920
aatttcagtt tcactgggaa tcctttagtt tatctactat gtagtagaga ggttttgttt 163980
tattgcatgt ttgacgtagg aacgtatata tgcaagacat ggaggaaaac caagtgggcc 164040
agagttttga aaattcttta tcttttcttt ctgccaaagt gagtctccca agtttgtctt 164100
tttttttca tttccactct tctatggttt ctagcattat ataaaccaaa caaaaaaaat 164160
acgttcagag attccttcag aaatgctgga tgatcttgat atcgatgctt ttcatatatg 164220
tgtttatgat gctggtttct ggggctggct ctcagtatca caaagatgtc tgtaaacaga 164280
atatgctatt tcttctttgt gacaaatttt gaacattatg tgaatgtcca agaaagagca 164340
aaagagggca aacttctcat acatttttga tgtcgaaacc aagagacgct tttattttcc 164400
taacttttct ttgaaagttc aaattaagta attttatcct gtcctaaagt ttaaaaagaa 164460
aaaaaaaagg aagaaggaat taaaaatcca aagaaaatta tgtttgtttg cttttctgtt 164520
tttttcttcc ttccaactcc gagactttgc aagggcatag ttctgaagat ctctgacact 164580
gagacattag agatctctgt atcaatggat catttgtttt cagacatatg aaacaggaac 164640
tttgaacaag aaatttcccc tctttttctc atagtgatcc tgagacatca gctgtggaat 164700
cacaacacgt cattagtttt ggcaggtcct tgcaggtgtt ttgttttgtt ttattaatgt 164760
tcttccctcc tgtagctaga cagcaatctt ggagaatctg ccagcttgga agactattgt 164820
gtaaatttca aggtggagcc tcctttaatt tgttctgtgt tacctgtgag ctgtgaggtc 164880
atgaagagga gacaatgagg ctaatcatga gagccccatt ggtttaggca attagaacaa 164940
caagatctaa aatggtttat tagccttgaa ttgtgttaag cacataattc ataaaaaaca 165000
gaaaaaatat ttttaaatgt atgtctaaat cttcagttac aagtttgaaa ggtgacaaac 165060
tattctgagg aaatgattag gcctattctt gcaacgagtc tttatgatct gaaaagaatc 165120
tatgtccaca cataactccc acctcaaaga tggggcatct tttgctctgg gagatatcaa 165180
atgcgaccaa aacaagtgtt tgtagatttg aatgatgatt cagcagtgta gcagttctca 165240
ctcattttat aataattaac aacttaataa ttaattatta aactcctaca tgcttaacat 165300
tataagtatg ataacttctg tggttacata aaagatatac atagcacttg tccttgatct 165360
gtcacagtga ggtcccaatc caacctatga gcttcaaatg aaaagttcaa aattacactc 165420
attgtcataa gtcagagatc aaaggaagaa aggatttaac caaaatgata aattaaaatat 165480
aggtgattaa atatagtcat ggttcaaggc atgggccagt tagggagtgt gatgtgggta 165540
attatgaaag gccagctccc aagccctgtt gttgctactc cccccacatca gtcatccttc 165600
ctttttttct acttctactg cagtgccttc ctcatctttt cccttgcatc cctccattat 165660
atgagtcata caaattagac ttttcaaagc aacattaaca ttgtgtgaat ttggggtttt 165720
tgactaatcc caacattcca cccccacatt ccagtcccac atgggatttg gagccttgtt 165780
tataaacctg gcacttctaa tatatcttat cttagagtaa tccttgtatt tgtttaattt 165840
ccacttagca ttgtaaatac ttgcaggtat cctagttaag aaagcaaggt ttaaacacaa 165900
aatcatcacc aattaaagca ggctagataa agaatgtaat agaaatgcta gataaaacag 165960
attttttctt actaagtttt ctgtccctta tagagtgcat aacacaataa cttgcttgat 166020
aagaattcaa tgtacattgt tttgtgctga atcactaaat gcttgatttc tgtaacaaga 166080
gattgtggtt ccatcagtat ctggatttta gtctgtgtaa tcttaggcaa gttatttgat 166140
ttctctgtgc ctctgttttc ttgtctgtaa aatgagtata atggtagtaa ctaattcatt 166200
gtgtttttgt gaggattaaa tgagttaata actagtactc ctccctggca catagtaagt 166260
acaatatgct gtgctgtggt ggttgttatt attttttata gttccttgag caaaagaaat 166320
aatgtcccca tcttagtata atattggagg tatataccat agaagtgaac aaaagaatat 166380
agtttcacaa agaaagtgat aattaaggcg gttcataaag ggtcataaag cttgtagatt 166440
ttagaaatgt gggggcatga ggatgtggag agggtattcc aggatgccag acagggagat 166500
tatggatgag tactaagatg agaactagaa aaagctgagg ggcaaaaggt cagaggaggc 166560
cacaagttag ggagtattag gaaaaagaag ttaatacttg acaagtgcca acatggcttc 166620
acgaggaatg ggttgggcct ttttgagtga ggaagaggct ggtgaaaggg tggtggagga 166680
cactgctgct gctgatggca tggggtgtag gtggcaggag aggcagggac atgagctagg 166740
aaactctcca gctatgaagt gatgagtctg gagtaatata aggacagtag gggtggagtg 166800
ctgaacttaa gggaggagag aaaaataatt ggtatggaag taggtacaat gcaattttat 166860
tatttctgag cctaaaaatg tgaaattttt gattatttgg tcagaccagg gaagtatttt 166920
cttttatgct atctctgaaa atgtatacac taaaaagttg tagtataaaa aggttgtaaa 166980
gcattaagta attttagagg aaacaataat ttggatattt tacatgcaat catttatatg 167040
caaatatatg taaatattac aaaattattc tctatttgtt acaaacctta aatatttttg 167100
actgaggaat attttattca tctaattata gctactttgt tctaactaat agatattctt 167160
gaaaacaaag caacactttt ttggagacag agtcttgcac tgtcacctag acttgagtgt 167220
gttaccttga actccagggc tccagtgatc ctcccacctc agtctcttgg gtaggtggat 167280
tacaggccca cactaccatg cccagctgta ttagtccatc ctttcattgc tataaagaaa 167340
taccggaaac tgggtaattt ataaagaaaa taaatgtaac tggctcacgg ttcttcaggc 167400
tgtacgggaa gcatagcagc atctgcttct gaggaggcct caggaagttt tcaatcatgg 167460
tggaaggcaa ataagaagca ggcatgttac acgacgaatc aggagcaaga caaagtgagg 167520
gaggaggtgc cacacacttt gaaatgagca gatctcatga gaacagcgcc aagaggatgg 167580
tgctataccg ttcatgagaa atccaccccc atgatccagt tacctcccac caggccccgc 167640
ctccaacact gggaattaca attcaacatg agatttgggc agagacacag atccaaacca 167700
taccaccagc taataccaaa aaaaaaaaaa aattttttttt ttaagacatg gtcttactat 167760
gttctacagg ctggtcttaa actcctggcc tcaagtgatc ctcccacctt ggcctcccaa 167820
agcactggga attcagacat gagtaacagt gcctggccaa tacttatttt taaacattct 167880
ctaccataaa cttaggatct tgatttgttc acattgaaca gatttttatt atacagattg 167940
aatttataag aaaatgttgc agacattgtc aaaaagggac gtccaaacca ctgtgatatt 168000
tataagcatt tgggccacat tttgatagaa ctatacacgg agtgtgtgtg tgtgtgtgtg 168060
tgtatatata tatacacaca cacattattt atatatatgt atatatgtat atatatatat 168120
gtatttatat atatatgtgt atatgtatgt acacattatt tacctaccta ctgtgtgagt 168180
gtgtgcatat atacacgcac acacacacac acaaatatat atatttccct tctgagacaa 168240
agccaaacag cactgtatgc ttaaagaaaa acagtcacac ttcccactta tgtaatttat 168300
attacatcca gtcaccacac cagccaaact gctttattgt tttttgtttg acatccaatg 168360
ctaaagcata atgcctgttg cagtgaaata tacatgagca accctgagaa ctcaatatag 168420
cctcacgtgt tgccactgag ttgagttgag gagtcaagct gtagcaaaaa ggtttgtcac 168480
cgggtgagta atggtgctct tatttttctc tgggtctcaa gaagtgctct ttatgacata 168540
tatggcatta aataaatatc agatatttgc acatcctaac tttcctattg gtgaagtttc 168600

-continued ttaaaagaga gataaagggc cattgtgtga ttgatagttt caggtatatt tttgctgcac 168660
agtcagtccg agtgtaccac gtagggcaaa ccacgtaact tctcagggcc ttgactgttt 168720
catttgtaaa ccagagaaaa ggacttgggt gacctccaaa gacctttcaa atttggagat 168780
gagtttgtgg aaagttcaaa cagtttagaa aacagaacta agacacccac tggcacccct 168840
ggaagcaaga gagtgccagg tactatttgt aatacaggaa tgaaatacct aattgtatga 168900
aattgaattc taactgaacc agtttgttca gttaaatttt ttttttcaat tagagtgctt 168960
acttcagtat ctaacactag acagtaaact gtagacaaaa gacctacaga atttctgaat 169020
ggtatcaaat tcaccacact taaaactttg ggatgtctaa tttcaaccaa cagctttctt 169080
tcttcataat gttgaatata tgtgtatcta ttttagctaa atttaatata tatcaatata 169140
ctttgataga tattttatat aaactattag actatagtat tatgagtaaa agacccacca 169200
tttcccaagc aattataaag aacgatcaaa attttaatgg gttgttagta ttatttcttt 169260
aaagattgtg atactgataa atatttggcc acattttaat agaattatac atgggatgtg 169320
tgtgtgtgtg tgtgtgtgtg tatatgtgtg tgtgtatata tatatggcag tagagatata 169380
tatatctaca cacatctaga tatatatata catgtatatc tatatataca cacatatatc 169440
tgtgtgtata tatacatatg tatatatacc tacatacata tgtacatata catacatgca 169500
tatatctgta catatatata tagtgtgtgt gtgtgtatat atatatatat atatatattt 169560
tttttttcct gagccaaaac aaaatactag gttgtaatag ctgttctttc agaaggaaga 169620
aaaacaacat gtgctgaact ctgagtttga tgtttttgta ttttacttcc tattttcata 169680
tcagtccatt tatttattca ggaagaattt attgagcata tattatgaac acagcttttg 169740
ctaaggacag ggtatgcagc agttatggcc tagtaggaga tatggatgtt aaaaacaaaa 169800
tgctcacaaa tgcacatata atcttaatac tcattgtaag ctatgaaagc agagtgtgag 169860
tattatgaga ccatatgttg ggagatttta tttggtattg aggatcagga aagatacccc 169920
tgaggaagtg atatttaatt tgaaacctaa agaaagcagt tggccatggg aagaaggtag 169980
ggaatgagat tcccaagcaa taggaatcca atgtgtgaag aagctgaggg agtgaaagaa 170040
agctagtgtg gtggcaggaa gaaagagaag agaatggaga agggcactaa atgagtcaga 170100
gaagtaggag gggctaaacc atgtagggtc gtgtaggcca tcttaaaggc ctgagtgtag 170160
tggaaaacct ttgaaggttt gttaaaaggt caatgaaatg ttctaatttc tgttgtagtg 170220
aattgctttg attgctgaat gcgaatggat gggtagagat gcaagagtga aagggaagaa 170280
atcaattagg aggctcttgc cctgctccag ataggactga taattaattt tatttgggaa 170340
gatcagggag aaagataagt catgaatgac tcccaagttt ctggattgaa gaaatgaagg 170400
taccatacac tgagatggga aagcctaggg gtagagtagc tttgagaaga aaggtagcat 170460
ttccccattt cataaaacat ggaagaacaa agaggctgga ttcctgtttg tagacatacc 170520
ttccaggcca gaactgcatt actacaacat ctttgcaagc cacattgcct ttcataactc 170580
tgtgtcagtg ttgatgccgt aacatctttg gccttccccc taccatcctc ccgcagtcct 170640
ccatgataat gccattattc cgtttcaaat tgtgtgcttc cattggatgt gtgagtctcc 170700
ttgaaagtta taatgaggct gtagcccata tgaaatgctt caactcaggt cctgcatagg 170760
aagaggaagc taatctctcc aggaactgag cctgtggcta gagggatgga taattgttta 170820
aataaagaat atgctgctga gtactgatgg gctctttatg tacccatttg gctgctgctg 170880
cccaaccttt aatctttcct gagctttaaa taggaaggaa aaaatggtcc acaaaggatt 170940
tgagccattt tgctgtggtg atgaggagca cgggtttaga gacaaacact cctgtgtttg 171000
aattccagct cctactatct cctagctaag tgaccttgga caagtcactt accttctcca 171060
acctgctgtt tcttcatgta cgtaatagga tttacctcat gaggttgaca tgaagattga 171120
aagaggtaac atatagaatg agcctgtccc aggacatggt tcatgataag tctgccataa 171180
atgggagcta tgtgtcccac ccttttggag gagataactg ttctgtagca ggtaatatat 171240
tgtttgatac ttggttaacc cttacaatta tcatttcctg ttcttctcaa taatgctaga 171300
aaccttttat ttaaagaacc acaatataaa atgaaaaata tataaaaaaa gcaaatggaa 171360
aaattctatt ggcaaggctt tttaacttta tatactaaat aaatccaatt gcttaaataa 171420
tgaactgact caagttctca gcactgcttc ttgtttaatt ctctttagtt tttcagaatt 171480
ctccaataat gacctttgtc tactctcttc agtttattca gaaattactt ttatttacat 171540
agaagtttgg aagtggatac acaaacatat ccctcacata tcttatgatc ctatgagtca 171600
tatactcatc tcttatattc cctctgtaaa gcaatgtagg tacctttcag gaaggtgatt 171660
tttatgtagg ttgagaaata tcagcatgga ggtcctagct gacctctcta gagagtttct 171720
gagacatttg acaacaactt tttctttaag tcatcagtta tgccccgggg tatgaaattt 171780
ctaacatgat cctcagtaaa cttggctgcc ttgctgagga tactctccat ctgcctgaga 171840
gacacagaca ccattaattg ggaattgact tgacttgtgt ggttccttgt ggaccagatg 171900
gccactaaat attctcattt caaggcaatt ggtaaaaact acacttcaag aaatttcatt 171960
cttaattccc cttagtggat gttattaacc aaaggcaaaa gaaaaaaagg gtaaaaaaaa 172020
tattctaaat gttaatatca aaaatattat tttcaattca ccccaggcac agagaactaa 172080
gtattattat tgctattgca ccggcattcc ccaatgagac agtgattttc ttttaagaca 172140
tttttaaata atataggcag aattaagtag acggtgatct ggtaagtaga tgtttcaggg 172200
taacagctgt gcaatgctcc atgcagggaa ttagattgtc attttattcc ttaccaggaa 172260
catacattca gttaaacaat tatttgactt ctgctcttcc actgatttct aagttgaggc 172320
tctctcttgt gcctgtctga tcagataagt agagttgtgc cttggtttat agatgagata 172380
aatgtgtatt tgaataagca taagttaaag aaattttaaa atcccttagg aagctaggct 172440
tatcagagaa atccaaggaa atacattaac aaactaggaa tttgttctaa caggttaatt 172500
ataactcata aacttattgg gttttttac cttttaattt tatattacat ttgcttataa 172560
taaggaatat tgctaggaat aaaatttttt aatattctac aattaacaat tatctcaatt 172620
tctttattct aaagacattg ggattagaaa aatgttcaca agggactcca aatattgctg 172680
tagtatttgt ttcttaaaag aatgatacaa agcagacatg ataaaatatt aaaatttgag 172740
agaacttgat ggtaagtaca tgggtgtttc ttattttaaa ataattttc tacttgaaat 172800
attttacaat acaataaggg aaaaataaaa agttatttaa gttattcata ctttcttctt 172860
cttttctttt ttgctataga aagtatttat tttttctgga acatttagaa aaaacttgga 172920
tccctatgaa cagtggagtg atcaagaaat atggaaagtt gcagatgagg taaggctgct 172980
aactgaaatg attttgaaag ggtaactca taccaacaca aatggctgat atagctgaca 173040
tcattctaca cactttgtgt gcatgtatgt gtgtgcacaa ctttaaaatg gagtacccta 173100
acatacctgg agcaacaggt acttttgact ggacctaccc ctaactgaaa tgattttgaa 173160
agaggtaact cataccaaca caaatggttg atatggctaa gatcattcta cacactttgt 173220
gtgcatgtat ttctgtgcac aacttcaaaa tggagtaccc taaaatacct ggcgcgacaa 173280
gtacttttga ctgagcctac ttctctcctc actggtatgg ctccaaccat caggccctat 173340
cttggtccat ttaggctgct aaaataaaat accaaagact gagctgctta taagcaatct 173400
ttggaggctg agaagtcaaa gatcaaggtg ccagcaggtt tgctgtctcg tgagagcata 173460
cttcctggtt cattgatggt gctttcttgc tgtgtcctca cataatggaa agggcaagac 173520
ctctctggtg tctcttttac aatggcacta atcccatcat gagggctttg ttctcatgac 173580
ctaatcacct cccacatgtc ctacattcta atactatcac cttgggggtt aggattttaa 173640
catatgaatt tgaggaggtg gcggggggga cacaaatatt tagaccatag catttcactc 173700
ctgacctcca aagttcatgt cttcttcaca tgcaaaatac attcattcca tcccaatagc 173760
ccccaaagtc ttaacttgtt ccagcatcaa cttacaaggc taaagtccaa ggtttcatct 173820
aaatatcagc taaatcagca caaacagcta aatcaggtag agtgggactt aaggtgtgat 173880
tcctctttag gcagattgct ctccaactat gaaattgtga aatcaaacct attatgtact 173940
ttcaaaataa aatggtgaaa caggcacagg ctagacagtc ccatttcaaa aaagagaaat 174000
agaaaagaaa aaaggagtga caggtctcta taagtctaaa actttaaggc ttgagaataa 174060
tttgctttgc tttgcctcca ggctcactgg ggtggtgtct tacctctgga cacactgggg 174120
tggaggctct atcctcatgg atttgagtgt ctcattcttt gtggcaggtc tgtgctccaa 174180
tcccacacct atggctccct gagtgtgcaa ttgcatgcct ggtggttcta ctggtctggg 174240
attgcatagg tggcccagcc ttcatagctc cactgggcat tgccctaatg tgggctctat 174300
gtggtgacct cacccctggg cctctacctg ggccctgtga ctccctgggt tcttgaaatc 174360
taggtggagg cagccatccc cctacagttg tgctgagtgt agtgcatgag tgctggggtc 174420
tgctagagct atacctaggg tggtggagat gtatggcaat ggagtatggg gagctgatat 174480
ggtttgggtg tgtccccacc caaatcttgt cttgaattat aatttccata atctccatgt 174540
gttgagggag ggacctggtg agaggtgact ggatcatggg catggttttc ccatgctgtt 174600
catgtgatag tgagtgagtt ctcacgagat ccaatggttt cataaggcag ttttccctgc 174660
tcttgcaccc tctttcttgc ctgtcaccat gtaagacata actctttccc ttccgccatg 174720
attgtaagtt tcctgaggcc ttcccagcca tgtggaactg tgagtcaatt aaacctcttt 174780
tctttataaa ttacccagtc tctttacagc aatgtgaaaa tgtgctaata caggagcaaa 174840
gactgcagtg tgaggtggca atgtgaagtc tgcaatgtga ggtggcacgg ggcagttgta 174900
gcccctcctt tgaaatcttt cttccctacc ccaggcctct gcactctgaa ctatgatggg 174960
aaaggcagct tggaagatct ccaaatggct ttggagtcat tcttccattg tcttggacta 175020
taaattctgg cttctgttta ggtggctgac taatatcccc actgtctgaa tgcatagcac 175080
ctagtttctg ttgagatggc tagtccatag taatttactt atcaaatttg gccacaccct 175140
ttgtattctc tcctgagcag gctttctcat ctttcacaat atggataggc tgagaatttt 175200
ccaaattttg aagttctgct tcccttttga tcaataattc cattttaaag tcatttctca 175260
tcttgaattt tactatgagc agtcaagagt aactaagctg ctccttcaac tttgcttgga 175320
tatttcctca gtcaaacatt caatttcatt gctttcaagt tctgccttcc acaaaacact 175380
aggacacaaa cagctcagcc aagttctttg acattttata agaaggatag cttttcctcc 175440
attgtccaat aacatgttcc tcatttccat ctgaaaaccc atcagattgg cctttaccgt 175500
ccatatttct gggaacattc tgctcatgac cacttaggta ttcggtaaga agatagtagc 175560
tttctctata gctctcctcc tctctggagc cctcaccaga atggccttta attgtccatt 175620
cacagcaatg taggcttttt ctagcatgta cctgaaaact cttccagcct ctactcatta 175680
ccttgttcca aagctgcttc cacattgagt atttgttaca gcagtaccca gatcccagta 175740
ccaatattct gtcttagtcc attggggcta ctacacgatg tcttataaac aacagtaaaa 175800

```
tttatttttc acagttgtgg aggctgggaa gttcaaaatc tggtgccagc agattttgtg 175860
tctggtgaag gccttcttcc tcacagatgg ctgtgttctc actgtgttgt tacatggcag 175920
aagagtgggc aggctagctc tctgggatgt cttttataag ggcagtaatc caaatcatgg 175980
gtttagggta gagccctcat gacctaaatc acctcccaaa ggccccacct cctaatacca 176040
gcatctttga agttaggatt tcaacatatg actttggcag gggacagaa gctttcagtt 176100
tatagcaaac cctataggta gcactacttt gtcctttcct aatcaatttg cgtcaatgaa 176160
acatgaatta gaagagacct aggcgactcc actatactgg gattattccc agtataaatt 176220
atcatctctc cacaccttct catctactcc ctatctgagt tctgaagctc tccactacaa 176280
gaaggaggct ttggtttgac ttgatatact tctctgggaa acaggtttag cataaaacag 176340
tgatgctcat tctagaacac ctgcaaatga caatagtttt ctttcgaagt cgccaggaat 176400
cgtctgcctt tgggtatgtg gctgtgagca ctgccgggca aaatgccata tgacctagat 176460
gaggcatatg ccatcctttg aagccattag gacattatat aggaaatata ttaactaaaa 176520
tggaataaaa ttttctaaat aacaccttat gtttatccaa caggtggttc attatacttg 176580
agagcattat acagaggaat ttgatgggga ggagagctgg agaaattctc gaaattctgg 176640
gtttctttaa cagaatactc tagctataaa cttataattt taaaaaataa gcattatatt 176700
aaagaaaagg gaacataaat tattttgttt tattaaactt aagtccaaag gtctggattg 176760
tggcagaata ggatcagggg acctaaaatg ttgagcctca aaggtcttct tagagaacaa 176820
ctgtattcca ctattagcgc ttttggtcct tttagcccaa tttctgttta tcccaaatgt 176880
tcttcccttt tctgccttcc ttcacagtgg accctgccag gagctttgaa atgcctgtga 176940
gtgttaaaca cttacccatt gagtgcccaa ccttaacatg cccctaataa aatgtactta 177000
gattaaccgt tttcattatc aaagtttcct tattacccaa caaacacagg cgctttaaag 177060
aaaacattaa ctaaattgca agtgacacat tttaagatct ttgatatgac ttcagagaat 177120
gcactatagg aacacaatgc aatgggaggg aaacttggga gggaagacat tagcctttat 177180
aaaatctgca agtattgcca aatcaaaata aaatttacag gaaagcagga tcataaatat 177240
aatctaaaat cttagaacct gtggttatga ttttaaatac taatacaatg caaaattttt 177300
acctgtttag gtttttattt catcagttca tatttaggta tatactttta ctgttctcct 177360
tttttataat ttaccattca caaagatgat gatgttagtc taactttaat gtcatgagtg 177420
ctttgagtag tagtgctaag tttttgttga gtagtagtgt gctttttttga ttagtagtga 177480
taggtttttg atgagtaagc ctgctagcag catacaaaca aacaagcaag tatcagccta 177540
gagaagcaga aaaggcattt gggtttcaaa gtcacaaggc ctaggcttta gtctaataca 177600
gctgataata caatttgtcc aaacaggaca tttttgggtg tgtcaaacac taaactggac 177660
aggacattat gacaaaagtg caaagcagga ctttccgggg caaaccagga tgtatgtcat 177720
ctcactgagt cctctctttg tccttgccat gactagtatc tctagaggta aatgaacaga 177780
gtaatgacaa atagccagac acctgaatct tatcccaaca gcacctccta cataattccc 177840
cattatccca aatggaaatt aaaaatatat acagtgataa ttccaggcca agaaatgctt 177900
tatttctagc ttggacttgg cttccatgtc cagtgtagaa tcttatcctt gctgatctgg 177960
actgtatctc atgaagccat gacttgtacc tagttactag ctggaaggct tagaacaaaa 178020
gctggtccag agagcctcct ttttccttat ttcctgggtc cacaccttta ccatggcagt 178080
ctgcctatca tttgatggag gaatttaaag caagtccaag ggaagggaag agagtttcta 178140
aaatctagaa cttggatagt ttaatttacc tatcccaaaa cagcttaggc ccagacagct 178200
```

tctctccaag attggtgcca aactgaaatt accagctgtg tagaccaaag agaatttcaa 178260
aagaaactga atcccaagag aaaaaaaaaa gacttctggc attgtggccc aataaattgg 178320
taggattgtt gtgacttttc aagtttacat gtaaaatggg cccagcgcag tgcctggcaa 178380
atatgggtac taagtaaaag taactataat catgtttttt taatctggac ttcacttggt 178440
catcctttaa atggtgtctg acagaatcct agttcttgtc tcactttact tagtttccct 178500
gggaaatttc atgtgtcctt ttggctttaa ttaatatctc tattttgatg acctccatta 178560
tctgcctatt cccagagctt tccacctgat atctcagcac atgaaaagca ccttatgtca 178620
ataagtgagt tccttccctg ccccaccaca tacctgtcct gtgttcctaa ttccactgaa 178680
tggcatccca tcctccagtt tcccaaggcc aagacctggg actcatcttt cactctcaag 178740
ttcctccacg ggtacccaca tgtcacatcc tgtcaatgct gtccctgggg agtatctgaa 178800
atatattcac ttttcttcat ttccacctga caccactatt aacacttgca caaatttctg 178860
aggttcctgg ctcatttccc tcattgaccc ccaatagttc attctgctct ttgcagctct 178920
ggtgatcttt ccaaacccca catctgatca cttgtttctt cccttcatat ggctccttaa 178980
tgccttctgg actaagtcca cactgcttaa ggtggcttac caggtccttc atgattttgt 179040
ctttgtttgg ctttctacac tcactgccca acttcccctt acttcccatg attcagttat 179100
actgaatttc tttggttctc taaagcacat gtgctttctg ttctgcagag gctttttttgt 179160 tcacttgcta ttctctacct gggaaactcc cccagccctt cactgcctcc ttctaccatc 179220
tttcaggcct ctccttacac atcacttctt tccaaaaatc tgccttgaca ctccaggtct 179280
cggtttccta ggtgtaccct ataactccac ccctttcata gcatttctca ctctggctgg 179340
agatttacct tttaacttgt ccatgtcccc cactggagtg gaagttcctg gaggtcaggg 179400
attatatcct attaattgtt gtatttccag tgcctagagt agtcttgcat acatggatgg 179460
tattcaataa atattggttg aatgaataag gagttctttc atttcatatg taatagatca 179520
tggaaatagc cttgtgattg atacacagca ggtattacca tcctcacttt agaatgagga 179580
ctcagagcct tgagatgtct gagggccttg actgggacag ctggcagatg caggagcaga 179640
gctgcatcac ccctgtgggc tatctcaggg ttgtctgtaa tctaagtaca atgtctgttg 179700
attttggact gaaggctttt tgggtaattg tttgcttttt caatacttat aaaatagttt 179760
ccatccttac tcattgatag taaggttagt tattttagaa aacaagctaa atagcagaaa 179820
tagtggcctt ttaagttgaa aatttaccct gaaaaatcta cagagtagca aacagagtat 179880
caaaaggagt tgactgtatc tatttttata actgccactt atggattatt cagtaaaacc 179940
acaattcact tttatgattt tttttcatgt ttctctgtca caagagcaaa ctcttgctcc 180000
ataataacat tccagaatac agcaatagca aaagtcaaca ttttgaatcc tttacaaact 180060
cttagacatt tttttttttt tagtttaaca tgttacaaaa caaaatttct tcttttttca 180120
cagcagtttg ggaagtacat actatttatt agctcatcag catgaagctg gaaaattctt 180180
tttcctaaag ttctttatat ctacaaactg ttgatgtttt catttattta tttttaatgc 180240
tacgttgtaa tgaaaatcat tggaaaactt tagattctag taattttgaa gtcttcttag 180300
tttggacagg actgagctaa agtttgtact ttttttaatt tattgaaaaa tggtttctaa 180360
tgatagtatt aacaagatta tattgggggc aggacgcagt ggctcacact tgtaatccta 180420
gcactttggg aggccgaggc ggttggatca cctgaggtca ggagttcaag accagcctgg 180480
ccaacatgta gaaatcccct ctccactaaa atacaaaaat tagctgggca tggtggcagg 180540
cactgtaatc ccagctactt gggaggctga ggcaggagaa ttgtttgaac ctgggagtcg 180600
gaggttgcag tgagcccaga tcgcaccact gcactccagc ctgggcaata gagcaagatt 180660
ctgtctcaaa aaggaagaaa gaaagattat attggggata tatatgtgtg tgtgtgtgtg 180720
tgtgtgtata tacacacaca tatatatata catatataca tatatataca tatttaaagg 180780
ataaaggatt ctgctgccac agatcactaa atcagatgat ctctagcaat ttcctgtttg 180840
tttgtttttt gcccatagtg cttatctctt tgaacagtaa ttttccactt actatttttc 180900
tccccttttg gaccataatt tcctttaagg cagagcctcc tgttactcat ctttgaatct 180960
ggggtctgtc agagtaccta gaatttaata aactctcatt aagagccagt tgaaagaata 181020
tatgactaag cagtcattta catccaaaag atccgtagga gaattcttat cagcacatgt 181080
gattggtaac aataactttg tacttttcaa aaacaattac taatctatct tgctttccat 181140
tatctcacca aaacctatta gcatgtctgg cagaaaatag atacttaata aatttcttaa 181200
atgtttactg acttcaattt taagttttat taactatgtt gacttttctc taatgaagat 181260
gattctaaaa agctttttac tatacttcac agtgaataaa acagtgagat aggaatattg 181320
caaaatgtcc cctgtgttgg tcagtcttag tgtcattcat tttaaaaatt ctgttctcta 181380
aatattgaca gttatatata aatttatgta attgtttact tctaataaag aatttcatct 181440
ggggaaaaac atactttgct cagctctttg ccacaagtgc aaagtctaag acagtcaaat 181500
agctttccta gtacggcctt aggaacttag tatatgactg gtgtgaatct agagggagca 181560
tactgcattc tgaccaaaat ctccaccctg ttactatggc catcactaac ttcgcagtat 181620
tgcagtactt cctgctagct tagttcccaa ggcaacttgt gaaggaaaat ttttacaaag 181680
ctgttgtcac acaaaggtag tgtttcagtt cctgagccca tgtccttgga gttgcccagg 181740
ctccaataat actaataatt actgtacatt aggtacttac catgtgccat attctgtggg 181800
agccgctttc cacaaattat ctctggtaat ccttgtaaca accctttgac atcaatatta 181860 ttatttctc catttttta catatgagat aaatgagact taaaataatg tgcctgatat 181920
catcagcaaa tgagctgagg agggcagatt caaagctgat tgtgtttgac tctagagctg 181980
cagtcttaag ccagaccttt tcttgctggt taattttact gaaaaaaaaa aaaaaaaaaa 182040
aaaaccctca aatactgctg attgatctaa agtactaaca tttctatcag tgttagggaa 182100 atttaattt tataatttga ttttgtgaga aatttatagc atcttgaata ctcacatgca 182160
aagtgatatg tcttagataa cattttacaa tggcagagct taagccagtg ctcagtcatt 182220
cattcatcct caagttttga ttcatttatc attcatcaaa actctgtttt gtttggccac 182280
ccacattcta ggagctcagt acatatttga taaatgaatg aattgttgag gttgacagtt 182340
acccaggact ggcattagga acacagagct gaagagcacg tttttaccct caagaagctt 182400
acagtctaac gagggaactt gcacaaatac tactatcact aggtgcctgg ttgaatggct 182460
taagagatga tcagggatat tcagaaggat atgtcaggct cagcaatggc atcacttgag 182520
agcatcaagg tgtttaggga actacaagat gtttggttct gctgggaata agagtgaagg 182580
gggctccatt tggatgcctc atacaccagg tgagagatct tagattttat tccaccagga 182640
ggagaactac cataggattt aaaacagaaa tgatatggtc aaacctacat cttaggaaga 182700
tccctggggt gtttgtatgg tggacttgca atttgactaa ttgagatttg taggatgatt 182760
cttaagagat gatgatgacc cagactggga tcactataat agagttggta aggaggagaa 182820
tgatttaaaa agtagttgga agaattctag ggatggagat aaacatttga aaattattaa 182880
cttataggtg gtcatcaata ccctgaaaat gactgggatc tcagaggaga gtctggagag 182940
ttggaaatga caaagactaa tattcaaggg ggcaggaaga gggagagttg ttcacacatg 183000
acaataggaa gaaatggcca tagagtgtgt ggtttctctc aagccaagga atagatgttt 183060
taagaaagga aaattcttgt ggtgggaagc agtagagatg acagatacac attaatttct 183120
tgagatttct agatgactaa atgggcagat gttgaatgat agctaaagga gaacccagaa 183180
acaagggagg gattttgttt ttgtttttta aaaaagatag accatagcag cttcatagac 183240
tgaaacaata aaaaagttga aggcacaaag aaagacacag gtcctctaac tccctgccca 183300
gtgcccttta ttcatattct cagcacttgt atttctaagt tttatgtttg agtcttcggg 183360
gatacatcag agtagtcccc cttgtctaat aaatgtgttt acatttcctg ccataccaga 183420
aacccttctc aaactttaat gaatttctac aaggtgagat tactttaatg agaaaccaac 183480
caaggaaagg agtatcatct gcaatatact ttcaaatgtt ttttgcttgt ttgtttcttg 183540
tccagctaaa aaaaaaaaaa aaaaacaagc cattggtcct aacacaactt tcatattcta 183600
ccccaatatc aaagaggctt aaaatctcct ggtcgtgtga tgggcacaca gttaattttt 183660
tgtgaacaaa cacagtgtta tgggccattt ctgaatttat ctctgaaatc ataagattct 183720
ttctgagcca ttatctcatt ctatattaca gtcaggtgga gcccatctta cctcctcata 183780
ctaaattcta gacttctcaa gggcaggaga caatcatctg tatatctctt tggccttcat 183840
acactcagga gtacttgcca aaaataaaca tttaatgcac atttatttga ataattgata 183900
agatccaata cttcaataac tttgtcatat ttttatagaa tgggtttcta tatctcattt 183960
gcattttcaa actttacttt tactgtctag ctttaaaaaa aaagcctttg actctaatac 184020
agccctcata ttctacccca atatctaaga ggctttatat ctcctagtgt tgtaccacta 184080
ttttaactcc agtatttttt acttcatagt tttacctatt tgttacagtt agtttttatg 184140
aattcaagag atgaatagca attttccata tgtaatttaa aaaaccccac agttgactat 184200
tttatgctat cttttgtcct cagtcatgac agagtagaag atgggaggta gcaccaagga 184260
tgatgtcata cctccatcct ttatgctaca ttctatcttc tgtctacata agatgtcata 184320
ctagagggca tatctgcaat gtatacatat tatcttttcc agcatgcatt cagttgtgtt 184380
ggaataattt atgtacacct ttataaacgc tgagcctcac aagagccatg tgccacgtat 184440
tgttttctta ctactttttg ggatacctgg cacgtaatag acactcattg aaagtttcct 184500
aatgaatgaa gtacaaagat aaaacaagtt atagactgat tcttttgagc tgtcaaggtt 184560
gtaaatagac ttttgctcaa tcaattcaaa tggtggcagg tagtgggggt agagggattg 184620
gtatgaaaaa cataagcttt cagaactcct gtgtttattt ttagaatgtc aactgcttga 184680
gtgtttttaa ctctgtggta tctgaactat cttctctaac tgcaggttgg gctcagatct 184740
gtgatagaac agtttcctgg gaagcttgac tttgtccttg tggatggggg ctgtgtccta 184800
agccatggcc acaagcagtt gatgtgcttg gctagatctg ttctcagtaa ggcgaagatc 184860
ttgctgcttg atgaacccag tgctcatttg gatccagtgt gagtttcaga tgttctgtta 184920
cttaatagca cagtgggaac agaatcatta tgcctgcttc atggtgacac atatttctat 184980
taggctgtca tgtctgcgtg tgggggtctc ccccaagata tgaaataatt gcccagtgga 185040
aatgagcata aatgcatatt tccttgctaa gagtcttgtg ttttcttccg aagatagttt 185100
ttagtttcat acaaactctt ccccccttgtc aacacatgat gaagctttta aatacatggg 185160
cctaatctga tccttatgat ttgcctttgt atcccattta taccataagc atgtttatag 185220
ccccaaataa agaagtactg gtgattctac ataatgaaaa atgtactcat ttattaaagt 185280
ttctttgaaa tatttgtcct gtttatttat ggatacttag agtctacccc atggttgaaa 185340
agctgattgt ggctaacgct atatcaacat tatgtgaaaa gaacttaaag aaataagtaa 185400
tttaaagaga taatagaaca atagacatat tatcaaggta aatacagatc attactgttc 185460
tgtgatatta tgtgtggtat tttctttctt ttctagaaca taccaaataa ttagaagaac 185520
tctaaaacaa gcatttgctg attgcacagt aattctctgt gaacacagga tagaagcaat 185580
gctggaatgc caacaatttt tggtgagtct ttataacttt acttaagatc tcattgccct 185640
tgtaattctt gataacaatc tcacatgtga tagttcctgc aaattgcaac aatgtacaag 185700
ttcttttcaa aaatatgtat catacagcca tccagcttta ctcaaaatag ctgcacaagt 185760
ttttcacttt gatctgagcc atgtggtgag gttgaaatat agtaaatcta aaatggcagc 185820
atattactaa gttatgttta taaataggat atatatactt tttgagccct ttatttgggg 185880
accaagtcat acaaaatact ctactgttta agattttaaa aaaggtccct gtgattcttt 185940
caataactaa atgtcccatg gatgtggtct gggacaggcc tagttgtctt acagtctgat 186000
ttatggtatt aatgacaaag ttgagaggca catttcattt ttctagccat gatttgggtt 186060
caggtagtac ctttctcaac caccttctca ctgttcttaa aaaaactgtc acatggccag 186120
gcacagtggc ttacatctgt aatcccaata ctttgggagg ctgaggtggg gggattactt 186180
gaggccagga attcaagacc agcccaggca acatagtgag gccccatctg tctttattaa 186240
aacaaaacaa aactgtcaca gcttctttca agtgatgttt acaaattccc tatggtttag 186300
tcacaaggaa gttctgagga tgatgtatca cgtcatttct gttcaggctt ttgagcctcc 186360
tggaggtaaa tggtttcctt actgaaggct tgttattacc atgattatca ctaagcttga 186420
agtaacaaat tagggggca gactcacaac ctcttgccct gccatggaca agttcaagaa 186480
tctaagtaaa gtcctctatt gtctgatctt ggatttgctc aacctgaaca agccaaggag 186540
gtgtattaaa ctcaggcaca tcctgaccaa tttggaattc ttaagcttca gatcactgtg 186600
gaagaggctc aactctttat ggtgctgtag acttacgctc attttctagg taatttataa 186660
gggacctaat attttgtttt caaagcaact tcagttctac taaacctccc tgaagaatct 186720
tccagctgct gagtagaaaa tcacaactaa tttcacagat ggtagaacct ccttagagca 186780
aaaggacaca gcagttaaat gtgacatacc tgattgttca aaatgcaagg ctctggacat 186840
tgcattcttt gacttttatt ttcctttgag cctgtgccag tttctgtccc tgctctggtc 186900
tgacctgcct tctgtcccag atctcactaa cagccatttc cctaggtcat agaagagaac 186960
aaagtgcggc agtacgattc catccagaaa ctgctgaacg agaggagcct cttccggcaa 187020
gccatcagcc cctccgacag ggtgaagctc tttccccacc ggaactcaag caagtgcaag 187080
tctaagcccc agattgctgc tctgaaagag gagacagaag aagaggtgca agatacaagg 187140
ctttagagag cagcataaat gttgacatgg gacatttgct catggaattg gagctcgtgg 187200
gacagtcacc tcatggaatt ggagctcgtg gaacagttac ctctgcctca gaaaacaagg 187260
atgaattaag tttttttta aaaaagaaac atttggtaag gggaattgag gacactgata 187320
tgggtcttga taaatggctt cctggcaata gtcaaattgt gtgaaaggta cttcaaatcc 187380
ttgaagattt accacttgtg ttttgcaagc cagattttcc tgaaaaccct tgccatgtgc 187440
tagtaattgg aaaggcagct ctaaatgtca atcagcctag ttgatcagct tattgtctag 187500
tgaaactcgt taatttgtag tgttggagaa gaactgaaat catacttctt agggttatga 187560
ttaagtaatg ataactggaa acttcagcgg tttatataag cttgtattcc tttttctctc 187620
ctctccccat gatgtttaga aacacaacta tattgtttgc taagcattcc aactatctca 187680
tttccaagca agtattagaa taccacagga accacaagac tgcacatcaa aatatgcccc 187740
attcaacatc tagtgagcag tcaggaaaga gaacttccag atcctggaaa tcagggttag 187800
tattgtccag gtctaccaaa aatctcaata tttcagataa tcacaataca tcccttacct 187860
gggaaagggc tgttataatc tttcacaggg gacaggatgg ttcccttgat gaagaagttg 187920
atatgccttt tcccaactcc agaaagtgac aagctcacag acctttgaac tagagtttag 187980
ctggaaaagt atgttagtgc aaattgtcac aggacagccc ttctttccac agaagctcca 188040
ggtagagggt gtgtaagtag ataggccatg ggcactgtgg gtagacacac atgaagtcca 188100
agcatttaga tgtataggtt gatggtggta tgttttcagg ctagatgtat gtacttcatg 188160
ctgtctacac taagagagaa tgagagacac actgaagaag caccaatcat gaattagttt 188220
tatatgcttc tgttttataa ttttgtgaag caaaattttt tctctaggaa atatttattt 188280
taataatgtt tcaaacatat ataacaatgc tgtattttaa aagaatgatt atgaattaca 188340
tttgtataaa ataattttta tatttgaaat attgactttt tatggcacta gtatttctat 188400
gaaatattat gttaaaactg ggacagggga gaacctaggg tgatattaac caggggccat 188460
gaatcacctt ttggtctgga gggaagcctt ggggctgatg cagttgttgc ccacagctgt 188520
atgattccca gccagcacag cctcttagat gcagttctga agaagatggt accaccagtc 188580
tgactgtttc catcaagggt acactgcctt ctcaactcca aactgactct taagaagact 188640
gcattatatt tattactgta agaaaatatc acttgtcaat aaaatccata catttgtgtg 188700
aaa 188703

<210> SEQ ID NO 2
<211> LENGTH: 6130
<212> TYPE: DNA
<213> ORGANISM: Homo sapiens

<400> SEQUENCE: 2
aattggaagc aaatgacatc acagcaggtc agagaaaaag ggttgagcgg caggcaccca 60
gagtagtagg tctttggcat taggagcttg agcccagacg gccctagcag ggaccccagc 120
gcccgagaga ccatgcagag gtcgcctctg gaaaaggcca gcgttgtctc caaacttttt 180
ttcagctgga ccagaccaat tttgaggaaa ggatacagac agcgcctgga attgtcagac 240
atataccaaa tcccttctgt tgattctgct gacaatctat ctgaaaaatt ggaaagagaa 300
tgggatagag agctggcttc aaagaaaaat cctaaactca ttaatgccct tcggcgatgt 360
tttttctgga gatttatgtt ctatggaatc tttttatatt taggggaagt caccaaagca 420
gtacagcctc tcttactggg aagaatcata gcttcctatg acccggataa caaggaggaa 480
cgctctatcg cgatttatct aggcataggc ttatgccttc tctttattgt gaggacactg 540
ctcctacacc cagccatttt tggccttcat cacattggaa tgcagatgag aatagctatg 600
tttagtttga tttataagaa gactttaaag ctgtcaagcc gtgttctaga taaaataagt 660
attggacaac ttgttagtct cctttccaac aacctgaaca aatttgatga aggacttgca 720
ttggcacatt tcgtgtggat cgctcctttg caagtggcac tcctcatggg gctaatctgg 780
gagttgttac aggcgtctgc cttctgtgga cttggtttcc tgatagtcct tgcccttttt 840
caggctgggc tagggagaat gatgatgaag tacagagatc agagagctgg gaagatcagt 900
gaaagacttg tgattacctc agaaatgatt gaaaatatcc aatctgttaa ggcatactgc 960
tgggaagaag caatggaaaa aatgattgaa aacttaagac aaacagaact gaaactgact 1020
cggaaggcag cctatgtgag atacttcaat agctcagcct tcttcttctc agggttcttt 1080
gtggtgtttt tatctgtgct tccctatgca ctaatcaaag gaatcatcct ccggaaaata 1140
ttcaccacca tctcattctg cattgttctg cgcatggcgg tcactcggca atttccctgg 1200

```
gctgtacaaa catggtatga ctctcttgga gcaataaaca aaatacagga tttcttacaa   1260
aagcaagaat ataagacatt ggaatataac ttaacgacta cagaagtagt gatggagaat   1320
gtaacagcct tctgggagga gggatttggg gaattatttg agaaagcaaa acaaaacaat   1380
aacaatagaa aaacttctaa tggtgatgac agcctcttct tcagtaattt ctcacttctt   1440
ggtactcctg tcctgaaaga tattaatttc aagatagaaa gaggacagtt gttggcggtt   1500
gctggatcca ctggagcagg caagacttca cttctaatga tgattatggg agaactggag   1560
ccttcagagg gtaaaattaa gcacagtgga agaatttcat tctgttctca gttttcctgg   1620
attatgcctg gcaccattaa agaaaatatc atctttggtg tttcctatga tgaatataga   1680
tacagaagcg tcatcaaagc atgccaacta gaagaggaca tctccaagtt tgcagagaaa   1740
gacaatatag ttcttggaga aggtggaatc acactgagtg gaggtcaacg agcaagaatt   1800
tctttagcaa gagcagtata caaagatgct gatttgtatt tattagactc tccttttgga   1860
tacctagatg ttttaacaga aaaagaaata tttgaaagct gtgtctgtaa actgatggct   1920
aacaaaacta ggattttggt cacttctaaa atggaacatt taaagaaagc tgacaaaata   1980
ttaattttgc atgaaggtag cagctatttt tatgggacat tttcagaact ccaaaatcta   2040
cagccagact ttagctcaaa actcatggga tgtgattctt tcgaccaatt tagtgcagaa   2100
agaagaaatt caatcctaac tgagacctta caccgtttct cattagaagg agatgctcct   2160
gtctcctgga cagaaacaaa aaaacaatct tttaaacaga ctggagagtt tggggaaaaa   2220
aggaagaatt ctattctcaa tccaatcaac tctatacgaa aattttccat tgtgcaaaag   2280
actcccttac aaatgaatgg catcgaagag gattctgatg agcctttaga gagaaggctg   2340
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgctt ttttgatgat   2640
atggagagca taccagcagt gactacatgg aacacatacc ttcgatatat tactgtccac   2700
aagagcttaa tttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgacctt ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gagcatattt cctccaaacc   3240
tcacagcaac tcaaacaact ggaatctgaa ggcaggagtc caattttcac tcatcttgtt   3300
acaagcttaa aaggactatg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttaccttc   3480
atttccattt taacaacagg agaaggagaa ggaagagttg gtattatcct gactttagcc   3540
atgaatatca tgagtacatt gcagtgggct gtaaactcca gcatagatgt ggatagcttg   3600
```

atgcgatctg tgagccgagt ctttaagttc attgacatgc caacagaagg taaacctacc 3660
aagtcaacca aaccatacaa gaatggccaa ctctcgaaag ttatgattat tgagaattca 3720
cacgtgaaga aagatgacat ctggccctca gggggccaaa tgactgtcaa agatctcaca 3780
gcaaaataca cagaaggtgg aaatgccata ttagagaaca tttccttctc aataagtcct 3840
ggccagaggg tgggcctctt gggaagaact ggatcaggga agagtacttt gttatcagct 3900
tttttgagac tactgaacac tgaaggagaa atccagatcg atggtgtgtc ttgggattca 3960
ataactttgc aacagtggag gaaagccttt ggagtgatac cacagaaagt atttattttt 4020
tctggaacat ttagaaaaaa cttggatccc tatgaacagt ggagtgatca agaaatatgg 4080
aaagttgcag atgaggttgg gctcagatct gtgatagaac agtttcctgg gaagcttgac 4140
tttgtccttg tggatggggg ctgtgtccta agccatggcc acaagcagtt gatgtgcttg 4200
gctagatctg ttctcagtaa ggcgaagatc ttgctgcttg atgaacccag tgctcatttg 4260
gatccagtaa cataccaaat aattagaaga actctaaaac aagcatttgc tgattgcaca 4320
gtaattctct gtgaacacag gatagaagca atgctggaat gccaacaatt tttggtcata 4380
gaagagaaca aagtgcggca gtacgattcc atccagaaac tgctgaacga gaggagcctc 4440
ttccggcaag ccatcagccc ctccgacagg gtgaagctct ttccccaccg gaactcaagc 4500
aagtgcaagt ctaagcccca gattgctgct ctgaaagagg agacagaaga agaggtgcaa 4560
gatacaaggc tttagagagc agcataaatg ttgacatggg acatttgctc atggaattgg 4620
agctcgtggg acagtcacct catggaattg gagctcgtgg aacagttacc tctgcctcag 4680
aaaacaagga tgaattaagt ttttttttaa aaaagaaaca tttggtaagg ggaattgagg 4740
acactgatat gggtcttgat aaatggcttc ctggcaatag tcaaattgtg tgaaaggtac 4800
ttcaaatcct tgaagattta ccacttgtgt tttgcaagcc agattttcct gaaaaccctt 4860
gccatgtgct agtaattgga aaggcagctc taaatgtcaa tcagcctagt tgatcagctt 4920
attgtctagt gaaactcgtt aatttgtagt gttggagaag aactgaaatc atacttctta 4980
gggttatgat taagtaatga taactggaaa cttcagcggt ttatataagc ttgtattcct 5040
ttttctctcc tctccccatg atgtttagaa acacaactat attgtttgct aagcattcca 5100
actatctcat ttccaagcaa gtattagaat accacaggaa ccacaagact gcacatcaaa 5160
atatgcccca ttcaacatct agtgagcagt caggaaagag aacttccaga tcctggaaat 5220
cagggttagt attgtccagg tctaccaaaa atctcaatat ttcagataat cacaatacat 5280
cccttacctg ggaaagggct gttataatct ttcacagggg acaggatggt tcccttgatg 5340
aagaagttga tatgcctttt cccaactcca gaaagtgaca agctcacaga cctttgaact 5400
agagtttagc tggaaaagta tgttagtgca aattgtcaca ggacagccct tctttccaca 5460
gaagctccag gtagagggtg tgtaagtaga taggccatgg gcactgtggg tagacacaca 5520
tgaagtccaa gcatttagat gtataggttg atggtggtat gttttcaggc tagatgtatg 5580
tacttcatgc tgtctacact aagagagaat gagagacaca ctgaagaagc accaatcatg 5640
aattagtttt atatgcttct gttttataat tttgtgaagc aaaatttttt ctctaggaaa 5700
tatttatttt aataatgttt caaacatata ttacaatgct gtattttaaa agaatgatta 5760
tgaattacat ttgtataaaa taatttttat atttgaaata ttgacttttt atggcactag 5820
tatttttatg aaatattatg ttaaaactgg gacaggggag aacctagggt gatattaacc 5880
aggggccatg aatcaccttt tggtctggag ggaagccttg gggctgatcg agttgttgcc 5940
cacagctgta tgattcccag ccagacacag cctcttagat gcagttctga agaagatggt 6000
accaccagtc tgactgtttc catcaagggt acactgcctt ctcaactcca aactgactct 6060
taagaagact gcattatatt tattactgta agaaaatatc acttgtcaat aaaatccata 6120
catttgtgta 6130

<210> SEQ ID NO 3
<211> LENGTH: 1477
<212> TYPE: PRT
<213> ORGANISM: Homo sapiens

<400> SEQUENCE: 3

Met Gln Arg Ser Pro Leu Glu Lys Ala Ser Val Val Ser Lys Leu Phe
1 5 10 15

Phe Ser Trp Thr Arg Pro Ile Leu Arg Lys Gly Tyr Arg Gln Arg Leu
20 25 30

Glu Leu Ser Asp Ile Tyr Gln Ile Pro Ser Val Asp Ser Ala Asp Asn
35 40 45

Leu Ser Glu Lys Leu Glu Arg Glu Trp Asp Arg Glu Leu Ala Ser Lys
50 55 60

Lys Asn Pro Lys Leu Ile Asn Ala Leu Arg Arg Cys Phe Phe Trp Arg
65 70 75 80

Phe Met Phe Tyr Gly Ile Phe Leu Tyr Leu Gly Glu Val Thr Lys Ala
85 90 95

Val Gln Pro Leu Leu Leu Gly Arg Ile Ile Ala Ser Tyr Asp Pro Asp
100 105 110

Asn Lys Glu Glu Arg Ser Ile Ala Ile Tyr Leu Gly Ile Gly Cys Phe
115 120 125

Ile Val Arg Thr Leu Leu Leu His Pro Ala Ile Phe Gly Leu His His
130 135 140

Ile Gly Met Gln Met Arg Ile Ala Met Phe Ser Leu Ile Tyr Lys Lys
145 150 155 160

Thr Leu Lys Leu Ser Ser Arg Val Leu Asp Lys Ile Ser Ile Gly Gln
165 170 175

Leu Val Ser Leu Leu Ser Asn Asn Leu Asn Lys Phe Asp Glu Gly Leu
180 185 190

Ala Leu Ala His Phe Val Trp Ile Ala Pro Leu Gln Val Ala Leu Leu
195 200 205

Met Gly Leu Ile Trp Glu Leu Leu Gln Ala Ser Ala Phe Cys Gly Leu
210 215 220

Gly Phe Leu Ile Val Leu Ala Leu Phe Gly Ala Gly Leu Gly Arg Met
225 230 235 240

Met Met Lys Tyr Arg Asp Gln Arg Ala Gly Lys Ile Ser Glu Arg Leu
245 250 255

Val Ile Thr Ser Glu Met Ile Glu Asn Ile Gln Ser Val Lys Ala Tyr
260 265 270

Cys Trp Glu Glu Ala Met Glu Lys Met Ile Glu Asn Leu Arg Gln Thr
275 280 285

Glu Leu Lys Leu Thr Arg Lys Ala Ala Tyr Val Arg Tyr Phe Asn Ser
290 295 300

Ser Ala Phe Phe Phe Ser Gly Phe Phe Val Val Phe Leu Ser Val Leu
305 310 315 320

Pro Tyr Ala Leu Ile Lys Gly Ile Ile Leu Arg Lys Ile Phe Thr Thr
325 330 335

Ile Ser Phe Cys Ile Val Leu Arg Met Ala Val Thr Arg Gln Phe Pro
340 345 350

```
Trp Ala Val Gln Thr Trp Tyr Asp Ser Leu Gly Ala Ile Asn Lys Ile
        355                 360                 365

Gln Asp Phe Leu Gln Lys Gln Glu Tyr Lys Thr Leu Glu Tyr Asn Leu
    370                 375                 380

Thr Thr Thr Glu Val Val Met Glu Asn Val Thr Ala Phe Trp Glu Glu
385                 390                 395                 400

Gly Phe Gly Glu Leu Phe Glu Lys Ala Lys Gln Asn Asn Asn Asn Arg
                405                 410                 415

Lys Thr Ser Asn Gly Asp Asp Ser Leu Phe Phe Ser Asn Phe Ser Leu
            420                 425                 430

Leu Gly Thr Pro Val Leu Lys Asp Ile Asn Phe Lys Ile Glu Arg Gly
        435                 440                 445

Gln Leu Leu Ala Val Ala Gly Ser Thr Gly Ala Gly Lys Thr Ser Leu
    450                 455                 460

Leu Met Met Ile Met Gly Glu Leu Glu Pro Ser Glu Gly Lys Ile Lys
465                 470                 475                 480

His Ser Gly Arg Ile Ser Phe Cys Ser Gln Phe Ser Trp Ile Met Pro
                485                 490                 495

Gly Thr Ile Lys Glu Asn Ile Ile Phe Gly Val Ser Tyr Asp Glu Tyr
            500                 505                 510

Arg Tyr Arg Ser Val Ile Lys Ala Cys Gln Leu Glu Glu Asp Ile Ser
        515                 520                 525

Lys Phe Ala Glu Lys Asp Asn Ile Val Leu Gly Glu Gly Gly Ile Thr
    530                 535                 540

Leu Ser Gly Gly Gln Arg Ala Arg Ile Ser Leu Ala Arg Ala Val Tyr
545                 550                 555                 560

Lys Asp Ala Asp Leu Tyr Leu Leu Asp Ser Pro Phe Gly Tyr Leu Asp
                565                 570                 575

Val Leu Thr Glu Lys Glu Ile Phe Glu Ser Cys Val Cys Lys Leu Met
            580                 585                 590

Ala Asn Lys Thr Arg Ile Leu Val Thr Ser Lys Met Glu His Leu Lys
        595                 600                 605

Lys Ala Asp Lys Ile Leu Ile Leu His Glu Gly Ser Ser Tyr Phe Tyr
    610                 615                 620

Gly Thr Phe Ser Glu Leu Gln Asn Leu Gln Pro Asp Phe Ser Ser Lys
625                 630                 635                 640

Leu Met Gly Cys Asp Ser Phe Asp Gln Phe Ser Ala Glu Arg Arg Asn
                645                 650                 655

Ser Ile Leu Thr Glu Thr Leu His Arg Phe Ser Leu Glu Gly Asp Ala
            660                 665                 670

Pro Val Ser Trp Thr Glu Thr Lys Lys Gln Ser Phe Lys Gln Thr Gly
        675                 680                 685

Glu Phe Gly Glu Lys Arg Lys Asn Ser Ile Leu Asn Pro Ile Asn Ser
    690                 695                 700

Ile Arg Lys Phe Ser Ile Val Gln Lys Thr Pro Leu Gln Met Asn Gly
705                 710                 715                 720

Ile Glu Glu Asp Ser Asp Glu Pro Leu Glu Arg Arg Leu Ser Leu Val
                725                 730                 735

Pro Asp Ser Glu Gln Gly Glu Ala Ile Leu Pro Arg Ile Ser Val Ile
            740                 745                 750

Ser Thr Gly Pro Thr Leu Gln Ala Arg Arg Arg Gln Ser Val Leu Asn
        755                 760                 765

Leu Met Thr His Ser Val Asn Gln Gly Gln Asn Ile His Arg Lys Thr
```

```
    770                 775                 780

Thr Ala Ser Thr Arg Lys Val Ser Leu Ala Pro Gln Ala Asn Leu Thr
785                 790                 795                 800

Glu Leu Asp Ile Tyr Ser Arg Arg Leu Ser Gln Glu Thr Gly Leu Glu
                805                 810                 815

Ile Ser Glu Glu Ile Asn Glu Glu Asp Leu Lys Glu Cys Phe Phe Asp
            820                 825                 830

Asp Met Glu Ser Ile Pro Ala Val Thr Thr Trp Asn Thr Tyr Leu Arg
        835                 840                 845

Tyr Ile Thr Val His Lys Ser Leu Ile Phe Val Leu Ile Trp Cys Leu
    850                 855                 860

Val Ile Phe Leu Ala Glu Val Ala Ala Ser Leu Val Val Leu Trp Leu
865                 870                 875                 880

Leu Gly Asn Thr Pro Leu Gln Asp Lys Gly Asn Ser Thr His Ser Arg
                885                 890                 895

Asn Asn Ser Tyr Ala Val Ile Ile Thr Ser Thr Ser Ser Tyr Tyr Val
            900                 905                 910

Phe Tyr Ile Tyr Val Gly Val Ala Asp Thr Leu Leu Ala Met Gly Phe
        915                 920                 925

Phe Arg Gly Leu Pro Leu Val His Thr Leu Ile Thr Val Ser Lys Ile
    930                 935                 940

Leu His His Lys Met Leu His Ser Val Leu Gln Ala Pro Met Ser Thr
945                 950                 955                 960

Leu Asn Thr Leu Lys Ala Gly Gly Ile Leu Asn Arg Phe Ser Lys Asp
                965                 970                 975

Ile Ala Ile Leu Asp Asp Leu Leu Pro Leu Thr Ile Phe Asp Phe Ile
            980                 985                 990

Gln Leu Leu Leu Ile Val Ile Gly  Ala Ile Ala Val Val  Ala Val Leu
        995                 1000                 1005

Gln Pro  Tyr Ile Phe Val Ala  Thr Val Pro Val Ile  Val Ala Phe
    1010                 1015                 1020

Ile Met  Leu Arg Ala Tyr Phe  Leu Gln Thr Ser Gln  Gln Leu Lys
    1025                 1030                 1035

Gln Leu  Glu Ser Glu Gly Arg  Ser Pro Ile Phe Thr  His Leu Val
    1040                 1045                 1050

Thr Ser  Leu Lys Gly Leu Trp  Thr Leu Arg Ala Phe  Gly Arg Gln
    1055                 1060                 1065

Pro Tyr  Phe Glu Thr Leu Phe  His Lys Ala Leu Asn  Leu His Thr
    1070                 1075                 1080

Ala Asn  Trp Phe Leu Tyr Leu  Ser Thr Leu Arg Trp  Phe Gln Met
    1085                 1090                 1095

Arg Ile  Glu Met Ile Phe Val  Ile Phe Phe Ile Ala  Val Thr Phe
    1100                 1105                 1110

Ile Ser  Ile Leu Thr Thr Gly  Glu Gly Glu Gly Arg  Val Gly Ile
    1115                 1120                 1125

Ile Leu  Thr Leu Ala Met Asn  Ile Met Ser Thr Leu  Gln Trp Ala
    1130                 1135                 1140

Val Asn  Ser Ser Ile Asp Val  Asp Ser Leu Met Arg  Ser Val Ser
    1145                 1150                 1155

Arg Val  Phe Lys Phe Ile Asp  Met Pro Thr Glu Gly  Lys Pro Thr
    1160                 1165                 1170

Lys Ser  Thr Lys Pro Tyr Lys  Asn Gly Gln Leu Ser  Lys Val Met
    1175                 1180                 1185
```

-continued

Ile Ile Glu Asn Ser His Val Lys Lys Asp Asp Ile Trp Pro Ser
1190 1195 1200

Gly Gly Gln Met Thr Val Lys Asp Leu Thr Ala Lys Tyr Thr Glu
1205 1210 1215

Gly Gly Asn Ala Ile Leu Glu Asn Ile Ser Phe Ser Ile Ser Pro
1220 1225 1230

Gly Gln Arg Val Gly Leu Leu Gly Arg Thr Gly Ser Gly Lys Ser
1235 1240 1245

Thr Leu Leu Ser Ala Phe Leu Arg Leu Leu Asn Thr Glu Gly Glu
1250 1255 1260

Ile Gly Ile Asp Gly Val Ser Trp Asp Ser Ile Thr Leu Gln Gln
1265 1270 1275

Trp Arg Lys Ala Phe Gly Val Ile Pro Gln Lys Val Phe Ile Phe
1280 1285 1290

Ser Gly Thr Phe Arg Lys Asn Leu Asp Pro Tyr Glu Gln Trp Ser
1295 1300 1305

Asp Gln Glu Ile Trp Lys Val Ala Asp Glu Val Gly Leu Arg Ser
1310 1315 1320

Val Ile Glu Gln Phe Pro Gly Lys Leu Asp Phe Val Leu Val Asp
1325 1330 1335

Gly Gly Cys Val Leu Ser His Gly His Lys Gln Leu Met Cys Leu
1340 1345 1350

Ala Arg Ser Val Leu Ser Lys Ala Lys Ile Leu Leu Leu Asp Glu
1355 1360 1365

Pro Ser Ala His Leu Asp Pro Val Thr Tyr Gln Ile Ile Arg Arg
1370 1375 1380

Thr Leu Lys Gln Ala Phe Ala Asp Cys Thr Val Ile Leu Cys Glu
1385 1390 1395

His Arg Ile Glu Ala Met Leu Glu Cys Gln Gln Phe Leu Val Ile
1400 1405 1410

Glu Glu Asn Lys Val Arg Gln Tyr Asp Ser Ile Gln Lys Leu Leu
1415 1420 1425

Asn Glu Arg Ser Leu Phe Arg Gln Ala Ile Ser Pro Ser Asp Arg
1430 1435 1440

Val Lys Leu Phe Pro His Arg Asn Ser Ser Lys Cys Lys Ser Lys
1445 1450 1455

Pro Gln Ile Ala Ala Leu Lys Glu Glu Thr Glu Glu Glu Val Gln
1460 1465 1470

Asp Thr Arg Leu
1475

<210> SEQ ID NO 4
<211> LENGTH: 4389
<212> TYPE: DNA
<213> ORGANISM: Homo sapiens

<400> SEQUENCE: 4
gaattcaaag gaaaacataa gatgcaattc gtgcctccaa ggaggttgta gggaagaggg 60
gttatgaatg tatgtaaata gaagttggtg tgcgtgtgtg tttataaaca gaattgtcag 120
accaaacatt attttggaag cagtaaaagt aaactagaat ctggcctagt catgtcccag 180
gacacctctt tcaagtcctg aaacatcttt gtaagactgt aatgtgtgtt tacatcctag 240
gtaatcactg tggcccactg ttgaagagct gtggctgttc ttacccttct agttagataa 300
acttataagc acaaccagac tacatatatg aagctgaaga gaccttgtct tttttaacg 360

-continued

```
agcttttctt cccgatagga gtgactattt cttttcttct tccacatttt caggttttag    420
tgtacttgtg attgctaccc acttatcact attaaagtct actcaggaga gaatctgaga    480
aacactctca aattaagttg aacatgatgg ataagtaaag tattgtgaaa gttcactctc    540
atgatttcta atggtgaaac ctggcagggt gactaatctt tgacgagaag gttatcactt    600
ataatctttc atatattgag atcatttgta agaagcaccc agcacattgc tgaacacaaa    660
gtaggtatta aataaatgtt ggcttccttt tctcctactc atcctcgctc ttctttttaa    720
tataccttta aaatgatgcc acagaaatgg ccacccaatc ttctatattt aaggtcagtt    780
cttgcattag gaaattctat aggggaagta tgtgaagtat gtgtagtcag tcattaaatg    840
cttgggctct ggccacagat tgtttaggtt taaatcccag tttcctcttt tattattaat    900
tgtgcaactt gcttgggaaa acatgaaact tgtttttcct caggttcatt atctgtaata    960
tatagtgaat gaagaagttt cctgtcccat gaaggtgttg taaagattaa aaaaggcaaa   1020
ttaggctgtg tatttgtcat aataattggc atatatggta agtgaccaac aaccataagg   1080
tattataaaa ttgttataaa atgatatgag ctatcattga gcagcatgaa agaagagctt   1140
cactgtttca cctactatca ccctggccca ttaatctctt tcctgttcct gacatttcag   1200
agatacgttt aggatttcaa tcatgacctt aagccacatt tgaacaattt tctggtggat   1260
aagtcctcat tcccacatta tgtatgtacc tagatgcaaa tcctgaatat catgtcgcaa   1320
ttagtgcatc tggacatgct tgctaactgt gttaaagctc tgaataatgg taaagtttta   1380
tttctaccaa aacaaatttg ggctgtaatg ttttatgata aaaatctgtg gtcttcctat   1440
gtacatgtgt gtgtacatgc ttaaaatgca atgttatagt taaatgtaat tcattaaaag   1500
tatgtaactc cagtggctac ttagtttggc tacttggttt gtagatttct gctttcctgt   1560
ttcattgtta aacaggtcta gaagttatta tttcatgaaa ctaatgtgag gaaaaagact   1620
atgttgatat ataagtgaca ttatataaat acatgaggga tgatttgatt agaagcagta   1680
ttacacagtg ataggagtaa tggtttagaa ctagactcag gtttgaatct tagctctatc   1740
attataggca tttacttaac ttttcttgtt tgcttaactg aaaactgaag ataataacac   1800
ctatttacat ggttgttata agggttatat gaataatgtc tggcaaatag taagaactca   1860
agtaactgtt tcactctttc cagaaggaga ttggctgaaa aatatttgga gtctcctcca   1920
gccatattcc ttggtcagct tctatgatcc tctttggagc ttaattctta atccctttat   1980
tttcacttgc ttgttgataa caaagaagaa ctaattatta atttatttca aaatgcatgt   2040
attatatttg atgggccaca ctaacagtta taaaccaaac aacagattgg gaatggggaa   2100
gtggatgtgg tgagttcaat cacatgtctg ggaaaagtca atagtgaaga cagagtctca   2160
caatttttg tcataatgga gagatgaaaa cacaggtaga ggatttcaaa caacagagtg   2220
gatggtgagt taaaaatgct gaaattcttt cctggtgtct aacttaatgc aatgtggttt   2280
atctctttgc tcttttctct actattcaaa tttaggataa taaagattaa atgtttctaa   2340
atcttacttt acaatatcaa gaaaaaaagg tatgcttttg cccacggaag ggcaaagcag   2400
agctatgaaa acctgctgaa cacattcttt attttcaaca caggttcttg tctttccatc   2460
atgaaatgca cattttattt gtactgtatt tgggtgacca caagtcaaca acaagataat   2520
tcacaagacc cttgccttag atgtgtcggc aataaagtaa tcaggccaaa atttttactt   2580
tcctttgaat ttttcaattc aaacacaatg tatgcttgct tttacacagt agggttcagg   2640
gattagaggg ttggctcctt taaaaccgtc agagacacag gcaatcctac acaaaattct   2700
cagaaggaag gcgcctacgc ctgggaatgc ccagatgccc ctcagagagt tgaagatggc   2760
```

gtttctctga gtcaggtcaa agttaacaca ttaccttcgc ttcaaagact gcttggcttc 2820
ctttcggtgg attagtcaag atgttttgct gactgagact aggaaatcta taggagggcg 2880
ggttagttta cattgttcct tgtcattatc gctaaaacac tccaaagcct tccttaaaaa 2940
tgcgcactgg gctaaaaagg atagacaagg aacacatcct gggccggtaa ttacgcaaag 3000
cattatctcc tcttacctcc ttgcagattt ttttttctct ttcagtacgt gtcctaagat 3060
ttctgtgcca cccttggagt tcactcacct aaacctgaaa ctaataaagc ttggttcttt 3120
tctccgacac gcaaaggaag cgctaaggta aatgcatcag acccacactg ccgcggaact 3180
tttcggctct ctaaggctgt attttgatat acgaaaggca cattttcctt ccctttttcaa 3240 aatgcacctt gcaaacgtaa caggaacccg actaggatca tcgggaaaag gaggaggagg 3300
aggaaggcag gctccgggga agctggtggc agcgggtcct gggtctggcg gaccctgacg 3360
cgaaggaggg tctaggaagc tctccgggga gccggttctc ccgccggtgg cttcttctgt 3420
cctccagcgt tgccaactgg acctaaagag aggccgcgac tgtcgcccac ctgcgggatg 3480
ggcctggtgc tgggcggtca ggacactgac ctggaaggag cgcgcgcgag ggagggaggc 3540
tgggagtcag aatcgggaaa gggaggtgcg gggcggcgag ggagcgaagg aggagaggag 3600
gaaggagcgg gaggggtgct ggcgggggtg cgtagtgggt ggagaaagcc gctagagcaa 3660
atttggggcc ggaccaggca gcactcggct tttaacctgg gcagtgaagg cgggggaaag 3720
agcaaaagga aggggtggtg tgcggagtag gggtgggtgg ggggaattgg aagcaaatga 3780
catcacagca ggtcagagaa aaagggttga gcggcaggca cccagagtag taggtctttg 3840
gcattaggag cttgagccca gacggcccta gcagggaccc cagcgcccga gagaccatgc 3900
agaggtcgcc tctggaaaag gccagcgttg tctccaaact ttttttcagg tgagaaggtg 3960
gccaaccgag cttcggaaag acacgtgccc acgaaagagg agggcgtgtg tatgggttgg 4020
gtttggggta aaggaataag cagtttttaa aaagatgcgc tatcattcat tgttttgaaa 4080
gaaaatgtgg gtattgtaga ataaaacaga aagcattaag aagagatgga agaatgaact 4140
gaagctgatt gaatagagag ccacatctac ttgcaactga aaagttagaa tctcaagact 4200
caagtacgct actatgcact tgttttattt catttttcta agaaactaaa aatacttgtt 4260
aataagtacc taagtatggt ttattggttt tccccccttca tgccttggac acttgattgt 4320
cttcttggca catacaggtg ccatgcctgc atatagtaag tgctcagaaa acatttcttg 4380
actgaattc 4389

<210> SEQ ID NO 5
<211> LENGTH: 19
<212> TYPE: DNA
<213> ORGANISM: Homo sapiens

<400> SEQUENCE: 5
tttaacctgg gcagtgaag 19

<210> SEQ ID NO 6
<211> LENGTH: 17
<212> TYPE: DNA
<213> ORGANISM: Homo sapiens

<400> SEQUENCE: 6
aacccaaccc atacaca 17

<210> SEQ ID NO 7
<211> LENGTH: 22
<212> TYPE: DNA

-continued

<213> ORGANISM: Homo sapiens

<400> SEQUENCE: 7
caaatcaagt gaatatctgt tc 22

<210> SEQ ID NO 8
<211> LENGTH: 21
<212> TYPE: DNA
<213> ORGANISM: Homo sapiens

<400> SEQUENCE: 8
agccaccata cttggctcct a 21

<210> SEQ ID NO 9
<211> LENGTH: 22
<212> TYPE: DNA
<213> ORGANISM: Homo sapiens

<400> SEQUENCE: 9
ctaaaatatt tgcacatgca ac 22

<210> SEQ ID NO 10
<211> LENGTH: 21
<212> TYPE: DNA
<213> ORGANISM: Homo sapiens

<400> SEQUENCE: 10
tttcttagtg tttggagttg g 21

<210> SEQ ID NO 11
<211> LENGTH: 22
<212> TYPE: DNA
<213> ORGANISM: Homo sapiens

<400> SEQUENCE: 11
tcattttaag tctcctctaa ag 22

<210> SEQ ID NO 12
<211> LENGTH: 21
<212> TYPE: DNA
<213> ORGANISM: Homo sapiens

<400> SEQUENCE: 12
cgatacagaa tatatgtgcc a 21

<210> SEQ ID NO 13
<211> LENGTH: 20
<212> TYPE: DNA
<213> ORGANISM: Homo sapiens

<400> SEQUENCE: 13
aacaactaga agcatgccag 20

<210> SEQ ID NO 14
<211> LENGTH: 24
<212> TYPE: DNA
<213> ORGANISM: Homo sapiens

<400> SEQUENCE: 14
gttgtataat ttataacaat agtg 24

<210> SEQ ID NO 15
<211> LENGTH: 20
<212> TYPE: DNA

<213> ORGANISM: Homo sapiens

<400> SEQUENCE: 15
ggaagataca atgacacctg 20

<210> SEQ ID NO 16
<211> LENGTH: 21
<212> TYPE: DNA
<213> ORGANISM: Homo sapiens

<400> SEQUENCE: 16
ctgaagatca ctgttctatg c 21

<210> SEQ ID NO 17
<211> LENGTH: 22
<212> TYPE: DNA
<213> ORGANISM: Homo sapiens

<400> SEQUENCE: 17
atgacttaaa accttgagca gt 22

<210> SEQ ID NO 18
<211> LENGTH: 22
<212> TYPE: DNA
<213> ORGANISM: Homo sapiens

<400> SEQUENCE: 18
ggaagtctac catgataaac at 22

<210> SEQ ID NO 19
<211> LENGTH: 21
<212> TYPE: DNA
<213> ORGANISM: Homo sapiens

<400> SEQUENCE: 19
gagaccatgc tcagatcttc c 21

<210> SEQ ID NO 20
<211> LENGTH: 23
<212> TYPE: DNA
<213> ORGANISM: Homo sapiens

<400> SEQUENCE: 20
acttttataa cttcctagtg aag 23

<210> SEQ ID NO 21
<211> LENGTH: 22
<212> TYPE: DNA
<213> ORGANISM: Homo sapiens

<400> SEQUENCE: 21
aagatgtagc acaatgagag ta 22

<210> SEQ ID NO 22
<211> LENGTH: 20
<212> TYPE: DNA
<213> ORGANISM: Homo sapiens

<400> SEQUENCE: 22
cagttaggtg tttagagcaa 20

<210> SEQ ID NO 23
<211> LENGTH: 22
<212> TYPE: DNA

<213> ORGANISM: Homo sapiens

<400> SEQUENCE: 23
gtatacagtg taatggatca tg 22

<210> SEQ ID NO 24
<211> LENGTH: 22
<212> TYPE: DNA
<213> ORGANISM: Homo sapiens

<400> SEQUENCE: 24
caccaaatta agttcttaat ag 22

<210> SEQ ID NO 25
<211> LENGTH: 22
<212> TYPE: DNA
<213> ORGANISM: Homo sapiens

<400> SEQUENCE: 25
ttctgcttag gatgataatt gg 22

<210> SEQ ID NO 26
<211> LENGTH: 22
<212> TYPE: DNA
<213> ORGANISM: Homo sapiens

<400> SEQUENCE: 26
gcataggtca tgtgttttat ta 22

<210> SEQ ID NO 27
<211> LENGTH: 22
<212> TYPE: DNA
<213> ORGANISM: Homo sapiens

<400> SEQUENCE: 27
cagattgagc atactaaaag tg 22

<210> SEQ ID NO 28
<211> LENGTH: 22
<212> TYPE: DNA
<213> ORGANISM: Homo sapiens

<400> SEQUENCE: 28
tacatgaatg acatttacag ca 22

<210> SEQ ID NO 29
<211> LENGTH: 21
<212> TYPE: DNA
<213> ORGANISM: Homo sapiens

<400> SEQUENCE: 29
gctacttctg caccactttt g 21

<210> SEQ ID NO 30
<211> LENGTH: 23
<212> TYPE: DNA
<213> ORGANISM: Homo sapiens

<400> SEQUENCE: 30
cagtctgtct ttcttttatt tta 23

<210> SEQ ID NO 31
<211> LENGTH: 21
<212> TYPE: DNA

<213> ORGANISM: Homo sapiens

<400> SEQUENCE: 31
caaaatgcta aaatacgaga c 21

<210> SEQ ID NO 32
<211> LENGTH: 19
<212> TYPE: DNA
<213> ORGANISM: Homo sapiens

<400> SEQUENCE: 32
tccaggagac aggagcatc 19

<210> SEQ ID NO 33
<211> LENGTH: 20
<212> TYPE: DNA
<213> ORGANISM: Homo sapiens

<400> SEQUENCE: 33
ctcatgggat gtgattcttt 20

<210> SEQ ID NO 34
<211> LENGTH: 22
<212> TYPE: DNA
<213> ORGANISM: Homo sapiens

<400> SEQUENCE: 34
gatacacctt atcctaatcc ta 22

<210> SEQ ID NO 35
<211> LENGTH: 18
<212> TYPE: DNA
<213> ORGANISM: Homo sapiens

<400> SEQUENCE: 35
accacaatgg tggcatga 18

<210> SEQ ID NO 36
<211> LENGTH: 21
<212> TYPE: DNA
<213> ORGANISM: Homo sapiens

<400> SEQUENCE: 36
tgtatacatc cccaaactat c 21

<210> SEQ ID NO 37
<211> LENGTH: 21
<212> TYPE: DNA
<213> ORGANISM: Homo sapiens

<400> SEQUENCE: 37
tgggcatggg aggaataggt g 21

<210> SEQ ID NO 38
<211> LENGTH: 24
<212> TYPE: DNA
<213> ORGANISM: Homo sapiens

<400> SEQUENCE: 38
ttacaataca tacaaacata gtgg 24

<210> SEQ ID NO 39
<211> LENGTH: 16
<212> TYPE: DNA

<213> ORGANISM: Homo sapiens

<400> SEQUENCE: 39
aagtaacttt ggctgc 16

<210> SEQ ID NO 40
<211> LENGTH: 17
<212> TYPE: DNA
<213> ORGANISM: Homo sapiens

<400> SEQUENCE: 40
ctgccattag aaaacca 17

<210> SEQ ID NO 41
<211> LENGTH: 22
<212> TYPE: DNA
<213> ORGANISM: Homo sapiens

<400> SEQUENCE: 41
aagtctatct gattctattt gc 22

<210> SEQ ID NO 42
<211> LENGTH: 25
<212> TYPE: DNA
<213> ORGANISM: Homo sapiens

<400> SEQUENCE: 42
gtttttttaa taatacagac atact 25

<210> SEQ ID NO 43
<211> LENGTH: 19
<212> TYPE: DNA
<213> ORGANISM: Homo sapiens

<400> SEQUENCE: 43
tgtccacttg caatgtgaa 19

<210> SEQ ID NO 44
<211> LENGTH: 24
<212> TYPE: DNA
<213> ORGANISM: Homo sapiens

<400> SEQUENCE: 44
caataaagaa tctcaaatag ctct 24

<210> SEQ ID NO 45
<211> LENGTH: 20
<212> TYPE: DNA
<213> ORGANISM: Homo sapiens

<400> SEQUENCE: 45
tagtcttttt caggtacaag 20

<210> SEQ ID NO 46
<211> LENGTH: 24
<212> TYPE: DNA
<213> ORGANISM: Homo sapiens

<400> SEQUENCE: 46
caatggaaat tcaaagaaat cact 24

<210> SEQ ID NO 47
<211> LENGTH: 23
<212> TYPE: DNA

<213> ORGANISM: Homo sapiens

<400> SEQUENCE: 47
gaatacttac tatatgcaga gca 23

<210> SEQ ID NO 48
<211> LENGTH: 22
<212> TYPE: DNA
<213> ORGANISM: Homo sapiens

<400> SEQUENCE: 48
gttcttcctc atgctattac tc 22

<210> SEQ ID NO 49
<211> LENGTH: 21
<212> TYPE: DNA
<213> ORGANISM: Homo sapiens

<400> SEQUENCE: 49
gcccgacaaa taaccaagtg a 21

<210> SEQ ID NO 50
<211> LENGTH: 21
<212> TYPE: DNA
<213> ORGANISM: Homo sapiens

<400> SEQUENCE: 50
ctaacacatt gcttcaggct a 21

<210> SEQ ID NO 51
<211> LENGTH: 22
<212> TYPE: DNA
<213> ORGANISM: Homo sapiens

<400> SEQUENCE: 51
aaggttgttt gtctccatat at 22

<210> SEQ ID NO 52
<211> LENGTH: 20
<212> TYPE: DNA
<213> ORGANISM: Homo sapiens

<400> SEQUENCE: 52
gcctatgaga aaactgcact 20

<210> SEQ ID NO 53
<211> LENGTH: 20
<212> TYPE: DNA
<213> ORGANISM: Homo sapiens

<400> SEQUENCE: 53
acatgggtgt ttcttattta 20

<210> SEQ ID NO 54
<211> LENGTH: 18
<212> TYPE: DNA
<213> ORGANISM: Homo sapiens

<400> SEQUENCE: 54
gttaggggta ggtccagt 18

<210> SEQ ID NO 55
<211> LENGTH: 23
<212> TYPE: DNA

<213> ORGANISM: Homo sapiens

<400> SEQUENCE: 55
gcttgagtgt ttttaactct gtg 23

<210> SEQ ID NO 56
<211> LENGTH: 21
<212> TYPE: DNA
<213> ORGANISM: Homo sapiens

<400> SEQUENCE: 56
atgattctgt tcccactgtg c 21

<210> SEQ ID NO 57
<211> LENGTH: 21
<212> TYPE: DNA
<213> ORGANISM: Homo sapiens

<400> SEQUENCE: 57
gttctgtgat attatgtgtg g 21

<210> SEQ ID NO 58
<211> LENGTH: 21
<212> TYPE: DNA
<213> ORGANISM: Homo sapiens

<400> SEQUENCE: 58
caagggcaat gagatcttaa g 21

<210> SEQ ID NO 59
<211> LENGTH: 18
<212> TYPE: DNA
<213> ORGANISM: Homo sapiens

<400> SEQUENCE: 59
agtttctgtc cctgctct 18

<210> SEQ ID NO 60
<211> LENGTH: 21
<212> TYPE: DNA
<213> ORGANISM: Homo sapiens

<400> SEQUENCE: 60
gagcaaatgt cccatgtcaa c 21

<210> SEQ ID NO 61
<211> LENGTH: 24
<212> TYPE: DNA
<213> ORGANISM: Homo sapiens

<400> SEQUENCE: 61
aatggtgttt acctacctag agaa 24

<210> SEQ ID NO 62
<211> LENGTH: 19
<212> TYPE: DNA
<213> ORGANISM: Homo sapiens

<400> SEQUENCE: 62
cctcctctga ttccacaag 19

<210> SEQ ID NO 63
<211> LENGTH: 22
<212> TYPE: DNA

<213> ORGANISM: Homo sapiens

<400> SEQUENCE: 63
ctgagattct gttctaggtg tg 22

<210> SEQ ID NO 64
<211> LENGTH: 21
<212> TYPE: DNA
<213> ORGANISM: Homo sapiens

<400> SEQUENCE: 64
cctacactca gaacccatca t 21

<210> SEQ ID NO 65
<211> LENGTH: 21
<212> TYPE: DNA
<213> ORGANISM: Homo sapiens

<400> SEQUENCE: 65
ttcagttgac ttgtcatctt g 21

<210> SEQ ID NO 66
<211> LENGTH: 23
<212> TYPE: DNA
<213> ORGANISM: Homo sapiens

<400> SEQUENCE: 66
aatatgttga aagttaaaca gtg 23

<210> SEQ ID NO 67
<211> LENGTH: 26
<212> TYPE: DNA
<213> ORGANISM: Homo sapiens

<400> SEQUENCE: 67
gttacactat aaaggttgtt ttagac 26

<210> SEQ ID NO 68
<211> LENGTH: 25
<212> TYPE: DNA
<213> ORGANISM: Homo sapiens

<400> SEQUENCE: 68
cacagttccc atattaatag aaatg 25

<210> SEQ ID NO 69
<211> LENGTH: 19
<212> TYPE: DNA
<213> ORGANISM: Homo sapiens

<400> SEQUENCE: 69
tttttaacag ggatttggg 19

<210> SEQ ID NO 70
<211> LENGTH: 20
<212> TYPE: DNA
<213> ORGANISM: Homo sapiens

<400> SEQUENCE: 70
gattgattga ttgattgatt 20

<210> SEQ ID NO 71
<211> LENGTH: 20
<212> TYPE: DNA

-continued

```
<213> ORGANISM: Homo sapiens

<400> SEQUENCE: 71

gcggtcgcat aagggtcagt                                              20


<210> SEQ ID NO 72
<211> LENGTH: 20
<212> TYPE: DNA
<213> ORGANISM: Homo sapiens

<400> SEQUENCE: 72

cgccagcgta ttcccagtca                                              20
```

MUTATIONS ASSOCIATED WITH CYSTIC FIBROSIS

This application claims priority to under 35 U.S.C. §119(e) to U.S. Patent Application Nos. 61/316,321, filed Mar. 22, 2010 and 61/359,029, filed on Jun. 28, 2010. The disclosures of each of U.S. Patent Application Nos. 61/316,321 and 61/359,029 are expressly incorporated by reference in their entireties herein.

BACKGROUND OF THE INVENTION

Cystic fibrosis (CF) is the most common severe autosomal recessive genetic disorder in the Caucasian population. It affects approximately 1 in 2,500 Caucasian live births in North America (Boat et al, The Metabolic Basis of Inherited Disease, 6th ed, pp 2649-2680, McGraw Hill, N.Y. (1989)). The incidence of disease is lower in African American, Hispanic and Asian individuals. Approximately 1 in 25 Caucasian persons are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). The CFTR gene contains 27 exons and encodes a protein of 1480 amino acids. Several regions are contemplated to have functional importance in the CFTR protein, including two areas for ATP binding, termed Nucleotide Binding Folds (NBF), a Regulatory (R) region that has multiple potential sites for phosphorylation by protein kinases A and C, and two hydrophobic regions believed to interact with cell membranes.

The major symptoms of classical cystic fibrosis include chronic pulmonary disease, pancreatic exocrine insufficiency, congenital absence of the vas deferens in males and elevated sweat electrolyte levels. The symptoms are consistent with CF being an exocrine disorder. Although recent advances have been made in the analysis of ion transport across the apical membrane of the epithelium of CF patient cells, it is not clear that the abnormal regulation of chloride channels represents the only defect in the disease. Mutations in the CFTR gene are also associated with atypical CF and monosymptomatic diseases such as congential absence of the vas deferens in males, idiopathic chronic pancreatitis and chronic sinusitis (Noone and Knowles, *Respir. Res*., vol. 2, p. 328 (2001); Southern, *Respiration*, vol. 74, p. 241 (2007)). A variety of CFTR gene mutations are known. One of them leads to the omission of phenylalanine residue 508 within the first putative NBF domain. This mutation, termed ΔF508, accounts for about 70% of the CFTR chromosomes in Caucasian patients and was highly associated with the predominant haplotype found on chromosomes of Caucasian CF patients (Kerem, et al., *Science*, vol. 245, p. 1073 (1989); Lemna, et al., *New Engl. J. Med*., vol. 322, p. 291 (1990)). However, the haplotypes associated with Caucasian CF chromosomes without ΔF508 also exist although less common, confirming that allelic heterogeneity is present in CF and CF related disorders.

Therefore, there is a need for more effective genetic screening for other CFTR mutant alleles which are present in the other 30% of Caucasian CF patients, as well as other alleles found in other racial and ethnic groups. Knowledge of such alleles can be used to design probes for screening and/or testing, as well as to devise other screening and/or testing methods. The more complete the set of probes available for CFTR mutant alleles, the more accurate the diagnoses.

SUMMARY OF THE INVENTION

The present invention provides methods, products and systems relating to novel mutations identified in the CFTR gene that can be used for more accurate diagnosis of CF and CF related disorders.

In one aspect, the present invention provides a method for testing for mutations in the CFTR gene, which comprises testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations.

Yet other embodiments of the present invention comprise systems for performing the method. For example, the system may comprise a station or device for testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations. Also, the system may comprise a device for analysis and/or interpretation of the data. For example, a computer having software to analyze the data for the presence of one of the mutations of the invention may be included in the system.

The following embodiments may be used in either the methods or the systems of the invention. In some embodiments, the sample contains an isolated nucleic acid. In some embodiments, the testing step comprises nucleic acid sequencing. In some embodiments, the testing step comprises hybridization. In some embodiments, the hybridization is performed using one or more oligonucleotide probes specific for a region in the CFTR gene (SEQ ID NO:1) (FIG. 1) corresponding to the one or more mutations selected from Table 1, 2, 3 or 4, and under conditions sufficiently stringent to disallow a single nucleotide mismatch. In some embodiments, the hybridization is performed with a microarray. In some embodiments, the testing step comprises restriction enzyme digestion. In some embodiments, the testing step comprises PCR amplification. In some embodiments, the PCR amplification is digital PCR amplification. In some embodiments, the testing step comprises primer extension. In some embodiments, the primer extension is single-base primer extension. In some embodiments, the testing step comprises performing a multiplex allele-specific primer extension (ASPE). In yet other embodiments, the testing step may comprise performing real-time PCR.

In some embodiments, the sample contains purified or partially purified protein. In some embodiments, the testing step comprises amino acid sequencing. For example, in certain embodiments, the system comprises a device for amino acid sequencing. In some embodiments, the testing step comprises performing an immuno assay using one or more antibodies that specifically recognize one or more epitopes corresponding to the one or more mutations selected from Table 1, 2, 3 or 4. In some embodiments, the testing step comprises protease digestion (e.g., trypsin digestion). In some embodiments, the testing step further comprises performing 2D-gel electrophoresis.

In some embodiments, the testing step comprises determining the presence of the one or more mutations using mass spectrometry. In some embodiments, the mass spectrometric format is selected from among Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

In some embodiments, the sample is obtained from cells, tissue, whole blood, mouthwash, plasma, serum, urine, stool, saliva, cord blood, chorionic villus sample, chorionic villus sample culture, amniotic fluid, amniotic fluid culture, transcervical lavage fluid, and combination thereof. In further embodiments, the sample is obtained from a pregnant woman, for testing the sample for the presence of one or more CFTR mutations in fetal nucleic acids contained therein. For example, in certain embodiments, the system comprises a station for processing of the samples.

In yet another aspect, the present invention provides a method for screening and/or testing for CFTR mutations, comprising steps of: (a) providing a sample obtained from a subject; (b) testing the sample for the presence of a mutation at a pre-determined position selected from Table 1, 2, 3 or 4, in the CFTR gene or protein; and wherein the presence of the mutation at the pre-determined position indicates that the subject has an increased risk of having CF or a CF related disorder, or being a carrier of a CFTR mutation.

Yet other embodiments of the present invention comprise systems for performing the method. For example, the system may comprise a station or device for testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations. Also, the system may comprise a device for analysis and/or interpretation of the data. For example, a computer having software to analyze the data for the presence of one of the mutations of the invention may be included in the system.

The following embodiments may be used in either the methods or the systems of the invention. In some embodiments, the testing step comprises determining the identity of the nucleotide and/or amino acid at the pre-determined position selected from Table 1, 2, 3 or 4.

In some embodiments, the presence of the mutation is determined by comparing the identity of the nucleotide and/or amino acid at the pre-determined position to a control.

In some embodiments, the method further comprises a step of determining if the mutation is listed in Table 1, 2, 3 or 4.

In another aspect, the present invention provides products, e.g., reagents, for detecting novel CFTR mutations described herein. Such reagents may be used for detection of the mutations described herein in the protein sequence and/or the nucleic acid sequence.

In some embodiments, the invention provides a nucleic acid probe that specifically binds to a normal CFTR gene but not to a mutant CFTR gene containing one or more mutations selected from Table 1, 2, 3, or 4. In some embodiments, the present invention provides a plurality of probes (e.g., as may be used for real-time PCR or sequencing), or an array containing one or more probes that specifically bind to a normal CFTR gene but not to a mutant CFTR gene containing one or more mutations selected from Table 1, 2, 3, or 4. In some embodiments, the present invention provides a nucleic acid probe that specifically binds to a mutant CFTR gene containing one or more mutations selected from Table 1, 2, 3, or 4 but not to a normal CFTR gene. In some embodiments, the array comprises one or more probes that specifically bind to a mutant CFTR gene containing one or more mutations selected from Table 1, 2, 3, or 4 but not to a normal CFTR gene.

In some embodiments, the present invention provides an antibody that specifically binds to a normal CFTR protein but not to a mutant CFTR protein containing one or more mutations selected from Table 1, 2, 3, or 4. In some embodiments, the present invention provides an antibody that specifically binds to a mutant CFTR protein containing one or more mutations selected from Table 1, 2, 3, or 4 but not to a normal CFTR protein.

In some embodiments, the present invention provides a kit for comprising one or more reagents that differentiate a normal CFTR gene or protein from a mutant CFTR gene or protein containing one or more mutations selected from Table 1, 2, 3, or 4. Such kits may be useful, e.g., for screening and/or testing for CFTR mutations. In some embodiments, the one or more reagents comprises one or more nucleic acid probes. In some embodiments, the one or more reagents comprises one or more antibodies. In some embodiments, the one or more reagents are provided in a form of microarray. In some embodiments, the kit further comprises reagents for primer extension. Or, probes for the detection of mutations may be provided. In some embodiments, the kit further comprises a control indicative of a healthy individual. In some embodiments, the kit further comprises an instruction on how to determine if an individual has CF or a CF related disorder, is at risk of developing CF or a CF related disorder, or is a carrier of a CFTR mutation.

In still another aspect, the present invention provides a computer readable medium encoding information corresponding to one or more mutations shown in Tables 1, 2, 3 and 4. Such computer readable media may be part of the systems as described herein.

Other features, objects, and advantages of the present invention are apparent in the detailed description and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

FIGURES

FIG. 1 is a genomic sequence of the CFTR gene according to an embodiment of the invention.

FIG. 2 is a cDNA sequence of CFTR according to an embodiment of the invention.

FIG. 3 is an amino acid sequence of CFTR according to an embodiment of the invention.

FIG. 4 is a nucleotide sequence of the 5' end of the CFTR gene according to an embodiment of the invention.

DEFINITIONS

Figure 5:
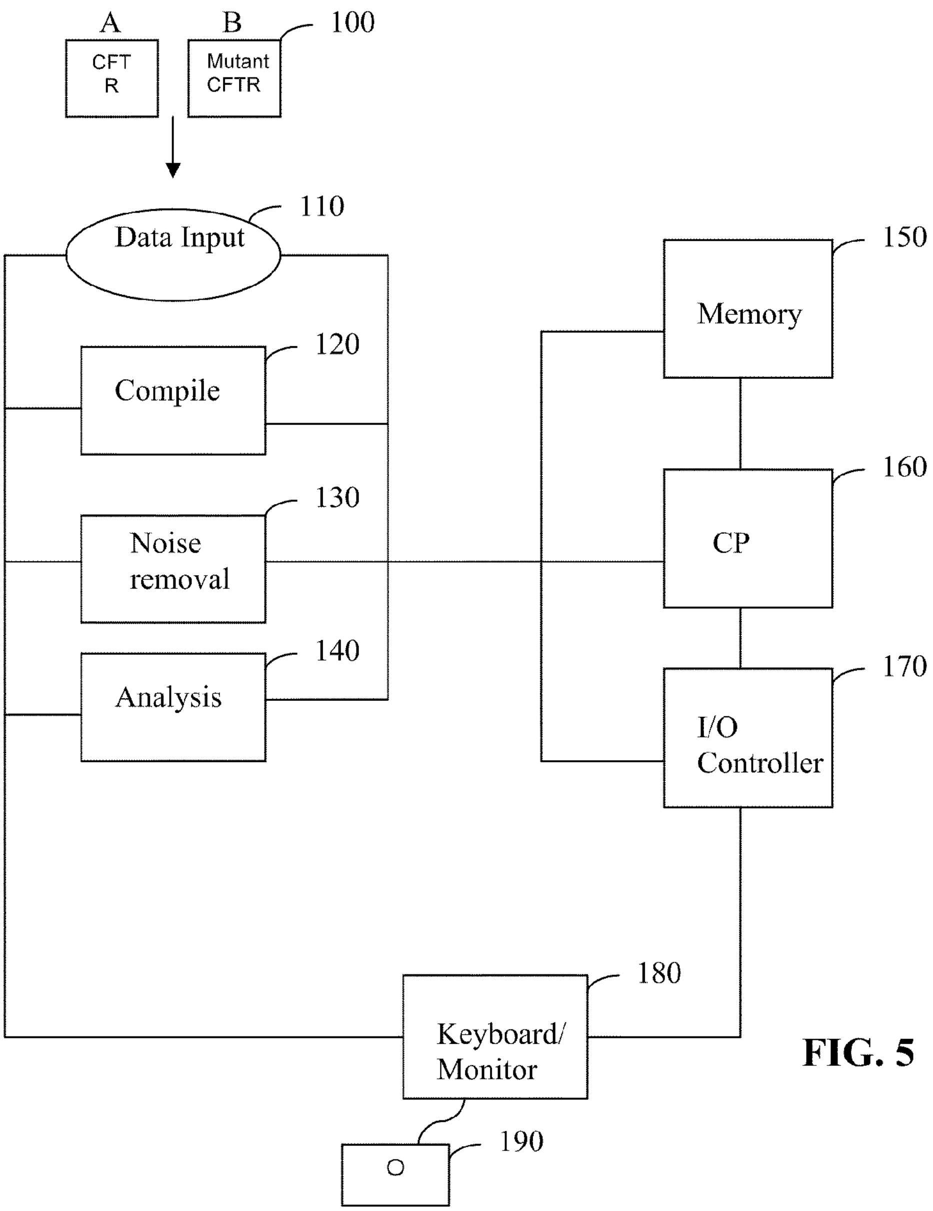
FIG. 5 is a schematic of a system according to an embodiment of the invention.

In order for the present invention to be more readily understood, certain terms are first defined. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Allele: As used herein, the term "allele" refers to different versions of a nucleotide sequence of a same genetic locus (e.g., a gene).

Allele specific primer extension (ASPE): As used herein, the term "allele specific primer extension (ASPE)" refers to a mutation detection method utilizing primers which hybridize to a corresponding DNA sequence and which are extended depending on the successful hybridization of the 3' terminal nucleotide of such primer. Typically, extension primers that possess a 3' terminal nucleotide which form a perfect match with the target sequence are extended to form extension products. Modified nucleotides can be incorporated into the extension product, such nucleotides effectively labeling the extension products for detection purposes. Alternatively, an extension primer may instead comprise a 3' terminal nucleotide which forms a mismatch with the target sequence. In this instance, primer extension does not occur unless the polymerase used for extension inadvertently possesses exonuclease activity.

Amplification: As used herein, the term "amplification" refers to any methods known in the art for copying a target nucleic acid, thereby increasing the number of copies of a selected nucleic acid sequence. Amplification may be exponential or linear. A target nucleic acid may be either DNA or RNA. Typically, the sequences amplified in this manner form an "amplicon." Amplification may be accomplished with various methods including, but not limited to, the polymerase chain reaction ("PCR"), transcription-based amplification, isothermal amplification, rolling circle amplification, etc. Amplification may be performed with relatively similar amount of each primer of a primer pair to generate a double stranded amplicon. However, asymmetric PCR may be used to amplify predominantly or exclusively a single stranded product as is well known in the art (e.g., Poddar et al. *Molec. And Cell. Probes* 14:25-32 (2000)). This can be achieved using each pair of primers by reducing the concentration of one primer significantly relative to the other primer of the pair (e.g., 100 fold difference). Amplification by asymmetric PCR is generally linear. Additionally, methods such as real-time PCR may be utilized. A skilled artisan will understand that different amplification methods may be used together.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological sample: As used herein, the term "biological sample" encompasses any sample obtained from a biological source. A biological sample can, by way of non-limiting example, include blood, amniotic fluid, sera, urine, feces, epidermal sample, skin sample, cheek swab, sperm, amniotic fluid, cultured cells, bone marrow sample and/or chorionic Convenient biological samples may be obtained by, for example, scraping cells from the surface of the buccal cavity. The term biological sample encompasses samples which have been processed to release or otherwise make available a nucleic acid or protein for detection as described herein. For example, a biological sample may include a cDNA that has been obtained by reverse transcription of RNA from cells in a biological sample. The biological sample may be obtained from a stage of life such as a fetus, young adult, adult, and the like. Fixed or frozen tissues also may be used.

Carrier: The term "carrier," as used in the context of CF, refers to a person who is symptom-free but carries a CFTR mutation that can be passed to his/her children. Typically, a carrier has one CFTR allele that contains a disease causing mutation and a second allele that is normal or not disease-related. CF and CF related disorders are "autosomal recessive" diseases, meaning that a mutation produces little or no phenotypic effect when present in a heterozygous configuration with a non-disease related allele, but produces a "disease state" when a person is homozygous, i.e., both CFTR alleles are mutant alleles that contain the same disease causing mutation or compound heterozygous, i.e., both CFTR alleles are mutant alleles that contain two different disease-causing mutations. A carrier status is whether or not one is a carrier.

Coding sequence vs. non-coding sequence: As used herein, the teem "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom. As used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Complement: As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Crude: As used herein, the term "crude," when used in connection with a biological sample, refers to a sample which is in a substantially unrefined state. For example, a crude sample can be cell lysates or biopsy tissue sample. A crude sample may exist in solution or as a dry preparation.

Deletion: As used herein, the term "deletion" encompasses a mutation that removes one or more nucleotides from a naturally-occurring nucleic acid.

Epitope: As used herein, the term "epitope" refers to a fragment or portion of a molecule or a molecule compound (e.g., a polypeptide or a protein complex) that makes contact with a particular antibody or antibody like proteins.

Familial history: As used herein, the term "familial history" typically refers to occurrence of events (e.g., CF disease, CF related disorder or CFTR mutation carrier) relating to an individual's immediate family members including parents and siblings. Sometimes, family history also may include grandparents.

Flanking: As used herein, the term "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase. For example, primers that flank mutant CTFR sequences do not actually anneal to the mutant sequence but rather anneal to sequence that adjoins the mutant sequence. In some cases, primers that flank a CFTR exon are generally designed not to anneal to the exon sequence but rather to anneal to sequence that adjoins the exon (e.g. intron sequence). However, in some cases, amplification primer may be designed to anneal to the exon sequence.

Genotype: As used herein, the term "genotype" refers to the genetic constitution of an organism. More specifically, the term refers to the identity of alleles present in an individual. "Genotyping" of an individual or a DNA sample refers to identifying the nature, in terms of nucleotide base, of the two alleles possessed by an individual at a known polymorphic site.

Heterozygous: As used herein, the term "heterozygous" or "HET" refers to an individual possessing two different alleles of the same gene. As used herein, the term "heterozygous" encompasses "compound heterozygous" or "compound heterozygous mutant." As used herein, the term "compound heterozygous" refers to an individual possessing two different alleles. As used herein, the term "compound heterozygous mutant" refers to an individual possessing two different copies of an allele, such alleles are characterized as mutant forms of a gene. The term "mutant" as used herein refers to a mutated, or potentially non-functional form of a gene. (See "mutations of the CFTR gene.")

Homozygous: As used herein, the term "homozygous" refers to an individual possessing two copies of the same allele. As used herein, the term "homozygous mutant" refers to an individual possessing two copies of the same allele, such allele being characterized as the mutant form of a gene. The term "mutant" as used herein refers to a mutated, or potentially non-functional form of a gene.

Hybridize: As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

Insertion or addition: As used herein, the term "insertion" or "addition" refers to a change in an amino acid or nucleotide sequence resulting in the addition of one or more amino acid residues or nucleotides, respectively, as compared to the naturally occurring molecule.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Labeled: The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

Multiplex PCR: As used herein, the term "multiplex PCR" refers to amplification of two or more regions which are each primed using a distinct primers pair.

Multiplex ASPE: As used herein, the term "multiplex ASPE" refers to an assay combining multiplex PCR and allele specific primer extension for detecting polymorphisms. Typically, multiplex PCR is used to first amplify regions of DNA that will serve as target sequences for ASPE primers. See the definition of allele specific primer extension.

Mutations of the CFTR gene: As used herein, the term "mutations of the CFTR gene" refers to one or more abnormal nucleic acid sequences as compared to a wild-type CFTR gene sequence. The "mutations of the CFTR gene" are also referred to as "mutant CF sequences." Mutations of the CFTR gene encompass substitutions (e.g., single nucleotide polymorphisms (SNP)), deletions, insertions, additions, and/or duplications.

Primer: As used herein, the term "primer" refers to a short single-stranded oligonucleotide capable of hybridizing to a complementary sequence in a nucleic acid sample. Typically, a primer serves as an initiation point for template dependent DNA synthesis. Deoxyribonucleotides can be added to a primer by a DNA polymerase. In some embodiments, such deoxyribonucleotides addition to a primer is also known as primer extension. The term primer, as used herein, includes all forms of primers that may be synthesized including peptide nucleic acid primers, locked nucleic acid primers, phosphorothioate modified primers, labeled primers, and the like. A "primer pair" or "primer set" for a PCR reaction typically refers to a set of primers typically including a "forward primer" and a "reverse primer." As used herein, a "forward primer" refers to a primer that anneals to the anti-sense strand of dsDNA. A "reverse primer" anneals to the sense-strand of dsDNA.

Polymorphism: As used herein, the term "polymorphism" refers to the coexistence of more than one form of a gene or portion thereof.

Pure or substantially pure: As used herein, the term "pure or substantially pure" refers to a compound, e.g., a protein or polypeptide that has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

Real-time PCR: As used herein, the term "real-time PCR" refers to quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

Sense strand vs. anti-sense strand: As used herein, the term "sense strand" refers to the strand of double-stranded DNA (dsDNA) that includes at least a portion of a coding sequence of a functional protein. As used herein, the term "anti-sense strand" refers to the strand of dsDNA that is the reverse complement of the sense strand.

Specific: As used herein, the term "specific," when used in connection with an oligonucleotide primer, refers to an oligonucleotide or primer, under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

Subject: As used herein, the term "subject" refers to a human or any non-human animal. A subject can be a patient, which refers to a human presenting to a medical provider for diagnosis or treatment of a disease. A human includes pre and post natal forms. Particularly preferred subjects are humans being tested for the existence of a CFTR carrier state, CF disease or CF related disorder state.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially complementary: As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

Substitution: As used herein, the term "substitution" refers to the replacement of one or more amino acids or nucleotides by different amino acids or nucleotides, respectively, as compared to the naturally occurring molecule.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Wild-type: As used herein, the term "wild-type" refers to the typical or the most common form existed in nature. For example, a wild-type CFTR gene or protein refers to the typical or the most common form of CFTR gene or protein existed in a natural population. As used herein, "wild-type" is used interchangeably with "naturally-occurring." In some embodiment, a wild-type CFTR gene or a locus thereof, refers to the CFTR gene sequence which is found in NCBI GenBank locus ID M58478 (HUMCFTC) (SEQ ID NO:4) (FIG. 4). The CFTR gene is located on chromosome 7, which may be found in NCBI GenBank locus AC000111 and AC000061, the contents of which are incorporated herein in their entirety by reference. The cDNA for the CFTR gene is found in Audrezet et al., *Hum. Mutat.* (2004) 23 (4), 343-357.

DETAILED DESCRIPTION

The present invention provides, among other things, methods, products and systems that use novel mutations in the cystic fibrosis transmembrane conductance regulator (CFTR) gene in screening and/or testing for CF and CF related diseases, disorders or conditions. For example, the novel mutations provided herein can be used to assist in clinical diagnosis of CF disease, CF related disease, disorder or condition, or carrier status and for genetic counseling (e.g., for evaluation of an individual's risk for developing CF or being a carrier of a CFTR mutation). The novel mutations provided herein can be used alone or in combination with other known CFTR mutations as part of a panel of CFTR mutations.

Various aspects of the invention are described in detail in the following sections. The use of sections is not meant to limit the invention. Each section can apply to any aspect of the invention. In this application, the use of "or" means "and/or" unless stated otherwise.

Novel Mutations in the CFTR Gene

The CFTR gene was mapped to chromosome 7 and described in, for example, U.S. Pat. No. 6,201,107 and U.S. Pat. No. 5,776,677, the disclosures of which are incorporated by reference herein in their entirety. The CFTR genomic sequence is described in GenBank Accession Number NC_000007 (range: 117120016.117308718; the entire contents of which are herein incorporated by reference) (SEQ ID NO:1) (FIG. 1). The CFTR gene contains 27 exons. The exons are numbered 1, 2, 3, 4, 5, 6a, 6b, 7, 8, 9, 10, 11, 12, 13, 14a, 14b, 15, 16, 17a, 17b, 18, 19, 20, 21, 22, 23, and 24. The CFTR cDNA sequence is described in GenBank Accession Number AR016032.1 (SEQ ID NO:2) (FIG. 2).

The CFTR protein is described in, for example, U.S. Pat. No. 5,543,399, the disclosure of which is incorporated by reference herein in its entirety. The CFTR protein sequence is also described in GenBank Accession Number AAC90840.1 (SEQ ID NO:3) (FIG. 3).

As described in Example 1, the inventors of the present application identified various novel mutations in the CFTR gene (Table 5). These mutations were identified by sequence analysis of the CFTR gene in specimens submitted for clinical testing obtained from individuals who were known to be affected with CF or likely to be a carrier because of familial history, or suspected to be affected with CF based on other CF testing (see Clinical Indication listed in Table 5). The mutations were identified by comparing the CFTR gene sequence from patient samples to the wild-type CFTR gene or protein sequence (see SEQ ID NO:1-3). As shown in Table 5, patients carrying these mutations were from different ethnic groups including Caucasians, African Americans, Hispanics, and Asians. Thus, these mutations may be particularly useful for developing more effective genetic testing for patients from non-Caucasian racial groups.

Novel mutations described herein are located in introns (e.g., intron 3, intron 6a, intron 11, intron 14a, intron 19, intron 20, intron 21, and intron 23) and exons (e.g., exon 2, exon 3, exon 4, exon 5, exon 6a, exon 6b, exon 7, exon 9, exon 10, exon 11, exon 12, exon 13, exon 14a, exon 14b, exon 15, exon 16, exon 17a, exon 17b, exon 19, exon 20, exon 21, exon 22, and exon 24). Some of the novel mutations are nonsense mutations, i.e., mutations that result in a stop codon. Some of the novel mutations are missense mutations, i.e., mutations that result in amino acid substitutions. Some of the novel mutations cause in-frame insertions and/or deletions. Some of the novel mutations delete one or more nucleotides in such a manner as to lead to a shift in the reading frame. Some of the novel mutations alter the sequence at a splice junction, for example, consensus splice site ag/gt or other splice sites. Thus, most of the novel mutations described herein are likely to disrupt CFTR gene or protein expression or function.

The "ACMG recommendations for standards for interpretation and reporting of sequence variations: Revisions 2007" (Richards S C et al. Genetics in Medicine, 10:294-300, which is incorporated herein by reference), provides interpretive categories and definitions of sequence variations which can be used, along with additional test results and clinical information to classify the novel mutations described herein into the following groups.

Group I:

Patient has a novel sequence change that can be classified as category 2 according to the ACMG guidelines (i.e., nonsense, frame shift (FS), consensus splice site ag/gt). Patient has another well established CF disease causing mutation (i.e. F508, W1282X, etc). Patient indication is suspected of having CF, known to be affected with CF or identified through newborn screening. The Group I mutations, which are of particular interest, are shown in Table 1 and these mutations are expected to cause CF or CF related diseases, disorders or conditions.

Group IIA:

Patient has novel sequence change that can be classified as category 3 according to the ACMG guidelines (i.e., missense, in-frame ins/del, other splice site mutations, etc). Patient has another well established CF disease causing mutation (i.e., F508, W1282X, etc.). Patient is suspected of having CF, known to be affected with CF, or identified through positive newborn screening. The Group IIA mutations are shown in Table 2 (under subsection Group IIA).

Group IIB:

Patent has a novel sequence change that can be classified as category 3 according to the ACMG guidelines (i.e., missense, in-frame ins/del, other splice site mutations, etc). Patient is suspected of having CF, known to be affected with CF, or identified through positive newborn screening. The Group IIB mutations are shown in Table 2 (under subsection Group IIB).

Group III:

Patient has novel sequence change that can be classified as category 3 according to the ACMG guidelines (i.e., missense, in-frame insertions/deletions, other splice site mutations, etc). Patient has another well established CF disease causing mutation (i.e. F508, W1282X, etc). Patient indication is suspected of having CF, known to be affected with CF, or identified through newborn screening. Patient has an additional change(s) of unknown clinical significance. The Group III mutations are shown in Table 3.

Group IV:

Mutations other than the Group I, II, and III mutations identified above. The Group IV mutations are shown in Table 4.

Novel CFTR mutations according to the invention however are not limited to the specific nucleotide or amino acid variations identified in Tables 1-4 and should encompass any abnormal nucleotides or amino acid residues, as compared to the wild-type CFTR gene or protein sequences, that may be present at any of the positions identified in Tables 1-4.

TABLE 1

Group I mutations

| Sequence Change | Type of mutation | AA Change | Ethnicity | Other Mutations | Clinical Information | Exon |
|---|---|---|---|---|---|---|
| 1824delA | Frameshift (FS) | n/a | Caucasian | F508del | Mutation was identified in a 22 year old patient with a known diagnosis of CF. This patient carried a second mutation known to cause CF (F508del). | el2 |
| 2957delT | FS | n/a | Caucasian | F508del | Mutation was identified in a 1 year old patient with a known diagnosis of CF. The patient carried a second mutation known to cause CF (F508del). | e15 |
| 4089ins4 | FS | n/a | Caucasian | F508del | Mutation was identified in a 7 year old patient with a known diagnosis of CF. The patient had a positive sweat chloride test. | e21 |

TABLE 1-continued

| Sequence Change | Type of mutation | AA Change | Ethnicity | Other Mutations | Clinical Information | Exon |
|---|---|---|---|---|---|---|
| Group I mutations | | | | | | |
| | | | | | The patient carried a second mutation known to cause CF (F508del). | |
| 4374 + 2T > C | Splice site mutation | n/a | 1. Caucasian | 1. F508del | Patient #1: Mutation was identified in a 45 year old patient with a suspected diagnosis of CF. The patient carried a second mutation known to cause CF (F508del). | i23 |
| | | | 2. Caucasian | 2. F508del | Patient #2: Mutation was identified in a 52 year old patient with a suspected diagnosis of CF. The patient carried a second mutation known to cause CF (F508del). | |
| 3064A > T | Nonsense | K978X | African American | Q1042X | Mutation was identified in a 26 year old patient with a known diagnosis of CF. The patient carried a second mutation likely to cause CF Q1042X. | e16 |
| 246C > G | Nonsense | Y38X | Caucasian | F508del | Mutation was identified in a 1 month old patient with a suspected diagnosis of CF. The patient had a positive sweat chloride test. The patient carried a second mutation known to cause CF (F508del). | e2 |
| Group IIA | | | | | | |
| 269C > T | Missense (MS) | A46V | 1) Caucasian | 1) 3849 + 1219 2G > A | Patient #1: Mutation was identified in a 32 year old patient who was tested due to abnormalities found on fetal ultrasound. The patient carried a second mutation of unknown clinical significance (3849 + 12192G > A). | e2 |
| | | | 2) Black | 2) F508del | Patient #2: Mutation was identified in a 2 month old patient who was tested based on follow-up for a positive newborn screen. The patient carried a second mutation known to cause cystic fibrosis (F508del). | |
| | | | 3) African American | 3) none | Patient #3: Mutation was identified in a 24 year old patient who was tested as a parental follow-up to a positive newborn screen. | |
| 2902 G > T | MS | D924Y | Caucasian | F508del | Mutation was identified in a 1 month old patient with a suspected diagnosis of CF. The patient also had a positive sweat chloride test and carried a second mutation known to cause CF (F508del) | e15 |
| 3814G > A | MS | E1228K | Caucasian | F508del | Mutation was identified in a 1 month old patient with a suspected diagnosis of CF. The patient had a borderline sweat chloride test. The patient carried a second mutation known to cause CF (F508del). | e19 |
| 502G > C | MS | G124R | Not Provided | F508del | Mutation was identified in a 2 month old patient with a suspected diagnosis of CF. The patient had a positive sweat chloride test. The patient carried a second mutation known to cause CF (F508del). | e4 |
| 1520G > T | MS | G463V | Caucasian | F508del | Mutation was identified in a 17 year old patient with a known diagnosis of CF. Patient carried a second mutation known to cause CF (F508del). | e9 |
| 511_513dup TTA | In frame duplication | L127dup | Caucasian, Asian | W1282X | Mutation was identified in a newborn with a suspected diagnosis of CF. The patient had clinical symptoms of CF including as a positive sweat chloride test, meconium ileus, echogenic bowel, and pancreatic insufficiency. The patient carried a second mutation known to cause CF (W1282X). | e4 |
| 978A > T | MS | E282D | 1. not provided | 1. 3120 + 1G > A | Patient #1: Mutation was identified in a 10 year old patient with a suspected diagnosis of CF. The patient had a positive sweat chloride test. The patient carried a second mutation known to cause CF (3120 + 1G > A). | e6b |
| | | | 2. not provided | 2) none | Patient #2: Mutation was identified in a 4 year old patient with a suspected diagnosis of CF and a family history of CF. | |
| 843G > C | MS | Q237H | Caucasian | F508del | Mutation was identified in a 2 month old patient with a known diagnosis of CF. The patient carried a second mutation known to cause CF (F508del). | e6a |
| 829C > T | MS | L233F | Caucasian | D1152H | Mutation was identified in a 1 month old patient who was tested following a positive | e6a |

TABLE 1-continued

| Sequence Change | Type of mutation | AA Change | Ethnicity | Other Mutations | Clinical Information | Exon |
|---|---|---|---|---|---|---|
| Group I mutations | | | | | | |
| | | | | | newborn screen. The patient carried a second mutation known to cause CF (D1152H). | |
| 4096 − 6C > T | Splice site mutation | None | Caucasian | F508del | Mutation was identified in a 58 year old patient with a suspected diagnosis of CF. The patient carried a second mutation known to cause CF (F508del). | i21 |
| 4375 − 7delT | Splice site mutation | None | Caucasian | F508del | Mutation was identified in a 6 year old patient with a suspected diagnosis of CF. Patient has a family history, a borderline sweat chloride test and recurrent pneumonia. The patient carried a second mutation known to cause CF (F508del). | i23 |
| 1586 G > C | MS | S485T | Caucasian | S1235R | Mutation was identified in a 2 year old patient with a suspected diagnosis of CF. The patient carried a second mutation S1235R (3837T > G) which has been reported in individuals with varying CF phenotypes. | e10 |
| Group IIB | | | | | | |
| 875 + 4G > T | Splice site mutation | n/a | African American | none | Mutation was identified in a 1 month old patient who had a positive newborn screening test. | i6a |
| 4005 + 3 G > T | Splice site mutation | n/a | Caucasian | none | Mutation was identified in a 40 year old patient who was tested to determine if they were a carrier, there was no family history of CF. | i20 |

TABLE 3

| Sequence Change | Type of mutation | AA Change | Ethnicity | Other Mutations | Clinical Information | Exon |
|---|---|---|---|---|---|---|
| Group III Mutations | | | | | | |
| 2711T > C | MS | 1860T | Caucasian | F508del, E528E | Mutation was identified in a 58 year old woman with a suspected diagnosis of CF. The patient carried a second mutation known to cause CF (F508del) and an additional mutation of unknown clinical significance (E528E) . . . | el4a |
| 3891G > C | MS | L1253F | Not provided | G85E, L15P | Mutation was identified in a 32 year old patient with a known diagnosis of CF. The patient carried a second mutation known to cause CF (G85E) and an additional mutation of unknown clinical significance (L15P). | e20 |
| 2524C > T | MS | P798S | African American | F508del, R74W, G921E, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, G921E, D1270N). | e13 |
| 2894G > A | MS | G921E | African American | F508del, R74W, P798S, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, P789S, D1270N). | e15 |

TABLE 4

| Sequence Change | Type of mutation | AA Change | Ethnicity | Other Mutations | Clinical Information | Exon |
|---|---|---|---|---|---|---|
| Group IV Mutations | | | | | | |
| 405 + 10247C > T | Possible splice site mutation | n/a | Caucasian | F508del | Mutation was identified in a 35 year old patient who was tested to determine if they were a carrier, there was no family history of CF. This patient carried a second mutation known to cause CF (F508del) | i3 |

TABLE 4-continued

| Group IV Mutations | | | | | | |
|---|---|---|---|---|---|---|
| Sequence Change | Type of mutation | AA Change | Ethnicity | Other Mutations | Clinical Information | Exon |
| 405 + 10255delC | Possible splice site mutation | n/a | Not Provided | F508del, 124del23bp | Mutation was identified in a 10 year old patient. The patient carries two mutations know to cause CF (F508del and 124del23). | i3 |
| 1811 + 1643 G > T | Possible splice site mutation | n/a | 1. Hispanic | 1. F508del | Patient #1: Mutation was identified in a 1 year old patient with a known diagnosis of CF. Patient had a positive sweat chloride test. The patient carried a second mutation known to cause CF (F508del). | i11 |
| | | | 2. Hispanic | 2. F508del | Patient #2: Mutation was identified in a 6 year old patient with a known diagnosis of CF. The patient carried a second mutation know to cause CF (F508del). | |
| | | | 3. Not provided | 3. none | Patient #3: Mutation was identified in an 8 month old patient with a suspected diagnosis of CF. | |
| 1812 − 13A > G | Splice site mutation | n/a | Caucasian | none | Mutation was identified in a 15 year old patient with a suspected diagnosis of CF. The patient has chronic sinusitis. | i11 |
| 2752 − 33insA | Possible splice site mutation | n/a | African American | F693L | Mutation was identified in a 6 year old patient with a known diagnosis of CF. The patient carries a second mutation of unknown clinical significance (F693L). | i14a |
| 3849 + 12192 G > A | Possible splice site mutation | n/a | Caucasian | A46V | Mutation was identified in a 32 year old patient who was tested due to abnormalities found on fetal ultrasound. The patient carried an additional mutation of known clinical significance (A46V). | i19 |
| 724G > A | MS | A198T | Hispanic | none | Mutation was identified in a 4 month old patient with a suspected diagnosis of CF. | e6a |
| 3899C > T | MS | A1256V | Guyanese | none | Mutation was identified in a 45 year old patient who was tested to determine if they were a carrier, there was no family history of CF. | e20 |
| 3986C > T | MS | A1285V | Not Provided | none | Mutation was identified in a 23 year old patient who was tested to determine if they were a carrier, there was no family history of CF. | e20 |
| 901G > A | MS | E257K | Hispanic | none | Mutation was identified in a 4 year old patient with a suspected diagnosis of CF. The patient has asthma and recurring pneumonia. | e6b |
| 392 T > C | MS | F87S | Not Provided | none | The mutation was identified in a 1 month old patient with a suspected diagnosis of CF. | e3 |
| 3463T > C | MS | F1111L | Hispanic | none | Mutation was identified in a 6 year old patient with a suspected diagnosis of CF. The patient has asthma. | e17b |
| 1757G > A | MS | G542E | Hispanic | none | Mutation was identified in a 25 year old patient who was tested to determine if they were a carrier, there was no family history of CF. The patient carried 2 copies of G542E . . . | e11 |
| 4025G > C | MS | G1298A | Asian | G970D, Q1352H | Mutation was identified in a 34 year old patient with congenital absence of the vas deferens. The patient carried two other mutations of unknown clinical significance (G970D and Q1352H) | e21 |
| 4129G > T | MS | G1333W | Not Provided | none | Mutation was identified in an 8 year old patient with a suspected diagnosis of CF. Patient had recurrent respiratory infections and chronic cough. | e22 |
| 663T > G | MS | I177M | Caucasian | none | Mutation was identified in a 34 year old patient who was tested to determine if they were a carrier, there was no family history of CF. | e5 |
| 3200T > C | MS | I1023T | Hispanic | none | Mutation was identified in a 34 year old patient who was tested to determine if they were a carrier, there was no family history of CF. | e17a |
| 4412 T > C | MS | I1427T | Asian | S1444S | Mutation was identified in a 34 year old patient who was tested to determine if they were a carrier, there was no family history of CF. The patient carried another mutation that is considered likely to be clinically benign (S144S). | e24 |
| 620A > C | MS | K163T | Caucasian | none | Mutation was identified in a 32 year old patient with a family history of CF. | e4 |
| 1738 A > G | MS | K536E | Hispanic | I488I | Mutation was identified in a 19 year old patient who's son had a positive newborn screening test. The patient carried another mutation that is considered likely to be clinically benign (I1488I) . . . | e11 |
| 3370A > C | MS | K1080Q | Caucasian | none | Mutation was identified in a 9 year old patient with a suspected diagnosis of CF. The patient had asthma and failure to thrive. | e17b |

TABLE 4-continued

| Group IV Mutations | | | | | | |
|---|---|---|---|---|---|---|
| Sequence Change | Type of mutation | AA Change | Ethnicity | Other Mutations | Clinical Information | Exon |
| 1129 C > T | MS | L333F | Asian | none | Mutation was identified in a 37 year old patient who tested to determine if they were a carrier, there was no family history of CF. | e7 |
| 2383C > T | MS | R751C | Caucasian | 2183delAA > G | Mutation was identified in a 36 year old patient who was being tested due to a partner being a CF carrier. The patient also carried a second mutation known to cause CF (2183delAA > G). | e13 |
| 2761delTCT | In frame deletion | S877del | Caucasian | F508del, D1152H | Mutation was identified in 1 month old patient who had a positive sweat chloride test. The patient carried two additional mutations known to cause CF (F508del and D1152H). | e14b |
| 1106A > G | MS | Y325C | Caucasian | R334W | Mutation was identified in a 35 year old patient who was tested to determine if they were a carrier, there was no family history of CF. Patient carried a second mutation known to cause CF (R334W). | e7 |
| 622A > G | MS | T164A | Caucasian | none | Mutation was identified in a 3 month old patient with a suspected diagnosis of CF. | e5 |

Detection of CFTR Mutations

A variety of methods known in the art can be used to detect CFTR gene mutations disclosed in the present invention. For example, methods that have been used to detect previously identified CFTR gene mutations have been described and are adaptable for use with the present invention. See e.g., Audrezet et al., "Genomic rearrangements in the CFTR gene: extensive allelic heterogeneity and diverse mutational mechanisms" *Hum Mutat.* 2004 April; 23(4):343-57; PCT WO 2004/040013 A1 and corresponding US application No. 20040110138; titled "Method for the detection of multiple genetic targets" by Spiegelman and Lem; US patent application No. 20030235834; titled "Approaches to identify cystic fibrosis" by Dunlop et al.; and US patent application No. 20040126760 titled "Novel compositions and methods for carrying out multiple PCR reactions on a single sample" by N. Broude, the entire contents of each of which are herein incorporated by reference.

Nucleic Acid Analyses

In certain embodiments, CFTR gene mutations disclosed herein are detected at the nucleic acid level. For example, nucleic acid can be analyzed by sequencing, hybridization, PCR amplification, restriction enzyme digestion, primer extension such as single-base primer extension or multiplex allele-specific primer extension (ASPE).

Nucleic acid analyses can be performed on genomic DNA, messenger RNAs, and/or cDNA. In many embodiments, nucleic acids are extracted from a biological sample. In some embodiments, nucleic acids are analyzed without having been amplified. In some embodiments, nucleic acids are amplified using techniques known in the art (such as polymerase chain reaction (PCR)) and amplified nucleic acids are used in subsequent analyses. Multiplex PCR, in which several amplicons (e.g., from different genomic regions) are amplified at once using multiple sets of primer pairs, may be employed. Additionally, methods such as real-time PCR, as are known in the art, may be used to perform nucleic acid analysis.

In some embodiments, nucleic acids are amplified in a manner such that the amplification product for a wild-type allele differs in size from that of a mutant allele. Thus, presence or absence of a particular mutant allele can be determined by detecting size differences in the amplification products, e.g., on an electrophoretic gel. For example, deletions or insertions of CFTR gene regions may be particularly amenable to using size-based approaches.

Certain exemplary nucleic acid analysis methods are described in detail below.

Allele-Specific Amplification

In some embodiments, CFTR gene mutations are detected using an allele-specific amplification assay. This approach is variously referred to as PCR amplification of specific allele (PASA) (Sarkar, et al., 1990 *Anal. Biochem.* 186:64-68), allele-specific amplification (ASA) (Okayama, et al., 1989 *J. Lab. Clin. Med.* 114:105-113), allele-specific PCR (ASPCR) (Wu, et al. 1989 *Proc. Natl. Acad. Sci. USA.* 86:2757-2760), and amplification-refractory mutation system (ARMS) (Newton, et al., 1989 *Nucleic Acids Res.* 17:2503-2516). The entire contents of each of these references is incorporated herein. This method is applicable for single base substitutions as well as micro deletions/insertions.

For example, for PCR-based amplification methods, amplification primers may be designed such that they can distinguish between different alleles (e.g., between a wild-type allele and a mutant allele). Thus, the presence or absence of amplification product can be used to determine whether a CFTR gene mutation is present in a given nucleic acid sample. In some embodiments, allele specific primers can be designed such that the presence of amplification product is indicative of a CFTR gene mutation. In some embodiments, allele specific primers can be designed such that the absence of amplification product is indicative of a CFTR gene mutation.

In some embodiments, two complementary reactions are used. One reaction employs a primer specific for the wild type allele ("wild-type-specific reaction") and the other reaction employs a primer for the mutant allele ("mutant-specific reaction"). The two reactions may employ a common second primer. PCR primers specific for a particular allele (e.g., the wild-type allele or mutant allele) generally perfectly match one allelic variant of the target, but are mismatched to other allelic variant (e.g., the mutant allele or wild-type allele). The mismatch may be located at/near the 3' end of the primer, leading to preferential amplification of the perfectly matched allele. Whether an amplification product can be detected from one or in both reactions indicates the absence or presence of the mutant allele. Detection of an amplification product only from the wild-type-specific reaction indicates presence of the wild-type allele only (e.g., homozygosity of the wild-type allele). Detection of an amplification product in the mutant-specific reaction only indicates presence of the mutant allele only (e.g. homozygosity of the mutant allele). Detection of amplification products from both reactions indicate (e.g., a heterozygote). As used herein, this approach will be referred to as "allele specific amplification (ASA)."

Allele-specific amplification can also be used to detect duplications, insertions, or inversions by using a primer that hybridizes partially across the junction. The extent of junction overlap can be varied to allow specific amplification.

Amplification products can be examined by methods known in the art, including by visualizing (e.g., with one or more dyes) bands of nucleic acids that have been migrated (e.g., by electrophoresis) through a gel to separate nucleic acids by size.

Allele-Specific Primer Extension

In some embodiments, an allele-specific primer extension (ASPE) approach is used to detect CFTR gene mutations. ASPE employs allele-specific primers that can distinguish between alleles (e.g., between a mutant allele and a wild-type allele) in an extension reaction such that an extension product is obtained only in the presence of a particular allele (e.g., mutant allele or wild-type allele). Extension products may be detectable or made detectable, e.g., by employing a labeled deoxynucleotide in the extension reaction. Any of a variety of labels are compatible for use in these methods, including, but not limited to, radioactive labels, fluorescent labels, chemiluminescent labels, enzymatic labels, etc. In some embodiments, a nucleotide is labeled with an entity that can then be bound (directly or indirectly) by a detectable label, e.g., a biotin molecule that can be bound by streptavidin-conjugated fluorescent dyes. In some embodiments, reactions are done in multiplex, e.g., using many allele-specific primers in the same extension reaction.

In some embodiments, extension products are hybridized to a solid or semi-solid support, such as beads, matrix, gel, among others. For example, the extension products may be tagged with a particular nucleic acid sequence (e.g., included as part of the allele-specific primer) and the solid support may be attached to an "anti-tag" (e.g., a nucleic acid sequence complementary to the tag in the extension product). Extension products can be captured and detected on the solid support. For example, beads may be sorted and detected. One such system that can be employed in this manner is the LUMINEX™ MAP system, which can be adapted for cystic fibrosis mutation detection by Luminex Corporation and is sold commercially as a universal bead array (TAG-IT™) (See, e.g., Example 2)

Additional ASPE methods and reagents are described in, e.g., U.S. patent publication number 2008/0138803 A1, the entire contents of which are herein incorporated by reference.

Single Nucleotide Primer Extension

In some embodiments, a single nucleotide primer extension (SNuPE) assay is used, in which the primer is designed to be extended by only one nucleotide. In such methods, the identity of the nucleotide just downstream (e.g., 3') of the 3' end of the primer is known and differs in the mutant allele as compared to the wild-type allele. SNuPE can be performed using an extension reaction in which the only one particular kind of deoxynucleotide is labeled (e.g., labeled dATP, labeled dCTP, labeled dGTP, or labeled dTTP). Thus, the presence of a detectable extension product can be used as an indication of the identity of the nucleotide at the position of interest (e.g., the position just downstream of the 3' end of the primer), and thus as an indication of the presence or absence of a mutation at that position. SNuPE can be performed as described in U.S. Pat. No. 5,888,819; U.S. Pat. No. 5,846,710; U.S. Pat. No. 6,280,947; U.S. Pat. No. 6,482,595; U.S. Pat. No. 6,503,718; U.S. Pat. No. 6,919,174; Piggee, C. et al. Journal of Chromatography A 781 (1997), p. 367-375 ("Capillary Electrophoresis for the Detection of Known Point Mutations by Single-Nucleotide Primer Extension and Laser-Induced Fluorescence Detection"); Hoogendoom, B. et al., *Human Genetics* (1999) 104:89-93, ("Genotyping Single Nucleotide Polymorphism by Primer Extension and High Performance Liquid Chromatography"), the entire contents of each of which are herein incorporated by reference.

In some embodiments, primer extension can be combined with mass spectrometry for accurate and fast detection of the presence or absence of a mutation. See, U.S. Pat. No. 5,885,775 to Haff et al. (analysis of single nucleotide polymorphism analysis by mass spectrometry); U.S. Pat. No. 7,501,251 to Koster (DNA diagnosis based on mass spectrometry); the teachings of both of which are incorporated herein by reference. Suitable mass spectrometric format includes, but is not limited to, Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

Oligonucleotide Ligation Assay

In some embodiments, an oligonucleotide ligation assay ("OLA" or "OL") is used. OLA employs two oligonucleotides that are designed to be capable of hybridizing to abutting sequences of a single strand of a target molecules. Typically, one of the oligonucleotides is biotinylated, and the other is detectably labeled, e.g., with a streptavidin-conjugated fluorescent moiety. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241:1077-1080 and U.S. Pat. No. 4,998,617, the entire contents of which are herein incorporated by reference in their entirety.

Hybridization Approach

In some embodiments, nucleic acids are analyzed by hybridization using one or more oligonucleotide probes specific for a region in the CFTR gene (SEQ ID NO:1) corresponding to the one or more mutations selected from Table 1, 2, 3 or 4, and under conditions sufficiently stringent to disallow a single nucleotide mismatch. In certain embodiments, suitable nucleic acid probes can distinguish between a normal CFTR gene and a mutant CFTR gene containing one or more mutations selected from Table 1, 2, 3, or 4. For example, suitable nucleic acid probes specifically bind to a normal CFTR gene but not to a mutant CFTR gene containing one or more mutations selected from Table 1, 2, 3, or 4. Alternatively, nucleic acid probes specifically bind to a mutant CFTR gene containing one or more mutations selected from Table 1, 2, 3, or 4 but not to a normal CFTR gene. Probes of the present invention include those that are capable of specifically hybridizing a mutant CFTR allele containing one or more mutations listed in Tables 1, 2, 3, or 4. Probes of the present invention also include those that are capable of specifically hybridizing a normal allele in a particular region of the CFTR gene and therefore capable of distinguishing a normal allele from a mutant CFTR allele containing one or more mutations listed in Tables 1, 2, 3, or 4. Thus, for example, one of ordinary skill in the art could use probes of the invention to determine whether an individual is homozygous or heterozygous for a particular allele.

Nucleic acid hybridization techniques are well known in the art. See, e.g., Sambrook, et al., 1989, Molecular Cloning:

A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

In some embodiments, probe molecules that hybridize to the mutant or wildtype CFTR sequences can be used for detecting such sequences in the amplified product by solution phase or, more preferably, solid phase hybridization. Solid phase hybridization can be achieved, for example, by attaching the CFTR probes to a microchip.

Nucleic acid probes may comprise ribonucleic acids and/or deoxyribonucleic acids. In some embodiments, provided nucleic acid probes are oligonucleotides (i.e., "oligonucleotide probes"). Generally, oligonucleotide probes are long enough to bind specifically to a homologous region of the CFTR gene, but short enough such that a difference of one nucleotide between the probe and the nucleic acid sample being tested disrupts hybridization. Typically, the sizes of oligonucleotide probes vary from approximately 10 to 100 nucleotides. In some embodiments, oligonucleotide probes vary from 15 to 90, 15 to 80, 15 to 70, 15 to 60, 15 to 50, 15 to 40, 15 to 35, 15 to 30, 18 to 30, or 18 to 26 nucleotides in length. As appreciated by those of ordinary skill in the art, the optimal length of an oligonucleotide probe may depend on the particular methods and/or conditions in which the oligonucleotide probe may be employed.

In some embodiments, nucleic acid probes are useful as primers, e.g., for nucleic acid amplification and/or extension reactions.

In some embodiments, nucleic acid probes are labeled with a detectable moiety as described herein.

Arrays

A variety of the methods mentioned herein may be adapted for use with arrays that allow sets of mutations to be analyzed and/or detected in a single experiment. For example, multiple novel CFTR mutations described herein (e.g., Tables 1, 2, 3 or 4) can be analyzed at the same time. Additionally or alternatively, one or more novel CFTR mutations described herein (e.g., Tables 1, 2, 3 or 4) can be analyzed together with other CFTR mutations known in the art at the same time. In particular, methods that involve use of nucleic acid reagents (e.g., probes, primers, oligonucleotides, etc.) are particularly amenable for adaptation to an array-based platform (e.g., microarray). In some embodiments, an array containing one or more probes specific for detecting CFTR mutations described herein (e.g., Tables 1, 2, 3 or 4) can be designed and adapted for various methods described herein. Additionally or alternatively, probes specific for detecting CFTR mutations described herein (e.g., Tables 1, 2, 3 or 4) can be combined with probes specific for CFTR mutations known in the art. In some embodiments, an array containing multiple probes are known as a mutation panel. See, e.g., Wall et al. "A 31-mutation assay for cystic fibrosis testing in the clinical molecular diagnostics laboratory," *Human Mutation,* 1995; 5(4):333-8, the entire contents of which are herein incorporated by reference. Other methods may include the use of real-time PCR with probes for detecting CFTR mutations as described herein.

Protein-Based Analyses

In certain embodiments, CFTR mutations are detected at the protein (or peptide or polypeptide level), that is, a gene product from a CFTR gene mutation is analyzed. For example, CFTR protein or fragment thereof can be analyzed by amino acid sequencing methods, or immuno assays using one or more antibodies that specifically recognize one or more epitopes corresponding to the one or more novel mutations described herein (e.g., Table 1, 2, 3 and 4). CFTR proteins can also be analyzed by protease digestion (e.g., trypsin digestion) and, in some embodiments, the digested protein products can be further analyzed by 2D-gel electrophoresis.

Antibody Detection of Mutant Proteins

For example, specific antibodies that can differentiate between a normal CFTR protein and a mutant CFTR protein can be employed in any of a variety of methods known in the art to detect CFTR mutations. In certain embodiments, suitable antibodies can distinguish between a normal CFTR protein and a mutant CFTR protein containing one or mutations selected from Tables 1, 2, 3, or 4. For example, suitable antibodies specifically bind to a normal CFTR protein but not to a mutant CFTR protein containing one or more mutations selected from Table 1, 2, 3, or 4. Alternatively, suitable antibodies specifically bind to a mutant CFTR protein containing one or more mutations selected from Table 1, 2, 3, or 4 but not to a normal CFTR protein.

Antibodies against particular epitopes, polypeptides, and/or proteins (e.g., mutant or normal CFTR proteins) can be generated using any of a variety of known methods in the art. For example, the epitope, polypeptide, or protein against which an antibody is desired can be produced and injected into an animal, typically a mammal (such as a donkey, mouse, rabbit, horse, chicken, etc.), and antibodies produced by the animal can be collected from the animal. Monoclonal antibodies can also be produced by generating hybridomas that express an antibody of interest with an immortal cell line. For more details on methods of producing, and uses of, antibodies to detect CFTR mutants, see, e.g., U.S. Pat. No. 5,776,677, the entire contents of which are herein incorporated by reference.

In some embodiments, antibodies are labeled with a detectable moiety as described herein.

Antibody detection methods are well known in the art including, but are not limited to, enzyme-linked immunosorbent assays (ELISAs) and Western blots. Some such methods are amenable to being performed in an array format. For example, a variety of different antibodies, each of which is specific for different epitopes within the CFTR protein, could be immobilized in an array and used in an assay such as an ELISA.

Detectable Moieties

In certain embodiments, certain molecules (e.g., nucleic acid probes, antibodies, etc.) used in accordance with and/or provided by the invention comprise one or more detectable entities or moieties, i.e., such molecules are "labeled" with such entities or moieties.

Any of a wide variety of detectable agents can be used in the practice of the present invention. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, SPECTRUM RED™, SPECTRUM GREEN™, cyanine dyes (e.g., CY-3™, CY-5™, CY-3.5™, CY5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm). For example, a suitable dye for use in real-time PCR procedures may include SYBR Green.

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92:4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al., the entire contents of which are herein incorporated by reference. Donor/acceptor pairs of dyes that can be used include, for example, fluorescein/tetramethylrohdamine, IAEDANS/fluoroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

Enzymes

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., $^{3}H$, $^{13}C$, $^{14}C$, $^{18}F$, $^{19}F$, $^{32}P$, $^{35}S$, $^{64}Cu$, $^{67}Cu$, $^{67}Ga$, $^{90}Y$, $^{99m}Tc$, $^{111}In$, $^{125}I$, $^{123}I$, $^{129}I$, $^{131}I$, $^{135}I$, $^{186}Re$, $^{187}Re$, $^{201}Tl$, $^{212}Bi$, $^{213}Bi$, $^{211}At$, $^{153}Sm$, $^{177}Lu$).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Kits

In certain embodiments, the invention provides kits for use in accordance with the invention. Generally, inventive kits comprise one or more reagents that differentiate a normal CFTR gene or protein from a mutant CFTR gene or protein containing one or more mutations selected from Table 1, 2, 3, or 4. For example, kits may comprise one or more (e.g., any combination of) reagents as described herein, and optionally additional components. For example, a kit according to the present invention may also include reagents that can detect other CFTR mutations well known in the art.

Suitable reagents may include nucleic acid probes and/or antibodies or fragments thereof. In some embodiments, suitable reagents are provided in a form of an array such as a microarray or a CFTR mutation panel.

In some embodiments, provided kits further comprise reagents for carried out various detection methods described herein (e.g., sequencing, hybridization, primer extension, multiplex ASPE, immuno assays, etc.). For example, kits according to the invention may optionally contain buffers, enzymes, and/or reagents for use in methods described herein, e.g., for amplifying nucleic acids via primer-directed amplification, for performing ELISA experiments, etc.

In some embodiments, provided kits further comprise a control indicative of a healthy individual, e.g., a nucleic acid and/or protein sample from an individual who does not carry a CFTR mutation associated with CF or a CF related disorder. In some embodiments, provided kits further comprise a control indicative of known CFTR mutant alleles (such as ΔF508). Kits may also contain instructions on how to determine if an individual has CF or a CF related disorder, is at risk of developing CF or a CF related disorder, or is a carrier of CFTR mutation.

In some embodiments, a computer readable medium encoding information corresponding to one or more mutations shown in Tables 1, 2, 3, and 4 is provided. Such computer readable medium may be included in a kit of the invention.

Systems

In an embodiment, the present invention provides systems for carrying out the analysis of the invention. Thus, in an embodiment, the present invention comprises a computer-readable medium on which is encoded programming code for the methods described herein. Also in an embodiment, present invention may comprise a system comprising a processor in communication with a computer-readable medium, the processor configured to perform the methods described herein. Suitable processors and computer-readable media for various embodiments of the present invention are described in greater detail below and are illustrated in FIG. 5.

Thus, in certain embodiments, the invention comprises a system for predicting the activity of at least one gene comprising: a computer readable medium; and a processor in communication with the computer readable medium, the processor configured to estimate the effects of individual mutations in the at least one gene. The processor may, in certain embodiments, be further in communication with a database comprising data for a plurality of sequences for the portion of the at least one gene, where the processor is configured to compare the nucleic acid and/or amino acid sequence of the portion of the at least one gene to the data of the plurality of sequences for the portion of the at least one gene to determine if there is a mutation in the portion of the at least one gene in the biological sample obtained from the subject.

In other embodiments, the invention comprises a computer readable medium on which is encoded program code for predicting the activity of at least one gene, the program code comprising code for applying a model to estimate the effects of individual mutations in the at least one gene. In certain embodiments, the programming code comprises code configured to compare the amino acid and/or nucleic acid sequence of the portion of the at least one gene to the data for a plurality of sequences for the portion of the at least one gene stored in a database to determine if there is a mutation in the portion of the at least one gene in the biological sample obtained from the subject.

Some embodiments of the systems and computer readable media of the invention may be applied to various genes. In certain embodiments, the at least one gene comprises the CFTR gene.

As noted herein, the sequence of the portion of the at least one gene and the biological activity of interest as assessed for a particular subject may be compared to a database of amino acid and/or nucleic acid sequences and biological activity as assess for a plurality of subjects. Thus, in certain embodiments of the systems and computer readable media, the database comprises data for the biological activity as measured in a plurality of samples from which the sequence of the portion of the at least one gene was determined.

Embodiments in accordance with aspects of the present subject matter can be implemented in digital electronic circuitry, in computer hardware, firmware, software, or in combinations of the preceding. In one embodiment, a computer may comprise a processor or processors. The processor may comprise, or have access to, a computer-readable medium, such as a random access memory coupled to the processor. The processor may execute computer-executable program instructions stored in memory, such as executing one or more computer programs including a sampling routine and suitable programming to produce output to generate the analysis described in detail herein.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media that may store instructions that when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing may be in one or more structures, and may be dispersed through one or more structures. The processor may comprise code for carrying out one or more of the methods (or parts of methods) described herein.

The system may comprise a data compiling system as well as a means for the user to interact with the system as the analysis proceeds. Thus, in an embodiment, the present invention may comprise a system for collecting and/or compiling data from a plurality of assay measurements and/or sequencing data and transmitting the data to a computer, and a system for transmitting the results of the analysis to a user. The systems of the present invention may be designed for high-throughput analysis of DNA and/or amino acid sequencing data. Thus, in an embodiment, the plurality of measured signals comprise a plurality of known DNA sequences isolated from at least one cell type.

FIG. 5 shows an embodiment of the flow of information in a system comprising the software of the present invention. As discussed above, a computer processor or CPU may include, for example, digital logic processors capable of processing input, executing algorithms, and generating output as necessary in response to the inputs received from the touch-sensitive input device. As detailed herein, such processors may include a microprocessor, such as an ASIC, and state machines, and/or other components. Such processors include, or may be in communication with, media, for example computer-readable media, which stores instructions that, when executed by the processor, cause the processor to perform the steps described herein.

Thus, in an embodiment, the starting point may comprise data (100) that may comprise a normal CFTR gene (100A) and mutant CFTR gene (100B). Once the data has been collected (110), it may be compiled (120) and/or transformed if necessary using any standard spreadsheet software such as Microsoft Excel, FoxPro, Lotus, or the like. In an embodiment, the data are entered into the system for each experiment. Alternatively, data from previous runs are stored in the computer memory (150) and used as required.

At each point in the analysis, the user may input instructions via a keyboard (180), floppy disk, remote access (e.g., via the internet) (190), or other access means. The user may enter instructions including options for the run, how reports should be printed out, and the like. Also, at each step in the analysis, the data may be stored in the computer using a storage device common in the art such as disks, drives or memory (150). As is understood in the art, the processor (160) and I/O controller (170) are required for multiple aspects of computer function. Also, in a embodiment, there may be more than one processor.

The data may also be processed to remove noise (130). In some cases, the user, via the keyboard (180), floppy disk, or remote access (190), may want to input variables or constraints for the analysis, as for example, the threshold for determining noise. The results of the analysis may then be compiled and provided in a form for review by a user (140).

The following examples serve to illustrate the present invention. These examples are in no way intended to limit the scope of the invention.

EXAMPLES

Example 1

Identification of Novel Mutations in the CFTR Gene

Novel mutations in the CFTR gene were identified using the CF full sequencing assay. Typically, samples submitted for CF full sequencing assays were from individuals for whom testing in CF mutation panels has been uninformative, or partially uninformative. These individuals include 1) patients with idiopathic chronic pancreatitis; 2) patients with congenital bilateral absence of the vas deferens (CBAVD); 3) couples who test positive/negative by mutation analysis; 4) CF-affected or suspected patients in whom one or no mutations have been identified; 5) obligate carriers of a rare familial mutation; 6) patients with a family history of CF, for whom mutation analysis by other methodologies is negative; 7) patients with a CF related disease or condition. Sequence changes in the CFTR gene were identified by comparing the patient gene sequence to the wild-type gene sequence. Novel mutations in the CFTR gene that were unreported previously are summarized in Table 5.

As shown in Table 5, patients carrying these novel mutations were from different ethnic groups including Caucasians, African Americans, Hispanics, and Asians. Some of the mutations are located in introns (e.g., intron 3, intron 6a, intron 11, intron 14a, intron 19, intron 20, intron 21, and intron 23). Some of the mutations are located in exons (e.g., exon 2, exon 3, exon 4, exon 5, exon 6a, exon 6b, exon 7, exon 9, exon 10, exon 11, exon 12, exon 13, exon 14a, exon 14b, exon 15, exon 16, exon 17a, exon 17b, exon 19, exon 20, exon 21, exon 22, and exon 24).

As shown in Table 5, most of the novel mutations identified result in codon changes or altered gene splicing sites, which will likely affect the CFTR gene expression and/or protein function. In particular, some of the mutations are nonsense mutations (i.e., mutations predicted to result in the introduction of a stop codon). Some of the mutations affect consensus splice site ag/gt. Some of these mutations are insertion or deletion of at least one nucleotide. These mutations are category 2 mutations according to the ACMG guidelines, and are of the type expected to cause CF or CF related disease, disorder or condition.

Some mutations are missense mutations. Some are predicted to cause in-frame insertions and/or deletions. Some are likely to affect splice sites. These mutations are category 3 mutations according to the ACMG guidelines.

Thus, the novel mutations provided herein can be used, alone or in combination with other known CF mutations, to detect CF or a CF related disorder in CFTR testing assays including carrier testing.

TABLE 5

Novel Mutations in the CFTR gene

| Sequence Change | Type of mutation | AA Change | Ethnicity | Other Mutations | Clinical Information | Exon |
|---|---|---|---|---|---|---|
| 1824delA | Frameshift (FS) | n/a | Caucasian | F508del | Mutation was identified in a 22 year old patient with a known diagnosis of CF. This patient carried a second mutation known to cause CF (F508del). | e12 |
| 2957delT | FS | n/a | Caucasian | F508del | Mutation was identified in a 1 year old patient with a known diagnosis of CF. The patient carried a second mutation known to cause CF (F508del). | e15 |
| 4089ins4 | FS | n/a | Caucasian | F508del | Mutation was identified in a 7 year old patient with a known diagnosis of CF. The patient had a positive sweat chloride test. The patient carried a second mutation known to cause CF (F508del). | e21 |
| 4374 + 2T > C | Splice site mutation | n/a | 1. Caucasian | 1. F508del | Patient #1: Mutation was identified in a 45 year old patient with a suspected diagnosis of CF. The patient carried a second mutation known to cause CF (F508del). | i23 |
| | | | 2. Caucasian | 2. F508del | Patient #2: Mutation was identified in a 52 year old patient with a suspected diagnosis of CF. The patient carried a second mutation known to cause CF (F508del). | |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 3064A > T | Nonsense | K978X | African American | Q1042X | Mutation was identified in a 26 year old patient with a known diagnosis of CF. The patient carried a second mutation likely to cause CF Q1042X. | e16 |
| 246C > G | Nonsense | Y38X | Caucasian | F508del | Mutation was identified in a 1 month old patient with a suspected diagnosis of CF. The patient had a positive sweat chloride test. The patient carried a second mutation known to cause CF (F508del). | e2 |
| 269C > T | Missense (MS) | A46V | 1) Caucasian | 1) 3849 + 12192G > A | Patient #1: Mutation was identified in a 32 year old patient who was tested due to abnormalities found on fetal ultrasound. The patient carried a second mutation of unknown clinical significance (3849 + 12192G > A). | e2 |
| | | | 2) Black | 2) F508del | Patient #2: Mutation was identified in a 2 month old patient who was tested based on follow-up for a positive newborn screen. The patient carried a second mutation known to cause cystic fibrosis (F508del). | |
| | | | 3) African American | 3) none | Patient #3: Mutation was identified in a 24 year old patient who was tested as a parental follow-up to a positive newborn screen. | |
| 2902 G > T | MS | D924Y | Caucasian | F508del | Mutation was identified in a 1 month old patient with a suspected diagnosis of CF. The patient also had a positive sweat chloride test and carried a second mutation known to cause CF (F508del) | e 15 |
| 3814G > A | MS | E1228K | Caucasian | F508del | Mutation was identified in a 1 month old patient with a suspected diagnosis of CF. The patient had a borderline sweat chloride test. The patient carried a second mutation known to cause CF (F508del). | e19 |
| 502G > C | MS | G124R | Not Provided | F508del | Mutation was identified in a 2 month old patient with a suspected diagnosis of CF. The patient had a positive sweat chloride test. The patient carried a second mutation known to cause CF (F508del). | e4 |
| 1520G > T | MS | G463V | Caucasian | F508del | Mutation was identified in a 17 year old patient with a known diagnosis of CF. Patient carried a second mutation known to cause CF (F508del). | e9 |
| 511__513dup TTA | In frame duplication | L127dup | Caucasian, Asian | W1282X | Mutation was identified in a newborn with a suspected diagnosis of CF. The patient had clinical symptoms of CF including as a positive sweat chloride test, meconium ileus, echogenic bowel, and pancreatic insufficiency. The patient carried a second mutation known to cause CF (W1282X). | e4 |
| 978A > T | MS | E282D | 1. not provided | 1. 3120 + 1G > A | Patient #1: Mutation was identified in a 10 year old patient with a suspected diagnosis of CF. The patient had a positive sweat chloride test. The patient carried a second mutation known to cause CF (3120 + 1G > A). | e6b |
| | | | 2. not provided | 2) none | Patient #2: Mutation was identified in a 4 year old patient with a suspected diagnosis of CF and a family history of CF. | |
| 843G > C | MS | Q237H | Caucasian | F508del | Mutation was identified in a 2 month old patient with a known diagnosis of CF. The patient carried a second mutation known to cause CF (F508del). | e6a |
| 829C > T | MS | L233F | Caucasian | D1152H | Mutation was identified in a 1 month old patient who was tested following a positive newborn screen. The patient carried a second mutation known to cause CF (D1152H). | e6a |
| 4096 − 6C > T | Splice site mutation | None | Caucasian | F508del | Mutation was identified in a 58 year old patient with a suspected diagnosis of CF. The patient carried a second mutation known to cause CF (F508del). | i21 |
| 4375 − 7delT | Splice site mutation | None | Caucasian | F508del | Mutation was identified in a 6 year old patient with a suspected diagnosis of CF. Patient has a family history, a borderline sweat chloride test and recurrent pneumonia. The patient carried a second mutation known to cause CF (F508del). | i23 |
| 1586 G > C | MS | S485T | Caucasian | S1235R | Mutation was identified in a 2 year old patient with a suspected diagnosis of CF. The patient carried a second mutation S1235R (3837T > G) which has been reported in individuals with varying CF phenotypes. | el0 |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 875 + 4G > T | Splice site mutation | n/a | African American | none | Mutation was identified in a 1 month old patient who had a positive newborn screening test. | i6a |
| 4005 + 3G > T | Splice site mutation | n/a | Caucasian | none | Mutation was identified in a 40 year old patient who was tested to determine if they were a carrier, there was no family history of CF. | i20 |
| 2711T > C | MS | I860T | Caucasian | F508del, E528E | Mutation was identified in a 58 year old woman with a suspected diagnosis of CF. The patient carried a second mutation known to cause CF (F508del) and an additional mutation of unknown clinical significance (E528E) . . . | el4a |
| 3891G > C | MS | L1253F | Not provided | G85E, L15P | Mutation was identified in a 32 year old patient with a known diagnosis of CF. The patient carried a second mutation known to cause CF (G85E) and an additional mutation of unknown clinical significance (L15P). | e20 |
| 2524C > T | MS | P798S | African American | F508del, R74W, G921E, DI270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, G921E, D1270N). | e13 |
| 2894G > A | MS | G921E | African American | F508del, R74W, P798S, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, P789S, D1270N). | e15 |
| 405 + 10247C > T | Possible splice site mutation | n/a | Caucasian | F508del | Mutation was identified in a 35 year old patient who was tested to determine if they were a carrier, there was no family history of CF. This patient carried a second mutation known to cause CF (F508del). | i3 |
| 405 + 10255delC | Possible splice site mutation | n/a | Not Provided | F508del, 124del23bp | Mutation was identified in a 10 year old patient. The patient carries two mutations know to cause CF (F508del and 124del23). | i3 |
| 1811 + 1643 G > T | Possible splice site mutation | n/a | 1. Hispanic | 1. F508del | Patient #1: Mutation was identified in a 1 year old patient with a known diagnosis of CF. Patient had a positive sweat chloride test. The patient carried a second mutation known to cause CF (F508del). | i11 |
| | | | 2. Hispanic | 2. F508del | Patient #2: Mutation was identified in a 6 year old patient with a known diagnosis of CF. The patient carried a second mutation know to cause CF (F508del). | |
| | | | 3. Not provided | 3. none | Patient #3: Mutation was identified in an 8 month old patient with a suspected diagnosis of CF. | |
| 1812 − 13A > G | Splice site mutation | n/a | Caucasian | none | Mutation was identified in a 15 year old patient with a suspected diagnosis of CF. The patient has chronic sinusitis. | i11 |
| 2752 − 33insA | Possible splice site mutation | n/a | African American | F693L | Mutation was identified in a 6 year old patient with a known diagnosis of CF. The patient carries a second mutation of unknown clinical significance (F693L). | i14a |
| 3849 + 12192 G > A | Possible splice site mutation | n/a | Caucasian | A46V | Mutation was identified in a 32 year old patient who was tested due to abnormalities found on fetal ultrasound. The patient carried an additional mutation of known clinical significance (A46V). | i19 |
| 724G > A | MS | A198T | Hispanic | none | Mutation was identified in a 4 month old patient with a suspected diagnosis of CF. | e6a |
| 3899C > T | MS | A1256V | Guyanese | none | Mutation was identified in a 45 year old patient who was tested to determine if they were a carrier, there was no family history of CF. | e20 |
| 3986C > T | MS | A1285V | Not Provided | none | Mutation was identified in a 23 year old patient who was tested to determine if they were a carrier, there was no family history of CF. | e20 |
| 901G > A | MS | E257K | Hispanic | none | Mutation was identified in a 4 year old patient with a suspected diagnosis of CF. The patient has asthma and recurring pneumonia. | e6b |
| 392 T > C | MS | F87S | Not Provided | none | The mutation was identified in a 1 month old patient with a suspected diagnosis of CF. | e3 |
| 3463T > C | MS | F1111L | Hispanic | none | Mutation was identified in a 6 year old patient with a suspected diagnosis of CF. The patient has asthma. | e17b |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 1757G > A | MS | G542E | Hispanic | none | Mutation was identified in a 25 year old patient who was tested to determine if they were a carrier, there was no family history of CF. The patient carried 2 copies of G542E. . . | e11 |
| 4025G > C | MS | G1298A | Asian | G970D, Q1352H | Mutation was identified in a 34 year old patient with congenital absence of the vas deferens. The patient carried two other mutations of unknown clinical significance (G970D and Q1352H) | e21 |
| 4129G > T | MS | G1333W | Not Provided | none | Mutation was identified in an 8 year old patient with a suspected diagnosis of CF. Patient had recurrent respiratory infections and chronic cough. | e22 |
| 663T > G | MS | I177M | Caucasian | none | Mutation was identified in a 34 year old patient who was tested to determine if they were a carrier, there was no family history of CF. | e5 |
| 3200T > C | MS | I1023T | Hispanic | none | Mutation was identified in a 34 year old patient who was tested to determine if they were a carrier, there was no family history of CF. | e17a |
| 4412 T > C | MS | I1427T | Asian | S1444S | Mutation was identified in a 34 year old patient who was tested to determine if they were a carrier, there was no family history of CF. The patient carried another mutation that is considered likely to be clinically benign (S144S). | e24 |
| 620A > C | MS | K163T | Caucasian | none | Mutation was identified in a 32 year old patient with a family history of CF. | e4 |

Example 2

CFTR Mutation Detection Assay

The present example demonstrates that multiplex ASPE assay can be used to detect novel cystic fibrosis mutations described herein. Multiplex ASPE combines multiplex PCR and allele-specific primer extension. Multiplex PCR is performed to amplify target regions in the CFTR gene containing novel sequence variations described herein from genomic DNA in a sample. Multiplex primer extension reactions are then performed using allele-specific primers, i.e., extension primers that possess a 3' terminal nucleotide, which form a perfect complement with the target sequence, are extended to form extension products and modified nucleotides (e.g., biotinylated dCTP) are incorporated into the extension product for detection purposes. Alternatively, an extension primer may instead contain a 3' terminal nucleotide which forms a mismatch with the target sequence. In this instance, primer extension does not occur. Primer extension products are then hybridized to universal array beads with “anti-tag” sequence (sequences complementary to the tag sequence) for capture and detection purposes.

In some cases, the novel mutations described herein can be detected in combination of other known CF mutations, for example, mutations recommended by the American College of Genetics and American College of Obstetricians and Gynecologists, as well as other common and clinically relevant mutations, such as, for example, ΔF508 (exon 10), G542X (exon 11), G551D (exon 11), R117H (exon 4), W1282X (exon 20), $N_{13}O_3K$ (exon 21), 3905insT (exon 20), 3849+10 KbC>T (intron 19), G85E (exon 3), R334W (exon 7), A455E (exon 9), 1898+1G>A (exon 12), and/or 2184delA (exon 13).

Various ASPE kits can be used to carry out the detection methods described herein. For example, Luminex’s TAG-IT™ kit and Data Analysis software can be modified to detect a panel of CF mutations including one or more novel mutations described herein. Mutation detection kit may use non-isotopic fluorescent technology, and a 96-well assay format that is compatible with automation such that result analyses and genotype calling are automated.

Allele Specific Primers

Allele specific primers can be designed based on the sequence variations shown in Table 5 and the CFTR genomic sequences (including exon and intron sequences) using various methods and software known in the art. A universal tag sequence can be added to allele specific primers.

Specimens and Assay Format

Specimens containing genomic DNA to be analyzed can be obtained from, but not limited to, the following sources: Whole blood (e.g., whole blood in EDTA, ACD-A, ACD-B), fresh or frozen tissue, amniotic fluid, CVS (chorionic villus sampling) tissue, cultured cells (e.g., CVS, amniotic fluid, fibroblasts, POC (product of conception)), blood spots, cord blood, mouthwash, genomic DNA extracted by an outside laboratory. Blood and bloodspot DNA samples are typically run undiluted at a 5 μL input volume. An amount of 5 to 200 ng DNA is used as input. For testing prenatal and mouthwash samples, generally between 20 ng and 150 ng is used as input, for example, about 20 ng, 25 ng, 30 ng, 35 ng, 40 ng, 45 ng, 50 ng, 55 ng, 60 ng, 65 ng, 70 ng, 75 ng, 80 ng, 85 ng, 90 ng, 95 ng, 100 ng, 110 ng, 120 ng, 130 ng, 140 ng, or 150 ng.

A 96-well assay plate is used. Two genomic DNA controls are included with each assay plate. The specific controls are rotated sequentially through assay plates. Each assay plate also includes two cocktail blanks and ASPE (Allele-Specific Primer Extension) controls. A calibrating 96-well filter plate is also used during data acquisition.

Single-Well Multiplex PCR

Multiplex PCR are performed to amplify exons containing mutations described herein using consensus flanking intron sequences. Generally, amplicons range in size between about 150 bp and 600 bp (inclusive of endpoints).

Typically, 5 ng-200 ng of DNA is amplified to produce a product containing multiple amplicons using PCR amplification conditions known in the art or optimized/modified using routine experimentation.

Enzymatic Post-PCR Cleanup

PCR products are treated with Exonuclease I and Shrimp Alkaline Phosphatase to remove residual primers that will interfere with allele-specific primer extension reactions. PCR products are incubated with enzyme and then enzyme is heat-deactivated, according to standard protocols or modified protocols readily developed by one of ordinary skill in the art.

Single Well Allele Specific Primer Extension (ASPE) Reactions

Typically up to 100 sequence variations can be distinguished in a single-well reaction; using the Luminex bead set. For example, a set of allele-specific oligonucleotide (ASO) primers (including wildtype control ASOs) with tag sequences are used.

The Exo-SAP-treated PCR product is subjected to an allele-specific primer extension reaction containing tagged primers and biotinylated dCTP using PCR reaction conditions known in the art or modified readily by one of ordinary skill in the art.

Universal Array Sorting and Detection

Each bead is coupled with an anti-tag sequence complementary to the tag sequence ASPE primers. Therefore, any ASPE products, if present, can be captured for genotype analysis. Wild-type control for each amplicon is included. The signals from wildtype alleles serve as a control for each amplicon and provide information for allelic ratio calculation (typically obtained by calculating the ratio of signal for the mutant allele over signal for the wildtype allele), for the detected mutations.

The ASPE product is added to the universal bead array containing anti-tags to the ASPE primers and incubated for hybridization. Hybridization reactions are then washed over a filter that captures the beads and removes any non-hybridized ASPE products containing biotin. Bead hybridization conditions are known in the art and can be adapted readily by one skilled in the art.

Strepatavidin R-Phycoerythrin conjugate is added to the hybridized products on the filter plate and incubated at room temperature, followed by bead sorting and detection. For example, a modified LUMINEX™ 100 IS™ or 200 IS™ can be used. The LUMINEX™ 100 IS™ can upload sample sheets from text files or barcodes. Detection time averages 20-100 seconds per well.

Results

In the LUMINEX™ system, results are generated as a <.csv> file and exported in batches. The batch output file (.csv) is opened in TAG-IT™ Data Analysis Software (TDAS) version 6.0 where results are automatically generated based on pre-determined algorithms for allelic ratios on certain individually tested mutations and the presence or absence of signal on the remaining mutations.

Mutation Confirmation

Samples positive for any of the mutations described herein can be confirmed by a second assay run. Positive samples can also be confirmed by direct DNA sequencing.

Example 3

Cystic Fibrosis Sequencing Assays

The Cystic Fibrosis full sequencing assay and single exon sequence assay can be used to detect mutations in the CFTR gene directly in a patient sample. The Cystic Fibrosis full sequencing assay and single exon sequence assay can also be used to complement CF screening panels, and/or to serve as a confirmatory assay for samples that are positive for multiplex mutations or those without a normal counterpart in the CF mutation detection assay.

The CF full sequencing assay sequences the entire coding region of the CFTR gene plus 15 bp at the 3' end of each intron (30 bp for e17b to cover a known mutation) and 6 bp at the 5' beginning of each intron.

In addition, the assay includes portions of introns 1, 3, 11, and 19 useful in identifying the exon 2, 3 deletion, the A>G mutation at 1811+1.6 kb, and the C>T mutation at 3849+10 kb. Typically, the assay comprises analysis of 31 amplicons: e1, i1, e2, e3, i3, e4, e5, e6a, e6b, e7, e8, e9, e10, e11, e12, e13a, e13b, e14a, e14b, e15, e16, e17a, e17b, e18, e19, i19, e20, e21, e22, e23, and e24. Each amplicon includes the complete coding region of the exon with the exception of 13.1 and 13.2, in which, due to the large size of the exon, the amplicon is divided into two fragments. The CF Single Exon Sequencing assay uses the same primers but on an individual basis as needed.

Samples tested in the CF single exon sequencing assay in this Example include those from individuals that 1) tested positive in a CF mutation detection assay (e.g., multiplex ASPE assay as described in Examples 2) but require confirmation; 2) tested positive in the CF full sequencing assay and require repeat testing; 3) are being tested for a known familial mutation(s); and/or 4) are being tested for a mutation that is not detectable in the CF mutation detection assay of Example 2.

Specimens and Assay Format

Specimens to be analyzed can be extracted genomic DNA from any of, but not limited to, the following sources: Whole blood (e.g., whole blood in EDTA, ACD-A, ACD-B), blood spots, amniotic fluid, chorionic villus samples (CVS) (for single exon sequencing only), cultured cells (e.g., CVS, amniotic fluid, fibroblasts, POC), mouthwash (for single exon sequencing only).

A 96-well format is used. Cocktail blanks are run for all amplicons on each assay.

PCR Amplification

Target regions containing mutations described herein are first amplified by PCR amplification. Typically, 5 ng-200 ng of DNA is amplified in a 25 μL volume reaction. PCR primers include 5' UPS tags-UPS1 for the Forward primers and UPS2 for the Reverse primers. Table 6 presents sequences of exemplary primers used in amplification of certain exemplary target exon or intron regions.

TABLE 6

Primer sequences

| Amplicon | Primer Name | Sequence (5'-3') | Amplicon Length | SEQ ID NO. |
|---|---|---|---|---|
| Primers for exonic sequences | | | | |
| CF exon 1 | UP1CFe1F | TTTAACCTGGGCAGTGAAG | 373 | 5 |
| | UP2CFe1R | AACCCAACCCATACACA | | 6 |

TABLE 6-continued

Primer sequences

| Amplicon | Primer Name | Sequence (5'-3') | Amplicon Length | SEQ ID NO. |
|---|---|---|---|---|
| CF exon 2 | UP1CFe2F | CAAATCAAGTGAATATCTGTTC | 316 | 7 |
| | UP2CFe2R | AGCCACCATACTTGGCTCCTA | | 8 |
| CF exon 3 | UP1CFe3F2 | CTAAAATATTTGCACATGCAAC | 333 | 9 |
| | UP2CFe3R | TTTCTTAGTGTTTGGAGTTGG | | 10 |
| CF exon 4 | UP1CFe4F2 | TCATTTTAAGTCTCCTCTAAAG | 407 | 11 |
| | UP2CFe4R | CGATACAGAATATATGTGCCA | | 12 |
| CF exon 5 | UP1CFe5F2 | AACAACTAGAAGCATGCCAG | 394 | 13 |
| | UP2CFe5R2 | GTTGTATAATTTATAACAATAGTG | | 14 |
| CF exon 6a | UP 1 CFe6aF2 | GGAAGATACAATGACACCTG | 353 | 15 |
| | UP2CFe6aR3 | CTGAAGATCACTGTTCTATGC | | 16 |
| CF exon 6b | UP1 CFe6bF3 | ATGACTTAAAACCTTGAGCAGT | 336 | 17 |
| | UP2CFe6bR2 | GGAAGTCTACCATGATAAACAT | | 18 |
| CF exon 7 | UP1CFe7F2 | GAGACCATGCTCAGATCTTCC | 507 | 19 |
| | UP2CFe7R | ACTTTTATAACTTCCTAGTGAAG | | 20 |
| CF exon 8 | UP1CFe8F2 | AAGATGTAGCACAATGAGAGTA | 268 | 21 |
| | UP2CFe8R | CAGTTAGGTGTTTAGAGCAA | | 22 |
| CF exon 9 | UP1CFe9F | GTATACAGTGTAATGGATCATG | 402 | 23 |
| | UP2CFe9R4 | CACCAAATTAAGTTCTTAATAG | | 24 |
| CF exon 10 | UP1CFe1OF | TTCTGCTTAGGATGATAATTGG | 479 | 25 |
| | UP2CFe1OR | GCATAGGTCATGTGTTTTATTA | | 26 |
| CF exon 11 | UP1CFe11F | CAGATTGAGCATACTAAAAGTG | 240 | 27 |
| | UTP2CFe11R | TACATGAATGACATTTACAGCA | | 28 |
| CF exon 12 | UP1CFe12F | GCTACTTCTGCACCACTTTTG | 344 | 29 |
| | UP2CFe12R | CAGTCTGTCTTTCTTTTATTTTA | | 30 |
| CF exon 13a | UP1CFe13F3 | CAAAATGCTAAAATACGAGAC | 388 | 31 |
| | UP2CFe13R5 | TCCAGGAGACAGGAGCATC | | 32 |
| CF exon 13b | UP1CFe13F4 | CTCATGGGATGTGATTCTTT | 714 | 33 |
| | UP2CFe13R2 | GATACACCTTATCCTAATCCTA | | 34 |
| CF exon 14a | UP1CFe14aF3 | ACCACAATGGTGGCATGA | 299 | 35 |
| | UP2CFe14aR | TGTATACATCCCCAAACTATC | | 36 |
| CF exon 14b | UP1CFe14bF2 | TGGGCATGGGAGGAATAGGTG | 228 | 37 |
| | UP2CFe14bR | TTACAATACATACAAACATAGTGG | | 38 |
| CF exon 15 | UP1CFe15F2 | AAGTAACTTTGGCTGC | 416 | 39 |
| | UP2CFe15R2 | CTGCCATTAGAAAACCA | | 40 |
| CF exon 16 | UP1CFe16F2 | AAGTCTATCTGATTCTATTTGC | 307 | 41 |
| | UP2CFe16R2 | GTTTTTTTAATAATACAGACATACT | | 42 |
| CF exon 17a | UP1CFe17aF3 | TGTCCACTITGCAATGTGAA | 317 | 43 |
| | UP2CFe17aR3 | CAATAAAGAATCTCAAATAGCTCT | | 44 |
| CF exon 17b | UP1CFe17bF3 | TAGTCTTTTTCAGGTACAAG | 516 | 45 |
| | UP2CFe 17bR6 | CAATGGAAATTCAAAGAAATCACT | | 46 |
| CF exon 18 | UP1CFe18F6 | GAATACTTACTATATGCAGAGCA | 416 | 47 |
| | UP2CFe18R3 | GTTCTTCCTCATGCTATTACTC | | 48 |
| CF exon 19 | UP1CFe19F | GCCCGACAAATAACCAAGTGA | 494 | 49 |
| | UP2CFe19R2 | CTAACACATTGCTTCAGGCTA | | 50 |
| CF exon 20 | UP1CFe2OF | AAGGTTGTTTGTCTCCATATAT | 544 | 51 |
| | UP2CFe2OR | GCCTATGAGAAAACTGCACT | | 52 |
| CF exon 21 | UP1 CFe21 F | ACATGGGTGTTTCTTATTTA | 428 | 53 |
| | UP2CFe21 R2 | GTTAGGGGTAGGTCCAGT | | 54 |
| CF exon 22 | UP1CFe22F | GCTTGAGTGTTTTTAACTCTGTG | 314 | 55 |
| | UP2CFe22R | ATGATTCTGTTCCCACTGTGC | | 56 |

TABLE 6-continued

| Primer sequences | | | | |
|---|---|---|---|---|
| Amplicon | Primer Name | Sequence (5'-3') | Amplicon Length | SEQ ID NO. |
| CF exon 23 | UP1CFe23F | GTTCTGTGATATTATGTGTGG | 226 | 57 |
| | UP2CFe23R | CAAGGGCAATGAGATCTTAAG | | 58 |
| CF exon 24 | UP1CFe24F2 | AGTTTCTGTCCCTGCTCT | 356 | 59 |
| | UP2CFe24R | GAGCAAATGTCCCATGTCAAC | | 60 |
| Primers for intronic sequences | | | | |
| CF intron 1 | UP1CFin1F2 | AATGGTGTTTACCTACCTAGAGAA | 250 | 61 |
| | UP4CFin1R2 | CCTCCTCTGATTCCACAAG | | 62 |
| CF intron 3 | UP3CFin3F3 | CTGAGATTCTGTTCTAGGTGTG | 366 | 63 |
| | UP2CFin3R | CCTACACTCAGAACCCATCAT | | 64 |
| CF intron 19 | UP1CFin19F | TTCAGTTGACTTGTCATCTTG | 223 | 65 |
| | UP2CFin19R | AATATGTTGAAAGTTAAACAGTG | | 66 |
| CF intron 11 | UP1CFin11F | GTTACACTATAAAGGTTGTTTTAGAC | 292 | 67 |
| | UP2CFin11R | CACAGTTCCCATATTAATAGAAATG | | 68 |
| (Seq) | CFe9.SEQ.F | TTTTTAACAGGGATTTGGG | N/A | 69 |
| (Seq) | CFe6bF2 | GATTGATTGATTGATTGATT | N/A | 70 |
| (Seq) | UPS1 | GCGGTCGCATAAGGGTCAGT | N/A | 71 |
| (Seq) | UPS2 | CGCCAGCGTATTCCCAGTCA | N/A | 72 |

PCR conditions are as shown in Table 7.

TABLE 7

| PCR amplification conditions for CF full sequencing assay | | | |
|---|---|---|---|
| Cycles | Temperature (° C.) | Time | Function |
| 1 | 95 | 5 min | Denaturation of enzyme |
| 35 | 95 | 20 sec | Denaturation of dsDNA |
| | 55 | 20 sec | Annealing |
| | 72 | 40 sec | Extension |
| 1 | 72 | 7 min | Final extension |
| 1 | 8 | Forever | End |

Enzymatic Post-PCR Clean Up

PCR products are treated with Exonuclease I (Exo) and Shrimp Alkaline Phosphatase (SAP) to remove residual primers that may interfere with sequencing. The following incubation conditions are used:

37° C. for 30 minutes (enzyme digestion)

99° C. for 15 minutes (enzyme deactivation)

Hold at 8° C. until storage

Products can be stored, e.g., at −80° C. or −20° C.

Sequencing

Exo-SAP treated products are diluted 1:2 in water, and 3 µL is added to 7 µL of each forward and reverse sequence cocktail containing Big Dye v3.1 (ABI). In order to obtain bidirectional sequencing results, two sequencing reactions are performed for each amplicon, using both UPS1 and UPS2 primers. An additional forward sequencing reaction using gene specific primers is performed for Exons 6b and 9 to obtain readable sequence beyond the repeat regions. Cycle sequencing is performed in a thermocycler with the conditions shown in Table 8.

TABLE 8

| Thermocycler conditions for sequencing reactions for CF full sequencing assay | | | |
|---|---|---|---|
| Cycles | Temperature (° C.) | Time | Function |
| 1 | 96 | 1 min | Denaturation of enzyme |
| 25 | 96 | 10 sec | Denaturation of dsDNA |
| | 53 | 5 sec | Annealing |
| | 60 | 3 sec | Extension |
| 1 | 8 | Forever | End |

Assay plates can be stored, e.g., at −80° C. for up to 2 weeks until analyzed or further manipulated.

Post-Sequencing Purification

Sequence products are purified using the Performa DTR Ultra 96 Well Plate (Edge Biosystems). Sequencing reactions are diluted 1:2 and 10 µL is purified through the Edge Plate.

Sequencing Run: ABI 3730 Genetic Analyzer and Data Analysis

A 1 kV/14 second injection is performed on the 3730x1 Genetic Analyzer. POP7 polymer and a 50 cm array are used for optimal resolution. Parameters for a typical sequencing run are shown in Table 9.

TABLE 9

| Parameters for typical sequencing runs | |
|---|---|
| Feature | Parameter for CF full sequencing |
| Run Temp | 60° C. |
| Pre Run Voltage | 15.0 Kvolts |
| Pre Run Time | 180 sec |
| Injection Voltage | 1.0 Kvolts |

TABLE 9-continued

| Parameters for typical sequencing runs | |
|---|---|
| Feature | Parameter for CF full sequencing |
| Injection Time | 14 sec |
| Voltage number of steps | 30 |
| Voltage Step Interval | 15 sec |
| Data Delay Time | 240 sec |
| Run Voltage | 13.4 Kvolts |
| Run Time | 2400 sec |

Sequence data Analysis is performed using SEQSCAPE™ software (ABI).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. A method comprising: detecting in a sample obtained from a human subject the presence of a 1824delA mutation in a cystic fibrosis transmembrane conductance regulator (CFTR) gene or protein; and indicating that the subject has cystic fibrosis, or is at risk of developing cystic fibrosis when the subject is homozygous for the 1824delA mutation, or is a carrier of cystic fibrosis when the subject is heterozygous for the 1824delA mutation.

2. The method of claim 1, further comprising detecting one or more of a 269C>T, 2902G>T, 3814G>A, 502G>C, 1520G>T, 511-513 dup TTA, 978A>T, 843G>C, 829C>T, 4096-6C>T, 4375-7delT, 1586G>C, 875+4G>T, or 4005+3G>T mutation of the cystic fibrosis transmembrane conductance regulator (CFTR) gene or protein.

3. The method of claim 1, further comprising detecting one or more of a 2711T>C, 3891G>C, 2524C>T or 2894G>A mutation of the cystic fibrosis transmembrane conductance regulator (CFTR) gene or protein.

4. The method of claim 1, further comprising detecting one or more of a 405+10247C>T, 405+10255 del C, 1811+1643 G>T, 1812-13A>G, 2752-33insA, 3849+12192 G>A, 724G>A, 3899C>T, 3986C>T, 901G>A, 392T>C, 3463T>C, 1757G>A, 4025G>C, 4129G>T, 663T>G, 3200T>C, 4412T>C, 620A>C, 1738A>G, 3370A>C, 1129C>T, 2383C>T, 2761delTCT, 1106A>G or 622A>G mutation of the cystic fibrosis transmembrane conductance regulator (CFTR) gene or protein.

5. The method of claim 1, wherein the 1824delA mutation is detected as part of a CFTR mutation panel.

6. The method of claim 1, wherein the sample comprises nucleic acid.

7. The method of claim 6, wherein the detecting step comprises nucleic acid sequencing.

8. The method of claim 6, wherein the detecting step comprises hybridization.

9. The method of claim 8, wherein the hybridization is performed using one or more oligonucleotide probes specific for SEQ ID NO:1 under conditions sufficiently stringent to disallow a single nucleotide mismatch.

10. The method of claim 8, wherein the hybridization is performed with a microarray.

11. The method of claim 6, wherein the detecting step comprises restriction enzyme digestion.

12. The method of claim 6, wherein the detecting step comprises PCR amplification.

13. The method of claim 12, wherein the PCR amplification is digital PCR amplification or real-time PCR.

14. The method of claim 6, wherein the detecting step comprises primer extension.

15. The method of claim 14, wherein the primer extension is single-base primer extension.

16. The method of claim 6, wherein the detecting step comprises performing a multiplex allele-specific primer extension (ASPE).

17. The method of claim 1, wherein the sample comprises protein.

18. The method of claim 17, wherein the detecting step comprises amino acid sequencing.

19. The method of claim 17, wherein the detecting step comprises performing an immunoassay using one or more antibodies that specifically recognize one or more epitopes corresponding to the 1824delA mutation.

20. The method of claim 17, wherein the detecting step comprises protease digestion.

21. The method of claim 20, wherein the protease digestion is trypsin digestion.

22. The method of claim 20, wherein the detecting step further comprises performing 2D-gel electrophoresis.

23. The method of claim 1, wherein the detecting step comprises determining the presence of the one or more mutations using mass spectrometry.

24. The method of claim 23, wherein the mass spectrometric format is selected from among Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

25. The method of claim 1, wherein the sample is obtained from cells, tissue, whole blood, mouthwash, plasma, serum, urine, stool, saliva, cord blood, chorionic villus sample, chorionic villus sample culture, amniotic fluid, amniotic fluid culture, or transcervical lavage fluid, or a combination thereof.

26. The method of claim 1, wherein the method is used in conjunction with an additional test for CFTR mutations.

27. The method of claim 1 further comprising providing a sample obtained from the subject.

28. The method of claim 1, wherein the presence of the mutation is determined by comparing the identity of the nucleotide and/or amino acid at the 1824delA mutation to a control.

29. The method of claim 1, further comprising detecting one or more of a 2957delT, 4089ins4, 4374+2T>C, 3064A>T, or 246C>G mutation of the cystic fibrosis transmembrane conductance regulator (CFTR) gene or protein.

* * * * *

UNITED STATES PATENT AND TRADEMARK OFFICE

CERTIFICATE OF CORRECTION

PATENT NO. : 8,728,731 B2
APPLICATION NO. : 13/053626
DATED : May 20, 2014
INVENTOR(S) : Elizabeth Rohlfs et al.

It is certified that error appears in the above-identified patent and that said Letters Patent is hereby corrected as shown below:

In the Specification

At column 7, line 45, Please delete “teem”, please insert -- term --.

At column 12, line 2, Please delete “5xDenhart’s”, please insert -- 5XDenhart’s --.

At column 12, line 3, Please delete “2xSSC”, please insert -- 2XSSC --.

At column 12, line 4, please delete “0.2xSSC”, please insert -- 0.2XSSC --.

At column 20, Table 4, Row “405+10255delC”, Column “Clinical Information”, Line 2, Please delete “know”, please insert -- known --.

Signed and Sealed this
First Day of September, 2015

Michelle K. Lee
*Director of the United States Patent and Trademark Office*